(12) United States Patent
Yang et al.

(10) Patent No.: US 12,390,532 B2
(45) Date of Patent: Aug. 19, 2025

(54) ALK PROTEIN REGULATOR AND ANTI-TUMOR APPLICATION THEREOF

(71) Applicant: SHANGHAITECH UNIVERSITY, Pudong Shanghai (CN)

(72) Inventors: Xiaobao Yang, Pudong Shanghai (CN); Biao Jiang, Pudong Shanghai (CN); Xiaoling Song, Pudong Shanghai (CN); Ning Sun, Pudong Shanghai (CN); Chaowei Ren, Pudong Shanghai (CN); Ying Kong, Pudong Shanghai (CN); Jianshui Zhang, Pudong Shanghai (CN); Jinju Chen, Pudong Shanghai (CN); Yan Li, Pudong Shanghai (CN); Yuedong Zhou, Pudong Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 841 days.

(21) Appl. No.: 17/618,685

(22) PCT Filed: Jun. 11, 2020

(86) PCT No.: PCT/CN2020/095616
§ 371 (c)(1),
(2) Date: Dec. 13, 2021

(87) PCT Pub. No.: WO2020/249048
PCT Pub. Date: Dec. 17, 2020

(65) Prior Publication Data
US 2022/0257776 A1  Aug. 18, 2022

(30) Foreign Application Priority Data
Jun. 12, 2019 (CN) .......................... 201910505073.9

(51) Int. Cl.
*A61K 47/55* (2017.01)
*A61K 47/54* (2017.01)
*A61P 35/00* (2006.01)

(52) U.S. Cl.
CPC .............. *A61K 47/55* (2017.08); *A61K 47/54* (2017.08); *A61K 47/545* (2017.08); *A61K 47/548* (2017.08); *A61P 35/00* (2018.01)

(58) Field of Classification Search
None
See application file for complete search history.

(56) References Cited

U.S. PATENT DOCUMENTS 11,771,709 B2 * 10/2023 Yang .................... C07D 417/14
514/142

FOREIGN PATENT DOCUMENTS

| CN | 106458993 A | 2/2017 | | |
|---|---|---|---|---|
| JP | 2017-513862 A | 6/2017 | | |
| JP | 2021-506820 A | 2/2021 | | |
| JP | 2021-521163 A | 8/2021 | | |
| WO | 2017011371 A1 | 1/2017 | | |
| WO | 2017079267 A1 | 5/2017 | | |
| WO | WO-2017180417 A1 | * 10/2017 | ......... | A61K 31/4745 |
| WO | 2017/204445 A2 | 11/2017 | | |
| WO | 2019/042444 A1 | 3/2019 | | |
| WO | 2019/094772 A1 | 5/2019 | | |
| WO | WO-2019114770 A1 | * 6/2019 | ......... | A61K 31/4025 |
| WO | 2019196812 A1 | 10/2019 | | |
| WO | 2020/069106 A1 | 4/2020 | | |
| WO | 2021/036922 A1 | 3/2021 | | |
| WO | 2021/173677 A1 | 9/2021 | | |

OTHER PUBLICATIONS

Golub, Science vol. 286 Oct. 15, 1999 (Year: 1999).*
Sep. 23, 2020 International Search Report issued in International Patent Application No. PCT/CN2020/095616.
Sep. 23, 2020 Written Opinion of the International Searching Authority issued in International Patent Application No. PCT/CN2020/095616.
Kang C.H. et al., "Induced protein degradation of anaplastic lymphoma kinase (ALK) by proteolysis targeting chimera (PROTAC)." Biochemical and Biophysical Research Communications. vol. 505, Sep. 28, 2018.
Notice of Reasons for Refusal dated May 25, 2023 issued in corresponding Japanese Application No. 2021-573949.
Extended Search Report dated Jun. 23, 2023 issued in corresponding European Application No. 20822481.6.
Office Action dated Feb. 7, 2023 issued in corresponding Canadian Application No. 3,141,413.
First Office Action dated Mar. 11, 2024 issued in Korean Patent Application No. 10-2022-7001070.

* cited by examiner

*Primary Examiner* — Kortney L. Klinkel
*Assistant Examiner* — Donna M Nestor
(74) *Attorney, Agent, or Firm* — Nath, Goldberg & Meyer; Joshua B. Goldberg

(57) ABSTRACT

A compound of general formula (I), a compound of general formula (III) and anti-tumor applications thereof. A series of compounds designed and synthesized have a wide range of pharmacological activities, have the function of degrading specific proteins and/or inhibiting activity, and can be used in related tumor and cancer treatments.

(I)

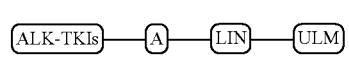

9 Claims, 2 Drawing Sheets

ALK PROTEIN REGULATOR AND ANTI-TUMOR APPLICATION THEREOF

This is a National Phase Application filed under 35 U.S.C. 371 as a national stage of PCT/CN2020/095616, filed Jun. 11, 2020, an application claiming the benefit of Chinese Application No. 201910505073.9, filed Jun. 12, 2019, the content of each of which is hereby incorporated by reference in its entirety.

TECHNICAL FIELD

The present disclosure relates to a compound represented by formula (I), a compound represented by formula (III) for the prevention or treatment of cancer and an anti-tumor application thereof, especially anti-tumor application for related proteins such as ALK, ROS1, MET, EGFR and FLT3.

Formula (I) or (III)

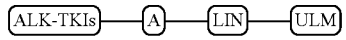

BACKGROUND

Lung cancer is the cancer with the highest total number of incidences and the highest number of deaths in the world. According to statistics from the American Cancer Center, about one in eight new cancer patients in 2020 was a lung cancer patient (13%), and one in five patients who were died of cancer was a lung cancer patient (22%). With the aging of the world, the incidence and mortality of lung cancer have increased year after year, which is of great significance to the research of lung cancer. At present, five-year survival rate of lung cancer is very low, only 18%, and this survival rate has not changed much since the 1970s. This is largely due to the fact that conventional treatment measures cannot effectively control lung cancer. Conventional radiotherapy and chemotherapy treatments kill cancer cells while also killing normal cells in the patient's body, reducing immunity and causing damage to the normal physiological functions of the patient.

In recent years, the precision medicine plan for patients with ALK (Anaplastic Lymphoma Kinase) mutation-positive non-small cell lung cancer using targeted small molecule inhibitors can specifically kill cancer cells, reduce toxic side effects, and significantly improve the clinical treatment effect and survival rate of this part of lung cancer patients. The number of patients with ALK fusion gene mutations accounts for 3-7% of the total number of patients with non-small cell lung cancer. It is clinically common in young lung cancer patients who do not smoke. It has been reported in lung adenocarcinoma and lung squamous cell carcinoma, lung adenocarcinoma is predominant, and the main existing form is EML4-ALK (Soda, M., et al., Nature, 2007. 448(7153): p. 561-6) (Inamura, K., et al., Mod Pathol, 2009.22(4):508-515) (Nishio, M., et al., Cancer Res Treat, 2018. 50(3): p. 691-700). This ratio is not significantly different between Asian and Western populations (Nishio, M., et al., Cancer Res Treat, 2018. 50(3): p. 691-700). ALK is a tyrosine kinase, which was first discovered that formed in anaplastic large cell lymphoma (ALCL) and gene rearranged with NPM to form a fusion gene (et al., 2007). Subsequently, many types of ALK gene rearrangements were also found in a variety of diseases including diffuse large B-cell lymphoma (ALCL) and inflammatory myofibroblastoma (IMT). These different forms of ALK fusion genes are a powerful oncogenic driver gene, which will cause the continuous activation of ALK kinase activity and transform normal cells into cancer cells (Soda, M., et al., Nature, 2007. 448(7153): p 561-6) (Choi et al., Cancer Research, 2008. 68(13): 4971-4976). Such cells strongly depend on ALK kinase activity, and inhibition of ALK activity will significantly inhibit the growth of these tumor cells. Based on the above findings, Pfizer developed the kinase inhibitor Crizotinib for ALK activity, which was approved by the FDA in 2011 for the treatment of non-small cell lung cancer patients with positive mutations in the ALK fusion gene.

Although the first-generation ALK inhibitor Crizotinib is highly effective for lung cancer patients with ALK fusion, patients usually develop resistance about 1 year after taking the drug. Part reason for drug resistance is the presence of ALK gene amplification or secondary drug resistance mutations in patients, including the site of L1196M, L1198F, L1152R, L1151TIN, C1156Y, F1174C, G1202R, D1203N, S1206Y, etc. (Bordi et al., Clin Lung Cancer, 2017. 18(6): 692-697; Dagogo-Jack and Shaw, Ann Oncol, 2016. 27 Suppl 3: iii42-iii50; Drizou et al., Clin Transl Oncol. 2017. 19(6):658-666). Among them, L1196M occurs more frequently and is also known as goalkeeper mutation. Because the ability of Crizotinib to enter the brain is relatively weak, some patients' tumors have brain metastases and developed drug resistance. In addition, part of the drug resistance mechanism is the conversion of driver genes in tumors, resulting in bypass activation mechanisms including EGFR mutation or activation (30-35%), c-KIT amplification (10%) or KRAS and other gene mutations (5%)), etc. (Bordi et al., Clin Lung Cancer, 2017. 18(6):692-697).

Research on drug resistance mechanisms has promoted the production of second and third generations of ALK inhibitors that have the ability to enter the brain, including Ceritinib (LDK378) developed by Novartis, and Alectinib (Code CH5424802) developed by Roche and Brigatinib (AP26113) produced by Takeda Pharmaceutical ariad company. These new drugs can overcome multiple drug-resistant mutations caused by the use of Crizotinib, including the common goalkeeper mutation Ll 196M; and these drugs also have a good ability to enter the brain, which can effectively control new brain lesions. For example, Brigatinib (AP26113) was approved by the FDA on Apr. 28, 2017 for the treatment of ALK mutation-positive non-small cell lung cancer patients who are resistant or intolerant to Crizotinib. Compared with the other two second-generation drugs, Brigatinib can effectively inhibit some of the known resistance mutations including G1269A, C1156Y, I1171S/T, and V1180L, and can also overcome the resistance to Crizotinib, Ceritinib and Alectinib caused by G1202R mutation (Zhang, S., et al., Clin Cancer Res, 2016. 22(22): p. 5527-5538). In addition, the drug can also target EGFR and FLT3 at the same time, with an effective rate of 55% and a control rate of 86% for lung cancer patients.

Although the second- and third-generation drugs subsequently developed are more effective and can overcome some of the drug resistance after the use of the previous generations of drugs, clinical results show that after the use of these small molecule inhibitor drugs, patients will have drug resistance without exception. Even though the newly launched third-generation ALK drug Lorlatinib (PF-06463922) can well fight against the known secondary drug resistance mutations of ALK, the problem of secondary drug resistance of tumors to kinase inhibitor drugs is still inevitable. Lung cancer patients with ALK gene rearrangement account for a high proportion of lung cancer patients in the world, and the number of lung cancer patients is increasing year by year. The emergence of drug resistance to targeted drugs has severely affected the needs of patients' survival and social development. Overcoming the drug resistance of tumors to targeted drug small molecule compounds in the treatment of lung cancer has also become an urgent problem.

ALK gene abnormality is not only critical to the occurrence of non-small cell lung cancer, but also plays an important role in many other diseases. ALK can not only form fusion mutations with EML4, but also form fusion mutations with dozens of other genes; ALK fusion mutations have not only been reported in lung cancer, but also in other diseases. For example, NPM-ALK fusions are mostly present in anaplastic large cell lymphoma. ALK mutations have also been reported in colorectal cancer (Lin et al., Mol Cancer Res, 2009. 7(9): 1466-1476; Lipson et al., Nat Met, 2012. 18(3): 382-384), breast cancer (Lin et al., Mol Cancer Res, 2009.7(9):1466-1476), inflammatory myofibroblastic tumor (Lawrence et al., Am JPathol, 2000.157(2):377-384), ovarian cancer (Ren et al., Cancer Res, 2012. 72(13):3312-3323) and many other diseases. In addition, the ALK gene is also found in gliomas in the form of amplification and gene activation mutations (Janoueix-Lerosey et al., Nature, 2008. 455(7215)967-970; Mosse et al., Nature, (7215)2008). These ALK mutant cells are also sensitive to ALK inhibitors, potentially benefiting from research on ALK inhibitors. ALK kinase inhibitors can not only inhibit the activity of ALK protein kinase, but also affect the activity of many other proteins. For example, in 2016, Crizotinib was also certified to treat ROS1 (c-ros oncogene I receptor tyrosine kinase, c-ros, proto-oncogene 1 tyrosine kinase) positive lung cancer patients with metastases.

Therefore, it is necessary to develop new treatment measures and a new class of drugs, which not only inhibit the occurrence and progression of tumors, but also potentially overcome the emergence of drug resistance to targeted drugs.

CONTENT OF THE PRESENT INVENTION

In one aspect, the present disclosure provides a compound represented by formula (I):

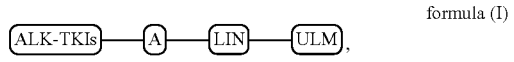

formula (I)

or a salt thereof, an enantiomer thereof, a stereoisomer thereof, a solvate thereof, a polymorph thereof, wherein the groups ALK-TKIs, A, LIN, ULM, and all substituents are as defined in Part I of the Detailed Description of the Disclosure.

The present disclosure also provides a pharmaceutical composition, comprising the compound represented by formula (I) or the pharmaceutically acceptable salt thereof, and at least one pharmaceutically acceptable carrier.

The present disclosure also provides the compound represented by formula (I), or the pharmaceutically acceptable salt thereof for use as a medicament:

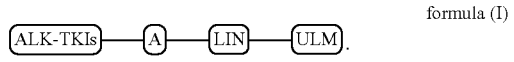

formula (I)

The compound represented by formula (I), or the pharmaceutically acceptable salt thereof described in the present disclosure for use in the prevention and/or treatment of cancer.

The present disclosure also provides a use of the compound represented by formula (I) or the pharmaceutically acceptable salt thereof in the preparation of a medicament for the prevention and/or treatment of cancer.

The present disclosure also provides a method for treating or preventing cancer, comprising administering a therapeutically effective amount of the compound represented by formula (I), or the pharmaceutically acceptable salt thereof, or the pharmaceutical composition to a subject.

In another aspect, the present disclosure provides a compound represented by formula (III):

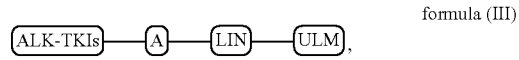

formula (III)

or a salt thereof, an enantiomer thereof, a stereoisomer thereof, a solvate thereof, a polymorph thereof, wherein the groups ALK-TKIS, A, LIN, ULM, and all substituents are as defined in Part II of the Detailed Description of the Disclosure.

The present disclosure also provides the compound represented by formula (III), or the pharmaceutically acceptable salt thereof for use as a medicament.

The present disclosure also provides the compound represented by formula (III), or the pharmaceutically acceptable salt thereof for use in the prevention and/or treatment of cancer.

The present disclosure also provides a use of the compound represented by formula (III) or the pharmaceutically acceptable salt thereof in the preparation of a medicament for the prevention and/or treatment of cancer.

The present disclosure also provides a method for treating or preventing cancer, comprising administering a therapeutically effective amount of the compound represented by formula (III), or the pharmaceutically acceptable salt thereof, or the pharmaceutical composition to a subject.

The present disclosure also provides a compound as listed in Table 3 or a pharmaceutically acceptable salt thereof for use in the prevention and/or treatment of cancer.

DETAILED DESCRIPTION OF THE PREFERRED EMBODIMENT

I. Compounds Represented by formula (I)

Figure 1:
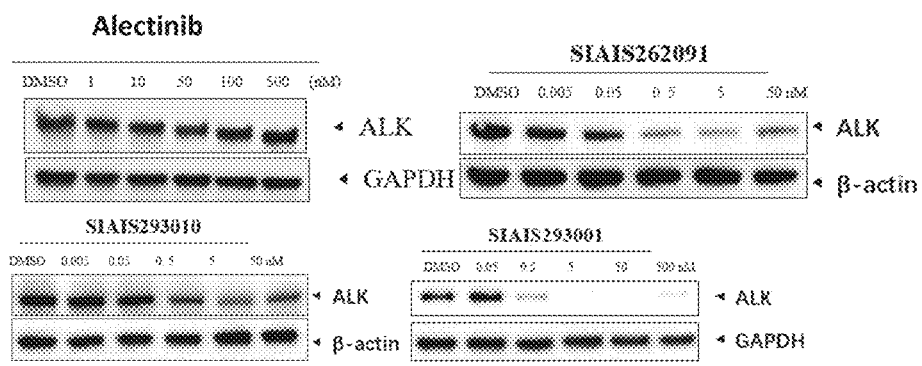
FIG. 1 shows the study of the Alectinib-derived compounds of the present disclosure (SR cell line) using Western-blot assay. Compared with the commercial parent inhibitor Alectinib, the compound of the present disclosure can effectively degrade ALK protein.

Therefore, one aspect of the present disclosure provides a compound represented by formula (I):

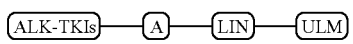

formula (I)

ALK-TKIs are covalently connected to LIN through group A, and wherein ULM is covalently connected to LIN;

wherein group A represents C(O) or is absent;

ALK-TKIs represent the structure of the following formula (Ia), formula (Ib), formula (Ic), formula (Id), formula (Ie) or formula (If):

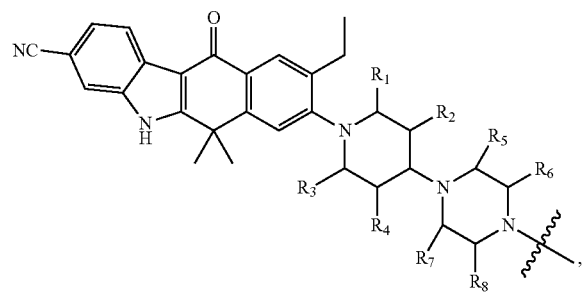

(Ia)

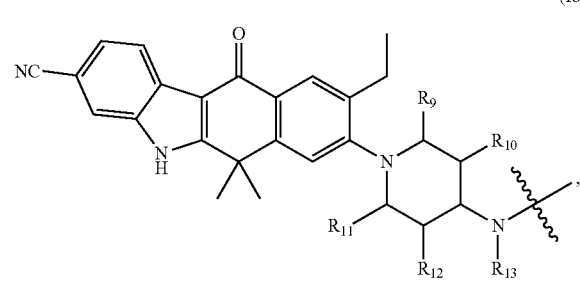

(Ib)

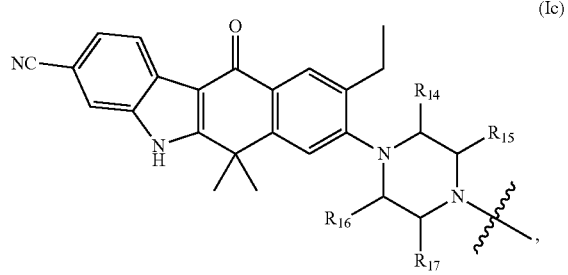

(Ic)

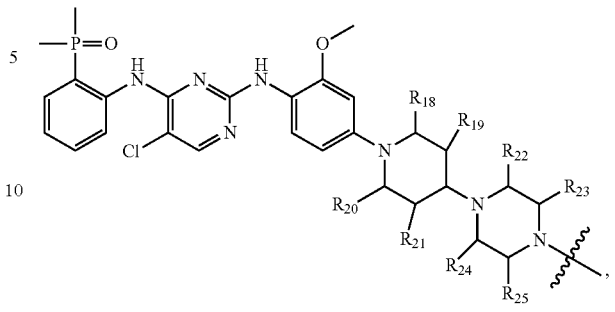

(Id)

(Ie)

(If)

wherein $R_1$, $R_2$, $R_3$, $R_4$, $R_5$, $R_6$, $R_7$, $R_8$, $R_9$, $R_{10}$, $R_{11}$, $R_{12}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{31}$, $R_{32}$, $R_{33}$ and $R_{34}$ each independently represents H or methyl, and $R_{13}$ and $R_{30}$ each independently represents H, methyl or ethyl;

the ULM represents the structure of the following formula (II):

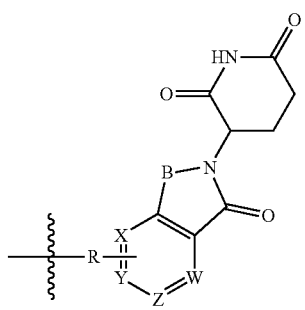

formula (II)

wherein, B represents $CH_2$ or C(O); X, Y, Z, and W are the same or different and each independently represents CH or N, and R represents vinylene or ethynylene; and LIN is a linking group and represents —U-alkylene-, wherein the alkylene is linear or branched alkylene optionally interrupted one or more times (e.g. 1-20, 1-15, 1-10, 1-9, 1-8, 1-7, 1-6,1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent;

or a salt thereof, an enantiomer thereof, a stereoisomer thereof, a solvate thereof, a polymorph thereof.

In the present disclosure, LIN in formula (I) is represented as —U-alkylene-, wherein one of the two ends of the —U-alkylene- (for example, group U) may be connected to group A, and the other end (alkylene) is connected to ULM; or one of the two ends of the —U-alkylene- (for example, alkylene) may be connected to group A, and the other end (group U) is connected to ULM. When group U is connected to the group A, group U and the group A are not C(O) at the same time. In an embodiment of the present disclosure, when group U is connected to group A, both group U and group A may be absent at the same time, or either of group U and group A is C(O), and the other is absent.

In an embodiment of the present disclosure, the ALK-TKIs are small molecule drugs targeting an ALK target.

In an embodiment of the present disclosure, the group A represents C(O).

In an embodiment of the present disclosure, the group A is absent.

In an embodiment of the present disclosure, in formula (II), B represents CH$_2$ or C(O); X, Y, Z, and W are the same and all represent CH, and R represents vinylene or ethynylene. In a sub-embodiment of the present disclosure, in formula (II), B represents CH$_2$ or C(O); X, Y, Z, and W are the same and all represent CH, and R represents vinylidene. In a sub-embodiment of the present disclosure, in formula (II), B represents CH$_2$ or C(O); X, Y, Z, and W are the same and all represent CH, and R represents ethynylene. In a sub-embodiment of the present disclosure, in formula (II), B represents CH$_2$; X, Y, Z, and W are the same and all represent CH, and R represents vinylidene. In a sub-embodiment of the present disclosure, in formula (II), B represents C(O); X, Y, Z, and W are the same and all represent CH, and R represents vinylidene. In a sub-embodiment of the present disclosure, in formula (II), B represents CH$_2$; X, Y, Z, and W are the same and all represent CH, and R represents ethynylene. In a sub-embodiment of the present disclosure, in formula (II), B represents C(O); X, Y, Z, and W are the same and all represent CH, and R represents ethynylene.

In an embodiment of the present disclosure, formula (II) is also the following structural formula:

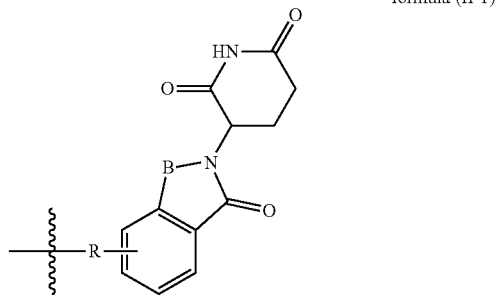

formula (II-1)

wherein group R represents vinylene or ethynylene, and B represents CH$_2$ or C(O).

In an embodiment of the present disclosure, formula (II) is also the following structural formula:

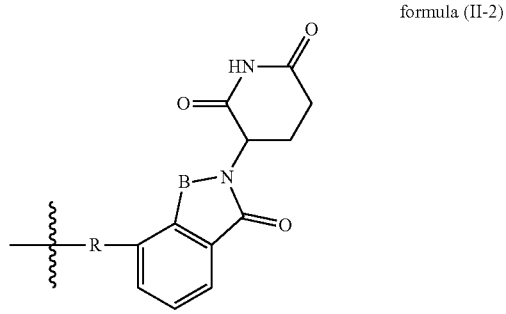

formula (II-2)

wherein group R represents vinylene or ethynylene, and B represents CH$_2$ or C(O).

In an embodiment of the present disclosure, formula (II) is also the following structural formula:

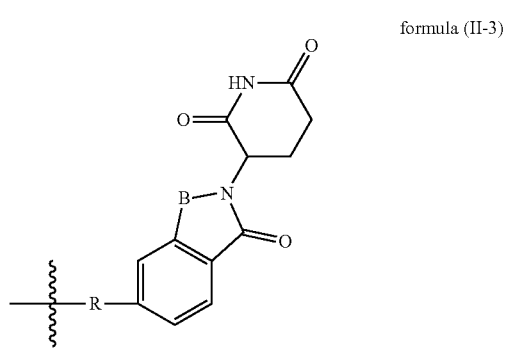

formula (II-3)

wherein group R represents vinylene or ethynylene, and B represents CH$_2$ or C(O).

In an embodiment of the present disclosure, formula (II) is also the following structural formula:

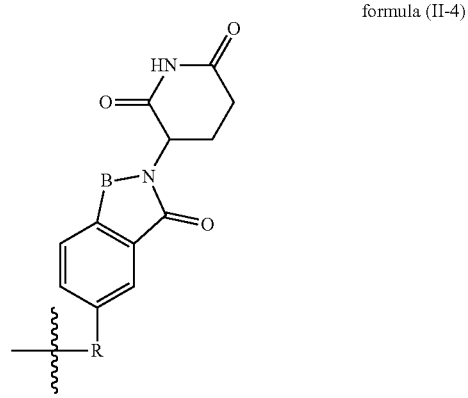

formula (II-4)

wherein group R represents vinylene or ethynylene, and B represents CH$_2$ or C(O).

In an embodiment of the present disclosure, formula (II) is also the following structural formula:

formula (II-5)

wherein group R represents vinylene or ethynylene, and B represents $CH_2$ or $C(O)$.

In an embodiment of the present disclosure, the LIN represents:

—U—$C_{1-30}$ alkylene-, —U—$(CH_2)_{n1}$—$(C(O)NH$—$(CH_2)_{n2})_{m1}$—, —U—$(CH_2)_{n1}$—$(NHC(O)$—$(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$(C(O)NH$—$(CH_2)_{n2})_{m1}$—$(O(CH_2)_{n3})_{m2}$—, —U—$(CH_2)_{n1}$—$(O(CH_2)_{n2})_{m1}$—$O$—$(CH_2)_{n3}$—$C(O)NH$—$(CH_2)_{n4}$—$(O(CH_2)_{n5})_{m2}$—$O$—$(CH_2)_{n6}$—, —U—$(CR_{a11}R_{a12})_{n1}$—$(O(CR_{a13}R_{a14})_{n2})_{m1}$—$O$—$(CR_{a15}R_{a16})_{n3}$—$C(O)NH$—$(CR_{a17}R_{a18})_{n4}$—$(O(CR_{a19}R_{a20})_{n5})_{m2}$—$O$—$(CR_{a21}R_{a22})_{n6}$—, —U—$(CR_{a23}R_{a24})_{n1}$—$C(O)NH$—$(O(CR_{a25}R_{a26})_{n2})_{m1}$—, —U—$(CH_2)_{n1}$—$(NHC(O)$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having alkylene carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

n1, n2, n3, n4, n5, n6, m1, m2 independently represent an integer of 1, 2, 3, 4, 5, 6, 7, 8, 9, 10, 11, 12, 13, 14, 15, 16, 17, 18, 19 or 20; and the group U represents $C(O)$, or the group U is absent; and wherein, the alkylene in the LIN is optionally substituted by one or more substituents.

In an embodiment of the present disclosure, the LIN represents —U—$C_{1-30}$ alkylene chain-, and the $C_{1-30}$ alkylene chain is optionally substituted by one or more substituents selected from hydroxyl, amino, mercapto, halogen or any combination thereof.

In an embodiment of the present disclosure, the LIN is preferably —U—$C_{1-30}$ alkylene-. In an embodiment of the present disclosure, the LIN is preferably —U-methylene or —U—$C_{1-30}$ alkylene-, wherein the $C_{2-30}$ alkylene is a linear or branched $C_{2-30}$ alkylene (e.g. $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents $C(O)$, or the group U is absent.

In an embodiment of the present disclosure, preferably, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—;

wherein the group U represents $C(O)$, or the group U is absent.

In an embodiment of the present disclosure, the LIN is preferably —U—$C_{2-40}$ alkylene- (for example, —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from $C(O)NH$, $NHC(O)$, O, NH, alkynylene, alkenylene, cycloalkylene, arylene, heterocyclylene or heteroarylene or any combination thereof, and the group U represents $C(O)$, or the group U is absent.

In an embodiment of the present disclosure, the LIN is —U-alkylene-, the alkylene (preferably $C_{1-30}$ alkylene chain, for example, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents $C(O)$, or the group U is absent.

In an embodiment of the present disclosure, the LIN is preferably —U—$C_{1-30}$ alkylene-, and the $C_{1-30}$ alkylene is a linear or branched $C_{1-30}$ alkylene chain (e.g. $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In an embodiment of the present disclosure, the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the present disclosure, the LIN represents:
—U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—;

wherein the group U represents C(O), or the group U is absent.

In an embodiment of the present disclosure, the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the present disclosure, the LIN represents: —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NFIC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_5NHC(O)(CH_2)_3$—, —U—$(CH_2)_8NHC(O)(CH_2)_8$—, —U—$(CH_2)_9NHC(O)CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—;

wherein the group U represents C(O), or the group U is absent.

In an embodiment of the present disclosure, the LIN means: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—

—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_3$—, or —U—(CH$_2$)$_5$—(O(CH$_2$)$_2$)$_2$—O—(CH$_2$)$_6$—;

wherein the group U represents C(O), or the group U is absent.

In an embodiment of the present disclosure, the LIN is —U—(CH$_2$)$_{n1}$—CH═CH—(CH$_2$)$_{n2}$—, wherein n1 and n2 each independently represents 1, 2, 3, 4, 5, 6, 7, 8, 9, 10, 11, 12, 13, 14, 15, 16, 17, 18, 19, or 20, and wherein the group U represents C(O), or the group U is absent.

In an embodiment of the present disclosure, the LIN is —U—CH$_2$CH═CHCH$_2$—, —U—CH$_2$CH═CH(CH$_2$)$_2$—, —U—CH$_2$CH═CH(CH$_2$)$_3$—, —U—CH$_2$CH═CH(CH$_2$)$_4$—, —U—CH$_2$CH═CH(CH$_2$)$_5$—, —U—CH$_2$CH═CH(CH$_2$)$_6$—, —U—CH$_2$CH═CH(CH$_2$)$_7$—, —U—CH$_2$CH═CH(CH$_2$)$_8$—, —U—CH$_2$CH═CH(CH$_2$)$_9$—, —U—CH$_2$CH═CH(CH$_2$)$_{10}$—, —U—(CH$_2$)$_2$CH═CHCH$_2$—, —U—(CH$_2$)$_2$CH═CH(CH$_2$)$_2$—, —U—(CH$_2$)$_2$CH═CH(CH$_2$)$_3$—, —U—(CH$_2$)$_2$CH═CH(CH$_2$)$_4$—, —U—(CH$_2$)$_2$CH═CH(CH$_2$)$_5$—, —U—(CH$_2$)$_2$CH═CH(CH$_2$)$_6$—, —U—(CH$_2$)$_2$CH═CH(CH$_2$)$_7$—, —U—(CH$_2$)$_2$CH═CH(CH$_2$)$_8$—, —U—(CH$_2$)$_3$CH═CHCH$_2$—, —U—(CH$_2$)$_3$CH═CH(CH$_2$)$_2$—, —U—(CH$_2$)$_3$CH═CH(CH$_2$)$_3$—, —U—(CH$_2$)$_3$CH═CH(CH$_2$)$_4$—, —U—(CH$_2$)$_3$CH═CH(CH$_2$)$_5$—, —U—(CH$_2$)$_3$CH═CH(CH$_2$)$_6$—, —U—(CH$_2$)$_3$CH═CH(CH$_2$)$_2$—, —U—(CH$_2$)$_4$CH═CHCH$_2$—, —U—(CH$_2$)$_4$CH═CH(CH$_2$)$_2$—, —U—(CH$_2$)$_4$CH═CH(CH$_2$)$_3$—, —U—(CH$_2$)$_4$CH═CH(CH$_2$)$_4$—, —U—(CH$_2$)$_4$CH═CH(CH$_2$)$_5$—, —U—(CH$_2$)$_5$CH═CHCH$_2$—, —U—(CH$_2$)$_5$CH═CH(CH$_2$)$_2$—, —U—(CH$_2$)$_5$CH═CH(CH$_2$)$_3$—, —U—(CH$_2$)$_5$CH═CH(CH$_2$)$_4$—, —U—(CH$_2$)$_5$CH═CH(CH$_2$)$_5$—, —U—(CH$_2$)$_6$CH═CHCH$_2$—, —U—(CH$_2$)$_6$CH═CH(CH$_2$)$_2$—, —U—(CH$_2$)$_6$CH═CH(CH$_2$)$_3$—, —U—(CH$_2$)$_7$CH═CHCH$_2$—, —U—(CH$_2$)$_7$CH═CH(CH$_2$)$_2$—, —U—(CH$_2$)$_7$CH═CH(CH$_2$)$_3$—, —U—(CH$_2$)$_8$CH═CHCH$_2$—, —U—(CH$_2$)$_8$CH═CH(CH$_2$)$_2$—, —U—(CH$_2$)$_8$CH═CH(CH$_2$)$_3$—, —U—(CH$_2$)$_9$CH═CHCH$_2$—, —U—(CH$_2$)$_9$CH═CH(CH$_2$)$_2$—, —U—(CH$_2$)$_9$CH═CH(CH$_2$)$_3$—, —U—(CH$_2$)$_{10}$CH═CHCH$_2$—, or —U—(CH$_2$)$_{10}$CH═CH(CH$_2$)$_2$—, and wherein the group U represents C(O), or the group U is absent.

In an embodiment of the present disclosure, the LIN is —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, and wherein the group U represents C(O), or the group U is absent.

In an embodiment of the present disclosure, the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C—C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, and the group U represents C(O), or the group U is absent.

In an embodiment of the present disclosure, the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the present disclosure, the LIN represents —U—CH$_2$-piperazinylidene-CH$_2$—, —U—

(CH$_2$)$_2$-piperazinylidene-(CH$_2$)$_2$—, —U—(CH$_2$)$_3$-piperazinylidene-(CH$_2$)$_3$—, —U—(CH$_2$)$_2$-piperazinylidene-(CH$_2$)$_3$—, —U—CH$_2$-piperazinylidene-(CH$_2$)$_2$—, —U—CH$_2$-piperazinylidene-(CH$_2$)$_3$— or —U—(CH$_2$)$_2$-piperazinylidene-(CH$_2$)$_3$—, wherein the group U represents C(O), or the group U is absent.

In an embodiment of the present disclosure, the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the present disclosure, the LIN represents —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In an embodiment of the present disclosure, the LIN represents:

—U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20;

wherein the group U represents C(O), or the group U is absent.

In an embodiment of the present disclosure, the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_5$—, —U—(CH$_2$)$_3$-triazolylidene-(CH$_2$)$_2$—O(CH$_2$)$_2$—, —U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In an embodiment of the present disclosure, the LIN represents:

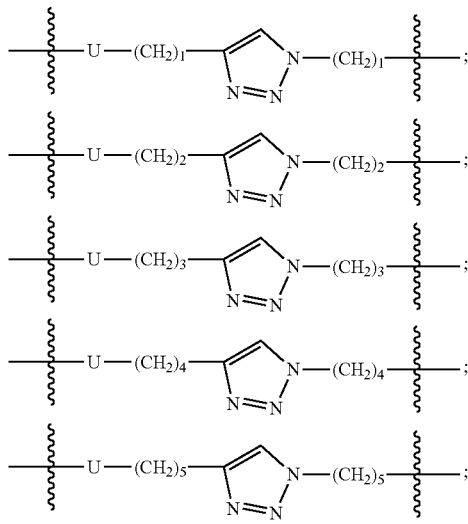

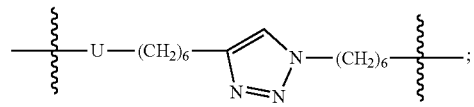

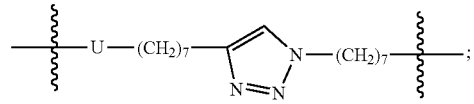

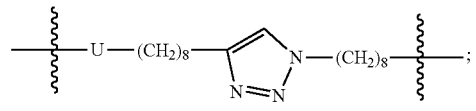

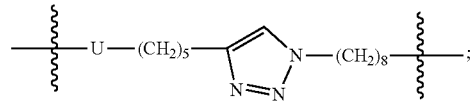

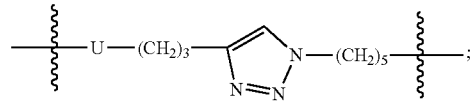

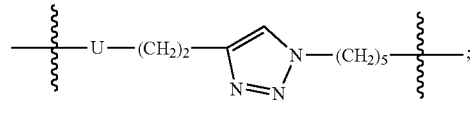

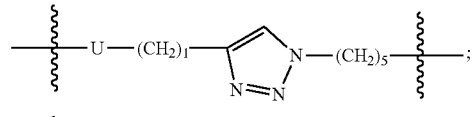

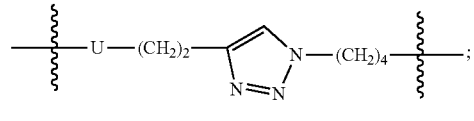

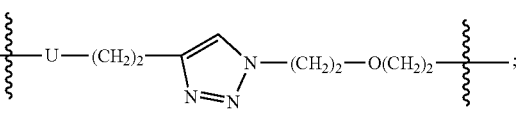

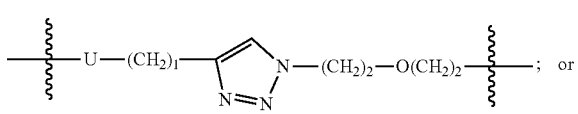

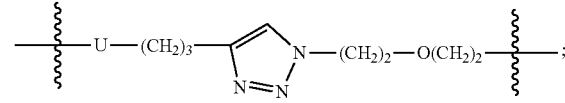

wherein the group U represents C(O), or the group U is absent.

In an embodiment of the present disclosure, the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the present disclosure, the compound represented by formula (I) is also a compound represented by formula (Ia-1):

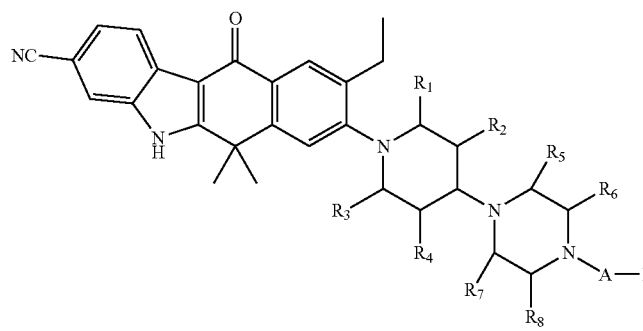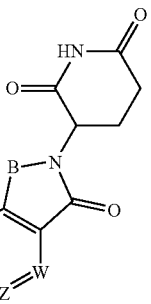

(Ia-1)

wherein, the groups LIN, A, R, $R_1$, $R_2$, $R_3$, $R_4$, $R_5$, $R_6$, $R_7$, $R_8$, and B, X, Y, Z, W are as defined herein.

In an embodiment of the present disclosure, the compound represented by formula (I) is also a compound represented by formula (Ia-2):

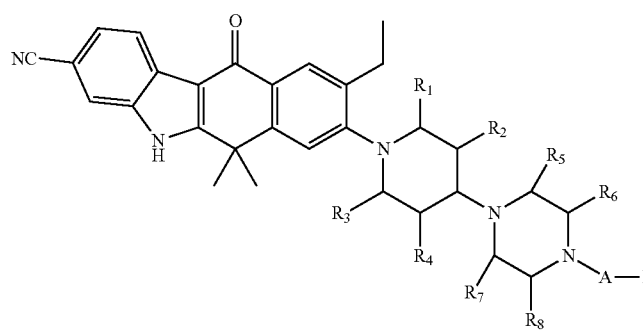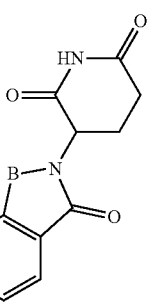

(Ia-2)

wherein, the groups LIN, A, R, and B are as defined herein, and the groups $R_1$, $R_2$, $R_3$, $R_4$, $R_5$, $R_6$, $R_7$, $R_8$ are as defined herein.

In an embodiment of the present disclosure, the compound represented by formula (I) is also a compound represented by formula (Ia-3):

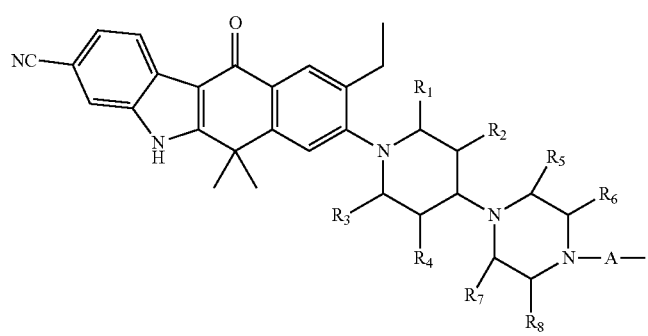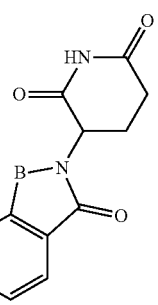

(Ia-3)

wherein, the groups LIN, A, R, and B are as defined herein, and the groups $R_1$, $R_2$, $R_3$, $R_4$, $R_5$, $R_6$, $R_7$, $R_8$ are as defined herein.

In an embodiment of the present disclosure, the compound represented by formula (I) is also a compound represented by formula (Ia-4):

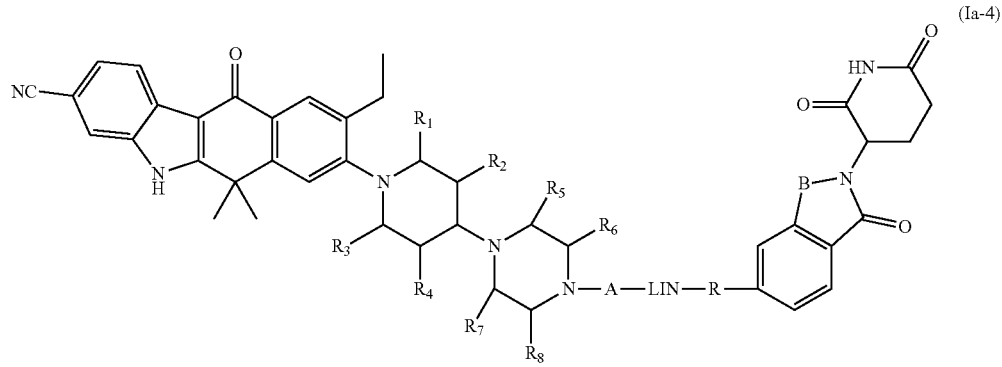

wherein, the groups LIN, A, R, and B are as defined herein, and the groups $R_1$, $R_2$, $R_3$, $R_4$, $R_5$, $R_6$, $R_7$, $R_8$ are as defined herein.

In an embodiment of the present disclosure, the compound represented by formula (I) is also a compound represented by formula (Ia-5):

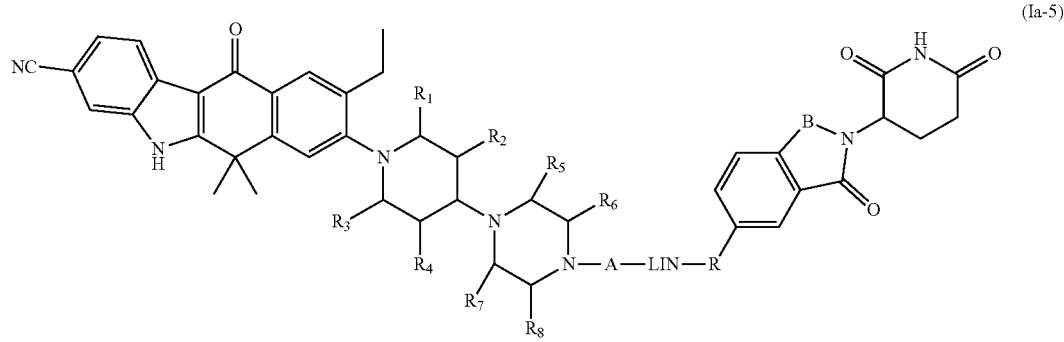

wherein, the groups LIN, A, R, and B are as defined herein, and the groups $R_1$, $R_2$, $R_3$, $R_4$, $R_5$, $R_6$, $R_7$, $R_8$ are as defined herein.

In an embodiment of the present disclosure, the compound represented by formula (I) is also a compound represented by formula (Ia-6):

wherein, the groups LIN, A, R, and B as defined herein, and the groups $R_1$, $R_2$, $R_3$, $R_4$, $R_5$, $R_6$, $R_7$, $R_8$ are as defined herein.

In a sub-embodiment of the compound of the present disclosure represented by formula (Ia-1), formula (Ia-2), formula (Ia-3), formula (Ia-4), formula (Ia-5), or formula (Ia-6), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene,

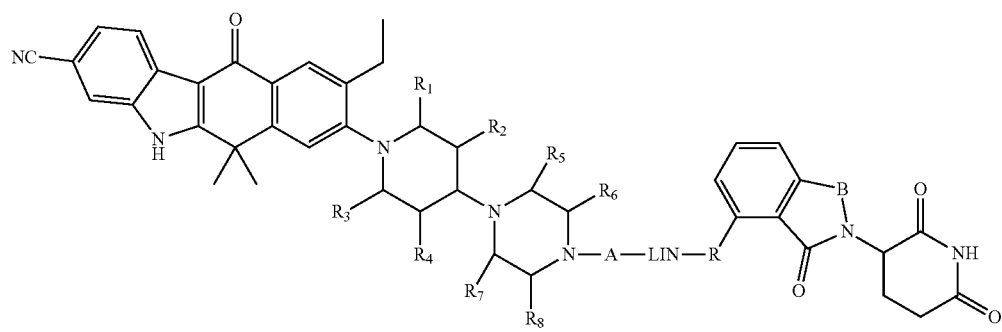

heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents —U—$C_{1\text{-}30}$ alkylene-, —U—$(CH_2)_{n1}$—$C(O)NH$—$(CH_2)_{n2})_{m1}$—, —U—$(CH_2)_{n1}$—$(NHC(O)$—$(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$C(O)NH$—$(CH_2)_{n2})_{m1}$—$(O(CH_2)_{n3})_{m2}$—, —U—$(CH_2)_{n1}$—$(O(CH_2)_{n2})_{m1}$—O—$(CH_2)_{n3}$—$C(O)NH$—$(CH_2)_{n4}$—$(O(CH_2)_{n5})_{m2}$—O—$(CH_2)_{n6}$—, —U—$(CR_{a11}R_{a12})_{n1}$—$(O(CR_{a13}R_{a14})_{n2})_{m1}$—O—$(CR_{a15}R_{a16})_{n3}$—C(O)NH—$(CR_{a17}R_{a18})_{n4}$—$(O(CR_{a19}R_{a20})_{n5})_{m2}$—O—$(CR_{21}R_{22})_{n6}$—, —U—$(CR_{a23}R_{a24})_{n1}$—C(O)NH—$(O(CR_{a25}R_{a26})_{n2})_{m1}$—, —U—$(CH_2)_{n1}$—$(NHC(O)$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound of the present disclosure represented by formula (Ia-1), formula (Ia-2), formula (Ia-3), formula (Ia-4), formula (Ia-5), or formula (Ia-6), the LIN represents —U—$C_{1\text{-}30}$ alkylene-; and the group U represents C(O), or the group U is absent; wherein the alkylene is optionally substituted by one or more substituents selected from hydroxyl, amino, mercapto, halogen or any combination thereof (wherein the number of substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1). In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN is preferably —U—$C_{2\text{-}40}$ alkylene-(preferably, —U—$C_{2\text{-}30}$ alkylene-), wherein the alkylene chain is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent, wherein the alkylene is optionally substituted by substituents selected from hydroxyl, amino, mercapto, halogen or any combination thereof.

In a sub-embodiment of the compound of the present disclosure represented by formula (Ia-1), formula (Ia-2), formula (Ia-3), formula (Ia-4), formula (Ia-5), or formula (Ia-6), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment, the LIN preferably represents: —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH$ $(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—; wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment of the present disclosure, the LIN preferably represents: —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_5$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—$(CH_2)_8NHC(O)(CH_2)_8$—, —U—$(CH_2)_9NHC(O)CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—; wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—(CH$_2$)$_{n1}$—CH═CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—CH$_2$CH═CHCH$_2$—, —U—CH$_2$CH═CH(CH$_2$)$_2$—, —U—CH$_2$CH═CH(CH$_2$)$_3$—, —U—CH$_2$CH═CH(CH$_2$)$_4$—, —U—CH$_2$CH═CH(CH$_2$)$_5$—, —U—CH$_2$CH═CH(CH$_2$)$_6$—, —U—CH$_2$CH═CH(CH$_2$)$_7$—, —U—CH$_2$CH═CH(CH$_2$)$_8$—, —U—CH$_2$CH═CH(CH$_2$)$_9$—, —U—CH$_2$CH═CH(CH$_2$)$_{10}$—, —U—(CH$_2$)$_2$CH═CHCH$_2$—, —U—(CH$_2$)$_2$CH═CH(CH$_2$)$_2$—, —U—(CH$_2$)$_2$CH═CH(CH$_2$)$_3$—, —U—(CH$_2$)$_2$CH═CH(CH$_2$)$_4$—, —U—(CH$_2$)$_2$CH═CH(CH$_2$)$_5$—, —U—(CH$_2$)$_2$CH═CH(CH$_2$)$_6$—, —U—(CH$_2$)$_2$CH═CH(CH$_2$)$_7$—, —U—(CH$_2$)$_2$CH═CH(CH$_2$)$_8$—, —U—(CH$_2$)$_3$CH═CHCH$_2$—, —U—(CH$_2$)$_3$CH═CH(CH$_2$)$_2$—, —U—(CH$_2$)$_3$CH═CH(CH$_2$)$_3$—, —U—(CH$_2$)$_3$CH═CH(CH$_2$)$_4$—, —U—(CH$_2$)$_3$CH═CH(CH$_2$)$_5$—, —U—(CH$_2$)$_3$CH═CH(CH$_2$)$_6$—, —U—(CH$_2$)$_3$CH═CH(CH$_2$)$_7$—, —U—(CH$_2$)$_4$CH═CHCH$_2$—, —U—(CH$_2$)$_4$CH═CH(CH$_2$)$_2$—, —U—(CH$_2$)$_4$CH═CH(CH$_2$)$_3$—, —U—(CH$_2$)$_4$CH═CH(CH$_2$)$_4$—, —U—(CH$_2$)$_4$CH═CH(CH$_2$)$_5$—, —U—(CH$_2$)$_5$CH═CHCH$_2$—, —U—(CH$_2$)$_5$CH═CH(CH$_2$)$_2$—, —U—(CH$_2$)$_5$CH═CH(CH$_2$)$_3$—, —U—(CH$_2$)$_5$CH═CH(CH$_2$)$_4$—, —U—(CH$_2$)$_5$CH═CH(CH$_2$)$_5$—, —U—(CH$_2$)$_6$CH═CHCH$_2$—, —U—(CH$_2$)$_6$CH═CH(CH$_2$)$_2$—, —U—(CH$_2$)$_6$CH═CH(CH$_2$)$_3$—, —U—(CH$_2$)$_7$CH═CHCH$_2$—, —U—(CH$_2$)$_7$CH═CH(CH$_2$)$_2$—, —U—(CH$_2$)$_7$CH═CH(CH$_2$)$_3$—, —U—(CH$_2$)$_5$CH═CHCH$_2$—, —U—(CH$_2$)$_8$CH═CH(CH$_2$)$_2$—, —U—(CH$_2$)$_8$CH═CH(CH$_2$)$_3$—, —U—(CH$_2$)$_9$CH═CHCH$_2$—U—(CH$_2$)$_9$CH═CH(CH$_2$)$_2$—, —U—(CH$_2$)$_9$CH═CH(CH$_2$)$_3$—, —U—(CH$_2$)$_{10}$CH═CHCH$_2$—, or —U—(CH$_2$)$_{10}$CH═CH(CH$_2$)$_2$—, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$CH≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, and wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—(CH$_2$)$_{n1}$-piperaziinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{n2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—; wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—(CH$_2$)$_3$-triazolylidene- (CH₂)₅—, —U—(CH₂)₂-triazolylidene-(CH₂)₅—, —U—CH₂-triazolylidene-(CH₂)₅—, —U—(CH₂)₂-triazolylidene-(CH₂)₄—, —U—(CH₂)₃-triazolylidene-(CH₂)₂—O(CH₂)₂—, —U—(CH₂)₂-triazolylidene-(CH₂)₂—O(CH₂)₂— or —U—CH₂-triazolylidene-(CH₂)₂—O(CH₂)₂—, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ta-6), the LIN represents:

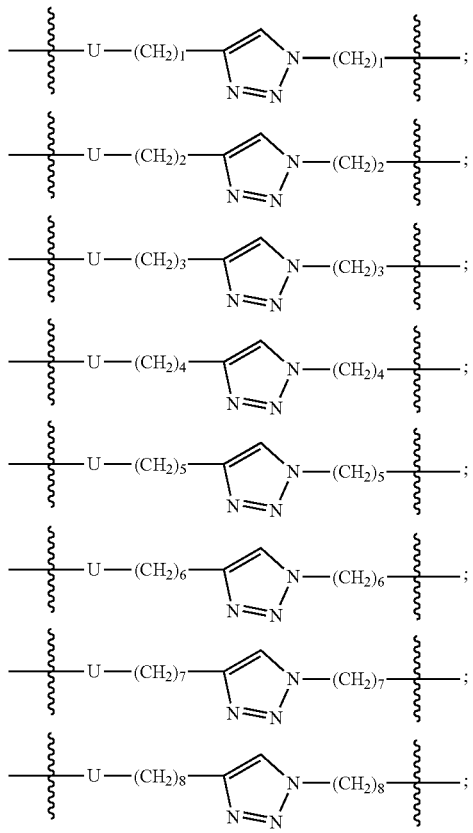

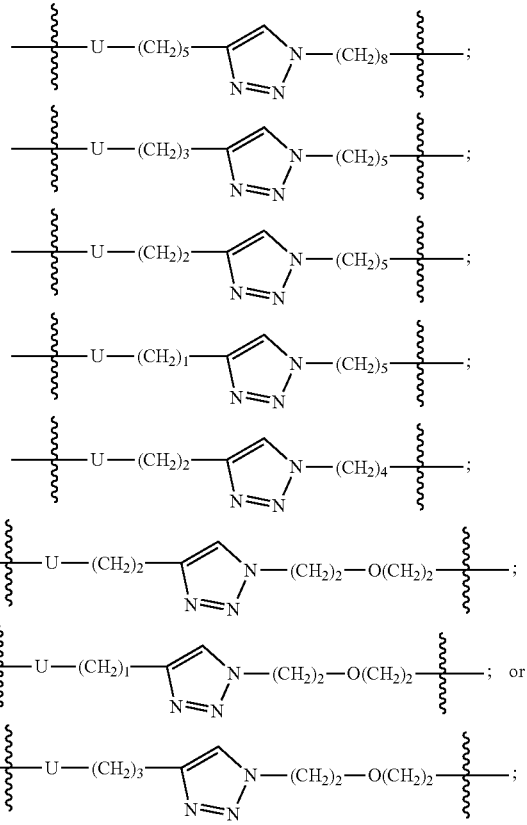

wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents —U—(CH₂)₂NHC(O)(CH₂)₂—O—(CH₂)₂— or —U—(CH₂)₂C(O)NH(CH₂)₂—O—(CH₂)₂—, wherein the group U represents C(O), or the group U is absent.

In an embodiment of the present disclosure, the compound represented by formula (I) is also a compound represented by formula (Ib-1):

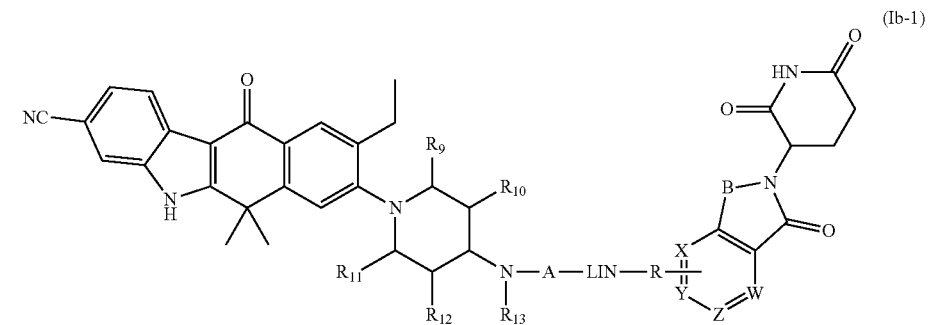

wherein, the groups LIN, A, R, R$_9$, R$_{10}$, R$_{11}$, R$_{12}$, R$_{13}$, and B, X, Y, Z, W are as defined herein.

In an embodiment of the present disclosure, the compound represented by formula (I) is also a compound represented by formula (Ib-2):

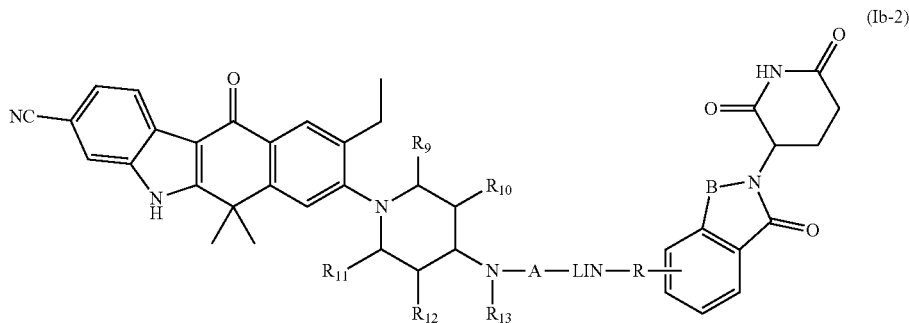

wherein, the groups LIN, A, R, R$_9$, R$_{10}$, R$_{11}$, R$_{12}$, R$_{13}$, and B are as defined herein.

In an embodiment of the present disclosure, the compound represented by formula (I) is also a compound represented by formula (Ib-3):

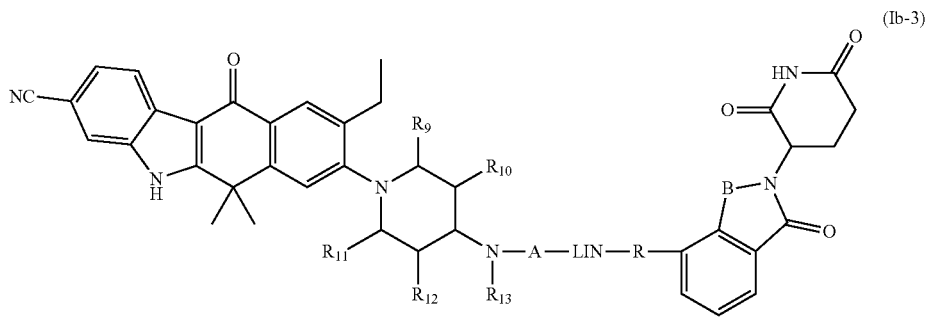

wherein, the groups LIN, A, R, R$_9$, R$_{10}$, R$_{11}$, R$_{12}$, R$_{13}$, and B are as defined herein.

In an embodiment of the present disclosure, the compound represented by formula (I) is also a compound represented by formula (Ib-4):

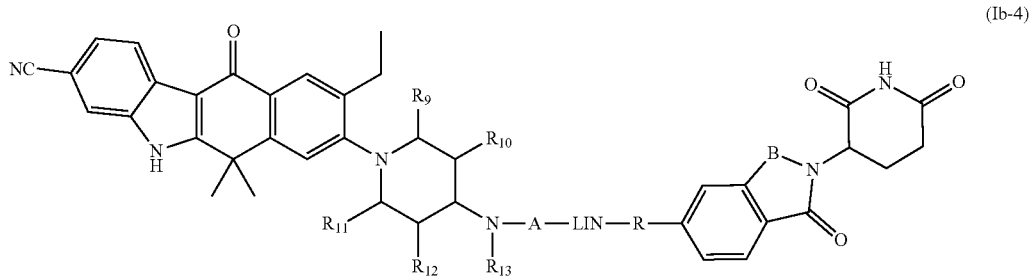

wherein, the groups LIN, A, R, R$_9$, R$_{10}$, R$_{11}$, R$_{12}$, R$_{13}$, and B are as defined herein.

In an embodiment of the present disclosure, the compound represented by formula (I) is also a compound represented by formula (Ib-5):

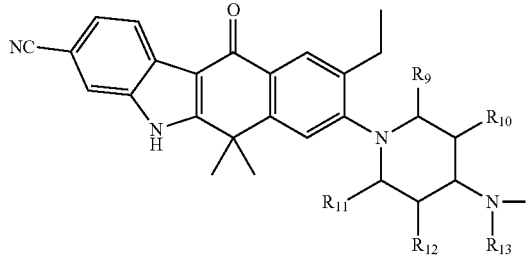
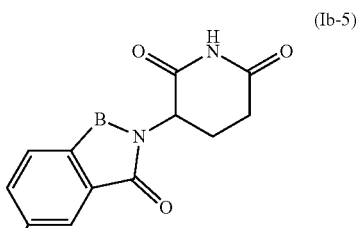

(Ib-5)

wherein, the groups LIN, A, R, $R_9$, $R_{10}$, $R_{11}$, $R_{12}$, $R_{13}$, and B are as defined herein.

In an embodiment of the present disclosure, the compound represented by formula (I) is also a compound represented by formula (Ib-6):

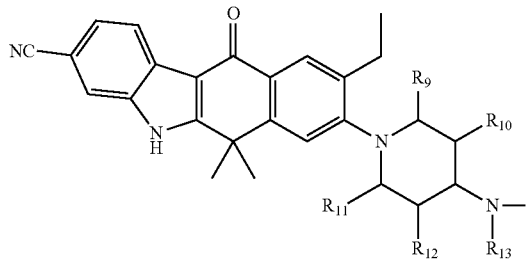

(Ib-6)

wherein, the groups LIN, A, $R_9$, $R_{10}$, $R_{11}$, $R_{12}$, $R_{13}$, and B are as defined herein.

In a sub-embodiment of the compound of the present disclosure represented by formula (Ib-1), formula (Ib-2), formula (Ib-3), formula (Ib-4), formula (Ib-5), or formula (Ib-6), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents —U—$C_{1-30}$ alkylene-, —U—$(CH_2)_{n1}$—$C(O)NH$—$(CH_2)_2)_{m1}$—, —U—$(CH_2)_{n1}$—$(NHC(O))$—$(CH_2)_{n2})_{m1}$—, —U—$(CH_2)_{n1}$—$(O(CH_2)_2)_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$C(O)NH$—$(CH_2)_{n2})_{m1}$—$(O(CH_2)_{n3})_{m2}$—, —U—$(CH_2)_{n1}$—$(O(CH_2)_{n2})_{m1}$—O—$(CH_2)_{n3}$—$C(O)NH$—$(CH_2)_{n4}$—$(O(CH_2)_{n5})_{m2}$—O—$(CH_2)_{n6}$—, —U—$(CR_{a11}R_{a12})_{n1}$—$(O(CR_{a13}R_{a14})_{n2})_{m1}$—O—$(CR_{a15}R_{a16})_{n3}$—$C(O)NH$—$(CR_{a17}R_{a18})_{n4}$—$(O(CR_{a19}R_{a20})_{n5})_{m2}$—O—$(CR_{a21}R_{a22})_6$—, —U—$(CR_{a23}R_{a24})_{n1}$—$C(O)NH$—$(O(CR_{a25}R_{a26})_{n2})_{m1}$—, —U—$(CH_2)_{n1}$—$(NHC(O))$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound of the present disclosure represented by formula (Ib-1), formula (Ib-2), formula (Ib-3), formula (Ib-4), formula (Ib-5), or formula (Ib-6), the LIN represents —U—$C_{1-30}$ alkylene-; and the group U represents C(O), or the group U is absent; wherein the alkylene is optionally substituted by one or more substituents selected from hydroxyl, amino, mercapto, halogen or any combination thereof (wherein the number of substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1). In a sub-embodiment, the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or —U—(CH$_2$)$_{30}$—; wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN is preferably —U—C$_{2-40}$ alkylene-(preferably, —U—C$_{2-30}$ alkylene-), wherein the alkylene chain is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent, wherein the alkylene is optionally substituted by substituents selected from hydroxyl, amino, mercapto, halogen or any combination thereof.

In a sub-embodiment of the compound represented by formula (Ib-1), formula (Ib-2), formula (Ib-3), formula (Ib-4), formula (Ib-5), or formula (Ib-6), the LIN represents —U—(CH$_2$)$_{n1}$—C(O)NH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment, the LIN preferably represents: —U—CH$_2$C(O)NHCH$_2$—, —U—CH$_2$C(O)NH(CH$_2$)$_2$—, —U—CH$_2$C(O)NH(CH$_2$)$_3$—, —U—CH$_2$C(O)NH(CH$_2$)$_4$—, —U—CH$_2$C(O)NH(CH$_2$)$_5$—, —U—CH$_2$C(O)NH(CH$_2$)$_6$—, —U—CH$_2$C(O)NH(CH$_2$)$_7$—, —U—CH$_2$C(O)NH(CH$_2$)$_8$—, —U—CH$_2$C(O)NH(CH$_2$)$_9$—, —U—CH$_2$C(O)NH(CH$_2$)$_{10}$—, —U—(CH$_2$)$_2$C(O)NHCH$_2$—, —U—(CH$_2$)$_2$C(O)NH(CH$_2$)$_2$—, —U—(CH$_2$)$_2$C(O)NH(CH$_2$)$_3$—, —U—(CH$_2$)$_2$C(O)NH(CH$_2$)$_4$—, —U—(CH$_2$)$_2$C(O)NH(CH$_2$)$_5$—, —U—(CH$_2$)$_2$C(O)NH(CH$_2$)$_6$—, —U—(CH$_2$)$_2$C(O)NH(CH$_2$)$_7$—, —U—(CH$_2$)$_2$C(O)NH(CH$_2$)$_8$—, —U—(CH$_2$)$_3$C(O)NHCH$_2$—, —U—(CH$_2$)$_3$C(O)NH(CH$_2$)$_2$—, —U—(CH$_2$)$_3$C(O)NH(CH$_2$)$_3$—, —U—(CH$_2$)$_3$C(O)NH(CH$_2$)$_4$—, —U—(CH$_2$)$_3$C(O)NH(CH$_2$)$_5$—, —U—(CH$_2$)$_3$C(O)NH(CH$_2$)$_6$—, —U—(CH$_2$)$_3$C(O)NH(CH$_2$)$_7$—, —U—(CH$_2$)$_3$C(O)NH(CH$_2$)$_8$—, —U—(CH$_2$)$_4$C(O)NHCH$_2$—, —U—(CH$_2$)$_4$C(O)NH(CH$_2$)$_2$—, —U—(CH$_2$)$_4$C(O)NH(CH$_2$)$_3$—, —U—(CH$_2$)$_4$C(O)NH(CH$_2$)$_4$—, —U—(CH$_2$)$_4$C(O)NH(CH$_2$)$_5$—, —U—(CH$_2$)$_4$C(O)NH(CH$_2$)$_6$—, —U—(CH$_2$)$_5$C(O)NHCH$_2$—, —U—(CH$_2$)OC(O)NH(CH$_2$)$_2$—, —U—(CH$_2$)OC(O)NH(CH$_2$)$_3$—, —U—(CH$_2$)$_5$C(O)NH(CH$_2$)$_4$—, —U—(CH$_2$)$_5$C(O)NH(CH$_2$)$_5$—, —U—(CH$_2$)$_5$C(O)NH(CH$_2$)$_6$—, —U—(CH$_2$)$_6$C(O)NHCH$_2$—, —U—(CH$_2$)$_6$C(O)NH(CH$_2$)$_2$—, —U—(CH$_2$)$_6$C(O)NH(CH$_2$)$_3$—, —U—(CH$_2$)$_6$C(O)NH(CH$_2$)$_4$—, —U—(CH$_2$)$_6$C(O)NH(CH$_2$)$_5$—, —U—(CH$_2$)$_6$C(O)NH(CH$_2$)$_6$—, —U—(CH$_2$)$_6$C(O)NH(CH$_2$)$_7$—, —U—(CH$_2$)$_7$C(O)NHCH$_2$—, —U—(CH$_2$)$_7$C(O)NH(CH$_2$)$_2$—, —U—(CH$_2$)$_7$C(O)NH(CH$_2$)$_3$—, —U—(CH$_2$)$_7$C(O)NH(CH$_2$)$_4$—, —U—(CH$_2$)$_7$C(O)NH(CH$_2$)$_5$—, —U—(CH$_2$)$_7$C(O)NH(CH$_2$)$_6$—, —U—(CH$_2$)$_7$C(O)NH(CH$_2$)$_7$—, —U—(CH$_2$)$_8$C(O)NHCH$_2$—, —U—(CH$_2$)$_8$C(O)NH(CH$_2$)$_2$—, —U—(CH$_2$)$_8$C(O)NH(CH$_2$)$_3$—, —U—(CH$_2$)$_8$C(O)NH(CH$_2$)$_4$—, —U—(CH$_2$)$_8$C(O)NH(CH$_2$)$_5$—, —U—(CH$_2$)$_8$C(O)NH(CH$_2$)$_6$—, —U—(CH$_2$)$_8$C(O)NH(CH$_2$)$_7$—, —U—(CH$_2$)$_8$C(O)NH(CH$_2$)$_8$—, —U—(CH$_2$)$_9$C(O)NHCH$_2$—, —U—(CH$_2$)$_9$C(O)NH(CH$_2$)$_2$—, —U—(CH$_2$)$_9$C(O)NH(CH$_2$)$_3$—, —U—(CH$_2$)$_9$C(O)NH(CH$_2$)$_4$—, —U—(CH$_2$)$_9$C(O)NH(CH$_2$)$_5$—, —U—(CH$_2$)$_9$C(O)NH(CH$_2$)$_6$—, —U—(CH$_2$)$_9$C(O)NH(CH$_2$)$_7$—, —U—(CH$_2$)$_9$C(O)NH(CH$_2$)$_8$—, —U—(CH$_2$)$_9$C(O)NH(CH$_2$)$_9$—, —U—(CH$_2$)$_{10}$C(O)NHCH$_2$—, —U—(CH$_2$)$_{10}$C(O)NH(CH$_2$)$_2$—, —U—(CH$_2$)$_{10}$C(O)NH(CH$_2$)$_3$—, —U—(CH$_2$)$_{10}$C(O)NH(CH$_2$)$_4$—, —U—(CH$_2$)$_{10}$C(O)NH(CH$_2$)$_5$— or —U—(CH$_2$)$_{10}$C(O)NH(CH$_2$)$_{10}$—; wherein the group U represents C(O), or the group U is absent.

In a sub-embodiment of the compound represented by formula (Ib-1), formula (Ib-2), formula (Ib-3), formula (Ib-4), formula (Ib-5), or formula (Ib-6), the LIN represents —U—(CH$_2$)$_{n1}$—NHC(O)—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment of the present disclosure, the LIN represents: —U—CH$_2$NHC(O)CH$_2$—, —U—CH$_2$NHC(O)(CH$_2$)$_2$—, —U—CH$_2$NHC(O)(CH$_2$)$_3$—, —U—CH$_2$NHC(O)(CH$_2$)$_4$—, —U—CH$_2$NHC(O)(CH$_2$)$_5$—, —U—CH$_2$NHC(O)(CH$_2$)$_6$—, —U—CH$_2$NHC(O)(CH$_2$)$_7$—, —U—CH$_2$NHC(O)(CH$_2$)$_8$—, —U—CH$_2$NHC(O)(CH$_2$)$_9$—, —U—CH$_2$NHC(O)(CH$_2$)$_{10}$—, —U—(CH$_2$)$_2$NHC(O)CH$_2$—, —U—(CH$_2$)$_2$NHC(O)(CH$_2$)$_2$—, —U—(CH$_2$)$_2$NHC(O)(CH$_2$)$_3$—, —U—(CH$_2$)$_2$NHC(O)(CH$_2$)$_4$—, —U—(CH$_2$)$_2$NHC(O)(CH$_2$)$_5$—, —U—(CH$_2$)$_3$NHC(O)CH$_2$—, —U—(CH$_2$)$_3$NHC(O)(CH$_2$)$_2$—, —U—(CH$_2$)$_3$NHC(O)(CH$_2$)$_3$—, —U—(CH$_2$)$_3$NHC(O)(CH$_2$)$_4$—, —U—(CH$_2$)$_3$NHC(O)(CH$_2$)$_5$—, —U—(CH$_2$)$_4$NHC(O)CH$_2$—, —U—(CH$_2$)$_4$NHC(O)(CH$_2$)$_2$—, —U—(CH$_2$)$_4$NHC(O)(CH$_2$)$_3$—, —U—(CH$_2$)$_4$NHC(O)(CH$_2$)$_4$—, —U—(CH$_2$)$_4$NHC(O)(CH$_2$)$_5$—, —U—(CH$_2$)$_4$NHC(O)(CH$_2$)$_6$—, —U—(CH$_2$)$_4$NHC(O)(CH$_2$)$_7$—, —U—(CH$_2$)$_5$NHC(O)CH$_2$—, —U—(CH$_2$)$_5$ONHC(O)(CH$_2$)$_2$—, —U—(CH$_2$)$_5$NHC(O)(CH$_2$)$_3$—, —U—(CH$_2$)$_5$NHC(O)(CH$_2$)$_4$—, —U—(CH$_2$)$_5$NHC(O)(CH$_2$)$_5$—, —U—(CH$_2$)$_5$NHC(O)(CH$_2$)$_6$—, —U—(CH$_2$)$_6$NHC(O)CH$_2$—, —U—(CH$_2$)$_6$NHC(O)(CH$_2$)$_2$—, —U—(CH$_2$)$_6$NHC(O)(CH$_2$)$_3$—, —U—(CH$_2$)$_6$NHC(O)(CH$_2$)$_4$—, —U—(CH$_2$)$_6$NHC(O)(CH$_2$)$_5$—, —U—(CH$_2$)$_6$NHC(O)(CH$_2$)$_6$—, —U—(CH$_2$)$_6$NHC(O)(CH$_2$)$_7$—, —U—(CH$_2$)$_7$NHC(O)CH$_2$—, —U—(CH$_2$)$_7$NHC(O)(CH$_2$)$_2$—, —U—(CH$_2$)$_7$NHC(O)(CH$_2$)$_3$—, —U—(CH$_2$)$_7$NHC(O)(CH$_2$)$_4$—, —U—(CH$_2$)$_7$NHC(O)(CH$_2$)$_5$—, —U—(CH$_2$)$_7$NHC(O)(CH$_2$)$_6$—, —U—(CH$_2$)$_7$NHC(O)(CH$_2$)$_7$—, —U—(CH$_2$)$_8$NHC(O)CH$_2$—, —U—(CH$_2$)$_8$NHC(O)(CH$_2$)$_2$—, —U—(CH$_2$)$_8$NHC(O)(CH$_2$)$_3$—, —U—(CH$_2$)$_8$NHC(O)(CH$_2$)$_8$—, —U—(CH$_2$)$_9$NHC(O)CH$_2$—, —U—(CH$_2$)$_9$NHC(O)(CH$_2$)$_2$—, —U—(CH$_2$)$_9$NHC(O)(CH$_2$)$_3$—, —U—(CH$_2$)$_9$NHC(O)(CH$_2$)$_9$—, or —U—(CH$_2$)$_{10}$NHC(O)(CH$_2$)$_{10}$—; wherein the group U represents C(O), or the group U is absent.

In a sub-embodiment of the compound represented by formula (Ib-1), formula (Ib-2), formula (Ib-3), formula (Ib-4), formula (Ib-5), or formula (Ib-6), the LIN represents —U—(CH$_2$)$_{n1}$—NHC(O)—(CH$_2$)$_{n2}$—, the LIN represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—CH$_2$—O—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiments of the compound represented by formula (Ib-1), formula (Ib-2), formula (Ib-3), formula (Ib-4), formula (Ib-5), or formula (Ib-6), the LIN represents —U—(CH$_2$)$_{n1}$—CH=CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—, —U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiments of the compound represented by formula (Ib-1), formula (Ib-2), formula (Ib-3), formula (Ib-4), formula (Ib-5), or formula (Ib-6), the LIN represents —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ia-1), formula (Ia-2), formula (Ia-3), formula (Ia-4), formula (Ia-5), or formula (Ia-6), the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—,
—U—(CH$_2$)$_2$C≡C(CH$_2$)$_2$—, —U—(CH$_2$)$_2$C≡C(CH$_2$)$_3$—,
—U—(CH$_2$)$_2$C≡C(CH$_2$)$_4$—, —U—(CH$_2$)$_2$C≡C(CH$_2$)$_5$—,
—U—(CH$_2$)$_2$C≡C(CH$_2$)$_6$—, —U—(CH$_2$)$_2$C≡C(CH$_2$)$_7$—,
—U—(CH$_2$)$_2$C≡C(CH$_2$)$_8$—, —U—(CH$_2$)$_3$C≡CCH$_2$—,
—U—(CH$_2$)$_3$C≡C(CH$_2$)$_2$—, —U—(CH$_2$)$_3$C≡C(CH$_2$)$_3$—,
—U—(CH$_2$)$_3$C≡C(CH$_2$)$_4$—, —U—(CH$_2$)$_3$C≡C(CH$_2$)$_5$—,
—U—(CH$_2$)$_3$C≡C(CH$_2$)$_6$—, —U—(CH$_2$)$_3$C≡C(CH$_2$)$_7$—,
—U—(CH$_2$)$_4$C≡CCH$_2$—, —U—(CH$_2$)$_4$C≡C(CH$_2$)$_2$—,
—U—(CH$_2$)$_4$C≡C(CH$_2$)$_3$—, —U—(CH$_2$)$_4$C≡C(CH$_2$)$_4$—,
—U—(CH$_2$)$_4$C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$CC(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$CC(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—, —U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—; wherein the group U represents C(O), or the group U is absent.

In a sub-embodiments of the compound represented by formula (Ib-1), formula (Ib-2), formula (Ib-3), formula (Ib-4), formula (Ib-5), or formula (Ib-6), the LIN represents —U—(CH$_2$)$_{n1}$-piperaziinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound represented by formula (Ib-1), formula (Ib-2), formula (Ib-3), formula (Ib-4), formula (Ib-5), or formula (Ib-6), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents: —U—(CH$_2$)$_{m1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—; wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_{m4}$—, —U—(CH$_2$)$_3$-triazolylidene-(CH$_2$)$_2$—O(CH$_2$)$_2$—, —U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents

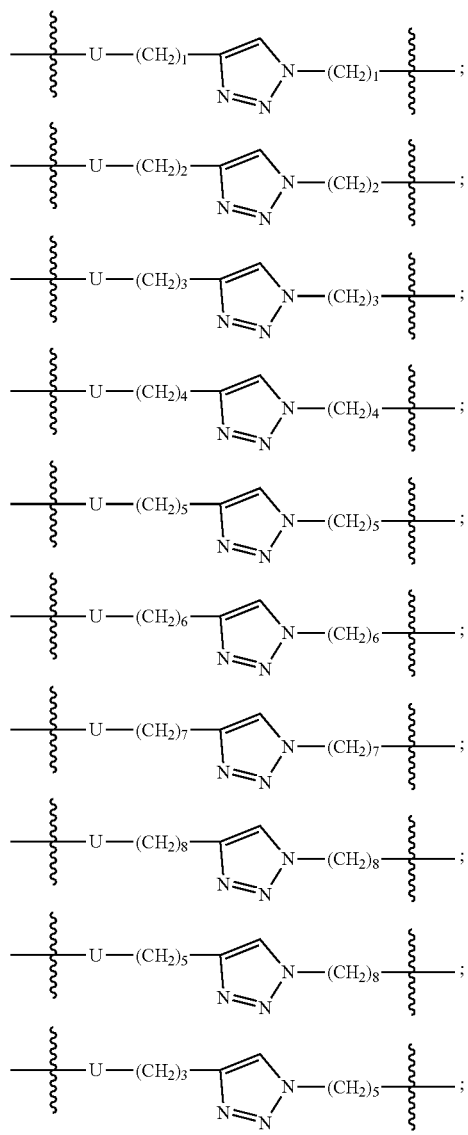

-continued

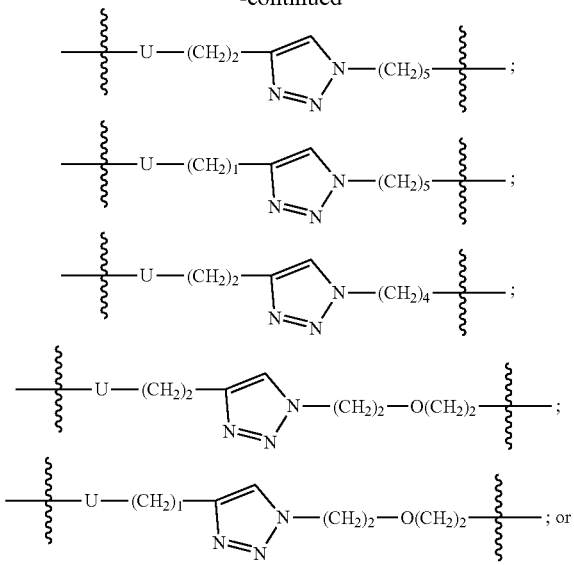

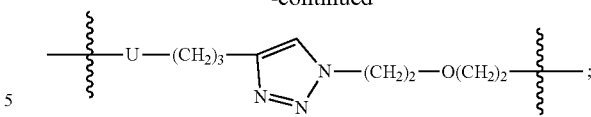

wherein the group U represents C(O), or the group U is absent.

In a sub-embodiment of the compound of the present disclosure represented by formula (Ib-1), formula (Ib-2), formula (Ib-3), formula (Ib-4), formula (Ib-5), or formula (Ib-6), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the present disclosure, the compound represented by formula (I) is also a compound represented by formula (Ic-1):

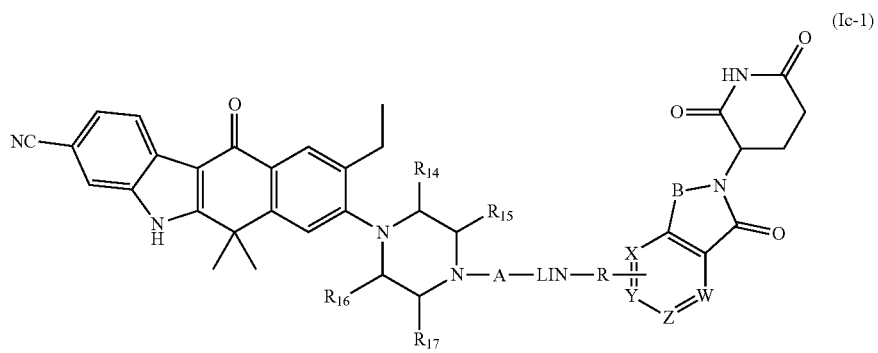

(Ic-1)

wherein, the groups LIN, A, R, R$_{14}$, R$_{15}$, R$_{16}$, R$_{17}$, and B, X, Y, Z, W are as defined herein.

In an embodiment of the present disclosure, the compound represented by formula (I) is also a compound represented by formula (Ic-2):

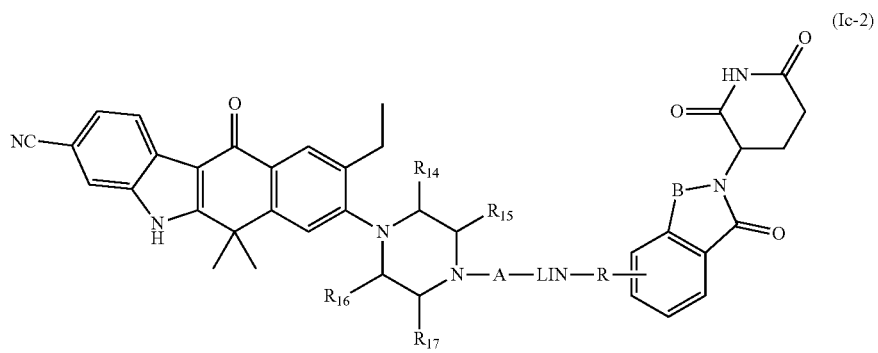

(Ic-2)

wherein, the groups LIN, A, R, $R_{14}$, $R_{15}$, $R_{16}$, $R_{17}$, and B are as defined herein.

In an embodiment of the present disclosure, the compound represented by formula (I) is also a compound represented by formula (Ic-3):

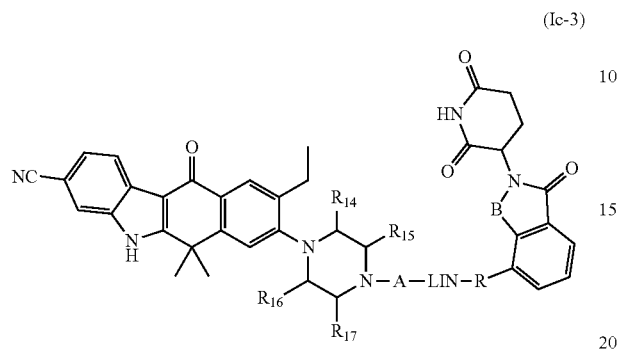

(Ic-3)

wherein, the groups LIN, A, R, $R_{14}$, $R_{15}$, $R_{16}$, $R_{17}$, and B are as defined herein.

In an embodiment of the present disclosure, the compound represented by formula (I) is also a compound represented by formula (Ic-4):

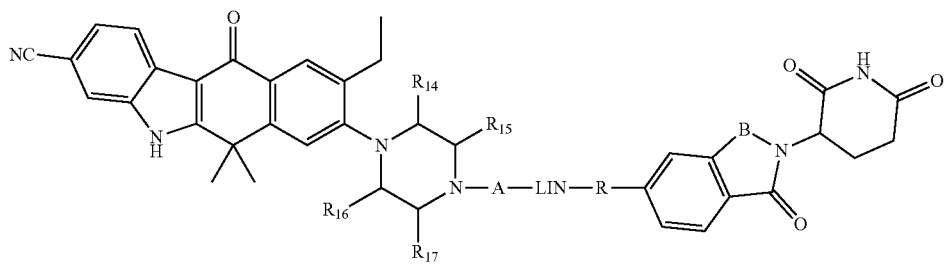

(Ic-4)

wherein, the groups LIN, A, R, $R_{14}$, $R_{15}$, $R_{16}$, $R_{17}$, and B are as defined herein.

In an embodiment of the present disclosure, the compound represented by formula (I) is also a compound represented by formula (Ic-5):

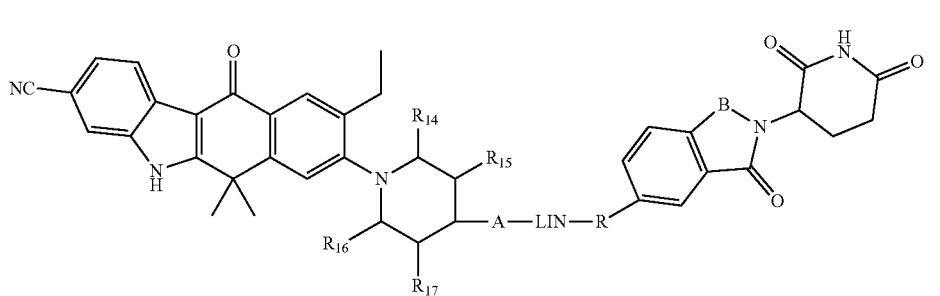

(Ic-5)

wherein, the groups LIN, A, R, $R_{14}$, $R_{15}$, $R_{16}$, $R_{17}$, and B are as defined herein.

In an embodiment of the present disclosure, the compound represented by formula (I) is also a compound represented by formula (Ic-6):

(Ic-6)

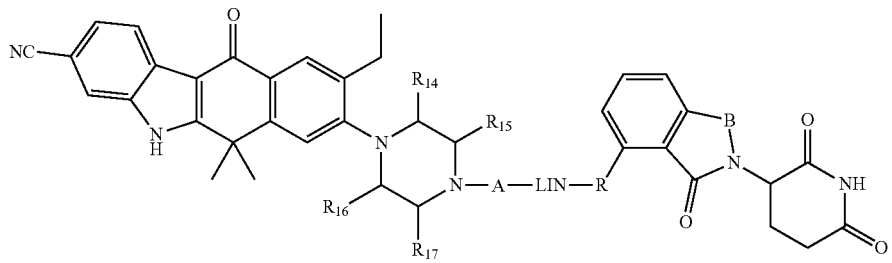

wherein, the groups LIN, A, R, $R_{14}$, $R_{15}$, $R_{16}$, $R_{17}$, and B are as defined herein.

In a sub-embodiment of the compound of the present disclosure represented by formula (Ic-1), formula (Ic-2), formula (Ic-3), formula (Ic-4), formula (Ic-5), or formula (Ic-6), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, O, NHC(O), NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—$C_{1-30}$ alkylene-, —U—$(CH_2)_{n1}$—$(C(O)NH$—$(CH_2)_{n2})_{m1}$—, —U—$(CH_2)_{n1}$—$(NHC(O)$—$(CH_2)_{n2})_{m1}$—, —U—$(CH_2)_{n1}$—$(O(CH_2)_2)_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$(C(O)NH$—$(CH_2)_{n2})_{m1}$—$(O(CH_2)_{n3})_{m2}$—, —U—$(CH_2)_{n1}$—$(O(CH_2)_{n2})_{m1}$—$O$—$(CH_2)_{n3}$—$C(O)NH$—$(CH_2)_{n4}$—$(O(CH_2)_{n5})_{m2}$—$O$—$(CH_2)_{n6}$—, —U—$(CR_{a11}R_{a12})_{n1}$—$(O(CR_{a13}R_{a14})_{n2})_{m1}$—$O$—$(CR_{a15}R_{a16})_{n3}$—$C(O)NH$—$(CR_{a17}R_{a18})_{n4}$—$(O(CR_{a19}R_{a20})_{n5})_{m2}$—$O$—$(CR_{a21}R_{a22})_{n6}$—, —U—$(CR_{a23}R_{a24})_{n1}$—$C(O)NH$—$(O(CR_{a25}R_{a26})_{n2})_{m1}$—, —U—$(CH_2)_{n1}$—$(NHC(O)$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$—, having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound of the present disclosure represented by formula (Ic-1), formula (Ic-2), formula (Ic-3), formula (Ic-4), formula (Ic-5), or formula (Ic-6), the LIN represents —U—$C_{1-30}$ alkylene-; and the group U represents C(O), or the group U is absent; wherein the alkylene is optionally substituted by one or more substituents selected from hydroxyl, amino, mercapto, halogen or any combination thereof (wherein the number of substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1). In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN is preferably —U—$C_{2-40}$ to alkylene-(preferably, —U—$C_{2-30}$ alkylene-), wherein the alkylene chain is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent, wherein the alkylene is optionally substituted by substituents selected from hydroxyl, amino, mercapto, halogen or any combination thereof.

In a sub-embodiment of the compound of the present disclosure represented by formula (Ic-1), formula (Ic-2), formula (Ic-3), formula (Ic-4), formula (Ic-5), or formula (Ic-6), the LIN represents —U—$(CH_2)_{n1}$—$C(O)NH$—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment, the LIN preferably represents: —U—$CH_2C(O)NHCH_2$—, —U—$CH_2C(O)NH(CH_2)_2$—, —U—$CH_2C(O)$ NH(CH$_2$)$_3$—, —U—CH$_2$C(O)NH(CH$_2$)$_4$—, —U—CH$_2$C(O)NH(CH$_2$)$_5$—, —U—CH$_2$C(O)NH(CH$_2$)$_6$—, —U—CH$_2$C(O)NH(CH$_2$)$_7$—, —U—CH$_2$C(O)NH(CH$_2$)$_8$—, —U—CH$_2$C(O)NH(CH$_2$)$_9$—, —U—CH$_2$C(O)NH(CH$_2$)$_{10}$—, —U—(CH$_2$)$_2$C(O)NHCH$_2$—, —U—(CH$_2$)$_2$C(O)NH(CH$_2$)$_2$—, —U—(CH$_2$)$_2$C(O)NH(CH$_2$)$_3$—, —U—(CH$_2$)$_2$C(O)NH(CH$_2$)$_4$—, —U—(CH$_2$)$_2$C(O)NH(CH$_2$)$_5$—, —U—(CH$_2$)$_2$C(O)NH(CH$_2$)$_6$—, —U—(CH$_2$)$_2$C(O)NH(CH$_2$)$_7$—, —U—(CH$_2$)$_2$C(O)NH(CH$_2$)$_8$—, —U—(CH$_2$)$_3$C(O)NHCH$_2$—, —U—(CH$_2$)$_3$C(O)NH(CH$_2$)$_2$—, —U—(CH$_2$)$_3$C(O)NH(CH$_2$)$_3$—, —U—(CH$_2$)$_3$C(O)NH(CH$_2$)$_4$—, —U—(CH$_2$)$_3$C(O)NH(CH$_2$)$_5$—, —U—(CH$_2$)$_3$C(O)NH(CH$_2$)$_6$—, —U—(CH$_2$)$_3$C(O)NH(CH$_2$)$_7$—, —U—(CH$_2$)$_3$C(O)NH(CH$_2$)$_8$—, —U—(CH$_2$)$_4$C(O)NHCH$_2$—, —U—(CH$_2$)$_4$C(O)NH(CH$_2$)$_2$—, —U—(CH$_2$)$_4$C(O)NH(CH$_2$)$_3$—, —U—(CH$_2$)$_4$C(O)NH(CH$_2$)$_4$—, —U—(CH$_2$)$_4$C(O)NH(CH$_2$)$_5$—, —U—(CH$_2$)$_4$C(O)NH(CH$_2$)$_6$—, —U—(CH$_2$)$_5$C(O)NHCH$_2$—, —U—(CH$_2$)$_5$C(O)NH(CH$_2$)$_2$—, —U—(CH$_2$)$_5$C(O)NH(CH$_2$)$_3$—, —U—(CH$_2$)$_5$C(O)NH(CH$_2$)$_4$—, —U—(CH$_2$)$_5$C(O)NH(CH$_2$)$_5$—, —U—(CH$_2$)$_5$C(O)NH(CH$_2$)$_6$—, —U—(CH$_2$)$_6$C(O)NHCH$_2$—, —U—(CH$_2$)$_6$C(O)NH(CH$_2$)$_2$—, —U—(CH$_2$)$_6$C(O)NH(CH$_2$)$_3$—, —U—(CH$_2$)$_6$C(O)NH(CH$_2$)$_4$—, —U—(CH$_2$)$_6$C(O)NH(CH$_2$)$_5$—, —U—(CH$_2$)$_6$C(O)NH(CH$_2$)$_6$—, —U—(CH$_2$)$_6$C(O)NH(CH$_2$)$_7$—, —U—(CH$_2$)$_7$C(O)NHCH$_2$—, —U—(CH$_2$)$_7$C(O)NH(CH$_2$)$_2$—, —U—(CH$_2$)$_7$C(O)NH(CH$_2$)$_3$—, —U—(CH$_2$)$_7$C(O)NH(CH$_2$)$_4$—, —U—(CH$_2$)$_7$C(O)NH(CH$_2$)$_5$—, —U—(CH$_2$)$_7$C(O)NH(CH$_2$)$_6$—, —U—(CH$_2$)$_7$C(O)NH(CH$_2$)$_7$—, —U—(CH$_2$)$_8$C(O)NHCH$_2$—, —U—(CH$_2$)$_8$C(O)NH(CH$_2$)$_2$—, —U—(CH$_2$)$_8$C(O)NH(CH$_2$)$_3$—, —U—(CH$_2$)$_8$C(O)NH(CH$_2$)$_4$—, —U—(CH$_2$)$_8$C(O)NH(CH$_2$)$_5$—, —U—(CH$_2$)$_8$C(O)NH(CH$_2$)$_6$—, —U—(CH$_2$)$_8$C(O)NH(CH$_2$)$_7$—, —U—(CH$_2$)$_8$C(O)NH(CH$_2$)$_8$—, —U—(CH$_2$)$_9$C(O)NHCH$_2$—, —U—(CH$_2$)$_9$C(O)NH(CH$_2$)$_2$—, —U—(CH$_2$)$_9$C(O)NH(CH$_2$)$_3$—, —U—(CH$_2$)$_9$C(O)NH(CH$_2$)$_4$—, —U—(CH$_2$)$_9$C(O)NH(CH$_2$)$_5$—, —U—(CH$_2$)$_9$C(O)NH(CH$_2$)$_6$—, —U—(CH$_2$)$_9$C(O)NH(CH$_2$)$_7$—, —U—(CH$_2$)$_9$C(O)NH(CH$_2$)$_8$—, —U—(CH$_2$)$_9$C(O)NH(CH$_2$)$_9$—, —U—(CH$_2$)$_{10}$C(O)NHCH$_2$—, —U—(CH$_2$)$_{10}$C(O)NH(CH$_2$)$_2$—, —U—(CH$_2$)$_{10}$C(O)NH(CH$_2$)$_3$—, —U—(CH$_2$)$_{10}$C(O)NH(CH$_2$)$_4$—, —U—(CH$_2$)$_{10}$C(O)NH(CH$_2$)$_5$— or —U—(CH$_2$)$_{10}$C(O)NH(CH$_2$)$_{10}$—; wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—(CH$_2$)$_{n1}$—NHC(O)—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment of the present disclosure, the LIN preferably represents: —U—CH$_2$NHC(O)CH$_2$—, —U—CH$_2$NHC(O)(CH$_2$)$_2$—, —U—CH$_2$NHC(O)(CH$_2$)$_3$—, —U—CH$_2$NHC(O)(CH$_2$)$_4$—, —U—CH$_2$NHC(O)(CH$_2$)$_5$—, —U—CH$_2$NHC(O)(CH$_2$)$_6$—, —U—CH$_2$NHC(O)(CH$_2$)$_7$—, —U—CH$_2$NHC(O)(CH$_2$)$_8$—, —U—CH$_2$NHC(O)(CH$_2$)$_9$—, —U—CH$_2$NHC(O)(CH$_2$)$_{10}$—, —U—(CH$_2$)$_2$NHC(O)CH$_2$—, —U—(CH$_2$)$_2$NHC(O)(CH$_2$)$_2$—, —U—(CH$_2$)$_2$NHC(O)(CH$_2$)$_3$—, —U—(CH$_2$)$_2$NHC(O)(CH$_2$)$_4$—, —U—(CH$_2$)$_2$NHC(O)(CH$_2$)$_5$—, —U—(CH$_2$)$_3$NHC(O)CH$_2$—, —U—(CH$_2$)$_3$NHC(O)(CH$_2$)$_2$—, —U—(CH$_2$)$_3$NHC(O)(CH$_2$)$_3$—, —U—(CH$_2$)$_3$NHC(O)(CH$_2$)$_4$—, —U—(CH$_2$)$_3$NHC(O)(CH$_2$)$_5$—, —U—(CH$_2$)$_4$NHC(O)CH$_2$—, —U—(CH$_2$)$_4$NHC(O)(CH$_2$)$_2$—, —U—(CH$_2$)$_4$NHC(O)(CH$_2$)$_3$—, —U—(CH$_2$)$_4$NHC(O)(CH$_2$)$_4$—, —U—(CH$_2$)$_4$NHC(O)(CH$_2$)$_5$—, —U—(CH$_2$)$_4$NHC(O)(CH$_2$)$_6$—, —U—(CH$_2$)$_4$NHC(O)(CH$_2$)$_7$—, —U—(CH$_2$)$_5$NHC(O)CH$_2$—, —U—(CH$_2$)$_5$NHC(O)(CH$_2$)$_2$—, —U—(CH$_2$)$_5$NHC(O)(CH$_2$)$_3$—, —U—(CH$_2$)$_5$NHC(O)(CH$_2$)$_4$—, —U—(CH$_2$)$_5$NHC(O)(CH$_2$)$_5$—, —U—(CH$_2$)$_5$NHC(O)(CH$_2$)$_6$—, —U—(CH$_2$)$_6$NHC(O)CH$_2$—, —U—(CH$_2$)$_6$NHC(O)(CH$_2$)$_2$—, —U—(CH$_2$)$_6$NHC(O)(CH$_2$)$_3$—, —U—(CH$_2$)$_6$NHC(O)(CH$_2$)$_4$—, —U—(CH$_2$)$_6$NHC(O)(CH$_2$)$_5$—, —U—(CH$_2$)$_6$NHC(O)(CH$_2$)$_6$—, —U—(CH$_2$)$_6$NHC(O)(CH$_2$)$_7$—, —U—(CH$_2$)$_7$NHC(O)CH$_2$—, —U—(CH$_2$)$_7$NHC(O)(CH$_2$)$_2$—, —U—(CH$_2$)$_7$NHC(O)(CH$_2$)$_3$—, —U—(CH$_2$)$_7$NHC(O)(CH$_2$)$_4$—, —U—(CH$_2$)$_7$NHC(O)(CH$_2$)$_5$—, —U—(CH$_2$)$_7$NHC(O)(CH$_2$)$_6$—, —U—(CH$_2$)$_7$NHC(O)(CH$_2$)$_7$—, —U—(CH$_2$)$_8$NHC(O)CH$_2$—, —U—(CH$_2$)$_8$NHC(O)(CH$_2$)$_2$—, —U—(CH$_2$)$_8$NHC(O)(CH$_2$)$_3$—, —U—(CH$_2$)$_8$NHC(O)(CH$_2$)$_8$—, —U—(CH$_2$)$_9$NHC(O)CH$_2$—, —U—(CH$_2$)$_9$NHC(O)(CH$_2$)$_2$—, —U—(CH$_2$)$_9$NHC(O)(CH$_2$)$_3$—, —U—(CH$_2$)$_9$NHC(O)(CH$_2$)$_9$—, or —U—(CH$_2$)$_{10}$NHC(O)(CH$_2$)$_{10}$—; wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —O—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_2$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_2$—(O(CH$_2$)$_3$)$_3$—, —U—(CH$_2$)$_2$—(O(CH$_2$)$_2$)$_2$—(O(CH$_2$)$_3$)$_4$—, —U—(CH$_2$)$_2$—(O(CH$_2$)$_2$)$_2$—(O(CH$_2$)$_3$)$_5$—, —U—(CH$_2$)$_2$—(O(CH$_2$)$_2$)$_2$—(O(CH$_2$)$_3$)$_6$—, —U—(CH$_2$)$_3$—O—(CH$_2$)$_2$—O—(CH$_2$)$_2$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—(CH$_2$)$_{n1}$—CH=CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—, —U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_9$C≡CCH$_2$—, —U—(CH$_2$)$_9$C≡C(CH$_2$)$_3$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, and wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O CH$_2$)$_{n3}$)$_{m1}$, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—; wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—, —U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents

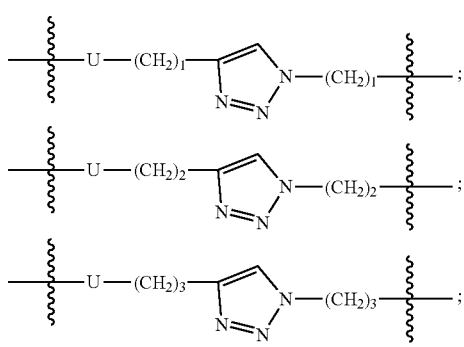

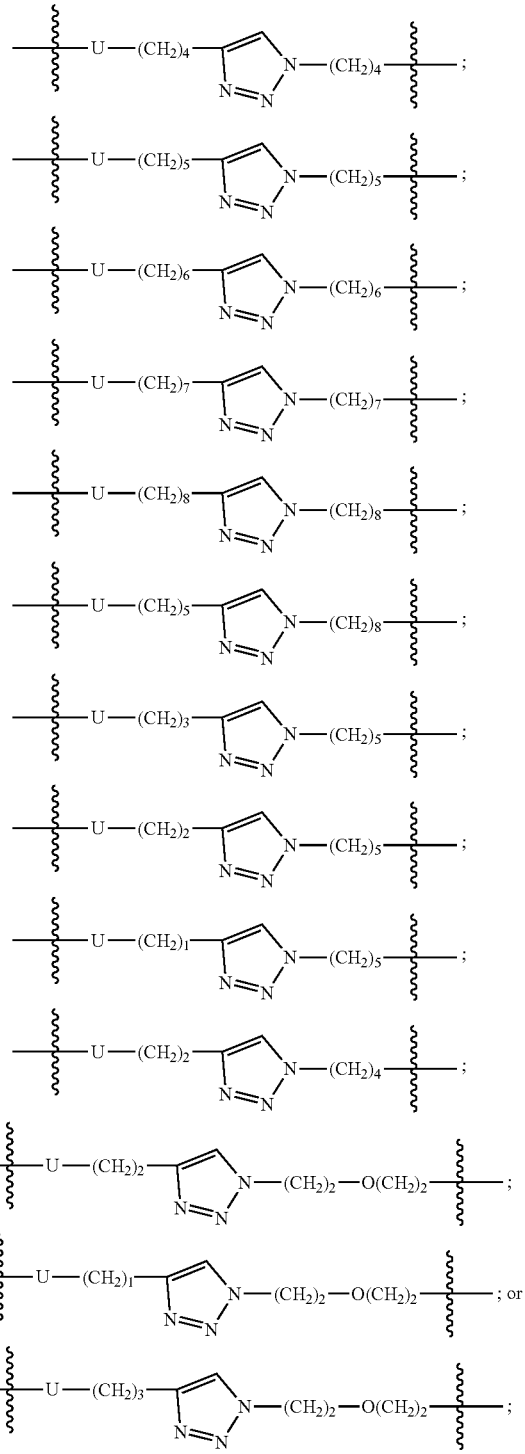

wherein the group U represents C(O), or the group U is absent.

In a sub-embodiment of the compound of the present disclosure represented by formula (Ic-1), formula (Ic-2), formula (Ic-3), formula (Ic-4), formula (Ic-5), or formula (Ic-6), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the present disclosure, the compound represented by formula (I) is also a compound represented by formula (Id-1), formula (Id-2), formula (Id-3), formula (Id-4), formula (Id-5), or formula (Id-6):
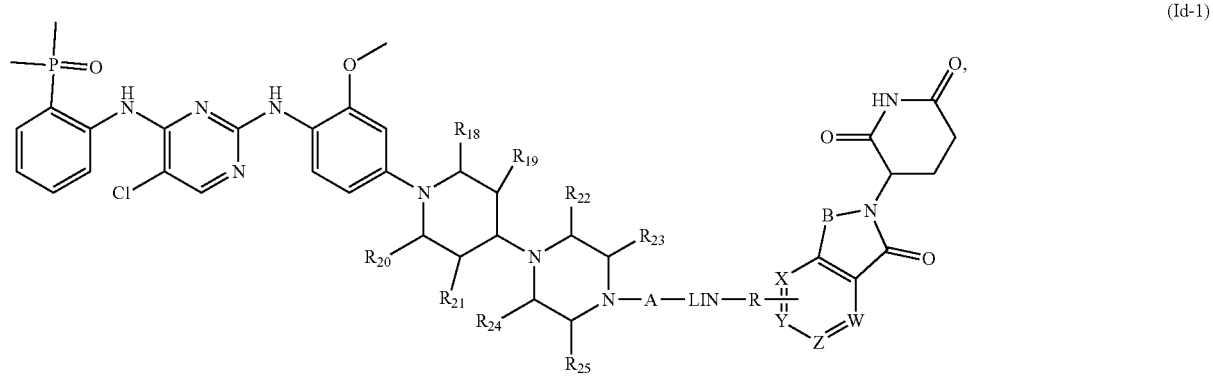
(Id-1)
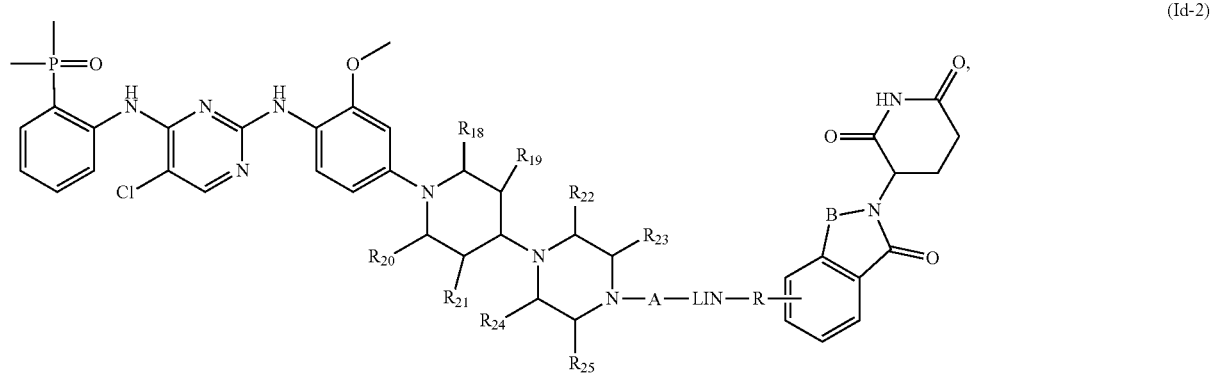
(Id-2)
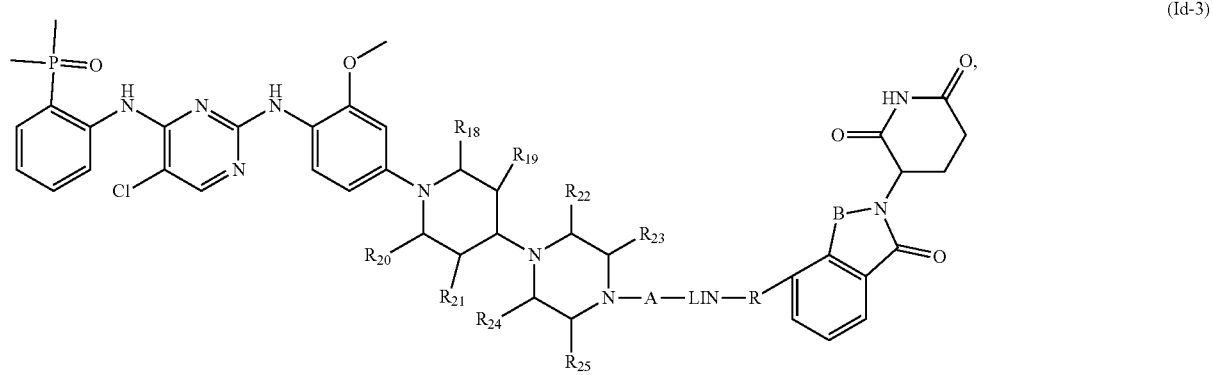
(Id-3)
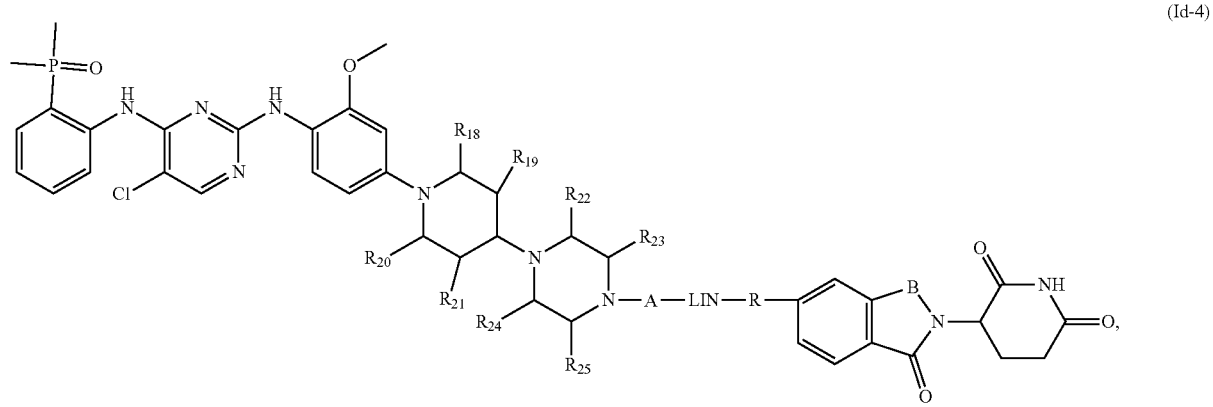
(Id-4)

-continued

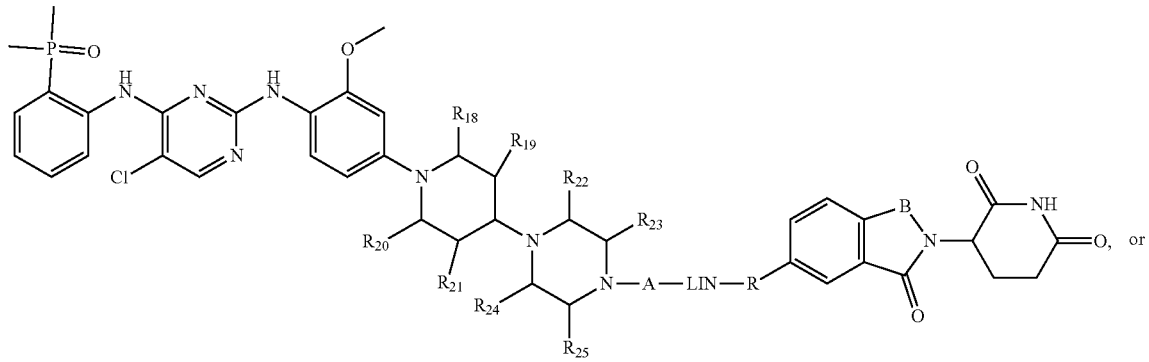

(Id-5)

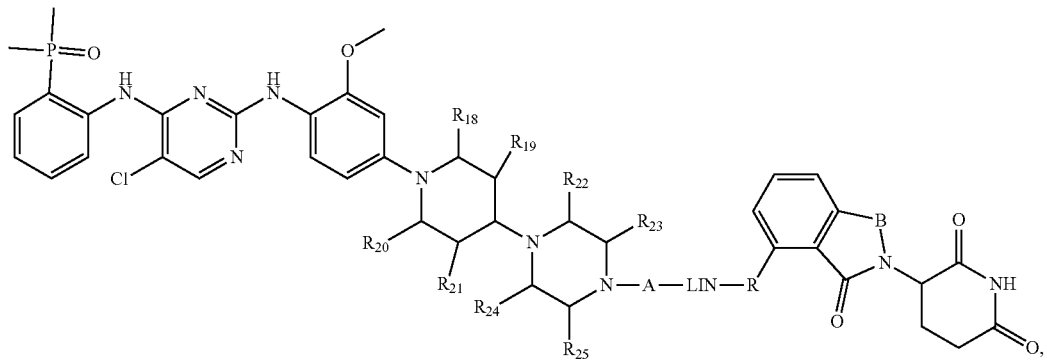

(Id-6)

wherein, the groups LIN, A, R, $R_{18}$, $R_{19}$, $R_{20}$, $R_{21}$, $R_{22}$, $R_{23}$, $R_{24}$, $R_{25}$, and B, X, Y, Z, W are as defined herein.

In a sub-embodiment of the compound of the present disclosure represented by formula (Id-1), formula (Id-2), formula (Id-3), formula (Id-4), formula (Id-5), or formula (Id-6), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, O, NHC(O), NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents —U—$C_{1-30}$ alkylene-, —U—$(CH_2)_{n1}$—$(C(O)NH$—$(CH_2)_{n2})_{m1}$—, —U—$(CH_2)_{n1}$—$(NHC(O)$—$(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$(C(O)NH$—$(CH_2)_{n2})_{m1}$—$(O(CH_2)_{n3})_{m2}$—, —U—$(CH_2)_{n1}$—$(O(CH_2)_{n2})_{m1}$—O—$(CH_2)_{n3}$—$C(O)NH$—$(CH_2)_{n4}$—$(O(CH_2)_{n5})_{m2}$—O—$(CH_2)_{n6}$—, —U—$(CR_{a11}R_{a12})_{n1}$—$(O(CR_{a13}R_{a14})_{n2})_{m1}$—O—$(CR_{a15}R_{a16})_{n3}$—$C(O)NH$—$(CR_{a17}R_{a18})_{n4}$—$(O(CR_{a19}R_{a20})_{n5})_{m2}$—O—$(CR_{a21}R_{a22})_{n6}$—, —U—$(CR_{a23}R_{a24})_{n1}$—$C(O)NH$—$(O(CR_{a25}R_{a26})_{n2})_{m1}$—, —U—$(CH_2)_{n1}$—$(NHC(O)$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound of the present disclosure represented by formula (Id-1), formula (Id-2), formula (Id-3), formula (Id-4), formula (Id-5), or formula (Id-6), the LIN represents —U—$C_{1-30}$ alkylene-; and the group U represents C(O), or the group U is absent; wherein the alkylene is optionally substituted by one or more substituents selected from hydroxyl, amino, mercapto, halogen or any combination thereof (wherein the number of substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1). In a sub-embodiment, the LIN represents: —U—$CH_2$—; —U—

$-(CH_2)_2-$; $-U-(CH_2)_3-$; $-U-(CH_2)_4-$; $-U-(CH_2)_5-$; $-U-(CH_2)_6-$; $-U-(CH_2)_7-$; $-U-(CH_2)_8-$; $-U-(CH_2)_9-$; $-U-(CH_2)_{10}-$; $-U-(CH_2)_{11}-$; $-U-(CH_2)_{12}-$; $-U-(CH_2)_{13}-$; $-U-(CH_2)_{14}-$; $-U-(CH_2)_{15}-$; $-U-(CH_2)_{16}-$; $-U-(CH_2)_{17}-$; $-U-(CH_2)_{18}-$; $-U-(CH_2)_{19}-$; $-U-(CH_2)_{20}-$; $-U-(CH_2)_{21}-$; $-U-(CH_2)_{22}-$; $-U-(CH_2)_{23}-$; $-U-(CH_2)_{24}-$; $-U-(CH_2)_{25}-$; $-U-(CH_2)_{26}-$; $-U-(CH_2)_{27}-$; $-U-(CH_2)_{28}-$; $-U-(CH_2)_{29}-$; or $-U-(CH_2)_{30}-$; wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN is preferably $-U-C_{2-40}$ alkylene- (preferably, $-U-C_{2-30}$ alkylene-), wherein the alkylene chain is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent, wherein the alkylene is optionally substituted by substituents selected from hydroxyl, amino, mercapto, halogen or any combination thereof.

In a sub-embodiment of the compound of the present disclosure represented by formula (Id-1), formula (Id-2), formula (Id-3), formula (Id-4), formula (Id-5), or formula (Id-6), the LIN represents $-U-(CH_2)_{n1}-C(O)NH-(CH_2)_{n2}-$, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment, the LIN preferably represents: $-U-CH_2C(O)NHCH_2-$, $-U-CH_2C(O)NH(CH_2)_2-$, $-U-CH_2C(O)NH(CH_2)_3-$, $-U-CH_2C(O)NH(CH_2)_4-$, $-U-CH_2C(O)NH(CH_2)_5-$, $-U-CH_2C(O)NH(CH_2)_6-$, $-U-CH_2C(O)NH(CH_2)_7-$, $-U-CH_2C(O)NH(CH_2)_8-$, $-U-CH_2C(O)NH(CH_2)_9-$, $-U-CH_2C(O)NH(CH_2)_{10}-$, $-U-(CH_2)_2C(O)NHCH_2-$, $-U-(CH_2)_2C(O)NH(CH_2)_2-$, $-U-(CH_2)_2C(O)NH(CH_2)_3-$, $-U-(CH_2)_2C(O)NH(CH_2)_4-$, $-U-(CH_2)_2C(O)NH(CH_2)_5-$, $-U-(CH_2)_2C(O)NH(CH_2)_6-$, $-U-(CH_2)_2C(O)NH(CH_2)_7-$, $-U-(CH_2)_2C(O)NH(CH_2)_8-$, $-U-(CH_2)_3C(O)NHCH_2-$, $-U-(CH_2)_3C(O)NH(CH_2)_2-$, $-U-(CH_2)_3C(O)NH(CH_2)_3-$, $-U-(CH_2)_3C(O)NH(CH_2)_4-$, $-U-(CH_2)_3C(O)NH(CH_2)_5-$, $-U-(CH_2)_3C(O)NH(CH_2)_6-$, $-U-(CH_2)_3C(O)NH(CH_2)_7-$, $-U-(CH_2)_3C(O)NH(CH_2)_8-$, $-U-(CH_2)_4C(O)NHCH_2-$, $-U-(CH_2)_4C(O)NH(CH_2)_2-$, $-U-(CH_2)_4C(O)NH(CH_2)_3-$, $-U-(CH_2)_4C(O)NH(CH_2)_4-$, $-U-(CH_2)_4C(O)NH(CH_2)_5-$, $-U-(CH_2)_4C(O)NH(CH_2)_6-$, $-U-(CH_2)_5C(O)NHCH_2-$, $-U-(CH_2)_5C(O)NH(CH_2)_2-$, $-U-(CH_2)_5C(O)NH(CH_2)_3-$, $-U-(CH_2)_5C(O)NH(CH_2)_4-$, $-U-(CH_2)_5C(O)NH(CH_2)_5-$, $-U-(CH_2)_5C(O)NH(CH_2)_6-$, $-U-(CH_2)_6C(O)NHCH_2-$, $-U-(CH_2)_6C(O)NH(CH_2)_2-$, $-U-(CH_2)_6C(O)NH(CH_2)_3-$, $-U-(CH_2)_6C(O)NH(CH_2)_4-$, $-U-(CH_2)_6C(O)NH(CH_2)_5-$, $-U-(CH_2)_6C(O)NH(CH_2)_6-$, $-U-(CH_2)_6C(O)NH(CH_2)_7-$, $-U-(CH_2)_7C(O)NHCH_2-$, $-U-(CH_2)_7C(O)NH(CH_2)_2-$, $-U-(CH_2)_7C(O)NH(CH_2)_3-$, $-U-(CH_2)_7C(O)NH(CH_2)_4-$, $-U-(CH_2)_7C(O)NH(CH_2)_5-$, $-U-(CH_2)_7C(O)NH(CH_2)_6-$, $-U-(CH_2)_7C(O)NH(CH_2)_7-$, $-U-(CH_2)_8C(O)NHCH_2-$, $-U-(CH_2)_8C(O)NH(CH_2)_2-$, $-U-(CH_2)_8C(O)NH(CH_2)_3-$, $-U-(CH_2)_8C(O)NH(CH_2)_4-$, $-U-(CH_2)_8C(O)NH(CH_2)_5-$, $-U-(CH_2)_8C(O)NH(CH_2)_6-$, $-U-(CH_2)_8C(O)NH(CH_2)_7-$, $-U-(CH_2)_8C(O)NH(CH_2)_8-$, $-U-(CH_2)_9C(O)NHCH_2-$, $-U-(CH_2)_9C(O)NH(CH_2)_2-$, $-U-(CH_2)_9C(O)NH(CH_2)_3-$, $-U-(CH_2)_9C(O)NH(CH_2)_4-$, $-U-(CH_2)_9C(O)NH(CH_2)_5-$, $-U-(CH_2)_9C(O)NH(CH_2)_6-$, $-U-(CH_2)_9C(O)NH(CH_2)_7-$, $-U-(CH_2)_9C(O)NH(CH_2)_8-$, $-U-(CH_2)_9C(O)NH(CH_2)_9-$, $-U-(CH_2)_{10}C(O)NHCH_2-$, $-U-(CH_2)_{10}C(O)NH(CH_2)_2-$, $-U-(CH_2)_{10}C(O)NH(CH_2)_3-$, $-U-(CH_2)_{10}C(O)NH(CH_2)_4-$, $-U-(CH_2)_{10}C(O)NH(CH_2)_5-$ or $-U-(CH_2)_{10}C(O)NH(CH_2)_{10}-$; wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents $-U-(CH_2)_{n1}-NHC(O)-(CH_2)_{n2}-$, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment of the present disclosure, the LIN preferably represents: $-U-CH_2NHC(O)CH_2-$, $-U-CH_2NHC(O)(CH_2)_2-$, $-U-CH_2NHC(O)(CH_2)_3-$, $-U-CH_2NHC(O)(CH_2)_4-$, $-U-CH_2NHC(O)(CH_2)_5-$, $-U-CH_2NHC(O)(CH_2)_6-$, $-U-CH_2NHC(O)(CH_2)_7-$, $-U-CH_2NHC(O)(CH_2)_8-$, $-U-CH_2NHC(O)(CH_2)_9-$, $-U-CH_2NHC(O)(CH_2)_{10}-$, $-U-(CH_2)_2NHC(O)CH_2-$, $-U-(CH_2)_2NHC(O)(CH_2)_2-$, $-U-(CH_2)_2NHC(O)(CH_2)_3-$, $-U-(CH_2)_2NHC(O)(CH_2)_4-$, $-U-(CH_2)_2NHC(O)(CH_2)_5-$, $-U-(CH_2)_3NHC(O)CH_2-$, $-U-(CH_2)_3NHC(O)(CH_2)_2-$, $-U-(CH_2)_3NHC(O)(CH_2)_3-$, $-U-(CH_2)_3NHC(O)(CH_2)_4-$, $-U-(CH_2)_3NHC(O)(CH_2)_5-$, $-U-(CH_2)_4NHC(O)CH_2-$, $-U-(CH_2)_4NHC(O)(CH_2)_2-$, $-U-(CH_2)_4NHC(O)(CH_2)_3-$, $-U-(CH_2)_4NHC(O)(CH_2)_4-$, $-U-(CH_2)_4NHC(O)(CH_2)_5-$, $-U-(CH_2)_4NHC(O)(CH_2)_6-$, $-U-(CH_2)_4NHC(O)(CH_2)_7-$, $-U-(CH_2)_5NHC(O)CH_2-$, $-U-(CH_2)_5NHC(O)(CH_2)_2-$, $-U-(CH_2)_5NHC(O)(CH_2)_3-$, $-U-(CH_2)_5NHC(O)(CH_2)_4-$, $-U-(CH_2)_5NHC(O)(CH_2)_5-$, $-U-(CH_2)_5NHC(O)(CH_2)_6-$, $-U-(CH_2)_6NHC(O)CH_2-$, $-U-(CH_2)_6NHC(O)(CH_2)_2-$, $-U-(CH_2)_6NHC(O)(CH_2)_3-$, $-U-(CH_2)_6NHC(O)(CH_2)_4-$, $-U-(CH_2)_6NHC(O)(CH_2)_5-$, $-U-(CH_2)_6NHC(O)(CH_2)_6-$, $-U-(CH_2)_6NHC(O)(CH_2)_7-$, $-U-(CH_2)_7NHC(O)CH_2-$, $-U-(CH_2)_7NHC(O)(CH_2)_2-$, $-U-(CH_2)_7NHC(O)(CH_2)_3-$, $-U-(CH_2)_7NHC(O)(CH_2)_4-$, $-U-(CH_2)_7NHC(O)(CH_2)_5-$, $-U-(CH_2)_7NHC(O)(CH_2)_6-$, $-U-(CH_2)_7NHC(O)(CH_2)_7-$, $-U-(CH_2)_8NHC(O)CH_2-$, $-U-(CH_2)_8NHC(O)(CH_2)_2-$, $-U-(CH_2)_8NHC(O)(CH_2)_3-$, $-U-(CH_2)_8NHC(O)(CH_2)_8-$, $-U-(CH_2)_9NHC(O)CH_2-$, $-U-(CH_2)_9NHC(O)(CH_2)_2-$, $-U-(CH_2)_9NHC(O)(CH_2)_3-$, $-U-(CH_2)_9NHC(O)(CH_2)_9-$, or $-U-(CH_2)_{10}NHC(O)(CH_2)_{10}-$; wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: $-U-CH_2-O-(CH_2)_2-$, $-U-CH_2-(O(CH_2)_2)_2-$, $-U-CH_2-(O(CH_2)_2)_3-$, $-U-CH_2-(O(CH_2)_2)_4-$, $-U-CH_2-(O(CH_2)_2)_5-$, $-U-CH_2-(O(CH_2)_2)_6-$, $-U-CH_2-(O(CH_2)_2)_7-$, $-U-CH_2-(O(CH_2)_2)_8-$, $-U-CH_2-(O(CH_2)_2)_9-$, $-U-CH_2-(O(CH_2)_2)_{10}-$, $-U-(CH_2)_2-O-(CH_2)_2-$, $-U-(CH_2)_2-(O(CH_2)_2)_2-$, $-U-(CH_2)_2-(O(CH_2)_2)_3-$, $-U-(CH_2)_2-(O(CH_2)_2)_4-$, $-U-(CH_2)_2-(O(CH_2)_2)_5-$, $-U-(CH_2)_2-(O(CH_2)_2)_6-$, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$) —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_2$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$(O(CH$_2$)$_2$)$_2$—O—(CH$_2$)$_3$—, —U—(CH$_2$)$_{241}$)(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents —U—(CH$_2$)$_{n1}$—CH=CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—, —U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH₂)₂C≡C(CH₂)₂—, —U—(CH₂)₂C≡C(CH₂)₃—, —U—(CH₂)₂C≡C(CH₂)₄—, —U—(CH₂)₂C≡C(CH₂)₅—, —U—(CH₂)₂C≡C(CH₂)₆—, —U—(CH₂)₂C≡C(CH₂)₇—, —U—(CH₂)₂C≡C(CH₂)₈—, —U—(CH₂)₃C≡CCH₂—, —U—(CH₂)₃C≡C(CH₂)₂—, —U—(CH₂)₃C≡C(CH₂)₃—, —U—(CH₂)₃C≡C(CH₂)₄—, —U—(CH₂)₃C≡C(CH₂)₅—, —U—(CH₂)₃C≡C(CH₂)₆—, —U—(CH₂)₃C≡C(CH₂)₇—, —U—(CH₂)₄C≡CCH₂—, —U—(CH₂)₄C≡C(CH₂)₂—, (CH₂)₄C≡C(CH₂)₃—, —U—(CH₂)₄C≡C(CH₂)₄—, —U—(CH₂)₄C≡C(CH₂)₅—, —U—(CH₂)₅C≡CCH₂—, —U—(CH₂)₅C≡C(CH₂)₂—, —U—(CH₂)₅C≡C(CH₂)₃—, —U—(CH₂)₅C≡C(CH₂)₄—, —U—(CH₂)₅C≡C(CH₂)₅—, —U—(CH₂)₆C≡CCH₂—, —U—(CH₂)₆C≡C(CH₂)₂—, —U—(CH₂)₆C≡C(CH₂)₃—, —U—(CH₂)₇C≡CCH₂—, —U—(CH₂)₇C≡C(CH₂)₂—, —U—(CH₂)₇C≡C(CH₂)₃—, —U—(CH₂)₈C≡CCH₂—, —U—(CH₂)₈C≡C(CH₂)₂—, —U—(CH₂)₈C≡C(CH₂)₃—, —U—(CH₂)₉C≡CCH₂—U—(CH₂)₉C≡C(CH₂)₂—, —U—(CH₂)₉C≡C(CH₂)₃—, —U—(CH₂)₁₀C≡CCH₂—, or —U—(CH₂)₁₀C≡C(CH₂)₂—, and wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents —U—(CH₂)$_{n1}$-piperazinylidene-(CH₂)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—CH₂-piperaziinylidene-CH₂—, —U—(CH₂)₂-piperaziinylidene-(CH₂)₂—, —U—(CH₂)₃-piperaziinylidene-(CH₂)₃—, —U—(CH₂)₂-piperaziinylidene-(CH₂)₃—, —U—CH₂-piperaziinylidene-(CH₂)₂—, —U—CH₂-piperaziinylidene-(CH₂)₃— or —U—(CH₂)₂-piperaziinylidene-(CH₂)₃—, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents —U—(CH₂)$_{n1}$-phenylene-(CH₂)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—CH₂-phenylene-CH₂—, —U—(CH₂)₂-phenylene-(CH₂)₂—, —U—CH₂-phenylene-(CH₂)₂—, —U—(CH₂)₂-phenylene-CH₂—, —U—(CH₂)₃-phenylene-(CH₂)₃—, —U—CH₂-phenylene-(CH₂)₃—, —U—(CH₂)₂-phenylene-(CH₂)₃—, —U—(CH₂)₃-phenylene-(CH₂)₂—, or —U—(CH₂)₃-phenylene-CH₂—, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—(CH₂)$_{n1}$-triazolylidene-(CH₂)$_{n2}$—, —U—(CH₂)$_{n1}$-triazolylidene-(CH₂)$_{n2}$—(O(CH₂)$_{n3}$)$_{m1}$—, —U—(CH₂)$_{n1}$—(O(CH₂)$_{n2}$)$_{m1}$—O—(CH₂)$_{n3}$-triazolylidene-(CH₂)$_{n4}$—(O(CH₂)$_{n5}$)$_{m2}$—O—(CH₂)$_{n6}$—, —U—(CH₂)$_{n1}$-triazolylidene-(CH₂)$_{n2}$—(O(CH₂)$_{n3}$)$_{m1}$—O—(CH₂)$_{n4}$— or —U—(CH₂)$_{n1}$—(O(CH₂)$_{n2}$)$_{m1}$—O—(CH₂)$_{n3}$-triazolylidene-(CH₂)$_{n4}$—; wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents: —U—(CH₂)₃-triazolylidene-(CH₂)₅—, —U—(CH₂)₂-triazolylidene-(CH₂)₅—, —U—CH₂-triazolylidene-(CH₂)₅—, —U—(CH₂)₂-triazolylidene-(CH₂)₄—, —U—(CH₂)₃-triazolylidene-(CH₂)₂—O(CH₂)₂—, —U—(CH₂)₂-triazolylidene-(CH₂)₂—O(CH₂)₂— or —U—CH₂-triazolylidene-(CH₂)₂—O(CH₂)₂—, wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents

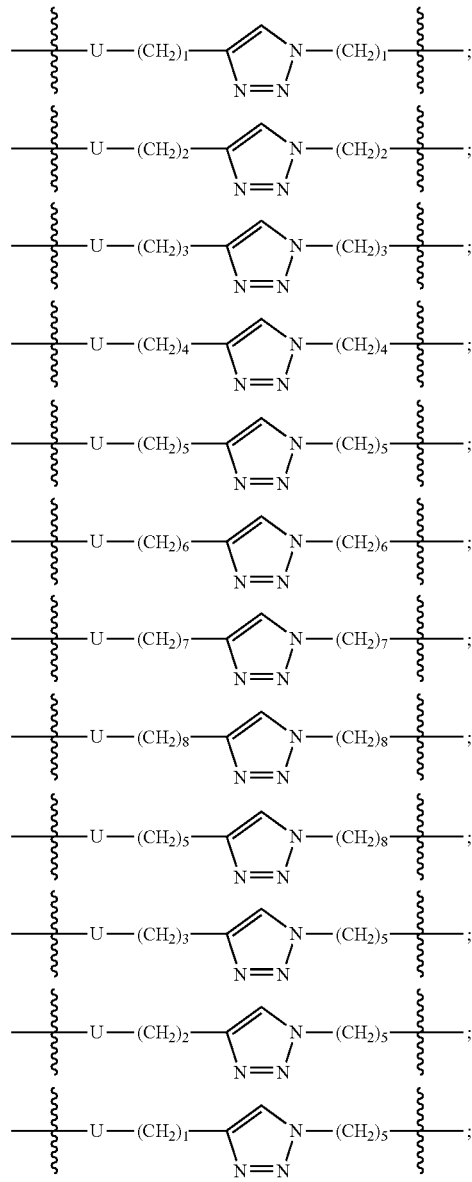

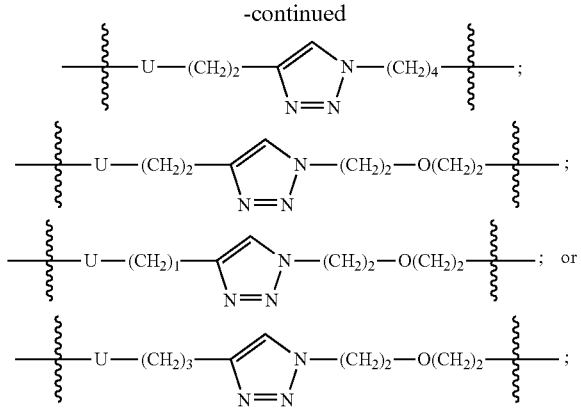

wherein the group U represents C(O), or the group U is absent.

In a sub-embodiment of the compound of the present disclosure represented by formula (Id-1), formula (Id-2), formula (Id-3), formula (Id-4), formula (Id-5), or formula (Id-6), the LIN represents —U—(CH₂)₂NHC(O)(CH₂)₂—O—(CH₂)₂— or —U—(CH₂)₂C(O)NH(CH₂)₂—O—(CH₂)₂—, wherein the group U represents C(O), or the group U is absent.

In an embodiment of the present disclosure, the compound represented by formula (I) is also a compound represented by formula (Ie-1), formula (Ie-2), formula (Ie-3), formula (Ie-4), formula (Ie-5), or formula (Ie-6):

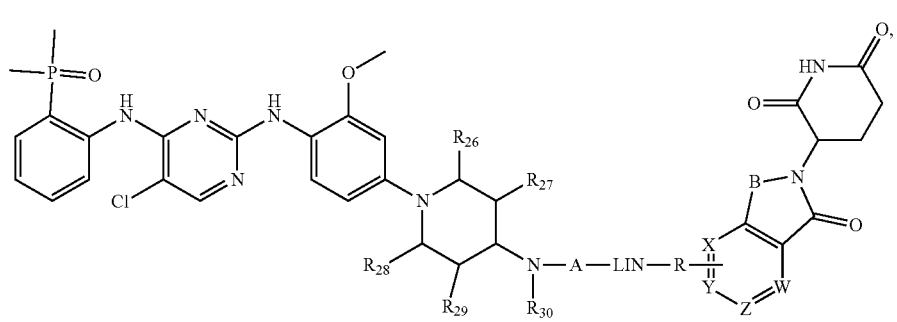

(Ie-1)

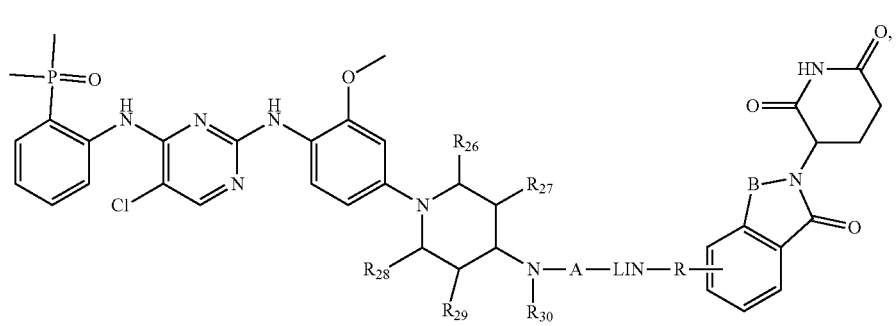

(Ie-2)

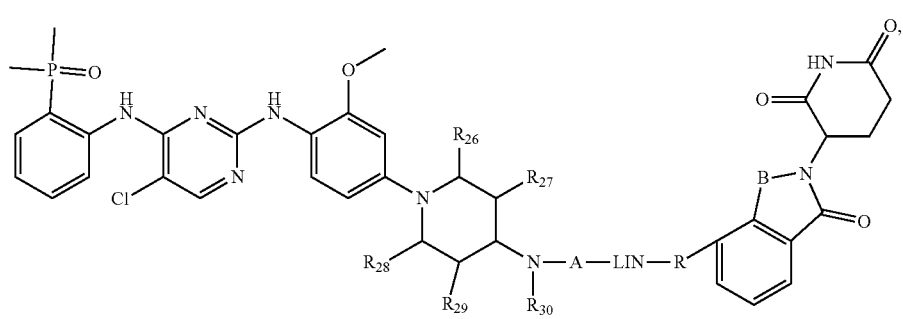

(Ie-3)

-continued

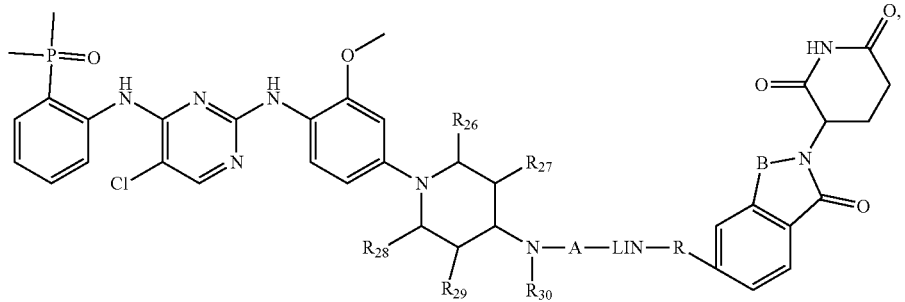

(Ie-4)

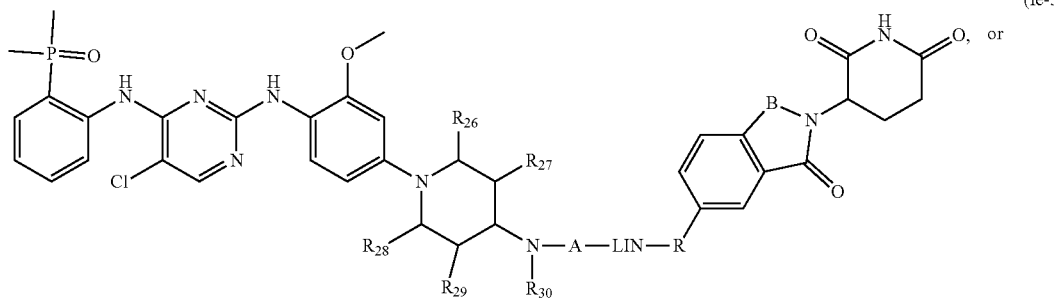

(Ie-5)

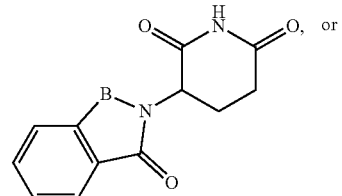, or

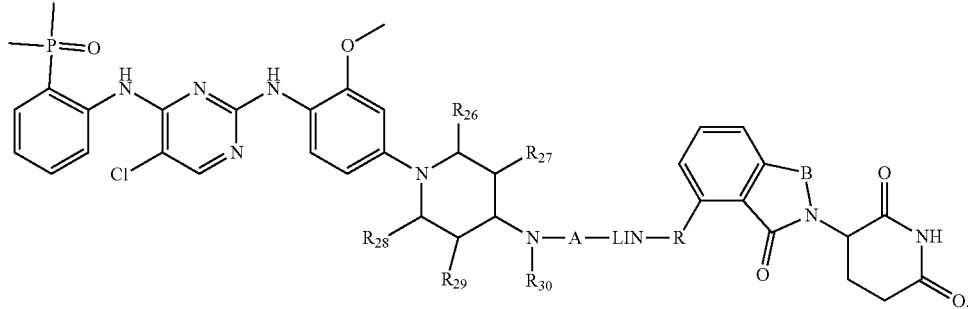

(Ie-6)

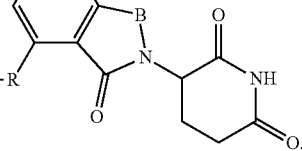, wherein, the groups LIN, A, R, $R_{26}$, $R_{27}$, $R_{28}$, $R_{29}$, $R_{30}$, and B, X, Y, Z, W are as defined herein.

In a sub-embodiment of the compound of the present disclosure represented by formula (Ie-1), formula (Ie-2), formula (Ie-3), formula (Ie-4), formula (Ie-5), or formula (Ie-6), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, O, NHC(O), NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents —U—$C_{1-30}$ alkylene-, —U—$(CH_2)_{n1}$—$(C(O)NH—(CH_2)_{n2})_{m1}$—, —U—$(CH_2)_{n1}$—$(NHC(O)—(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$(C(O)NH—(CH_2)_{n2})_{m1}$—$(O(CH_2)_{n3})_{m2}$—, —U—$(CH_2)_{n1}$—$(O(CH_2)_{n2})_{m1}$—$O—(CH_2)_{n3}$—$C(O)NH—(CH_2)_{n4}$—$(O(CH_2)_{n5})_{m2}$—$O—(CH_2)_{n6}$—, —U—$(CR_{a11}R_{a12})_{n1}$—$(O(CR_{a13}R_{a14})_{n2})_{m1}$—$O—(CR_{a15}R_{a16})_{n3}$—$C(O)NH—(CR_{a17}R_{a18})_{n4}$—$(O(CR_{a19}R_{a20})_{n5})_{m2}$—$O—(CR_{a21}R_{a22})_{n6}$—, —U—$(CR_{a23}R_{a24})_{n1}$—$C(O)NH—(O(CR_{a25}R_{a26})_{n2})_{m1}$—, —U—$(CH_2)_{m1}$—$(NHC(O)—(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound of the present disclosure represented by formula (Ie-1), formula (Ie-2), formula (Ie-3), formula (Ie-4), formula (Ie-5), or formula (Ie-6), the LEN represents —U—$C_{1-30}$ alkylene-; and the group U represents C(O), or the group U is absent; wherein the alkylene is optionally substituted by one or more substituents selected from hydroxyl, amino, mercapto, halogen or any combination thereof (wherein the number of substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1). In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN is preferably —U—$C_{2-40}$ alkylene- (e.g. —U—$C_{2-30}$ alkylene-), wherein the alkylene chain is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent, wherein the alkylene is optionally substituted by substituents selected from hydroxyl, amino, mercapto, halogen or any combination thereof.

In a sub-embodiment of the compound of the present disclosure represented by formula (Ie-1), formula (Ie-2), formula (Ie-3), formula (Ie-4), formula (Ie-5), or formula (Ie-6), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment, the LIN preferably represents: —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—; wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment of the present disclosure, the LIN preferably represents: —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—(CH$_2$)$_8$NHC(O)(CH$_2$)$_8$—, —U—(CH$_2$)$_9$NHC(O)CH$_2$—, —U—(CH$_2$)$_9$NHC(O)(CH$_2$)$_2$—, —U—(CH$_2$)$_9$NHC(O)(CH$_2$)$_3$—, —U—(CH$_2$)$_9$NHC(O)(CH$_2$)$_9$—, or —U—(CH$_2$)$_{10}$NHC(O)(CH$_2$)$_{10}$—; wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, (O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_{m4}$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents —U—(CH$_2$)$_{n1}$—CH=CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—(CH$_2$)$_{n1}$—C≡C—

$(CH_2)_{n2}$—  or  —U—$(CH_2)_{n1}$—C≡C—C≡C—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—$CH_2C\equiv CCH_2$—, —U—$CH_2C\equiv C(CH_2)_2$—, —U—$CH_2C\equiv C(CH_2)_3$—, —U—$CH_2C\equiv C(CH_2)_4$—, —U—$CH_2C\equiv C(CH_2)_5$—, —U—$CH_2C\equiv C(CH_2)_6$—, —U—$CH_2C\equiv C(CH_2)_7$—, —U—$CH_2C\equiv C(CH_2)_8$—, —U—$CH_2C\equiv C(CH_2)_9$—, —U—$CH_2C\equiv C(CH_2)_{10}$—, —U—$(CH_2)_2C\equiv CCH_2$—, —U—$(CH_2)_2C\equiv C(CH_2)_2$—, —U—$(CH_2)_2C\equiv C(CH_2)_3$—, —U—$(CH_2)_2C\equiv C(CH_2)_4$—, —U—$(CH_2)_2C\equiv C(CH_2)_5$—, —U—$(CH_2)_2C\equiv C(CH_2)_6$—, —U—$(CH_2)_2C\equiv C(CH_2)_7$—, —U—$(CH_2)_2C\equiv C(CH_2)_8$—, —U—$(CH_2)_3C\equiv CCH_2$—, —U—$(CH_2)_3C\equiv C(CH_2)_2$—, —U—$(CH_2)_3C\equiv C(CH_2)_3$—, —U—$(CH_2)_3C\equiv C(CH_2)_4$—, —U—$(CH_2)_3C\equiv C(CH_2)_5$—, —U—$(CH_2)_3C\equiv C(CH_2)_6$—, —U—$(CH_2)_3C\equiv C(CH_2)_7$—, —U—$(CH_2)_4C\equiv CCH_2$—, —U—$(CH_2)_4C\equiv C(CH_2)_2$—, —U—$(CH_2)_4C\equiv C(CH_2)_3$—, —U—$(CH_2)_4C\equiv C(CH_2)_4$—, —U—$(CH_2)_4C\equiv C(CH_2)_5$—, —U—$(CH_2)_5C\equiv CCH_2$—, —U—$(CH_2)_5C\equiv C(CH_2)_2$—, —U—$(CH_2)_5C\equiv C(CH_2)_3$—, —U—$(CH_2)_5C\equiv C(CH_2)_4$—, —U—$(CH_2)_5C\equiv C(CH_2)_5$—, —U—$(CH_2)_6C\equiv CCH_2$—, —U—$(CH_2)_6C\equiv C(CH_2)_2$—, —U—$(CH_2)_6C\equiv C(CH_2)_3$—, —U—$(CH_2)_7C\equiv CCH_2$—, —U—$(CH_2)_7C\equiv C(CH_2)_2$—, —U—$(CH_2)_7C\equiv C(CH_2)_3$—, —U—$(CH_2)_8C\equiv CCH_2$—, —U—$(CH_2)_8C\equiv C(CH_2)_2$—, —U—$(CH_2)_8C\equiv C(CH_2)_3$—, —U—$(CH_2)_9C\equiv CCH_2$—, —U—$(CH_2)_9C\equiv C(CH_2)_2$—, —U—$(CH_2)_9C\equiv C(CH_2)_3$—, —U—$(CH_2)_{10}C\equiv CCH_2$—, or —U—$(CH_2)_{10}C\equiv C(CH_2)_2$—, and wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents —U—$(CH_2)_{n1}$-piperazinylidene-$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—$CH_2$-piperaziinylidene-$CH_2$—, —U—$(CH_2)_2$-piperaziinylidene-$(CH_2)_2$—, —U—$(CH_2)_3$-piperaziinylidene-$(CH_2)_3$—, —U—$(CH_2)_2$-piperaziinylidene-$(CH_2)_3$—, —U—$CH_2$-piperaziinylidene-$(CH_2)_2$—, —U—$CH_2$-piperaziinylidene-$(CH_2)_3$— or —U—$(CH_2)_2$-piperaziinylidene-$(CH_2)_3$—, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents —U—$(CH_2)_{n1}$-phenylene-$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—$CH_2$-phenylene-$CH_2$—, —U—$(CH_2)_2$-phenylene-$(CH_2)_2$—, —U—$CH_2$-phenylene-$(CH_2)_2$—, —U—$(CH_2)_2$-phenylene-$CH_2$—, —U—$(CH_2)_3$-phenylene-$(CH_2)_3$—, —U—$CH_2$-phenylene-$(CH_2)_3$—, —U—$(CH_2)_2$-phenylene-$(CH_2)_3$—, —U—$(CH_2)_3$-phenylene-$(CH_2)_2$—, or —U—$(CH_2)_3$-phenylene-$CH_2$—, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—$(CH_2)_{n1}$-triazolylidene-$(CH_2)_{n2}$—, —U—$(CH_2)_{n1}$-triazolylidene-$(CH_2)_{n2}$—(O$(CH_2)_{n3})_{m1}$—, —U—$(CH_2)_{n1}$—(O$(CH_2)_{n2})_{m1}$—O—$(CH_2)_{n3}$-triazolylidene-$(CH_2)_{n4}$—(O$(CH_2)_{n5})_{m2}$—O—$(CH_2)_{n6}$—, —U—$(CH_2)_{n1}$-triazolylidene-$(CH_2)_{n2}$—(O$(CH_2)_{n3})_{m1}$—, O—$(CH_2)_{n4}$— or —U—$(CH_2)_{n1}$—(O$(CH_2)_{n2})_{m1}$—O—$(CH_2)_{n3}$-triazolylidene-$(CH_2)_{m4}$—; wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents: —U—$(CH_2)_3$-triazolylidene-$(CH_2)_5$—, —U—$(CH_2)_2$-triazolylidene-$(CH_2)_5$—, —U—$CH_2$-triazolylidene-$(CH_2)_5$—, —U—$(CH_2)_2$-triazolylidene-$(CH_2)_4$—, —U—$(CH_2)_3$-triazolylidene-$(CH_2)_2$—O$(CH_2)_2$—, —U—$(CH_2)_2$-triazolylidene-$(CH_2)_2$—O$(CH_2)_2$— or —U—$CH_2$-triazolylidene-$(CH_2)_2$—O$(CH_2)_2$—, wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents:

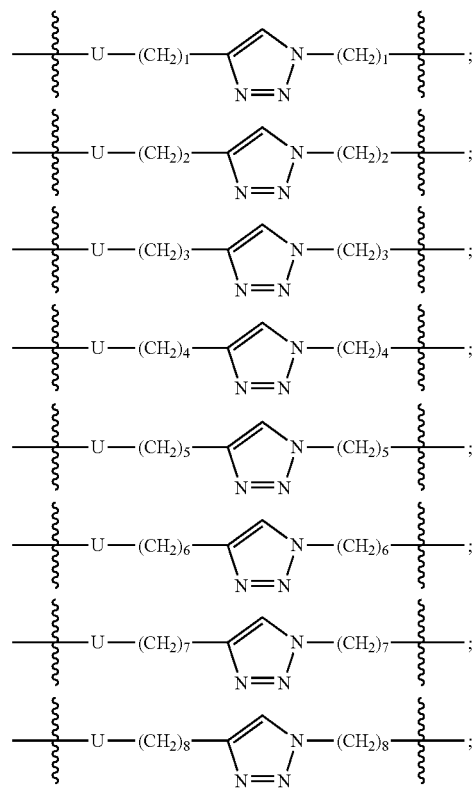

-continued

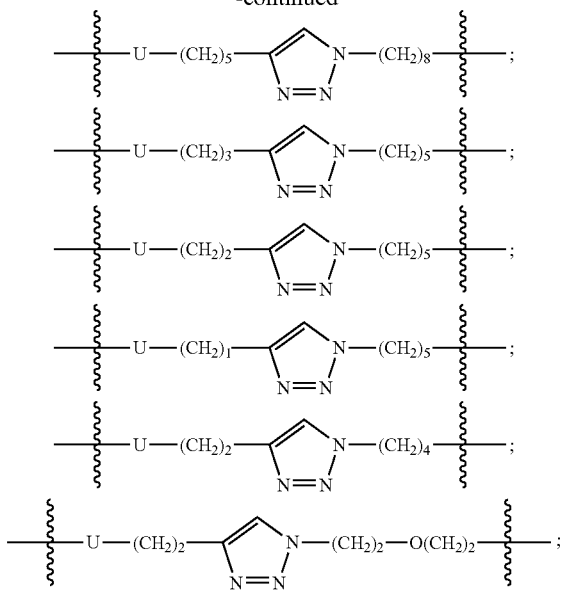

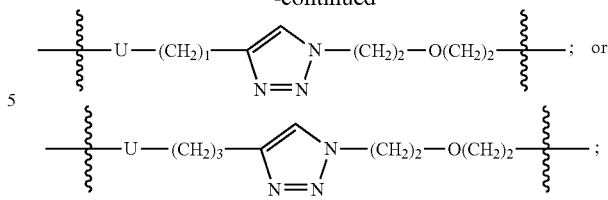

wherein the group U represents C(O), or the group U is absent.

In a sub-embodiment of the compound of the present disclosure represented by formula (Ie-1), formula (Ie-2), formula (Ie-3), formula (Ie-4), formula (Ie-5), or formula (Ie-6), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the present disclosure, the compound represented by formula (I) is also a compound represented by formula (If-1), formula (If-2), formula (If-3), formula (If-4), formula (If-5), or formula (If-6):

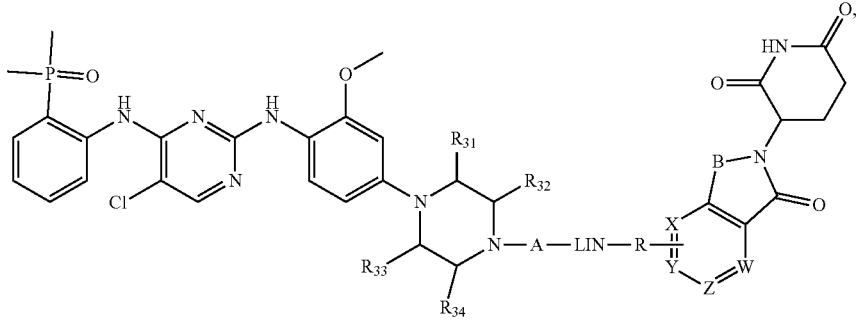

(If-1)

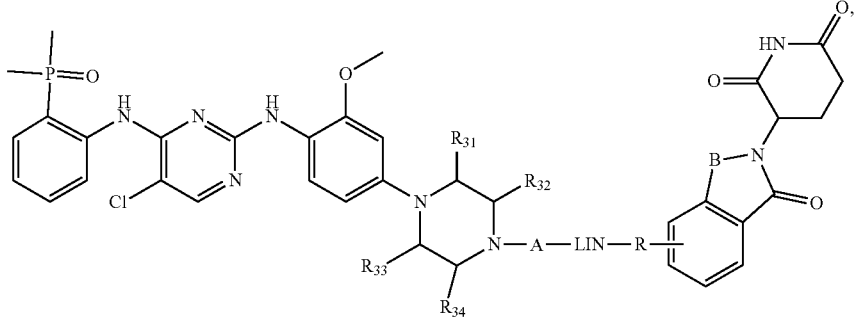

(If-2)

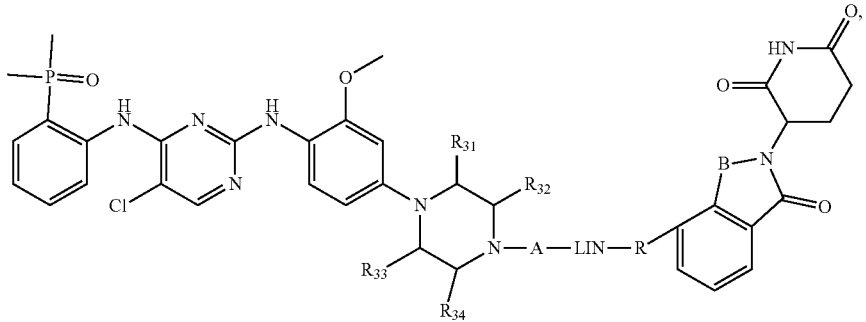

(If-3)

-continued (If-4)
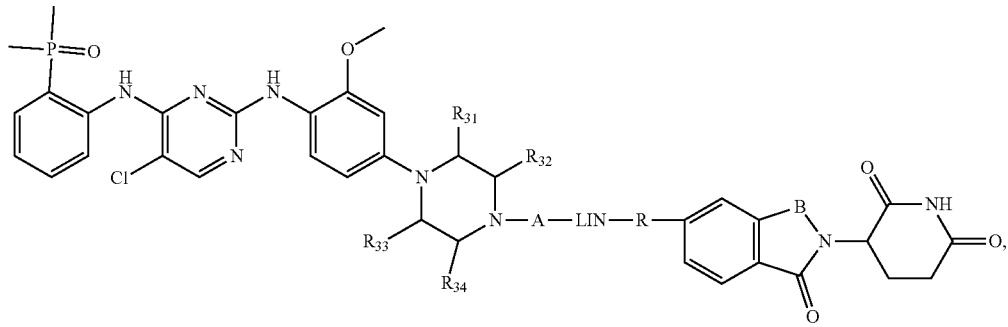

(If-5)
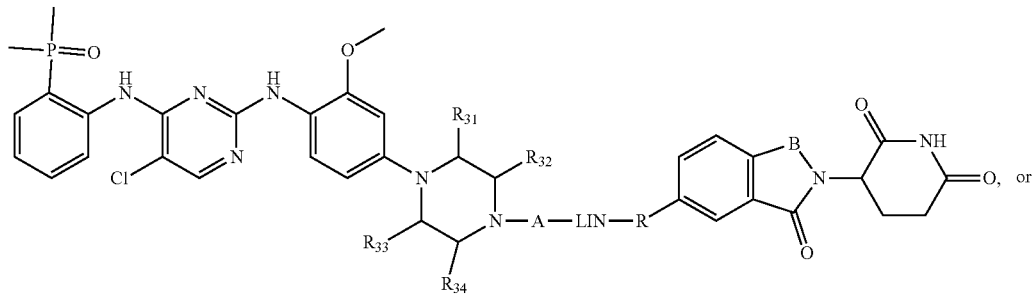

(If-6)
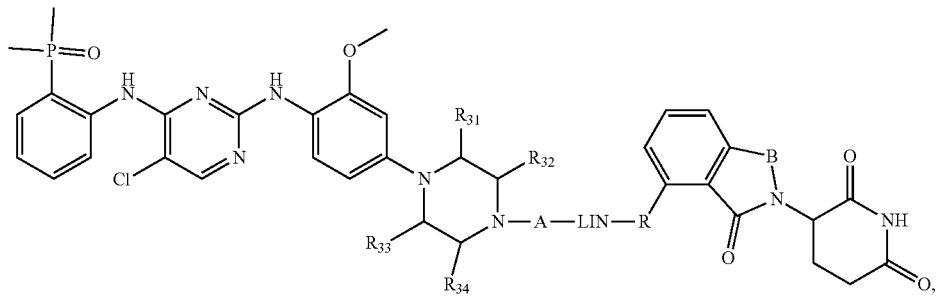

wherein, the groups LIN, A, R, $R_{31}$, $R_{32}$, $R_{33}$, $R_{34}$, and B, X, Y, Z, W are as defined herein.

In a sub-embodiment of the compound of the present disclosure represented by formula (If-1), formula (If-2), formula (If-3), formula (If-4), formula (If-5), or formula (If-6), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, O, NHC(O), NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—$C_{1-30}$ alkylene-, —U—$(CH_2)_{n1}$—$(C(O)NH$—$(CH_2)_{n2})_{m1}$—, —U—$(CH_2)_{n1}$—$(NHC(O)$—$(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$C(O)NH$—$(CH_2)_{n2})_{m1}$—$(O(CH_2)_{n3})_{m2}$—, —U—$(CH_2)_{n1}$—$(O(CH_2)_{n2})_{m1}$—O—$(CH_2)_{n3}$—$C(O)NH$—$(CH_2)_{n4}$—$(O(CH_2)_{n5})_{m2}$—O—$(CH_2)_{n6}$—, —U—$(CR_{a11}R_{a12})_{n1}$—$(O(CR_{a13}R_{a14})_{n2})_{m1}$—O—$(CR_{a15}R_{a16})_{n3}$—$C(O)NH$—$(CR_{a17}R_{a18})_{n4}$—$(O(CR_{a19}R_{a20})_{n5})_{m2}$—O—$(CR_{a21}R_{a22})_{n6}$—, —U—$(CR_{a23}R_{a24})_{n1}$—$C(O)NH$—$(O(CR_{a25}R_{a26})_{n2})_{m1}$—, —U—$(CH_2)_{n1}$—$(NHC(O)$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound of the present disclosure represented by formula (If-1), formula (If-2), formula (If-3), formula (If-4), formula (If-5), or formula (If-6), the LIN represents —U—$C_{1-30}$ alkylene-; and the group U represents C(O), or the group U is absent; wherein the alkylene is optionally substituted by one or more substituents selected from hydroxyl, amino, mercapto, halogen or any combination thereof (wherein the number of substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1). In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN is preferably —U—$C_{2-40}$ alkylene- (e.g. —U—$C_{2-30}$ alkylene-), wherein the alkylene chain is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent, wherein the alkylene is optionally substituted by substituents selected from hydroxyl, amino, mercapto, halogen or any combination thereof.

In a sub-embodiment of the compound represented by formula (If-1), formula (If-2), formula (If-3), formula (If-4), formula (If-5), or formula (If-6), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment, the LIN preferably represents: —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_9C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—; wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent. In a sub-embodiment of the present disclosure, the LIN preferably represents: —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—$(CH_2)_8NHC(O)(CH_2)_8$—, —U—$(CH_2)_9NHC(O)

$CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—; wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_{24}$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$(CH_2)_2$—O—$(CH_2)_2$—O—$CH_2$—, —U—$(CH_2)_2$—O—$(CH_2)_2$—O—$CH_2$—, —U—$(CH_2)_2$—O—$(CH_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—$(CH_2)_{n1}$—CH=CH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—$CH_2CH=CHCH_2$—, —U—$CH_2CH=CH(CH_2)_2$—, —U—$CH_2CH=CH(CH_2)_3$—, —U—$CH_2CH=CH(CH_2)_4$—, —U—$CH_2CH=CH(CH_2)_5$—, —U—$CH_2CH=CH(CH_2)_6$—, —U—$CH_2CH=CH(CH_2)_7$—, —U—$CH_2CH=CH(CH_2)_8$—, —U—$CH_2CH=CH(CH_2)_9$—, —U—$CH_2CH=CH(CH_2)_{10}$—, —U—$(CH_2)_2CH=CHCH_2$—, —U—$(CH_2)_2CH=CH(CH_2)_2$—, —U—$(CH_2)_2CH=CH(CH_2)_3$—, —U—$(CH_2)_2CH=CH(CH_2)_4$—, —U—$(CH_2)_2CH=CH(CH_2)_5$—, —U—$(CH_2)_2CH=CH(CH_2)_6$—, —U—$(CH_2)_2CH=CH(CH_2)_7$—, —U—$(CH_2)_2CH=CH(CH_2)_8$—, —U—$(CH_2)_3CH=CHCH_2$—, —U—$(CH_2)_3CH=CH(CH_2)_2$—, —U—$(CH_2)_3CH=CH(CH_2)_3$—, —U—$(CH_2)_3CH=CH(CH_2)_4$—, —U—$(CH_2)_3CH=CH(CH_2)_5$—, —U—$(CH_2)_3CH=CH(CH_2)_6$—, —U—$(CH_2)_3CH=CH(CH_2)_7$—, —U—$(CH_2)_4CH=CHCH_2$—, —U—$(CH_2)_4CH=CH(CH_2)_2$—, —U—$(CH_2)_4CH=CH(CH_2)_3$—, —U—$(CH_2)_4CH=CH(CH_2)_4$—, —U—$(CH_2)_4CH=CH(CH_2)_5$—, —U—$(CH_2)_5CH=CHCH_2$—, —U—$(CH_2)_5CH=CH(CH_2)_2$—, —U—$(CH_2)_5CH=CH(CH_2)_3$—, —U—$(CH_2)_5CH=CH(CH_2)_4$—, —U—$(CH_2)_5CH=CH(CH_2)_5$—, —U—$(CH_2)_6CH=CHCH_2$—, —U—$(CH_2)_6CH=CH(CH_2)_2$—, —U—$(CH_2)_6CH=CH(CH_2)_3$—, —U—$(CH_2)_7CH=CHCH_2$—, —U—$(CH_2)_7CH=CH(CH_2)_2$—, —U—$(CH_2)_7CH=CH(CH_2)_3$—, —U—$(CH_2)_8CH=CHCH_2$—, —U—$(CH_2)_8CH=CH(CH_2)_2$—, —U—$(CH_2)_8CH=CH(CH_2)_3$—, —U—$(CH_2)_9CH=CHCH_2$—U—$(CH_2)_9CH=CH(CH_2)_2$—, —U—$(CH_2)_9CH=CH(CH_2)_3$—, —U—$(CH_2)_{10}CH=CHCH_2$—, or —U—$(CH_2)_{10}CH=CH(CH_2)_2$—, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—$(CH_2)_{n1}$—C≡C—$(CH_2)_{n2}$— or —U—$(CH_2)_{n1}$—C≡C—C≡C—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$CC(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—(CH$_2$)$_{n1}$-piperaziinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{m4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—; wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—, —U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound represented by formula (If-1), formula (If-2), formula (If-3), formula (If-4), formula (If-5), or formula (If-6), the LIN represents:

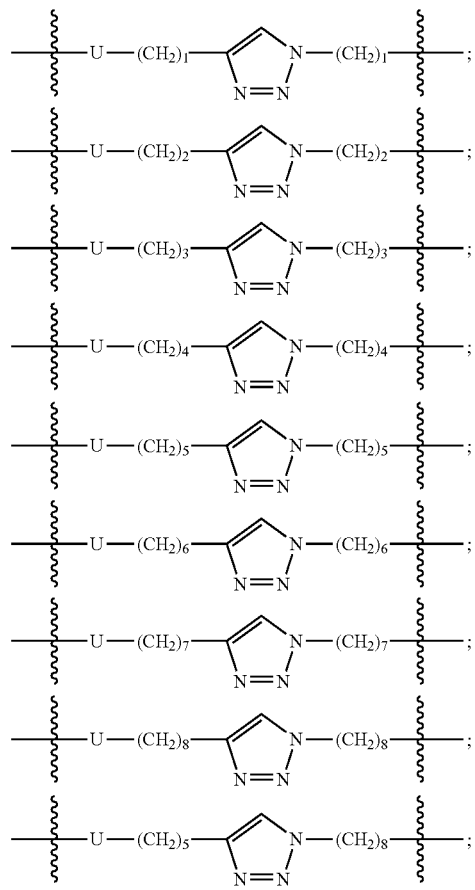

-continued

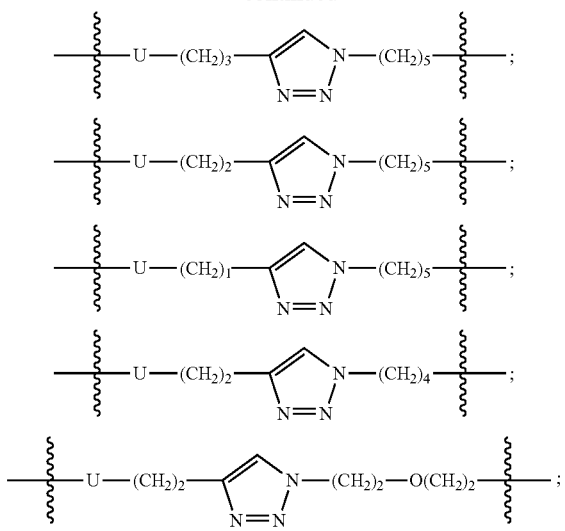

-continued

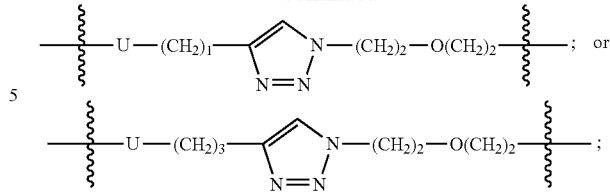

wherein the group U represents C(O), or the group U is absent.

In a sub-embodiment of the compound of the present disclosure represented by formula (If-1), formula (If-2), formula (If-3), formula (If-4), formula (If-5), or formula (If-6), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

The following compound represented by formula (I) of the present disclosure in Table 1 and the salt thereof (especially the pharmaceutically acceptable salt) is particularly preferred:

TABLE 1

The compounds represented by formula (I) of the present disclosure and their names

| Compound number | Structural formula | Compound name |
|---|---|---|
| | | 8-(4-(4-(4-(2-(2,6-dioxopiperidin-3-yl)-1-oxoisoindolin-4-yl)but-3-yn-1-yl)piperazin-1-yl)piperidin-1-yl)-9-ethyl-6,6-dimethyl-11-oxo-6,11-dihydro-5H-benzo[b]carbazole-3-carbonitrile |
| SIAIS293001 | | 8-(4-(4-(5-(2-(2,6-dioxopiperidin-3-yl)-1-oxoisoindolin-4-yl)pent-4-yn-1-yl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds represented by formula (I) of the present disclosure and their names

| Compound number | Structural formula | Compound name |
| --- | --- | --- |
| SIAIS293002 | | 8-(4-(4-(6-(2-(2,6-dioxopiperidin-3-yl)-1-oxoisoindolin-4-yl)hex-5-yn-1-yl)piperazin-1-yl)piperidin-1-yl)-9-ethyl-6,6-dimethyl-11-oxo-6,11-dihydro-5H-benzo[b]carbazole-3-carbonitrile |
| SIAIS293014 | | 8-(4-(4-(7-(2-(2,6-dioxopiperidin-3-yl)-1-oxoisoindolin-4-yl)hept-6-yn-1-yl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds represented by formula (I) of the present disclosure and their names

| Compound number | Structural formula | Compound name |
|---|---|---|
| SIAIS293003 | | 8-(4-(4-(8-(2-(2,6-dioxopiperidin-3-yl)-1-oxoisoindolin-4-yl)oct-7-yn-1-yl)piperazin-1-yl)piperidin-1-yl)-9-ethyl-6,6-dimethyl-11-oxo-6,11-dihydro-5H-benzo[b]carbazole-3-carbonitrile |
| SIAIS293004 | | 8-(4-(4-(9-(2-(2,6-dioxopiperidin-3-yl)-1-oxoisoindolin-4-yl)non-8-yn-1-yl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds represented by formula (I) of the present disclosure and their names

| Compound number | Structural formula | Compound name |
|---|---|---|
|  | 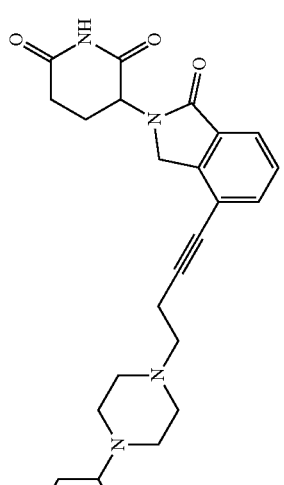 | 3-(4-(4-(4-(1-(4-(5-chloro-4-((2-(dimethylphosphono)phenyl)amino)pyrimidin-2-yl)amino)-3-methoxyphenyl)piperidin-4-yl)piperazin-1-yl)but-1-yn-1-yl)-1-oxoisoindolin-2-yl)piperidine-2,6-dione |
| SIAIS262039 | 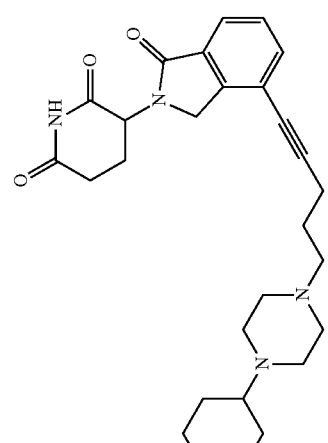 | 3-(4-(5-(4-(1-(4-(5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| SIAIS352010 | | 4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-2-(2,6-dioxopiperidin-3-yl)isoindoline-1,3-dione |
| SIAIS262040 | | 3-(4-(6-(4-(1-(4-((5-chloro-4-((2-(dimethylphosphono)phenyl)amino)pyrimidin-2-yl)amino)-3-methoxyphenyl)piperazin-1-yl)hex-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| SIAIS293015 | | 3-(4-(7-(4-(1-(4-(5-chloro-4-((2-(dimethylphosphonophenyl)amino)pyrimidin-2-yl)amino)-3-methoxyphenyl)piperidin-4-yl)piperazin-1-yl)hept-1-yn-1-yl)-1-oxoisoindolin-2-yl)piperidine-2,6-dione |
| SIAIS293017 | | 3-(4-(8-(4-(1-(4-(5-chloro-4-((2-(dimethylphosphonophenyl)amino)pyrimidin-2-yl)amino)-3-methoxyphenyl)piperidin-4-yl)piperazin-1-yl)oct-1-yn-1-yl)-1-oxoisoindolin-2-yl)piperidine-2,6-dione |
| SIAIS293018 | | 3-(4-(9-(4-(1-(4-(5-chloro-4-((2-(dimethylphosphonophenyl)amino)pyrimidin-2-yl)amino)-3-methoxyphenyl)piperidin-4-yl)piperazin-1-yl)non-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| | | 8-(4-(4-(6-(2-(2,6-dioxopiperidin-3-yl)-1-oxoisoindolin-5-yl)hex-5-ynoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(7-(2-(2,6-dioxopiperidin-3-yl)-1-oxoisoindolin-5-yl)hept-6-ynoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds represented by formula (I) of the present disclosure and their names

| Compound number | Structural formula | Compound name |
|---|---|---|
| | 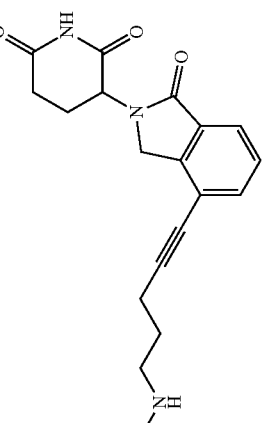 | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(5-(2-(2,6-dioxopiperidin-3-yl)-1-oxoisoindolin-4-yl)pent-4-yn-1-yl)acetamide |
| | 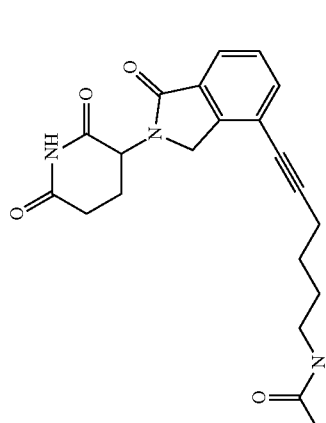 | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(6-(2-(2,6-dioxopiperidin-3-yl)-1-oxoisoindolin-4-yl)hex-5-yn-1-yl)acetamide |

TABLE 1-continued

The compounds represented by formula (I) of the present disclosure and their names

| Compound number | Structural formula | Compound name |
|---|---|---|
|  |  | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(5-(2-(2,6-dioxopiperidin-3-yl)-1-oxoisoindolin-4-yl)pent-4-yn-1-yl)acetamide |
|  |  | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(6-(2-(2,6-dioxopiperidin-3-yl)-1-oxoisoindolin-4-yl)hex-5-yn-1-yl)acetamide |

TABLE 1-continued

The compounds represented by formula (I) of the present disclosure and their names

| Compound number | Structural formula | Compound name |
|---|---|---|
|  |  | 3-(4-(4-((1-(4-((5-chloro-4-((2-(dimethylphosphonophenyl)amino)pyrimidin-2-yl)amino)-3-methoxyphenyl)piperidin-4-yl)amino)but-1-yn-1-yl)-1-oxoisoindolin-2-yl)piperidine-2,6-dione |
| SLAIS293093 |  | 3-(4-(5-((1-(4-((5-chloro-4-((2-(dimethylphosphonophenyl)amino)pyrimidin-2-yl)amino)-3-methoxyphenyl)piperidin-4-yl)amino)pent-1-yn-1-yl)-1-oxoisoindolin-2-yl)piperidine-2,6-dione |
| SLAIS353050 |  | 3-(4-(5-((1-(4-((5-chloro-4-((2-(dimethylphosphonophenyl)amino)pyrimidin-2-yl)amino)-3-methoxyphenyl)piperidin-4-yl)(methyl)amino)pent-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| | 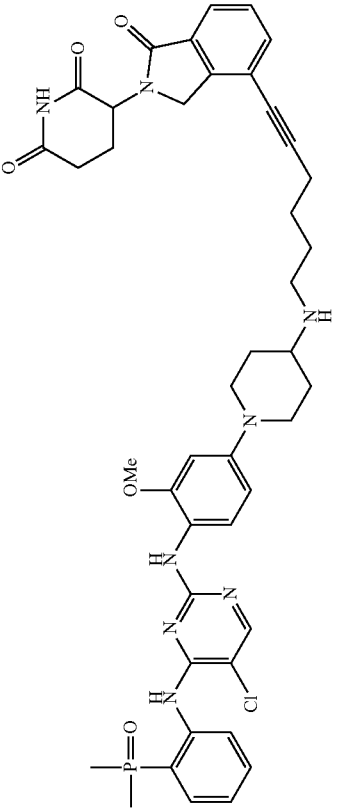 | 3-(4-(6-((1-(4-((5-chloro-4-((2-(dimethylphosphonophenyl)amino)pyrimidin-2-yl)amino)-3-methoxyphenyl)piperidin-4-yl)amino)hex-1-yn-1-yl)-1-oxoisoindolin-2-yl)piperidine-2,6-dione |
| | 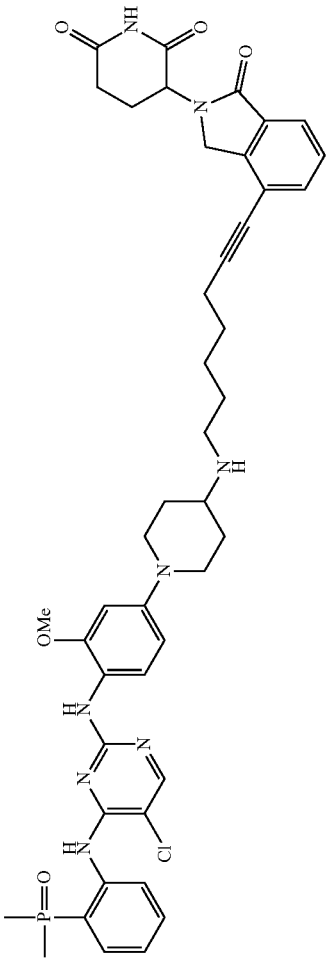 | 3-(4-(7-((1-(4-((5-chloro-4-((2-(dimethylphosphonophenyl)amino)pyrimidin-2-yl)amino)-3-methoxyphenyl)piperidin-4-yl)amino)hept-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| | 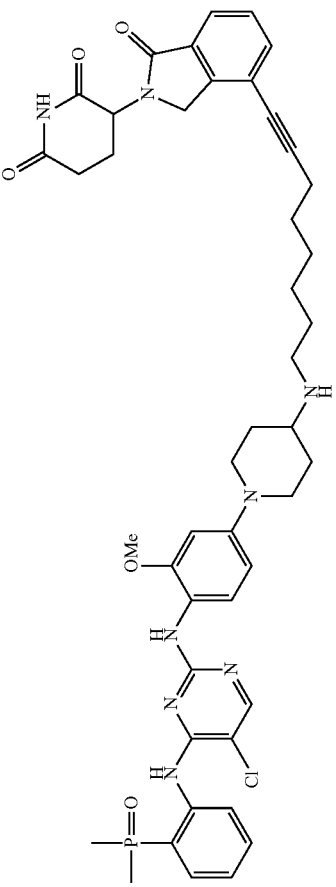 | 3-(4-(8-((1-(4-((5-chloro-4-((2-(dimethylphosphono)phenyl)amino)pyrimidin-2-yl)amino)-3-(methoxyphenyl)piperidin-4-yl)amino)oct-1-yn-1-yl)-1-oxoisoindolin-2-yl)piperidine-2,6-dione |
| | 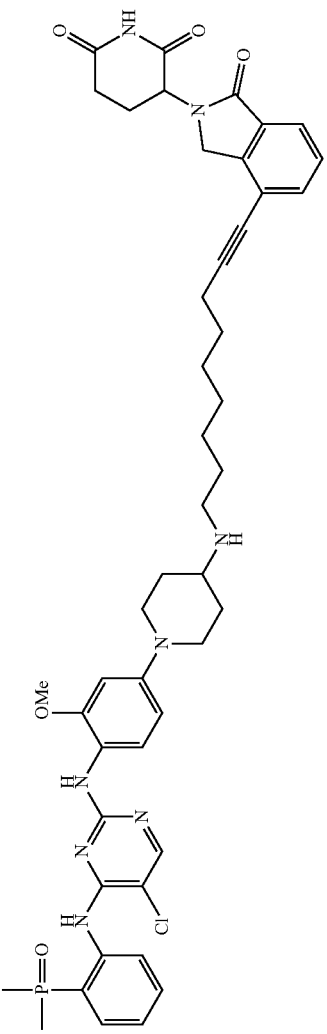 | 3-(4-(9-((1-(4-((5-chloro-4-((2-(dimethylphosphono)phenyl)amino)pyrimidin-2-yl)amino)-3-methoxyphenyl)piperidin-4-yl)amino)non-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| | 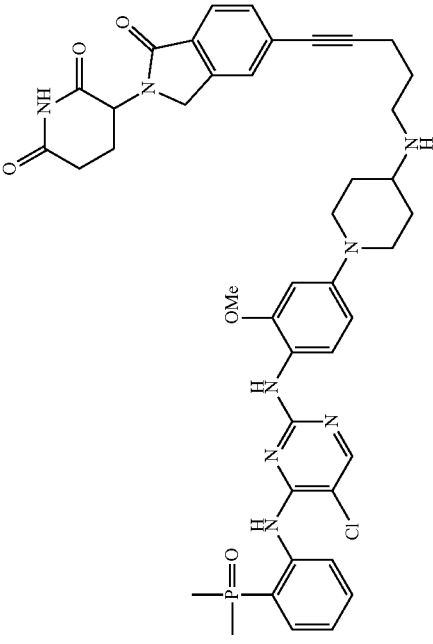 | 3-(5-(5-((1-(4-((5-chloro-4-((2-(dimethylphosphono)phenyl)amino)pyrimidin-2-yl)amino)-3-methoxyphenyl)piperidin-4-yl)amino)pent-1-yn-1-yl)-1-oxoisoindolin-2-yl)piperidine-2,6-dione |
| | 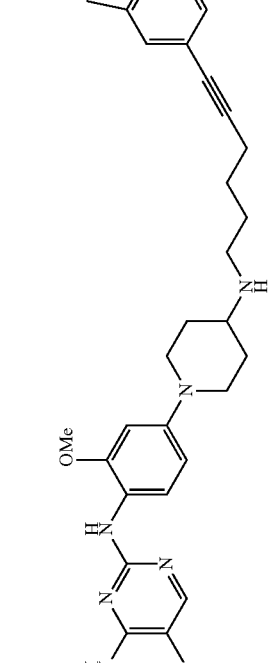 | 3-(5-(6-((1-(4-((5-chloro-4-((2-(dimethylphosphono)phenyl)amino)pyrimidin-2-yl)amino)-3-methoxyphenyl)piperidin-4-yl)amino)hex-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
|  | 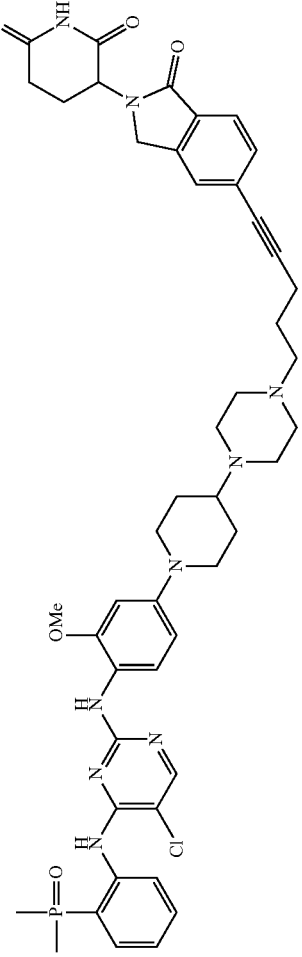 | 3-(5-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-1-oxoisoindolin-2-yl)piperidine-2,6-dione |
|  | 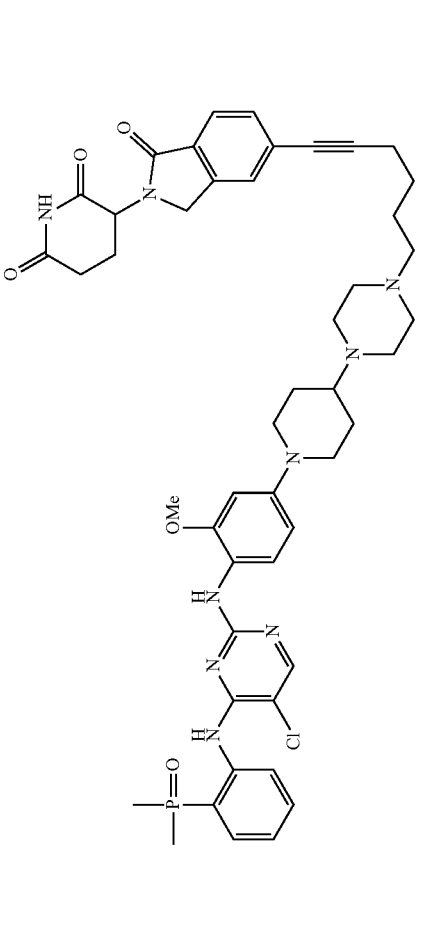 | 3-(5-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)hex-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| | | 8-(4-(4-(5-(2-(2,6-dioxopiperidin-3-yl)-1-oxoisoindolin-4-yl)pent-4-ynoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(6-(2-(2,6-dioxopiperidin-3-yl)-1-oxoisoindolin-4-yl)hex-5-ynoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds represented by formula (I) of the present disclosure and their names

| Compound number | Structural formula | Compound name |
|---|---|---|
| | | 8-(4-(4-(7-(2-(2,6-dioxopiperidin-3-yl)-1-oxoisoindolin-4-yl)hept-6-ynoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(8-(2-(2,6-dioxopiperidin-3-yl)-1-oxoisoindolin-4-yl)oct-7-ynoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds represented by formula (I) of the present disclosure and their names

| Compound number | Structural formula | Compound name |
|---|---|---|
| | 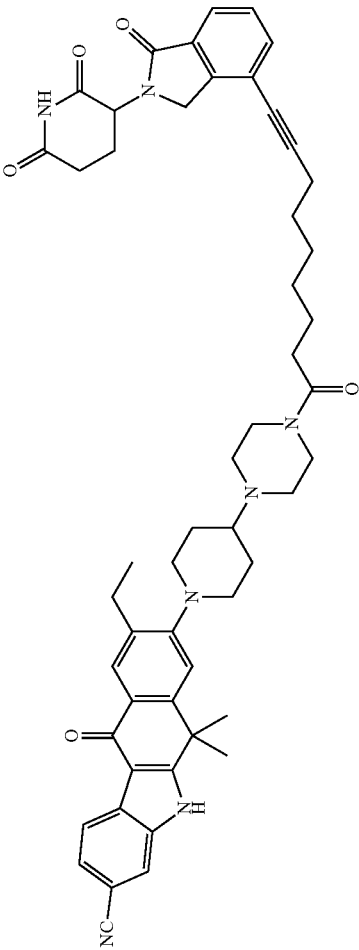 | 8-(4-(4-(9-(2-(2,6-dioxopiperidin-3-yl)-1-oxoisoindolin-4-yl)non-8-ynoyl)piperazin-1-yl)piperidin-1-yl)-9-ethyl-6,6-dimethyl-11-oxo-6,11-dihydro-5H-benzo[b]carbazole-3-carbonitrile |
| | 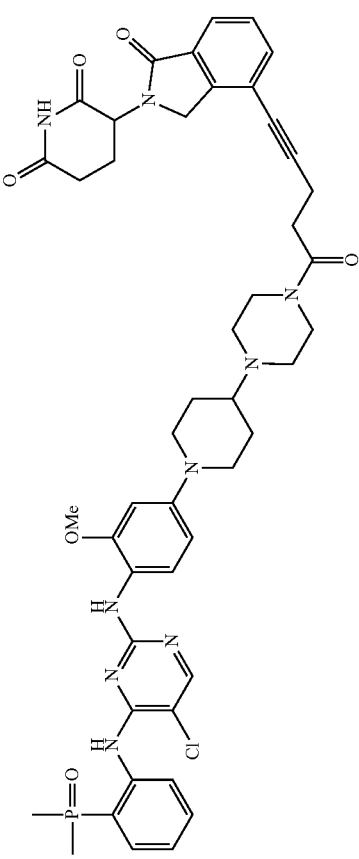 | 3-(4-(5-(4-(1-(4-(4-((5-chloro-4-((2-(dimethylphosphonophenyl)amino)pyrimidin-2-yl)amino)-3-methoxyphenyl)piperidin-4-yl)piperazin-1-yl)-5-oxopent-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
| | 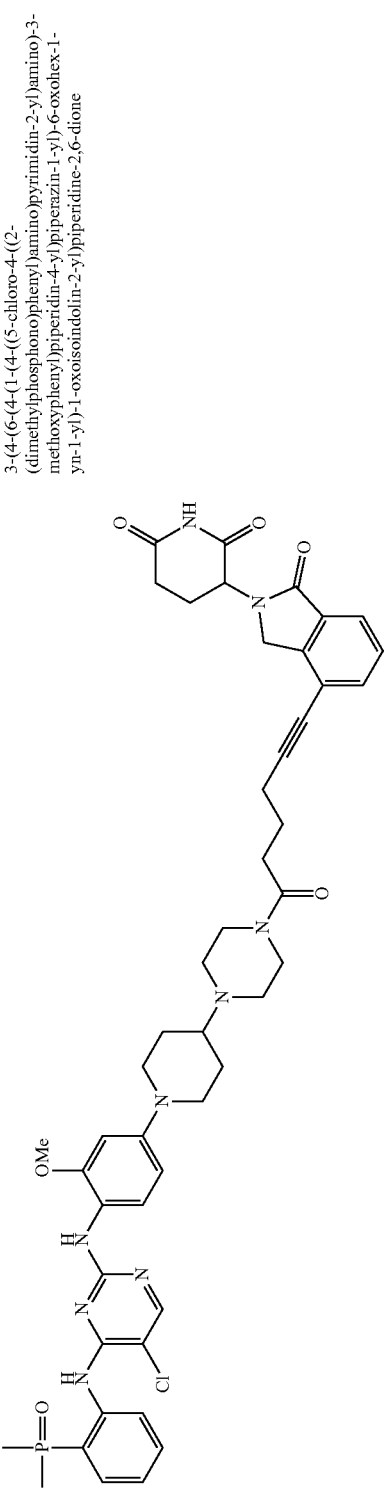 | 3-(4-(6-(4-(1-(4-(5-chloro-4-((2-(dimethylphosphono)phenyl)amino)pyrimidin-2-yl)amino)-3-methoxyphenyl)piperidin-4-yl)piperazin-1-yl)-6-oxohex-1-yn-1-yl)-1-oxoisoindolin-2-yl)piperidine-2,6-dione |
| | 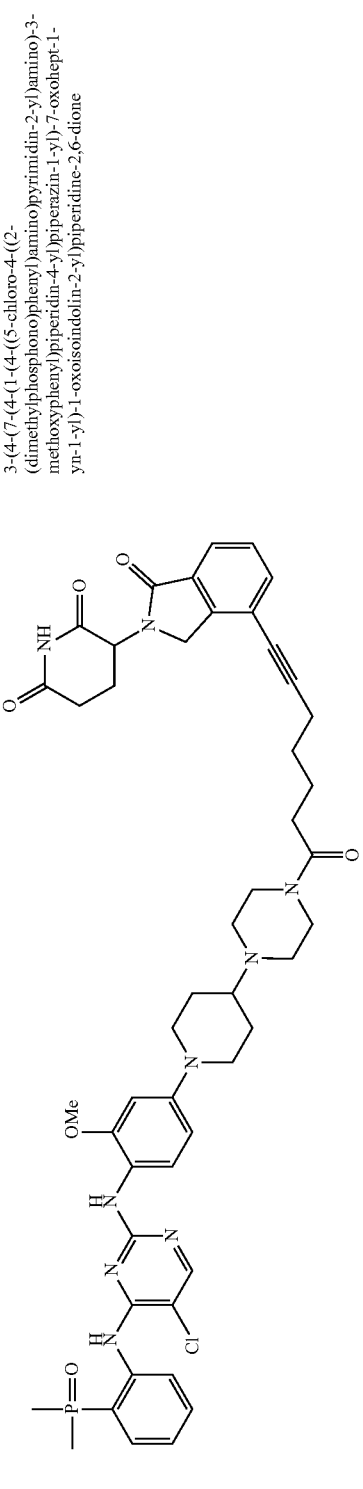 | 3-(4-(7-(4-(1-(4-(5-chloro-4-((2-(dimethylphosphono)phenyl)amino)pyrimidin-2-yl)amino)-3-methoxyphenyl)piperidin-4-yl)piperazin-1-yl)-7-oxohept-1-yn-1-yl)-1-oxoisoindolin-2-yl)piperidine-2,6-dione |

TABLE 1-continued

The compounds represented by formula (I) of the present disclosure and their names

| Compound number | Structural formula | Compound name |
|---|---|---|
|  | 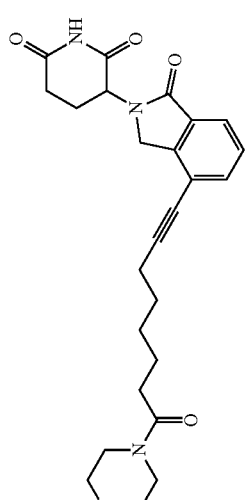 | 3-(4-(8-(4-(1-(4-((5-chloro-4-((2-(dimethylphosphono)phenyl)amino)pyrimidin-2-yl)amino)-3-methoxyphenyl)piperidin-4-yl)piperazin-1-yl)-8-oxooct-1-yn-1-yl)-1-oxoisoindolin-2-yl)piperidine-2,6-dione |
|  | 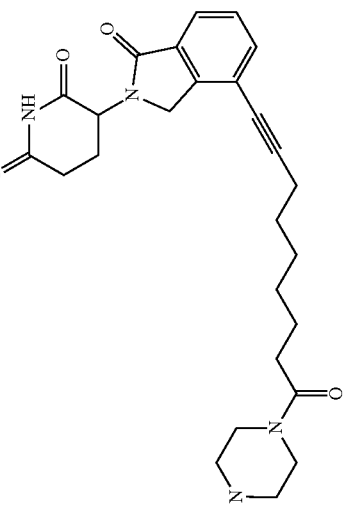 | 3-(4-(9-(4-(1-(4-((5-chloro-4-((2-(dimethylphosphono)phenyl)amino)pyrimidin-2-yl)amino)-3-methoxyphenyl)piperidin-4-yl)piperazin-1-yl)-9-oxonon-1-yn-1-yl)-1-oxoisoindolin-2-yl)piperidine-2,6-dione |

Another aspect of the present disclosure also provides a pharmaceutical composition, comprising the compound represented by formula (I) of the present disclosure or the pharmaceutically acceptable salt thereof, and a pharmaceutically acceptable carrier.

The pharmaceutical composition described in the present disclosure further comprises at least one additional medicament for the treatment or prevention of cancer.

In another aspect of the present disclosure, the compound represented by formula (I) of the present disclosure, or the pharmaceutically acceptable salt thereof for use as a medicament.

In another aspect of the present disclosure, the compound represented by formula (I), or the pharmaceutically acceptable salt thereof described in the present disclosure for use in the prevention and/or treatment of cancer.

In an embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus) large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, smoldering myeloma, smoldering multiple myeloma and myelofibrosis; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that dependent on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that dependent on the protein. In a sub-embodiment, the lung cancer is selected from the group consisting of: small cell lung cancer; and non-small cell lung cancer, including lung adenocarcinoma, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

As used herein, the term "tumors or diseases dependent on a protein selected from ALK, ROS1, MET, EGFR, FLT3 or any combination thereof" refers to a tumor, cancer or disease mediated or caused with the participation of the protein selected from ALK protein, ROS1, MET, EGFR and/or FLT3 or any combination thereof. "Tumors or diseases dependent on protein selected from ALK, ROS1, MET, EGFR, FLT3, or any combination thereof" includes, but is not limited to, the following tumor, cancer or disease dependent on protein selected from ALK, ROS1, MET, EGFR, FLT3, or any combination thereof: lung cancer, lymphoma, inflammatory myofibroblastoma tumor, colorectal cancer, glioma, astrocytome, ovarian cancer, leukemia, breast cancer, thyroid cancer, neuroblastoma, extramedullary plasmacytoma, plasma cell tumor, esophageal squamous cell carcinoma, renal cell carcinoma, bronchial carcinoma, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc.

In another aspect of the present disclosure, the compound represented by formula (I), or the pharmaceutically acceptable salt thereof described in the present disclosure for use in the preparation of a medicament for the prevention and/or treatment of cancer. In a sub-embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus) large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma and refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, myelofibrosis, smoldering myeloma and smoldering multiple myeloma; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/ primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

Another aspect of the present disclosure also provides a method for treating or preventing cancer, comprising administering a therapeutically effective amount of the compound represented by formula (I) of the present disclosure, or the pharmaceutically acceptable salt thereof, or the pharmaceutical composition to a subject. In an embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus) large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, smoldering myeloma, smoldering multiple myeloma and myelofibrosis; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

In the method for treating or preventing cancer described in the present disclosure, the compound represented by formula (I) described in the present disclosure, or the pharmaceutically acceptable salt thereof, or the pharmaceutical composition is administrated to a subject by at least one administration mode selected from nasal administration, inhalation administration, topical administration, oral administration, oral mucosal administration, rectal administration, pleural cavity administration, peritoneal administration, vaginal administration, intramuscular administration, subcutaneous administration, transdermal administration, epidural administration, intrathecal administration and intravenous administration.

II. Compounds Represented by Formula (III)

Another aspect of the present disclosure provides a compound represented by formula (III):

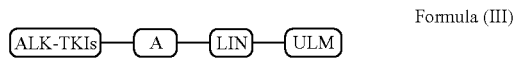

Formula (III)

wherein ALK-TKIs are covalently connected to LIN through group A, and ULM is covalently connected to LIN;

wherein group A represents C(O) or is absent;

ALK-TKIs represent the structure of the following formula (IIIa), formula (IIIb), formula (IIIc), formula (IIId), formula (IIIe) or formula (IIIf):

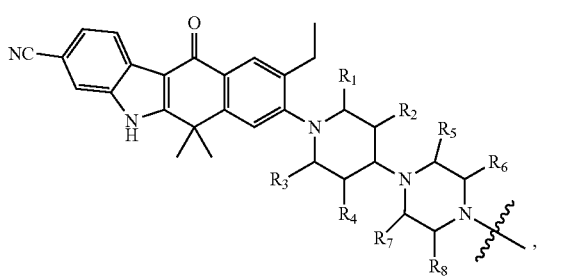

(IIIa)

-continued

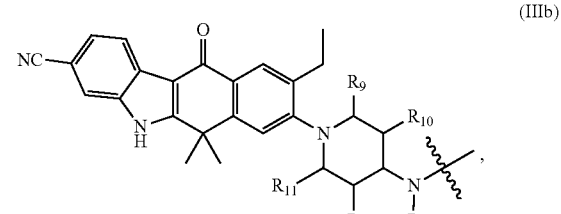
(IIIb)

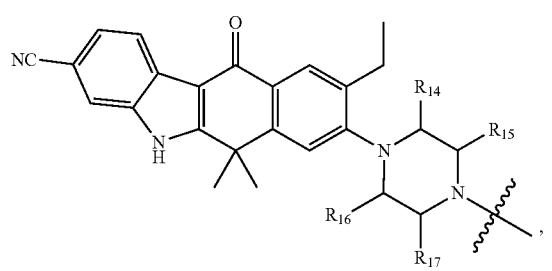
(IIIc)

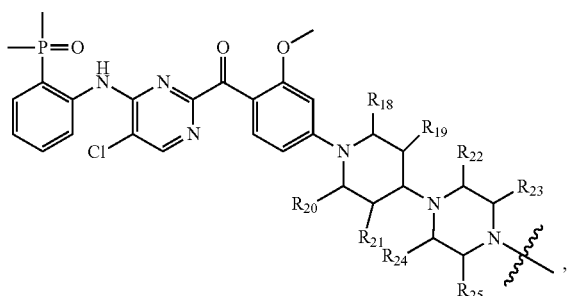
(IIId)

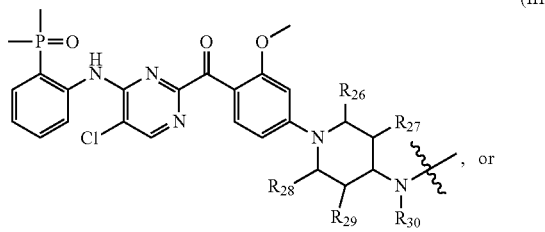
(IIIe)

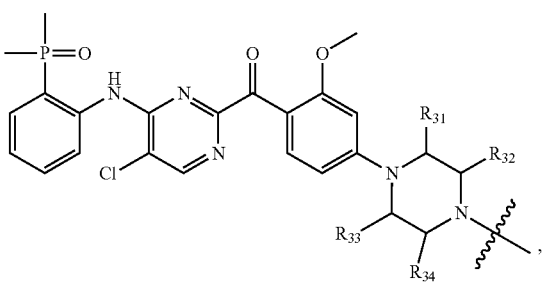
(IIIf)

wherein $R_1$, $R_2$, $R_3$, $R_4$, $R_5$, $R_6$, $R_7$, $R_8$, $R_9$, $R_{10}$, $R_{11}$, $R_{12}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{31}$, $R_{32}$, $R_{33}$ and $R_{34}$ each independently represents H or methyl, and $R_{13}$ and $R_{30}$ each independently represents H, methyl or ethyl;

the ULM represents the structure of the following formula (IV):

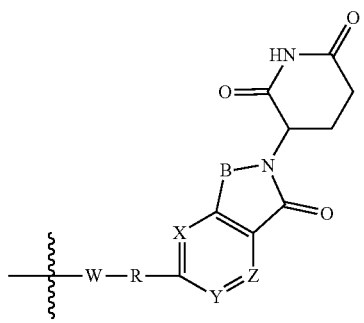
formula (IV)

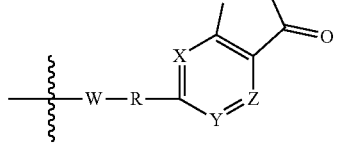

wherein

B represents $CH_2$ or $C(O)$, X, Y, Z are the same or different and each independently represents CH or N, R represents $CH_2$, NH or O, and W represents carbonyl or W is absent; and LIN is a linking group and represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, O, NHC(O), NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent;

or a salt thereof, an enantiomer thereof, a stereoisomer thereof, a solvate thereof, a polymorph thereof.

In the present disclosure, LIN in formula (III) is represented as —U-alkylene-, wherein one of the two ends of the —U-alkylene- (for example, group U) may be connected to group A, and the other end (alkylene) is connected to ULM; or one of the two ends of the —U-alkylene- (for example, alkylene) may be connected to group A, and the other end (group U) is connected to ULM. When group U is connected to the group A, group U and the group A are not C(O) at the same time. In an embodiment of the present disclosure, when group U is connected to group A, both group U and group A may be absent at the same time, or either of group U and group A is C(O), and the other is absent.

In an embodiment of the compound represented by formula (III) of the present disclosure, the ALK-TKIs are small molecule drugs targeting an ALK target.

In an embodiment of the compound represented by formula (III) of the present disclosure, the group A represents C(O).

In an embodiment of the compound represented by formula (III) of the present disclosure, the group A is absent.

In an embodiment of the compound represented by formula (III) of the present disclosure, in formula (IV), B represents $CH_2$ or C(O); X, Y, Z are the same and all represent CH, R represents $CH_2$, NH or O, and W represents carbonyl or W is absent. In a sub-embodiment of the present disclosure, in formula (IV), B represents $CH_2$; X, Y, Z are the same and all represent CH, R represents $CH_2$, NH or O, and W represents carbonyl or W is absent. In a sub-embodiment of the present disclosure, in formula (IV), B represents C(O); X, Y, Z are the same and all represent CH, R represents $CH_2$, NH or O, and W represents carbonyl or W is absent. In a sub-embodiment of the present disclosure, in formula (IV), B represents $CH_2$ or C(O); X, Y, Z are the same and all represent CH, R represents $CH_2$, and W represents carbonyl or W is absent. In a sub-embodiment of the present disclosure, in formula (IV), B represents $CH_2$ or C(O), X, Y, Z are the same and all represent CH, R represents NH, and W represents carbonyl or W is absent. In a sub-embodiment of the present disclosure, in formula (IV), B represents $CH_2$ or C(O); X, Y, Z are the same and all represent CH, R represents O, and W represents carbonyl or W is absent.

In an embodiment of the compound represented by formula (III) of the present disclosure, formula (IV) is also the following structural formula:

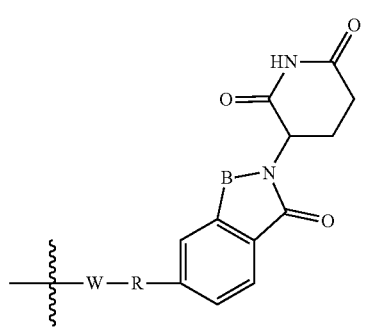

formula (IV-1)

wherein B represents $CH_2$ or C(O), R represents $CH_2$, NH or O, and W represents carbonyl or W is absent.

In an embodiment of the compound represented by formula (III) of the present disclosure, the LIN represents:
—U—$C_{1-30}$ alkylene-, —U—$(CH_2)_{n1}$—C(O)NH—$(CH_2)_{n2})_{m1}$—, —U—$(CH_2)_{n1}$—(NHC(O)—$(CH_2)_{n2})_{m1}$—, —U—$(CH_2)_{n1}$—(O$(CH_2)_{n2})_{m1}$—, —U—$(CH_2)_{n1}$—(O$(CH_2)_{n2})_{m1}$—(O$(CH_2)_{n3})_{m2}$—, —U—$(CR_{a1}R_{a2})_{n1}$—(O$(CR_{a3}R_{a4})_{n2})_{m1}$—, —U—$(CR_{a5}R_{a6})_{n1}$—(O$(CR_{a7}R_{a8})_{n2})_{m1}$—(O$(CR_{a9}R_{a10})_{n3})_{m2}$—, —U—$(CH_2)_{n1}$—C(O)NH—$(CH_2)_{n2})_{m1}$—(O$(CH_2)_{n3})_{m2}$—, —U—$(CH_2)_{n1}$—(O$(CH_2)_{n2})_{m1}$—O—$(CH_2)_{n3}$—C(O)NH—$(CH_2)_{n4}$—(O$(CH_2)_{n5})_{m2}$—O—$(CH_2)_{n6}$—, —U—$(CR_{a11}R_{a12})_{n1}$—(O$(CR_{a13}R_{a14})_{n2})_{m1}$—O—$(CR_{a15}R_{a16})_{n3}$—C(O)NH—$(CR_{a17}R_{a18})_{n4}$—(O$(CR_{a19}R_{a20})_{n5})_{m2}$—O—$(CR_{a21}R_{a22})_{n6}$—, —U—$(CR_{a23}R_{a24})_{n1}$—C(O)NH—(O$(CR_{a25}R_{a26})_{n2})_{m1}$—, —U—$(CH_2)_{n1}$—(NHC(O)—$(CH_2)_{n2})_{m1}$—(O$(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—(O$(CH_2)_{n2})_{m1}$— having alkylene carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

n1, n2, n3, n4, n5, n6, m1, m2 independently represent an integer of 1, 2, 3, 4, 5, 6, 7, 8, 9, 10, 11, 12, 13, 14, 15, 16, 17, 18, 19 or 20; and the group U represents C(O), or the group U is absent; and wherein, when the LIN represents —U—$C_{1-30}$ alkylene-, the $C_{1-30}$ alkylene is optionally substituted by one or more substituents.

In an embodiment of the compound represented by formula (III) of the present disclosure, the LIN represents —U—$C_{1-30}$ alkylene chain-, and the $C_{1-30}$ alkylene chain is optionally substituted by one or more substituents selected from hydroxyl, amino, mercapto, halogen or any combination thereof. In a sub-embodiment, the LIN represents —$(CH_2)_3CH(OH)CH(OH)(CH_2)_4$—.

In an embodiment of the compound represented by formula (III) of present disclosure, the LIN is preferably —U—$C_{1-30}$ alkylene-. In an embodiment of the present disclosure, the LIN is preferably —U-methylene or —U—$C_{2-30}$ alkylene-, wherein the $C_{1-30}$ alkylene is a linear or branched $C_{2-30}$ alkylene (e.g. $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent.

In an embodiment of the compound represented by formula (III) of the present disclosure, preferably, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—;

wherein the group U represents C(O), or the group U is absent.

In an embodiment of the compound represented by formula (III) of the present disclosure, the LIN is preferably —U—$C_{2-40}$ alkylene- (for example, —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In an embodiment of the compound represented by formula (III) of the present disclosure, the LIN is —U-alkylene-, the alkylene (e.g. $C_{1-30}$ alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents C(O), or the group U is absent.

In an embodiment of the compound represented by formula (III) of the present disclosure, the LIN is preferably —U—$C_{1-30}$ alkylene-, and the $C_{1-30}$ alkylene is a linear or branched $C_1$-$C_{30}$ alkylene chain (e.g. $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In an embodiment of the compound represented by formula (III) of the present disclosure, the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the compound represented by formula (III) of the present disclosure, the LIN preferably represents:
—U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—;

wherein the group U represents C(O), or the group U is absent.

In an embodiment of the compound represented by formula (III) of the present disclosure, the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the compound represented by formula (III) of the present disclosure, the LIN preferably represents: —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—$(CH_2)_8NHC(O)(CH_2)_8$—, —U—$(CH_2)_9NHC(O)CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—;

wherein the group U represents C(O), or the group U is absent.

In an embodiment of the compound represented by formula (III) of the present disclosure, the LIN represents:
—U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—

—(O(CH₂)₂)₂—, —U—(CH₂)₂—(O(CH₂)₂)₃—, —U—(CH₂)₂—(O(CH₂)₂)₄—, —U—(CH₂)₂—(O(CH₂)₂)₅—, —U—(CH₂)₂—(O(CH₂)₂)₆—, —U—(CH₂)₂—(O(CH₂)₂)₇—, —U—(CH₂)₂—(O(CH₂)₂)₈—, —U—(CH₂)₂—(O(CH₂)₂)₉—, —U—(CH₂)₂—(O(CH₂)₂)₁₀—, —U—(CH₂)₃—O—(CH₂)₂—, —U—(CH₂)₃—(O(CH₂)₂)₂—, —U—(CH₂)₃—(O(CH₂)₂)₃—, —U—(CH₂)₃—(O(CH₂)₂)₄—, —U—(CH₂)₃—(O(CH₂)₂)₅—, —U—(CH₂)₃—(O(CH₂)₂)₆—, —U—(CH₂)₃—(O(CH₂)₂)₇—, —U—(CH₂)₃—(O(CH₂)₂)₈—, —U—(CH₂)₃—(O(CH₂)₂)₉—, —U—(CH₂)₃—(O(CH₂)₂)₁₀—, —U—(CH₂)₄—O—(CH₂)₂—, —U—(CH₂)₄—(O(CH₂)₂)₂—, —U—(CH₂)₄—(O(CH₂)₂)₃—, —U—(CH₂)₄—(O(CH₂)₂)₄—, —U—(CH₂)₄—(O(CH₂)₂)₅—, —U—(CH₂)₄—(O(CH₂)₂)₆—, —U—(CH₂)₄—(O(CH₂)₂)₇—, —U—(CH₂)₄—(O(CH₂)₂)₈—, —U—(CH₂)₄—(O(CH₂)₂)₉—, —U—(CH₂)₄—(O(CH₂)₂)₁₀—, —U—CH₂—O—(CH₂)₃—, —U—CH₂—(O(CH₂)₃)₂—, —U—CH₂—(O(CH₂)₃)₃—, —U—CH₂—(O(CH₂)₃)₄—, —U—CH₂—(O(CH₂)₃)₅—, —U—CH₂—(O(CH₂)₃)₆—, —U—CH₂—(O(CH₂)₃)₇—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₂—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)—O—(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—; wherein the group U represent C(O), or the Group U is absent.

In an embodiment of the compound represented by formula (III) of the present disclosure, the LIN represents —U—(CH₂)$_{n1}$—CH=CH—(CH₂)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the compound represented by formula (III) of the present disclosure, the LIN represents: —U—CH₂CH=CHCH₂—, —U—CH₂CH=CH(CH₂)₂—, —U—CH₂CH=CH(CH₂)₃—, —U—CH₂CH=CH(CH₂)₄—, —U—CH₂CH=CH(CH₂)₅—, —U—CH₂CH=CH(CH₂)₆—, —U—CH₂CH=CH(CH₂)₇—, —U—CH₂CH=CH(CH₂)₈—, —U—CH₂CH=CH(CH₂)₉—, —U—CH₂CH=CH(CH₂)₁₀—, —U—(CH₂)₂CH=CHCH₂—, —U—(CH₂)₂CH=CH(CH₂)₂—, —U—(CH₂)₂CH=CH(CH₂)₃—, —U—(CH₂)₂CH=CH(CH₂)₄—, —U—(CH₂)₂CH=CH(CH₂)₅—, —U—(CH₂)₂CH=CH(CH₂)₆—, —U—(CH₂)₂CH=CH(CH₂)₇—, —U—(CH₂)₂CH=CH(CH₂)₈—, —U—(CH₂)₃CH=CHCH₂—, —U—(CH₂)₃CH=CH(CH₂)₂—, —U—(CH₂)₃CH=CH(CH₂)₃—, —U—(CH₂)₃CH=CH(CH₂)₄—, —U—(CH₂)₃CH=CH(CH₂)₅—, —U—(CH₂)₃CH=CH(CH₂)₆—, —U—(CH₂)₃CH=CH(CH₂)₇—, —U—(CH₂)₄CH=CHCH₂—, —U—(CH₂)₄CH=CH(CH₂)₂—, —U—(CH₂)₄CH=CH(CH₂)₃—, —U—(CH₂)₄CH=CH(CH₂)₄—, —U—(CH₂)₄CH=CH(CH₂)₅—, —U—(CH₂)₅CH=CHCH₂—, —U—(CH₂)₅CH=CH(CH₂)₂—, —U—(CH₂)₅CH=CH(CH₂)₃—, —U—(CH₂)₅CH=CH(CH₂)₄—, —U—(CH₂)₅CH=CH(CH₂)₅—, —U—(CH₂)₆CH=CHCH₂—, —U—(CH₂)₆CH=CH(CH₂)₂—, —U—(CH₂)₆CH=CH(CH₂)₃—, —U—(CH₂)₇CH=CHCH₂—, —U—(CH₂)₇CH=CH(CH₂)₂—, —U—(CH₂)₇CH=CH(CH₂)₃—, —U—(CH₂)₈CH=CHCH₂—, —U—(CH₂)₈CH=CH(CH₂)₂—, —U—(CH₂)₈CH=CH(CH₂)₃—, —U—(CH₂)₉CH=CHCH₂—U—(CH₂)₉CH=CH(CH₂)₂—, —U—(CH₂)₉CH=CH(CH₂)₃—, —U—(CH₂)₁₀CH=CHCH₂—, or —U—(CH₂)₁₀CH=CH(CH₂)₂—, wherein the group U represent C(O), or the group U is absent.

In an embodiment of the compound represented by formula (III) of the present disclosure, the LIN represents —U—(CH₂)$_{n1}$—C≡C—(CH₂)$_{n2}$— or —U—(CH₂)$_{n1}$—C≡C—C≡C—(CH₂)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, and wherein the group U represents C(O), or the group U is absent.

In an embodiment of the compound represented by formula (III) of the present disclosure, the LIN represents: —U—CH₂C≡CCH₂—, —U—CH₂C≡C(CH₂)₂—, —U—CH₂C≡C(CH₂)₃—, —U—CH₂C≡C(CH₂)₄—, —U—CH₂C≡C(CH₂)₅—, —U—CH₂C≡C(CH₂)₆—, —U—CH₂C≡C(CH₂)₇—, —U—CH₂C≡C(CH₂)₈—, —U—CH₂C≡C(CH₂)₉—, —U—CH₂C≡C(CH₂)₁₀—, —U—(CH₂)₂C≡CCH₂—, —U—(CH₂)₂C≡C(CH₂)₂—, —U—(CH₂)₂C≡C(CH₂)₃—, —U—(CH₂)₂C≡C(CH₂)₄—, —U—(CH₂)₂C≡C(CH₂)₅—, —U—(CH₂)₂C≡C(CH₂)₆—, —U—(CH₂)₂C≡C(CH₂)₇—, —U—(CH₂)₂C≡C(CH₂)₈—, —U—(CH₂)₃C≡CCH₂—, —U—(CH₂)₃C≡C(CH₂)₂—, —U—(CH₂)₃C≡C(CH₂)₃—, —U—(CH₂)₃C≡C(CH₂)₄—, —U—(CH₂)₃C≡C(CH₂)₅—, —U—(CH₂)₃C≡C(CH₂)₆—, —U—(CH₂)₃C≡C(CH₂)₇—, —U—(CH₂)₄C≡CCH₂—, —U—(CH₂)₄C≡C(CH₂)₂—, —U—(CH₂)₄C≡C(CH₂)₃—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, wherein the group U represents C(O), or the group U is absent.

In an embodiment of the compound represented by formula (III) of the present disclosure, the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the compound represented by formula (III) of the present disclosure, the LIN represents —U—CH$_2$-piperazinylidene-CH$_2$—, —U—(CH$_2$)$_2$-piperazinylidene-(CH$_2$)$_2$—, —U—(CH$_2$)$_3$-piperazinylidene-(CH$_2$)$_3$—, —U—(CH$_2$)$_2$-piperazinylidene-(CH$_2$)$_3$—, —U—CH$_2$-piperazinylidene-(CH$_2$)$_2$—, —U—CH$_2$-piperazinylidene-(CH$_2$)$_3$— or —U—(CH$_2$)$_2$-piperazinylidene-(CH$_2$)$_3$—, wherein the group U represents C(O), or the group U is absent.

In an embodiment of the compound represented by formula (III) of the present disclosure, the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In an embodiment of the compound represented by formula (III) of the present disclosure, the LIN represents —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In an embodiments of the compound represented by formula (III) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_3$-triazolylidene-(CH$_2$)$_{n4}$—(O(CH$_2$)$_{n5}$)$_{n2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_4$— or —U—(CH$_2$)$_{n1}$—(O(CH$_2$)$_{n2}$)$_{m1}$—O—(CH$_2$)$_{n3}$-triazolylidene-(CH$_2$)$_{n4}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In an embodiment of the compound represented by formula (III) of the present disclosure, the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In an embodiment of the compound represented by formula (III) of the present disclosure, the LIN represents:

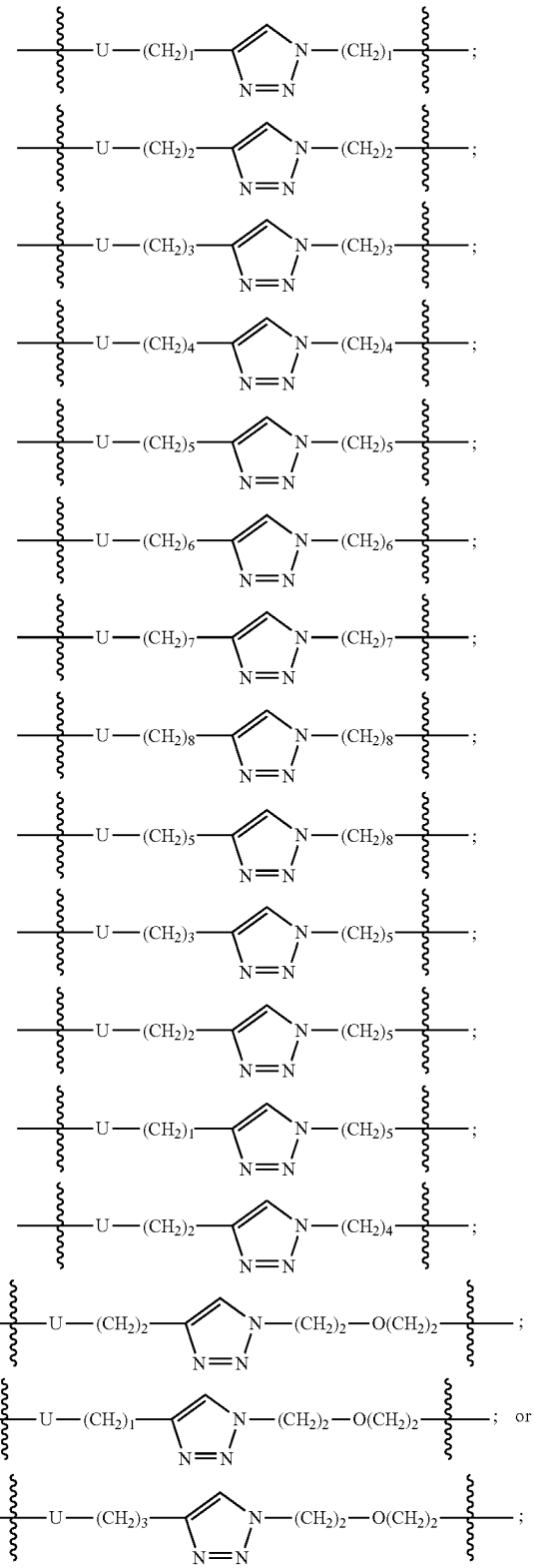

wherein the group U represents C(O), or the group U is absent.

In an embodiment of the compound represented by formula (III) of the present disclosure, the LIN: represents —U—(CH$_2$)$_2$NHC(O)(CH$_2$)$_2$—O—(CH$_2$)$_2$— or —U—

(CH$_2$)$_2$C(O)NH(CH$_2$)$_2$—O—(CH$_2$)$_2$—, wherein the group U represents C(O), or the group U is absent.

In an embodiment of the compound represented by formula (III) of the present disclosure, the compound represented by formula (III) is also a compound represented by formula (IIIa-1) or formula (IIIa-2):

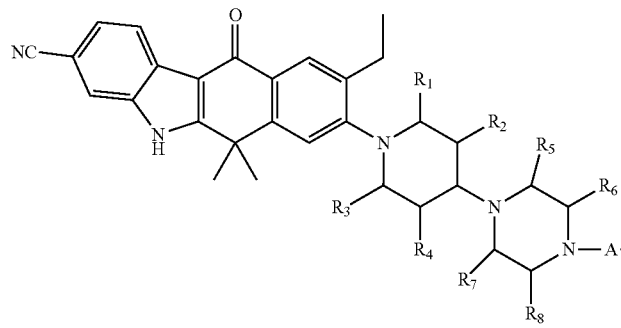
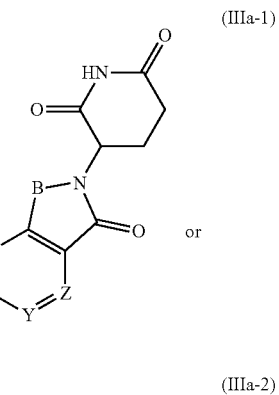

(IIIa-1)

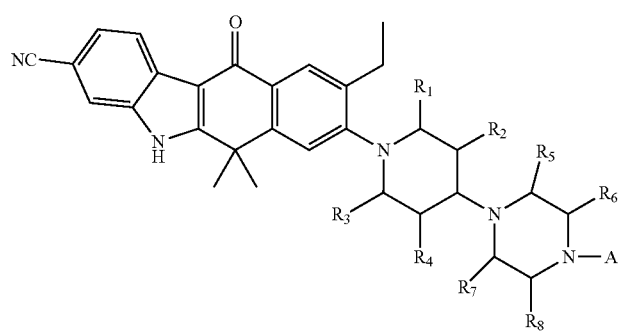
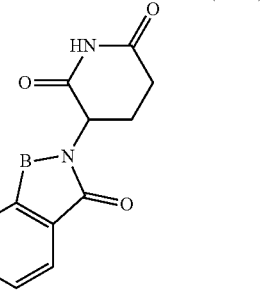

(IIIa-2)

wherein, the groups LIN, A, W, R, R$_1$, R$_2$, R$_3$, R$_4$, R$_5$, R$_6$, R$_7$, R$_8$, and B, X, Y, Z are as defined herein.

In a sub-embodiment of the compound of the present disclosure represented by formula (IIIa-1) or formula (IIIa-2), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (IIIa-1) or formula (IIIa-2), the LIN represents —U—C$_{1-30}$ alkylene-, —U—(CH$_2$)$_{n1}$—(C(O)NH—(CH$_2$)$_{n2}$)$_{m1}$—, —U—(CH$_2$)$_{n1}$—(NHC(O)—(CH$_2$)$_{n2}$)$_{m1}$—, —U—(CH$_2$)$_{n1}$—(O(CH$_2$)$_{n2}$)$_{m1}$—, —U—(CH$_2$)$_{n1}$—(O(CH$_2$)$_{n2}$)$_{m1}$—(O(CH$_2$)$_{n3}$)$_{m2}$—, —U—(CR$_{a1}$R$_{a2}$)$_{n1}$—(O(CR$_{a3}$R$_{a4}$)$_{n2}$)$_{m1}$—, —U—(CR$_{a5}$R$_{a6}$)$_{n1}$—(O(CR$_{a7}$R$_{a8}$)$_{n2}$)$_{m1}$—(O(CR$_{a9}$R$_{a10}$)$_{n3}$)$_{m2}$—, —U—(CH$_2$)$_{n1}$—(C(O)NH—(CH$_2$)$_{n2}$)$_{m1}$—(O(CH$_2$)$_{n3}$)$_{m2}$—, —U—(CH$_2$)$_{n1}$—(O(CH$_2$)$_{n2}$)$_{m1}$—O—(CH$_2$)$_{n3}$—C(O)NH—(CH$_2$)$_{n4}$—(O(CH$_2$)$_{n5}$)$_{m2}$—O—(CH$_2$)$_{n6}$—, —U—(CR$_{a11}$R$_{a12}$)$_{n1}$—(CR$_{a13}$R$_{a14}$)$_{n2}$)$_{m2}$—C(O)NH—(CR$_{a15}$R$_{a16}$)$_{n3}$—C(O)NH—(CR$_{a17}$R$_{a18}$)$_{n4}$—(O(CR$_{a19}$R$_{a20}$)$_{n5}$)$_{m2}$—O—(CR$_{a21}$R$_{a22}$)$_{n6}$—, —U—(CR$_{23}$R$_{24}$)$_{n1}$—C(O)NH—(O(CR$_{25}$R$_{26}$)$_{n2}$)$_{m1}$—, —U—(CH$_2$)$_{n1}$—(NHC(O)—(CH$_2$)$_{n2}$)$_{m1}$—(O(CH$_2$)$_{n3}$)$_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—(CH$_2$)$_{n1}$—(O(CH$_2$)$_{n2}$)$_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein R$_{a1}$, R$_{a2}$, R$_{a3}$, R$_{a4}$, R$_{a5}$, R$_{a6}$, R$_{a7}$, R$_{a8}$, R$_{a9}$, R$_{a10}$, R$_{a11}$, R$_{a12}$, R$_{a13}$, R$_{a14}$, R$_{a15}$, R$_{a16}$, R$_{a17}$, R$_{a18}$, R$_{a19}$, R$_{a20}$, R$_{a21}$, R$_{a22}$, R$_{a23}$, R$_{a24}$, R$_{a25}$, R$_{a26}$ each independently represents H, linear or branched C$_1$-C$_{10}$ alkyl or C$_3$-C$_{10}$ cycloalkyl, wherein in the same LIN, R$_{a1}$, R$_{a2}$, R$_{a3}$, R$_{a4}$, R$_{a5}$, R$_{a6}$, R$_{a7}$, R$_{a8}$, R$_{a9}$, R$_{a10}$, R$_{a11}$, R$_{a12}$, R$_{a13}$, R$_{a14}$, R$_{a15}$, R$_{a16}$, R$_{a17}$, R$_{a18}$, R$_{a19}$, R$_{a20}$, R$_{a21}$, R$_{a22}$, or R$_{a23}$, R$_{a24}$, R$_{a25}$, R$_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound represented by formula (IIIa-1) or formula (IIIc-2) of the present disclosure, the LIN represents —U—C$_{1-30}$ alkylene-; and the group U represents C(O), or the group U is absent. In a sub-embodiment of the present disclosure, the LIN is —U-methylene or —U—C$_{2-30}$ alkylene-, wherein the C$_{2-30}$ alkylene is a linear or branched C$_{2-30}$ alkylene (preferably C$_2$-C$_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent. In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent. In a sub-embodiment, the group U represents C(O). In a sub-embodiment, the group U is absent.

In an embodiment of the compound represented by formula (IIIa-1) or formula (IIIa-2) of the present disclosure, the LIN represents —U—$C_{1-30}$ alkylene chain-, and the $C_{1-30}$ alkylene chain is optionally substituted by one or more substituents selected from hydroxyl, amino, mercapto, halogen or any combination thereof. In a sub-embodiment, the LIN represents —$(CH_2)_3CH(OH)CH(OH)(CH_2)_4$—.

In a sub-embodiment of the compound represented by formula (IIIa-1) or formula (IIIa-2) of the present disclosure, the LIN represents —U—$C_{2-40}$ alkylene- (preferably, —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In a sub-embodiment of the compound represented by formula (IIIa-1) or formula (IIIa-2) of the present disclosure, the LIN represents —U-alkylene-, the alkylene (preferably $C_{1-30}$ alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents C(O), or the group U is absent.

In a sub-embodiment of the compound represented by formula (IIIa-1) or formula (IIIa-2) of the present disclosure, the LIN represents —U—$C_{1-30}$ alkylene-, and the $C_{1-30}$ alkylene is a linear or branched $C_{1-30}$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In a sub-embodiment of the compound of the present disclosure represented by formula (IIIa-1) or formula (IIIa-2), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIa-1) or formula (IIIa-2), the LIN represents: —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH$ (CH$_2$)$_2$—, —U—(CH$_2$)$_{10}$C(O)NH(CH$_2$)$_3$—, —U—(CH$_2$)$_{10}$C(O)NH(CH$_2$)$_4$—, —U—(CH$_2$)$_{10}$C(O)NH(CH$_2$)$_5$— or —U—(CH$_2$)$_{10}$C(O)NH(CH$_2$)$_{10}$—; wherein the group U represents C(O), or the group U is absent.

In a sub-embodiment of the compound of the present disclosure represented by formula (IIIa-1) or formula (IIIa-2), the LIN represents —U—(CH$_2$)$_{n1}$—NHC(O)—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIa-1) or formula (IIIa-2), the LIN represents —U—CH$_2$NHC(O)CH$_2$—, —U—CH$_2$NHC(O)(CH$_2$)$_2$—, —U—CH$_2$NHC(O)(CH$_2$)$_3$—, —U—CH$_2$NHC(O)(CH$_2$)$_4$—, —U—CH$_2$NHC(O)(CH$_2$)$_5$—, —U—CH$_2$NHC(O)(CH$_2$)$_6$—, —U—CH$_2$NHC(O)(CH$_2$)$_7$—, —U—CH$_2$NHC(O)(CH$_2$)$_8$—, —U—CH$_2$NHC(O)(CH$_2$)$_9$—, —U—CH$_2$NHC(O)(CH$_2$)$_{10}$—, —U—(CH$_2$)$_2$NHC(O)CH$_2$—, —U—(CH$_2$)$_2$NHC(O)(CH$_2$)$_2$—, —U—(CH$_2$)$_2$NHC(O)(CH$_2$)$_3$—, —U—(CH$_2$)$_2$NHC(O)(CH$_2$)$_4$—, —U—(CH$_2$)$_2$NHC(O)(CH$_2$)$_5$—, —U—(CH$_2$)$_3$NHC(O)CH$_2$—, —U—(CH$_2$)$_3$NHC(O)(CH$_2$)$_2$—, —U—(CH$_2$)$_3$NHC(O)(CH$_2$)$_3$—, —U—(CH$_2$)$_3$NHC(O)(CH$_2$)$_4$—, —U—(CH$_2$)$_3$NHC(O)(CH$_2$)$_5$—, —U—(CH$_2$)$_4$NHC(O)CH$_2$—, —U—(CH$_2$)$_4$NHC(O)(CH$_2$)$_2$—, —U—(CH$_2$)$_4$NHC(O)(CH$_2$)$_3$—, —U—(CH$_2$)$_4$NHC(O)(CH$_2$)$_4$—, —U—(CH$_2$)$_4$NHC(O)(CH$_2$)$_5$—, —U—(CH$_2$)$_4$NHC(O)(CH$_2$)$_6$—, —U—(CH$_2$)$_4$NHC(O)(CH$_2$)$_7$—, —U—(CH$_2$)$_5$NHC(O)CH$_2$—, —U—(CH$_2$)$_5$NHC(O)(CH$_2$)$_2$—, —U—(CH$_2$)$_5$NHC(O)(CH$_2$)$_3$—, —U—(CH$_2$)$_5$NHC(O)(CH$_2$)$_4$—, —U—(CH$_2$)$_5$NHC(O)(CH$_2$)$_5$—, —U—(CH$_2$)$_5$NHC(O)(CH$_2$)$_6$—, —U—(CH$_2$)$_6$NHC(O)CH$_2$—, —U—(CH$_2$)$_6$NHC(O)(CH$_2$)$_2$—, —U—(CH$_2$)$_6$NHC(O)(CH$_2$)$_3$—, —U—(CH$_2$)$_6$NHC(O)(CH$_2$)$_4$—, —U—(CH$_2$)$_6$NHC(O)(CH$_2$)$_5$—, —U—(CH$_2$)$_6$NHC(O)(CH$_2$)$_6$—, —U—(CH$_2$)$_6$NHC(O)(CH$_2$)$_7$—, —U—(CH$_2$)$_7$NHC(O)CH$_2$—, —U—(CH$_2$)$_7$NHC(O)(CH$_2$)$_2$—, —U—(CH$_2$)$_7$NHC(O)(CH$_2$)$_3$—, —U—(CH$_2$)$_7$NHC(O)(CH$_2$)$_4$—, —U—(CH$_2$)$_7$NHC(O)(CH$_2$)$_5$—, —U—(CH$_2$)$_7$NHC(O)(CH$_2$)$_6$—, —U—(CH$_2$)$_7$NHC(O)(CH$_2$)$_7$—, —U—(CH$_2$)$_8$NHC(O)CH$_2$—, —U—(CH$_2$)$_8$NHC(O)(CH$_2$)$_2$—, —U—(CH$_2$)$_8$NHC(O)(CH$_2$)$_3$—, —U—(CH$_2$)$_8$NHC(O)(CH$_2$)$_8$—, —U—(CH$_2$)$_9$NHC(O)CH$_2$—, —U—(CH$_2$)$_9$NHC(O)(CH$_2$)$_2$—, —U—(CH$_2$)$_9$NHC(O)(CH$_2$)$_3$—, —U—(CH$_2$)$_9$NHC(O)(CH$_2$)$_9$—, or —U—(CH$_2$)$_{10}$NHC(O)(CH$_2$)$_{10}$—; wherein the group U represents C(O), or the group U is absent.

In a sub-embodiment of the compound of the present disclosure represented by formula (IIIa-1) or formula (IIIa-2), the LIN represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiment of the compound of the present disclosure represented by formula (IIIa-1) or formula (IIIa-2), the LIN represents —U—(CH$_2$)$_{n1}$—CH=CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIa-1) or formula (IIIa-2), the LIN represents —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—, —U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiment of the compound of the present disclosure represented by formula (IIIa-1), or formula (IIIa-2), the LIN represents: —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (IIIa-1), or formula (IIIa-2), the LIN represents: —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—, —U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, and wherein the group U represents C(O), or the group U is absent.

In a sub-embodiment of the compound of the present disclosure represented by formula (IIIa-1) or formula (IIIa-2), the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIa-1) or formula (IIIa-2), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (IIIa-1) or formula (IIIa-2), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIa-1) or formula (IIIa-2), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound represented by formula (IIIa-1) or formula (IIIa-2) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{n2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In a sub-embodiment of the compound of the present disclosure represented by formula (IIIa-1) or formula (IIIa-2), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—, —U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (IIIa-1) or formula (IIIa-2), the LIN represents

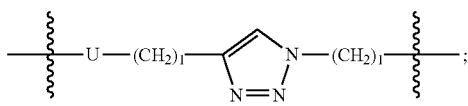

-continued

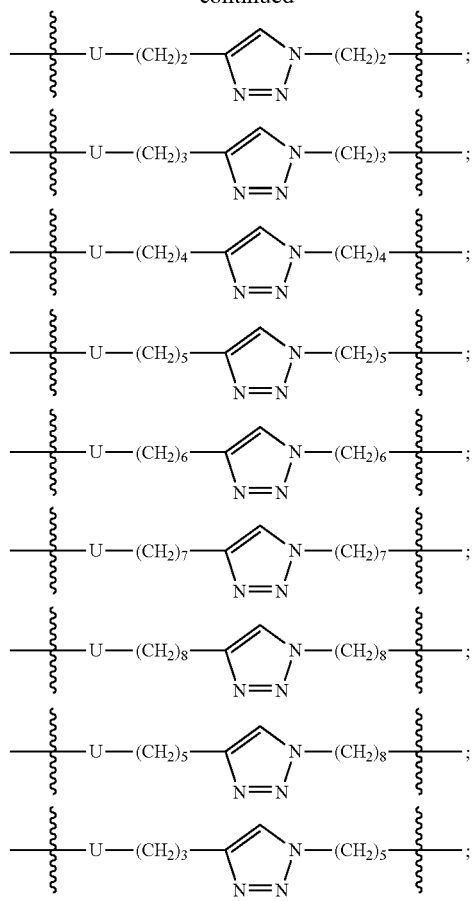

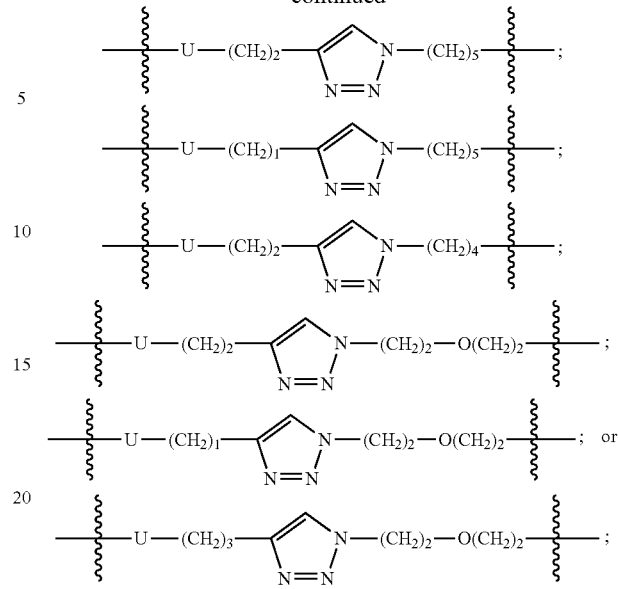

wherein the group U represents C(O), or the group U is absent.

In a sub-embodiment of the compound of the present disclosure represented by formula (IIIa-1) or formula (IIIa-2), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the compound represented by formula (III) of the present disclosure, the compound represented by formula (III) is also a compound represented by formula (IIIb-1) or formula (IIIb-2):

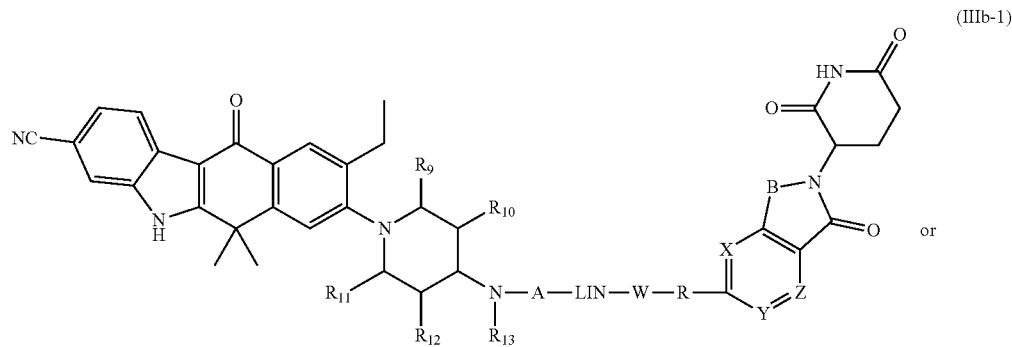

(IIIb-1)

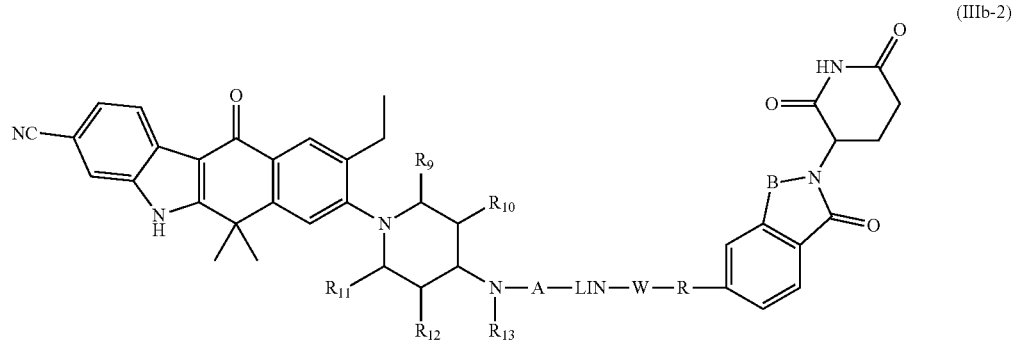

(IIIb-2)

wherein, the groups LIN, A, W, R, $R_9$, $R_{10}$, $R_{11}$, $R_{12}$, $R_{13}$, and B, X, Y, Z are as defined herein.

In a sub-embodiment of the compound of the present disclosure represented by formula (IIIb-1) or formula (IIIb-2), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (IIIb-1) or formula (IIIb-2), the LIN represents —U—$C_{1-30}$ alkylene-, —U—$(CH_2)_{n1}$—(C(O)NH—$(CH_2)_{n2})_{m1}$—, —U—$(CH_2)_{n1}$—(NHC(O)—$(CH_2)_{n2})_{m1}$—, —U—$(CH_2)_{n1}$—(O$(CH_2)_{n2})_{m1}$—, —U—$(CH_2)_{n1}$—(O$(CH_2)_{n2})_{m1}$—(O$(CH_2)_{n3})_{m2}$—, —U—$(CR_{a1}R_{a2})_{n1}$—(O$(CR_{a3}R_{a4})_{n2})_{m1}$—, —U—$(CR_{a5}R_{a6})_{n1}$—(O$(CR_{a7}R_{a8})_{n2})_{m1}$—(O$(CR_{a9}R_{a10})_{n3})_{m2}$—, —U—$(CH_2)_{n1}$—C(O)NH—$(CH_2)_{n2})_{m1}$—(O$(CH_2)_{n3})_{m2}$—, —U—$(CH_2)_{n1}$—(O$(CH_2)_{n2})_{m1}$—O—$(CH_2)_{n3}$—C(O)NH—$(CH_2)_{n4}$—(O$(CH_2)_{n5})_{m2}$—O—$(CH_2)_{n6}$—, —U—$(CR_{a11}R_{a12})_{n1}$—$(CR_{a13}R_{a14})_{n2})_{m2}$—C(O)NH—$(CR_{a15}R_{a16})_{n3}$—C(O)NH—$(CR_{a17}R_{a18})_{n4}$—(O$(CR_{a19}R_{a20})_{n5})_{m2}$—O—$(CR_{a21}R_{a22})_{n6}$—, —U—$(CR_{23}R_{24})_{n1}$—C(O)NH—(O$(CR_{25}R_{26})_{n2})_{m1}$—, —U—$(CH_2)_{n1}$—(NHC(O)—$(CH_2)_{n2})_{m1}$—(O$(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—(O$(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound represented by formula (IIIb-1) or formula (IIIb-2) of the present disclosure, the LIN represents —U—$C_1$-30 alkylene-; and the group U represents C(O), or the group U is absent. In a sub-embodiment of the present disclosure, the LIN is preferably —U-methylene or —U—$C_{2-30}$ alkylene-, wherein the $C_{2-30}$ alkylene is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent. In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent. In a sub-embodiment, the group U represents C(O). In a sub-embodiment, the group U is absent.

In an embodiment of the compound represented by formula (IIIb-1) or formula (IIIb-2) of the present disclosure, the LIN represents —U—$C_{1-30}$ alkylene chain-, and the $C_1$-30 alkylene chain is optionally substituted by one or more substituents selected from hydroxyl, amino, mercapto, halogen or any combination thereof. In a sub-embodiment, the LIN represents —$(CH_2)_3$CH(OH)CH(OH)$(CH_2)_4$—.

In a sub-embodiment of the compound represented by formula (IIIb-1) or formula (IIIb-2) of the present disclosure, the LIN represents —U—$C_{2-40}$ alkylene-(preferably, —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In a sub-embodiment of the compound represented by formula (IIIb-1) or formula (IIIb-2) of the present disclosure, the LIN represents —U-alkylene-, the alkylene (preferably $C_{1-30}$ alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents C(O), or the group U is absent.

In a sub-embodiment of the compound represented by formula (IIIb-1) or formula (IIIb-2) of the present disclosure, the LIN represents —U—$C_{1-30}$ alkylene-, and the $C_{1-30}$ alkylene is a linear or branched $C_{1-30}$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In a sub-embodiment of the compound of the present disclosure represented by formula (IIIb-1) or formula (IIIb-2), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIb-1) or formula (IIIb-2), the LIN represents —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$—, or —U—$(CH_2)_{10}C(O)NH(CH_2)_{10}$—; wherein the group U represents C(O), or the group U is absent.

In a sub-embodiment of the compound of the present disclosure represented by formula (IIIb-1) or formula (IIIb-2), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIb-1) or formula (IIIb-2), the LIN represents —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—$(CH_2)_8NHC(O)(CH_2)_8$—, —U—$(CH_2)_9NHC(O)CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—; wherein the group U represents C(O), or the group U is absent.

In a sub-embodiment of the compound of the present disclosure represented by formula (IIIb-1) or formula (IIIb-2), the LIN represents —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—

—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(C$_{142}$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—C$_{112}$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiment of the compound of the present disclosure represented by formula (IIIb-1) or formula (IIIb-2), the LIN represents —U—(CH$_2$)$_{n1}$—CH=CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIb-1) or formula (IIIb-2), the LIN represents —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiment of the compound of the present disclosure represented by formula (IIIb-1), or formula (IIIb-2), the LIN represents: —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (IIIb-1) or formula (IIIb-2), the LIN represents —U—CH$_2$C≡CCH$_2$—, —U—CH$_2$C≡C(CH$_2$)$_2$—, —U—CH$_2$C(CH$_2$)$_3$—, —U—CH$_2$CC(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, wherein the group U represents C(O), or the group U is absent.

In a sub-embodiment of the compound of the present disclosure represented by formula (IIIb-1) or formula (IIIb-2), the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIb-1) or formula (IIIb-2), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (IIIb-1) or formula (IIIb-2), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIb-1) or formula (IIIb-2), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound represented by formula (IIIb-1) or formula (IIIb-2) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_4$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In a sub-embodiment of the compound of the present disclosure represented by formula (IIIb-1) or formula (IIIb-2), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (IIIb-1) or formula (IIIb-2), the LIN represents

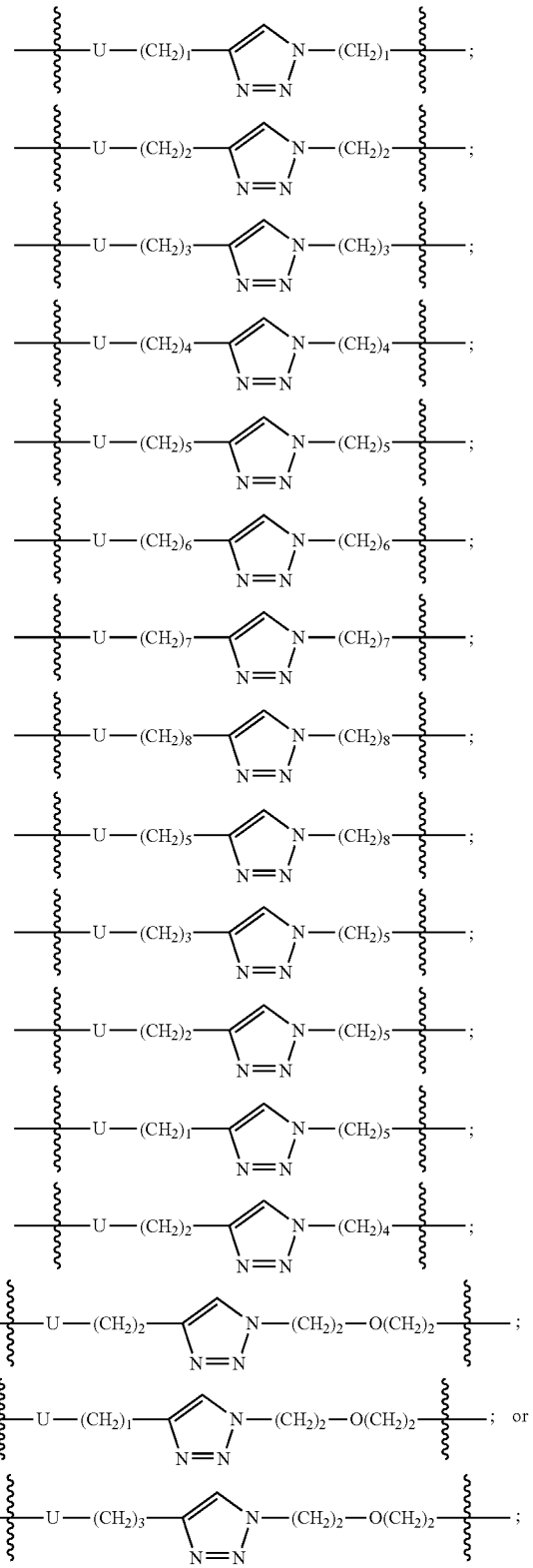

wherein the group U represents C(O), or the group U is absent.

In a sub-embodiment of the compound of the present disclosure represented by formula (IIIb-1) or formula (IIIb-2), the LIN represents —U—(CH$_2$)$_2$NHC(O)(CH$_2$)$_2$—O—

(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the compound represented by formula (III) of the present disclosure, the compound represented by formula (III) is also a compound represented by formula (IIIc-1) or formula (IIIc-2):

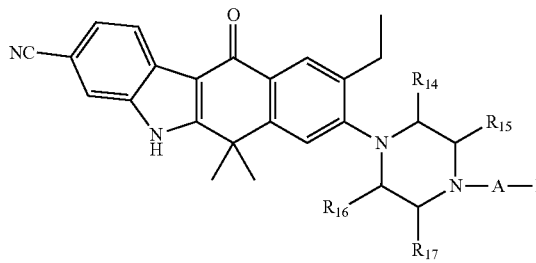
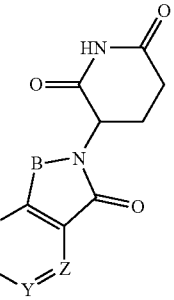

(IIIc-1)

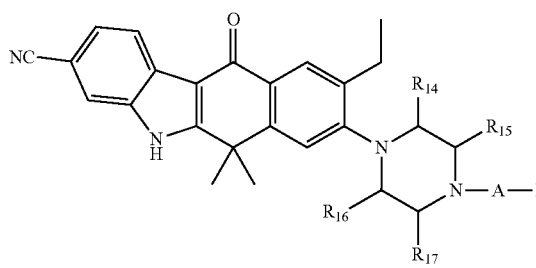
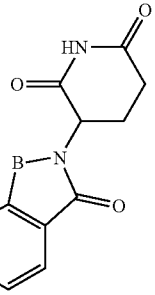

(IIIc-2)

wherein, the groups LIN, A, W, R, R$_{14}$, R$_{15}$, R$_{16}$, R$_{17}$, and B, X, Y, Z are as defined herein.

In a sub-embodiment of the compound of the present disclosure represented by formula (IIIc-1) or formula (IIIc-2), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (IIIc-1) or formula (IIIc-2), the LIN represents —U—C$_{1-30}$ alkylene-, —U—(CH$_2$)$_{n1}$—(C(O)NH—(CH$_2$)$_{n2}$)$_{m1}$—, —U—(CH$_2$)$_{n1}$—(NHC(O)—(CH$_2$)$_{n2}$)$_{m1}$—, —U—(CH$_2$)$_{n1}$—(O(CH$_2$)$_{n2}$)$_{m1}$—, —U—(CH$_2$)$_{n1}$—(O(CH$_2$)$_{n2}$)$_{m1}$—(O(CH$_2$)$_{n3}$)$_{m2}$—, —U—(CR$_{a1}$R$_{a2}$)$_{n1}$—(O(CR$_{a3}$R$_{a4}$)$_{n2}$)$_{m1}$—, —U—(CR$_{a5}$R$_{a6}$)$_{n1}$—(O(CR$_{a7}$R$_{a8}$)$_{n2}$)$_{m1}$—(O(CR$_{a9}$R$_{a10}$)$_{n3}$)$_{m2}$—, —U—(CH$_2$)$_{n1}$—C(O)NH—(CH$_2$)$_{n2}$)$_{m1}$—(O(CH$_2$)$_{n3}$)$_{m2}$—, —U—(CH$_2$)$_{n1}$—(O(CH$_2$)$_{n2}$)$_{m1}$—O—(CH$_2$)$_{n3}$—C(O)NH—(CH$_2$)$_{n4}$—(O(CH$_2$)$_{n5}$)$_{m2}$—O—(CH$_2$)$_{n6}$—, —U—(CR$_{a11}$R$_{a12}$)$_{n1}$—(CR$_{a13}$R$_{a14}$)$_{n2}$)$_{m2}$—C(O)NH—(CR$_{a15}$R$_{a16}$)$_{n3}$—C(O)NH—(CR$_{a17}$R$_{a18}$)$_{n4}$—(O(CR$_{a19}$R$_{a20}$)$_{n5}$)$_{m2}$—O—(CR$_{a21}$R$_{a22}$)$_{n6}$—, —U—(CR$_{23}$R$_{24}$)$_{n1}$—C(O)NH—(O(CR$_{25}$R$_{26}$)$_{n2}$)$_{m1}$—, —U—(CH$_2$)$_{n1}$—(NHC(O)—(CH$_2$)$_{n2}$)$_{m1}$—(O(CH$_2$)$_{n3}$)$_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—(CH$_2$)$_{n1}$—(O(CH$_2$)$_{n2}$)$_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein R$_{a1}$, R$_{a2}$, R$_{a3}$, R$_{a4}$, R$_{a5}$, R$_{a6}$, R$_{a7}$, R$_{a8}$, R$_{a9}$, R$_{a10}$, R$_{a11}$, R$_{a12}$, R$_{a13}$, R$_{a14}$, R$_{a15}$, R$_{a16}$, R$_{a17}$, R$_{a18}$, R$_{a19}$, R$_{a20}$, R$_{a21}$, R$_{a22}$, R$_{a23}$, R$_{a24}$, R$_{a25}$, R$_{a26}$ each independently represents H, linear or branched C$_1$-C$_{10}$ alkyl or C$_3$-C$_{10}$ cycloalkyl, wherein in the same LIN, R$_{a1}$, R$_{a2}$, R$_{a3}$, R$_{a4}$, R$_{a5}$, R$_{a6}$, R$_{a7}$, R$_{a8}$, R$_{a9}$, R$_{a10}$, R$_{a11}$, R$_{a12}$, R$_{a13}$, R$_{a14}$, R$_{a15}$, R$_{a16}$, R$_{a17}$, R$_{a18}$, R$_{a19}$, R$_{a20}$, R$_{a21}$, R$_{a22}$, or R$_{a23}$, R$_{a24}$, R$_{a25}$, R$_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound represented by formula (IIIc-1) or formula (IIIc-2) of the present disclosure, the LIN represents —U—C$_{1-30}$ alkylene-; and the group U represents C(O), or the group U is absent. In a sub-embodiment of the present disclosure, the LIN is preferably —U-methylene or —U—C$_{2-30}$ alkylene-, wherein the C$_{2-30}$ alkylene is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_1$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent. In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent. In a sub-embodiment, the group U represents C(O). In a sub-embodiment, the group U is absent.

In an embodiment of the compound represented by formula (IIIc-1) or formula (IIIc-2) of the present disclosure, the LIN represents —U—$C_{1-30}$ alkylene chain-, and the $C_{1-30}$ alkylene chain is optionally substituted by one or more substituents selected from hydroxyl, amino, mercapto, halogen or any combination thereof. In a sub-embodiment, the LIN represents —$(CH_2)_3$CH(OH)CH(OH)$(CH_2)_4$—.

In a sub-embodiment of the compound represented by formula (IIIc-1) or formula (IIIc-2) of the present disclosure, the LIN represents —U—$C_{2-40}$ alkylene- (preferably, —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In a sub-embodiment of the compound represented by formula (IIIc-1) or formula (IIIc-2) of the present disclosure, the LIN represents —U-alkylene-, the alkylene (preferably $C_1$-30 alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents C(O), or the group U is absent.

In a sub-embodiment of the compound represented by formula (IIIc-1) or formula (IIIc-2) of the present disclosure, the LIN represents —U—$C_{1-30}$ alkylene-, and the $C_{1-30}$ alkylene is a linear or branched $C_{1-30}$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In a sub-embodiment of the compound of the present disclosure represented by formula (IIIc-1) or formula (IIIc-2), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIc-1) or formula (IIIc-2), the LIN represents —U—$CH_2$C(O)NH$CH_2$—, —U—$CH_2$C(O)NH$(CH_2)_2$—, —U—$CH_2$C(O)NH$(CH_2)_3$—, —U—$CH_2$C(O)NH$(CH_2)_4$—, —U—$CH_2$C(O)NH$(CH_2)_5$—, —U—$CH_2$C(O)NH$(CH_2)_6$—, —U—$CH_2$C(O)NH$(CH_2)_2$—, —U—$CH_2$C(O)NH$(CH_2)_8$—, —U—$CH_2$C(O)NH$(CH_2)_9$—, —U—$CH_2$C(O)NH$(CH_2)_{10}$—, —U—$(CH_2)_2$C(O)NH$CH_2$—, —U—$(CH_2)_2$C(O)NH$(CH_2)_2$—, —U—$(CH_2)_2$C(O)NH$(CH_2)_3$—, —U—$(CH_2)_2$C(O)NH$(CH_2)_4$—, —U—$(CH_2)_2$C(O)NH$(CH_2)_5$—, —U—$(CH_2)_2$C(O)NH$(CH_2)_6$—, —U—$(CH_2)_2$C(O)NH$(CH_2)_7$—, —U—$(CH_2)_2$C(O)NH$(CH_2)_8$—, —U—$(CH_2)_3$C(O)NH$CH_2$—, —U—$(CH_2)_3$C(O)NH$(CH_2)_2$—, —U—$(CH_2)_3$C(O)NH$(CH_2)_3$—, —U—$(CH_2)_3$C(O)NH$(CH_2)_4$—, —U—$(CH_2)_3$C(O)NH$(CH_2)_5$—, —U—$(CH_2)_3$C(O)NH$(CH_2)_6$—, —U—$(CH_2)_3$C(O)NH$(CH_2)_2$—, —U—$(CH_2)_3$C(O)NH$(CH_2)_8$—, —U—$(CH_2)_4$C(O)NH$CH_2$—, —U—$(CH_2)_4$C(O)NH$(CH_2)_2$—, —U—$(CH_2)_4$C(O)NH$(CH_2)_3$—, —U—$(CH_2)_4$C(O)NH$(CH_2)_4$—, —U—$(CH_2)_4$C(O)NH$(CH_2)_5$—, —U—$(CH_2)_4$C(O)NH$(CH_2)_6$—, —U—$(CH_2)_5$C(O)NH$CH_2$—, —U—$(CH_2)_5$C(O)NH$(CH_2)_2$—, —U—$(CH_2)_5$C(O)NH$(CH_2)_3$—, —U—$(CH_2)_5$C(O)NH$(CH_2)_4$—, —U—$(CH_2)_5$C(O)NH$(CH_2)_5$—, —U—$(CH_2)_5$C(O)NH$(CH_2)_6$—, —U—$(CH_2)_6$C(O)NH$CH_2$—, —U—$(CH_2)_6$C(O)NH$(CH_2)_2$—, —U—$(CH_2)_6$C(O)NH$(CH_2)_3$—, —U—$(CH_2)_6$C(O)NH$(CH_2)_4$—, —U—$(CH_2)_6$C(O)NH$(CH_2)_5$—, —U—$(CH_2)_6$C(O)NH$(CH_2)_6$—, —U—$(CH_2)_6$C(O)NH$(CH_2)_7$—, —U—$(CH_2)_7$C(O)NH$CH_2$—, —U—$(CH_2)_7$C(O)NH$(CH_2)_2$—, —U—$(CH_2)_7$C(O)NH$(CH_2)_3$—, —U—$(CH_2)_7$C(O)NH$(CH_2)_4$—, —U—$(CH_2)_7$C(O)NH$(CH_2)_8$—, —U—$(CH_2)_7$C(O)NH$(CH_2)_6$—, —U—$(CH_2)_7$C(O)NH$(CH_2)_7$—, —U—$(CH_2)_8$C(O)NH$CH_2$—, —U—$(CH_2)_8$C(O)NH$(CH_2)_2$—, —U—$(CH_2)_8$C(O)NH$(CH_2)_3$—, —U—$(CH_2)_8$C(O)NH$(CH_2)_4$—, —U—$(CH_2)_8$C(O)NH$(CH_2)_5$—, —U—$(CH_2)_8$C(O)NH$(CH_2)_6$—, —U—$(CH_2)_8$C(O)NH$(CH_2)_7$—, —U—$(CH_2)_8$C(O)NH$(CH_2)_8$—, —U—$(CH_2)_9$C(O)NH$CH_2$—, —U—$(CH_2)_9$C(O)NH$(CH_2)_2$—, —U—$(CH_2)_9$C(O)NH$(CH_2)_3$—, —U—$(CH_2)_9$C(O)NH$(CH_2)_4$—, —U—$(CH_2)_9$C(O)NH$(CH_2)_5$—, —U—$(CH_2)_9$C(O)NH$(CH_2)_6$—, —U—$(CH_2)_9$C(O)NH$(CH_2)_7$—, —U—

$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—; wherein the group U represents C(O), or the group U is absent.

In a sub-embodiment of the compound of the present disclosure represented by formula (IIIc-1) or formula (IIIc-2), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIc-1) or formula (IIIc-2), the LIN represents —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—$(CH_2)_8NHC(O)(CH_2)_8$—, —U—$(CH_2)_9NHC(O)CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—; wherein the group U represents C(O), or the group U is absent.

In a sub-embodiment of the compound of the present disclosure represented by formula (IIIc-1) or formula (IIIc-2), the LIN represents —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents C(O), or the group U is absent.

In a sub-embodiment of the compound of the present disclosure represented by formula (IIIc-1) or formula (IIIc-2), the LIN represents —U—$(CH_2)_{n1}$—CH=CH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIc-1) or formula (IIIc-2), the LIN represents —U—CH$_2$CH=CHCH$_2$—, —U—CH$_2$CH=CH(CH$_2$)$_2$—, —U—CH$_2$CH=CH(CH$_2$)$_3$—, —U—CH$_2$CH=CH(CH$_2$)$_4$—, —U—CH$_2$CH=CH(CH$_2$)$_5$—, —U—CH$_2$CH=CH(CH$_2$)$_6$—, —U—CH$_2$CH=CH(CH$_2$)$_7$—, —U—CH$_2$CH=CH(CH$_2$)$_8$—, —U—CH$_2$CH=CH(CH$_2$)$_9$—, —U—CH$_2$CH=CH(CH$_2$)$_{10}$—, —U—(CH$_2$)$_2$CH=CHCH$_2$—, —U—(CH$_2$)$_2$CH=CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, wherein the group U represents C(O), or the group U is absent.

In a sub-embodiment of the compound of the present disclosure represented by formula (IIIc-1), or formula (IIIc-2), the LIN represents: —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (IIIc-1) or formula (IIIc-2), the LIN represents —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, and wherein the group U represents C(O), or the group U is absent.

In a sub-embodiment of the compound of the present disclosure represented by formula (IIIc-1) or formula (IIIc-2), the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIc-1) or formula (IIIc-2), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (IIIc-1) or formula (IIIc-2), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIc-1) or formula (IIIc-2), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound represented by formula (IIIc-1) or formula (IIIc-2) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{n2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In a sub-embodiment of the compound of the present disclosure represented by formula (IIIc-1) or formula (IIIc-2), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (IIIc-1) or formula (IIIc-2), the LIN represents

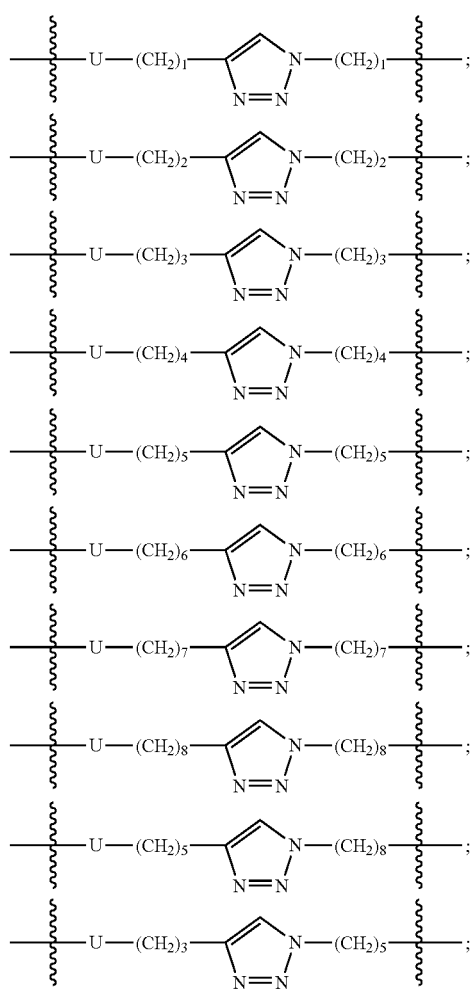

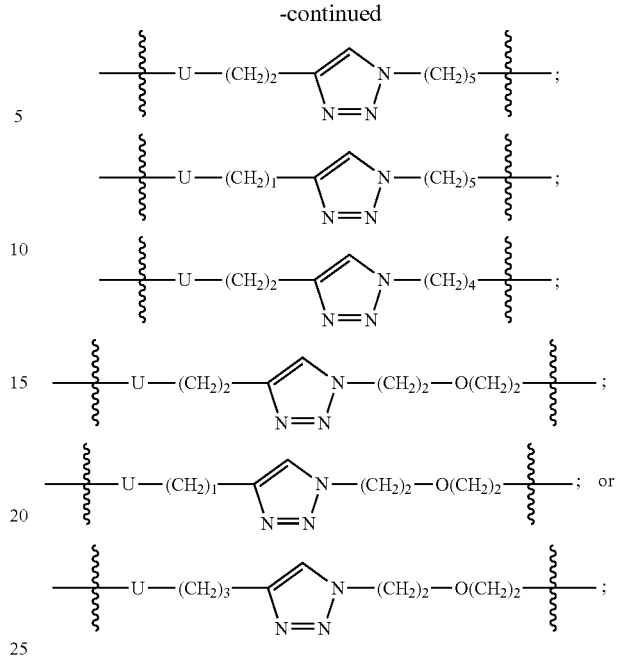

wherein the group U represents C(O), or the group U is absent.

In a sub-embodiment of the compound of the present disclosure represented by formula (IIIc-1) or formula (IIIc-2), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the compound represented by formula (III) of the present disclosure, the compound represented by formula (III) is also a compound represented by formula (IIId-1) or formula (IIId-2):

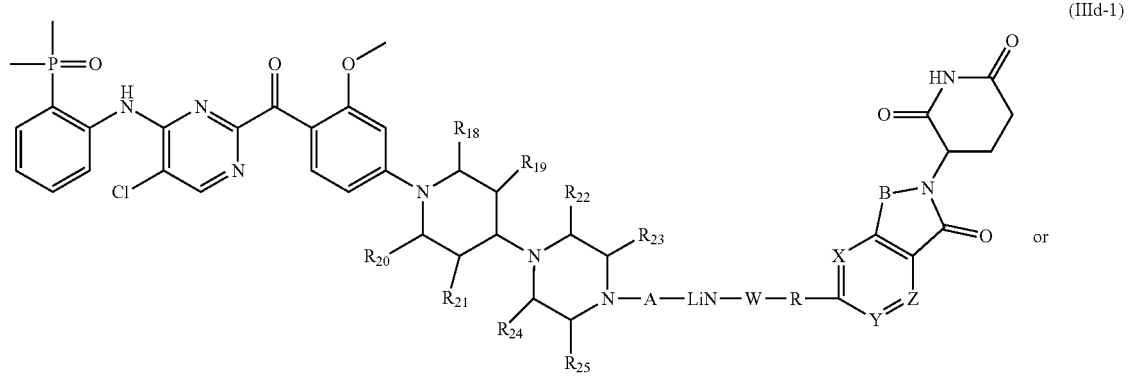

(IIId-1)

or

-continued (IIId-2)

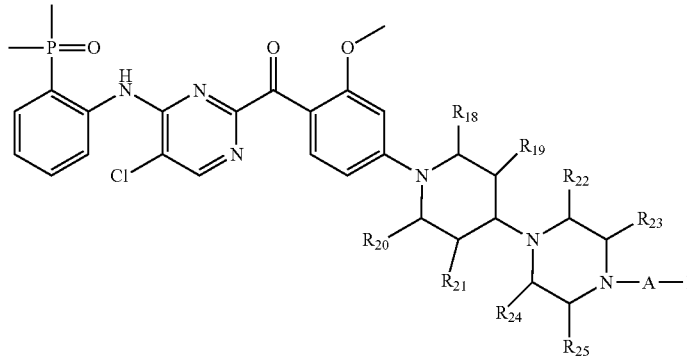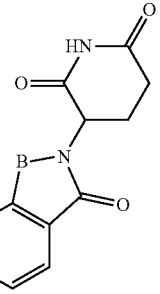

wherein, the groups LIN, A, W, R, $R_{18}$, $R_{19}$, $R_{20}$, $R_{21}$, $R_{22}$, $R_{23}$, $R_{24}$, $R_{25}$, and B, X, Y, Z are as defined herein.

In a sub-embodiment of the compound of the present disclosure represented by formula (IIId-1) or formula (IIId-2), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (IIId-1) or formula (IIId-2), the LIN represents —U—$C_{1-30}$ alkylene-, —U—$(CH_2)_{n1}$—$(C(O)NH—(CH_2)_{n2})_{m1}$—, —U—$(CH_2)_{n1}$—$(NHC(O)—(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$(C(O)NH—(CH_2)_{n2})_{m1}$—$(O(CH_2)_{n3})_{m2}$—, —U—$(CH_2)_{n1}$—$(O(CH_2)_{n2})_{m1}$—O—$(CH_2)_{n3}$—$C(O)NH—(CH_2)_{n4}$—$(O(CH_2)_{n5})_{m2}$—O—$(CH_2)_{n6}$—, —U—$(CR_{a11}R_{a12})_{n1}$—$(CR_{a13}R_{a14})_{n2})_{m2}$—$C(O)NH—(CR_{a15}R_{a16})_{n3}$—$C(O)NH—(CR_{a17}R_{a18})_{n4}$—$(O(CR_{a19}R_{a20})_{n5})_{m2}$—O—$(CR_{a21}R_{a22})_{n6}$—, —U—$(CR_{23}R_{24})_{n1}$—$C(O)NH—(O(CR_{25}R_{26})_{n2})_{m1}$—, —U—$(CH_2)_{n1}$—$(NHC(O)—(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound represented by formula (IIId-1) or formula (IIId-2) of the present disclosure, the LIN represents —U—$C_{1-30}$ alkylene-; and the group U represents C(O), or the group U is absent. In a sub-embodiment of the present disclosure, the LIN is preferably —U-methylene or —U—$C_{2-30}$ alkylene-, wherein the $C_{1-30}$ alkylene is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent. In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent. In a sub-embodiment, the group U represents C(O). In a sub-embodiment, the group U is absent.

In a sub-embodiment of the compound represented by formula (IIId-1) or formula (IIId-2) of the present disclosure, the LIN represents —U—$C_{2-40}$ alkylene-(preferably, —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In a sub-embodiment of the compound represented by formula (IIId-1) or formula (IIId-2) of the present disclosure, the LIN represents —U-alkylene-, the alkylene (preferably $C_{1-30}$ alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents C(O), or the group U is absent.

In a sub-embodiment of the compound represented by formula (IIId-1) or formula (IIId-2) of the present disclosure, the LIN represents —U—$C_{1-30}$ alkylene-, and the $C_{1-30}$ alkylene is a linear or branched $C_{1-30}$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In a sub-embodiment of the compound of the present disclosure represented by formula (IIId-1) or formula (IIId-2), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIId-1) or formula (IIId-2), the LIN represents —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—; wherein the group U represents C(O), or the group U is absent.

In a sub-embodiment of the compound of the present disclosure represented by formula (IIId-1) or formula (IIId-2), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIId-1) or formula (IIId-2), the LIN represents —U—$CH_2NHC(O)CH_2$—, —U—$CH_2NHC(O)(CH_2)_2$—, —U—$CH_2NHC(O)(CH_2)_3$—, —U—$CH_2NHC(O)(CH_2)_4$—, —U—$CH_2NHC(O)(CH_2)_5$—, —U—$CH_2NHC(O)(CH_2)_6$—, —U—$CH_2NHC(O)(CH_2)_7$—, —U—$CH_2NHC(O)(CH_2)_8$—, —U—$CH_2NHC(O)(CH_2)_9$—, —U—$CH_2NHC(O)(CH_2)_{10}$—, —U—$(CH_2)_2NHC(O)CH_2$—, —U—$(CH_2)_2NHC(O)(CH_2)_2$—, —U—$(CH_2)_2NHC(O)(CH_2)_3$—, —U—$(CH_2)_2NHC(O)(CH_2)_4$—, —U—$(CH_2)_2NHC(O)(CH_2)_5$—, —U—$(CH_2)_3NHC(O)CH_2$—, —U—$(CH_2)_3NHC(O)(CH_2)_2$—, —U—$(CH_2)_3NHC(O)(CH_2)_3$—, —U—$(CH_2)_3NHC(O)(CH_2)_4$—, —U—$(CH_2)_3NHC(O)(CH_2)_5$—, —U—$(CH_2)_4NHC(O)CH_2$—, —U—$(CH_2)_4NHC(O)(CH_2)_2$—, —U—$(CH_2)_4NHC(O)(CH_2)_3$—, —U—$(CH_2)_4NHC(O)(CH_2)_4$—, —U—$(CH_2)_4NHC(O)(CH_2)_5$—, —U—$(CH_2)_4NHC(O)(CH_2)_6$—, —U—$(CH_2)_4NHC(O)(CH_2)_7$—, —U—$(CH_2)_5NHC(O)CH_2$—, —U—$(CH_2)_5NHC(O)(CH_2)_2$—, —U—$(CH_2)_5NHC(O)(CH_2)_3$—, —U—$(CH_2)_5NHC(O)(CH_2)_4$—, —U—$(CH_2)_5NHC(O)(CH_2)_5$—, —U—$(CH_2)_5NHC(O)(CH_2)_6$—, —U—$(CH_2)_6NHC(O)CH_2$—, —U—$(CH_2)_6NHC(O)(CH_2)_2$—, —U—$(CH_2)_6NHC(O)(CH_2)_3$—, —U—$(CH_2)_6NHC(O)(CH_2)_4$—, —U—$(CH_2)_6NHC(O)(CH_2)_5$—, —U—$(CH_2)_6NHC(O)(CH_2)_6$—, —U—$(CH_2)_6NHC(O)(CH_2)_7$—, —U—$(CH_2)_7NHC(O)CH_2$—, —U—$(CH_2)_7NHC(O)(CH_2)_2$—, —U—$(CH_2)_7NHC(O)(CH_2)_3$—, —U—$(CH_2)_7NHC(O)(CH_2)_4$—, —U—$(CH_2)_7NHC(O)(CH_2)_5$—, —U—

$(CH_2)_7NHC(O)(CH_2)_6$—, —U—$(CH_2)_7NHC(O)(CH_2)_7$—, —U—$(CH_2)_8NHC(O)CH_2$—, —U—$(CH_2)_8NHC(O)(CH_2)_2$—, —U—$(CH_2)_8NHC(O)(CH_2)_3$—, —U—$(CH_2)_8NHC(O)(CH_2)_8$—, —U—$(CH_2)_9NHC(O)CH_2$—, —U—$(CH_2)_9NHC(O)(CH_2)_2$—, —U—$(CH_2)_9NHC(O)(CH_2)_3$—, —U—$(CH_2)_9NHC(O)(CH_2)_9$—, or —U—$(CH_2)_{10}NHC(O)(CH_2)_{10}$—; wherein the group U represents C(O), or the group U is absent.

In a sub-embodiment of the compound of the present disclosure represented by formula (IIId-1) or formula (IIId-2), the LIN represents —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(C_{142})_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents C(O), or the group U is absent.

In a sub-embodiment of the compound of the present disclosure represented by formula (IIId-1) or formula (IIId-2), the LIN represents —U—$(CH_2)_{n1}$—CH=CH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIId-1) or formula (IIId-2), the LIN represents —U—$CH_2CH=CHCH_2$—, —U—$CH_2CH=CH(CH_2)_2$—, —U—$CH_2CH=CH(CH_2)_3$—, —U—$CH_2CH=CH(CH_2)_4$—, —U—$CH_2CH=CH(CH_2)_5$—, —U—$CH_2CH=CH(CH_2)_6$—, —U—$CH_2CH=CH(CH_2)_7$—, —U—$CH_2CH=CH(CH_2)_8$—, —U—$CH_2CH=CH(CH_2)_9$—, —U—$CH_2CH=CH(CH_2)_{10}$—, —U—$(CH_2)_2CH=CHCH_2$—, —U—$(CH_2)_2CH=CH(CH_2)_2$—, —U—$(CH_2)_2CH=CH(CH_2)_3$—, —U—$(CH_2)_2CH=CH(CH_2)_4$—, —U—$(CH_2)_2CH=CH(CH_2)_5$—, —U—$(CH_2)_2CH=CH(CH_2)_6$—, —U—$(CH_2)_2CH=CH(CH_2)_7$—, —U—$(CH_2)_2CH=CH(CH_2)_8$—, —U—$(CH_2)_3CH=CHCH_2$—, —U—$(CH_2)_3CH=CH(CH_2)_2$—, —U—$(CH_2)_3CH=CH(CH_2)_3$—, —U—$(CH_2)_3CH=CH(CH_2)_4$—, —U—$(CH_2)_3CH=CH(CH_2)_5$—, —U—$(CH_2)_3CH=CH(CH_2)_6$—, —U—$(CH_2)_3C=CH(CH_2)_7$—, —U—$(CH_2)_4CH=CHCH_2$—, —U—$(CH_2)_4CH=CH(CH_2)_2$—, —U—$(CH_2)_4CH=CH(CH_2)_3$—, —U—$(CH_2)_4CH=CH(CH_2)_4$—, —U—$(CH_2)_4CH=CH(CH_2)_5$—, —U—$(CH_2)_5CH=CHCH_2$—, —U—$(CH_2)_5CH=CH(CH_2)_2$—, —U—$(CH_2)_5CH=CH(CH_2)_3$—, —U—$(CH_2)_5CH=CH(CH_2)_4$—, —U—$(CH_2)_5CH=CH(CH_2)_5$—, —U—$(CH_2)_6CH=CHCH_2$—, —U—$(CH_2)_6CH=CH(CH_2)_2$—, —U—$(CH_2)_6CH=CH(CH_2)_3$—, —U—$(CH_2)_7CH=CHCH_2$—, —U—$(CH_2)_7CH=CH(CH_2)_2$—, —U—$(CH_2)_7CH=CH(CH_2)_3$—, —U—$(CH_2)_8CH=CHCH_2$—, —U—$(CH_2)_8CH=CH(CH_2)_2$—, —U—$(CH_2)_8CH=CH(CH_2)_3$—, —U—$(CH_2)_9CH=CHCH_2$—U—$(CH_2)_9CH=CH(CH_2)_2$—, —U—$(CH_2)_9CH=CH(CH_2)_3$—, —U—$(CH_2)_{10}CH=CHCH_2$—, or —U—$(CH_2)_{10}CH=CH(CH_2)_2$—, and wherein the group U represents C(O), or the group U is absent.

In a sub-embodiment of the compound of the present disclosure represented by formula (IIId-1), or formula (IIId-2), the LIN represents: —U—$(CH_2)_{m1}$—C≡$(CH_2)_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (IIId-1), or formula (IIId-2), the LIN represents —U—CH$_2$C≡CCH$_2$—, —U—CH$_2$C≡C(CH$_2$)$_2$—, —U—CH$_2$C≡C(CH$_2$)$_3$—, —U—CH$_2$C≡C(CH$_2$)$_4$—, —U—CH$_2$CC(CH$_2$)$_5$—, —U—CH$_2$C≡C(CH$_2$)$_6$—, —U—CH$_2$C≡C(CH$_2$)$_7$—, —U—CH$_2$C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$CCCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, wherein the group U represents C(O), or the group U is absent.

In a sub-embodiment of the compound of the present disclosure represented by formula (IIId-1) or formula (IIId-2), the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIId-1) or formula (IIId-2), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_2$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (IIId-1) or formula (IIId-2), the LIN represents —U—(CH$_2$)$_{m1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIId-1) or formula (IIId-2), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound represented by formula (IIId-1) or formula (IIId-2) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O (CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O (CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In a sub-embodiment of the compound of the present disclosure represented by formula (IIId-1) or formula (IIId-2), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (IIId-1) or formula (IIId-2) the LIN represents

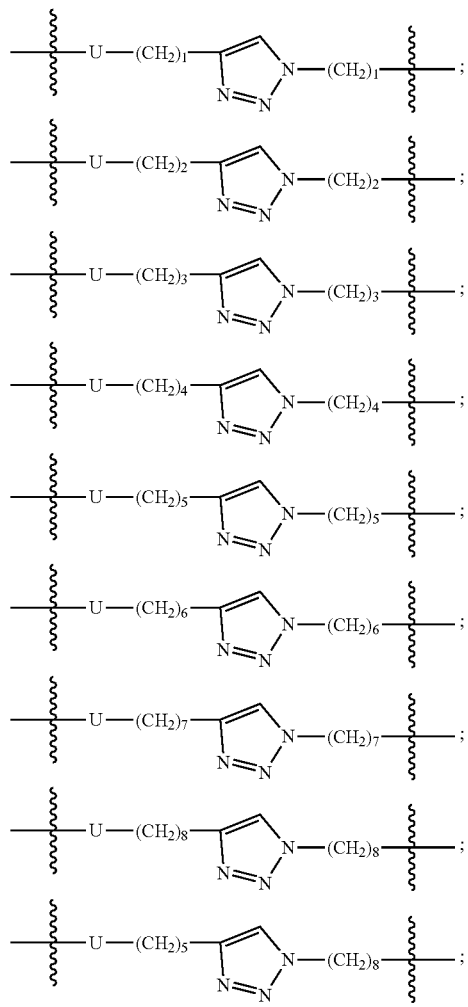

-continued

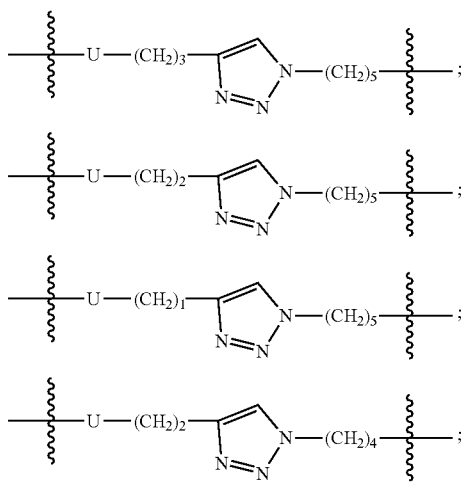

wherein the group U represents C(O), or the group U is absent.

In a sub-embodiment of the compound of the present disclosure represented by formula (IIId-1) or formula (IIId-2), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the compound represented by formula (III) of the present disclosure, the compound represented by formula (III) is also a compound represented by formula (IIIe-1) or formula (IIIe-2):

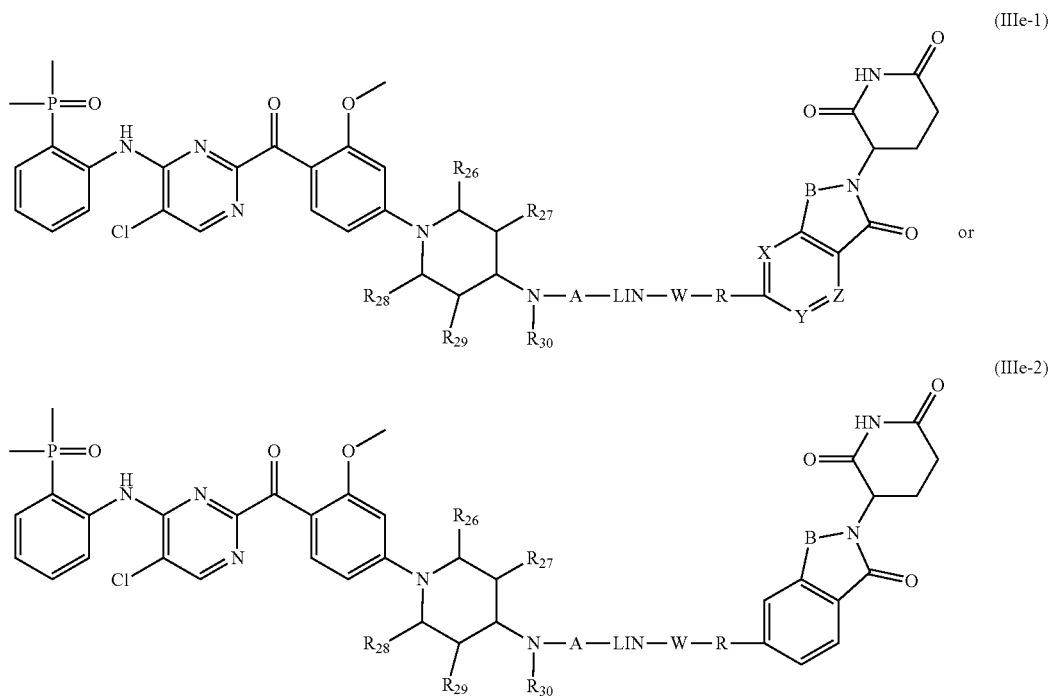

wherein, the groups LIN, A, W, R, R$_{26}$, R$_{27}$, R$_{28}$, R$_{29}$, R$_{30}$, and B, X, Y, Z are as defined herein.

In a sub-embodiment of the compound of the present disclosure represented by formula (IIIe-1) or formula (IIIe-2), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (IIIe-1) or formula (IIIe- -continued

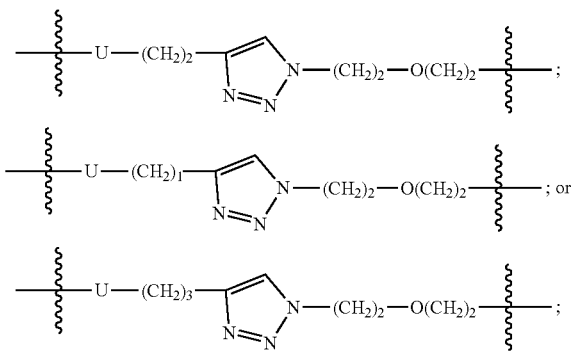

2), the LIN represents —U—$C_{1-30}$ alkylene-, —U—$(CH_2)_{n1}$—C(O)NH—$(CH_2)_{n2})_{m1}$—, —U—$(CH_2)_{n1}$—(NHC(O)—$(CH_2)_{n2})_{m1}$—, —U—$(CH_2)_{n1}$—(O($CH_2)_{n2})_{m1}$—, —U—$(CH_2)_{n1}$—(O($CH_2)_{n2})_{m1}$—(O($CH_2)_{n3})_{m2}$—, —U—$(CR_{a1}R_{a2})_{n1}$—(O($CR_{a3}R_{a4})_{n2})_{m1}$—, —U—$(CR_{a5}R_{a6})_{n1}$—(O($CR_{a7}R_{a8})_{n2})_{m1}$—(O($CR_{a9}R_{a10})_{n3})_{m2}$—, —U—$(CH_2)_{n1}$—C(O)NH—$(CH_2)_{n2})_{m1}$—(O($CH_2)_{n3})_{m2}$—, —U—$(CH_2)_{n1}$—(O($CH_2)_{n2})_{m1}$—O—$(CH_2)_{n3}$—C(O)NH—$(CH_2)_{n4}$—(O($CH_2)_{n5})_{m2}$—O—$(CH_2)_{n6}$—, —U—$(CR_{a11}R_{a12})_{n1}$—($CR_{a13}R_{a14})_{n2})_{m2}$—C(O)NH—$(CR_{a15}R_{a16})_{n3}$—C(O)NH—$(CR_{a17}R_{a18})_{n4}$—(O($CR_{a19}R_{a20})_{n5})_{m2}$—O—$(CR_{a21}R_{a22})_{n6}$—, —U—$(CR_{23}R_{24})_{n1}$—C(O)NH—(O($CR_{25}R_{26})_{n2})_{m1}$—, —U—$(CH_2)_{n1}$—(NHC(O)—$(CH_2)_{n2})_{m1}$—(O($CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—(O($CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound represented by formula (IIIe-1) or formula (IIIe-2) of the present disclosure, the LIN represents —U—$C_{1-30}$ alkylene-; and the group U represents C(O), or the group U is absent. In a sub-embodiment of the present disclosure, the LIN is preferably —U-methylene or —U—$C_{2-30}$ alkylene-, wherein the $C_{2-30}$ alkylene is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_5$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent. In a sub-embodiment, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent. In a sub-embodiment, the group U represents C(O). In a sub-embodiment, the group U is absent.

In a sub-embodiment of the compound represented by formula (IIIe-1) or formula (IIIe-2) of the present disclosure, the LIN represents —U—$C_{2-40}$ alkylene- (e.g. —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In a sub-embodiment of the compound represented by formula (IIIe-1) or formula (IIIe-2) of the present disclosure, the LIN represents —U-alkylene-, the alkylene (preferably $C_{1-30}$ alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof wherein the group U represents C(O), or the group U is absent.

In a sub-embodiment of the compound represented by formula (IIIe-1) or formula (IIIe-2) of the present disclosure, the LIN represents —U—$C_{1-30}$ alkylene-, and the $C_{1-30}$ alkylene is a linear or branched $C_{1-30}$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In a sub-embodiment of the compound of the present disclosure represented by formula (IIIe-1) or formula (IIIe-2), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIe-1) or formula (IIIe- 2), the LIN represents —U—CH$_2$C(O)NHCH$_2$—, —U—CH$_2$C(O)NH(CH$_2$)$_2$—, —U—CH$_2$C(O)NH(CH$_2$)$_3$—, —U—CH$_2$C(O)NH(CH$_2$)$_4$—, —U—CH$_2$C(O)NH(CH$_2$)$_5$—, —U—CH$_2$C(O)NH(CH$_2$)$_6$—, —U—CH$_2$C(O)NH(CH$_2$)$_7$—, —U—CH$_2$C(O)NH(CH$_2$)$_8$—, —U—CH$_2$C(O)NH(CH$_2$)$_9$—, —U—CH$_2$C(O)NH(CH$_2$)$_{10}$—, —U—(CH$_2$)$_2$C(O)NHCH$_2$—, —U—(CH$_2$)$_2$C(O)NH(CH$_2$)$_2$—, —U—(CH$_2$)$_2$C(O)NH(CH$_2$)$_3$—, —U—(CH$_2$)$_2$C(O)NH(CH$_2$)$_4$—, —U—(CH$_2$)$_2$C(O)NH(CH$_2$)$_5$—, —U—(CH$_2$)$_2$C(O)NH(CH$_2$)$_6$—, —U—(CH$_2$)$_2$C(O)NH(CH$_2$)$_7$—, —U—(CH$_2$)$_2$C(O)NH(CH$_2$)$_8$—, —U—(CH$_2$)$_3$C(O)NHCH$_2$—, —U—(CH$_2$)$_3$C(O)NH(CH$_2$)$_2$—, —U—(CH$_2$)$_3$C(O)NH(CH$_2$)$_3$—, —U—(CH$_2$)$_3$C(O)NH(CH$_2$)$_4$—, —U—(CH$_2$)$_3$C(O)NH(CH$_2$)$_5$—, —U—(CH$_2$)$_3$C(O)NH(CH$_2$)$_6$—, —U—(CH$_2$)$_3$C(O)NH(CH$_2$)$_7$—, —U—(CH$_2$)$_3$C(O)NH(CH$_2$)$_8$—, —U—(CH$_2$)$_4$C(O)NHCH$_2$—, —U—(CH$_2$)$_4$C(O)NH(CH$_2$)$_2$—, —U—(CH$_2$)$_4$C(O)NH(CH$_2$)$_3$—, —U—(CH$_2$)$_4$C(O)NH(CH$_2$)$_4$—, —U—(CH$_2$)$_4$C(O)NH(CH$_2$)$_5$—, —U—(CH$_2$)$_4$C(O)NH(CH$_2$)$_6$—, —U—(CH$_2$)$_5$C(O)NHCH$_2$—, —U—(CH$_2$)$_5$C(O)NH(CH$_2$)$_2$—, —U—(CH$_2$)$_5$C(O)NH(CH$_2$)$_3$—, —U—(CH$_2$)$_5$C(O)NH(CH$_2$)$_4$—, —U—(CH$_2$)$_5$C(O)NH(CH$_2$)$_5$—, —U—(CH$_2$)$_5$C(O)NH(CH$_2$)$_6$—, —U—(CH$_2$)$_6$C(O)NHCH$_2$—, —U—(CH$_2$)$_6$C(O)NH(CH$_2$)$_2$—, —U—(CH$_2$)$_6$C(O)NH(CH$_2$)$_3$—, —U—(CH$_2$)$_6$C(O)NH(CH$_2$)$_4$—, —U—(CH$_2$)$_6$C(O)NH(CH$_2$)$_5$—, —U—(CH$_2$)$_6$C(O)NH(CH$_2$)$_6$—, —U—(CH$_2$)$_6$C(O)NH(CH$_2$)$_7$—, —U—(CH$_2$)$_7$C(O)NHCH$_2$—, —U—(CH$_2$)$_7$C(O)NH(CH$_2$)$_2$—, —U—(CH$_2$)$_7$C(O)NH(CH$_2$)$_3$—, —U—(CH$_2$)$_7$C(O)NH(CH$_2$)$_4$—, —U—(CH$_2$)$_7$C(O)NH(CH$_2$)$_5$—, —U—(CH$_2$)$_7$C(O)NH(CH$_2$)$_6$—, —U—(CH$_2$)$_7$C(O)NH(CH$_2$)$_7$—, —U—(CH$_2$)$_8$C(O)NHCH$_2$—, —U—(CH$_2$)$_8$C(O)NH(CH$_2$)$_2$—, —U—(CH$_2$)$_8$C(O)NH(CH$_2$)$_3$—, —U—(CH$_2$)$_8$C(O)NH(CH$_2$)$_4$—, —U—(CH$_2$)$_8$C(O)NH(CH$_2$)$_5$—, —U—(CH$_2$)$_8$C(O)NH(CH$_2$)$_6$—, —U—(CH$_2$)$_8$C(O)NH(CH$_2$)$_7$—, —U—(CH$_2$)$_8$C(O)NH(CH$_2$)$_8$—, —U—(CH$_2$)$_9$C(O)NHCH$_2$—, —U—(CH$_2$)$_9$C(O)NH(CH$_2$)$_2$—, —U—(CH$_2$)$_9$C(O)NH(CH$_2$)$_3$—, —U—(CH$_2$)$_9$C(O)NH(CH$_2$)$_4$—, —U—(CH$_2$)$_9$C(O)NH(CH$_2$)$_5$—, —U—(CH$_2$)$_9$C(O)NH(CH$_2$)$_6$—, —U—(CH$_2$)$_9$C(O)NH(CH$_2$)$_7$—, —U—(CH$_2$)$_9$C(O)NH(CH$_2$)$_8$—, —U—(CH$_2$)$_9$C(O)NH(CH$_2$)$_9$—, —U—(CH$_2$)$_{10}$C(O)NHCH$_2$—, —U—(CH$_2$)$_{10}$C(O)NH(CH$_2$)$_2$—, —U—(CH$_2$)$_{10}$C(O)NH(CH$_2$)$_3$—, —U—(CH$_2$)$_{10}$C(O)NH(CH$_2$)$_4$—, —U—(CH$_2$)$_{10}$C(O)NH(CH$_2$)$_5$— or —U—(CH$_2$)$_{10}$C(O)NH(CH$_2$)$_{10}$—; wherein the group U represents C(O), or the group U is absent.

In a sub-embodiment of the compound of the present disclosure represented by formula (IIIe-1) or formula (IIIe-2), the LIN represents —U—(CH$_2$)$_{n1}$—NHC(O)—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIe-1) or formula (IIIe-2), the LIN represents —U—CH$_2$NHC(O)CH$_2$—, —U—CH$_2$NHC(O)(CH$_2$)$_2$—, —U—CH$_2$NHC(O)(CH$_2$)$_3$—, —U—CH$_2$NHC(O)(CH$_2$)$_4$—, —U—CH$_2$NHC(O)(CH$_2$)$_5$—, —U—CH$_2$NHC(O)(CH$_2$)$_6$—, —U—CH$_2$NHC(O)(CH$_2$)$_7$—, —U—CH$_2$NHC(O)(CH$_2$)$_8$—, —U—CH$_2$NHC(O)(CH$_2$)$_9$—, —U—CH$_2$NHC(O)(CH$_2$)$_{10}$—, —U—(CH$_2$)$_2$NHC(O)CH$_2$—, —U—(CH$_2$)$_2$NHC(O)(CH$_2$)$_2$—, —U—(CH$_2$)$_2$NHC(O)(CH$_2$)$_3$—, —U—(CH$_2$)$_2$NHC(O)(CH$_2$)$_4$—, —U—(CH$_2$)$_2$NHC(O)(CH$_2$)$_5$—, —U—(CH$_2$)$_3$NHC(O)CH$_2$—, —U—(CH$_2$)$_3$NHC(O)(CH$_2$)$_2$—, —U—(CH$_2$)$_3$NHC(O)(CH$_2$)$_3$—, —U—(CH$_2$)$_3$NHC(O)(CH$_2$)$_4$—, —U—(CH$_2$)$_3$NHC(O)(CH$_2$)$_5$—, —U—(CH$_2$)$_4$NHC(O)CH$_2$—, —U—(CH$_2$)$_4$NHC(O)(CH$_2$)$_2$—, —U—(CH$_2$)$_4$NHC(O)(CH$_2$)$_3$—, —U—(CH$_2$)$_4$NHC(O)(CH$_2$)$_4$—, —U—(CH$_2$)$_4$NHC(O)(CH$_2$)$_5$—, —U—(CH$_2$)$_4$NHC(O)(CH$_2$)$_6$—, —U—(CH$_2$)$_4$NHC(O)(CH$_2$)$_7$—, —U—(CH$_2$)$_5$NHC(O)CH$_2$—, —U—(CH$_2$)$_5$NHC(O)(CH$_2$)$_2$—, —U—(CH$_2$)$_5$NHC(O)(CH$_2$)$_3$—, —U—(CH$_2$)$_5$NHC(O)(CH$_2$)$_4$—, —U—(CH$_2$)$_5$NHC(O)(CH$_2$)$_5$—, —U—(CH$_2$)$_5$NHC(O)(CH$_2$)$_6$—, —U—(CH$_2$)$_6$NHC(O)CH$_2$—, —U—(CH$_2$)$_6$NHC(O)(CH$_2$)$_2$—, —U—(CH$_2$)$_6$NHC(O)(CH$_2$)$_3$—, —U—(CH$_2$)$_6$NHC(O)(CH$_2$)$_4$—, —U—(CH$_2$)$_6$NHC(O)(CH$_2$)$_5$—, —U—(CH$_2$)$_6$NHC(O)(CH$_2$)$_6$—, —U—(CH$_2$)$_6$NHC(O)(CH$_2$)$_7$—, —U—(CH$_2$)$_7$NHC(O)CH$_2$—, —U—(CH$_2$)$_7$NHC(O)(CH$_2$)$_2$—, —U—(CH$_2$)$_7$NHC(O)(CH$_2$)$_3$—, —U—(CH$_2$)$_7$NHC(O)(CH$_2$)$_4$—, —U—(CH$_2$)$_7$NHC(O)(CH$_2$)$_5$—, —U—(CH$_2$)$_7$NHC(O)(CH$_2$)$_6$—, —U—(CH$_2$)$_7$NHC(O)(CH$_2$)$_7$—, —U—(CH$_2$)$_8$NHC(O)CH$_2$—, —U—(CH$_2$)$_8$NHC(O)(CH$_2$)$_2$—, —U—(CH$_2$)$_8$NHC(O)(CH$_2$)$_3$—, —U—(CH$_2$)$_8$NHC(O)(CH$_2$)$_8$—, —U—(CH$_2$)$_9$NHC(O)CH$_2$—, —U—(CH$_2$)$_9$NHC(O)(CH$_2$)$_2$—, —U—(CH$_2$)$_9$NHC(O)(CH$_2$)$_3$—, —U—(CH$_2$)$_9$NHC(O)(CH$_2$)$_9$—, or —U—(CH$_2$)$_{10}$NHC(O)(CH$_2$)$_{10}$—; wherein the group U represents C(O), or the group U is absent.

In a sub-embodiment of the compound of the present disclosure represented by formula (IIIe-1) or formula (IIIe-2), the LIN represents —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—C$_{112}$—(O(CH$_2$)$_2$)$_9$—, —U—C$_{112}$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_7$—, —U—(CH$_2$)$_4$—(O(CH$_2$)$_2$)$_6$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_7$—, —U—(CH$_2$)$_2$—(O(CH$_2$)$_3$)$_8$—, —U—(CH$_2$)$_2$—(O(CH$_2$)$_9$—, —U—(CH$_2$)$_2$)$_3$, —(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —O—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —O—(CH$_2$)$_3$—(O(CH$_2$)$_3$)$_{10}$—, —O—CH$_2$—O—(CH$_2$)$_2$—O—

$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2)_3$—, —U—$(CH_2)_2$—$(O(CH_2)_2)_2$—$(O(CH_2)_3)_2$—, —U—$(CH_2)_2$—$(O(CH_2)_3)_2$—, —U—$(CH_2)_2$—$(O(CH_2)_2)_3$—, —U—$(CH_2)_2$—$(O(CH_2)_3)_3$—, —U—$(CH_2)_2$—$(O(CH_2)_2)_4$—, —U—$(CH_2)_2$—$(O(CH_2)_3)_4$—, —U—$(CH_2)_2$—$(O(CH_2)_2)_5$—, —U—$(CH_2)_2$—$(O(CH_2)_3)_5$—, —U—$(CH_2)_2$—$(O(CH_2)_2)_6$—, —U—$(CH_2)_2$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, $(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_2$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —O—$(CH_2)_3$—$(O(CH_2)_2)_2$—O—$(CH_2)_5$—, or —U—$(CH_2)_5$—$(O(CH_2)_2)_2$—O—$(CH_2)_6$—; wherein the group U represents C(O), or the group U is absent.

In a sub-embodiment of the compound of the present disclosure represented by formula (IIIe-1) or formula (IIIe-2), the LIN represents —U—$(CH_2)_{n1}$—CH=CH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIe-1) or formula (IIIe-2), the LIN represents —U—$CH_2CH=CHCH_2$—, —U—$CH_2CH=CH(CH_2)_2$—, —U—$CH_2CH=CH(CH_2)_3$—, —U—$CH_2CH=CH(CH_2)_4$—, —U—$CH_2CH=CH(CH_2)_5$—, —U—$CH_2CH=CH(CH_2)_6$—, —U—$CH_2CH=CH(CH_2)_7$—, —U—$CH_2CH=CH(CH_2)_8$—, —U—$CH_2CH=CH(CH_2)_9$—, —U—$CH_2CH=CH(CH_2)_{10}$—, —U—$(CH_2)_2CH=CHCH_2$—, —U—$(CH_2)_2CH=CH(CH_2)_2$—, —U—$(CH_2)_2CH=CH(CH_2)_3$—, —U—$(CH_2)_2CH=CH(CH_2)_4$—, —U—$(CH_2)_2CH=CH(CH_2)_5$—, —U—$(CH_2)_2CH=CH(CH_2)_6$—, —U—$(CH_2)_2CH=CH(CH_2)_7$—, —U—$(CH_2)_2CH=CH(CH_2)_8$—, —U—$(CH_2)_3CH=CHCH_2$—, —U—$(CH_2)_3C=CH(CH_2)_2$—, —U—$(CH_2)_3CH=CH(CH_2)_3$—, —U—$(CH_2)_3CH=CH(CH_2)_4$—, —U—$(CH_2)_3CH=CH(CH_2)_5$—, —U—$(CH_2)_3CH=CH(CH_2)_6$—, —U—$(CH_2)_3CH=CH(CH_2)_7$—, —U—$(CH_2)_4CH=CHCH_2$—, —U—$(CH_2)_4CH=CH(CH_2)_2$—, —U—$(CH_2)_4CH=CH(CH_2)_3$—, —U—$(CH_2)_4CH=CH(CH_2)_4$—, —U—$(CH_2)_4CH=CH(CH_2)_5$—, —U—$(CH_2)_5CH=CHCH_2$—, —U—$(CH_2)_5CH=CH(CH_2)_2$—, —U—$(CH_2)_5CH=CH(CH_2)_3$—, —U—$(CH_2)_5CH=CH(CH_2)_4$—, —U—$(CH_2)_5CH=CH(CH_2)_5$—, —U—$(CH_2)_6CH=CHCH_2$—, —U—$(CH_2)_6CH=CH(CH_2)_2$—, —U—$(CH_2)_6CH=CH(CH_2)_3$—, —U—$(CH_2)_7CH=CHCH_2$—, —U—$(CH_2)_7CH=CH(CH_2)_2$—, —U—$(CH_2)_7CH=CH(CH_2)_3$—, —U—$(CH_2)_8CH=CHCH_2$—, —U—$(CH_2)_8CH=CH(CH_2)_2$—, —U—$(CH_2)_8CH=CH(CH_2)_3$—, —U—$(CH_2)_9CH=CHCH_2$—U—$(CH_2)_9CH=CH(CH_2)_2$—, —U—$(CH_2)_9CH=CH(CH_2)_3$—, —U—$(CH_2)_{10}CH=CHCH_2$—, or —U—$(CH_2)_{10}CH=CH(CH_2)_2$—, wherein the group U represents C(O), or the group U is absent.

In a sub-embodiment of the compound of the present disclosure represented by formula (IIIe-1), or formula (IIIe-2), the LIN represents: —U—$(CH_2)_{n1}$—C≡C—$(CH_2)_{n2}$— or —U—$(CH_2)_{n1}$—C≡C—C≡C—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (IIIe-1), or formula (IIIe-2), the LIN represents —U—$CH_2C≡CCH_2$—, —U—$CH_2C≡C(CH_2)_2$—, —U—$CH_2CC(CH_2)_3$—, —U—$CH_2C≡C(CH_2)_4$—, —U—$CH_2C≡C(CH_2)_5$—, —U—$CH_2C≡C(CH_2)_6$—, —U—$CH_2C≡C(CH_2)_7$—, —U—$CH_2C≡C(CH_2)_8$—, —U—$CH_2C≡C(CH_2)_9$—, —U—$CH_2C≡C(CH_2)_{10}$—, —U—$(CH_2)_2C≡CCH_2$—, —U—$(CH_2)_2C≡C(CH_2)_2$—, —U—$(CH_2)_2C≡C(CH_2)_3$—, —U—$(CH_2)_2C≡C(CH_2)_4$—, —U—$(CH_2)_2C≡C(CH_2)_5$—, —U—$(CH_2)_2C≡C(CH_2)_6$—, —U—$(CH_2)_2C≡C(CH_2)_7$—, —U—$(CH_2)_2C≡C(CH_2)_8$—, —U—$(CH_2)_3C≡CCH_2$—, —U—$(CH_2)_3C≡C(CH_2)_2$—, —U—$(CH_2)_3C≡C(CH_2)_3$—, —U—$(CH_2)_3C≡C(CH_2)_4$—, —U—$(CH_2)_3C≡C(CH_2)_5$—, —U—$(CH_2)_3C≡C(CH_2)_6$—, —U—$(CH_2)_3C≡C(CH_2)_7$—, —U—$(CH_2)_4C≡CCH_2$—, —U—$(CH_2)_4C≡C(CH_2)_2$—, —U—$(CH_2)_4C≡C(CH_2)_3$—, —U—$(CH_2)_4C≡C(CH_2)_4$—, —U—$(CH_2)_4C≡C(CH_2)_5$—, —U—$(CH_2)_5C≡CCH_2$—, —U—$(CH_2)_5C≡C(CH_2)_2$—, —U—$(CH_2)_5C≡C(CH_2)_3$—, —U—$(CH_2)_5C≡C(CH_2)_4$—, —U—$(CH_2)_5C≡C(CH_2)_5$—, —U—$(CH_2)_6C≡CCH_2$—, —U—$(CH_2)_6C≡C(CH_2)_2$—, —U—$(CH_2)_6C≡C(CH_2)_3$—, —U—$(CH_2)_7C≡CCH_2$—, —U—$(CH_2)_7C≡C(CH_2)_2$—, —U—$(CH_2)_7C≡C(CH_2)_3$—, —U—$(CH_2)_8C≡CCH_2$—, —U—$(CH_2)_8C≡C(CH_2)_2$—, —U—$(CH_2)_8C≡C(CH_2)_3$—, —U—$(CH_2)_9C≡CCH_2$—U—$(CH_2)_9C≡C(CH_2)_2$—, —U—$(CH_2)_9C≡C(CH_2)_3$—, —U—$(CH_2)_{10}C≡CCH_2$—, or —U—$(CH_2)_{10}C≡C(CH_2)_2$—, wherein the group U represents C(O), or the group U is absent.

In a sub-embodiment of the compound of the present disclosure represented by formula (IIIe-1) or formula (IIIe-2), the LIN represents —U—$(CH_2)_{n1}$-piperazinylidene-$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIe-1) or formula (IIIe-2), the LIN represents: —U—$CH_2$-piperaziinylidene-$CH_2$—, —U—$(CH_2)_2$-piperaziinylidene-$(CH_2)_2$—, —U—$(CH_2)_3$-piperaziinylidene-$(CH_2)_3$—, —U—$(CH_2)_2$-piperaziinylidene-$(CH_2)_3$—, —U—$CH_2$-piperaziinylidene-$(CH_2)_2$—, —U—$CH_2$-piperaziinylidene-$(CH_2)_3$— or —U—$(CH_2)_2$-piperaziinylidene-$(CH_2)_3$—, wherein the group U represents C(O), or the group U is absent.

In a sub-embodiment of the compound of the present disclosure represented by formula (IIIe-1) or formula (IIIe- 2), the LIN represents —U—(CH$_2$)$_{b1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIe-1) or formula (IIIe-2), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound represented by formula (IIIe-1) or formula (IIIe-2) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{n4}$— or —U—(CH$_2$)$_{n1}$—(O(CH$_2$)$_{n2}$)$_{m1}$—O—(CH$_2$)$_{n3}$-triazolylidene-(CH$_2$)$_{m1}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In a sub-embodiment of the compound of the present disclosure represented by formula (IIIe-1) or formula (IIIe-2), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —

U—(CH$_2$)$_2$-triazolylidene-(CH$_2$)$_4$—, —U—(CH$_2$)$_3$-triazolylidene-(CH$_2$)$_2$—O(CH$_2$)$_2$—, —U—(CH$_2$)$_2$-triazolylidene-(CH$_2$)$_2$—O(CH$_2$)$_2$— or —

U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (IIIe-1) or formula (IIIe-2), the LIN represents

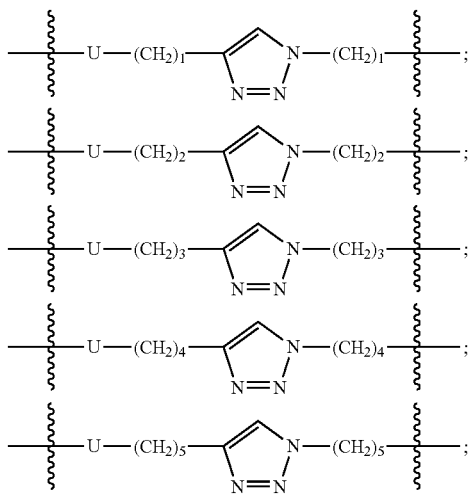

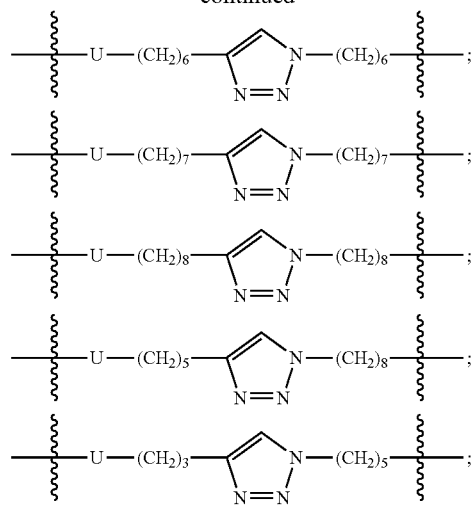

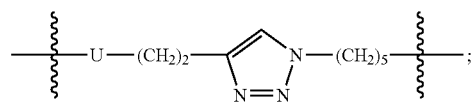

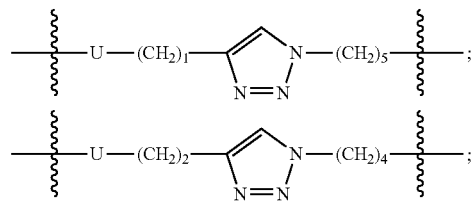

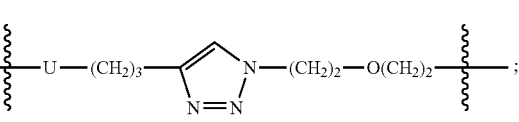

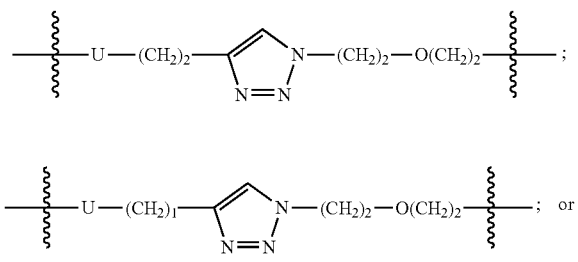

wherein the group U represents C(O), or the group U is absent.

In a sub-embodiment of the compound of the present disclosure represented by formula (IIIe-1) or formula (IIIe-2), the LIN represents —U—(CH$_2$)$_2$NHC(O)(CH$_2$)$_2$—O—(CH$_2$)$_2$— or —U—(CH$_2$)$_2$C(O)NH(CH$_2$)$_2$—O—(CH$_2$)$_2$—, wherein the group U represents C(O), or the group U is absent.

In an embodiment of the compound represented by formula (III) of the present disclosure, the compound represented by formula (III) is also a compound represented by formula (IIIf-1) or formula (IIIf-2):

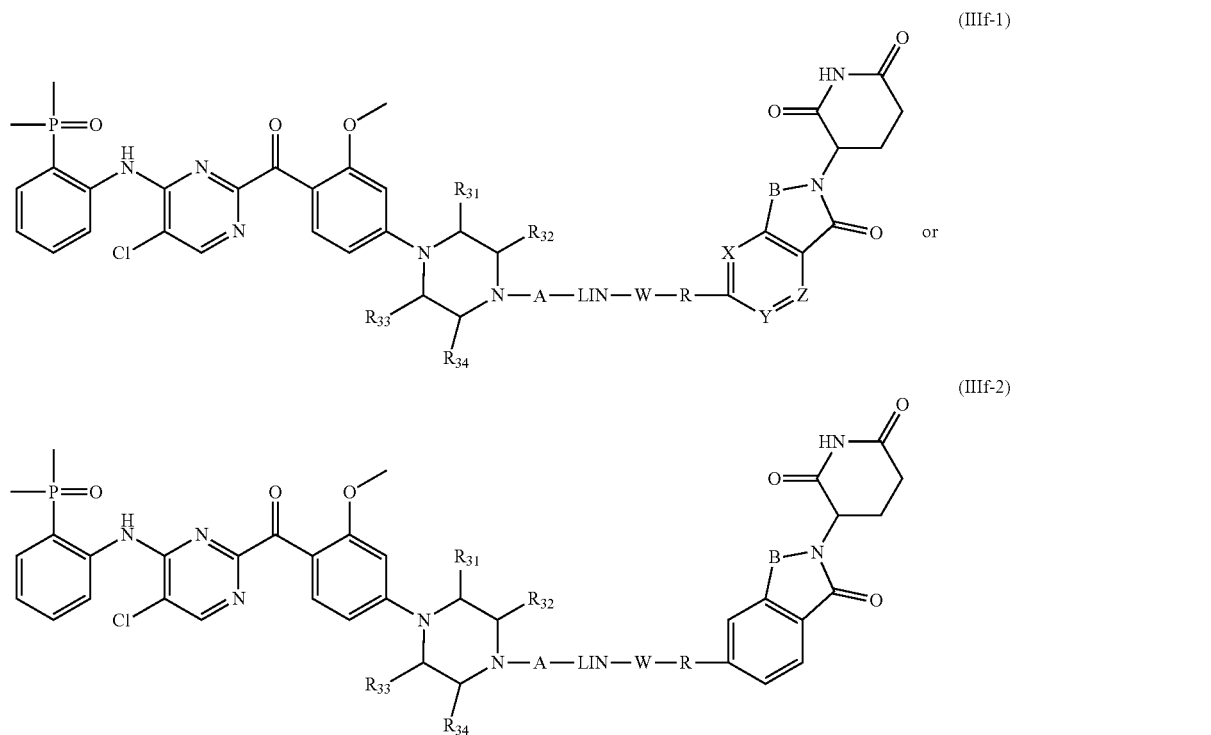

wherein, the groups LIN, A, W, R, $R_{31}$, $R_{32}$, $R_{33}$, $R_{34}$, and B, X, Y, Z are as defined herein.

In a sub-embodiment of the compound of the present disclosure represented by formula (IIIf-1) or formula (IIIf-2), the LIN represents —U-alkylene-, wherein the alkylene is linear or branched alkylene optionally interrupted one or more times (e.g. 1-20, 1-15, 1-10, 1-9, 1-8, 1-7, 1-6, 1-5, 1-4, 1-3 or 1-2 times, or 1 time) by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent.

In a sub-embodiment of the compound of the present disclosure represented by formula (IIIf-1) or formula (IIIf-2), the LIN represents —U—$C_{1-30}$ alkylene-, —U—$(CH_2)_{n1}$—$(C(O)NH$—$(CH_2)_{n2})_{m1}$—, —U—$(CH_2)_{n1}$—$(NHC(O)$—$(CH_2)_{n2})_{m1}$—, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—$(C(O)NH$—$(CH_2)_{n2})_{m1}$—$(O(CH_2)_{n3})_{m2}$—, —U—$(CH_2)_{n1}$—$(O(CH_2)_{n2})_{m1}$—$O$—$(CH_2)_{n3}$—$C(O)NH$—$(CH_2)_{n4}$—$(O(CH_2)_{n5})_{m2}$—$O$—$(CH_2)_{n6}$—, —U—$(CR_{a11}R_{a12})_{n1}$—$(CR_{a13}R_{a14})_{n2})_{m2}$—$C(O)NH$—$(CR_{a15}R_{a16})_{n3}$—$C(O)NH$—$(CR_{a17}R_{a18})_{n4}$—$(O(CR_{a19}R_{a20})_{n5})_{m2}$—$O$—$(CR_{a21}R_{a22})_{n6}$—, —U—$(CR_{23}R_{24})_{n1}$—$C(O)NH$—$(O(CR_{25}R_{26})_{n2})_{m1}$—, —U—$(CH_2)_{n1}$—$(NHC(O)$—$(CH_2)_{n2})_{m1}$—$(O(CH_2)_{n3})_{m2}$—, linear or branched —U-alkylene chain-interrupted one or more times (e.g. 1-20, 1-15, 1-10, 1-9, 1-8, 1-7, 1-6, 1-5, 1-4, 1-3 or 1-2 times, or 1 time) by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$— having carbon chain interrupted one or more times (e.g. 1-20, 1-15, 1-10, 1-9, 1-8, 1-7, 1-6, 1-5, 1-4, 1-3 or 1-2 times, or 1 time) by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

wherein n1, n2, n3, n4, n5, n6, m1, m2 each independently represents an integer of 1, 2, 3, 4, 5, 6, 7, 8, 9, 10, 11, 12, 13, 14, 15, 16, 17, 18, 19, or 20, and the group U represents C(O), or the group U is absent; wherein the alkylene in the LIN is optionally substituted by one or more substituents (in particular, substituents selected from hydroxyl, amino, mercapto, halogen or any combination thereof).

In a sub-embodiment of the compound represented by formula (IIIf-1) or formula (IIIf-2) of the present disclosure, the LIN represents —U—$C_{1-30}$ alkylene-; and the group U represents C(O), or the group U is absent. In a sub-embodiment of the present disclosure, the LIN is —U-methylene or —U—$C_{2-30}$ alkylene-, wherein the $C_{2-30}$ alkylene is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents C(O), or the group U is absent. In a sub-embodiment, the UN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents C(O), or the group U is absent. In a sub-embodiment, the group U represents C(O). In a sub-embodiment, the group U is absent.

In a sub-embodiment of the compound represented by formula (IIIf-1) or formula (IIIf-2) of the present disclosure, the LIN represents —U—$C_{2-40}$ alkylene- (e.g. —U—$C_{2-30}$ alkylene-), wherein the alkylene is optionally interrupted one or more times (e.g. 1-20, 1-15, 1-10, 1-9, 1-8, 1-7, 1-6, 1-5, 1-4, 1-3, or 1-2 times, or 1 time) by one or more group selected from C(O)NH, NHC(O), O, NH, alkynylene, alkenylene, cycloalkylene, arylene, heterocyclylene or heteroarylene or any combination thereof, and the group U represents C(O), or the group U is absent.

In a sub-embodiment of the compound represented by formula (IIIf-1) or formula (IIIf-2) of the present disclosure, the LIN represents —U-alkylene-, the alkylene (preferably $C_{1-30}$ alkylene chain, particularly preferably $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents, wherein the substituent is selected from hydroxyl, amino, mercapto, halogen or any combination thereof; wherein the group U represents C(O), or the group U is absent.

In a sub-embodiment of the compound represented by formula (IIIf-1) or formula (IIIf-2) of the present disclosure, the LIN represents —U—$C_{1-30}$ alkylene-, and the $C_{1-30}$ alkylene is a linear or branched $C_{1-30}$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$ alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) substituted by one or more substituents selected from hydroxyl, amino, mercapto, halogen or any combination thereof, wherein the group U represents C(O), or the group U is absent. In a sub-embodiment of the present disclosure, the number of the substituents can be, e.g. 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In a sub-embodiment of the compound of the present disclosure represented by formula (IIIf-1) or formula (IIIf-2), the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIf-1) or formula (IIIf-2), the LIN represents —U—$CH_2C(O)NHCH_2$—, —U—$CH_2C(O)NH(CH_2)_2$—, —U—$CH_2C(O)NH(CH_2)_3$—, —U—$CH_2C(O)NH(CH_2)_4$—, —U—$CH_2C(O)NH(CH_2)_5$—, —U—$CH_2C(O)NH(CH_2)_6$—, —U—$CH_2C(O)NH(CH_2)_7$—, —U—$CH_2C(O)NH(CH_2)_8$—, —U—$CH_2C(O)NH(CH_2)_9$—, —U—$CH_2C(O)NH(CH_2)_{10}$—, —U—$(CH_2)_2C(O)NHCH_2$—, —U—$(CH_2)_2C(O)NH(CH_2)_2$—, —U—$(CH_2)_2C(O)NH(CH_2)_3$—, —U—$(CH_2)_2C(O)NH(CH_2)_4$—, —U—$(CH_2)_2C(O)NH(CH_2)_5$—, —U—$(CH_2)_2C(O)NH(CH_2)_6$—, —U—$(CH_2)_2C(O)NH(CH_2)_7$—, —U—$(CH_2)_2C(O)NH(CH_2)_8$—, —U—$(CH_2)_3C(O)NHCH_2$—, —U—$(CH_2)_3C(O)NH(CH_2)_2$—, —U—$(CH_2)_3C(O)NH(CH_2)_3$—, —U—$(CH_2)_3C(O)NH(CH_2)_4$—, —U—$(CH_2)_3C(O)NH(CH_2)_5$—, —U—$(CH_2)_3C(O)NH(CH_2)_6$—, —U—$(CH_2)_3C(O)NH(CH_2)_7$—, —U—$(CH_2)_3C(O)NH(CH_2)_8$—, —U—$(CH_2)_4C(O)NHCH_2$—, —U—$(CH_2)_4C(O)NH(CH_2)_2$—, —U—$(CH_2)_4C(O)NH(CH_2)_3$—, —U—$(CH_2)_4C(O)NH(CH_2)_4$—, —U—$(CH_2)_4C(O)NH(CH_2)_5$—, —U—$(CH_2)_4C(O)NH(CH_2)_6$—, —U—$(CH_2)_5C(O)NHCH_2$—, —U—$(CH_2)_5C(O)NH(CH_2)_2$—, —U—$(CH_2)_5C(O)NH(CH_2)_3$—, —U—$(CH_2)_5C(O)NH(CH_2)_4$—, —U—$(CH_2)_5C(O)NH(CH_2)_5$—, —U—$(CH_2)_5C(O)NH(CH_2)_6$—, —U—$(CH_2)_6C(O)NHCH_2$—, —U—$(CH_2)_6C(O)NH(CH_2)_2$—, —U—$(CH_2)_6C(O)NH(CH_2)_3$—, —U—$(CH_2)_6C(O)NH(CH_2)_4$—, —U—$(CH_2)_6C(O)NH(CH_2)_5$—, —U—$(CH_2)_6C(O)NH(CH_2)_6$—, —U—$(CH_2)_6C(O)NH(CH_2)_7$—, —U—$(CH_2)_7C(O)NHCH_2$—, —U—$(CH_2)_7C(O)NH(CH_2)_2$—, —U—$(CH_2)_7C(O)NH(CH_2)_3$—, —U—$(CH_2)_7C(O)NH(CH_2)_4$—, —U—$(CH_2)_7C(O)NH(CH_2)_5$—, —U—$(CH_2)_7C(O)NH(CH_2)_6$—, —U—$(CH_2)_7C(O)NH(CH_2)_7$—, —U—$(CH_2)_8C(O)NHCH_2$—, —U—$(CH_2)_8C(O)NH(CH_2)_2$—, —U—$(CH_2)_8C(O)NH(CH_2)_3$—, —U—$(CH_2)_8C(O)NH(CH_2)_4$—, —U—$(CH_2)_8C(O)NH(CH_2)_5$—, —U—$(CH_2)_8C(O)NH(CH_2)_6$—, —U—$(CH_2)_8C(O)NH(CH_2)_7$—, —U—$(CH_2)_8C(O)NH(CH_2)_8$—, —U—$(CH_2)_9C(O)NHCH_2$—, —U—$(CH_2)_9C(O)NH(CH_2)_2$—, —U—$(CH_2)_9C(O)NH(CH_2)_3$—, —U—$(CH_2)_9C(O)NH(CH_2)_4$—, —U—$(CH_2)_9C(O)NH(CH_2)_5$—, —U—$(CH_2)_9C(O)NH(CH_2)_6$—, —U—$(CH_2)_9C(O)NH(CH_2)_7$—, —U—$(CH_2)_9C(O)NH(CH_2)_8$—, —U—$(CH_2)_9C(O)NH(CH_2)_9$—, —U—$(CH_2)_{10}C(O)NHCH_2$—, —U—$(CH_2)_{10}C(O)NH(CH_2)_2$—, —U—$(CH_2)_{10}C(O)NH(CH_2)_3$—, —U—$(CH_2)_{10}C(O)NH(CH_2)_4$—, —U—$(CH_2)_{10}C(O)NH(CH_2)_5$— or —U—$(CH_2)_{10}C(O)NH(CH_2)_{10}$—; wherein the group U represents C(O), or the group U is absent.

In a sub-embodiment of the compound of the present disclosure represented by formula (IIIf-1) or formula (IIIf-2), the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIf-1) or formula (IIIf-2), the LIN represents —U—$CH_2NHC(O)CH_2$—, —U—CH$_2$NHC(O)(CH$_2$)$_2$—, —U—CH$_2$NHC(O)(CH$_2$)$_3$—, —U—CH$_2$NHC(O)(CH$_2$)$_4$—, —U—CH$_2$NHC(O)(CH$_2$)$_5$—, —U—CH$_2$NHC(O)(CH$_2$)$_6$—, —U—CH$_2$NHC(O)(CH$_2$)$_7$—, —U—CH$_2$NHC(O)(CH$_2$)$_8$—, —U—CH$_2$NHC(O)(CH$_2$)$_9$—, —U—CH$_2$NHC(O)(CH$_2$)$_{10}$—, —U—(CH$_2$)$_2$NHC(O)CH$_2$—, —U—(CH$_2$)$_2$NHC(O)(CH$_2$)$_2$—, —U—(CH$_2$)$_2$NHC(O)(CH$_2$)$_3$—, —U—(CH$_2$)$_2$NHC(O)(CH$_2$)$_4$—, —U—(CH$_2$)$_2$NHC(O)(CH$_2$)$_5$—, —U—(CH$_2$)$_3$NHC(O)CH$_2$—, —U—(CH$_2$)$_3$NHC(O)(CH$_2$)$_2$—, —U—(CH$_2$)$_3$NHC(O)(CH$_2$)$_3$—, —U—(CH$_2$)$_3$NHC(O)(CH$_2$)$_4$—, —U—(CH$_2$)$_3$NHC(O)(CH$_2$)$_5$—, —U—(CH$_2$)$_4$NHC(O)CH$_2$—, —U—(CH$_2$)$_4$NHC(O)(CH$_2$)$_2$—, —U—(CH$_2$)$_4$NHC(O)(CH$_2$)$_3$—, —U—(CH$_2$)$_4$NHC(O)(CH$_2$)$_4$—, —U—(CH$_2$)$_4$NHC(O)(CH$_2$)$_5$—, —U—(CH$_2$)$_4$NHC(O)(CH$_2$)$_6$—, —U—(CH$_2$)$_4$NHC(O)(CH$_2$)$_7$—, —U—(CH$_2$)$_5$NHC(O)CH$_2$—, —U—(CH$_2$)$_5$NHC(O)(CH$_2$)$_2$—, —U—(CH$_2$)$_5$NHC(O)(CH$_2$)$_3$—, —U—(CH$_2$)$_5$NHC(O)(CH$_2$)$_4$—, —U—(CH$_2$)$_5$NHC(O)(CH$_2$)$_5$—, —U—(CH$_2$)$_5$NHC(O)(CH$_2$)$_6$—, —U—(CH$_2$)$_6$NHC(O)CH$_2$—, —U—(CH$_2$)$_6$NHC(O)(CH$_2$)$_2$—, —U—(CH$_2$)$_6$NHC(O)(CH$_2$)$_3$—, —U—(CH$_2$)$_6$NHC(O)(CH$_2$)$_4$—, —U—(CH$_2$)$_6$NHC(O)(CH$_2$)$_5$—, —U—(CH$_2$)$_6$NHC(O)(CH$_2$)$_6$—, —U—(CH$_2$)$_6$NHC(O)(CH$_2$)$_7$—, —U—(CH$_2$)$_7$NHC(O)CH$_2$—, —U—(CH$_2$)$_7$NHC(O)(CH$_2$)$_2$—, —U—(CH$_2$)$_7$NHC(O)(CH$_2$)$_3$—, —U—(CH$_2$)$_7$NHC(O)(CH$_2$)$_4$—, —U—(CH$_2$)$_7$NHC(O)(CH$_2$)$_5$—, —U—(CH$_2$)$_7$NHC(O)(CH$_2$)$_6$—, —U—(CH$_2$)$_7$NHC(O)(CH$_2$)$_7$—, —U—(CH$_2$)$_8$NHC(O)CH$_2$—, —U—(CH$_2$)$_8$NHC(O)(CH$_2$)$_2$—, —U—(CH$_2$)$_8$NHC(O)(CH$_2$)$_3$—, —U—(CH$_2$)$_5$NHC(O)(CH$_2$)$_8$—, —U—(CH$_2$)$_9$NHC(O)CH$_2$—, —U—(CH$_2$)$_9$NHC(O)(CH$_2$)$_2$—, —U—(CH$_2$)$_9$NHC(O)(CH$_2$)$_3$—, —U—(CH$_2$)$_9$NHC(O)(CH$_2$)$_9$—, or —U—(CH$_2$)$_{10}$NHC(O)(CH$_2$)$_{10}$—; wherein the group U represents C(O), or the group U is absent.

In a sub-embodiment of the compound of the present disclosure represented by formula (IIIf-1) or formula (IIIf-2), the LIN represents —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_2$—O—CH$_2$—, —U—(CH$_2$)$_2$—O—(CH$_2$)$_2$—O(CH$_2$)$_2$—O—(CH$_2$)$_3$—, —U—(CH$_2$)$_2$—(O(CH$_2$)$_2$)$_2$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents C(O), or the group U is absent.

In a sub-embodiment of the compound of the present disclosure represented by formula (IIIf-1) or formula (IIIf-2), the LIN represents —U—(CH$_2$)$_{n1}$—CH═CH—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIf-1) or formula (IIIf-2), the LIN represents —U—CH$_2$CH═CHCH$_2$—, —U—CH$_2$CH═CH(CH$_2$)$_2$—, —U—CH$_2$CH═CH(CH$_2$)$_3$—, —U—CH$_2$CH═CH(CH$_2$)$_4$—, —U—CH$_2$CH═CH(CH$_2$)$_5$—, —U—CH$_2$CH═CH(CH$_2$)$_6$—, —U—CH$_2$CH═CH(CH$_2$)$_7$—, —U—CH$_2$CH═CH(CH$_2$)$_8$—, —U—CH$_2$CH═CH(CH$_2$)$_9$—, —U—CH$_2$CH═CH(CH$_2$)$_{19}$—, —U—(CH$_2$)$_2$CH═CHCH$_2$—, —U—(CH$_2$)$_2$CH═CH(CH$_2$)$_2$—, —U—(CH$_2$)$_2$CH=CH(CH$_2$)$_3$—, —U—(CH$_2$)$_2$CH=CH(CH$_2$)$_4$—, —U—(CH$_2$)$_2$CH=CH(CH$_2$)$_5$—, —U—(CH$_2$)$_2$CH=CH(CH$_2$)$_6$—, —U—(CH$_2$)$_2$CH=CH(CH$_2$)$_7$—, —U—(CH$_2$)$_2$CH=CH(CH$_2$)$_8$—, —U—(CH$_2$)$_3$CH=CHCH$_2$—, —U—(CH$_2$)$_3$CH=CH(CH$_2$)$_2$—, —U—(CH$_2$)$_3$CH=CH(CH$_2$)$_3$—, —U—(CH$_2$)$_3$CH=CH(CH$_2$)$_4$—, —U—(CH$_2$)$_3$CH=CH(CH$_2$)$_5$—, —U—(CH$_2$)$_3$CH=CH(CH$_2$)$_6$—, —U—(CH$_2$)$_3$CH=CH(CH$_2$)$_7$—, —U—(CH$_2$)$_4$CH=CHCH$_2$—, —U—(CH$_2$)$_4$CH=CH(CH$_2$)$_2$—, —U—(CH$_2$)$_4$CH=CH(CH$_2$)$_3$—, —U—(CH$_2$)$_4$CH=CH(CH$_2$)$_4$—, —U—(CH$_2$)$_4$CH=CH(CH$_2$)$_5$—, —U—(CH$_2$)$_5$CH=CHCH$_2$—, —U—(CH$_2$)$_5$CH=CH(CH$_2$)$_2$—, —U—(CH$_2$)$_5$CH=CH(CH$_2$)$_3$—, —U—(CH$_2$)$_5$CH=CH(CH$_2$)$_4$—, —U—(CH$_2$)$_5$CH=CH(CH$_2$)$_5$—, —U—(CH$_2$)$_6$CH=CHCH$_2$—, —U—(CH$_2$)$_6$CH=CH(CH$_2$)$_2$—, —U—(CH$_2$)$_6$CH=CH(CH$_2$)$_3$—, —U—(CH$_2$)$_7$CH=CHCH$_2$—, —U—(CH$_2$)$_7$CH=CH(CH$_2$)$_2$—, —U—(CH$_2$)$_7$CH=CH(CH$_2$)$_3$—, —U—(CH$_2$)$_8$CH=CHCH$_2$—, —U—(CH$_2$)$_8$CH=CH(CH$_2$)$_2$—, —U—(CH$_2$)$_8$CH=CH(CH$_2$)$_3$—, —U—(CH$_2$)$_9$CH=CHCH$_2$—U—(CH$_2$)$_9$CH=CH(CH$_2$)$_2$—, —U—(CH$_2$)$_9$CH=CH(CH$_2$)$_3$—, —U—(CH$_2$)$_{10}$CH=CHCH$_2$—, or —U—(CH$_2$)$_{10}$CH=CH(CH$_2$)$_2$—, and wherein the group U represents C(O), or the group U is absent.

In a sub-embodiment of the compound of the present disclosure represented by formula (IIIf-1), or formula (IIIf-2), the LIN represents: —U—(CH$_2$)$_{n1}$—C≡C—(CH$_2$)$_{n2}$— or —U—(CH$_2$)$_{n1}$—C≡C—C≡C—(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19 or 20, wherein the group U represents C(O), or the group U is absent.

In a sub-embodiment of the compound of the present disclosure represented by formula (IIIf-1), or formula (IIIf-2), the LIN represents: —U—CH$_2$C≡CCH$_2$—, —U—CH$_2$C≡C(CH$_2$)$_2$—, —U—CH$_2$C—C(CH$_2$)$_3$—, —U—CH$_2$C≡C(CH$_2$)$_4$—, —U—CH$_2$C≡C(CH$_2$)$_5$—, —U—CH$_2$C≡C(CH$_2$)$_6$—, —U—CH$_2$C≡C(CH$_2$)$_7$—, —U—CH$_2$C≡C(CH$_2$)$_8$—, —U—CH$_2$C≡C(CH$_2$)$_9$—, —U—CH$_2$C≡C(CH$_2$)$_{10}$—, —U—(CH$_2$)$_2$C≡CCH$_2$—, —U—(CH$_2$)$_2$C≡C(CH$_2$)$_2$—, —U—(CH$_2$)$_2$C≡C(CH$_2$)$_3$—, —U—(CH$_2$)$_2$C≡C(CH$_2$)$_4$—, —U—(CH$_2$)$_2$C≡C(CH$_2$)$_5$—, —U—(CH$_2$)$_2$C≡C(CH$_2$)$_6$—, —U—(CH$_2$)$_2$C≡C(CH$_2$)$_7$—, —U—(CH$_2$)$_2$C≡C(CH$_2$)$_8$—, —U—(CH$_2$)$_3$C≡CCH$_2$—, —U—(CH$_2$)$_3$C≡C(CH$_2$)$_2$—, —U—(CH$_2$)$_3$C≡C(CH$_2$)$_3$—, —U—(CH$_2$)$_3$C≡C(CH$_2$)$_4$—, —U—(CH$_2$)$_3$C≡C(CH$_2$)$_5$—, —U—(CH$_2$)$_3$C≡C(CH$_2$)$_6$—, —U—(CH$_2$)$_3$C≡C(CH$_2$)$_7$—, —U—(CH$_2$)$_4$C≡CCH$_2$—, —U—(CH$_2$)$_4$C≡C(CH$_2$)$_2$—, —U—(CH$_2$)$_4$C≡C(CH$_2$)$_3$—, —U—(CH$_2$)$_4$C≡C(CH$_2$)$_4$—, —U—(CH$_2$)$_4$C≡C(CH$_2$)$_5$—, —U—(CH$_2$)$_5$C≡CCH$_2$—, —U—(CH$_2$)$_5$C≡C(CH$_2$)$_2$—, —U—(CH$_2$)$_5$C≡C(CH$_2$)$_3$—, —U—(CH$_2$)$_5$C≡C(CH$_2$)$_4$—, —U—(CH$_2$)$_5$C≡C(CH$_2$)$_5$—, —U—(CH$_2$)$_6$C≡CCH$_2$—, —U—(CH$_2$)$_6$C≡C(CH$_2$)$_2$—, —U—(CH$_2$)$_6$C≡C(CH$_2$)$_3$—, —U—(CH$_2$)$_7$C≡CCH$_2$—, —U—(CH$_2$)$_7$C≡C(CH$_2$)$_2$—, —U—(CH$_2$)$_7$C≡C(CH$_2$)$_3$—, —U—(CH$_2$)$_8$C≡CCH$_2$—, —U—(CH$_2$)$_8$C≡C(CH$_2$)$_2$—, —U—(CH$_2$)$_8$C≡C(CH$_2$)$_3$—, —U—(CH$_2$)$_9$C≡CCH$_2$—U—(CH$_2$)$_9$C≡C(CH$_2$)$_2$—, —U—(CH$_2$)$_9$C≡C(CH$_2$)$_3$—, —U—(CH$_2$)$_{10}$C≡CCH$_2$—, or —U—(CH$_2$)$_{10}$C≡C(CH$_2$)$_2$—, and wherein the group U represents C(O), or the group U is absent.

In a sub-embodiment of the compound of the present disclosure represented by formula (IIIf-1) or formula (IIIf-2), the LIN represents —U—(CH$_2$)$_{n1}$-piperazinylidene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIf-1) or formula (IIIf-2), the LIN represents: —U—CH$_2$-piperaziinylidene-CH$_2$—, —U—(CH$_2$)$_2$-piperaziinylidene-(CH$_2$)$_2$—, —U—(CH$_2$)$_3$-piperaziinylidene-(CH$_2$)$_3$—, —U—(CH$_2$)$_2$-piperaziinylidene-(CH$_2$)$_3$—, —U—CH$_2$-piperaziinylidene-(CH$_2$)$_2$—, —U—CH$_2$-piperaziinylidene-(CH$_2$)$_3$— or —U—(CH$_2$)$_2$-piperaziinylidene-(CH$_2$)$_3$—, wherein the group U represents C(O), or the group U is absent.

In a sub-embodiment of the compound of the present disclosure represented by formula (IIIf-1) or formula (IIIf-2), the LIN represents —U—(CH$_2$)$_{n1}$-phenylene-(CH$_2$)$_{n2}$—, wherein n1 and n2 each independently represents an integer of 1, 2, 3, 4, 5, 6, 7, 8, 9, 10, 11, 12, 13, 14, 15, 16, 17, 18, 19, or 20, wherein the group U represents C(O), or the group U is absent.

In a sub-embodiment of the compound of the present disclosure represented by formula (IIIf-1) or formula (IIIf-2), the LIN represents: —U—CH$_2$-phenylene-CH$_2$—, —U—(CH$_2$)$_2$-phenylene-(CH$_2$)$_2$—, —U—CH$_2$-phenylene-(CH$_2$)$_2$—, —U—(CH$_2$)$_2$-phenylene-CH$_2$—, —U—(CH$_2$)$_3$-phenylene-(CH$_2$)$_3$—, —U—CH$_2$-phenylene-(CH$_2$)$_3$—, —U—(CH$_2$)$_2$-phenylene-(CH$_2$)$_3$—, —U—(CH$_2$)$_3$-phenylene-(CH$_2$)$_2$—, or —U—(CH$_2$)$_3$-phenylene-CH$_2$—, wherein the group U represents C(O), or the group U is absent.

In a sub-embodiment of the compound represented by formula (IIIf-1) or formula (IIIf-2) of the present disclosure, the LIN represents: —U—(CH$_2$)$_{n1}$-triazolylidene-(CH$_2$)$_{n2}$—, —U—(CH$_2$)$_{n1}$-triazolylidene-(CH$_2$)$_{n2}$—(O(CH$_2$)$_{n3}$)$_{m1}$—, —U—(CH$_2$)$_{n1}$—(O(CH$_2$)$_{n2}$)$_{m1}$—O—(CH$_2$)$_{n3}$-triazolylidene-(CH$_2$)$_{n4}$—(O(CH$_2$)$_{n5}$)$_{m2}$—O—(CH$_2$)$_{n6}$—, —U—(CH$_2$)$_{n1}$-triazolylidene-(CH$_2$)$_{n2}$—(O(CH$_2$)$_{n3}$)$_{m1}$—O—(CH$_2$)$_{m1}$— or —U—(CH$_2$)$_{n1}$—(O(CH$_2$)$_{n2}$)$_{m1}$—O—(CH$_2$)$_{n3}$-triazolylidene-(CH$_2$)$_{n4}$—;

wherein n1, n2, n3, n4, n5, n6, m1 and m2 each independently represents an integer of 1, 2, 3, 4, 5, 6, 7, 8, 9, 10, 11, 12, 13, 14, 15, 16, 17, 18, 19 or 20; wherein the group U represents C(O), or the group U is absent.

In a sub-embodiment of the compound of the present disclosure represented by formula (IIIf-1) or formula (IIIf-2), the LIN represents: —U—(CH$_2$)$_3$-triazolylidene-(CH$_2$)$_5$—, —U—(CH$_2$)$_2$-triazolylidene-(CH$_2$)$_5$—, —U—CH$_2$-triazolylidene-(CH$_2$)$_5$—, —U—(CH$_2$)$_2$-triazolylidene-(CH$_2$)$_4$—, —U—(CH$_2$)$_3$-triazolylidene-(CH$_2$)$_2$—O(CH$_2$)$_2$—U—(CH$_2$)$_2$-triazolylidene-(CH$_2$)$_2$—O(CH$_2$)$_2$— or —U—CH$_2$-triazolylidene-(CH$_2$)$_2$—O(CH$_2$)$_2$—, wherein the group U represents C(O), or the group U is absent.

In a sub-embodiment of the compound of the present disclosure represented by formula (IIIf-1) or formula (IIIf-2), the LIN represents

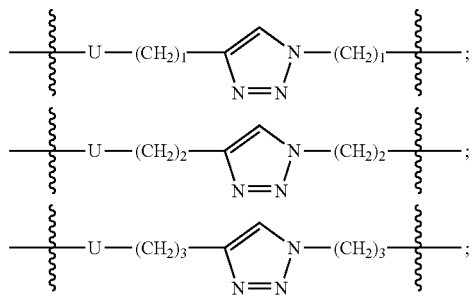

-continued

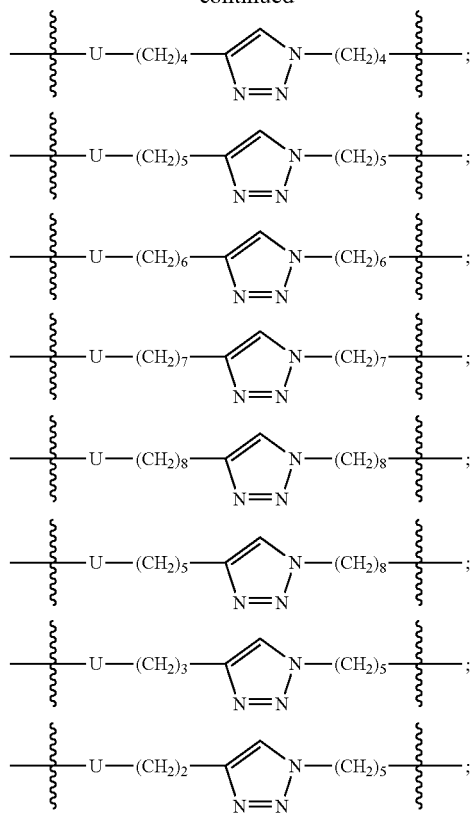

-continued

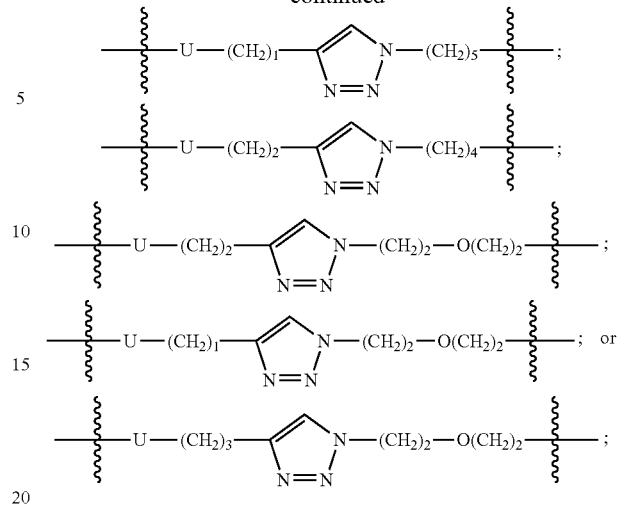

wherein the group U represents C(O), or the group U is absent.

In a sub-embodiment of the compound of the present disclosure represented by formula (IIIf-1) or formula (IIIf-2), the LIN represents —U—$(CH_2)_2$NHC(O)$(CH_2)_2$—O—$(CH_2)_2$— or —U—$(CH_2)_2$C(O)NH$(CH_2)_2$—O—$(CH_2)_2$—, wherein the group U represents C(O), or the group U is absent.

The following compound represented by formula (III) of the present disclosure in Table 2 and the salt thereof (especially the pharmaceutically acceptable salt) are particularly preferred:

TABLE 2

| Compound number | Structural formula | Compound name |
|---|---|---|
| | | 8-(4-(4-(4-((2-(2,6-dioxopiperidin-3-yl)-1-oxoisoindolin-5-yl)aminoacetyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(3-((2-(2,6-dioxopiperidin-3-yl)-1-oxoisoindolin-5-yl)amino)propionyl)piperazin-1-yl)piperidin-1-yl)-9-ethyl-6,6-dimethyl-11-oxo-6,11-dihydro-5H-benzo[b]carbazole-3-carbonitrile |

TABLE 2-continued

| Compound number | Structural formula | Compound name |
|---|---|---|
| | 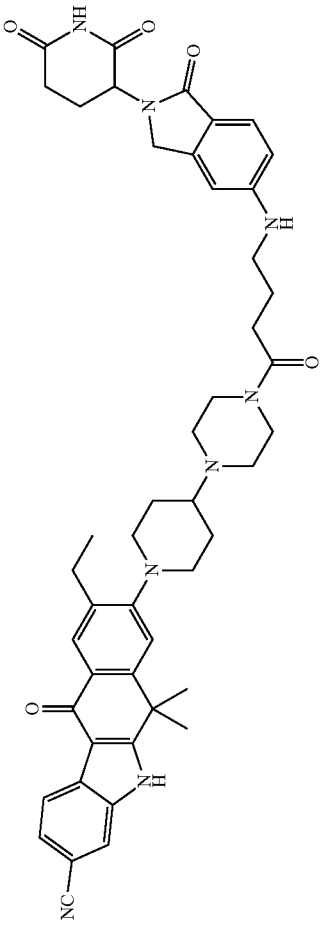 | 8-(4-(4-(4-((2-(2,6-dioxopiperidin-3-yl)-1-oxoisoindolin-5-yl)amino)butyryl)piperazin-1-yl)piperidin-1-yl)-9-ethyl-6,6-dimethyl-11-oxo-6,11-dihydro-5H-benzo[b]carbazole-3-carbonitrile |
| | 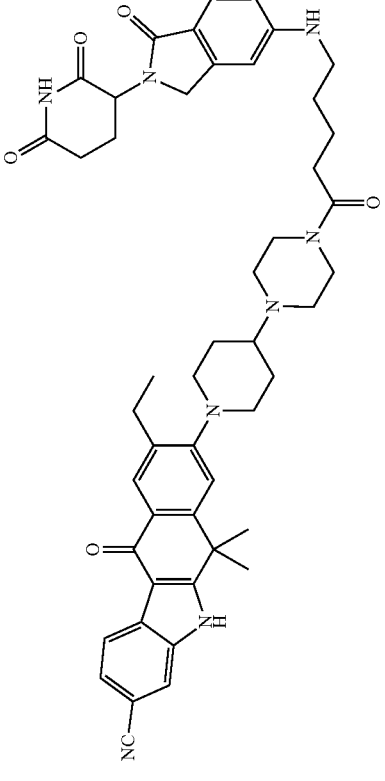 | 8-(4-(4-(5-((2-(2,6-dioxopiperidin-3-yl)-1-oxoisoindolin-5-yl)amino)valeryl)piperazin-1-yl)piperidin-1-yl)-9-ethyl-6,6-dimethyl-11-oxo-6,11-dihydro-5H-benzo[b]carbazole-3-carbonitrile |
| | 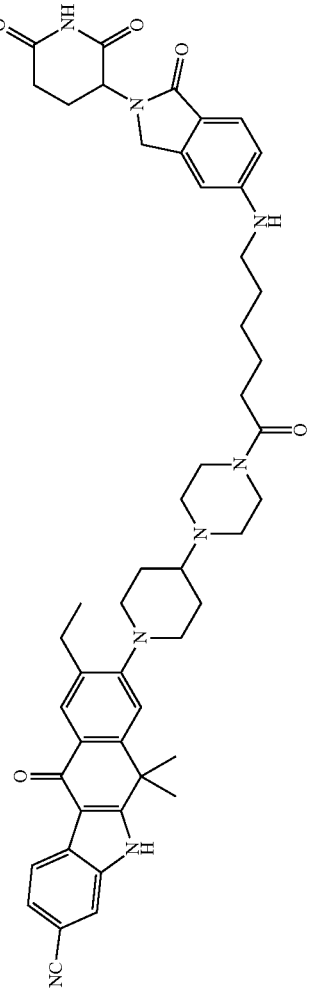 | 8-(4-(4-(6-((2-(2,6-dioxopiperidin-3-yl)-1-oxoisoindolin-5-yl)amino)hexanoyl)piperazin-1-yl)piperidin-1-yl)-9-ethyl-6,6-dimethyl-11-oxo-6,11-dihydro-5H-benzo[b]carbazole-3-carbonitrile |

TABLE 2-continued

| Compound number | Structural formula | Compound name |
|---|---|---|
| | | 8-(4-(4-(7-((2-(2,6-dioxopiperidin-3-yl)-1-oxoisoindolin-5-yl)amino)heptanoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(2-((2-(2,6-dioxopiperidin-3-yl)-1-oxoisoindolin-5-yl)amino)ethyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(2-((2-(2,6-dioxopiperidin-3-yl)-1-oxoisoindolin-5-yl)oxy)acetyl)piperazin-1-yl)piperidin-1-yl)-9-ethyl-6,6-dimethyl-11-oxo-6,11-dihydro-5H-benzo[b]carbazole-3-carbonitrile |

| Compound number | Structural formula | Compound name |
|---|---|---|
| | 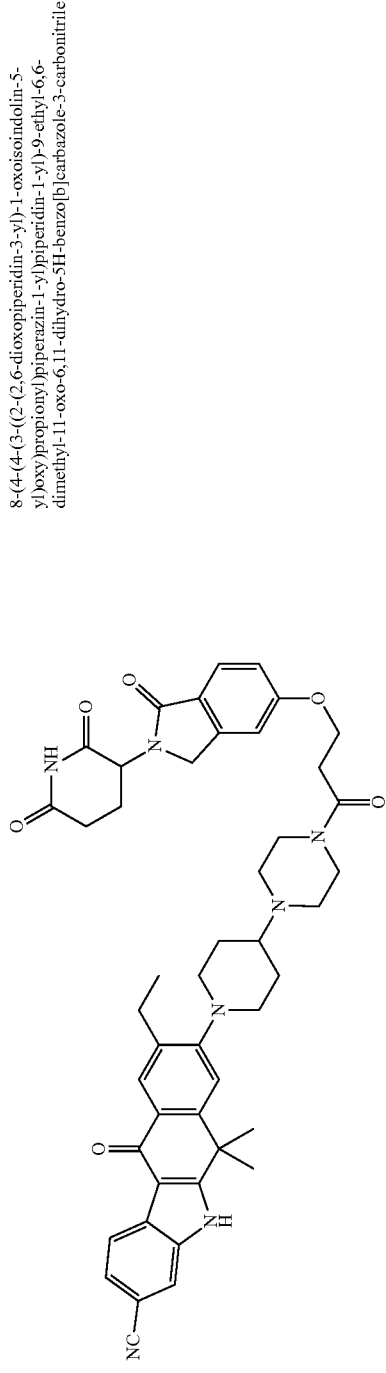 | 8-(4-(4-(3-((2-(2,6-dioxopiperidin-3-yl)-1-oxoisoindolin-5-yl)oxy)propionyl)piperazin-1-yl)piperidin-1-yl)-9-ethyl-6,6-dimethyl-11-oxo-6,11-dihydro-5H-benzo[b]carbazole-3-carbonitrile<br><br>8-(4-(4-(5-((2-(2,6-dioxopiperidin-3-yl)-1-oxoisoindolin-5-yl)oxy)valeryl)piperazin-1-yl)piperidin-1-yl)-9-ethyl-6,6-dimethyl-11-oxo-6,11-dihydro-5H-benzo[b]carbazole-3-carbonitrile |

TABLE 2-continued

| Compound number | Structural formula | Compound name |
|---|---|---|
| | 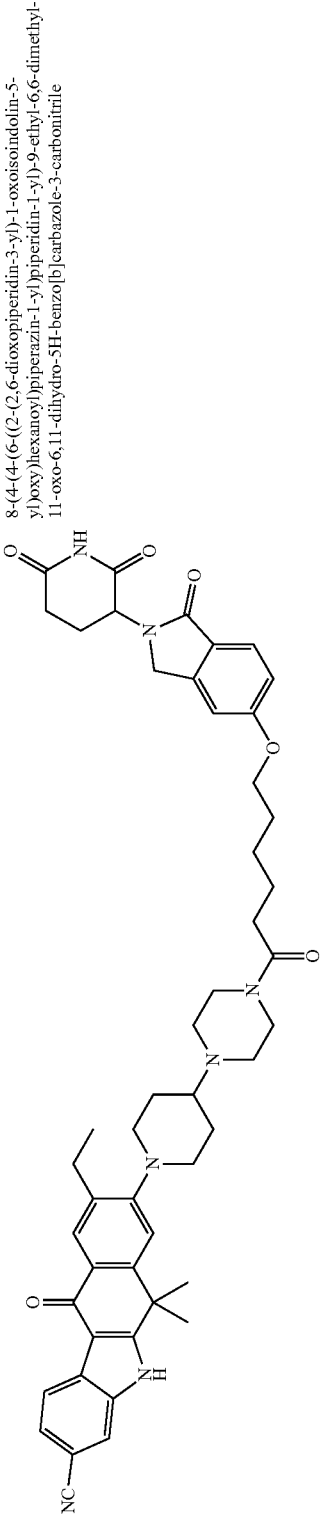 | 8-(4-(4-(6-((2-(2,6-dioxopiperidin-3-yl)-1-oxoisoindolin-5-yl)oxy)hexanoyl)piperazin-1-yl)piperidin-1-yl)-9-ethyl-6,6-dimethyl-11-oxo-6,11-dihydro-5H-benzo[b]carbazole-3-carbonitrile |
| | 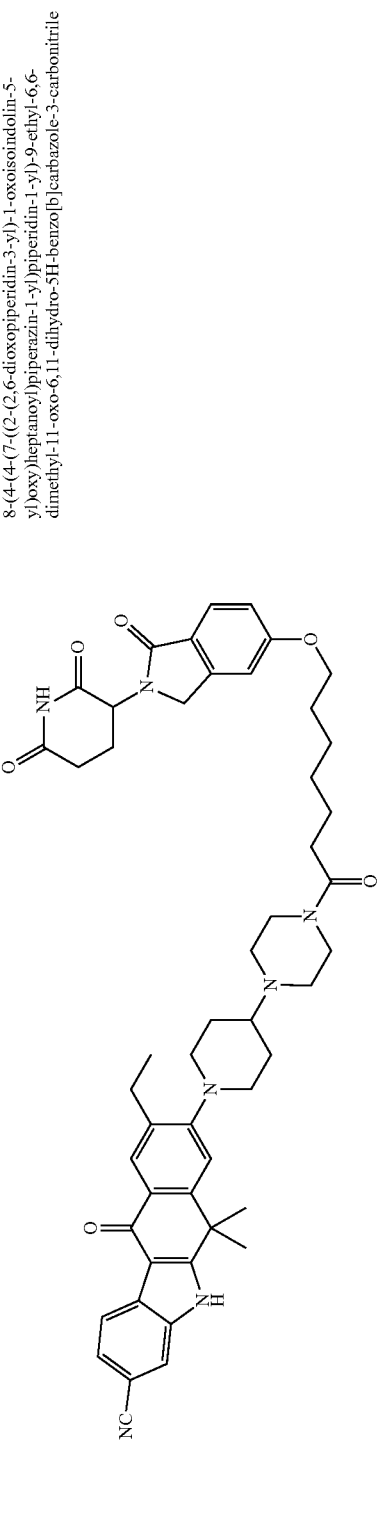 | 8-(4-(4-(7-((2-(2,6-dioxopiperidin-3-yl)-1-oxoisoindolin-5-yl)oxy)heptanoyl)piperazin-1-yl)piperidin-1-yl)-9-ethyl-6,6-dimethyl-11-oxo-6,11-dihydro-5H-benzo[b]carbazole-3-carbonitrile |
| | 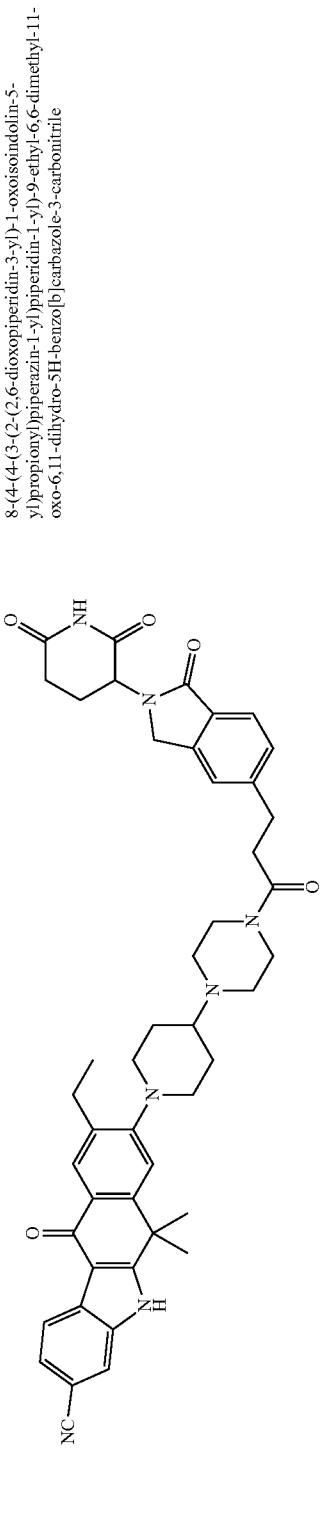 | 8-(4-(4-(3-(2-(2,6-dioxopiperidin-3-yl)-1-oxoisoindolin-5-yl)propionyl)piperazin-1-yl)piperidin-1-yl)-9-ethyl-6,6-dimethyl-11-oxo-6,11-dihydro-5H-benzo[b]carbazole-3-carbonitrile |

TABLE 2-continued
| Compound number | Structural formula | Compound name |
|---|---|---|
| | 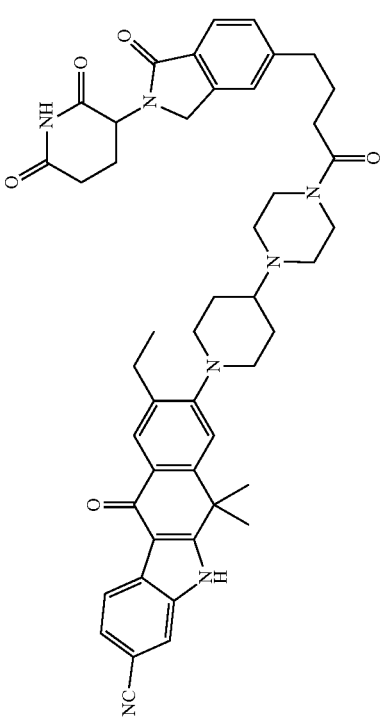 | 8-(4-(4-(4-(2-(2,6-dioxopiperidin-3-yl)-1-oxoisoindolin-5-yl)butyryl)piperazin-1-yl)piperidin-1-yl)-9-ethyl-6,6-dimethyl-11-oxo-6,11-dihydro-5H-benzo[b]carbazole-3-carbonitrile |
| | 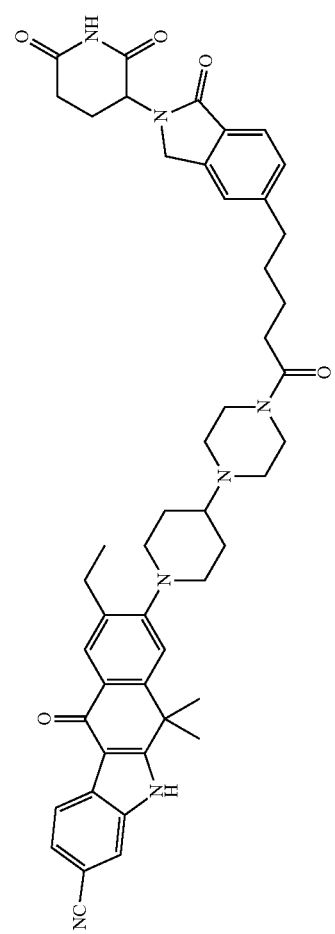 | 8-(4-(4-(5-(2-(2,6-dioxopiperidin-3-yl)-1-oxoisoindolin-5-yl)valeryl)piperazin-1-yl)piperidin-1-yl)-9-ethyl-6,6-dimethyl-11-oxo-6,11-dihydro-5H-benzo[b]carbazole-3-carbonitrile |

TABLE 2-continued

| Compound number | Structural formula | Compound name |
|---|---|---|
| | | 8-(4-(4-((2-(2,6-dioxopiperidin-3-yl)-1,3-dioxoisoindolin-5-yl)aminoacetyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(3-((2-(2,6-dioxopiperidin-3-yl)-1,3-dioxoisoindolin-5-yl)amino)propionyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(4-((2-(2,6-dioxopiperidin-3-yl)-1,3-dioxoisoindolin-5-yl)amino)butyryl)piperazin-1-yl)piperidin-1-yl)-9-ethyl-6,6-dimethyl-11-oxo-6,11-dihydro-5H-benzo[b]carbazole-3-carbonitrile |

TABLE 2-continued
| Compound number | Structural formula | Compound name |
|---|---|---|
| | 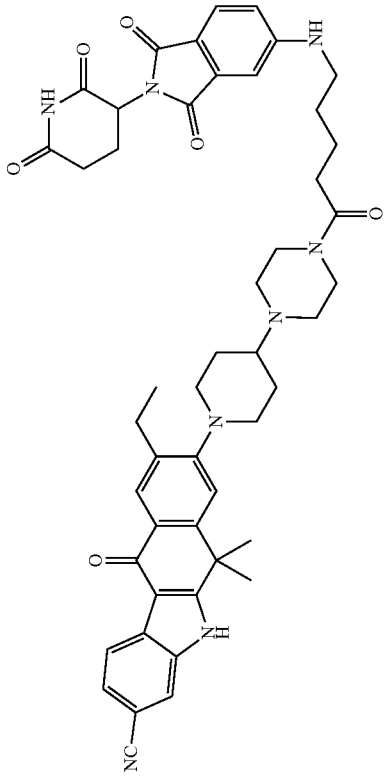 | 8-(4-(4-(5-((2-(2,6-dioxopiperidin-3-yl)-1,3-dioxoisoindolin-5-yl)amino)valeryl)piperazin-1-yl)piperidin-1-yl)-9-ethyl-6,6-dimethyl-11-oxo-6,11-dihydro-5H-benzo[b]carbazole-3-carbonitrile |
| | 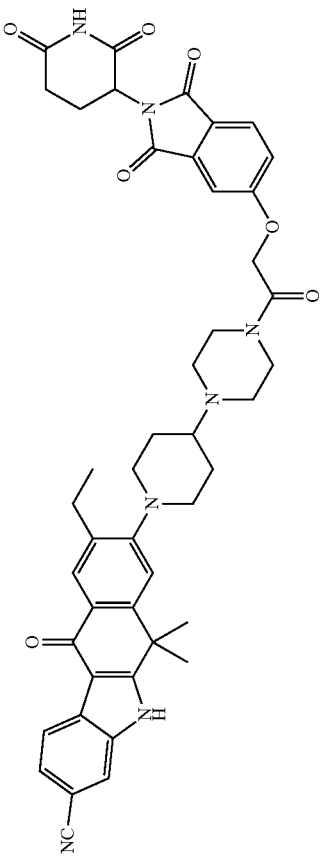 | 8-(4-(4-(2-((2-(2,6-dioxopiperidin-3-yl)-1,3-dioxoisoindolin-5-yl)oxy)acetyl)piperazin-1-yl)piperidin-1-yl)-9-ethyl-6,6-dimethyl-11-oxo-6,11-dihydro-5H-benzo[b]carbazole-3-carbonitrile |

TABLE 2-continued
| Compound number | Structural formula | Compound name |
|---|---|---|
|  | 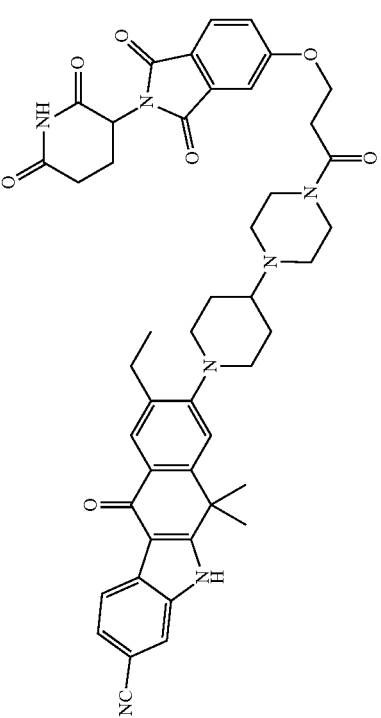 | 8-(4-(4-(3-((2-(2,6-dioxopiperidin-3-yl)-1,3-dioxoisoindolin-5-yl)oxy)propionyl)piperazin-1-yl)piperidin-1-yl)-9-ethyl-6,6-dimethyl-11-oxo-6,11-dihydro-5H-benzo[b]carbazole-3-carbonitrile |
|  | 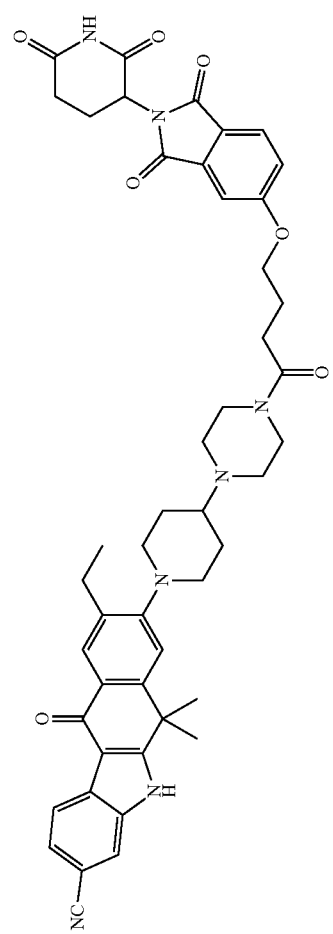 | 8-(4-(4-(4-((2-(2,6-dioxopiperidin-3-yl)-1,3-dioxoisoindolin-5-yl)oxy)butyryl)piperazin-1-yl)piperidin-1-yl)-9-ethyl-6,6-dimethyl-11-oxo-6,11-dihydro-5H-benzo[b]carbazole-3-carbonitrile |

TABLE 2-continued

| Compound number | Structural formula | Compound name |
|---|---|---|
| | | 8-(4-(4-(5-((2-(2,6-dioxopiperidin-3-yl)-1,3-dioxoisoindolin-5-yl)oxy)valeryl)piperazin-1-yl)piperidin-1-yl)-9-ethyl-6,6-dimethyl-11-oxo-6,11-dihydro-5H-benzo[b]carbazole-3-carbonitrile |
| | | 3-(5-((2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethyl)amino)-1-oxoisoindolin-2-yl)piperidine-2,6-dione |

| Compound number | Structural formula | Compound name |
|---|---|---|
| | 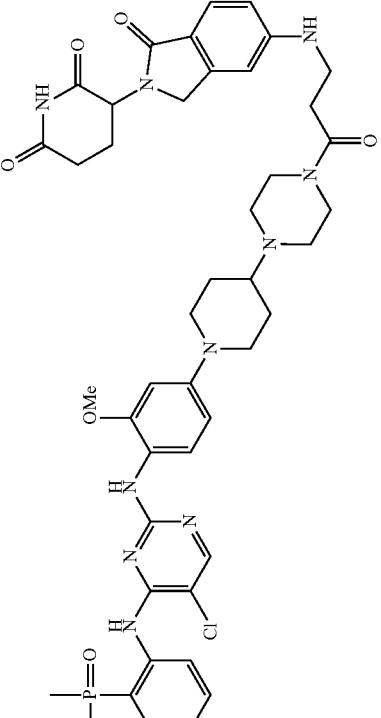 | 3-(5-((3-(4-(1-(4-((5-chloro-4-((2-(dimethylphosphono)phenyl)amino)pyrimidin-2-yl)amino)-3-methoxyphenyl)piperidin-4-yl)piperazin-1-yl)-3-oxopropyl)amino)-1-oxoisoindolin-2-yl)piperidine-2,6-dione |
| | 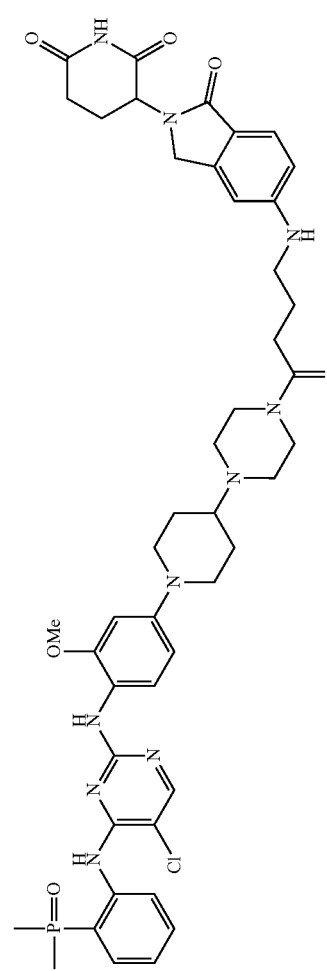 | 3-(5-((4-(1-(4-((5-chloro-4-((2-(dimethylphosphono)phenyl)amino)pyrimidin-2-yl)amino)-3-methoxyphenyl)piperidin-4-yl)piperazin-1-yl)-4-oxobutyl)amino)-1-oxoisoindolin-2-yl)piperidine-2,6-dione |

TABLE 2-continued

| Compound number | Structural formula | Compound name |
|---|---|---|
| | 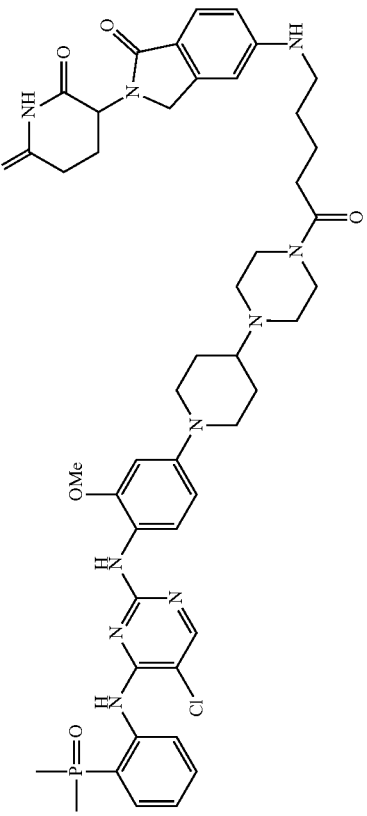 | 3-(5-((5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)amino)-1-oxoisoindolin-2-yl)piperidine-2,6-dione<br><br>3-(5-((6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)amino)-1-oxoisoindolin-2-yl)piperidine-2,6-dione |

| Compound number | Structural formula | Compound name |
|---|---|---|
| | 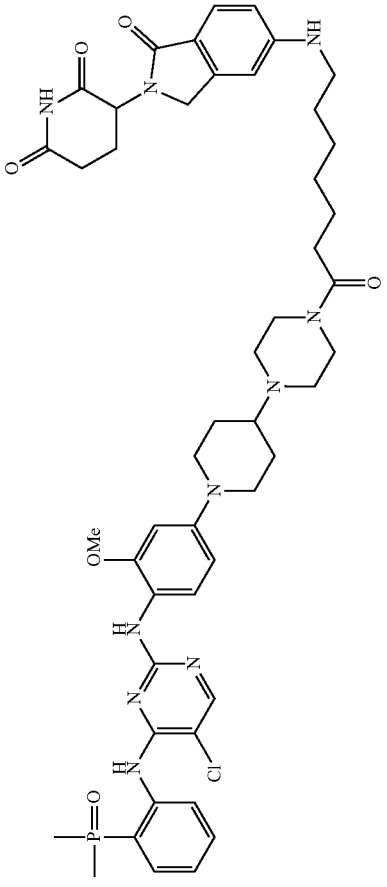 | 3-(5-((7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxoheptyl)amino)-1-oxoisoindolin-2-yl)piperidine-2,6-dione |
| | 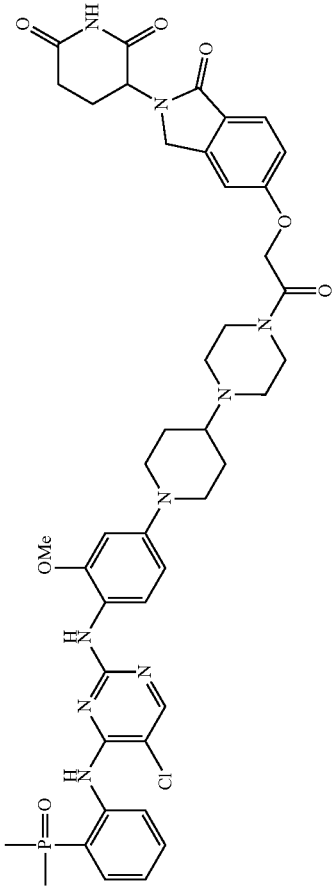 | 3-(5-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethoxy)-1-oxoisoindolin-2-yl)piperidine-2,6-dione |

TABLE 2-continued

| Compound number | Structural formula | Compound name |
|---|---|---|
| | 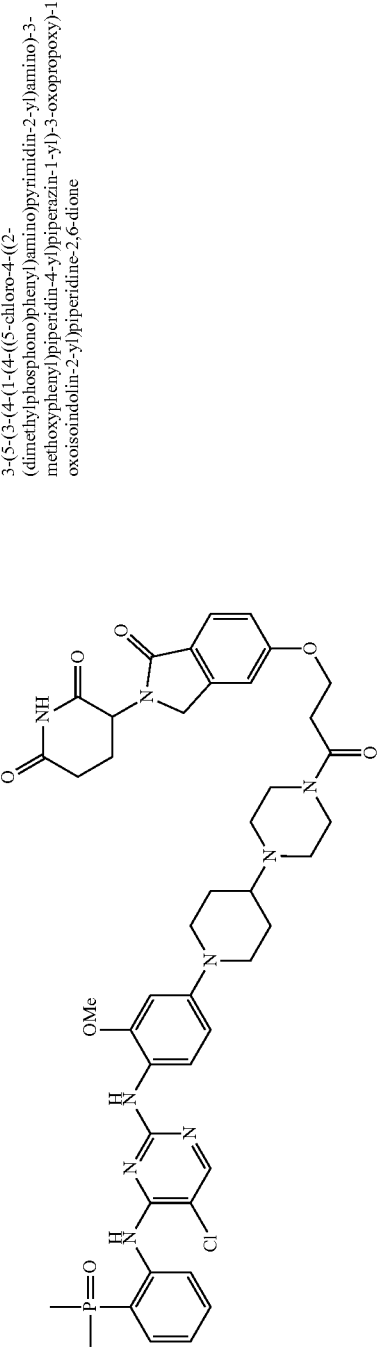 | 3-(5-(3-(4-(1-(4-((5-chloro-4-((2-(dimethylphosphono)phenyl)amino)pyrimidin-2-yl)amino)-3-methoxyphenyl)piperidin-4-yl)piperazin-1-yl)-3-oxopropoxy)-1-oxoisoindolin-2-yl)piperidine-2,6-dione |
| | 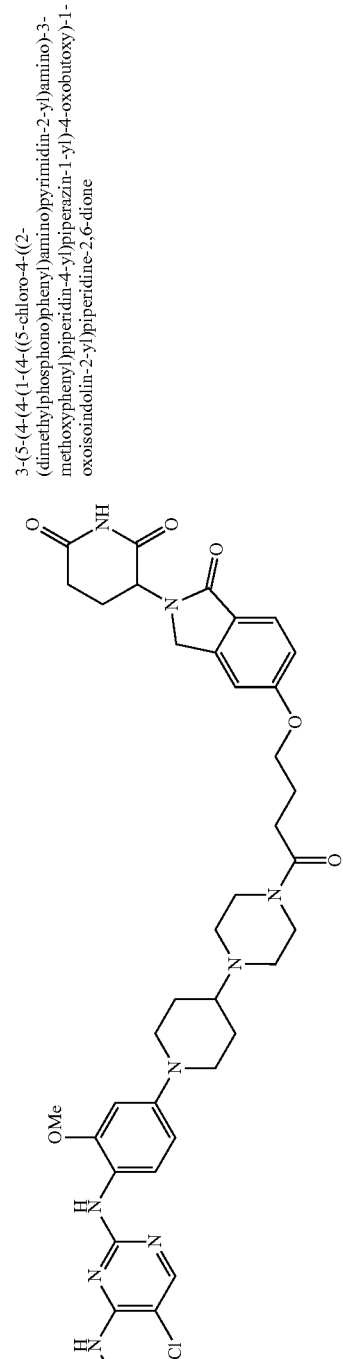 | 3-(5-(4-(4-(1-(4-((5-chloro-4-((2-(dimethylphosphono)phenyl)amino)pyrimidin-2-yl)amino)-3-methoxyphenyl)piperidin-4-yl)piperazin-1-yl)-4-oxobutoxy)-1-oxoisoindolin-2-yl)piperidine-2,6-dione |

TABLE 2-continued

| Compound number | Structural formula | Compound name |
|---|---|---|
| | 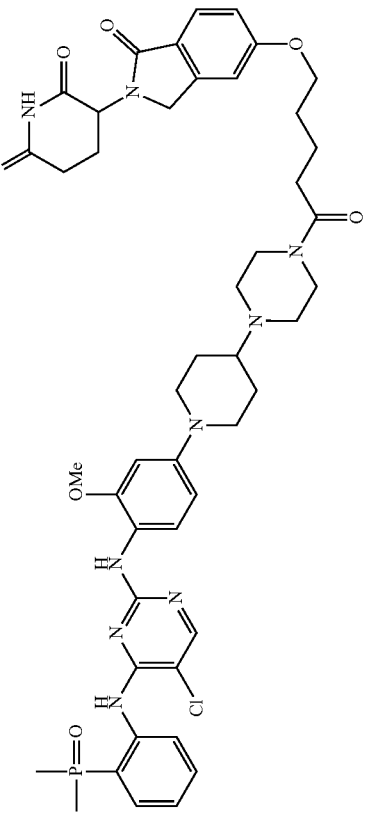 | 3-(5-((5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)oxy)-1-oxoisoindolin-2-yl)piperidine-2,6-dione<br><br>3-(5-((6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)oxy)-1-oxoisoindolin-2-yl)piperidine-2,6-dione |

TABLE 2-continued

| Compound number | Structural formula | Compound name |
|---|---|---|
| | 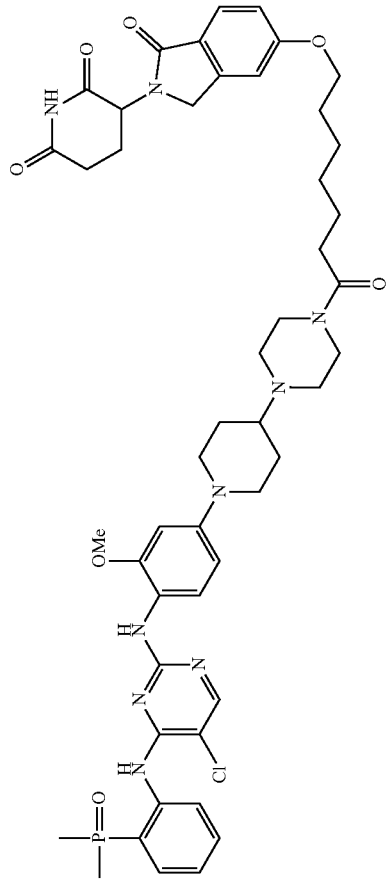 | 3-(5-((7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxoheptyl)oxy)-1-oxoisoindolin-2-yl)piperidine-2,6-dione |
| | 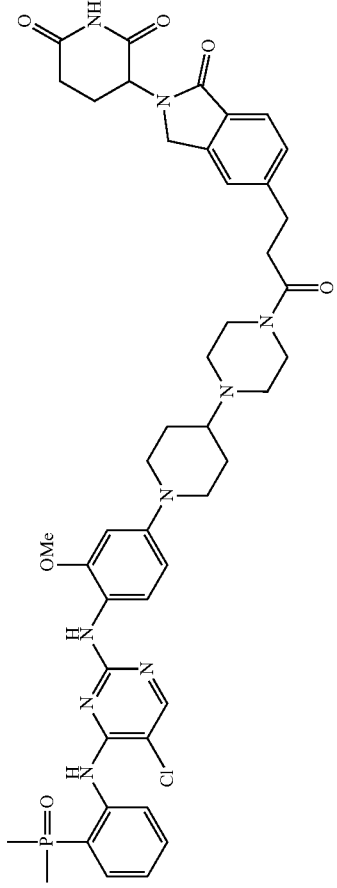 | 3-(5-(3-(4-(1-(4-((5-chloro-4-((2-(dimethylphosphono)phenyl)amino)pyrimidin-2-yl)amino)-3-methoxyphenyl)piperidin-4-yl)piperazin-1-yl)-3-oxopropyl)-1-oxoisoindolin-2-yl)piperidine-2,6-dione |

TABLE 2-continued

| Compound number | Structural formula | Compound name |
|---|---|---|
| | 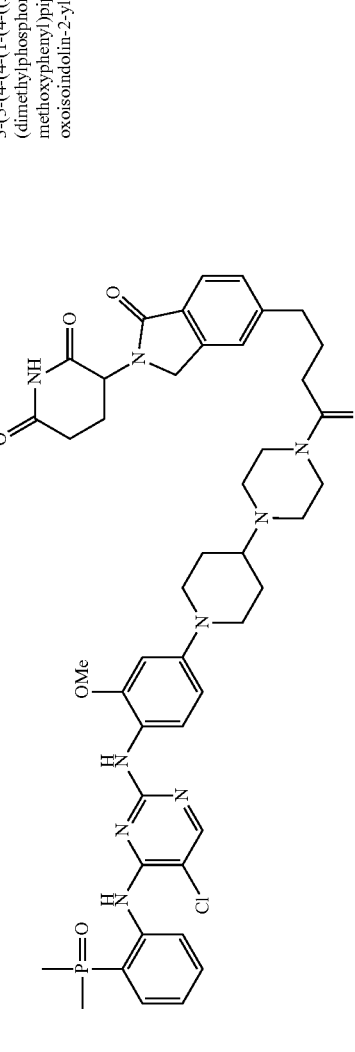 | 3-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)-4-oxobutyl)-1-oxoisoindolin-2-yl)piperidine-2,6-dione |
| | 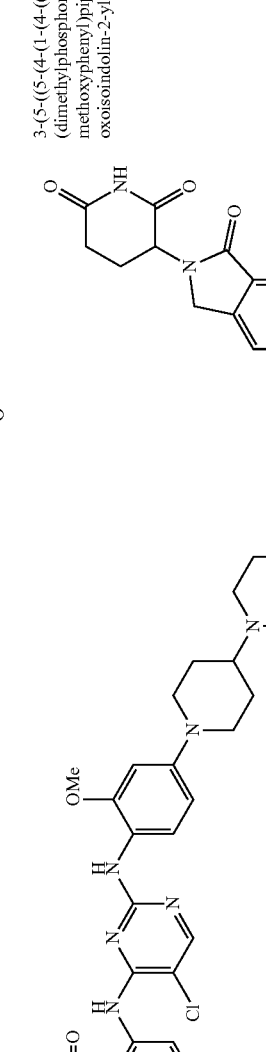 | 3-(5-((5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)-1-oxoisoindolin-2-yl)piperidine-2,6-dione |

| Compound number | Structural formula | Compound name |
|---|---|---|
| | 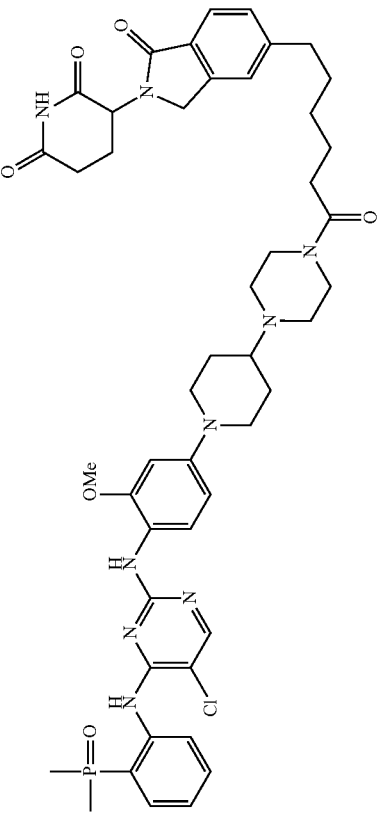 | 3-(5-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)-1-oxoisoindolin-2-yl)piperidine-2,6-dione<br><br>3-(5-(7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxoheptyl)-1-oxoisoindolin-2-yl)piperidine-2,6-dione |

TABLE 2-continued

| Compound number | Structural formula | Compound name |
|---|---|---|
| | 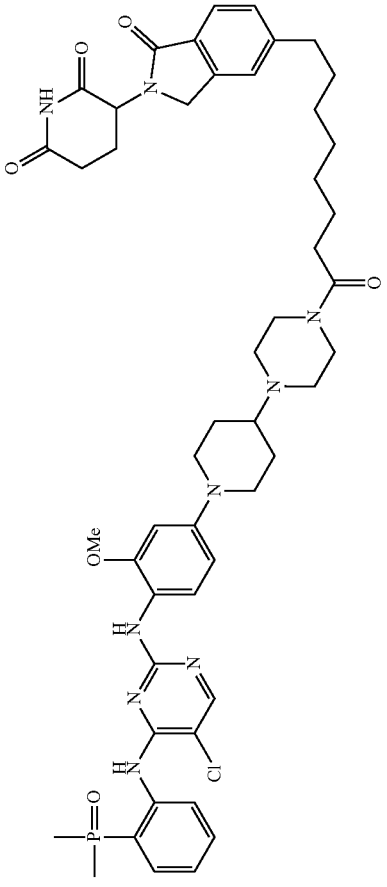 | 3-(5-(8-(4-(1-(4-((5-chloro-4-((2-(dimethylphosphono)phenyl)amino)pyrimidin-2-yl)amino)-3-methoxyphenyl)piperidin-4-yl)piperazin-1-yl)-8-oxooctyl)-1-oxoisoindolin-2-yl)piperidine-2,6-dione |
| | 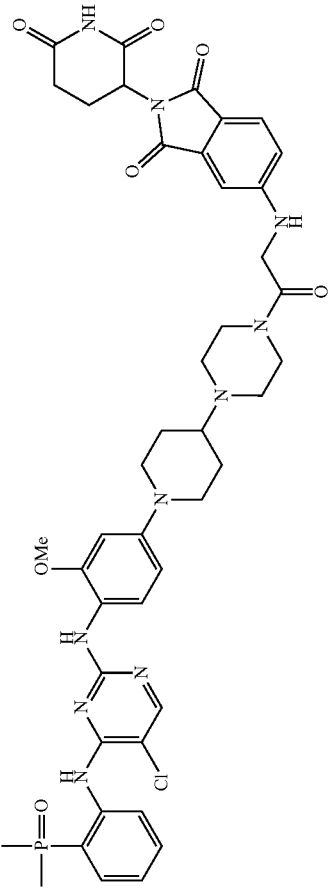 | 5-((2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethyl)amino)-2-(2,6-dioxopiperidin-3-yl)isoindoline-1,3-dione |

TABLE 2-continued

| Compound number | Structural formula | Compound name |
|---|---|---|
| | 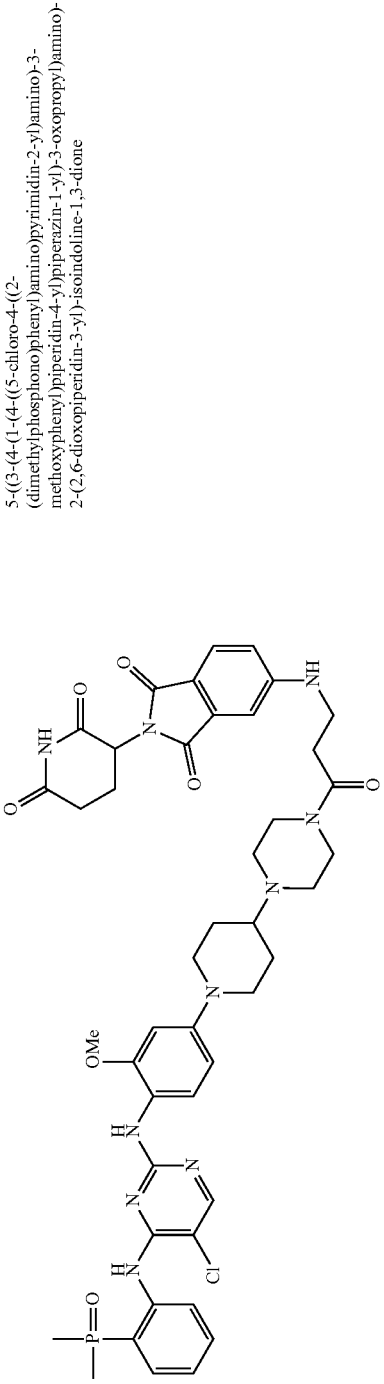 | 5-(3-(4-(1-(4-((5-chloro-4-((2-(dimethylphosphono)phenyl)amino)pyrimidin-2-yl)amino)-3-methoxyphenyl)piperidin-4-yl)piperazin-1-yl)-3-oxopropyl)amino)-2-(2,6-dioxopiperidin-3-yl)-isoindoline-1,3-dione<br><br>5-((4-(4-(1-(4-((5-chloro-4-((2-(dimethylphosphono)phenyl)amino)pyrimidin-2-yl)amino)-3-methoxyphenyl)piperidin-4-yl)piperazin-1-yl)-4-oxobutyl)amino)-2-(2,6-dioxopiperidin-3-yl)-isoindoline-1,3-dione |

TABLE 2-continued

| Compound number | Structural formula | Compound name |
|---|---|---|
| | 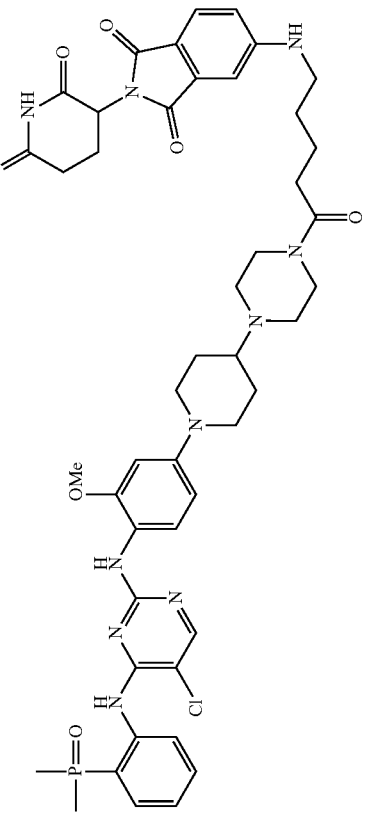 | 5-((5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)amino)-2-(2,6-dioxopiperidin-3-yl)-isoindoline-1,3-dione<br><br>5-((6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)amino)-2-(2,6-dioxopiperidin-3-yl)-isoindoline-1,3-dione |

TABLE 2-continued

| Compound number | Structural formula | Compound name |
|---|---|---|
| | 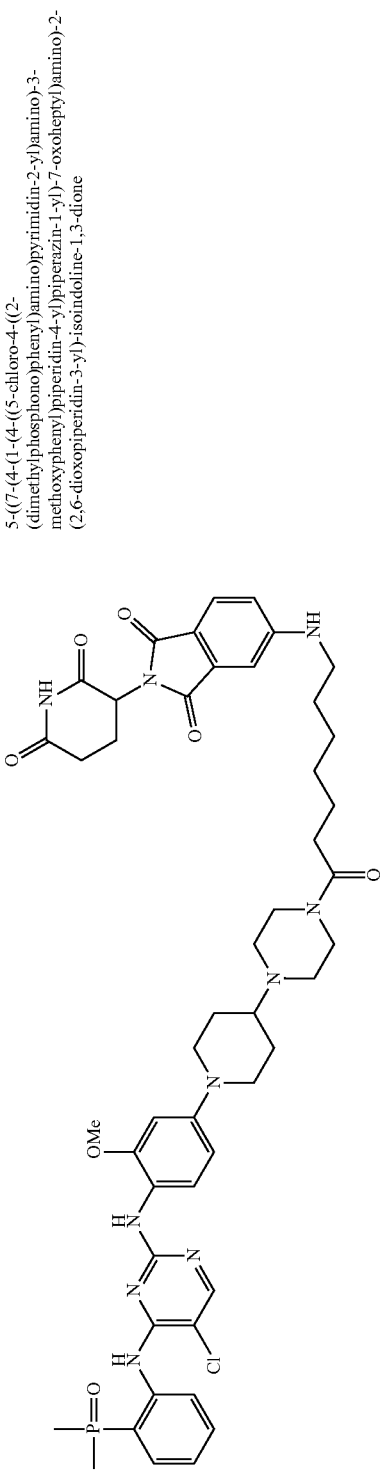 | 5-((7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxoheptyl)amino)-2-(2,6-dioxopiperidin-3-yl)-isoindoline-1,3-dione |
| | 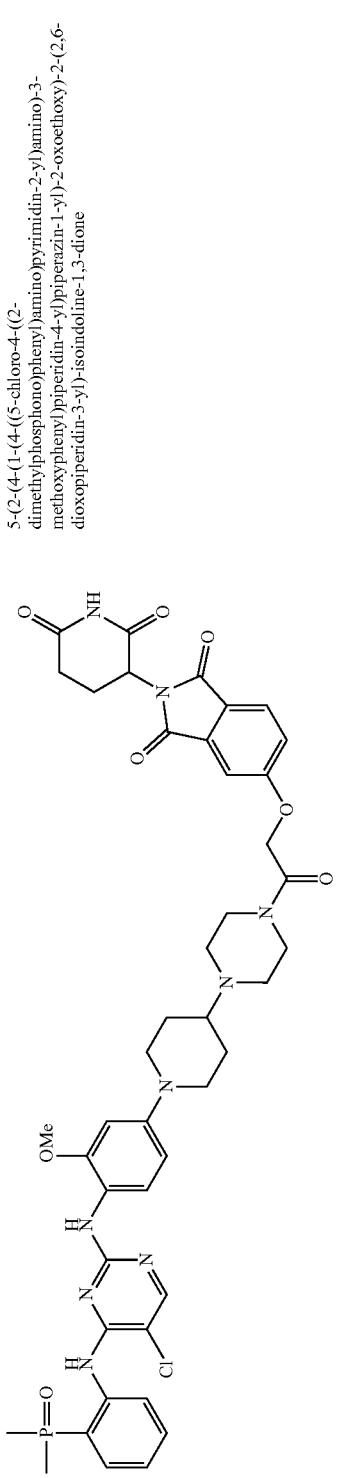 | 5-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethoxy)-2-(2,6-dioxopiperidin-3-yl)-isoindoline-1,3-dione |

TABLE 2-continued

| Compound number | Structural formula | Compound name |
|---|---|---|
| | 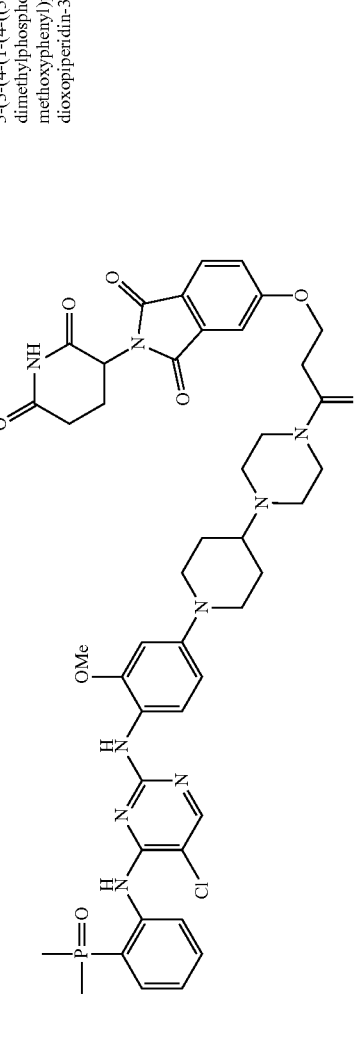 | 5-(3-(4-(1-(4-((5-chloro-4-((2-dimethylphosphono)phenyl)amino)pyrimidin-2-yl)amino)-3-methoxyphenyl)piperidin-4-yl)piperazin-1-yl)-3-oxopropoxy)-2-(2,6-dioxopiperidin-3-yl)-isoindoline-1,3-dione |
| | 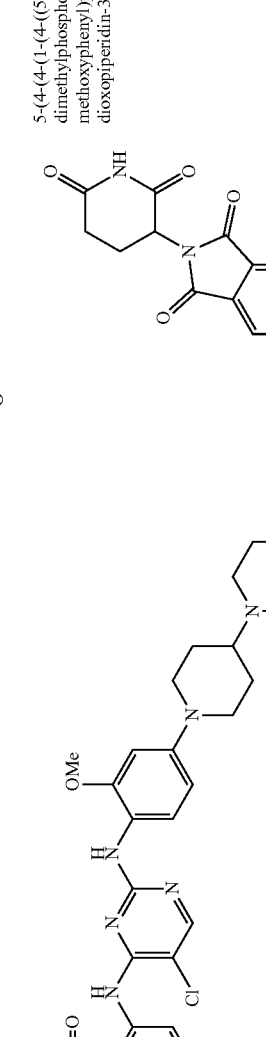 | 5-(4-(4-(1-(4-((5-chloro-4-((2-dimethylphosphono)phenyl)amino)pyrimidin-2-yl)amino)-3-methoxyphenyl)piperidin-4-yl)piperazin-1-yl)-4-oxobutoxy)-2-(2,6-dioxopiperidin-3-yl)-isoindoline-1,3-dione |

| Compound number | Structural formula | Compound name |
|---|---|---|
| | 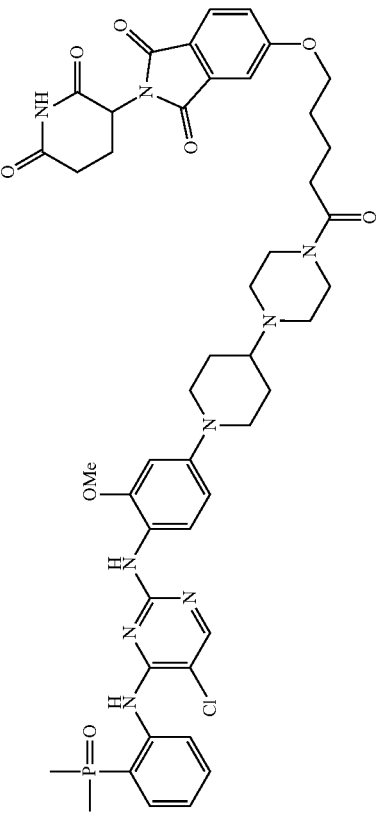 | 5-(5-(4-(1-(4-((5-chloro-4-((2-(dimethylphosphonophenyl)amino)pyrimidin-2-yl)amino)-3-methoxyphenyl)piperidin-4-yl)piperazin-1-yl)-5-oxopentyl)oxy)-2-(2,6-dioxopiperidin-3-yl)isoindoline-1,3-dione |
| | | 3-(5-(((1-(4-((5-chloro-4-((2-(dimethylphosphonophenyl)amino)pyrimidin-2-yl)amino)-3-methoxyphenyl)piperidin-4-yl)amino)methyl)amino)-1-oxoisoindolin-2-yl)piperidine-2,6-dione |
| | 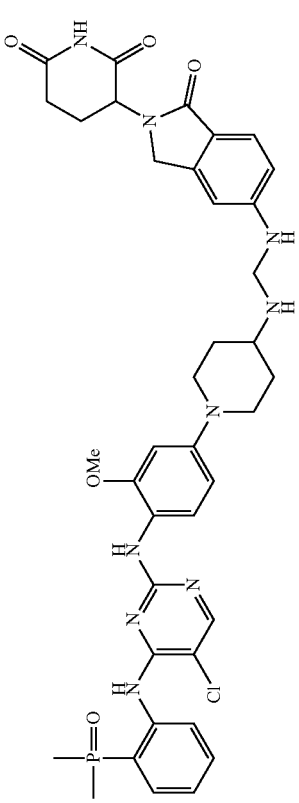 | 3-(5-((2-((1-(4-((5-chloro-4-((2-(dimethylphosphonophenyl)amino)pyrimidin-2-yl)amino)-3-methoxyphenyl)piperidin-4-yl)amino)ethyl)amino)-1-oxoisoindolin-2-yl)piperidine-2,6-dione |

TABLE 2-continued

| Compound number | Structural formula | Compound name |
|---|---|---|
| | | 3-(5-((3-((1-(4-((5-chloro-4-((2-(dimethylphosphonophenyl)amino)pyrimidin-2-yl)amino)-3-methoxyphenyl)piperidin-4-yl)amino)propyl)amino)-1-oxoisoindolin-2-yl)piperidine-2,6-dione |
| | | 3-(5-((4-((1-(4-((5-chloro-4-((2-(dimethylphosphonophenyl)amino)pyrimidin-2-yl)amino)-3-methoxyphenyl)piperidin-4-yl)amino)butyl)amino)-1-oxoisoindolin-2-yl)piperidine-2,6-dione |
| | | 3-(5-((5-((1-(4-((5-chloro-4-((2-(dimethylphosphonophenyl)amino)pyrimidin-2-yl)amino)-3-methoxyphenyl)piperidin-4-yl)amino)pentyl)amino)-1-oxoisoindolin-2-yl)piperidine-2,6-dione |

TABLE 2-continued

| Compound number | Structural formula | Compound name |
|---|---|---|
| | | 3-(5-((6-((1-(4-((5-chloro-4-((2-(dimethylphosphono)phenyl)amino)pyrimidin-2-yl)amino)-3-methoxyphenyl)piperidin-4-yl)amino)hexyl)amino)-1-oxoisoindolin-2-yl)piperidine-2,6-dione |
| | | 3-(5-((7-((1-(4-((5-chloro-4-((2-(dimethylphosphono)phenyl)amino)pyrimidin-2-yl)amino)-3-methoxyphenyl)piperidin-4-yl)amino)heptyl)amino)-1-oxoisoindolin-2-yl)piperidine-2,6-dione |
| | | 3-(5-(((1-(4-((5-chloro-4-((2-(dimethylphosphono)phenyl)amino)pyrimidin-2-yl)amino)-3-methoxyphenyl)piperidin-4-yl)amino)methoxy)-1-oxoisoindolin-2-yl)piperidine-2,6-dione |

TABLE 2-continued

| Compound number | Structural formula | Compound name |
|---|---|---|
| | | 3-(5-(2-((1-(4-((5-chloro-4-((2-(dimethylphosphono)phenyl)amino)pyrimidin-2-yl)amino)-3-methoxyphenyl)piperidin-4-yl)amino)ethoxy)-1-oxoisoindolin-2-yl)piperidine-2,6-dione |
| | | 3-(5-(3-((1-(4-((5-chloro-4-((2-(dimethylphosphono)phenyl)amino)pyrimidin-2-yl)amino)-3-methoxyphenyl)piperidin-4-yl)amino)propoxy)-1-oxoisoindolin-2-yl)piperidine-2,6-dione |
| | | 3-(5-(4-((1-(4-((5-chloro-4-((2-(dimethylphosphono)phenyl)amino)pyrimidin-2-yl)amino)-3-methoxyphenyl)piperidin-4-yl)amino)butoxy)-1-oxoisoindolin-2-yl)piperidine-2,6-dione |

| Compound number | Structural formula | Compound name |
|---|---|---|
| | 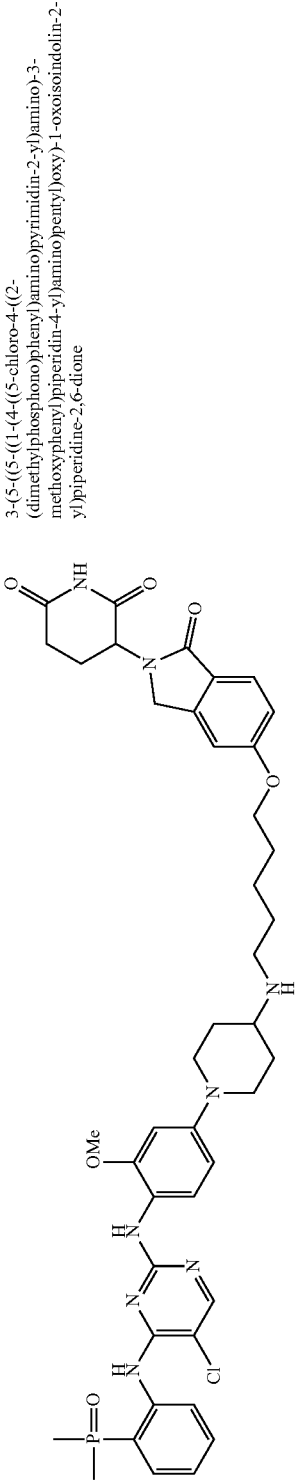 | 3-(5-((5-(1-(4-((5-chloro-4-((2-(dimethylphosphono)phenyl)amino)pyrimidin-2-yl)amino)-3-methoxyphenyl)piperidin-4-yl)amino)pentyl)oxy)-1-oxoisoindolin-2-yl)piperidine-2,6-dione |
| | | 3-(5-((6-(1-(4-((5-chloro-4-((2-(dimethylphosphono)phenyl)amino)pyrimidin-2-yl)amino)-3-methoxyphenyl)piperidin-4-yl)amino)hexyl)oxy)-1-oxoisoindolin-2-yl)piperidine-2,6-dione |
| | 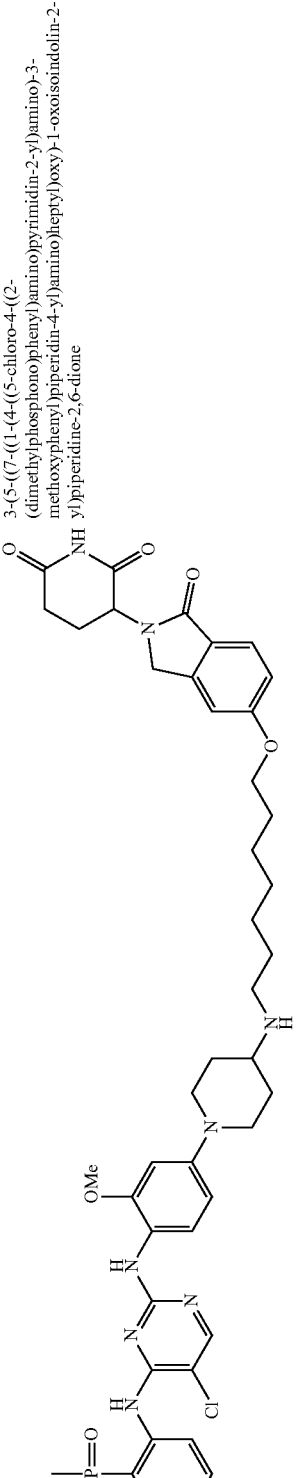 | 3-(5-((7-(1-(4-((5-chloro-4-((2-(dimethylphosphono)phenyl)amino)pyrimidin-2-yl)amino)-3-methoxyphenyl)piperidin-4-yl)amino)heptyl)oxy)-1-oxoisoindolin-2-yl)piperidine-2,6-dione |

TABLE 2-continued

| Compound number | Structural formula | Compound name |
|---|---|---|
| | | 3-(5-(2-((1-(4-((5-chloro-4-((2-(dimethylphosphonophenyl)amino)pyrimidin-2-yl)amino)-3-methoxyphenyl)piperidin-4-yl)amino)ethyl)-1-oxoisoindolin-2-yl)piperidine-2,6-dione |
| | | 3-(5-(3-((1-(4-((5-chloro-4-((2-(dimethylphosphonophenyl)amino)pyrimidin-2-yl)amino)-3-methoxyphenyl)piperidin-4-yl)amino)propyl)-1-oxoisoindolin-2-yl)piperidine-2,6-dione |
| | | 3-(5-(4-((1-(4-((5-chloro-4-((2-(dimethylphosphonophenyl)amino)pyrimidin-2-yl)amino)-3-methoxyphenyl)piperidin-4-yl)amino)butyl)-1-oxoisoindolin-2-yl)piperidine-2,6-dione |

TABLE 2-continued

| Compound number | Structural formula | Compound name |
|---|---|---|
| | | 3-{5-(5-((1-(4-((5-chloro-4-((2-(dimethylphosphonophenyl)amino)pyrimidin-2-yl)amino-3-methoxyphenyl)piperidin-4-yl)amino)pentyl)-1-oxoisoindolin-2-yl)piperidine-2,6-dione |
| | | 3-{5-(6-((1-(4-((5-chloro-4-((2-(dimethylphosphonophenyl)amino)pyrimidin-2-yl)amino)-3-methoxyphenyl)piperidin-4-yl)amino)hexyl)-1-oxoisoindolin-2-yl)piperidine-2,6-dione |
| | | 3-{5-(7-((1-(4-((5-chloro-4-((2-(dimethylphosphonophenyl)amino)pyrimidin-2-yl)amino)-3-methoxyphenyl)piperidin-4-yl)amino)heptyl)-1-oxoisoindolin-2-yl)piperidine-2,6-dione |

TABLE 2-continued
| Compound number | Structural formula | Compound name |
|---|---|---|
| | 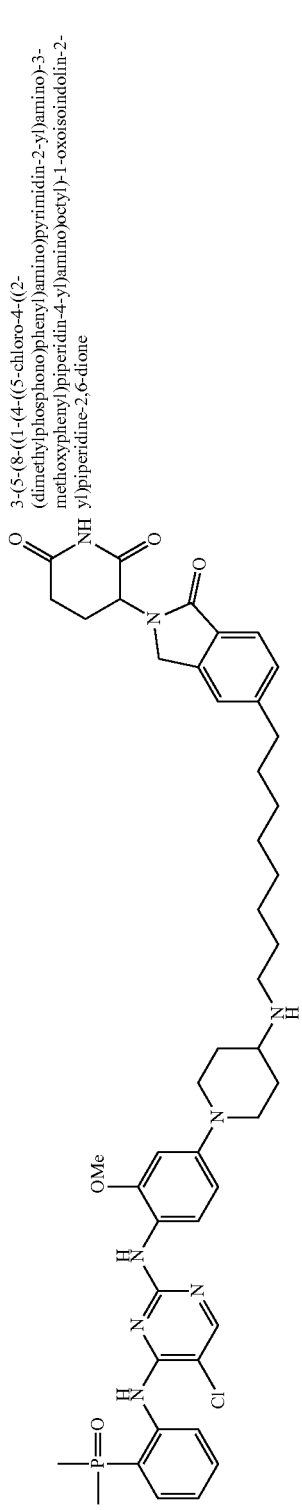 | 3-(5-(8-((1-(4-((5-chloro-4-((2-(dimethylphosphono)phenyl)amino)pyrimidin-2-yl)amino)-3-methoxyphenyl)piperidin-4-yl)amino)octyl)-1-oxoisoindolin-2-yl)piperidine-2,6-dione |

Another aspect of the present disclosure also provides a pharmaceutical composition, comprising the compound represented by formula (III) of the present disclosure or the pharmaceutically acceptable salt thereof, and a pharmaceutically acceptable carrier.

The pharmaceutical composition described in the present disclosure further comprises at least one additional medicament for the treatment or prevention of cancer.

In another aspect of the present disclosure, the compound represented by formula (III) of the present disclosure, or the pharmaceutically acceptable salt thereof for use as a medicament.

In another aspect of the present disclosure, the compound represented by formula (III), or the pharmaceutically acceptable salt thereof described in the present disclosure for use in the prevention and/or treatment of cancer. In an embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus)large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, smoldering myeloma, smoldering multiple myeloma and myelofibrosis; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK)mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

In another aspect of the present disclosure, the compound represented by formula (III), or the pharmaceutically acceptable salt thereof described in the present disclosure for use in the preparation of a medicament for the prevention and/or treatment of cancer. In a sub-embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus)large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus)large B-cell lymphoma and refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, myelofibrosis, smoldering myeloma and smoldering multiple myeloma; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/ primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK)mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

Another aspect of the present disclosure also provides a method for treating or preventing cancer, comprising administering a therapeutically effective amount of the compound represented by formula (III) of the present disclosure, or the pharmaceutically acceptable salt thereof, or the pharmaceutical composition to a subject. In an embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus)large B-cell lymphoma, primary mediastinal (thymus))large B-cell lymphoma, recurrent transformed non-Hodgkin's lymphoma, refractory B-cell non-Hodgkin's lymphoma, refractory diffuse large B-cell lymphoma, refractory primary mediastinal (thymus)large B-cell lymphoma and refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, myelofibrosis, smoldering myeloma and smoldering multiple myeloma; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

In the method for treating or preventing cancer described in the present disclosure, the compound represented by formula (III) described in the present disclosure, or the pharmaceutically acceptable salt thereof, or the pharmaceutical composition is administrated to a subject by at least one administration mode selected from nasal administration, inhalation administration, topical administration, oral administration, oral mucosal administration, rectal administration, pleural cavity administration, peritoneal administration, vaginal administration, intramuscular administration, subcutaneous administration, transdermal administration, epidural administration, intrathecal administration and intravenous administration.

III. Another Aspect of the Present Disclosure Provides the Following Compound Represented in Table 3 and the Salt Thereof (Especially the Pharmaceutically Acceptable Salt) are Particularly Preferred:

TABLE 3

| Compound number | Structural formula | Compound name |
|---|---|---|
| SIAIS262091 | (structure) | 8-(4-(4-(4-[(2-(2,6-dioxopiperidin-3-yl)-1-oxoisoindolin-4-yl)aminoacetyl]piperazin-1-yl)piperidin-1-yl)-9-ethyl-6,6-dimethyl-11-oxo-6,11-dihydro-5H-benzo[b]carbazole-3-carbonitrile |
| SIAIS262092 | (structure) | 8-(4-(4-(4-((2-(2,6-dioxopiperidin-3-yl)-1-oxoisoindolin-4-yl)amino)butyryl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| SIAIS262093 | | 8-(4-(4-(5-((2-(2,6-dioxopiperidin-3-yl)-1-oxoisoindolin-4-yl)amino)pentanoyl)piperazin-1-yl)piperidin-1-yl)-9-ethyl-6,6-dimethyl-11-oxo-6,11-dihydro-5H-benzo[b]carbazole-3-carbonitrile |
| SIAIS262095 | | 8-(4-(4-(7-((2-(2,6-dioxopiperidin-3-yl)-1-oxoisoindolin-4-yl)amino)heptanoyl)piperazin-1-yl)piperidin-1-yl)-9-ethyl-6,6-dimethyl-1-oxo-6,11-dihydro-5H-benzo[b]carbazole-3-carbonitrile |
| | | 8-(4-(4-(2-((2-(2,6-dioxopiperidin-3-yl)-1-oxoisoindolin-4-yl)amino)ethyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | | 8-(4-(4-(3-((2-(2,6-dioxopiperidin-3-yl)-1-oxoisoindolin-4-yl)amino)propyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(4-((2-(2,6-dioxopiperidin-3-yl)-1-oxoisoindolin-4-yl)amino)butyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(5-((2-(2,6-dioxopiperidin-3-yl)-1-oxoisoindolin-4-yl)amino)pentyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| 263 | 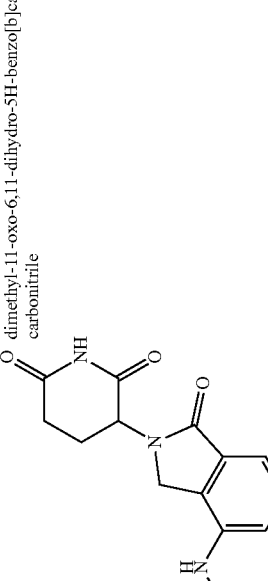 | 8-(4-(4-(7-((2-(2,6-dioxopiperidin-3-yl)-1-oxoisoindolin-4-yl)amino)heptyl)piperazin-1-yl)piperidin-1-yl)-9-ethyl-6,6-dimethyl-11-oxo-6,11-dihydro-5H-benzo[b]carbazole-3-carbonitrile |
| 264 | 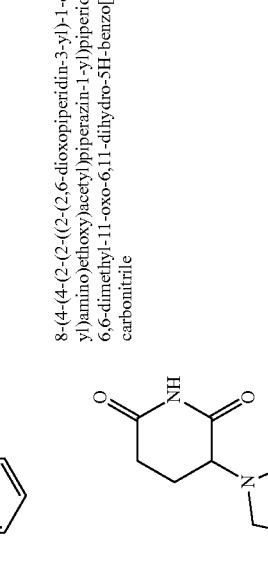 | 8-(4-(4-(2-(2-((2-(2,6-dioxopiperidin-3-yl)-1-oxoisoindolin-4-yl)amino)ethoxy)acetyl)piperazin-1-yl)piperidin-1-yl)-9-ethyl-6,6-dimethyl-11-oxo-6,11-dihydro-5H-benzo[b]carbazole-3-carbonitrile |
|  | 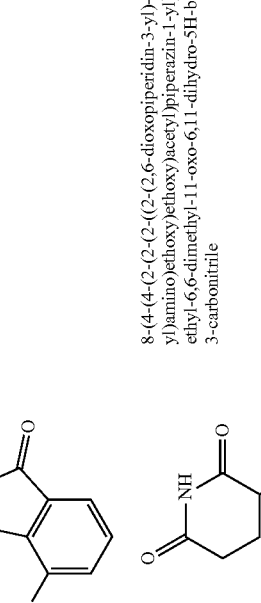 | 8-(4-(4-(2-(2-(2-((2-(2,6-dioxopiperidin-3-yl)-1-oxoisoindolin-4-yl)amino)ethoxy)ethoxy)acetyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | 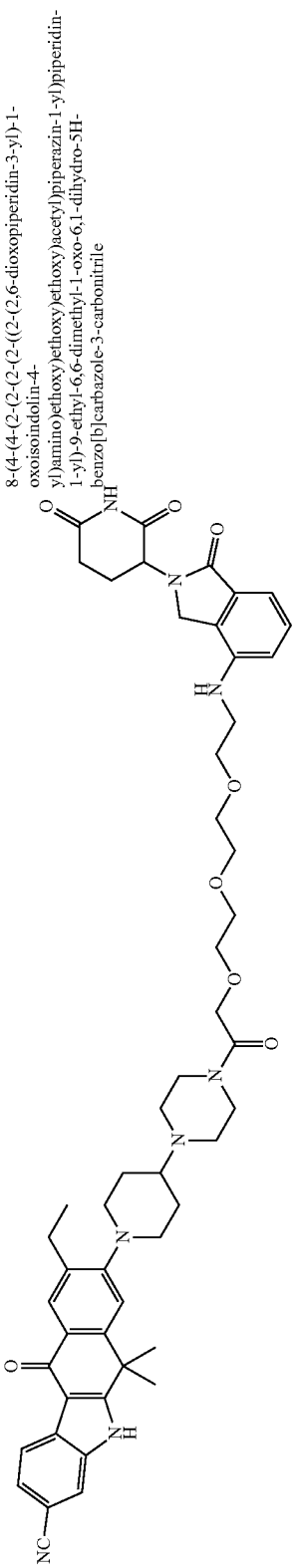 | 8-(4-(4-(2-(2-(2-(2-((2-(2,6-dioxopiperidin-3-yl)-1-oxoisoindolin-4-yl)amino)ethoxy)ethoxy)ethoxy)acetyl)piperazin-1-yl)piperidin-1-yl)-9-ethyl-6,6-dimethyl-1-oxo-6,1-dihydro-5H-benzo[b]carbazole-3-carbonitrile |
| | | 8-(4-(4-(14-((2-(2,6-dioxopiperidin-3-yl)-1-oxoisoindolin-4-yl)amino)-3,6,9,12-tetraoxatetradecanoyl-1-acyl)piperazin-1-yl)piperidin-1-yl)-9-ethyl-6,6-dimethyl-11-oxo-6,11-dihydro-5H-benzo[b]carbazole-3-carbonitrile |
| | 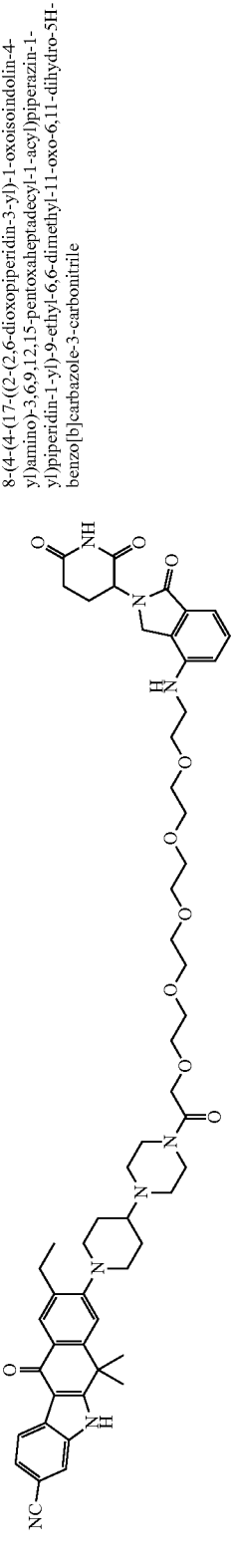 | 8-(4-(4-(17-((2-(2,6-dioxopiperidin-3-yl)-1-oxoisoindolin-4-yl)amino)-3,6,9,12,15-pentoxaheptadecyl-1-acyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| SIAIS293010 | 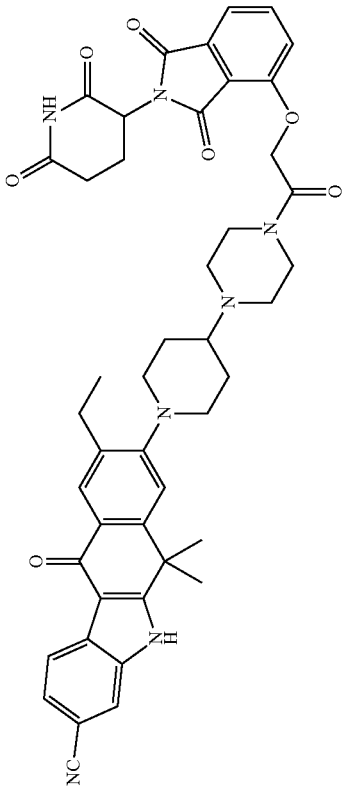 | 8-(4-(4-(2-((2-(2,6-dioxopiperidin-3-yl)-1,3-dioxoisoindolin-4-yl)oxy)acetyl)piperazin-1-yl)piperidin-1-yl)-9-ethyl-6,6-dimethyl-11-oxo-6,11-dihydro-5H-benzo[b]carbazole-3-carbonitrile |
| | 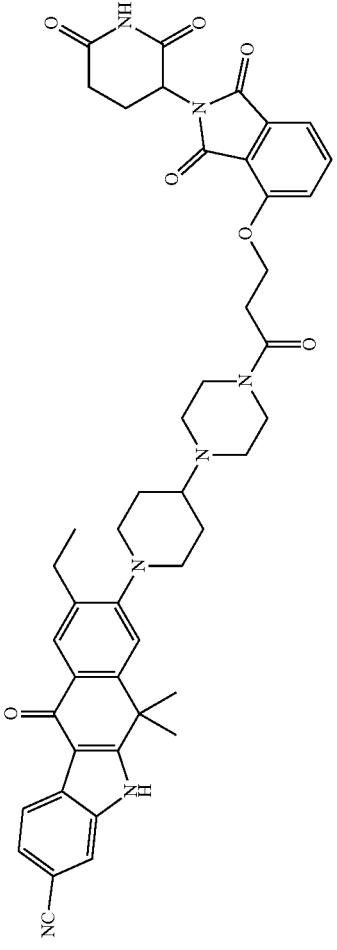 | 8-(4-(4-(3-((2-(2,6-dioxopiperidin-3-yl)-1,3-dioxoisoindolin-4-yl)oxy)propionyl)piperazin-1-yl)piperidin-1-yl)-9-ethyl-6,6-dimethyl-11-oxo-6,11-dihydro-5H-benzo[b]carbazole-3-carbonitrile |
| | 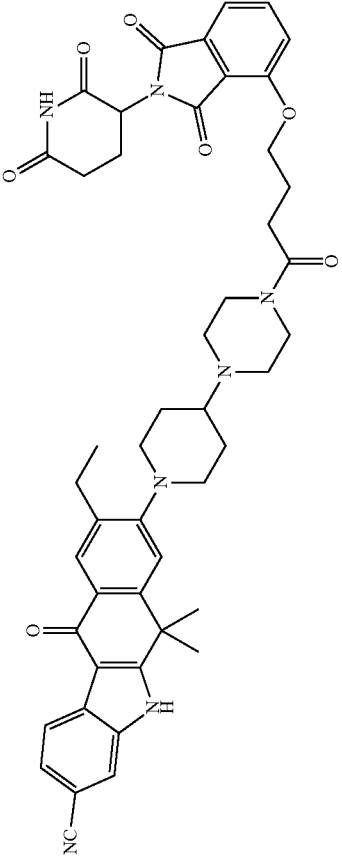 | 8-(4-(4-(4-((2-(2,6-dioxopiperidin-3-yl)-1,3-dioxoisoindolin-4-yl)oxy)butyryl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | | 8-(4-(4-(5-((2-(2,6-dioxopiperidin-3-yl)-1,3-dioxoisoindolin-4-yl)oxy)pentanoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(7-((2-(2,6-dioxopiperidin-3-yl)-1,3-dioxoisoindolin-4-yl)oxy)heptanoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(2-((2-(2,6-dioxopiperidin-3-yl)-1-oxoisoindolin-4-yl)oxy)acetyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| 271 | | 8-(4-(4-(3-((2-(2,6-dioxopiperidin-3-yl)-1-oxoisoindolin-4-yl)oxy)propionyl)piperazin-1-yl)piperidin-1-yl)-9-ethyl-6,6-dimethyl-11-oxo-6,11-dihydro-5H-benzo[b]carbazole-3-carbonitrile |
| 272 | | 8-(4-(4-(4-((2-(2,6-dioxopiperidin-3-yl)-1-oxoisoindolin-4-yl)oxy)butyryl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(5-((2-(2,6-dioxopiperidin-3-yl)-1-oxoisoindolin-4-yl)oxy)pentanoyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | | 8-(4-(4-(6-((2-(2,6-dioxopiperidin-3-yl)-1-oxoisoindolin-4-yl)oxy)hexanoyl)piperazin-1-yl)piperidin-1-yl)-9-ethyl-6,6-dimethyl-11-oxo-6,1-dihydro-5H-benzo[b]carbazole-3-carbonitrile |
| | | 8-(4-(4-(7-((2-(2,6-dioxopiperidin-3-yl)-1-oxoisoindolin-4-yl)oxy)heptanoyl)piperazin-1-yl)piperidin-1-yl)-9-ethyl-6,6-dimethyl-11-oxo-6,1-dihydro-5H-benzo[b]carbazole-3-carbonitrile |
| | | 8-(4-(4-(2-(2-(2,6-dioxopiperidin-3-yl)-1-oxoisoindolin-4-yl)ethyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| SIAIS293005 | 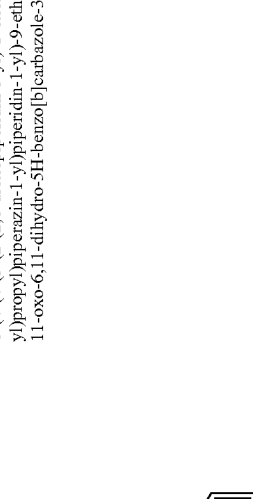 | 8-(4-(4-(3-(2-(2,6-dioxopiperidin-3-yl)-1-oxoisoindolin-4-yl)propyl)piperazin-1-yl)piperidin-1-yl)-9-ethyl-6,6-dimethyl-11-oxo-6,11-dihydro-5H-benzo[b]carbazole-3-carbonitrile |
| | 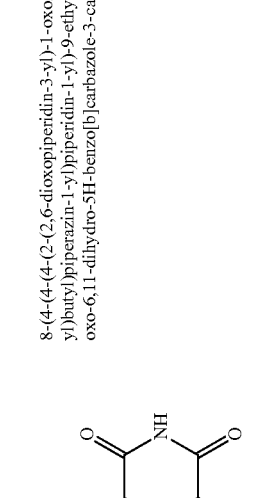 | 8-(4-(4-(4-(2-(2,6-dioxopiperidin-3-yl)-1-oxoisoindolin-4-yl)butyl)piperazin-1-yl)piperidin-1-yl)-9-ethyl-6,6-dimethyl-11-oxo-6,11-dihydro-5H-benzo[b]carbazole-3-carbonitrile |
| SIAIS350083 | 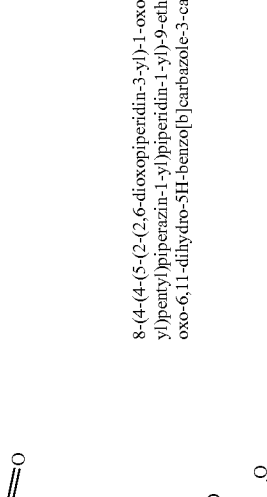 | 8-(4-(4-(5-(2-(2,6-dioxopiperidin-3-yl)-1-oxoisoindolin-4-yl)pentyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| 277 | | 8-(4-(4-(6-(2-(2,6-dioxopiperidin-3-yl)-1-oxoisoindolin-4-yl)hexyl)piperazin-1-yl)piperidin-1-yl)-9-ethyl-6,6-dimethyl-11-oxo-6,11-dihydro-5H-benzo[b]carbazole-3-carbonitrile |
| 278 | | 8-(4-(4-(3-((2-(2,6-dioxopiperidin-3-yl)-1,3-dioxoisoindolin-4-yl)amino)propyl)piperazin-1-yl)piperidin-1-yl)-9-ethyl-6,6-dimethyl-11-oxo-6,11-dihydro-5H-benzo[b]carbazole-3-carbonitrile |
|  | | 8-(4-(4-((2-(2,6-dioxopiperidin-3-yl)-1,3-dioxoisoindolin-4-yl)amino)butyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| SIAIS293008 | | 8-(4-(4-(5-((2-(2,6-dioxopiperidin-3-yl)-1,3-dioxoisoindolin-4-yl)amino)pentyl)piperazin-1-yl)piperidin-1-yl)-9-ethyl-6,6-dimethyl-11-oxo-6,11-dihydro-5H-benzo[b]carbazole-3-carbonitrile |
| SIAIS293009 | | 8-(4-(4-(6-((2-(2,6-dioxopiperidin-3-yl)-1,3-dioxoisoindolin-4-yl)amino)hexyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | | 8-(4-(4-(2-(2-(2,6-dioxopiperidin-3-yl)-1-oxoisoindolin-4-yl)ethyl)phenethyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(2-(4-(2-(2-(2,6-dioxopiperidin-3-yl)-1-oxoisoindolin-4-yl)ethyl)piperazin-1-yl)ethyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| SIAIS293012 | | N-(1-(3-cyano-9-ethyl-6,6-dimethyl-11-oxo-6,11-dihydro-5H-benzo[b]carbazol-8-yl)piperidin-4-yl)-5-((2-(2,6-dioxopiperidin-3-yl)-1-oxoisoindolin-4-yl)amino)pentanamide |
| SIAIS352107 | | 8-(4-(5-((2-(2,6-dioxopiperidin-3-yl)-1-oxoisoindolin-4-yl)amino)pentanoyl)piperazin-1-yl)-9-ethyl-6,6-dimethyl-11-oxo-6,11-dihydro-5H-benzo[b]carbazole-3-carbonitrile |
| SIAIS350081 | | 8-(4-(5-(2-(2,6-dioxopiperidin-3-yl)-1-oxoisoindolin-4-yl)pentyl)piperazin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| SLAIS293060 | 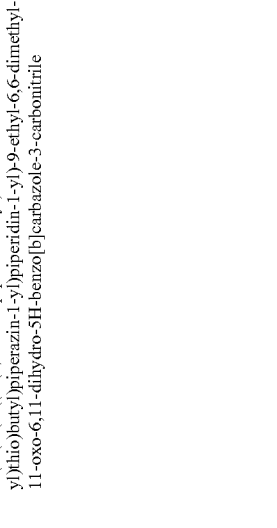 | 8-(4-(4-(4-((2-(2,6-dioxopiperidin-3-yl)-1-oxoisoindolin-4-yl)thio)butyl)piperazin-1-yl)piperidin-1-yl)-9-ethyl-6,6-dimethyl-11-oxo-6,11-dihydro-5H-benzo[b]carbazole-3-carbonitrile |
| SLAIS352054 | 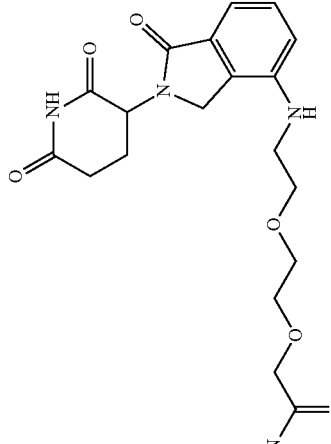 | 3-(4-((2-(2-(2-(4-(1-(4-((5-chloro-4-((2-(dimethylphosphono)phenyl)amino)pyrimidine-2-yl)amino)-3-methoxyphenyl)piperidin-4-yl)piperazin-1-yl)-2-oxoethoxy)ethoxy)ethyl)amino)-1-oxoisoindolin-2-yl)piperidine-2,6-dione |
| SLAIS352055 | 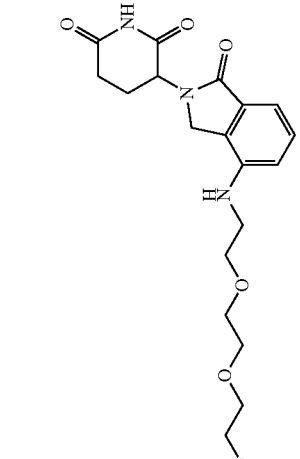 | 3-(4-((2-(2-(2-(2-(4-(1-(4-((5-chloro-4-((2-(dimethylphosphono)phenyl)amino)pyrimidine-2-yl)amino)-3-methoxyphenyl)piperidin-4-yl)piperazin-1-yl)-2-oxoethoxy)ethoxy)ethoxy)ethyl)amino)-1-oxoisoindolin-2-yl)piperidine-2,6-dione |

TABLE 3-continued

| Compound number | Structural formula | Compound name |
|---|---|---|
| SIAIS352056 | | 3-(4-((14-(4-(1-(4-((5-chloro-4-((2-(dimethylphosphono)phenyl)amino)pyrimidin-2-yl)amino)-3-methoxyphenyl)piperidin-4-yl)piperazin-1-yl)-14-oxo-3,6,9,12-tetraoxatetradecyl)amino)-1-oxoisoindolin-2-yl)piperidine-2,6-dione |
| SIAIS352057 | | 3-(4-((17-(4-(1-(4-((5-chloro-4-((2-(dimethylphosphono)phenyl)amino)pyrimidin-2-yl)amino)-3-methoxyphenyl)piperidin-4-yl)piperazin-1-yl)-17-oxo-3,6,9,12,15-pentaoxaheptadecyl)amino)-1-oxoisoindolin-2-yl)piperidine-2,6-dione |
| SIAIS293016 | | 4-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethoxy)-2-(2,6-dioxopiperidin-3-yl)isoindoline-1,3-dione |

TABLE 3-continued

| Compound number | Structural formula | Compound name |
|---|---|---|
| | 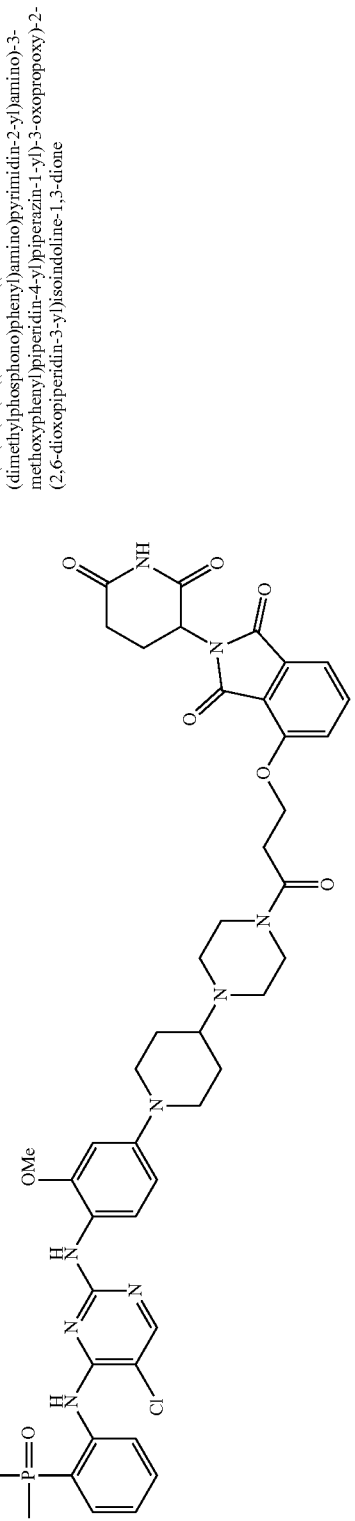 | 4-(3-(4-(1-(4-((5-chloro-4-((2-(dimethylphosphono)phenyl)amino)pyrimidin-2-yl)amino)-3-methoxyphenyl)piperidin-4-yl)piperazin-1-yl)-3-oxopropoxy)-2-(2,6-dioxopiperidin-3-yl)isoindoline-1,3-dione |
| | | 4-((5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)oxy)-2-(2,6-dioxopiperidin-3-yl)isoindoline-1,3-dione |

TABLE 3-continued

| Compound number | Structural formula | Compound name |
|---|---|---|
| | 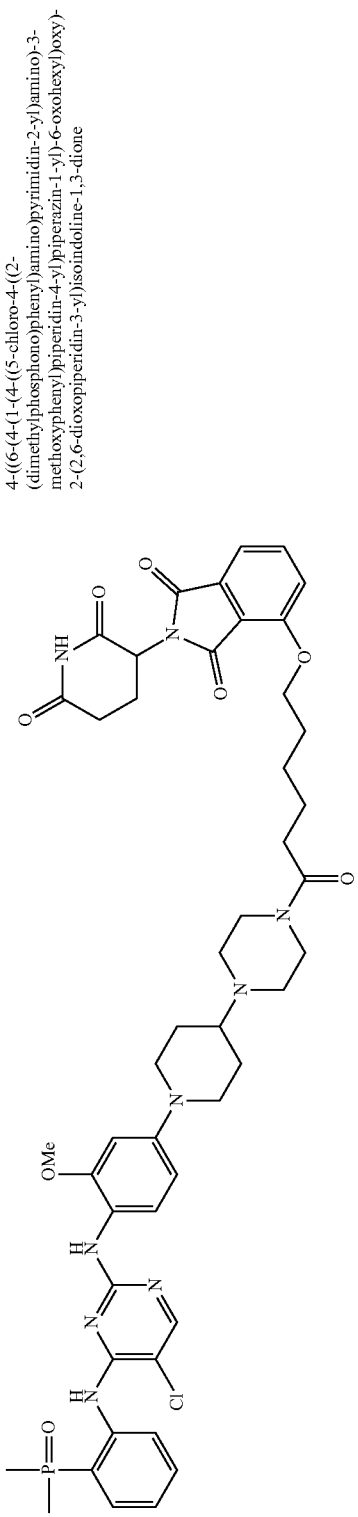 | 4-((6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)oxy)-2-(2,6-dioxopiperidin-3-yl)isoindoline-1,3-dione |
| | | 4-((7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxoheptyl)oxy)-2-(2,6-dioxopiperidin-3-yl)isoindoline-1,3-dione |

TABLE 3-continued

| Compound number | Structural formula | Compound name |
|---|---|---|
| | 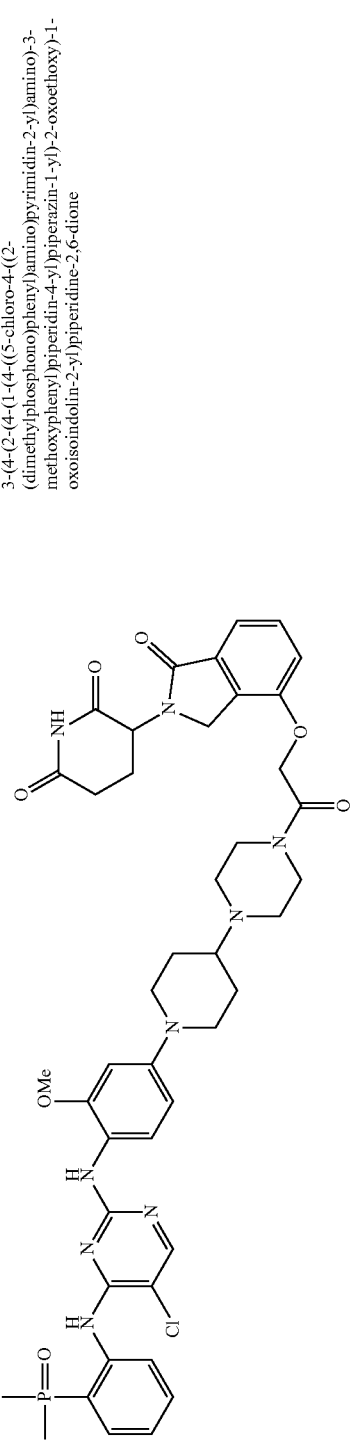 | 3-(4-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethoxy)-1-oxoisoindolin-2-yl)piperidine-2,6-dione |
| | | 3-(4-(3-(4-(1-(4-((5-chloro-4-((2-(dimethylphosphono)phenyl)amino)pyrimidin-2-yl)amino)-3-methoxyphenyl)piperidin-4-yl)piperazin-1-yl)-3-oxopropoxy)-1-oxoisoindolin-2-yl)piperidine-2,6-dione |

TABLE 3-continued

| Compound number | Structural formula | Compound name |
|---|---|---|
| | | 3-(4-((5-chloro-4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)oxy)-1-oxoisoindolin-2-yl)piperidine-2,6-dione |
| | | 3-(4-((6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)oxy)-1-oxoisoindolin-2-yl)piperidine-2,6-dione |

| Compound number | Structural formula | Compound name |
|---|---|---|
| | 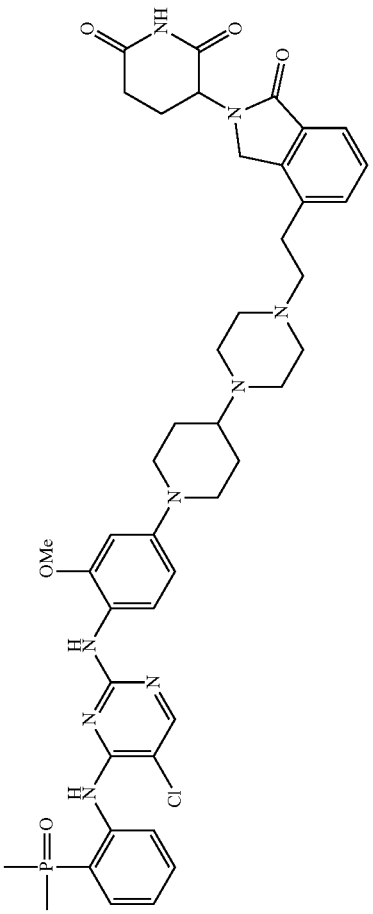 | 3-(4-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)ethyl)-1-oxoisoindolin-2-yl)piperidine-2,6-dione
3-(4-(3-(4-(1-(4-((5-chloro-4-((2-(dimethylphosphono)phenyl)amino)pyrimidin-2-yl)amino)-3-methoxyphenyl)piperidin-4-yl)piperazin-1-yl)ethyl)-1-oxoisoindolin-2-yl)piperidine-2,6-dione |

TABLE 3-continued

| Compound number | Structural formula | Compound name |
|---|---|---|
| SIAIS352059 | 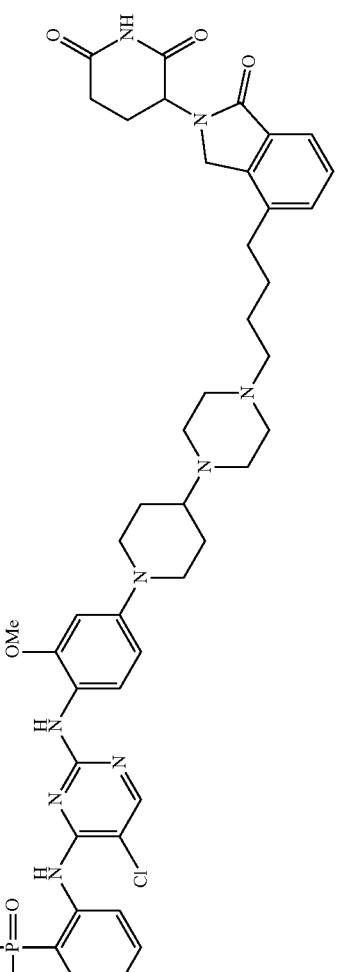 | 3-(4-(4-(1-(4-(5-chloro-4-((2-(dimethylphosphono)phenyl)amino)pyrimidin-2-yl)amino)-3-methoxyphenyl)piperidin-4-yl)piperazin-1-yl)butyl)-1-oxoisoindolin-2-yl)piperidine-2,6-dione |
| SIAIS352008 | 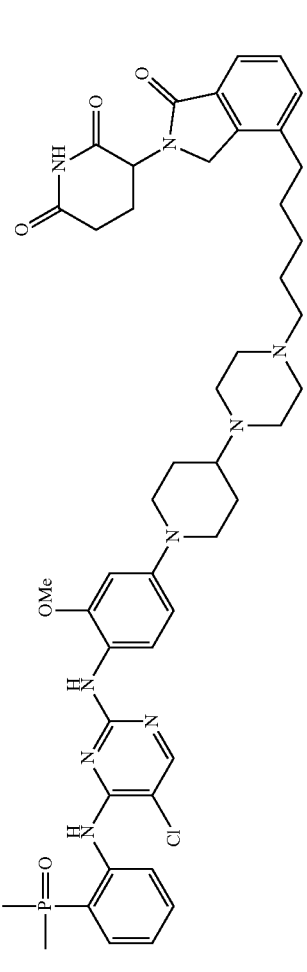 | 3-(4-(5-(4-(1-(4-(5-chloro-4-((2-(dimethylphosphono)phenyl)amino)pyrimidin-2-yl)amino)-3-methoxyphenyl)piperidin-4-yl)piperazin-1-yl)pentyl)-1-oxoisoindolin-2-yl)piperidine-2,6-dione |

TABLE 3-continued

| Compound number | Structural formula | Compound name |
|---|---|---|
| | 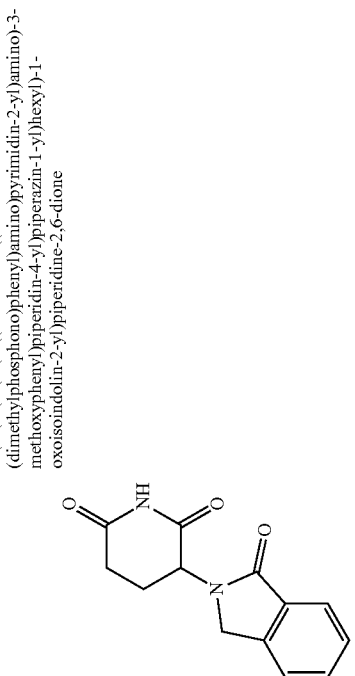 | 3-(4-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)hexyl)-1-oxoisoindolin-2-yl)piperidine-2,6-dione |
| | | 3-(4-(4-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)ethyl)phenethyl)-1-oxoisoindolin-2-yl)piperidine-2,6-dione |

TABLE 3-continued

| Compound number | Structural formula | Compound name |
|---|---|---|
| | 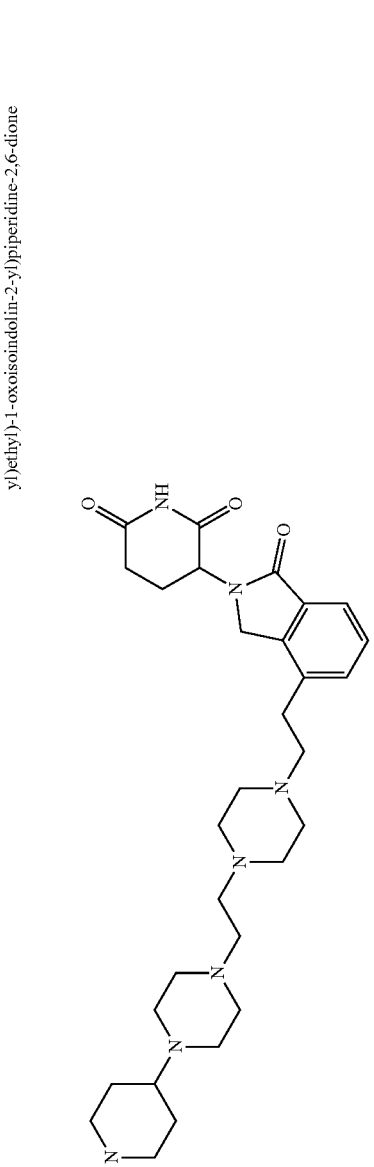 | 3-(4-(2-(4-(2-(4-(1-(4-((5-chloro-4-((2-(dimethyl)phosphono)phenyl)amino)pyrimidin-2-yl)amino)-3-methoxyphenyl)piperidin-4-yl)piperazin-1-yl)ethyl)piperazin-1-yl)ethyl)-1-oxoisoindolin-2-yl)piperidine-2,6-dione |
| | 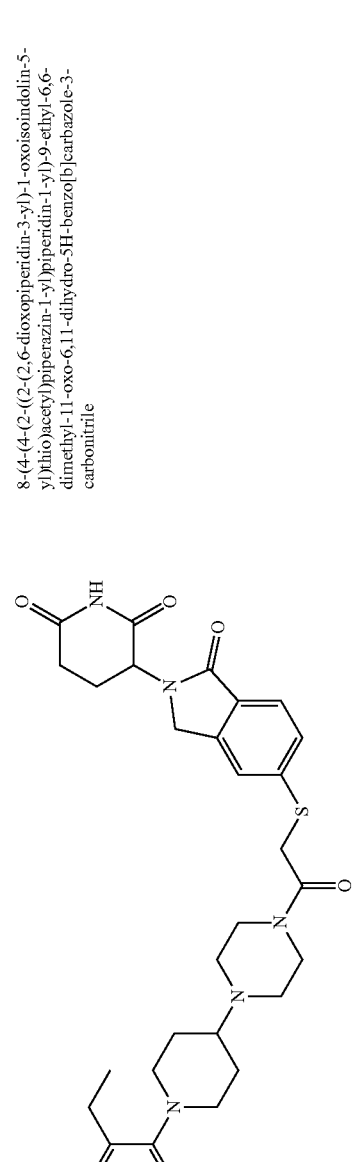 | 8-(4-(4-(2-((2-(2,6-dioxopiperidin-3-yl)-1-oxoisoindolin-5-yl)thio)acetyl)piperazin-1-yl)piperidin-1-yl)-9-ethyl-6,6-dimethyl-11-oxo-6,11-dihydro-5H-benzo[b]carbazole-3-carbonitrile |

TABLE 3-continued
| Compound number | Structural formula | Compound name |
|---|---|---|
| | 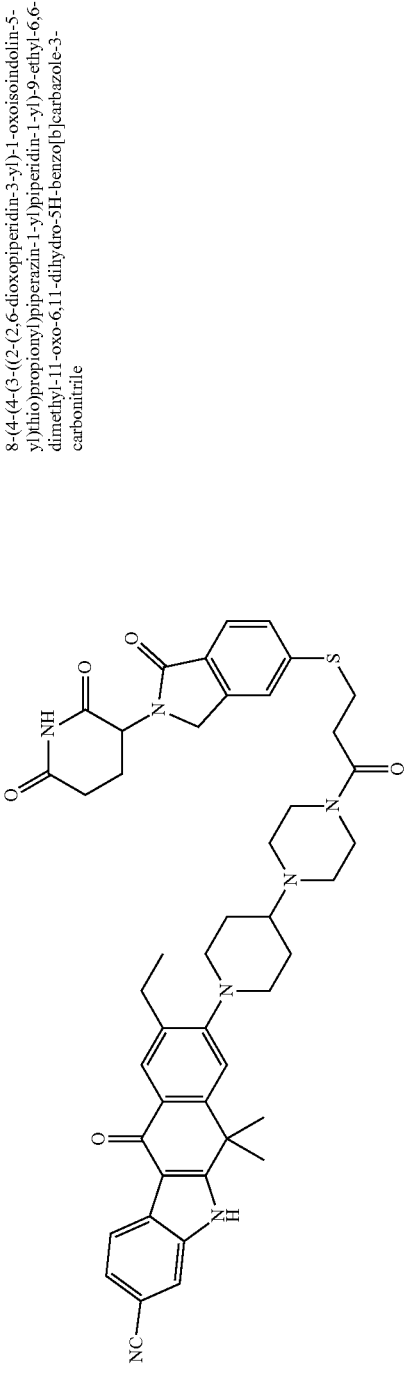 | 8-(4-(4-(3-((2-(2,6-dioxopiperidin-3-yl)-1-oxoisoindolin-5-yl)thio)propionyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(4-((2-(2,6-dioxopiperidin-3-yl)-1-oxoisoindolin-5-yl)thio)butyryl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | | 8-(4-(4-(5-((2-(2,6-dioxopiperidin-3-yl)-1-oxoisoindolin-5-yl)thio)pentanoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(6-((2-(2,6-dioxopiperidin-3-yl)-1-oxoisoindolin-5-yl)thio)hexanoyl)piperazin-1-yl)piperidin-1-yl)-9-ethyl-6,6-dimethyl-11-oxo-6,11-dihydro-5H-benzo[b]carbazole-3-carbonitrile |

TABLE 3-continued
| Compound number | Structural formula | Compound name |
|---|---|---|
| | 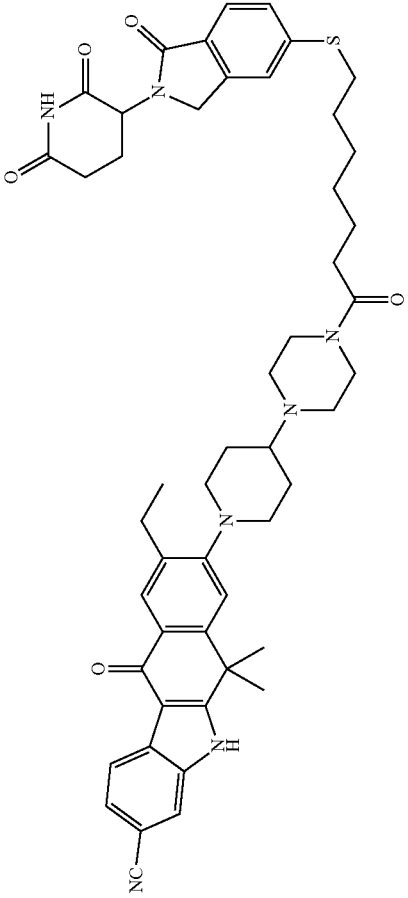 | 8-(4-(4-(7-((2-(2-(2,6-dioxopiperidin-3-yl)-1-oxoisoindolin-5-yl)thio)heptanoyl)piperazin-1-yl)piperidin-1-yl)-9-ethyl-6,6-dimethyl-11-oxo-6,11-dihydro-5H-benzo[b]carbazole-3-carbonitrile |
| | 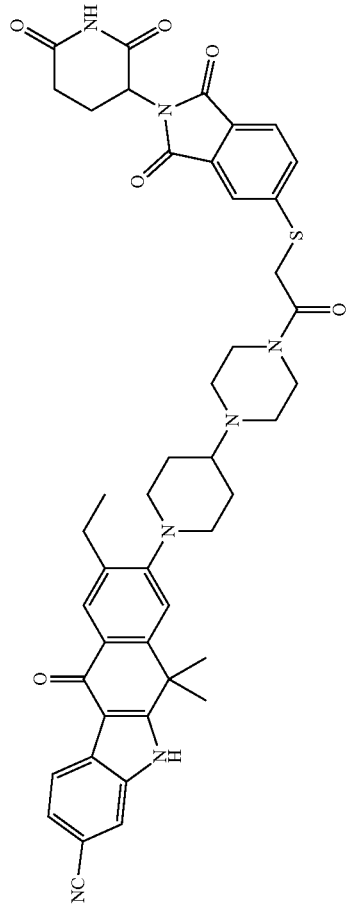 | 8-(4-(4-(2-((2-(2-(2,6-dioxopiperidin-3-yl)-1,3-dioxoisoindolin-5-yl)thio)acetyl)piperazin-1-yl)piperidin-1-yl)-9-ethyl-6,6-dimethyl-11-oxo-6,11-dihydro-5H-benzo[b]carbazole-3-carbonitrile |

TABLE 3-continued
| Compound number | Structural formula | Compound name |
|---|---|---|
| | 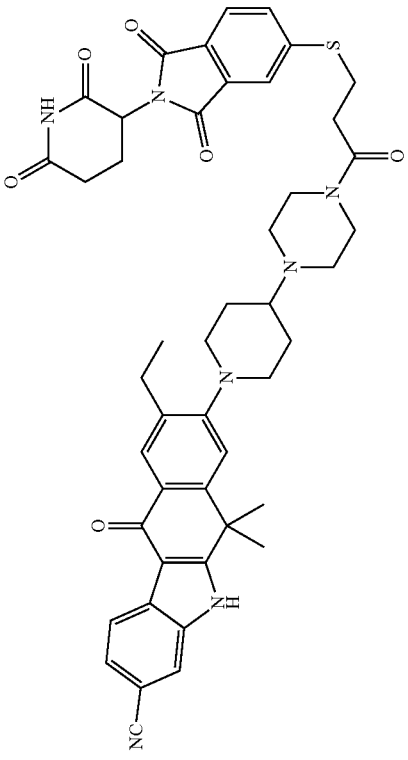 | 8-(4-(4-(3-((2-(2,6-dioxopiperidin-3-yl)-1,3-dioxoisoindolin-5-yl)thio)propionyl)piperazin-1-yl)piperidin-1-yl)-9-ethyl-6,6-dimethyl-11-oxo-6,11-dihydro-5H-benzo[b]carbazole-3-carbonitrile |
| | 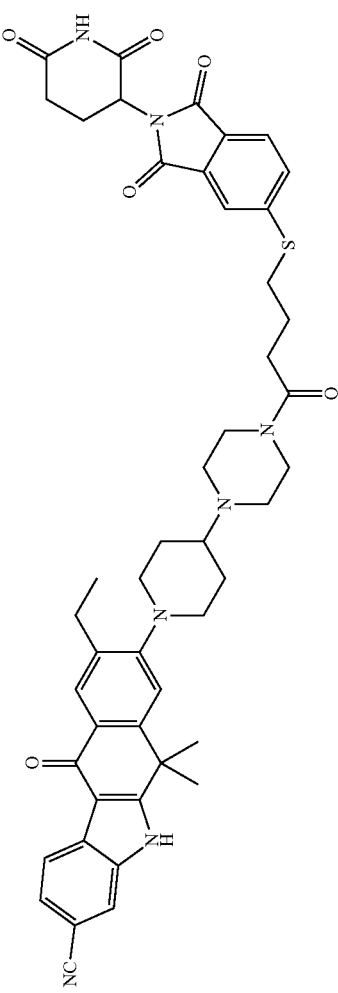 | 8-(4-(4-(4-((2-(2,6-dioxopiperidin-3-yl)-1,3-dioxoisoindolin-5-yl)thio)butyryl)piperazin-1-yl)piperidin-1-yl)-9-ethyl-6,6-dimethyl-11-oxo-6,11-dihydro-5H-benzo[b]carbazole-3-carbonitrile |

TABLE 3-continued
| Compound number | Structural formula | Compound name |
|---|---|---|
| | 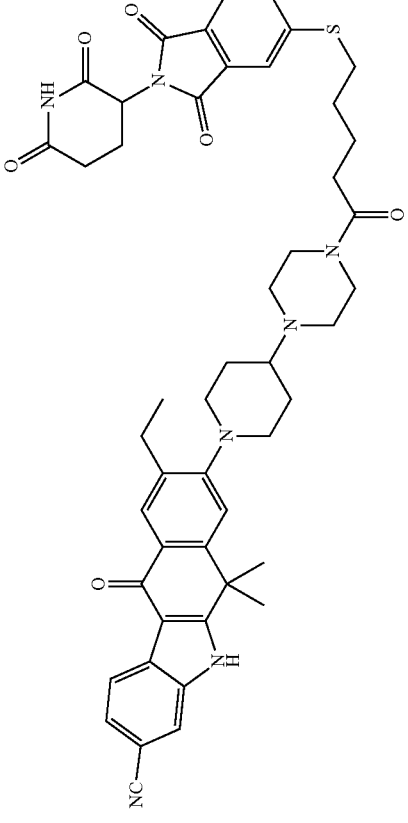 | 8-(4-(4-(5-((2-(2,6-dioxopiperidin-3-yl)-1,3-dioxoisoindolin-5-yl)thio)pentanoyl)piperazin-1-yl)piperidin-1-yl)-9-ethyl-6,6-dimethyl-11-oxo-6,11-dihydro-5H-benzo[b]carbazole-3-carbonitrile |
| | 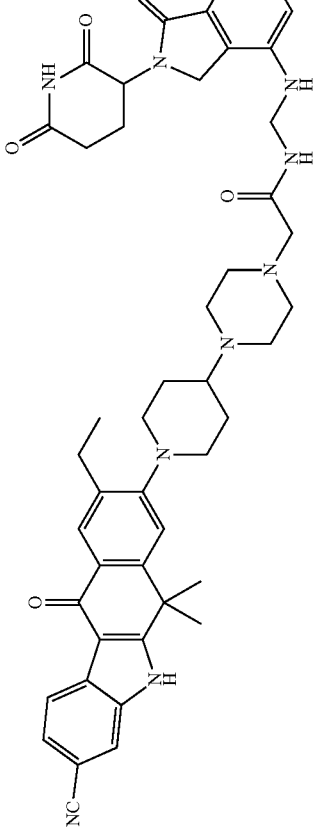 | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-((2-(2,6-dioxopiperidin-3-yl)-1-oxoisoindolin-4-yl)amino)methyl)acetamide |

TABLE 3-continued

| Compound number | Structural formula | Compound name |
|---|---|---|
| | | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-(2-((2-(2,6-dioxopiperidin-3-yl)-1-oxoisoindolin-4-yl)amino)ethyl)acetamide |
| | | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-(3-((2-(2,6-dioxopiperidin-3-yl)-1-oxoisoindolin-4-yl)amino)propyl)acetamide |
| | | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-(4-((2-(2,6-dioxopiperidin-3-yl)-1-oxoisoindolin-4-yl)amino)butyl)acetamide |

TABLE 3-continued

| Compound number | Structural formula | Compound name |
|---|---|---|
| | | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-(((2-(2,6-dioxopiperidin-3-yl)-1-oxoisoindolin-4-yl)oxy)methyl)acetamide |
| | | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-(2-((2-(2,6-dioxopiperidin-3-yl)-1-oxoisoindolin-4-yl)oxy)ethyl)acetamide |
| | | 2-(4-(1-(3-cyano-9-ethyl-6,6-dimethyl-11-oxo-6,11-dihydro-5H-benzo[b]carbazol-8-yl)piperidin-4-yl)piperazin-1-yl)-N-(3-((2-(2,6-dioxopiperidin-3-yl)-1-oxoisoindolin-4-yl)oxy)propyl)acetamide |

TABLE 3-continued

| Compound number | Structural formula | Compound name |
|---|---|---|
| | | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(4-((2-(2,6-dioxopiperidin-3-yl)-1-oxoisoindolin-4-yl)oxy)butyl)acetamide |
| | | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(((2-(2,6-dioxopiperidin-3-yl)-1-oxoisoindolin-4-yl)thio)methyl)acetamide |
| | | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(2-((2-(2,6-dioxopiperidin-3-yl)-1-oxoisoindolin-4-yl)thio)ethyl)acetamide |

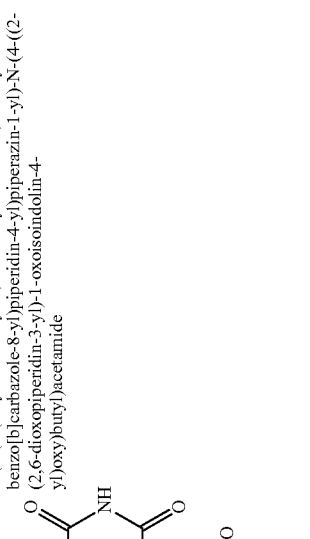
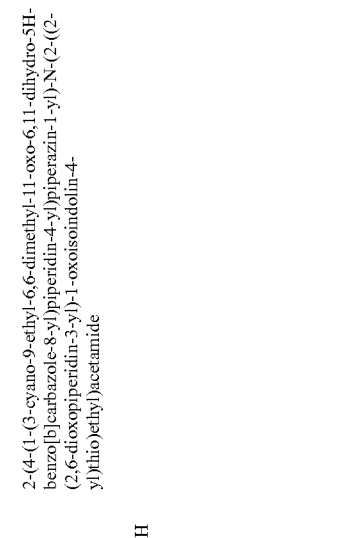

TABLE 3-continued

| Compound number | Structural formula | Compound name |
|---|---|---|
| | 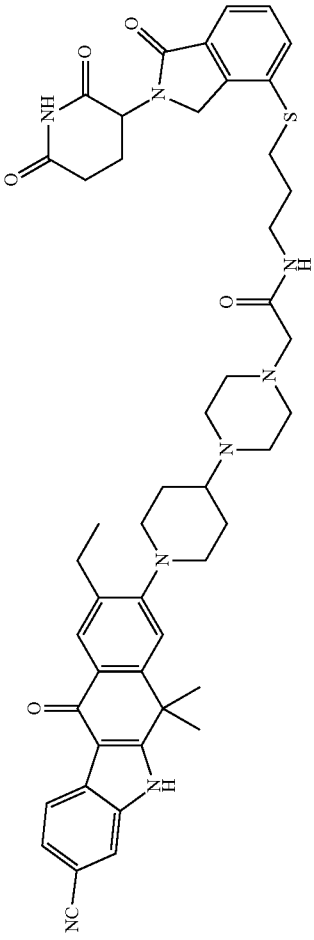 | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(3-((2-(2,6-dioxopiperidin-3-yl)-1-oxoisoindolin-4-yl)thio)propyl)acetamide |
| | | 2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(4-((2-(2,6-dioxopiperidin-3-yl)-1-oxoisoindolin-4-yl)thio)butyl)acetamide |
| SIAIS353007 | 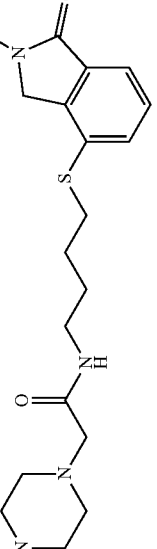 | N-(1-(4-((5-chloro-4-((2-(dimethyl)phosphonophenyl)amino)pyrimidin-2-yl)amino)-3-methoxyphenyl)piperidin-4-yl)-2-((2-(2,6-dioxopiperidin-3-yl)-1-oxoisoindolin-4-yl)thio)-N-methyl acetamide |

TABLE 3-continued

| Compound number | Structural formula | Compound name |
|---|---|---|
| SLAIS353009 | | N-(1-(4-((5-chloro-4-((2-(dimethylphosphono)phenyl)amino)pyrimidin-2-yl)amino)-3-methoxyphenyl)piperidin-4-yl)-6-((2-(2,6-dioxopiperidin-3-yl)-1-oxoisoindolin-4-yl)thio)-N-methyl hexanamide |
| SLAIS353043 | | 3-(4-((1-(4-((5-chloro-4-((2-(dimethylphosphono)phenyl)amino)pyrimidin-2-yl)amino)-3-methoxyphenyl)piperidin-4-yl)(methyl)amino)butyl)thio)-1-oxoisoindolin-2-yl)piperidine-2,6-dione |
| SLAIS353044 | | 3-(4-((5-((1-(4-((5-chloro-4-((2-(dimethylphosphono)phenyl)amino)pyrimidin-2-yl)amino)-3-methoxyphenyl)piperidin-4-yl)(methyl)amino)pentyl)thio)-1-oxoisoindolin-2-yl)piperidine-2,6-dione |

TABLE 3-continued

| Compound number | Structural formula | Compound name |
|---|---|---|
| SIAIS353041 | | 3-(4-((6-((1-(4-((5-chloro-4-((2-(dimethylphosphono)phenyl)amino)pyrimidin-2-yl)amino)-3-methoxyphenyl)piperidin-4-yl)(methyl)amino)hexyl)thio)-1-oxoisoindolin-2-yl)piperidine-2,6-dione |
| SIAIS353062 | | 4-(1-(4-((5-chloro-4-((2-(dimethylphosphono)phenyl)amino)pyrimidin-4-yl)amino)-3-methoxyphenyl)pyridin-4-yl)-N-(4-((2-(2,6-dioxopiperidin-3-yl)-1-oxoisoindolin-4-yl)thio)butyl)piperazine-1-carboxamide |
| SIAIS352011 | | 3-(4-((2-(4-(1-(4-((5-chloro-4-((2-(dimethylphosphono)phenyl)amino)pyrimidin-2-yl)amino)-3-methoxyphenyl)piperidin-4-yl)piperazin-1-yl)ethyl)thio)-1-oxoisoindolin-2-yl)piperidine-2,6-dione |

TABLE 3-continued

| Compound number | Structural formula | Compound name |
|---|---|---|
| SIAIS293189 | | 3-(4-((4-((4-(1-(4-((5-chloro-4-((2-(dimethylphosphono)phenyl)amino)pyrimidin-2-yl)amino)-3-methoxyphenyl)piperidin-4-yl)piperazin-1-yl)methyl)benzyl)thio)-1-oxoisoindolin-2-yl)piperidine-2,6-dione |
| | | 3-(5-((2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethyl)thio)-1-oxoisoindolin-2-yl)piperidine-2,6-dione |

TABLE 3-continued

| Compound number | Structural formula | Compound name |
|---|---|---|
| | 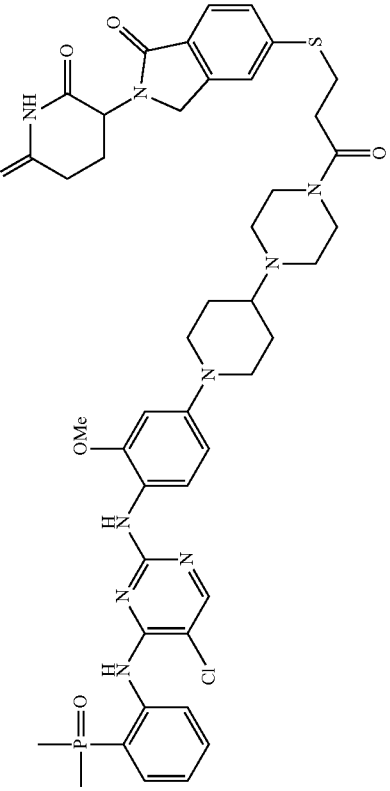 | 3-(5-((3-(4-((5-chloro-4-(1-(4-(4-((5-chloro-4-((2-(dimethylphosphono)phenyl)amino)pyrimidin-2-yl)amino)-3-methoxyphenyl)piperidin-4-yl)piperazin-1-yl)-3-oxopropyl)thio)-1-oxoisoindolin-2-yl)piperidine-2,6-dione |
| | 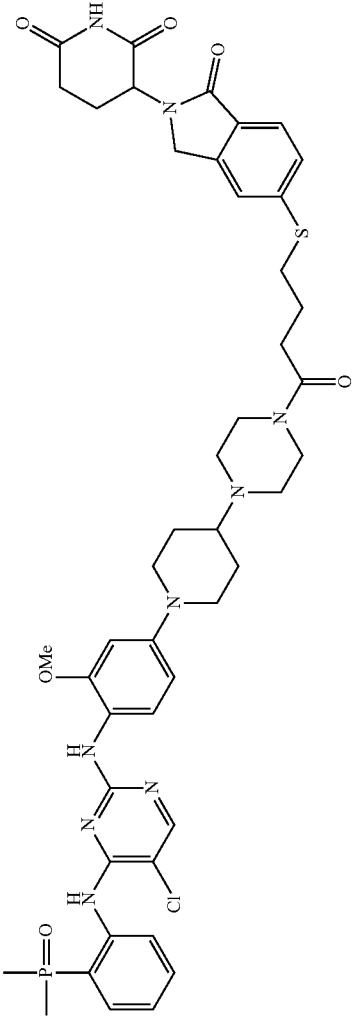 | 3-(5-((4-(4-(1-(4-(4-((5-chloro-4-((2-(dimethylphosphono)phenyl)amino)pyrimidin-2-yl)amino)-3-methoxyphenyl)piperidin-4-yl)piperazin-1-yl)-4-oxobutyl)thio)-1-oxoisoindolin-2-yl)piperidine-2,6-dione |

| Compound number | Structural formula | Compound name |
|---|---|---|
| | 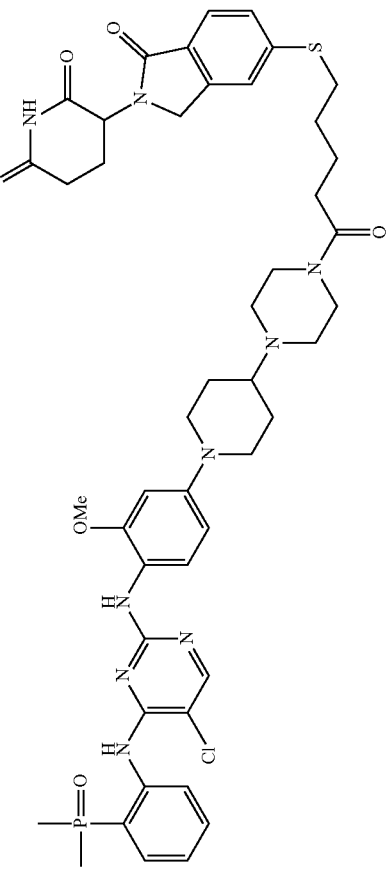 | 3-(5-((5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopentyl)thio)-1-oxoisoindolin-2-yl)piperidine-2,6-dione |
| | | 3-(5-((6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohexyl)thio)-1-oxoisoindolin-2-yl)piperidine-2,6-dione |

TABLE 3-continued

| Compound number | Structural formula | Compound name |
|---|---|---|
| | 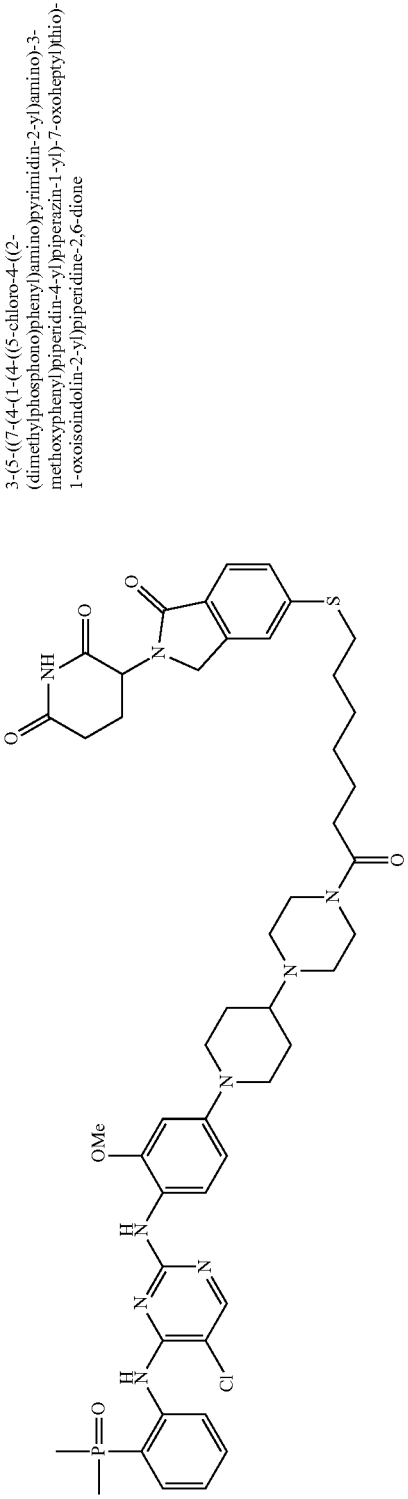 | 3-(5-((7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxoheptyl)thio)-1-oxoisoindolin-2-yl)piperidine-2,6-dione |
| | 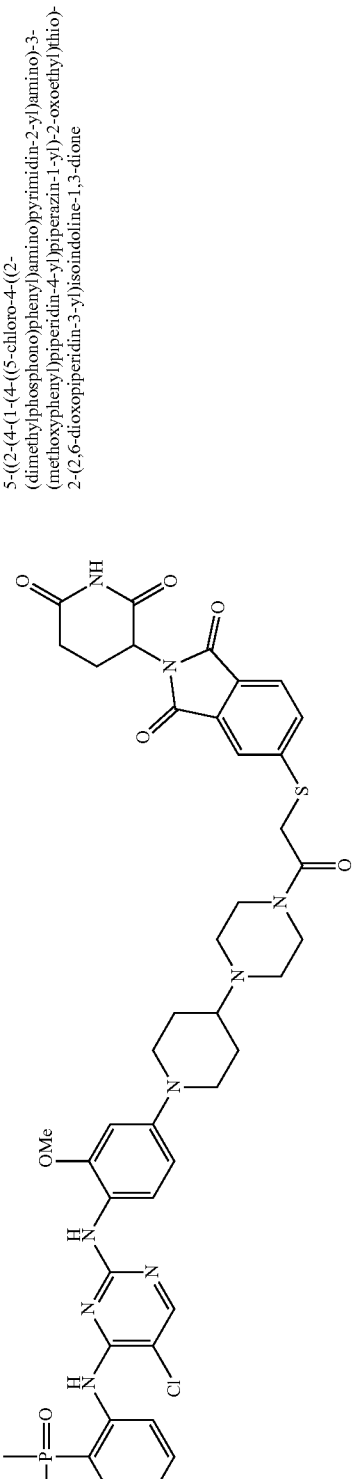 | 5-((2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethyl)thio)-2-(2,6-dioxopiperidin-3-yl)isoindoline-1,3-dione |

TABLE 3-continued

| Compound number | Structural formula | Compound name |
|---|---|---|
| | 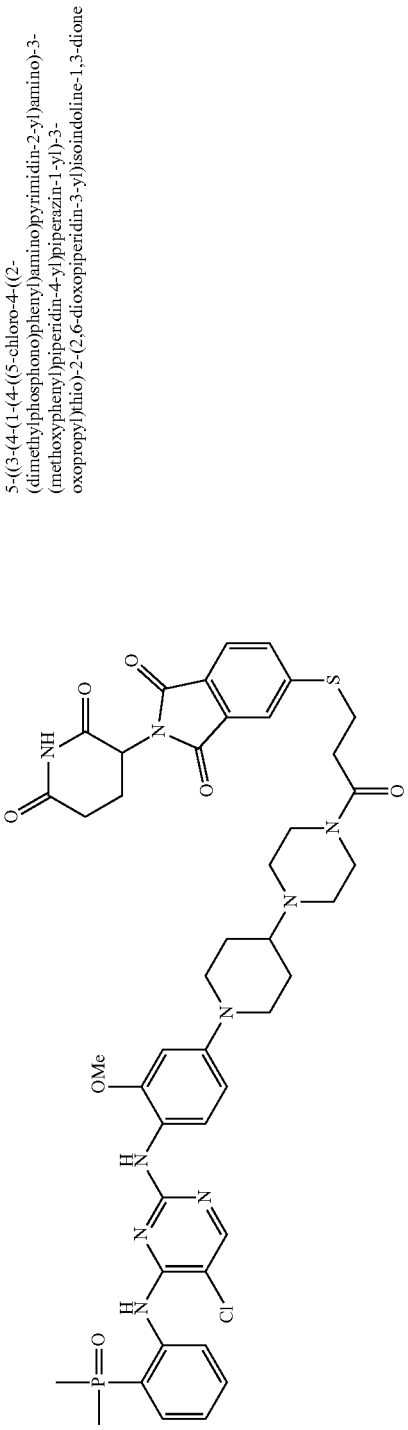 | 5-((3-(4-(1-(4-((5-chloro-4-((2-(dimethylphosphono)phenyl)amino)pyrimidin-2-yl)amino)-3-(methoxyphenyl)piperidin-4-yl)piperazin-1-yl)-3-oxopropyl)thio)-2-(2,6-dioxopiperidin-3-yl)isoindoline-1,3-dione |
| | | 5-((4-(4-(1-(4-((5-chloro-4-((2-(dimethylphosphono)phenyl)amino)pyrimidin-2-yl)amino)-3-(methoxyphenyl)piperidin-4-yl)piperazin-1-yl)-4-oxobutyl)thio)-2-(2,6-dioxopiperidin-3-yl)isoindoline-1,3-dione |

TABLE 3-continued

| Compound number | Structural formula | Compound name |
|---|---|---|
| | 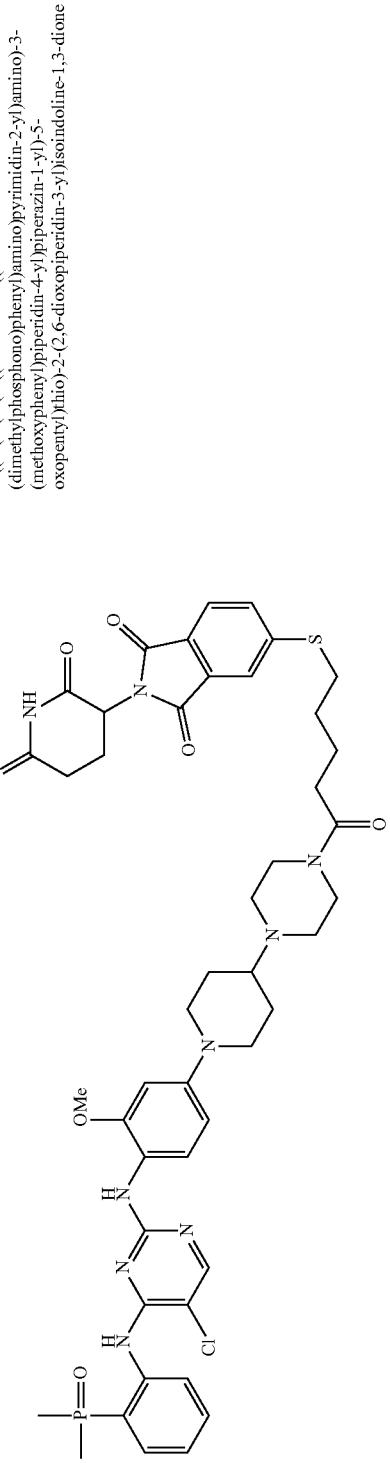 | 5-((5-(4-(1-(4-((5-chloro-4-((2-(dimethylphosphono)phenyl)amino)pyrimidin-2-yl)amino)-3-(methoxyphenyl)piperidin-4-yl)piperazin-1-yl)-5-oxopentyl)thio)-2-(2,6-dioxopiperidin-3-yl)isoindoline-1,3-dione |
| | 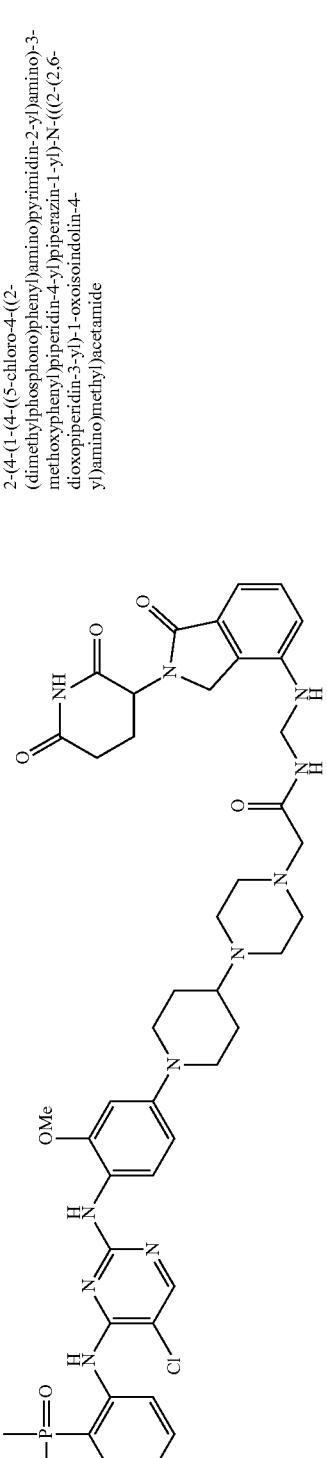 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-((2-(2,6-dioxopiperidin-3-yl)-1-oxoisoindolin-4-yl)amino)methyl)acetamide |

TABLE 3-continued

| Compound number | Structural formula | Compound name |
|---|---|---|
| | 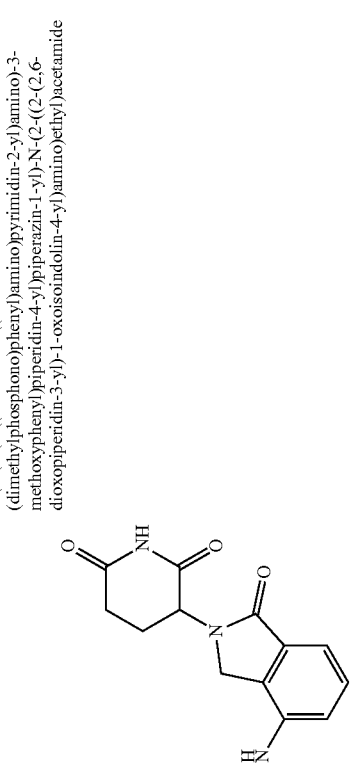 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(2-((2-(2,6-dioxopiperidin-3-yl)-1-oxoisoindolin-4-yl)amino)ethyl)acetamide |
| | 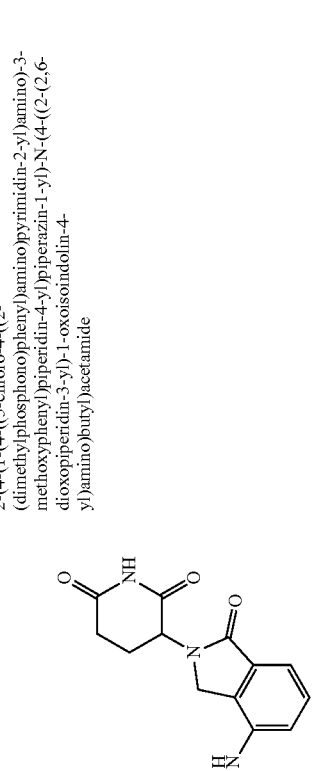 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(3-((2-(2,6-dioxopiperidin-3-yl)-1-oxoisoindolin-4-yl)amino)propyl)acetamide |
| | 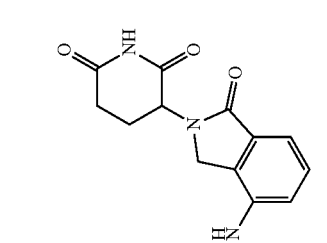 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(4-((2-(2,6-dioxopiperidin-3-yl)-1-oxoisoindolin-4-yl)amino)butyl)acetamide |

TABLE 3-continued

| Compound number | Structural formula | Compound name |
|---|---|---|
| | 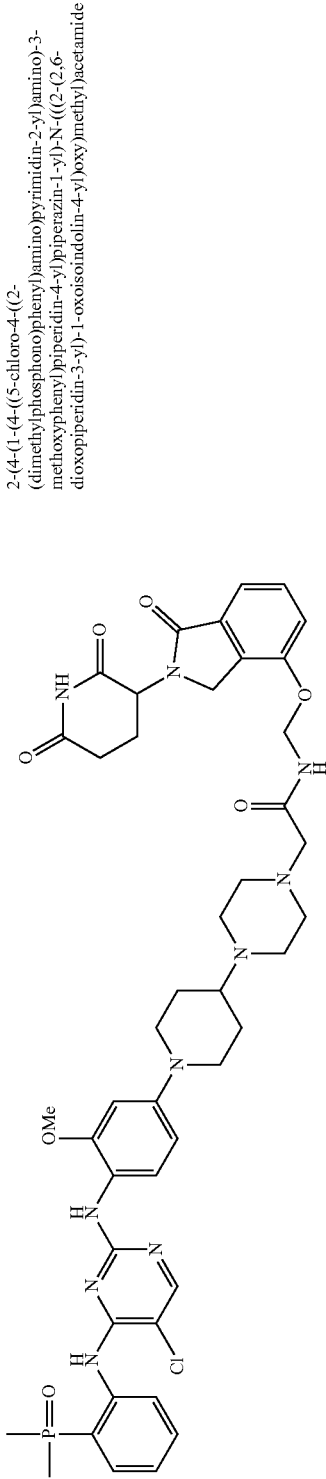 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(((2-(2,6-dioxopiperidin-3-yl)-1-oxoisoindolin-4-yl)oxy)methyl)acetamide |
| | 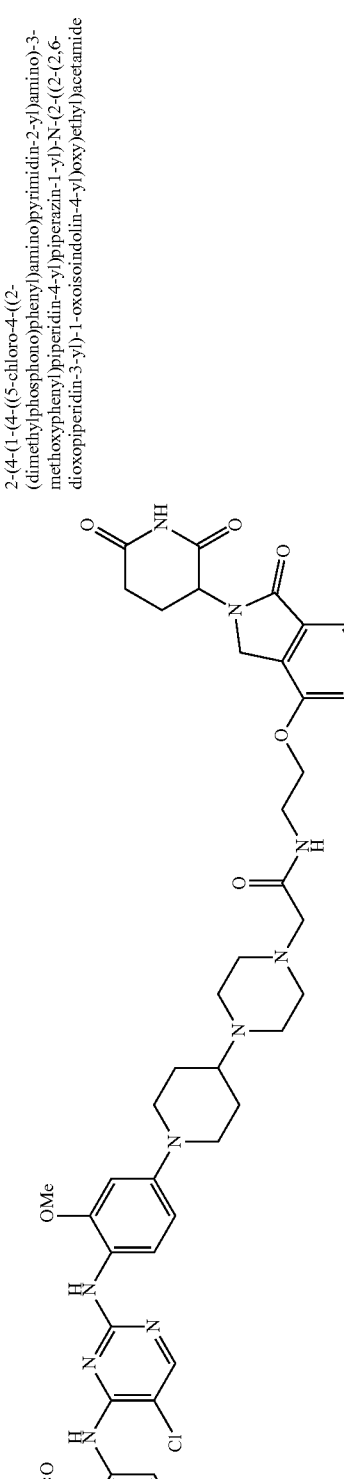 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(2-((2-(2,6-dioxopiperidin-3-yl)-1-oxoisoindolin-4-yl)oxy)ethyl)acetamide |

TABLE 3-continued

| Compound number | Structural formula | Compound name |
|---|---|---|
| | | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(3-((2-(2,6-dioxopiperidin-3-yl)-1-oxoisoindolin-4-yl)oxy)propyl)acetamide |
| | | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(4-((2-(2,6-dioxopiperidin-3-yl)-1-oxoisoindolin-4-yl)oxy)butyl)acetamide |
| | | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(4-((2-(2,6-dioxopiperidin-3-yl)-1-oxoisoindolin-4-yl)thio)methyl)acetamide |

| Compound number | Structural formula | Compound name |
|---|---|---|
| | 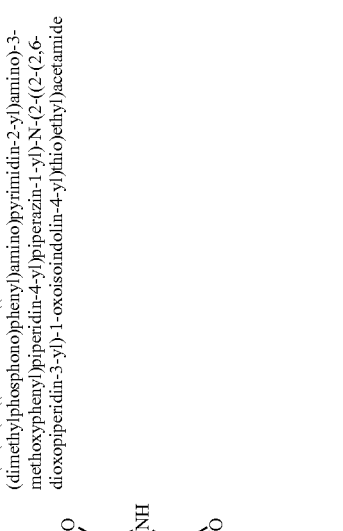 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(2-((2-(2,6-dioxopiperidin-3-yl)-1-oxoisoindolin-4-yl)thio)ethyl)acetamide |
| | 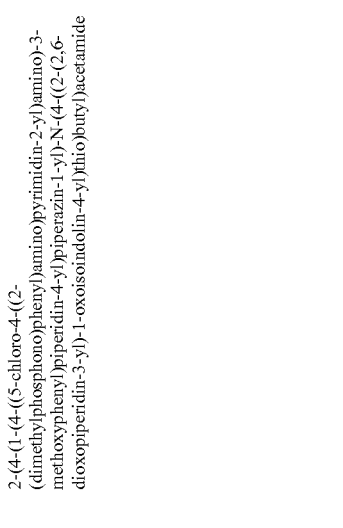 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(3-((2-(2,6-dioxopiperidin-3-yl)-1-oxoisoindolin-4-yl)thio)propyl)acetamide |
| | 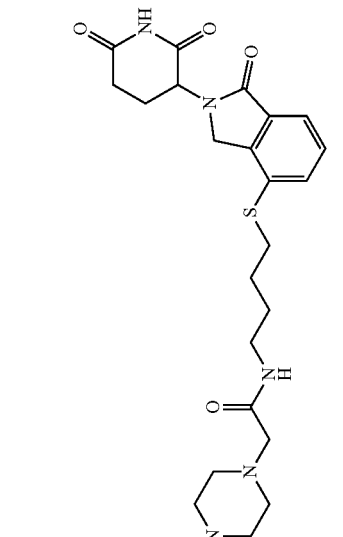 | 2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(4-((2-(2,6-dioxopiperidin-3-yl)-1-oxoisoindolin-4-yl)thio)butyl)acetamide |

TABLE 3-continued

| Compound number | Structural formula | Compound name |
|---|---|---|
| | 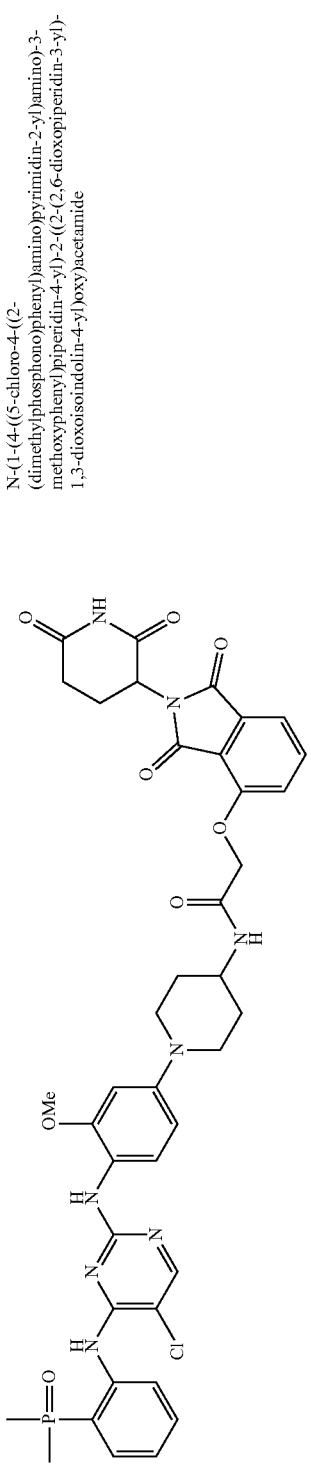 | N-(1-(4-((5-chloro-4-((2-(dimethylphosphono)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)oxy)acetamide |
| | 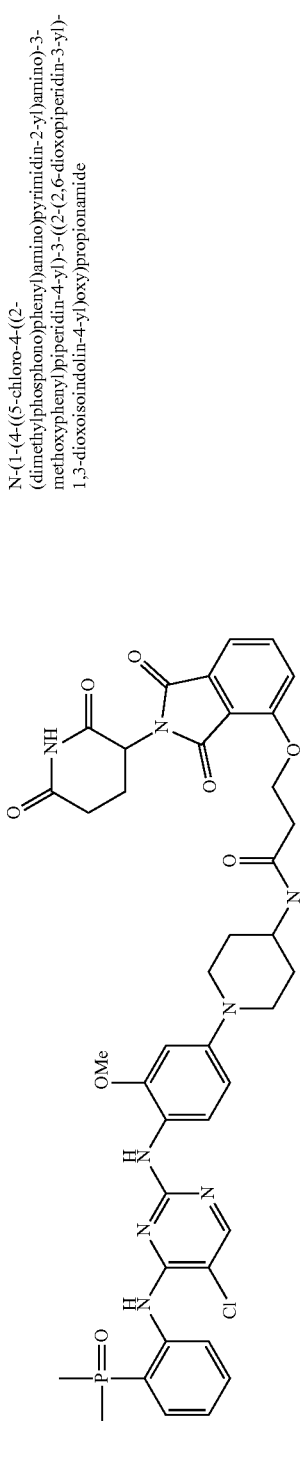 | N-(1-(4-((5-chloro-4-((2-(dimethylphosphono)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)oxy)propionamide |
| | 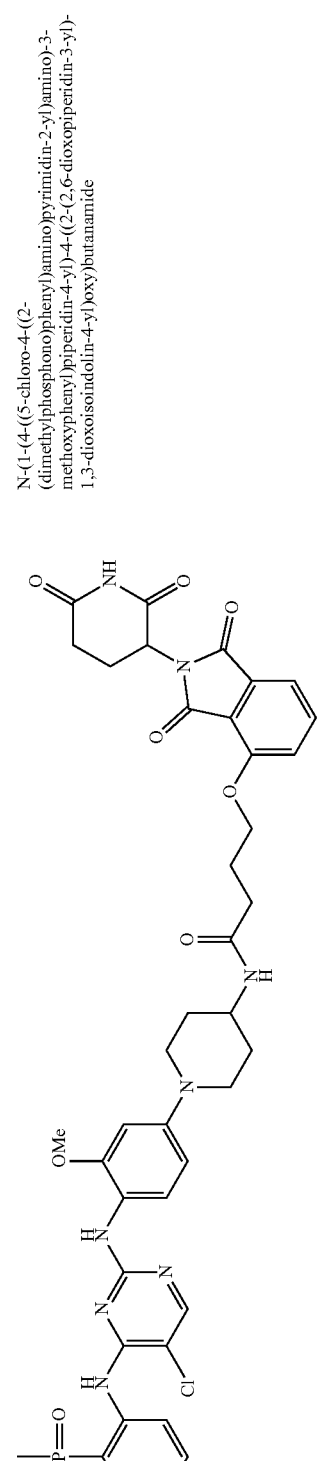 | N-(1-(4-((5-chloro-4-((2-(dimethylphosphono)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)oxy)butanamide |

TABLE 3-continued

| Compound number | Structural formula | Compound name |
|---|---|---|
| | | N-(1-(4-((5-chloro-4-((2-(dimethyl)phosphono)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)oxy)pentanamide |
| | | N-(1-(4-((5-chloro-4-((2-(dimethyl)phosphono)phenyl)amino)pyrimidin-2-yl)amino)-3-methoxyphenyl)piperidin-4-yl)-6-((2-(2,6-dioxopiperidin-3-yl)-1,3-dioxoisoindolin-4-yl)oxy)hexanamide |
| | | 3-(4-(2-((1-(4-((5-chloro-4-((2-(dimethyl)phosphono)phenyl)amino)pyrimidin-2-yl)amino)-3-(methoxyphenyl)piperidin-4-yl)amino)ethoxy)-1-oxoisoindolin-2-yl)piperidine-2,6-dione |

TABLE 3-continued

| Compound number | Structural formula | Compound name |
|---|---|---|
| | 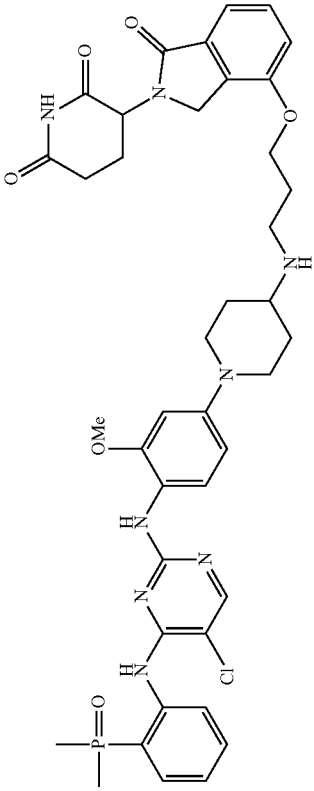 | 3-(4-(3-((1-(4-((5-chloro-4-((2-(dimethylphosphono)phenyl)amino)pyrimidin-2-yl)amino)-3-(methoxyphenyl)piperidin-4-yl)amino)propoxy)-1-oxoisoindolin-2-yl)piperidine-2,6-dione |
| | | 3-(4-(4-((1-(4-((5-chloro-4-((2-(dimethylphosphono)phenyl)amino)pyrimidin-2-yl)amino)-3-(methoxyphenyl)piperidin-4-yl)amino)butoxy)-1-oxoisoindolin-2-yl)piperidine-2,6-dione |
| | 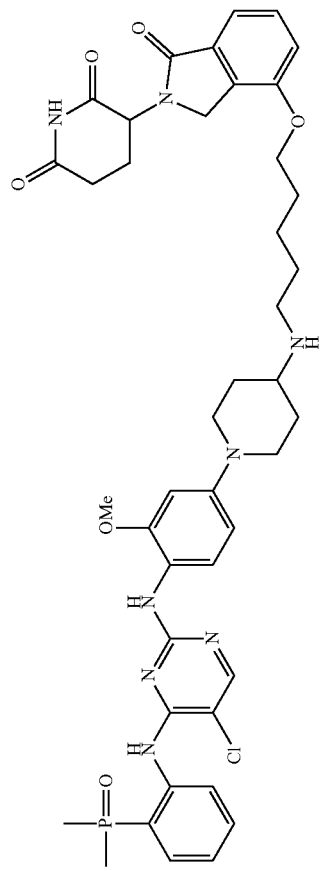 | 3-(4-((5-((1-(4-((5-chloro-4-((2-(dimethylphosphono)phenyl)amino)pyrimidin-2-yl)amino)-3-methoxyphenyl)piperidin-4-yl)amino)pentyl)oxy)-1-oxoisoindolin-2-yl)piperidine-2,6-dione |

TABLE 3-continued

| Compound number | Structural formula | Compound name |
|---|---|---|
| | | 3-(4-((6-((1-(4-((5-chloro-4-((2-(dimethylphosphono)phenyl)amino)pyrimidin-2-yl)amino)-3-methoxyphenyl)piperidin-4-yl)amino)hexyl)oxy)-1-oxoisoindolin-2-yl)piperidine-2,6-dione |
| | | 3-(4-((7-((1-(4-((5-chloro-4-((2-(dimethylphosphono)phenyl)amino)pyrimidin-2-yl)amino)-3-methoxyphenyl)piperidin-4-yl)amino)heptyl)oxy)-1-oxoisoindolin-2-yl)piperidine-2,6-dione |
| | | 3-(5-(((1-(4-((5-chloro-4-((2-(dimethylphosphono)phenyl)amino)pyrimidin-2-yl)amino)-3-methoxyphenyl)piperidin-4-yl)amino)methyl)thio)-1-oxoisoindolin-2-yl)piperidine-2,6-dione |

TABLE 3-continued

| Compound number | Structural formula | Compound name |
|---|---|---|
| | | 3-(4-((2-((1-(4-((5-chloro-4-((2-(dimethylphosphono)phenyl)amino)pyrimidin-2-yl)amino)-3-methoxyphenyl)piperidin-4-yl)amino)ethyl)thio)-1-oxoisoindolin-2-yl)piperidine-2,6-dione |
| | | 3-(4-((3-((1-(4-((5-chloro-4-((2-(dimethylphosphono)phenyl)amino)pyrimidin-2-yl)amino)-3-methoxyphenyl)piperidin-4-yl)amino)propyl)thio)-1-oxoisoindolin-2-yl)piperidine-2,6-dione |
| | | 3-(4-((4-((1-(4-((5-chloro-4-((2-(dimethylphosphono)phenyl)amino)pyrimidin-2-yl)amino)-3-methoxyphenyl)piperidin-4-yl)amino)butyl)thio)-1-oxoisoindolin-2-yl)piperidine-2,6-dione |

TABLE 3-continued

| Compound number | Structural formula | Compound name |
|---|---|---|
| | | 3-(4-((5-chloro-4-((2-(dimethylphosphono)phenyl)amino)pyrimidin-2-yl)amino)-3-methoxyphenyl)piperidin-4-yl)amino)pentyl)thio)-1-oxoisoindolin-2-yl)piperidine-2,6-dione |
| | | 3-(4-((6-((1-(4-((5-chloro-4-((2-(dimethylphosphono)phenyl)amino)pyrimidin-2-yl)amino)-3-methoxyphenyl)piperidin-4-yl)amino)hexyl)thio)-1-oxoisoindolin-2-yl)piperidine-2,6-dione |
| | | 3-(4-((2-((1-(4-((5-chloro-4-((2-(dimethylphosphono)phenyl)amino)pyrimidin-2-yl)amino)-3-methoxyphenyl)piperidin-4-yl)amino)ethyl)amino)-1-oxoisoindolin-2-yl)piperidine-2,6-dione |

TABLE 3-continued

| Compound number | Structural formula | Compound name |
|---|---|---|
| | | 3-(4-((1-(4-((5-chloro-4-((2-(dimethylphosphono)phenyl)amino)pyrimidin-2-yl)amino)-3-methoxyphenyl)piperidin-4-yl)amino)propyl)amino)-1-oxoisoindolin-2-yl)piperidine-2,6-dione |
| | | 3-(4-((5-((1-(4-((5-chloro-4-((2-(dimethylphosphono)phenyl)amino)pyrimidin-2-yl)amino)-3-methoxyphenyl)piperidin-4-yl)amino)pentyl)amino)-1-oxoisoindolin-2-yl)piperidine-2,6-dione |
| | | 3-(4-((6-((1-(4-((5-chloro-4-((2-(dimethylphosphono)phenyl)amino)pyrimidin-2-yl)amino)-3-methoxyphenyl)piperidin-4-yl)amino)hexyl)amino)-1-oxoisoindolin-2-yl)piperidine-2,6-dione |

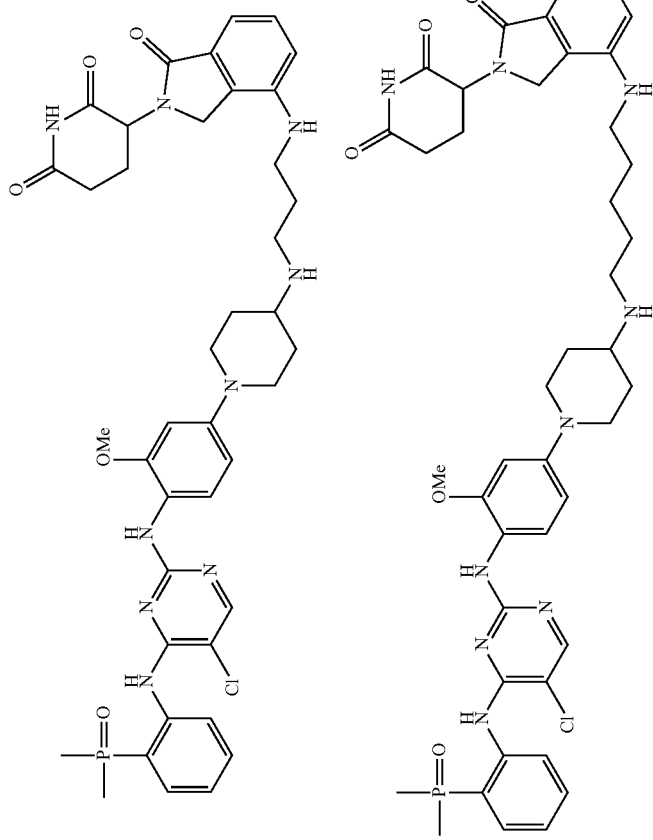
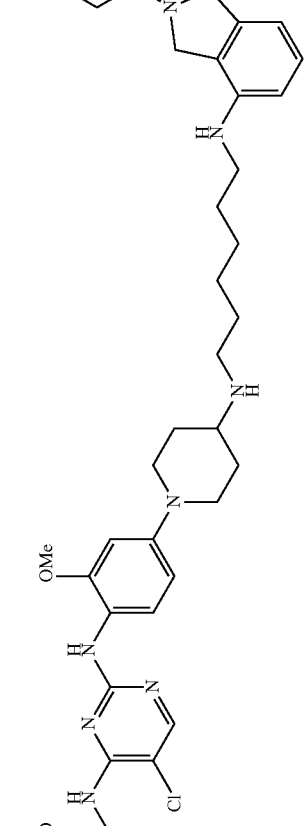

TABLE 3-continued

| Compound number | Structural formula | Compound name |
|---|---|---|
| 361 | 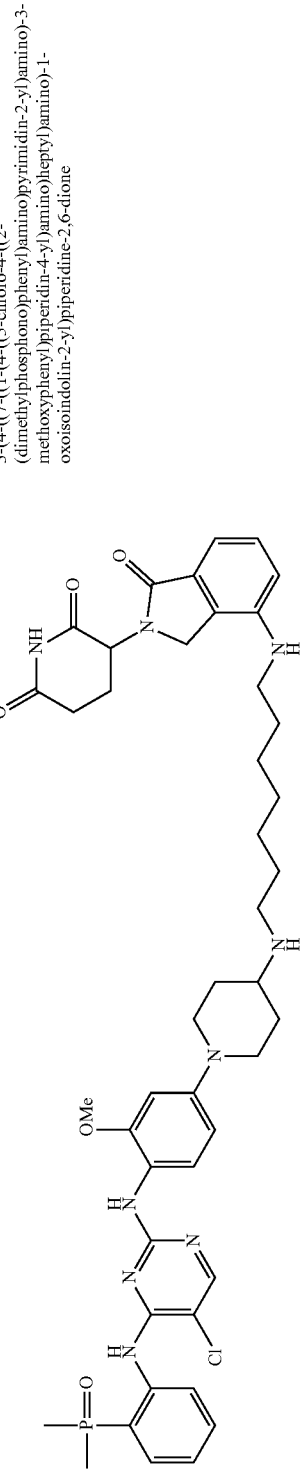 | 3-(4-((7-((1-(4-((5-chloro-4-((2-(dimethylphosphono)phenyl)amino)pyrimidin-2-yl)amino)-3-methoxyphenyl)piperidin-4-yl)amino)heptyl)amino)-1-oxoisoindolin-2-yl)piperidine-2,6-dione |
| | 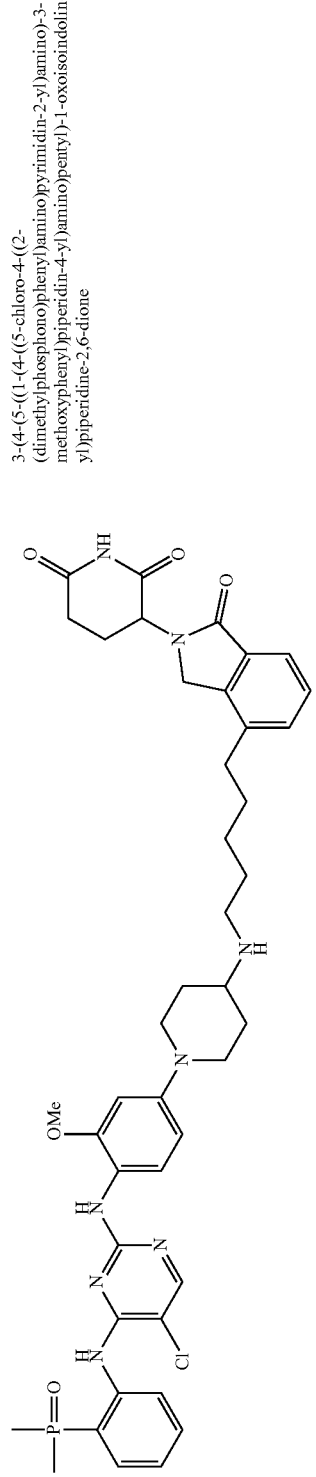 | 3-(4-(4-((1-(4-((5-chloro-4-((2-(dimethylphosphono)phenyl)amino)pyrimidin-2-yl)amino)-3-methoxyphenyl)piperidin-4-yl)amino)butyl)-1-oxoisoindolin-2-yl)piperidine-2,6-dione |
| 362 | 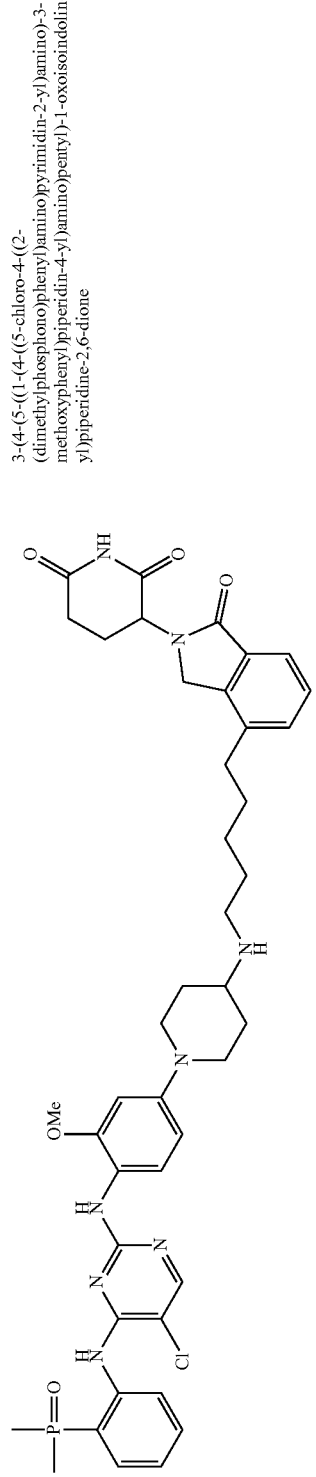 | 3-(4-(5-((1-(4-((5-chloro-4-((2-(dimethylphosphono)phenyl)amino)pyrimidin-2-yl)amino)-3-methoxyphenyl)piperidin-4-yl)amino)pentyl)-1-oxoisoindolin-2-yl)piperidine-2,6-dione |

TABLE 3-continued

| Compound number | Structural formula | Compound name |
|---|---|---|
| | 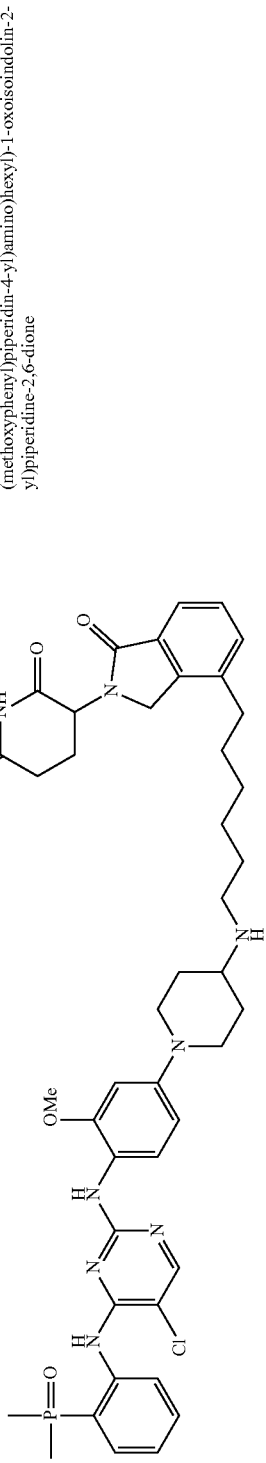 | 3-(4-(6-((1-(4-((5-chloro-4-((2-(dimethylphosphono)phenyl)amino)pyrimidin-2-yl)amino)-3-(methoxy)phenyl)piperidin-4-yl)amino)hexyl)-1-oxoisoindolin-2-yl)piperidine-2,6-dione |
| | | 3-(4-(7-((1-(4-((5-chloro-4-((2-(dimethylphosphono)phenyl)amino)pyrimidin-2-yl)amino)-3-(methoxy)phenyl)piperidin-4-yl)amino)heptyl)-1-oxoisoindolin-2-yl)piperidine-2,6-dione |
| | 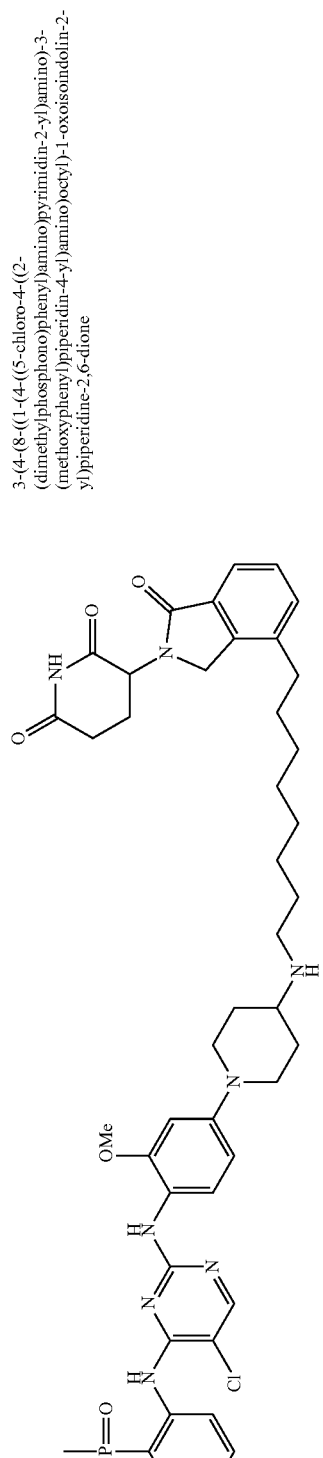 | 3-(4-(8-((1-(4-((5-chloro-4-((2-(dimethylphosphono)phenyl)amino)pyrimidin-2-yl)amino)-3-(methoxy)phenyl)piperidin-4-yl)amino)octyl)-1-oxoisoindolin-2-yl)piperidine-2,6-dione |

TABLE 3-continued
| Compound number | Structural formula | Compound name |
|---|---|---|
|  | 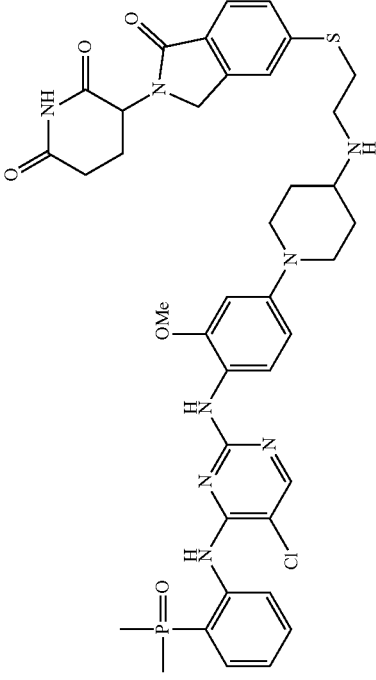 | 3-(5-((2-((1-(4-((5-chloro-4-((2-(dimethylphosphono)phenyl)amino)pyrimidin-2-yl)amino)-3-methoxyphenyl)piperidin-4-yl)amino)ethyl)thio)-1-oxoisoindolin-2-yl)piperidine-2,6-dione |
|  | 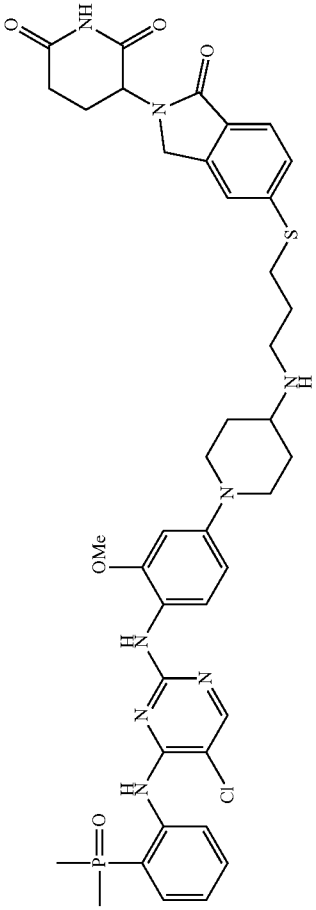 | 3-(5-((3-((1-(4-((5-chloro-4-((2-(dimethylphosphono)phenyl)amino)pyrimidin-2-yl)amino)-3-methoxyphenyl)piperidin-4-yl)amino)propyl)thio)-1-oxoisoindolin-2-yl)piperidine-2,6-dione |

TABLE 3-continued
| Compound number | Structural formula | Compound name |
|---|---|---|
| | 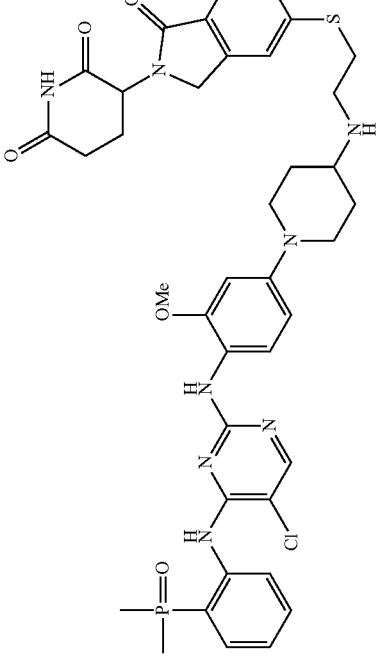 | 3-(5-((4-((1-(4-((5-chloro-4-((2-(dimethylphosphono)phenyl)amino)pyrimidin-2-yl)amino)-3-methoxyphenyl)piperidin-4-yl)amino)butyl)thio)-1-oxoisoindolin-2-yl)piperidine-2,6-dione |
| | | 3-(5-((5-((1-(4-((5-chloro-4-((2-(dimethylphosphono)phenyl)amino)pyrimidin-2-yl)amino)-3-methoxyphenyl)piperidin-4-yl)amino)pentyl)thio)-1-oxoisoindolin-2-yl)piperidine-2,6-dione |

TABLE 3-continued

| Compound number | Structural formula | Compound name |
|---|---|---|
| | 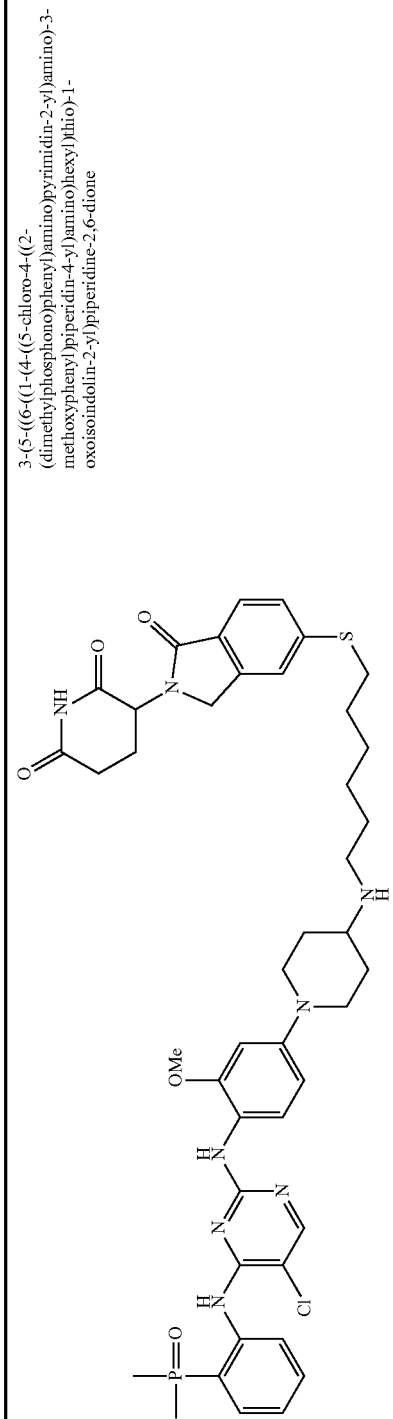 | 3-(5-((6-((1-(4-((5-chloro-4-((2-(dimethylphosphono)phenyl)amino)pyrimidin-2-yl)amino)-3-methoxyphenyl)piperidin-4-yl)amino)hexyl)thio)-1-oxoisoindolin-2-yl)piperidine-2,6-dione |
| | 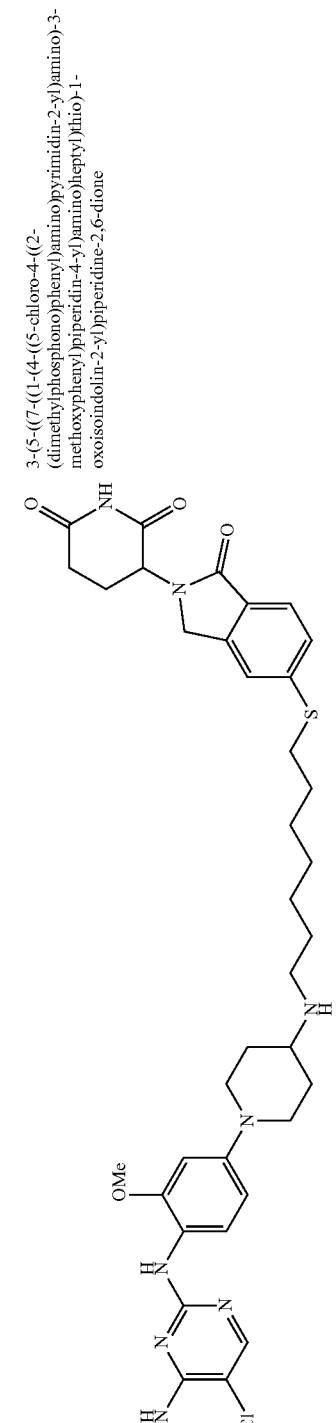 | 3-(5-((7-((1-(4-((5-chloro-4-((2-(dimethylphosphono)phenyl)amino)pyrimidin-2-yl)amino)-3-methoxyphenyl)piperidin-4-yl)amino)heptyl)thio)-1-oxoisoindolin-2-yl)piperidine-2,6-dione |
| | 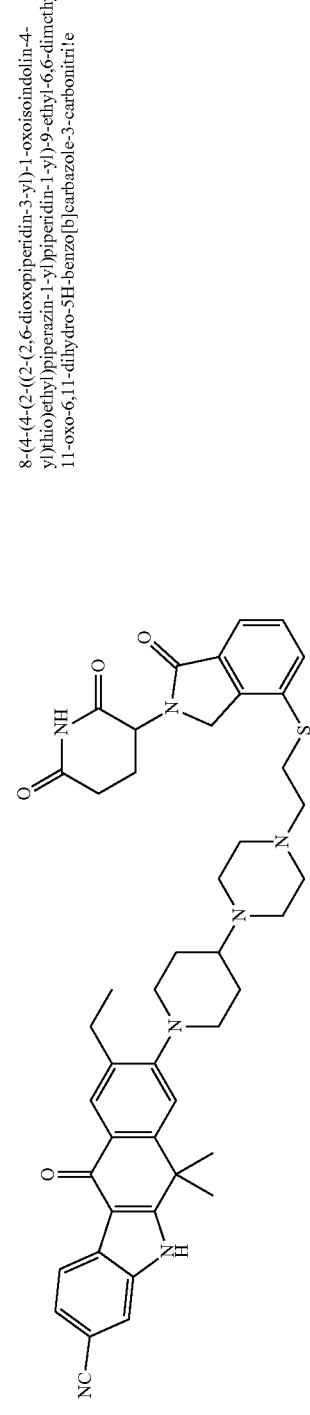 | 8-(4-(4-(2-((2-(2,6-dioxopiperidin-3-yl)-1-oxoisoindolin-4-yl)thio)ethyl)piperazin-1-yl)piperidin-1-yl)-9-ethyl-6,6-dimethyl-11-oxo-6,11-dihydro-5H-benzo[b]carbazole-3-carbonitrile |

TABLE 3-continued
| Compound number | Structural formula | Compound name |
|---|---|---|
| | 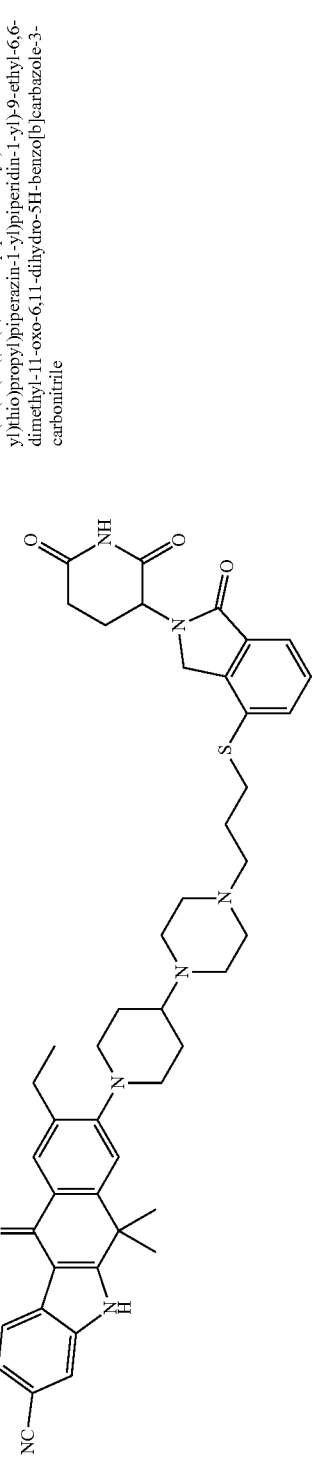 | 8-(4-(4-(3-((2-(2,6-dioxopiperidin-3-yl)-1-oxoisoindolin-4-yl)thio)propyl)piperazin-1-yl)piperidin-1-yl)-9-ethyl-6,6-dimethyl-11-oxo-6,11-dihydro-5H-benzo[b]carbazole-3-carbonitrile |
| | 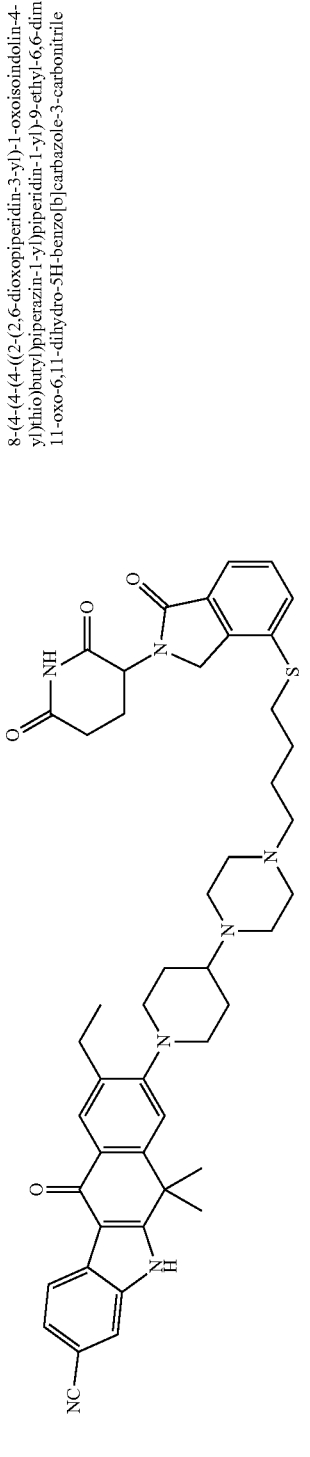 | 8-(4-(4-(4-((2-(2,6-dioxopiperidin-3-yl)-1-oxoisoindolin-4-yl)thio)butyl)piperazin-1-yl)piperidin-1-yl)-9-ethyl-6,6-dimethyl-11-oxo-6,11-dihydro-5H-benzo[b]carbazole-3-carbonitrile |

TABLE 3-continued
| Compound number | Structural formula | Compound name |
|---|---|---|
| | 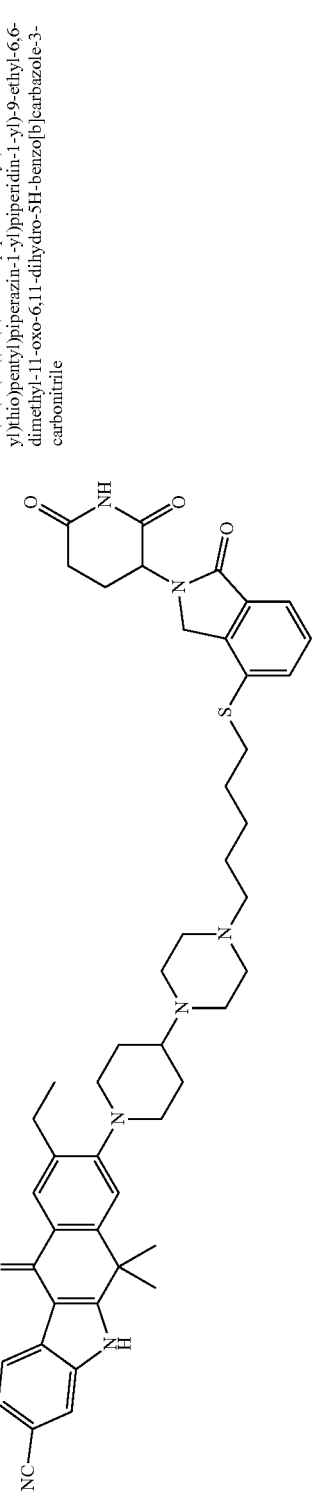 | 8-(4-(4-(5-((2-(2,6-dioxopiperidin-3-yl)-1-oxoisoindolin-4-yl)thio)pentyl)piperazin-1-yl)piperidin-1-yl)-9-ethyl-6,6-dimethyl-11-oxo-6,11-dihydro-5H-benzo[b]carbazole-3-carbonitrile |
| | 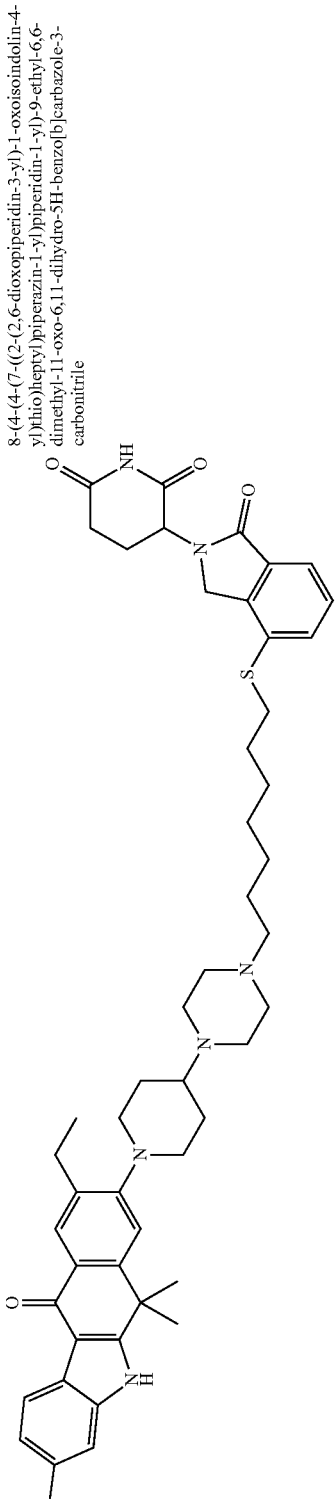 | 8-(4-(4-(7-((2-(2,6-dioxopiperidin-3-yl)-1-oxoisoindolin-4-yl)thio)heptyl)piperazin-1-yl)piperidin-1-yl)-9-ethyl-6,6-dimethyl-11-oxo-6,11-dihydro-5H-benzo[b]carbazole-3-carbonitrile |

TABLE 3-continued

| Compound number | Structural formula | Compound name |
|---|---|---|
| | | 4-((3-((1-(4-((5-chloro-4-((2-(dimethylphosphono)phenyl)amino)pyrimidin-2-yl)amino)-3-methoxyphenyl)piperidin-4-yl)amino)propyl)amino)-2-(2,6-dioxopiperidin-3-yl)isoindolin-1,3-dione |
| | | 4-((5-((1-(4-((5-chloro-4-((2-(dimethylphosphono)phenyl)amino)pyrimidin-2-yl)amino)-3-methoxyphenyl)piperidin-4-yl)amino)pentyl)amino)-2-(2,6-dioxopiperidin-3-yl)isoindolin-1,3-dione |
| | | 4-((6-((1-(4-((5-chloro-4-((2-(dimethylphosphono)phenyl)amino)pyrimidin-2-yl)amino)-3-methoxyphenyl)piperidin-4-yl)amino)hexyl)amino)-2-(2,6-dioxopiperidin-3-yl)isoindolin-1,3-dione |

Another aspect of the present disclosure also provides a pharmaceutical composition, comprising any one of the compounds of the present disclosure in Table 3 or the pharmaceutically acceptable salt thereof, and a pharmaceutically acceptable carrier.

The pharmaceutical composition described in the present disclosure further comprises at least one additional medicament for the treatment or prevention of cancer.

In another aspect of the present disclosure, any one of the compounds of the present disclosure in Table 3, or the pharmaceutically acceptable salt thereof for use as a medicament.

In another aspect of the present disclosure, the compounds of the present disclosure in Table 3, or the pharmaceutically acceptable salt thereof described in the present disclosure for use in the prevention and/or treatment of cancer. In an embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal(thymus)large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma and refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, myelofibrosis, smoldering myeloma and smoldering multiple myeloma; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

In another aspect of the present disclosure, the compounds of the present disclosure in Table 3, or the pharmaceutically acceptable salt thereof for use in the preparation of a medicament for the prevention and/or treatment of cancer. In a sub-embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus) large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma and refractory transformed non-Hodgkin's lymphoma; inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, myelofibrosis, smoldering myeloma and smoldering multiple myeloma; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer; and non-small cell lung cancer, including lung adenocarcinoma, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

Another aspect of the present disclosure also provides a method for treating or preventing cancer, comprising administering a therapeutically effective amount of any one of the compounds of the present disclosure in Table 3 of the present disclosure, or the pharmaceutically acceptable salt thereof, or the pharmaceutical composition to a subject. In an embodiment, the cancer is selected from: lung cancer; lymphoma, including diffuse large B cell lymphoma, non-Hodgkin's lymphoma, anaplastic lymphoma, anaplastic large cell lymphoma, CD20 positive lymphoma, primary lymphoma, B-cell lymphoma, recurrent B-cell non-Hodgkin's lymphoma, recurrent diffuse large B-cell lymphoma, recurrent mediastinal (thymus) large B-cell lymphoma, primary mediastinal (thymus) large B-cell lymphoma, recurrent transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, inflammatory myofibroblastic tumor; colorectal cancer; brain glioma; astrocytome; ovarian cancer; bone marrow diseases, including multiple myeloma, myelodysplastic syndrome (MDS), previously treated myelodysplastic syndrome, plasma cell myeloma, smoldering myeloma, smoldering multiple myeloma and myelofibrosis; transplant-related cancer; neutropenia; leukemia, including acute myeloid leukemia (AML), leukemia-related anemia, chronic myelogenous leukemia, and B-cell chronic lymphocytic leukemia; Unverricht syndrome; bronchial cancer; prostate cancer; breast cancer, including patients with triple-negative breast cancer, incident breast cancer and Cowden's disease; thyroid cancer; pancreatic cancer; neuroblastoma; extramedullary plasmacytoma; plasmacytoma; gastric cancer; gastrointestinal stromal tumor; esophageal cancer; colorectal adenocarcinoma; esophageal squamous cell carcinoma; liver cancer; renal cell carcinoma; bladder cancer; endometrial cancer; melanoma; brain cancer; oral cancer; sarcoma, including rhabdomyosarcoma, various fatty tumors, Ewing's sarcoma/primitive neuroectodermal tumors (Ewing/PNETs), and leiomyosarcoma; tumors resistant to targeted drugs, including tumors resistant to EGFR or ALK targeted drugs, such as lung cancer resistant to EGFR or ALK targeted drugs, lymphoma resistant to ALK-targeted drugs; or tumors or diseases that rely on protein selected from ALK, ROS1, MET, EGFR, FLT3 or any combination thereof, including but not limited to lung cancer, lymphoma, inflammatory myofibroblastic tumor, colorectal cancer, brain glioma, astrocytome, ovarian cancer, leukemia, breast cancer, thyroid cancer, neuroblastoma, extramedullary plasmacytoma, plasmacytoma, esophageal squamous cell carcinoma, renal cell carcinoma, bronchial cancer, prostate cancer, breast cancer, thyroid cancer, pancreatic cancer, neuroblastoma, extramedullary plasmacytoma, plasmacytoma, gastric cancer, gastrointestinal stromal tumor, esophageal cancer, colorectal adenocarcinoma, esophageal squamous cell carcinoma, liver cancer, renal cell carcinoma, bladder cancer, endometrial cancer, melanoma, brain cancer, oral cancer and sarcoma, etc. that rely on the protein. In a sub-embodiment, the lung cancer is selected from the group consisting of: small cell lung cancer, non-small cell lung cancer, anaplastic lymphoma kinase (ALK) mutation-positive non-small cell lung cancer (NSCLC), ROS1-positive non-small cell lung cancer, MET-mutated or amplified lung cancer, and EGFR-mutated non-small cell lung cancer. In a sub-embodiment, the lung cancer is lung adenocarcinoma.

In the method for treating or preventing cancer described in the present disclosure, the compounds of the present disclosure in Table 3, or the pharmaceutically acceptable salt thereof, or the pharmaceutical composition is administrated to a subject by at least one administration mode selected from nasal administration, inhalation administration, topical administration, oral administration, oral mucosal administration, rectal administration, pleural cavity administration, peritoneal administration, vaginal administration, intramuscular administration, subcutaneous administration, transdermal administration, epidural administration, intrathecal administration and intravenous administration.

IV. Definition

Generally, the nomenclature used herein and the nomenclature of laboratory procedures described below (including the nomenclature used for cell culture, organic chemistry, analytical chemistry, pharmacology, etc.) are well-known and commonly used in the art. Unless clearly defined otherwise, all scientific and technical terms used herein in and in this disclosure have the same meaning as commonly understood by those skilled in the art. In addition, in the claims and/or specification, when the term "a" or "an" is used in combination with the term "comprising" or "including" or a noun, its meaning can be "one", but it also has the same meaning with "one or more", "at least one" and "one or more than one". Similarly, the word "another" or "other" can represent at least a second or more.

It should be understood that whenever the terms "including" or "comprising" are used herein to describe various aspects of the present disclosure, other similar aspects described with "consisting of" and/or "essentially consisting of" are also provided.

As used herein, the term "about" refers to approximately, about, or around. When the term "about" is used in conjunction with a numerical range, it modifies the numerical range by extending the upper and lower limits of the specified numerical value. For example, the term "about" as used herein is intended to include variations of ±20%, ±15%, ±10%, ±5%, ±1%, and +0.1% above and below the specified value, because such changes are appropriate.

The term "absent" used in combination with a substituent or a group means that the substituent or the group does not exist. In other words, when the substituent or group does not exist, it becomes a bond or bond linker. For example, in the compound represented by formula (I) according to the present disclosure, when the group A does not exist, the ALK-TKI moiety is directly covalently bonded (or connected) to LIN.

As used herein, the term "interrupted" in the "linear or branched alkylene chain interrupted one or more times by one or more groups selected from . . . " used alone or in combination has the known definition in the art, that is, can mean that a group as defined herein (for example, a group selected from C(O)NH, NHC(O), O, NH, alkynylene, alkenylene, cycloalkylene, arylene, heterocyclylene, heteroarylene, or any combination thereof as described herein) is inserted between any two adjacent carbon atoms in the carbon chain backbone of a linear or branched alkylene chain. Herein, examples of the term "interrupted one or more times" may include, but are not limited to, interrupted 1-20 times, or 1-15, 1-10, 1-9, 1-8, 1-7, 1-6, 1-5, 1-4, 1-3 or 1-2 times, or 1 time. Herein, examples of the term "one or more groups selected from . . . " in the above "interrupted one or more times by one or more groups selected from . . . " may include, but are not limited to 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1. For example, the term "linear or branched alkylene chain interrupted one or more times by one or more groups O" used alone or in combination refers to —O— groups are inserted between one or more pairs of any two adjacent carbon atoms in the carbon chain backbone of the linear or branched alkylene chain to form linear or linear oxaalkylene including one or more (e.g. 1-20, 1-15, 1-10, 1-8, 1-7, 1-6, 1-5, 1-4, 1-3, 1-2 or 1) "—CH$_2$—O—CH$_2$—" segments.

Herein, the compounds represented by formula (I) and (III) of the present disclosure and the compounds listed in Tables 1-3 are also referred to as degrading agents, protein degradation targeted drugs PROTAD, or PROTAD small molecules (PROTAD compounds), these names can be used interchangeably.

Herein, the part of monovalent compound (or monovalent group) represented by formula (Id), formula (Ie) and formula (If):

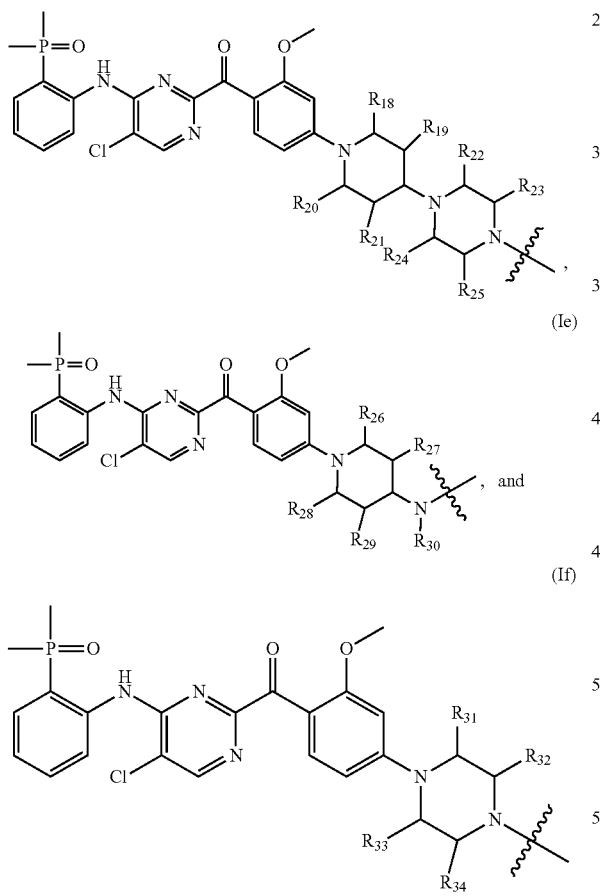

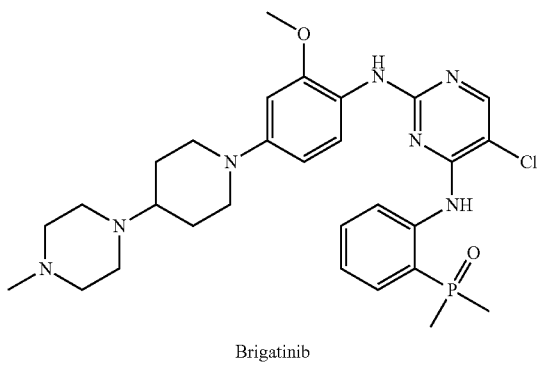 [SMILES: COc1cc(N2CCC(N3CCN(C)CC3)CC2)ccc1Nc1ncc(Cl)c(Nc2ccccc2P(C)(C)=O)n1]

Brigatinib

Herein, the part of monovalent compound (or monovalent group) represented by formula (Ia), formula (Ib) and formula (Ic):

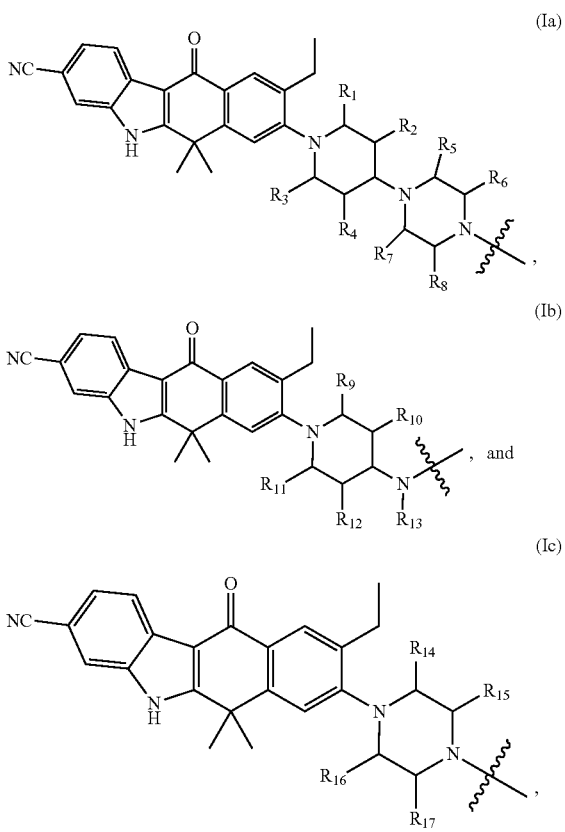

all are structures derived from the piperidine-piperazine group of Brigatinib, wherein $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{31}$, $R_{32}$, $R_{33}$ and $R_{34}$ each independently represents H or methyl, and $R_{30}$ represents H, methyl or ethyl.

all are structures derived from the modification of the piperidine-morpholine group of Alectinib, wherein $R_1$, $R_2$, $R_3$, $R_4$, $R_5$, $R_6$, $R_7$, $R_8$, $R_9$, $R_{10}$, $R_{11}$, $R_{12}$, $R_{14}$, $R_{15}$, $R_{16}$ and $R_{17}$ each independently represents H or methyl, and $R_{13}$, represents H, methyl or ethyl.

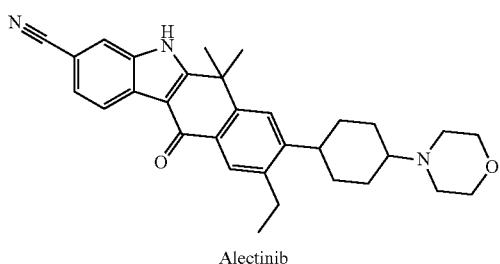 [SMILES: CCc1cc2c(cc1C1CCC(N3CCOCC3)CC1)C(C)(C)c1[nH]c3cc(C#N)ccc3c1C2=O]

Alectinib

Herein, the bond broken by the wavy line shows the point at which the depicted group is connected to the other part of the molecule. For example, the depicted group shown below

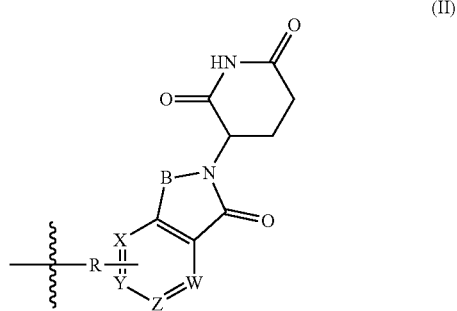

(II)

it means that the compound part of formula (II) is connected to the linking group LIN part of the compound represented by formula (I) through the group R.

Herein, the terms "LIN" and "linker" are used interchangeably, and both represent a linking group or linking unit in a compound represented by formula (I) or a compound represented by formula (III).

In the present disclosure, the term "halogen atom" or "halogen" used alone or in combination means fluorine, chlorine, bromine or iodine, and is, for example, F, Cl or Br.

In the present disclosure, the term "alkyl" used alone or in combination refers to a linear or branched alkyl. The term "$C_x$-$C_y$ alkyl" or "$C_{x-y}$ alkyl" (x and y are each an integer) refers to a linear or branched chain alkyl containing x to y carbon atoms. The term "$C_{1-10}$ alkyl" used alone or in combination in the present disclosure refers to a linear or branched chain alkyl group containing 1 to 10 carbon atoms. Examples of $C_{1-10}$ alkyl groups in the present disclosure include, but are not limited to, $C_{1-9}$ alkyl groups, $C_{1-8}$ alkyl groups, $C_{2-8}$ alkyl groups, $C_{1-7}$ alkyl groups, $C_{1-6}$ alkyl groups, $C_{1-5}$ alkyl groups, or $C_{1-4}$ alkyl. Representative examples include, but are not limited to, methyl, ethyl, n-propyl, isopropyl, n-butyl, isobutyl, sec-butyl, tert-butyl, pentyl, isopentyl, neopentyl, ter-pentyl, hexyl, heptyl, octyl, nonyl and decyl. The term "$C_{1-3}$ alkyl" in the present disclosure refers to an alkyl containing 1 to 3 carbon atoms, and representative examples thereof include methyl, ethyl, n-propyl, and isopropyl.

In the present disclosure, the "alkyl" is optionally substituted, and the substituent may be one or more substituents selected from halogen, cyano, $C_{1-3}$ alkyl, $C_{1-3}$ alkoxy, trifluoromethyl, heterocyclyl or any combination thereof.

In the present disclosure, the term "alkylene" (which is used interchangeably with "alkylene chain") used alone or in combination refers to a linear or branched divalent saturated hydrocarbon group composed of carbon and hydrogen atoms. The term "$C_x$-$C_y$ alkylene" or "$C_{x-y}$ alkylene" (x and y are each an integer) refers to a linear or branched alkylene containing x toy carbon atoms. Examples of the $C_{1-30}$ alkylene of the present disclosure include, but are not limited to, $C_1$-$C_{29}$ alkylene, $C_1$-$C_{28}$ alkylene, $C_1$-$C_{27}$ alkylene, $C_1$-$C_{26}$ alkylene, $C_1$-$C_{25}$ alkylene, $C_1$-$C_{24}$ alkylene, $C_1$-$C_{23}$ alkylene, $C_1$-$C_{22}$ alkylene, $C_1$-$C_{21}$ alkylene, $C_1$-$C_{20}$ alkylene, $C_1$-$C_{19}$ alkylene, $C_1$-$C_{18}$ alkylene, $C_1$-$C_{17}$ alkylene, $C_1$-$C_{16}$ alkylene, $C_1$-$C_{15}$ alkylene, $C_1$-$C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene. Representative examples include, but are not limited to, methylene, ethylene, propylene, isopropylene, butylene, isobutylene, sec-butylene, tert-butylene, pentylene, isopentylene, neopentylene, ter-pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, cerylene, heptacosylene, octacosylene, nonacosylene, and triacontylene.

In the present disclosure, the "alkylene" is optionally substituted, and the substituent may be one or more selected from hydroxyl, amino, mercapto, halogen, cyano, $C_{1-3}$ alkyl, $C_{1-3}$ alkoxy, trifluoromethyl, heterocyclic group or any combination thereof.

In the present disclosure, the term "arylene" used alone or in combination refers to a divalent aromatic hydrocarbon group containing 5 to 14 carbon atoms and optionally containing one or more fused rings, such as phenylene or naphthylene or fluorenylene. In the present disclosure, the "arylene" is an optionally substituted arylene. The substituted arylene refers to an arylene substituted 1-3 times with a substituent (that is, the arylene is mono-substituted, di-substituted or tri-substituted with a substituent), wherein the substituent may be selected from, for example, $C_{1-3}$ alkyl, $C_{1-3}$ alkoxy, trifluoromethyl, mercapto, cyano, halogen, amino, hydroxyl, or any combination thereof.

In the present disclosure, the term "$C_{1-3}$ alkoxy" used alone or in combination refers to a linear or branched chain alkoxy containing 1 to 3 carbon atoms. Representative examples of $C_{1-3}$ alkoxy include, but are not limited to, methoxy, ethoxy, n-propoxy, and isopropoxy, preferably methoxy and ethoxy.

In the present disclosure, the term "cycloalkyl" used alone or in combination refers to a saturated and partially unsaturated (that is, with one or more double bonds, but not a fully conjugated rt-electron system) monovalent monocyclic or bicyclic cycloalkyl group with 3 to 12 carbons (for example, 3-10, 3-8, or 3-6 carbon atoms), which may contain a fused ring, a bridged ring or a spiro ring system. The term "$C_3$-$C_{10}$ cycloalkyl" refers to a saturated and partially unsaturated (that is, with one or more double bonds, but not a fully conjugated π-electron system) monocyclic or bicyclic cycloalkyl group with 3 to 10 carbon atoms. Representative examples of cycloalkyl include, but are not limited to, cyclopropyl, cyclobutyl, cyclopentyl, cyclopentenyl, cyclohexyl, cyclohexenyl, cycloheptyl, cyclooctyl, decahydronaphthalene, octahydrocyclopentadiene, octahydro-1H-indene, spirocyclic group. In the present disclosure, the "cycloalkyl" is optionally mono-, di-, tri-, or poly-substituted, and the substituent may be selected from trifluoromethyl, mercapto, hydroxyl, amino, halogen, cyano, $C_{1-3}$ alkyl, $C_{1-3}$ alkoxy, trifluoromethyl, heterocyclyl or any combination thereof.

In the present disclosure, the term "cycloalkylene" used alone or in combination refers to a saturated and partially unsaturated (that is, with one or more double bonds, but not a fully conjugated π-electron system) monocyclic or bicyclic cyclic hydrocarbon divalent group with 3 to 12 carbon atoms (for example, 3-10, 3-8, or 3-6 carbon atoms), which may include a fused ring, a bridged ring or a spiro ring system. Representative examples of cycloalkylene include, but are not limited to, cyclopropylene, cyclobutylene, cyclopentylene, cyclopentenylene, cyclohexylene, cyclohexenylene, cycloheptylene, cyclooctylene, decahydronaphthylene, octahydrocyclopentadienylene, octahydro-1H-indenylene, spirocyclylene. According to a clear definition, a cycloalkylene can be unsubstituted or mono-, di-, tri-, or poly-substituted. In the present disclosure, the substituent of the substituted "cycloalkylene" can be one or more substituents selected from halogen, mercapto, hydroxyl, amino, cyano, $C_{1-3}$ alkyl, $C_{1-3}$ alkoxy, trifluoromethyl, heterocyclyl or any combination thereof.

In the present disclosure, the term "heteroarylene" used alone or in combination refers to 5- to 10-membered monocyclic or bicyclic divalent aromatic ring group containing one or more (for example, 1 to 6, or 1 to 5, or 1 to 4, or 1 to 3) heteroatoms independently selected from oxygen, nitrogen and sulfur. Representative examples of heteroarylene include, but are not limited to, furanylene, oxazolylidene, isoxazolylidene, oxadiazolylidene, thienylene, thiazolylidene, isothiazolylidene, thiadiazolylidene, pyrrolylene, imidazolylidene, pyrazolylidene, triazolylidene, pyridinylene, pyrimidinylene, pyridazinylene, pyrazinylene, indolylene, isoindolylene, benzofuranylene, isobenzofuranylene, benzothienylene, indazolylidene, benzimidazolylidene, benzoxazolylidene, benzisoxazolylidene, benzothiazolylene, benzoisothiazolylene, benzotriazolylidene, benzo[2,1,3]oxadiazolylene, benzo[2,1,3]thiadiazolylene, benzo[1,2,3]thiadiazolylene, quinolinylene, isoquinolinylene, naphthyridinylene, cinolinylene, quinazolinylene, quinoxalinylene, phthalazinylene, pyrazolo[1,5-a]pyridine subunit, pyrazolo[1,5-a]pyrimidine subunit, imidazo[1,2-a]pyridine subunit, 1H-pyrrolo[3,2-b]pyridine subunit, 1H-pyrrolo[2,3-b]pyridine subunit, 4H-fluoro[3,2-b]pyrrole subunits, pyrrolo[2,1-b]thiazole subunit and imidazo[2,1-b]thiazole subunit. According to a clear definition, heteroarylene can be unsubstituted or mono-, di-, tri-, or poly-substituted. The substituent of the substituted heteroarylene can be selected from, for example, $C_{1-3}$ alkyl, $C_{1-3}$ alkoxy, cyano, trifluoromethyl, heterocyclyl, halogen, amino, hydroxyl, or any combination thereof.

In the present disclosure, the term "heterocyclylene" used alone or in combination refers to a 4- to 6-membered saturated or partially unsaturated (that is, with one or more double bonds, but not a fully conjugated rt-electron system) divalent monocyclic group containing one or more (for example, 1-4, 1-3, 1-2, or 1) heteroatoms independently selected from sulfur, oxygen, and nitrogen. Representative examples of the heterocyclylene include, but are not limited to, azetidinylene, oxetanylene, pyrrolidinylene, imidazolidinylene, pyrazolidinylene, triazolylidene, tetrahydrofimanylene, tetrahydrothienylene, tetrahydrothiopyranylene, oxazolidinylene, thiazolidinylene, piperidinylene, piperazinylene, morpholinylene, thiomorpholinylene and dioxacyclohexylene. The heterocyclylene can be unsubstituted or mono-, di-, tri-, or poly-substituted as clearly defined. The substituent of the substituted heterocyclylene can be, for example, one or more substituents selected from $C_{1-3}$ alkyl, $C_{1-3}$ alkoxy, cyano, trifluoromethyl, heterocyclyl, halogen, amino, hydroxyl or any combination thereof.

In the present disclosure, the term "alkynylene" used alone or in combination refers to a linear or branched divalent hydrocarbon group with one or more carbon-carbon triple bonds containing 2 to 8 (preferably 2 to 6, more preferably 2 to 4) carbon atoms. Examples of alkynylene include, but are not limited to, ethynylene (i.e. —C≡C—), 1-propynylene, 1-butynylene, and 1,3-diynylene.

In the present disclosure, the term "alkenylene" used alone or in combination refers to a linear or branched divalent hydrocarbon group with one or more carbon-carbon double bonds containing 2 to 8 (preferably 2 to 6, more preferably 2 to 4) carbon atoms. Examples of alkenylene include, but are not limited to, vinylene (i.e. —CH=CH—), 1-propenylene, and 1-butenylene.

The salts or pharmaceutically acceptable salts, enantiomers, stereoisomers, solvates, and polymorphs of the compounds represented by formula I described in the present disclosure are also encompassed within the scope of the present disclosure.

In all embodiments of the present disclosure, the salt or pharmaceutically acceptable salt of the compound represented by formula I refers to a non-toxic inorganic or organic acid and/or base addition salt. Examples include: sulfate, hydrochloride, citrate, maleate, sulfonate, or p-toluenesulfonate.

The salts or pharmaceutically acceptable salts, enantiomers, stereoisomers, solvates, polymorphs of the compounds represented by formula III described in the present disclosure are also encompassed within the scope of the present disclosure.

In all embodiments of the present disclosure, the salt or pharmaceutically acceptable salt of the compound represented by formula III refers to a non-toxic inorganic or organic acid and/or base addition salt. Examples include: sulfate, hydrochloride, citrate, maleate, sulfonate, or p-toluenesulfonate.

"Pharmaceutically acceptable carrier" refers to pharmaceutically acceptable materials, such as fillers, stabilizers, dispersants, suspending agents, diluents, excipients, thickeners, solvents, or encapsulating materials. The compounds useful in the present disclosure are carried or transported into the patient's body or administered to the patient so that it can perform intended function thereof. Generally, such constructs are carried or transported from one organ or part of the body to another organ or part of the body. The carrier is compatible with other ingredients of the formulation (including the compounds useful in the present disclosure) and is not harmful to the patient, the carrier must be "acceptable." Some examples of materials that can be used as pharmaceutically acceptable carriers include: sugar, such as lactose, glucose, and sucrose; starch, such as corn starch and potato starch; cellulose and derivatives thereof, such as sodium carboxymethyl cellulose, ethyl cellulose and acetate cellulose; powdered tragacanth; malt; gelatin; talc; excipients, such as cocoa butter and suppository wax; oil, such as peanut oil, cottonseed oil, safflower oil, sesame oil, olive oil, corn oil and soybean oil; glycols, such as propylene glycol; polyols, such as glycerin, sorbitol, mannitol, and polyethylene glycol; esters, such as ethyl oleate and ethyl laurate; agar; buffers, such as magnesium hydroxide and aluminum hydroxide; surfactant phosphate buffer solution; and other non-toxic compatible substances used in pharmaceutical formulations.

The term "treat" or "treatment" refers to the administration of a compound represented by formula I or a compound represented by formula IV or a pharmaceutically acceptable salt thereof in the present disclosure, or a pharmaceutical composition comprising a compound represented by formula I or a compound represented by formula IV or a pharmaceutically acceptable salt thereof as an active ingredient to the subject to slow down (alleviate) unwanted diseases or conditions, such as the development of cancer or tumors. The beneficial or desired clinical results of the present disclosure include but are not limited to: alleviating symptoms, reducing the severity of the disease, stabilizing the state of the disease, delaying or slowing down the progression of the disease, improving or alleviating the disease, and alleviating the disease.

The "therapeutically effective amount" of the compound of the present disclosure depends on the age, sex, and weight of the patient, the patient's current medical condition, and the cancer progression of the patient being treated. Those skilled in the art can determine the appropriate amount based on these and other factors.

The term "room temperature" in the present disclosure refers to surrounding temperature, for example, a temperature of 20-30° C.

The compound developed by the present disclosure belongs to a degradant that targets a specific protein, which is composed of four parts: a small molecule compound (ALK-TKIS, Small Molecules Binding Protein) capable of binding protein, and an E3 ligase ligand with ubiquitination function and linking unit (linker or LIN), and group A. The present disclosure selects a small molecule compound (ALK-TKIS) that can bind to a protein as an anchoring element, and the E3 ligase ligand is combined with the ALK-TKIS through a linker and group A to develop a degradant which can target specific protein. The specific recognition of the target protein by ALK-TKIS inhibits the activity of the target protein. At the same time, the E3 ligase specifically ubiquitinates the target protein to degrade and clear the target protein, and finally the target protein can be eliminated from the tumor cells. The compounds of the present disclosure can not only inhibit the occurrence and progression of tumors, but also can potentially overcome the development of drug resistance to targeted drugs. The E3 ligase ligand with a novel structure designed and developed in the present disclosure has been successfully applied to a degradant targeting a specific protein, providing a new treatment strategy for tumor patients in the background of precision medicine.

Detailed Description of the Preferred Embodiment

In the following description, many specific details are proposed in order to provide a thorough understanding of the present disclosure. The present disclosure may be implemented without some or all of these specific details. In other cases, in order not to cause unnecessary confusion to the present disclosure, the well-known process operations are not described in detail. Although the present disclosure will be described in conjunction with specific embodiments, it should be understood that this is not intended to limit the present disclosure to these embodiments.

The following abbreviations are used throughout the specification and embodiments:
Boc Tert-butoxycarbonyl
Con. Concentration
 DCM Dichloromethane
 DMF N,N-dimethylformamide
 DMSO Dimethyl sulfoxide
 DIPEA N,N-diisopropylethylamine
 EA Ethyl acetate
EDCI Carbodiimide
 ESI Electrospray ionization
 equiv Equivalent
EtOH Ethanol
 HOAT 1-Hydroxy-7-azobenzotriazole
 HATU 2-(7-Azobenzotriazole)-N,N,N',N'-tetramethylurea hexafluorophosphate
 OMs Mesylate
 HPLC High performance liquid chromatography
 HRMS High resolution mass spectrometry
 LC-MS Liquid chromatography-mass spectrometry
 LRMS Low resolution mass spectrometry
 LC Liquid chromatography
Me Methyl
 MeCN Acetonitrile
McOH Methanol
 MS Mass spectrometry
MW Microwave
 NaHMDS Sodium hexamethyldisilazide
 NMM N-methylmorpholine
 NMP N-methylpyrrolidone
 $^1$H NMR Nuclear Magnetic Resonance Hydrogen Spectroscopy
 rt Room temperature
TEA Triethylamine
 TFA Trifluoroacetate
 TLC Thin layer chromatography
TMS Trimethylsilyl
 Xantphos 4,5-bis(diphenylphosphino)-9,9-dimethylxanthene
 X-Phos 2-dicyclohexylphosphino-2,4,6-triisopropylbiphenyl In the embodiments, the $^1$H NMR spectrum was measured with a Bruker-500 MHz nuclear magnetic resonance instrument, and CD$_3$OD containing 0.1% TMS was used as the solvent, and CD$_3$OD (δ=3.31 ppm) was used as the internal standard in the $^1$H NMR spectrum; or CDCl$_3$ containing 0.1% TMS was used as the solvent, CDCl$_3$ (δ=7.26 ppm) was used as the internal standard in the $^1$H NMR spectrum; or DMSO-d$_6$ containing 0.03% TMS was used as the solvent, and DMSO-d$_6$ (δ=2.50 ppm) was used as the internal standard in the $^1$H NMR spectrum; LRMS spectrum was measured on AB Triple 4600 mass spectrometer, HPLC preparation was measured on SHIMADZU LC-20AP instrument, and HPLC purity was measured on SHIMADZU LC-30AP or Waters 1525 instrument. All reactions were carried out under air atmosphere unless otherwise specified; the reactions were followed by TLC or LC-MS.

Solvents and reagents were treated as follows:
 the solvents DCM, DMF, anhydrous EtOH, and anhydrous MeOH used in the reactions were all purchased from Sinopharm;
 preparative CH$_3$CN and deionized water were used in HPLC preparation;
 unless otherwise specified, Alectinib, Alectinib Derivative A, Brigatinib and various carbon chain linking unit linkers of different lengths (linking groups of the compound represented by formula I or compound represented by formula III of the present disclosure) were all directly purchased.
 Other reagents and medicines were purchased directly from the manufacturer unless otherwise specified.

General Synthetic Method

General Preparation Method of Brigatinib Derivatives A, B, C (ALK Inhibitors)

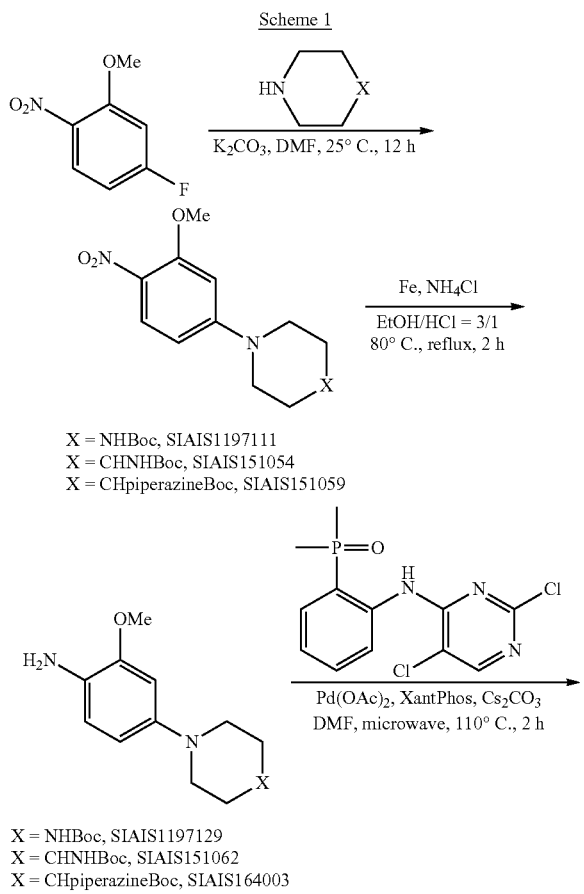

X = NHBoc, SIAIS1197129
X = CHNHBoc, SIAIS151062
X = CHpiperazineBoc, SIAIS164003

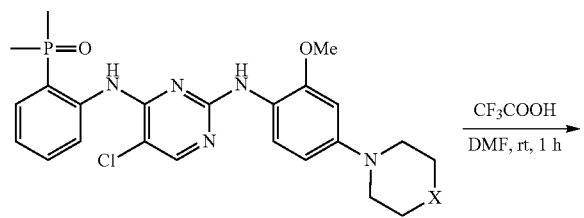

Y = NH, SIAIS1197135, brigatinib derivative A
Y = CHNH₂, SIAIS151101, brigatinib derivative B
Y = CHpiperazine, SIAIS164005, brigatinib derivative C The groups X and Y were as shown in Scheme 1.

General Preparation Method of Alectinib Derivatives B, C (ALK Inhibitors):

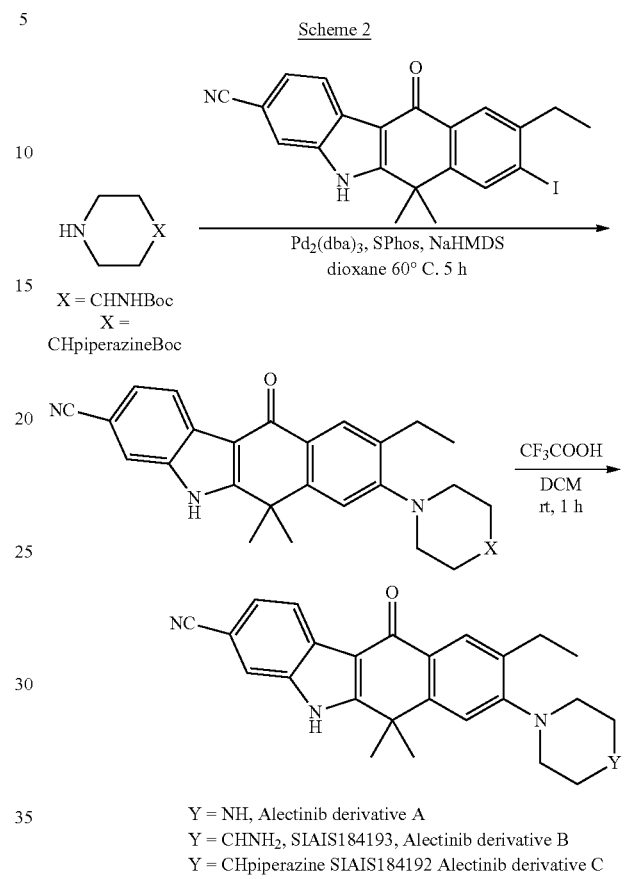

Y = NH, Alectinib derivative A
Y = CHNH₂, SIAIS184193, Alectinib derivative B
Y = CHpiperazine SIAIS184192 Alectinib derivative C The groups X and Y were as shown in Scheme 2.

In addition, the Alectinib derivative A (9-ethyl-6,6-dimethyl-11-oxo-8-(piperazin-1-yl)-6,11-dihydro-5H-benzo[b]carbazole-3-carbonitrile) could also be purchased directly.

General Preparation Method of Intermediate LM (Terminal Lenalidomide Alkyl Carbon Chain Linker Substituted by Acid, Namely Len-NH—$C_n$COOH Linker):

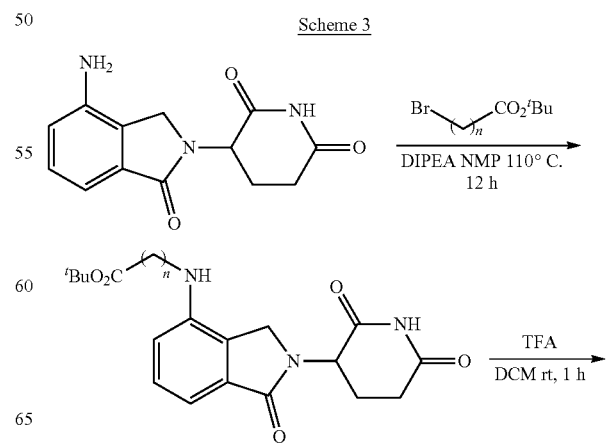

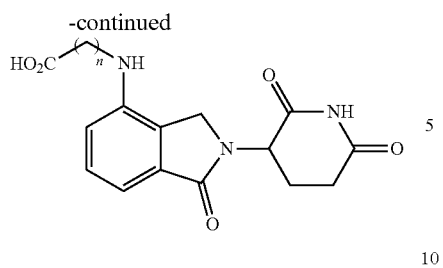

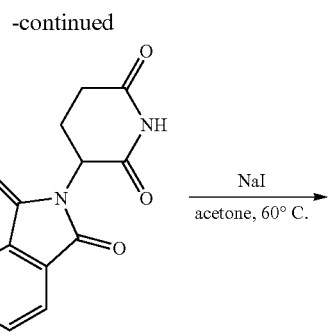

Wherein n is an integer of 1-20, as shown in Scheme 3.

General Preparation Method of Intermediate LM (Terminal Lenalidomide Alkyl PEG Chain Linker Substituted by Acid, Namely Len-NH-PEG$_n$COOH Linker):

Scheme 4

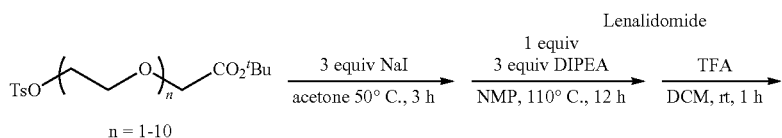

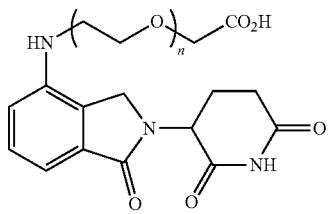

Wherein n is an integer of 1-10, as shown in Scheme 4.

General Preparation Method of Intermediate LM (Terminal Pomalidomide Alkyl Carbon Chain Linker Substituted by Iodine, Namely Poma-NH-C$_n$I):

Scheme 5

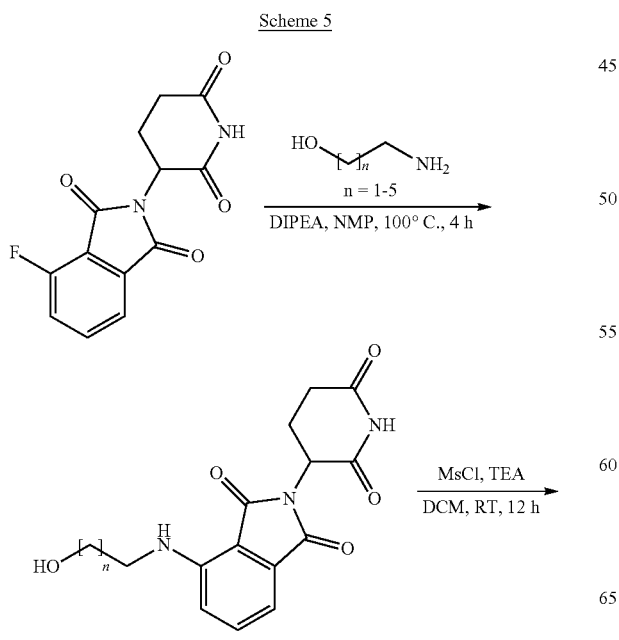

-continued

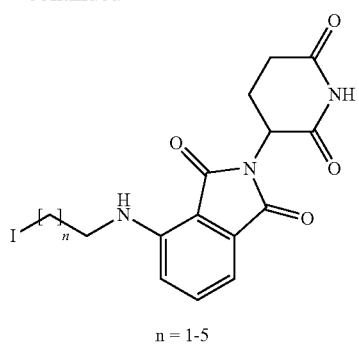

General Preparation Method of Intermediate LM (Terminal Lenalidomide or Pomalidomide Alkynyl Carbon Chain Linker Substituted by OMs, Namely Len/Poma-CC-C$_n$-OMs Linker):

Scheme 6
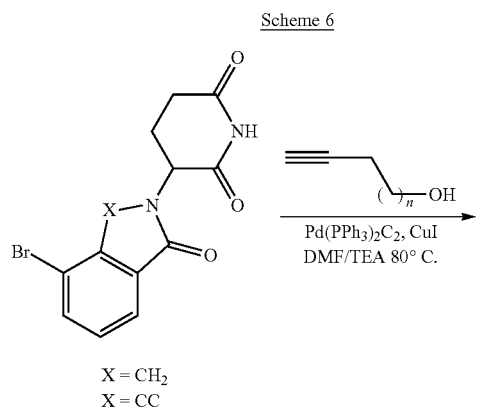
X = CH₂
X = CC
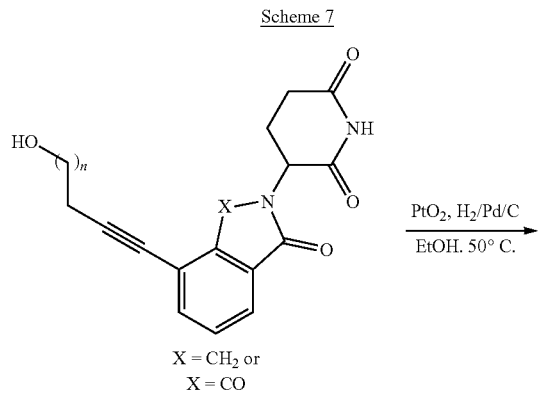
X = CH₂ or
X = CO
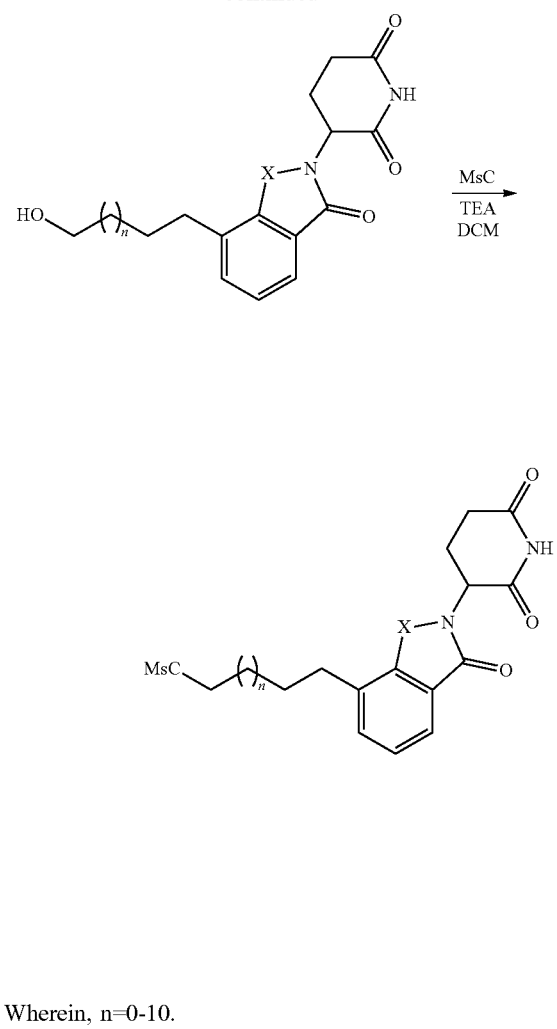
Wherein, n=0-10.
General Preparation Method of Intermediate LM (Len/Poma-O—$C_n$ Linker):
Scheme 8
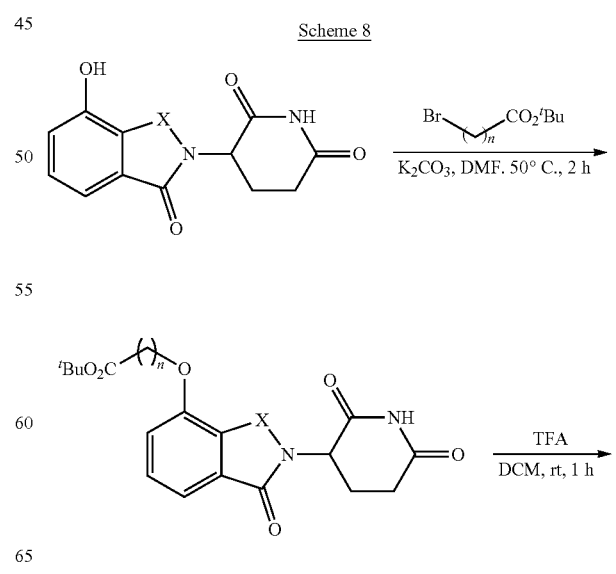
Wherein, n=0-10.
General Preparation Method of Intermediate LM (Len/Poma-CH₂-$C_n$ Linker):
Scheme 7

395
-continued
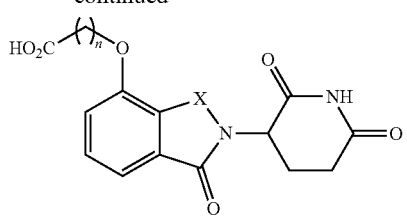
General Synthetic Method of the Compounds of the Present Disclosure (Constructed by Condensation Reaction):
Scheme 9
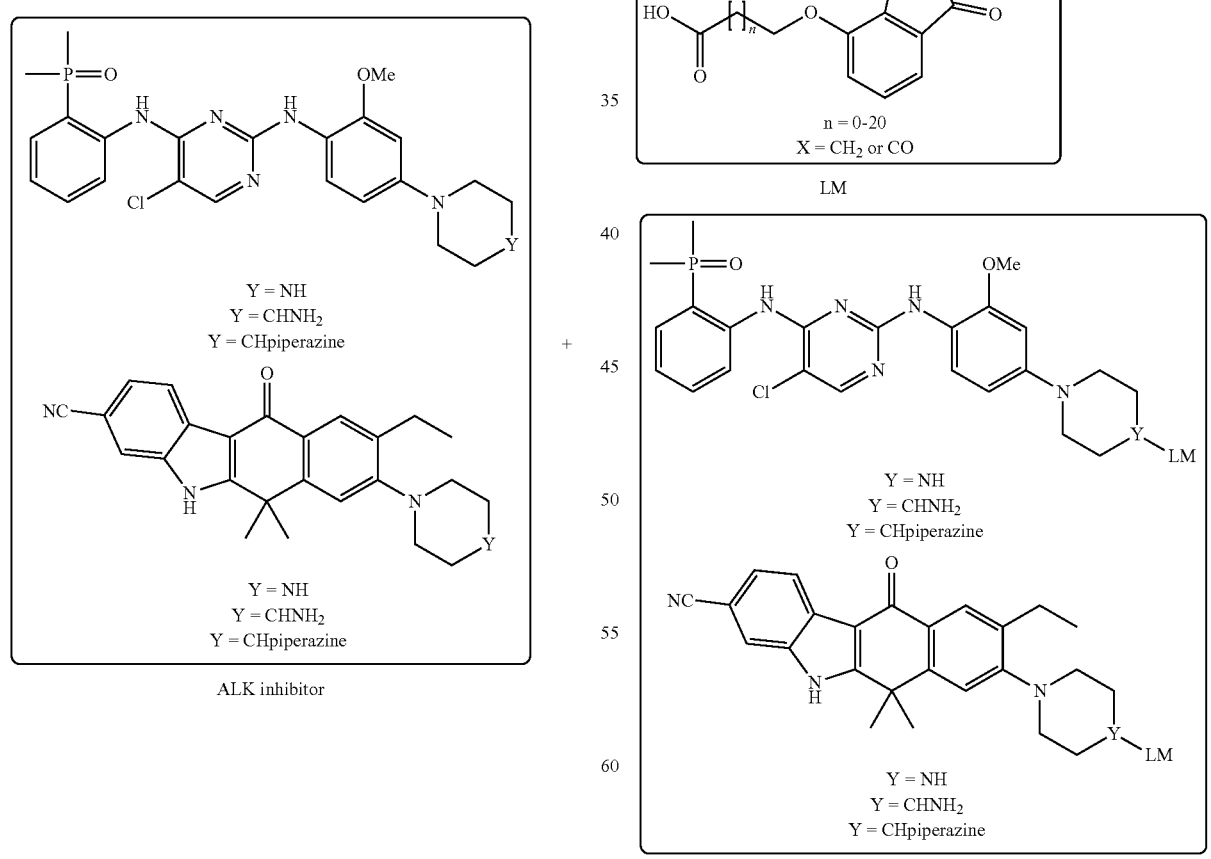
ALK inhibitor
396
-continued
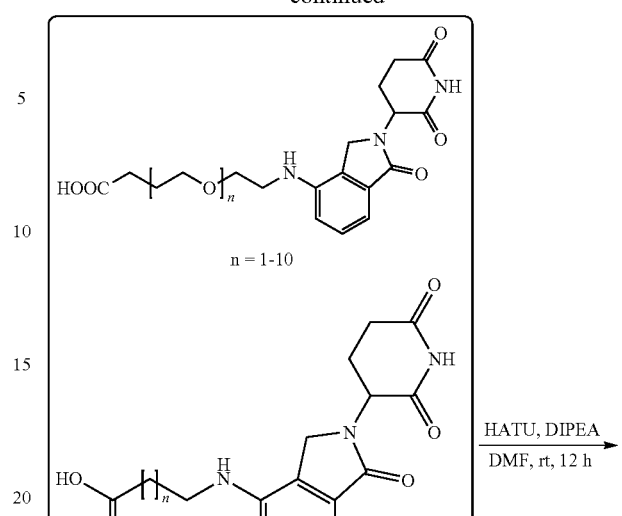
Compounds of the present disclosure General Synthetic Method of the Compounds of the Present Disclosure (Constructed by Nucleophilic Substitution Reaction):
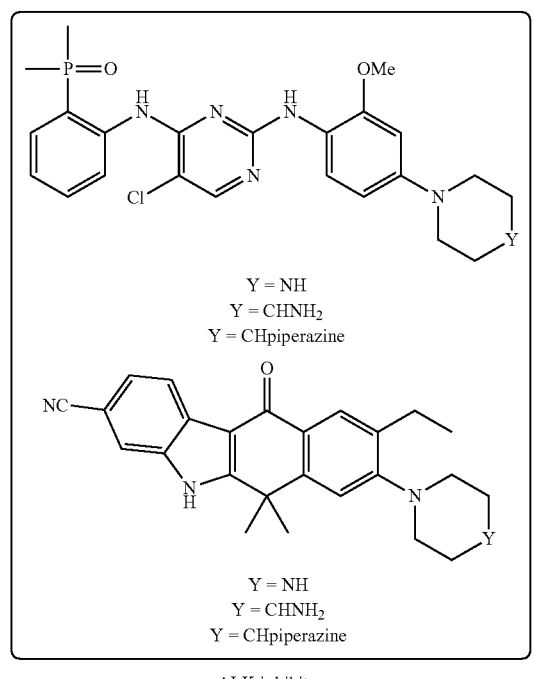
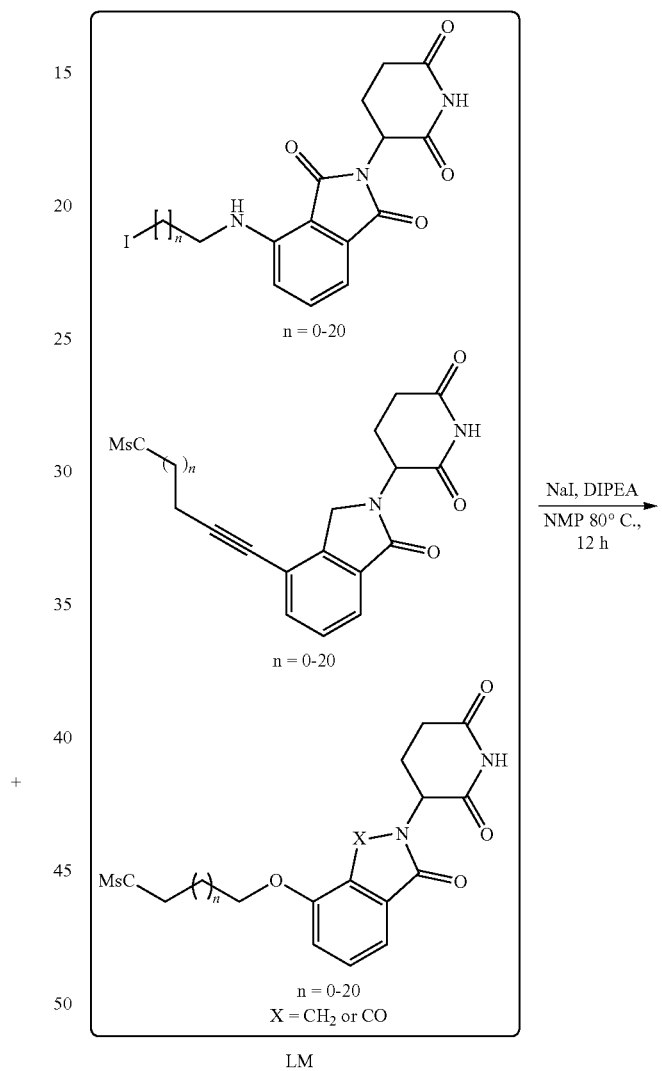

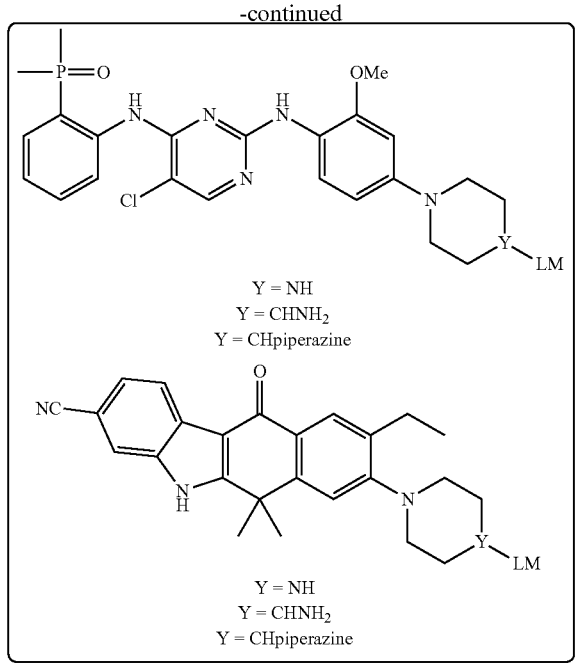

Compounds of the present disclosure

General Preparation Method of Intermediate LM (Lenalidomide PEG Chain Carboxylic Acid Linker Substituted by Thiol):

Scheme 11

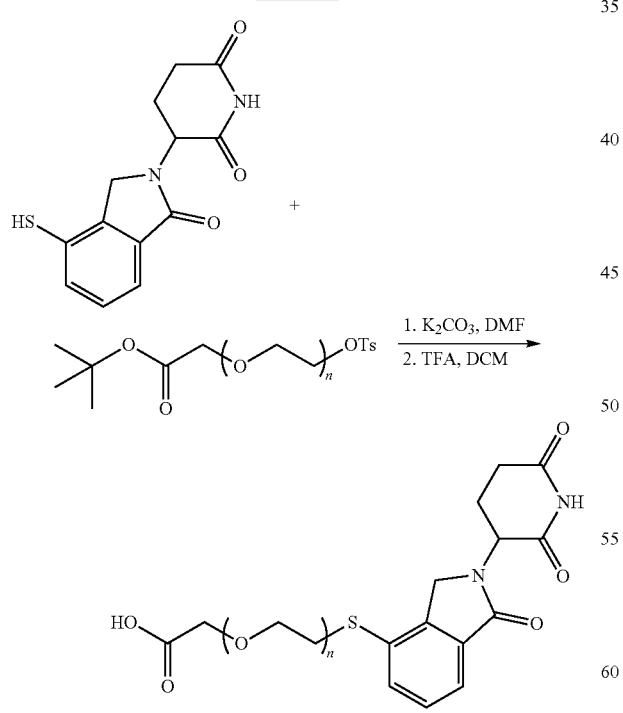

Wherein, n is an integer of 1-5, as shown in Scheme 11.

General Preparation Method of Intermediate LM (Lenalidomide Carbon Chain Carboxylic Acid Linker Substituted by Thiol):

Scheme 12

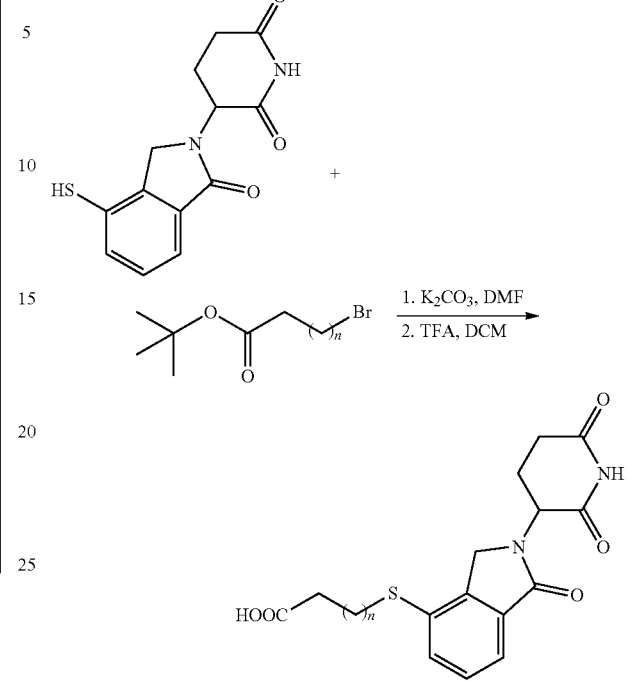

Wherein, n is an integer of 0-10, as shown in Scheme 12.

General Preparation Method of Intermediate LM (Terminal Thio-Lenalidomide Carbon Chain Linker Substituted by Bromine):

Scheme 13

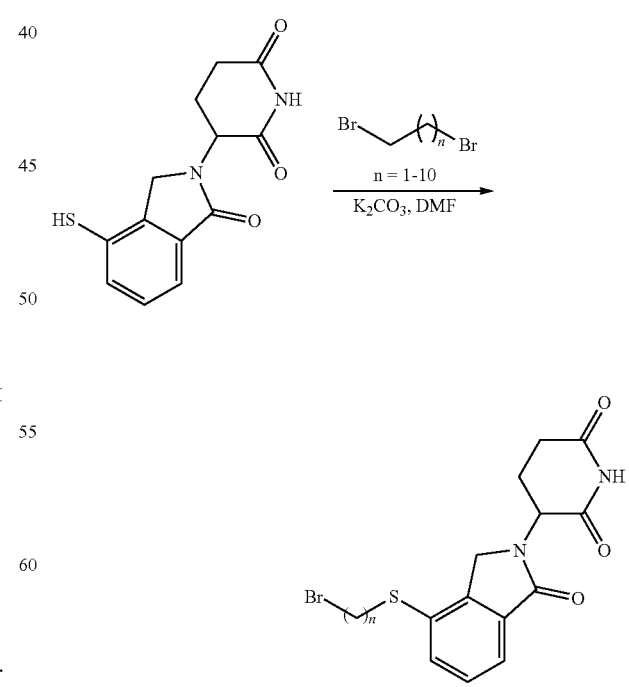

Wherein, n is an integer of 0-11, as shown in Scheme 13.

General Synthetic Method of the Compounds of the Present Disclosure (Constructed by Condensation Reaction):
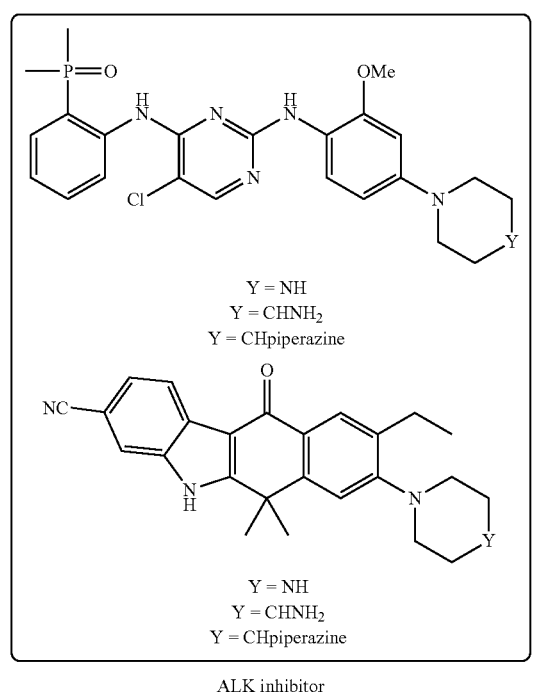
ALK inhibitor
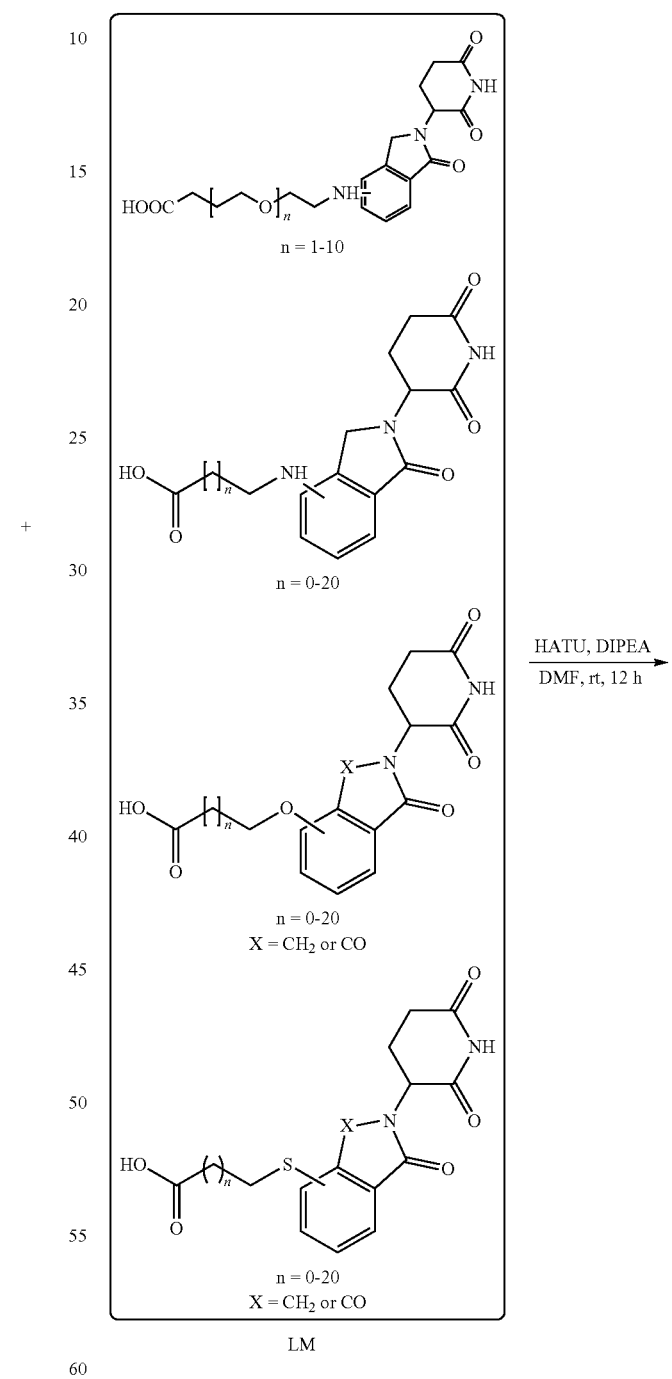
LM

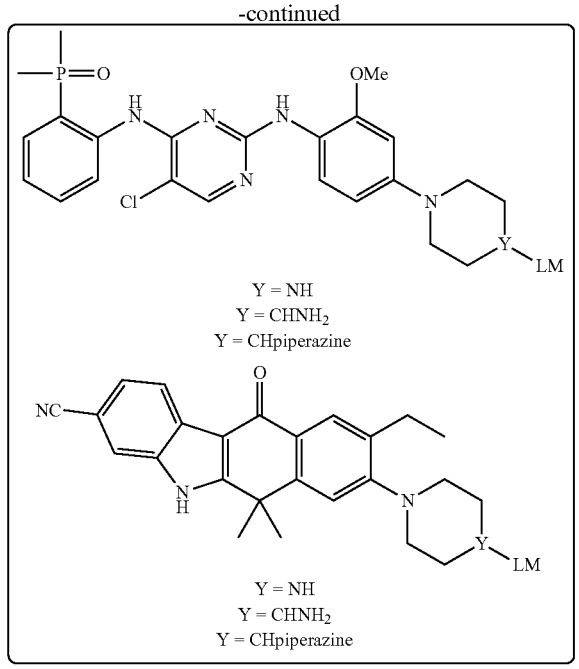
Compounds of the present disclosure
General Synthetic Method of the Compounds of the Present Disclosure (constructed by Nucleophilic Substitution Reaction):
Scheme 15
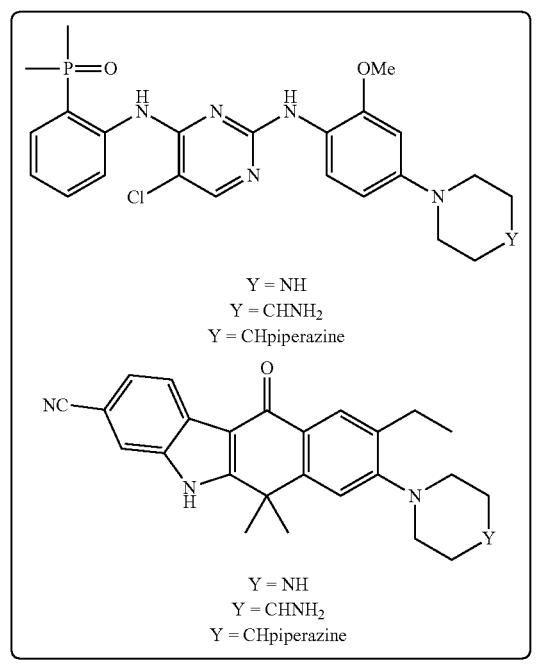
ALK inhibitor
+
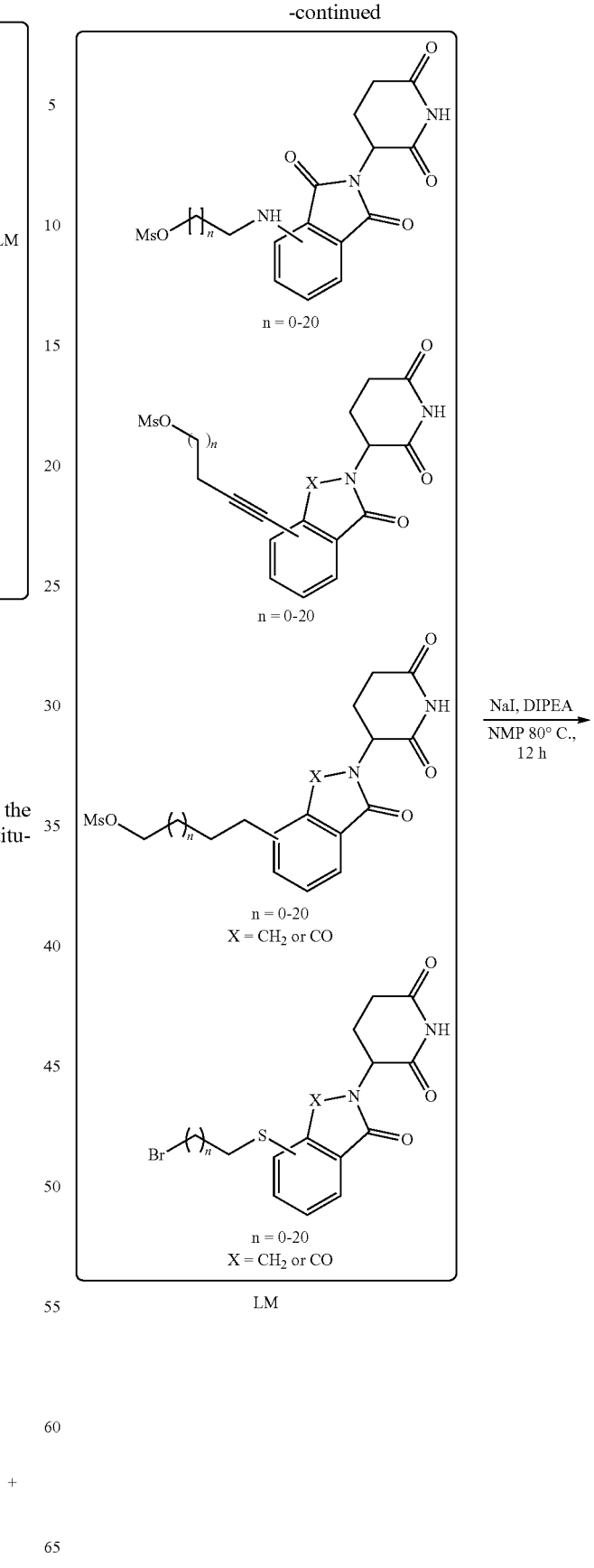
LM
$\xrightarrow{\text{NaI, DIPEA}}_{\text{NMP 80° C., 12 h}}$

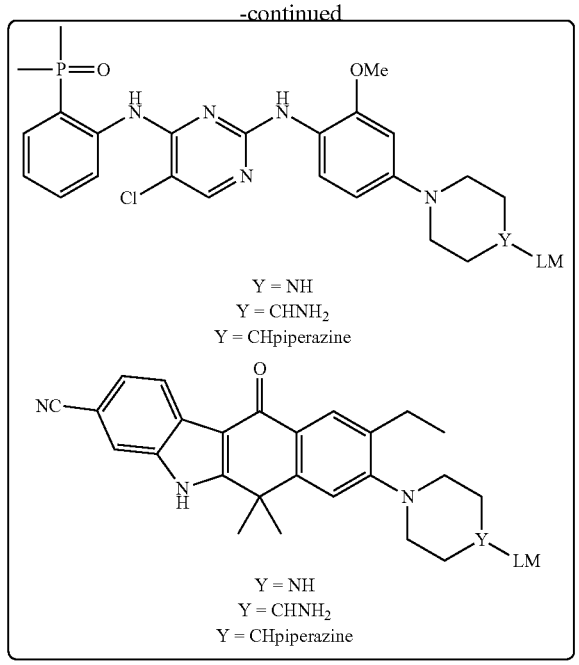

Compounds of the present disclosure

Embodiments of Intermediate Preparation

Intermediate Preparation Embodiment 1:
Preparation of Brigatinib Derivative A
(SIAIS1197135)

The Brigatinib derivative A (SIAIS1197135) was prepared according to Scheme 1.

Preparation of tert-butyl 4-(3-methoxy-4-nitrophenyl)piperazine-1-carboxylate (SIAIS1197111)

Under open conditions, 5-fluoro-2-nitroanisole (7 g, 40.9 mmol) was dissolved in 60 mL of DMF solution, and $K_2CO_3$ (8.4 g, 60.8 mmol), N-tert-butoxycarbonylpiperazidine (9.1 g, 48.9 mmol) were added sequentially, and the mixture was stirred at room temperature overnight. After the reaction was completed, quenched with water, extracted with ethyl acetate, organic phase was washed with water, washed with saturated brine, dried over anhydrous sodium sulfate, spin-dried, beaten with mixed solvent of petroleum ether: ethyl acetate=5:1, filtered with sand core, and 11.1 g of yellow target solid SIAIS1197111 was obtained, with a yield of 80%. $^1$H NMR (500 MHz, DMSO) δ 7.89 (d, J=9.3 Hz, 1H), 6.57 (d, J=9.5 Hz, 1H), 6.52 (s, 1H), 3.90 (s, 3H), 3.46 (s, 8H), 1.42 (s, 9H). HRMS (ESI) $C_{16}H_{24}N_3O_5^+$ [M+H]$^+$, calculated: 338.1710; found: 338.1610.

Preparation of tert-butyl 4-(4-amino-3-methoxyphenyl)piperazine-1-carboxylate (SIAIS1197129)

Under open conditions at room temperature, in an egg-shaped flask, SIAIS1197111 (10 g, 29.6 mmol), 90 mL of EtOH, 30 mL of $H_2O$, $NH_4Cl$ (6.3 g, 118.6 mmol), Fe powder (8.3 g, 148.2 mmol) were added sequentially, then, the system was ventilated with argon, and refluxed at 80° C. for 2 h. The reaction was detected by TLC until the reaction was completed, filtered by silica gel, concentrated and concentrated to remove the ethanol, extracted with dichloromethane, dried over anhydrous sodium sulfate, and spin-dried to obtain 7.7 g of gray-blue solid SIAIS1197129, with a yield of 85%. $^1$H NMR (500 MHz, MeOD) δ 6.72 (d, J=8.3 Hz, 1H), 6.63 (d, J=2.2 Hz, 1H), 6.47 (d, J=7.0 Hz, 1H), 3.86 (s, 3H), 3.57 (s, 4H), 2.99 (s, 4H), 1.50 (s, 9H). HRMS (ESI) $C_{16}H_{26}N_3O_3^+$ [M+H]$^+$, calculated: 308.1969; found: 308.1882.

Preparation of (2-((5-chloro-2-((2-methoxy-4-(piperazin-1-yl)phenyl)amino) pyrimidin-4-yl)amino) phenyl) dimethylphosphine oxide (SIAIS1197135)

At room temperature, in a standard microwave reaction tube, AP26113 intermediate (2 g, 6.3 mmol), SIAIS1197129 (2.4 g, 7.8 mmol), Pd(OAc)$_2$ (176 mg, 0.78 mmol), Xantphos (810 mg, 1.4 mmol), cesium carbonate (6.4 g, 19.6 mmol), 30 mL of DMF were added sequentially, then the system was ventilated with argon, the reaction was carried out under microwave at 110° C. for 1.5 h. The reaction was detected by TLC until the reaction was completed, filtered by silica gel, quenched with water, extracted with ethyl acetate, washed with water, dried over anhydrous sodium sulfate, and separated with a reversed phase C18 column. The eluents were methanol and water, 900 mg of reddish-brown solid was obtained and directly used for the next step.

Under open conditions at room temperature, in an egg-shaped flask, reddish-brown solid (900 mg), 6 mL of DCM, 20 mL of $CF_3COOH$ were added sequentially, and then the mixture was reacted at room temperature for 2 h. The reaction was detected by LC-MS until the reaction was completed, most of the $CF_3COOH$ was spun off, saturated sodium bicarbonate solution was added to adjust the pH value of the solution to alkaline, then the mixture was extracted with dichloromethane, the organic phase was dried over anhydrous sodium sulfate, spin-dried, separated with a reversed-phase C18 column, and the eluents were methanol and water, and 701 mg of SIAIS1197135 was obtained as reddish-brown solid. The total yield of the two steps was 23%. $^1$H NMR (500 MHz, MeOD) δ 8.32 (dd, J=8.2, 4.4 Hz, 1H), 8.04 (s, 1H), 7.70 (d, J=8.7 Hz, 1H), 7.61 (dd, J=14.1, 7.7 Hz, 1H), 7.52 (t, J=7.9 Hz, 1H), 7.26 (t, J=7.5, 1H), 6.67 (d, J=2.5 Hz, 1H), 6.45 (dd, J=8.8, 2.5 Hz, 1H), 3.86 (s, 3H), 3.24-3.17 (m, 4H), 3.17-3.11 (m, 4H), 1.83 (d, J=13.5 Hz, 6H). HRMS (ESI) $C_{23}H_{29}ClN_6O_2P^+$ (M+H)$^+$, calculated: 487.1773; found: 487.1773.

Intermediate Preparation Embodiment 2:
Preparation of Brigatinib Derivative B

The Brigatinib derivative B was prepared according to Scheme 1 using a similar method to that of the intermediate preparation embodiment 1 of Brigatinib derivative A. The intermediate synthesis data and structural characterization data of the Brigatinib derivative B were as follows:

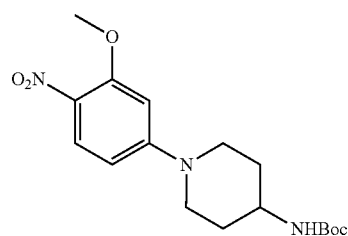

Tert-butyl (1-(3-methoxy-4-nitrophenyl)piperidin-4-yl) carbamate (SIAIS151054). (Yellow solid, 1.81 g, yield: 88%) $^1$H NMR (500 MHz, CDCl$_3$) δ 7.99 (t, J=8.9 Hz, 1H), 6.41 (dd, J=9.4, 2.5 Hz, 1H), 6.30 (d, J=2.5 Hz, 1H), 4.49 (s, 1H), 3.94 (s, 3H), 3.86-3.82 (m, 2H), 3.71 (s, 1H), 3.09-3.00 (m, 2H), 2.11-2.03 (m, 2H), 1.89-1.75 (m, 2H), 1.45 (s, 9H).

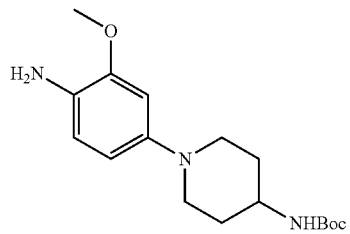 [SMILES: COc1cc(N2CCC(NC(=O)OC(C)(C)C)CC2)ccc1N]

Tert-butyl (1-(4-amino-3-methoxyphenyl)piperidin-4-yl) carbamate (SIAIS151062). (Gray purple solid, 411.6 mg, 90%) $^1$H NMR (500 MHz, DMSO) δ 6.82 (d, J=7.6 Hz, 1H), 6.50 (d, J=8.5 Hz, 1H), 6.48 (d, J=2.5 Hz, 1H), 6.28 (dd, J=8.4, 2.4 Hz, 1H), 4.20 (s, 2H), 3.73 (s, 3H), 3.33-3.26 (m, 3H), 2.56-2.50 (m, 2H), 1.77 (d, J=11.4 Hz, 2H), 1.53-1.45 (m, 2H), 1.39 (s, 9H).

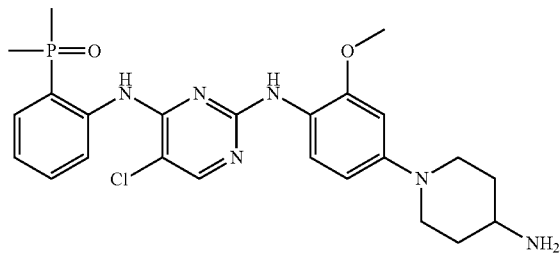 [SMILES: COc1cc(N2CCC(N)CC2)ccc1Nc1ncc(Cl)c(Nc2ccccc2P(C)(C)=O)n1]

(2-((2-((4-(4-Aminopiperidin-1-yl)-2-methoxyphenyl) amino)-5-chloropyrimidin-4-yl)amino)phenyl)dimethyl phosphine oxide (SIAIS151101). (Yellow solid, 330 mg, total yield of two steps: 33%) $^1$H NMR (500 MHz, DMSO) δ 8.49 (s, 1H), 8.08 (s, 1H), 8.06 (s, 1H), 7.53 (ddd, J=14.0, 7.7, 1.3 Hz, 1H), 7.38-7.32 (m, 2H), 7.10 (t, J=7.1 Hz, 1H), 6.62 (d, J=2.5 Hz, 1H), 6.46 (dd, J=8.7, 2.5 Hz, 1H), 3.75 (s, 3H), 3.65-3.61 (m, 2H), 2.78-2.67 (m, 3H), 1.82-1.79 (m, 2H), 1.78 (s, 3H), 1.75 (s, 3H), 1.42-1.34 (m, 2H). HRMS (ESI) C$_{24}$H$_{31}$ClN$_6$O$_2$P [M+H]$^+$: calculated: 501.1913, found: 501.1900.

Intermediate Preparation Embodiment 3:
Preparation of Brigatinib Derivative C
(SIAIS164005)

The Brigatinib derivative C (SIAIS164005) was prepared according to scheme 1 using a similar method to that of the intermediate preparation embodiment 1 of Brigatinib derivative A. The intermediate synthesis data and structural characterization data of the Brigatinib derivative C were as follows:

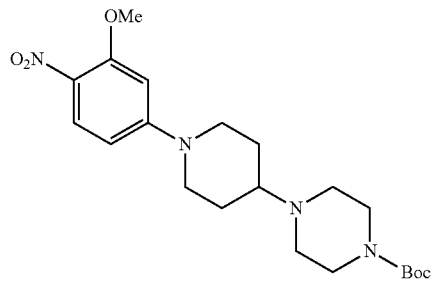 [SMILES: COc1cc(N2CCC(N3CCN(C(=O)OC(C)(C)C)CC3)CC2)ccc1[N+](=O)[O-]]

Tert-butyl 4-(1-(3-methoxy-4-nitrophenyl)piperidin-4-yl) piperazine-1-carboxylate (SIAIS151059). (Yellow solid, 1.02 g, yield: 83%). $^1$H NMR (500 MHz, MeOD) δ 7.93 (d, J=9.4 Hz, 1H), 6.55 (dt, J=13.4, 6.7 Hz, 1H), 6.50 (d, J=2.5 Hz, 1H), 4.10 (s, 1H), 4.07 (s, 1H), 3.94 (d, J=6.6 Hz, 3H), 3.43 (s, 4H), 3.02-2.93 (m, 2H), 2.60-2.55 (m, 5H), 2.02-1.95 (m, 2H), 1.57 (qd, J=12.4, 4.0 Hz, 2H), 1.46 (s, 9H). HRMS (ESI) C$_{21}$H$_{33}$N$_4$O$_5$ [M+H]$^+$: calculated: 421.2445, found: 421.2442.

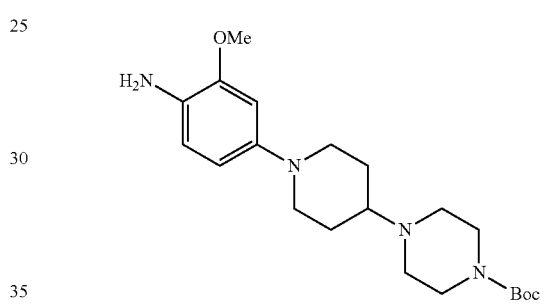

Tert-Butyl 4-(1-(4-amino-3-methoxyphenyl)piperidin-4-yl)piperazine-1-carboxylate (SIAIS164003). (Off-white solid, 745 mg, yield: 79%). $^1$H NMR (500 MHz, MeOD) δ 6.59 (t, J=56.8 Hz, 3H), 3.78 (s, 3H), 3.46 (s, 6H), 2.62 (d, J=4.3 Hz, 6H), 2.42 (s, 1H), 1.98 (s, 2H), 1.69 (d, J=9.7 Hz, 2H), 1.46 (s, 9H). HRMS (ESI) C$_{21}$H$_{35}$N$_4$O$_3$ [M+H]$^+$: calculated: 391.2704, found: 391.3048.

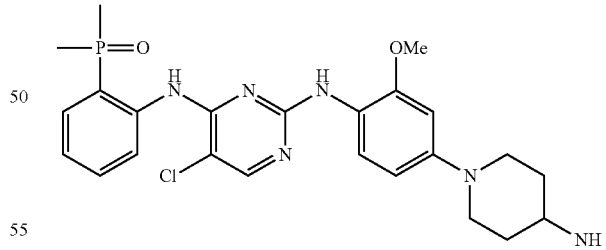

(2-((5-Chloro-2-((2-methoxy-4-(4-(piperazin-1-yl)piperidin-1-yl)phenyl)amino) pyrimidin-4-yl)amino) phenyl) dimethyl phosphine oxide (SIAIS164005). (Yellow solid, 350 mg, total yield of two steps: 37%). $^1$H NMR (500 MHz. MeOD) δ 8.33 (dd, J=8.2, 4.4 Hz, 1H), 8.03 (s, 1H), 7.69-7.64 (m, 1H), 7.60 (ddd, J=14.0, 7.7, 1.4 Hz, 1H), 7.51 (t, J=7.9 Hz, 1H), 7.26 (td, J=7.6, 1.2 Hz, 1H), 6.66 (d, J=2.4 Hz, 1H), 6.45 (dd, J=8.8, 2.5 Hz, 1H), 3.85 (s, 3H), 3.73-3.63 (m, 2H), 3.11-3.02 (m, 4H), 2.79-2.66 (m, 6H), 2.48-2.43 (m, 1H), 1.99 (d, J=12.5 Hz, 2H), 1.84 (d, J=13.5 Hz,

Intermediate Preparation Embodiment 4: Preparation of Alectinib Derivative B (SIAIS184193)

Preparation of Alectinib derivative B (8-(4-aminopiperidin-1-yl)-9-ethyl-6,6-dimethyl-11-oxo-6,11-dihydro-5H-benzo[b]carbazole-3-carbonitrile (SIAIS184193)) according to scheme 2

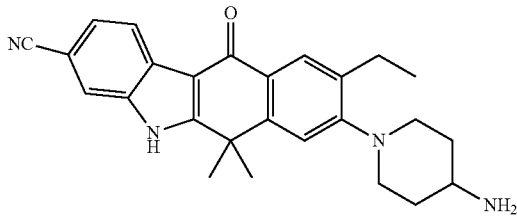 [SMILES: CCc1cc2c(cc1N1CCC(N)CC1)C(C)(C)c1[nH]c3cc(C#N)ccc3c1C2=O]

At room temperature, in a 25 mL egg-shaped flask, 9-ethyl-8-iodo-6,6-dimethyl-11-oxo-6,11-dihydro-5H-benzo[b]carbazole-3-carbonitrile (440 mg, 1 mmol), 4-tert-butoxycarbonylaminopiperidine (377.2 mg, 1.4 mmol), Pd$_2$(dba)$_3$ (45.8 mg, 0.05 mmol), Sphos (82.1 mg, 0.2 mmol), 10 mL of 1,4-dioxane were added sequentially, then the system was ventilated with argon, NaHMDS (4 mL, 4 mmol, 1.0 M in THF) was added, and the reaction was carried out in an oil bath at 60° C. for 5 h. The reaction was detected by TLC until the reaction was completed, spin-dried, separated with a normal phase column, eluent was petroleum ether: ethyl acetate=1:3, the residue was spin-dried to obtain a reddish-brown solid.

In an egg-shaped flask at room temperature, the reddish-brown solid (350 mg), 6 mL of DCM, 2 mL of CF$_3$COOH were added sequentially, and then the mixture was reacted at room temperature for 1 h. The reaction was detected by LC-MS until the reaction was completed, most of the CF$_3$COOH was spun off, saturated sodium bicarbonate solution was added to adjust the pH of the solution to alkaline, the mixture was extracted with dichloromethane, the organic phase was dried over anhydrous sodium sulfate, spin-dried, separated with a reversed-phase C18 column, and eluents were methanol and water, and 310 mg of a yellow solid SIAIS184193 was obtained. The total yield of the two steps was 60%. $^1$H NMR (500 MHz, DMSO) δ 12.91 (s, 1H), 8.32 (d, J=8.1 Hz, 1H), 8.17 (d, J=4.2 Hz, 2H), 8.05 (d, J=8.2 Hz, 1H), 8.01 (s, 1H), 7.61 (dd, J=8.1, 1.3 Hz, 1H), 7.38 (s, 1H), 3.22 (d, J=12.2 Hz, 3H), 2.86 (t, J=11.4 Hz, 2H), 2.70 (q, J=7.5 Hz, 2H), 2.06 (d, J=10.0 Hz, 2H), 1.81-1.73 (m, 8H), 1.28 (t, J=7.5 Hz, 3H). HRMS (ESI) Calculated for C$_{26}$H$_{29}$N$_4$O [M+H]$^+$: 413.2336, found: 413.2339.

Intermediate Preparation Embodiment 5: Preparation of Alectinib Derivative C (SIAIS184192)

The Alectinib Derivative C was prepared according to Scheme 2 using a method similar to that of Intermediate Preparation Embodiment 4 of the Alectinib Derivative B. The structure characterization data of the Alectinib Derivative C was as follows:

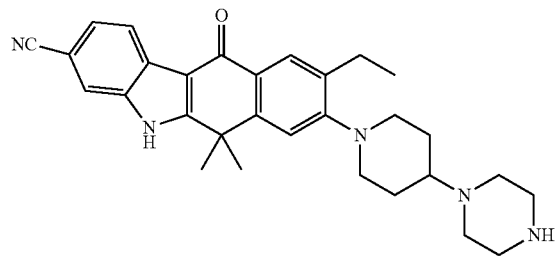 [SMILES: CCc1cc2c(cc1N1CCC(N3CCNCC3)CC1)C(C)(C)c1[nH]c3cc(C#N)ccc3c1C2=O]

9-Ethyl-6,6-dimethyl-11-oxo-8-(4-(piperazin-1-yl)piperidin-1-yl)-6,11-dihydro-5H-benzo[b]carbazole-3-carbonitrile (SIAIS184192). (Yellow solid, 280 mg, yield: 48%) $^1$H NMR (500 MHz, DMSO) δ 12.76 (s, 1H), 8.32 (d, J=8.1 Hz, 1H), 8.06 (s, 1H), 8.01 (s, 1H), 7.61 (d, J=9.0 Hz, 1H), 6.69 (d, J=8.4 Hz, 1H), 3.94 (s, 8H), 3.61 (s, 1H), 3.49-3.29 (m, 4H), 2.70 (q, J=7.8 Hz, 2H), 1.76 (s, 6H), 1.61 (s, 4H), 1.28 (t, J=7.5 Hz, 3H). HRMS (ESI) Calculated for C$_{30}$H$_{36}$N$_5$O [M+H]$^-$: 482.2914, found: 482.2911.

Intermediate Preparation Embodiment 6: Preparation of (2-(2,6-dioxopiperidin-3-yl)-1-oxoisoindolin-4-yl)aminoacetic acid (SIAIS1204057)

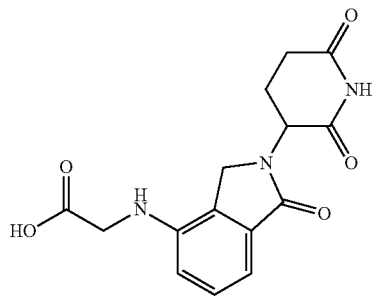 [SMILES: O=C(O)CNc1cccc2c1CN(C1CCC(=O)NC1=O)C2=O]

According to Scheme 3, Lenalidomide (2 mmol, 1 equiv), NMP (8 mL), and the corresponding raw material bromo-tert-butyl ester (2.4 mmol, 1.2 equiv) and N,N-diisopropylethylamine (6 mmol, 3 equiv) were added to a single-necked flask and the mixture was reacted at 110° C. for 12 h. After the reaction solution was cooled to room temperature, prepared by a C$_{18}$ reversed phase column, eluent (v/v): acetonitrile/(water+0.1% TFA)=10% -100%, the obtained compound was added into a single-neck flask, and then DCM (6 mL) and TFA (2 mL) were added and the mixture was stirred at room temperature for 1 h. The reaction solvent was evaporated under reduced pressure, and water was added to freeze-dry to obtain the final target compound (SIAIS1204057). The target product was a yellow solid, 1.0 g, with a yield of 48%. $^1$H NMR (500 MHz, DMSO) δ 11.01 (s, 1H), 7.28 (t, J=7.7 Hz, 1H), 6.98 (d, J=7.3 Hz, 1H), 6.66 (d, J=8.0 Hz, 1H), 5.94 (s, 1H), 5.12 (dd, J=13.3, 5.1 Hz, 1H), 4.26 (d, J=17.0 Hz, 1H), 4.16 (d, J=17.0 Hz, 1H), 3.92 (s, 2H), 2.98-2.85 (m, 1H), 2.62 (d, J=17.3 Hz, 1H), 2.39-2.26 (m, 1H), 2.08-1.99 (m, 1H). HRMS (ESI) m/z: Calculated for C$_{15}$H$_{16}$N$_3$O$_5^+$ [M+H]$^+$, 318.1084; found: 318.1098.

Intermediate Preparation Embodiment 7: Preparation of 4-((2-(2,6-dioxopiperidin-3-yl)-1-oxoisoindolin-4-yl)amino)butyric acid (SIAIS1204085)

According to the method of intermediate preparation embodiment 6, SIAIS1204085 was prepared. The difference (Previous column top:)
6H), 1.72-1.63 (m, 2H). HRMS (ESI) C$_{28}$H$_{38}$ClN$_7$O$_2$P [M+H]$^+$: calculated: 570.2508, found: 570.2498.

was that the raw material used was tert-butyl 4-bromobutyrate. The target product was a yellow solid, 215 mg, with a yield of 62%. $^1$H NMR (500 MHz, DMSO) δ 11.01 (s, 1H), 7.28 (t, J=7.7 Hz, 1H), 6.93 (d, J=7.3 Hz, 1H), 6.77 (d, J=8.0 Hz, 1H), 5.11 (dd, J=13.3, 5.1 Hz, 1H), 4.23 (d, J=17.0 Hz, 1H), 4.13 (d, J=17.0 Hz, 1H), 4.01 (s, 1H), 3.14 (t, J=7.0 Hz, 2H), 2.98-2.86 (m, 1H), 2.66-2.58 (d, J=17.6 Hz, 1H), 2.34 (t, J=7.3 Hz, 2H), 2.32-2.24 (m, 1H), 2.08-1.98 (m, 1H), 1.85-1.75 (m, 2H). HRMS (ESI) m/z: Calculated for $C_{17}H_{20}N_3O_5^+$ [M+H]$^+$, 346.1379; found: 346.1414.

Intermediate Preparation Embodiment 8: Preparation of 5-((2-(2,6-dioxopiperidin-3-yl)-1-oxoisoindolin-4-yl)amino)pentanoic acid (SIAIS1210133)

According to the method of intermediate preparation embodiment 6, SIAIS1210133 was prepared. The difference was that the raw material diacid used was tert-butyl 5-bromovalerate. The target product was a yellow solid, 215 mg, with a yield of 60%. $^1$H NMR (500 MHz, DMSO) δ 11.00 (s, 1H), 7.28 (t, J=7.7 Hz, 1H), 6.92 (t, J=10.9 Hz, 1H), 6.76 (d, J=8.0 Hz, 1H), 5.11 (dd, J=13.3, 5.1 Hz, 1H), 5.07 (s, 1H), 4.23 (d, J=17.2 Hz, 1H), 4.13 (d, J=17.1 Hz, 1H), 3.13 (d, J=6.4 Hz, 2H), 2.97-2.87 (m, 1H), 2.61 (d, J=16.7 Hz, 1H), 2.38-2.21 (m, 3H), 2.06-1.98 (m, 1H), 1.67-1.55 (m, 4H). HRMS (ESI) m/z: Calculated for $C_{18}H_{22}N_3O_5^+$ [M+H]$^+$, 360.1554; found: 360.1551.

Intermediate Preparation Embodiment 9: Preparation of 6-((2-(2,6-dioxopiperidin-3-yl)-1-oxoisoindolin-4-yl)amino)hexanoic acid (SIAIS1204061)

According to the method of intermediate preparation embodiment 6, SIAIS1204061 was prepared, the difference was that the raw material diacid used was tert-butyl 6-bromohexanoate. The target product was a yellow solid, 268 mg, with a yield of 72%. $^1$H NMR (500 MHz, DMSO) δ 11.01 (s, 1H), 7.29 (t, J=7.7 Hz, 1H), 6.94 (d, J=7.4 Hz, 1H), 6.76 (d, J=8.0 Hz, 1H), 5.11 (dd, J=13.3, 5.1 Hz, 1H), 4.24 (d, J=17.0 Hz, 1H), 4.14 (d, J=17.0 Hz, 1H), 4.05 (s, 1H), 3.12 (t, J=7.0 Hz, 2H), 2.98-2.87 (m, 1H), 2.66-2.58 (m, 1H), 2.35-2.25 (m, 1H), 2.22 (t, J=7.0 Hz, 2H), 2.07-2.00 (m, 1H), 1.63-1.50 (m, 4H), 1.43-1.37 (m, 2H). HRMS (ESI) m/z: Calculated for $C_{19}H_{24}N_3O_5^+$ [M+H]$^+$, 374.1710; found: 374.1720.

Intermediate Preparation Embodiment 10: Preparation of 7-((2-(2,6-dioxopiperidin-3-yl)-1-oxoisoindolin-4-yl)amino)heptanoic acid (SIAIS1204063)

According to the method of intermediate preparation embodiment 6, SIAIS1204063 was prepared, the difference was that the raw material diacid used was tert-butyl 6-bromoheptanoate. The target product was a yellow solid, 252 mg, with a yield of 65%. $^1$H NMR (500 MHz, DMSO) δ 11.00 (s, 1H), 7.28 (t, J=7.7 Hz, 1H), 6.93 (d, J=7.3 Hz, 1H), 6.75 (d, J=8.0 Hz, 1H), 5.11 (dd, J=13.2, 5.0 Hz, 1H), 4.23 (d, J=17.0 Hz, 1H), 4.13 (d, J=17.0 Hz, 1H), 3.11 (t, J=7.0 Hz, 2H), 2.98-2.84 (m, 1H), 2.67-2.57 (m, 1H), 2.35-2.25 (m, 1H), 2.20 (t, J=7.3 Hz, 2H), 2.07-1.99 (m, 1H), 1.63-1.46 (m, 4H), 1.42-1.27 (m, 4H). HRMS (ESI) m/z: Calculated for $C_{20}H_{26}N_3O_5^+$ [M+H]$^+$, 388.1867; found: 388.1878.

Intermediate Preparation Embodiment 11: Preparation of 2-(2-((2-(2,6-dioxopiperidin-3-yl)-1-oxoisoindolin-4-yl)amino)ethoxy)acetic acid (SIAIS1204115)

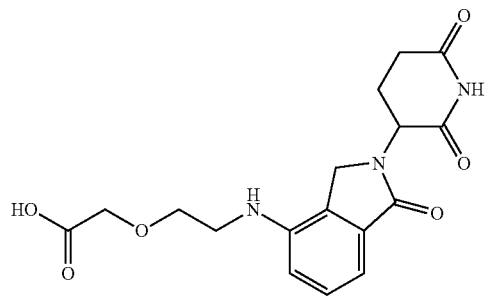 [SMILES: O=C(O)COCCNc1cccc2c1CN(C1CCC(=O)NC1=O)C2=O]

According to the method of Scheme 4, tert-butyl 2-(2-(toluenesulfonyloxy)ethoxy)acetate (1 equiv) and sodium iodide (2 equiv) were added together into a 25 mL egg-shaped flask, and then acetone (5 mL) was added, and the mixture was refluxed in an oil bath at 60° C. for 2 h. The acetone was spin-dried, then NMP (3 mL), Lenalidomide (0.8 equiv) and N, N-diisopropylethylamine (3 equiv) were added, and the mixture was reacted in an oil bath at 110° C. for 12 h. The reaction solution was cooled to room temperature, and then prepared by a $C_{18}$ reversed-phase column. The eluent (v/v): acetonitrile/(water+0.1% TFA)=10%-100%, acetonitrile was evaporated under reduced pressure, and intermediate was obtained by freeze-drying; then the intermediate was added to a 25 mL single-necked flask, 1 mL dichloromethane and 3 mL trifluoroacetic acid were added sequentially, and the mixture was stirred at room temperature for 1 h. The reaction solvent was evaporated under reduced pressure, and water was added to the residue to freeze-dry to obtain the target compound SIAIS1204115 (yellow solid, 134 mg, yield: 77%); $^1$H NMR (500 MHz, DMSO) δ 11.00 (s, 1H)), 7.29 (t, J=7.7 Hz, 1H), 6.95 (d, J=6.9 Hz, 1H), 6.80 (d, J=8.0 Hz, 1H), 5.12 (dd, J=13.3, 5.1 Hz, 1H), 4.24 (d, J=17.1 Hz, 1H), 4.13 (d, J=17.0 Hz, 1H), 4.02 (s, 2H), 3.65 (t, J=5.9 Hz, 2H), 3.32 (t, J=5.9 Hz, 2H), 2.97-2.89 (m, 1H), 2.65-2.58 (m, 1H), 2.33-2.25 (m, 1H), 2.06-2.02 (m, 1H); HRMS (ESI) m/z: calculated: $C_{17}H_{20}N_3O_6^+$ [M+H]$^+$, 362.1347; found: 362.1344.

Intermediate Preparation Embodiment 12: Preparation of 2-(2-(2-((2-(2,6-dioxopiperidin-3-yl)-1-oxoisoindolin-4-yl)amino)ethoxy)ethoxy)acetic acid (SIMS1204123)

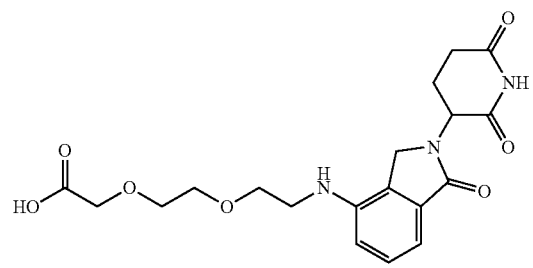 [SMILES: O=C(O)COCCOCCNc1cccc2c1CN(C1CCC(=O)NC1=O)C2=O]

SIAIS1204123 was prepared according to the method of intermediate preparation embodiment 11, the difference was that the tert-butyl ester substituted by OTs was tort-butyl 2-(2-(2-(toluenesulfonyloxy)ethoxy)ethoxy) acetate. The obtained target compound SIAIS1204123 was a yellow liquid, 139 mg, with a yield of 80%; $^1$H NMR (500 MHz, DMSO) δ 11.00 (s, 1H), 7.33-7.24 (m, 1H), 6.94 (t, J=8.2 Hz, 1H), 6.81 (d, J=7.9 Hz, 1H), 5.11 (dd, J=13.3, 5.1 Hz, 1H), 4.23 (d, J=17.1 Hz, 1H), 4.14 (d, J=17.1 Hz, 1H), 4.04-4.01 (m, 2H), 3.62-3.56 (m, 6H), 3.32 (t, J=5.9 Hz, 2H), 2.95-2.88 (m, 1H), 2.62 (d, J=17.6 Hz, 1H), 2.35-2.28 (m, 1H), 2.07-2.00 (m, 1H); HRMS (ESI) m/z: Calculated for $C_{19}H_{24}N_3O_7^+$ [M+H]$^+$, 406.1609; found: 406.1618.

Intermediate Preparation Embodiment 13: Preparation of 2-(2-(2-(2-((2-(2,6-dioxopiperidin-3-yl)-1-oxoisoindolin-4-yl)amino)ethoxy)ethoxy)ethoxy) acetic acid (SIAIS1204127)

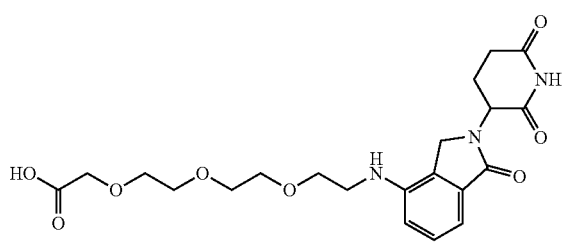 [SMILES: O=C(O)COCCOCCOCCNc1cccc2c1CN(C1CCC(=O)NC1=O)C2=O]

SIAIS1204127 was prepared according to the method of intermediate preparation embodiment 11, the difference was that the tert-butyl ester substituted by OTs was tert-butyl 2-(2-(2-(2-(toluenesulfonyloxy)ethoxy)ethoxy)ethoxy) acetate. The obtained target compound SIAIS1204127 was a yellow liquid, 124 mg, with a yield of 72%; $^1$H NMR (500 MHz, DMSO) δ 11.00 (s, 1H), 7.29 (t, J=7.7 Hz, 1H), 6.94 (d, J=7.4 Hz, 1H), 6.81 (d, J=8.0 Hz, 1H), 5.11 (dd, J=13.3, 5.1 Hz, 1H), 4.23 (d, J=17.1 Hz, 1H), 4.13 (d, J=17.1 Hz, 1H), 4.01 (s, 2H), 3.60-3.51 (m, 10H), 3.34-3.30 (m, 2H), 2.97-2.87 (m, 1H), 2.62 (d, J=16.9 Hz, 1H), 2.36-2.28 (m, 1H), 2.07-2.01 (m, 1H); HRMS (ESI) m/z: calculated: $C_{21}H_{28}N_3O_8^+$ [M+H]$^+$, 450.1871; found: 450.1879.

Intermediate Preparation Embodiment 14: Preparation of 14-((2-(2,6-dioxopiperidin-3-yl)-1-oxoisoindolin-4-yl)amino)-3,6,9,12-tetraoxatetradecanoic acid (SIAIS1204131)

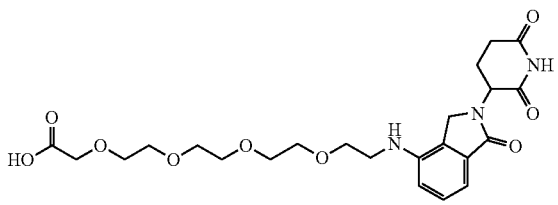 [SMILES: O=C(O)COCCOCCOCCOCCNc1cccc2c1CN(C1CCC(=O)NC1=O)C2=O]

SIAIS1204131 was prepared according to the method of the intermediate preparation embodiment 11. The difference was that the tert-butyl ester substituted by OTs was tert-butyl 14-(toluenesulfonyloxy)-3,6,9,12-tetraoxatetradecanoate. The obtained target compound SIAIS1204131 was a yellow liquid, 134 mg, with a yield of 79%. $^1$H NMR (500 MHz, DMSO) δ 11.00 (s, 1H), 7.29 (t, J=7.7 Hz, 1H), 6.96 (d, J=7.3 Hz, 1H), 6.82 (d, J=8.0 Hz, 1H), 5.11 (dd, J=13.3, 5.1 Hz, 2H), 4.24 (d, J=17.1 Hz, 1H), 4.13 (d, J=17.1 Hz, 1H), 4.01 (s, 2H), 3.64-3.46 (m, 14H), 3.32 (t, J=5.9 Hz, 2H), 2.99-2.86 (m, 1H), 2.62 (d, J=16.9 Hz, 1H), 2.31 (qd, J=13.3, 4.4 Hz, 1H), 2.07-2.00 (m, 1H); HRMS (ESI) m/z: Calculated for $C_{23}H_{32}N_3O_9^+$[M+H]$^+$, 494.2133; found: 494.2144.

Intermediate Preparation Embodiment 15: Preparation of 14-((2-(2,6-dioxopiperidin-3-yl)-1-oxoisoindolin-4-yl)amino)-3,6,9,12-tetraoxaheptadecanoic acid (SIAIS1204135)

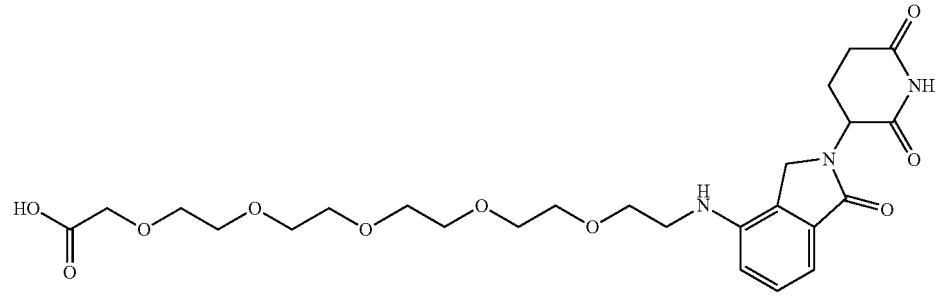 [SMILES: O=C(O)COCCOCCOCCOCCOCCNc1cccc2c1CN(C1CCC(=O)NC1=O)C2=O]

SIAIS1204135 was prepared according to the method of intermediate preparation embodiment 11. The difference was that the tert-butyl ester substituted by OTs was tert-butyl 17-(toluenesulfonyloxy)-3,6,9,12,15-pentaoxaheptadecanoate. The obtained target compound SIAIS1204135 was a yellow liquid, 127 mg, with a yield of 75%. $^1$H NMR (500 MHz, DMSO) δ 11.01 (s, 1H), 7.29 (t, J=7.7 Hz, 1H), 6.95 (d, J=6.9 Hz, 1H), 6.80 (d, J=6.9 Hz, 1H), 5.11 (dd, J=13.3, 5.1 Hz, 1H), 4.24 (d, J=17.1 Hz, 1H), 4.14 (d, J=17.1 Hz, 1H), 4.01 (s, 2H), 3.62-3.46 (m, 18H), 3.32 (t, J=5.9 Hz, 2H), 2.96-2.88 (m, 1H), 2.62 (d, J=16.6 Hz, 1H), 2.37-2.25 (m, 1H), 2.08-2.00 (m, 1H); HRMS (ESI) m/z: Calculated for $C_{25}H_{36}N_3O_{10}^+$[M+H]$^+$, 538.2395; found: 538.2403.

Intermediate Preparation Embodiment 16: Preparation of 2-(2,6-dioxopiperidin-3-yl)-4-((2-iodoethyl)amino)isoindoline-1,3-dione (SIAIS268006)

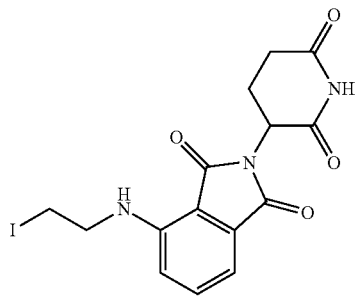 [SMILES: O=C1CCC(N2C(=O)c3cccc(NCCI)c3C2=O)C(=O)N1]

According to Scheme 5, in step 1, 2-(2,6-dioxopiperidin-3-yl)-4-fluoroisoindoline-1,3-dione (16.8 mmol, 1 equiv) was dissolved in 25 mL of NMP, 2-(tert-butyldimethylsiloxy)ethylamine (16.8 mmol, 1.0 equiv) and N, N-diisopropylethylamine (25.2 mmol, 1.5 equiv) were added successively, and the mixture was reacted at 90° C. for 4 h. The reaction was completed. The reaction solution was cooled to room temperature, poured into saturated brine, the mixture was extracted with ethyl acetate (4×50 mL), the organic phases were combined, washed with water (2×30 mL), washed with saturated brine (50 mL), dried over anhydrous $Na_2SO_4$, and the solvent was evaporated under reduced pressure, and the crude product was purified by column chromatography (eluent (v/v): petroleum ether/ethyl acetate=1:1) to obtain an intermediate. The intermediate was dissolved in 50 mL of tetrahydrofuran, tetrabutylammonium fluoride (16.8 mmol) was added, and the mixture was stirred at room temperature for 2 h. The reaction was completed. 200 mL of saturated brine was added, the mixture was extracted with ethyl acetate (4×50 mL), the organic phases were combined, washed with water (2×30 mL), washed with saturated brine (50 mL), dried over anhydrous $Na_2SO_4$, and the solvent was evaporated under reduced pressure to obtain the crude product of SIAIS255178, m=1.0 g, which was put into the next step directly.

In step 2, SIAIS255178 was dissolved in 40 mL mixed solvent (DCM/Pyridine=3/1), triethylamine (0.52 mL, 3.8 mmol) and methanesulfonyl chloride (0.30 mL, 3.8 mmol) were added sequentially, and the mixture was heated to 40° C., reacted for 2 h, the reaction was completed. The mixture was washed with saturated brine, the solvent was evaporated under reduced pressure, and the residue was purified by column chromatography to obtain SIAIS255180 as a yellow powder, m=0.80 g.

In step 3, SIAIS255180 was dissolved in 10 mL of acetone, sodium iodide (3.0 equiv) was added, and the reaction was heated to 60° C. for 24 h, and the conversion was completed. The mixture was cooled to room temperature, diluted with 40 mL of ethyl acetate, washed with saturated brine, dried over anhydrous sodium sulfate, and the solvent was evaporated under reduced pressure to obtain the crude product of SIAIS268006 as a yellow solid, which was put into use directly.

$^1$H NMR (500 MHz, DMSO-d$_6$) δ 11.10 (s, 1H), 7.60 (dd, J=8.6, 7.1 Hz, 1H), 7.19 (dd, J=18.6, 8.6 Hz, 1H), 7.08 (d, J=7.0 Hz, 1H), 6.81 (t, J=6.3 Hz, 1H), 5.06 (dd, J=12.8, 5.4 Hz, 1H), 3.81 (t, J=6.1 Hz, 1H), 3.75-3.64 (m, 2H), 3.39 (t, J=6.3 Hz, 2H), 2.89 (ddd, J=16.9, 13.8, 5.5 Hz, 1H), 2.64-2.53 (m, 1H), 2.04 (m, 1H).

Intermediate Preparation Embodiment 17: Preparation of 2-(2,6-dioxopiperidin-3-yl)-4-((3-iodopropyl)amino)isoindoline-1,3-dione (SIAIS268007)

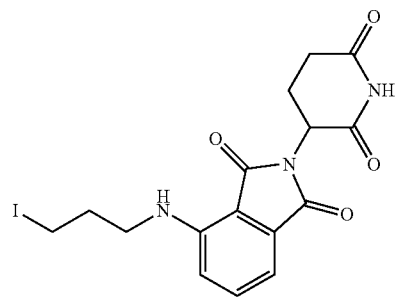 [SMILES: O=C1CCC(N2C(=O)c3cccc(NCCCI)c3C2=O)C(=O)N1]

SIAIS268007 was prepared according to the method of intermediate preparation embodiment 16. The difference was that 3-(tert-butyldimethylsiloxy)propylamine was used as the starting material in step 1, and dichloromethane was used as the solvent in step 2. The final product was purified by column chromatography of DCM/EA=5/1.

$^1$H NMR (500 MHz, DMSO-d$_6$) δ 11.09 (s, 1H), 7.60 (dd, J=8.5, 7.0 Hz, 1H), 7.14 (d, J=8.5 Hz, 1H), 7.04 (d, J=7.0 Hz, 1H), 6.68 (t, J=6.2 Hz, 1H), 5.05 (dd, J=12.8, 5.4 Hz, 1H), 3.39 (q, J=6.6 Hz, 2H), 3.31 (t, J=6.9 Hz, 2H), 2.88 (ddd, J=16.9, 13.8, 5.4 Hz, 1H), 2.62-2.52 (m, 1H), 2.12-2.01 (m, 3H).

Intermediate Preparation Embodiment 18: Preparation of 2-(2,6-dioxopiperidin-3-yl)-4-((4-iodobutyl)amino)isoindoline-1,3-dione (SIAIS255191)

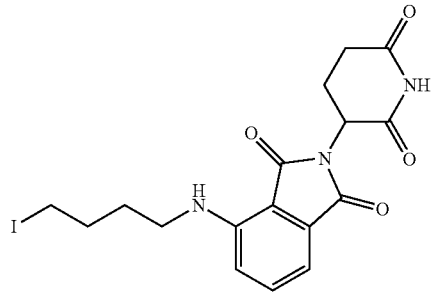 [SMILES: O=C1CCC(N2C(=O)c3cccc(NCCCCI)c3C2=O)C(=O)N1]

SIAIS255191 was prepared according to the method of intermediate preparation embodiment 16. The difference was that 4-aminobutanol was used as the starting material, and dichloromethane was used as the solvent in step 2.

$^1$H NMR (500 MHz, DMSO-d$_6$) δ 11.05 (s, 1H), 7.83-7.68 (m, 1H), 7.56 (dd, J=8.6, 6.9 Hz, 1H), 7.11 (dd, J=7.7, 6.0 Hz, 2H), 5.06 (dd, J=12.8, 5.4 Hz, 1H), 3.35-3.26 (m, 1H), 2.97-2.81 (m, 2H), 2.65-2.53 (m, 2H), 2.18 (t, J=8.1 Hz, 1H), 2.11-1.97 (m, 2H), 1.96-1.85 (m, 4H).

Intermediate Preparation Embodiment 19: Preparation of 2-(2,6-dioxopiperidin-3-yl)-4-((5-iodopentyl)amino)isoindoline-1,3-dione (SIAIS264016)

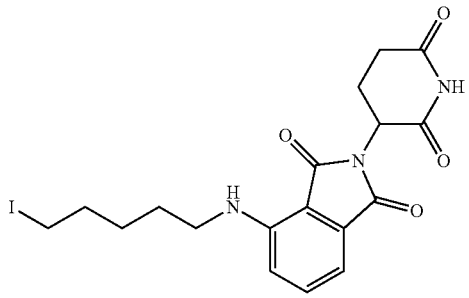 [SMILES: O=C1CCC(N2C(=O)c3cccc(NCCCCCI)c3C2=O)C(=O)N1]

SIAIS264016 was prepared according to the method of intermediate preparation embodiment 16. The difference was that 5-aminopentanol was used as the starting material, and dichloromethane was used as the solvent in step 2.

$^1$H NMR (500 MHz, DMSO-d$_6$) δ 11.09 (s, 1H), 7.58 (dd, J=8.6, 7.0 Hz, 1H), 7.11 (d, J=8.7 Hz, 1H), 7.02 (d, J=7.0 Hz, 1H), 5.05 (dd, J=12.8, 5.4 Hz, 1H), 3.29 (t, J=6.9 Hz, 4H), 2.88 (ddd, J=16.6, 13.6, 5.2 Hz, 1H), 2.64-2.55 (m, 1H), 2.07-1.99 (m, 1H), 1.86-1.75 (m, 2H), 1.68 (s, 1H), 1.59 (q, J=7.4 Hz, 2H), 1.43 (dd, J=8.5, 6.3 Hz, 2H).

Intermediate Preparation Embodiment 20: Preparation of 2-(2,6-dioxopiperidin-3-yl)-4-((6-iodohexyl)amino)isoindoline-1,3-dione (SIAIS264018)

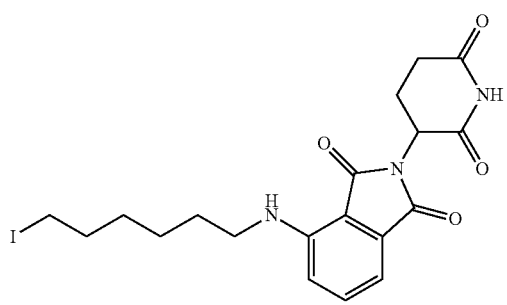 [SMILES: O=C1CCC(N2C(=O)c3cccc(NCCCCCCI)c3C2=O)C(=O)N1]

SIAIS264018 was prepared according to the method of intermediate preparation embodiment 16. The difference was that 6-aminohexanol was used as the starting material, and dichloromethane was used as the solvent in step 2.

$^1$H NMR (500 MHz, DMSO-d$_6$) δ 11.09 (s, 1H), 7.58 (dd, J=8.5, 7.0 Hz, 1H), 7.10 (d, J=8.6 Hz, 1H), 7.02 (d, J=7.0 Hz, 1H), 6.54 (t, J=5.9 Hz, 1H), 5.05 (dd, J=12.7, 5.4 Hz, 1H), 3.28 (q, J=6.7 Hz, 4H), 2.95-2.83 (m, 1H), 2.63-2.55 (m, 1H), 2.08 (d, J=4.9 Hz, 1H), 2.06-1.99 (m, 1H), 1.77 (t, J=7.0 Hz, 2H), 1.57 (t, J=7.1 Hz, 2H), 1.38 (p, J=5.0 Hz, 4H).

Intermediate Preparation Embodiment 21: Preparation of 4-(2-(2,6-dioxopiperidin-3-yl)-1-oxoisoindolin-4-yl)but-3-yn-1-yl methanesulfonate (SIAIS255120)

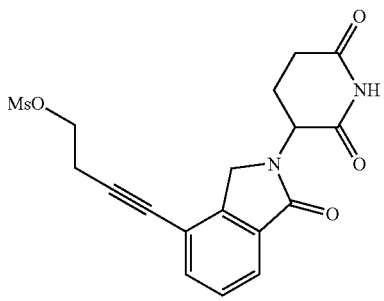 [SMILES: CS(=O)(=O)OCCC#Cc1cccc2c1CN(C1CCC(=O)NC1=O)C2=O]

According to Scheme 6, in step 1, 3-(4-bromo-1-oxoisoindolin-2-yl)piperidine-2,6-dione (0.50 g, 1.5 mmol) was dissolved in 5 mL of DMF, Ar gas was used for bubbling for 5 minutes, and 3-alkynylbutanol (0.21 g, 3.0 mmol), Pd(PPh$_3$)$_2$Cl$_2$ (0.10 g, 0.15 mmol) and CuI (57 mg, 0.30 mmol) were added sequentially. The mixture was stirred for 5 min, 2.5 mL of triethylamine was added, then the mixture was heated to 80° C., and reacted overnight. The mixture was cooled to room temperature, the reaction was quenched with 50 mL of water, extracted with ethyl acetate (3×50 mL), the organic phases were combined, washed with water (2×30 mL) and saturated brine (50 mL), dried over anhydrous Na$_2$SO$_4$, and the solvent was evaporated under reduced pressure, and the crude product was purified by column chromatography (DCM/MeOH=5/1) to obtain an alcohol intermediate as a light yellow solid, m=0.50 g.

In step 2, the above intermediate was dissolved in 15 mL of DCM, and triethylamine (0.44 g, 4.4 mmol) and methanesulfonyl chloride (0.25 g, 2.2 mmol) were added sequentially. The system became clear and reacted overnight. The reaction solution was washed with saturated brine, the solvent was evaporated under reduced pressure, and purified by column chromatography (DCM/MeOH=20/1) to obtain SIAIS255120 as a light yellow solid, m=0.35 g.

$^1$H NMR (500 MHz, DMSO-d$_6$) δ 11.01 (s, 1H), 7.74 (dd, J=7.6, 1.0 Hz, 1H), 7.67 (dd, J=7.6, 1.0 Hz, 1H), 7.54 (t, J=7.6 Hz, 1H), 5.16 (dd, J=13.4, 5.1 Hz, 1H), 4.52-4.27 (m, 4H), 3.24 (s, 3H), 3.02-2.87 (m, 3H), 2.67-2.57 (m, 1H), 2.42 (qd, J=13.3, 4.4 Hz, 1H), 2.03 (m, 1H).

Intermediate Preparation Embodiment 22: Preparation of 5-(2-(2,6-dioxopiperidin-3-yl)-1-oxoisoindolin-4-yl)pent-4-yn-1-yl methanesulfonate (SIAIS255121)

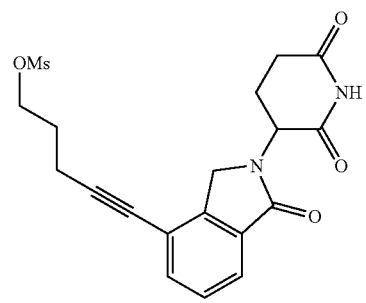 [SMILES: CS(=O)(=O)OCCCC#Cc1cccc2c1CN(C1CCC(=O)NC1=O)C2=O]

SIAIS255121 was prepared according to the method of intermediate preparation embodiment 21. The difference was that 4-alkynyl pentanol was used as the starting material.

$^1$H NMR (500 MHz, DMSO-d$_6$) δ 11.00 (s, 1H), 7.72 (dd, J=7.6, 1.0 Hz, 1H), 7.66 (dd, J=7.8, 1.0 Hz, 1H), 7.53 (t, J=7.6 Hz, 1H), 5.15 (dd, J=13.3, 5.1 Hz, 1H), 4.48 (d, J=17.8 Hz, 1H), 4.38 4.28 (m, 3H), 3.20 (s, 3H), 3.00 2.86 (m, 1H), 2.61 in, 3H), 2.45 (dd, J=13.1, 4.5 Hz, 1H), 2.00 (m, 3H).

Intermediate Preparation Embodiment 23: Preparation of 6-(2-(2,6-dioxopiperidin-3-yl)-1-oxoisoindolin-4-yl)hex-5-yn-1-yl methanesulfonate (SIAIS255119)

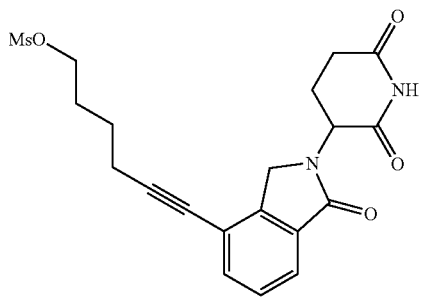 [SMILES: CS(=O)(=O)OCCCCC#Cc1cccc2c1CN(C1CCC(=O)NC1=O)C2=O]

SIAIS255119 was prepared according to the method of intermediate preparation embodiment 21. The difference was that 5-alkynyl hexanol was used as the starting material.
$^1$H NMR (500 MHz, DMSO-d$_6$) δ 10.99 (s, 1H), 7.71 (dd, J=7.6, 1.1 Hz, 1H), 7.65 (dd, J=7.7, 1.0 Hz, 1H), 7.52 (t, J=7.6 Hz, 1H), 5.14 (dd, J=13.4, 5.1 Hz, 1H), 4.46 (d, J=17.7 Hz, 1H), 4.31 (d, J=17.7 Hz, 1H), 4.27 (t, J=6.4 Hz, 2H), 3.17 (s, 3H), 2.91 (m, 1H), 2.55 (m, 3H), 2.48-2.42 (n, 1H), 2.01 (m, 1H), 1.88-1.80 (n, 2H), 1.67 (m, 2H).

Intermediate Preparation Embodiment 24: Preparation of 7-(2-(2,6-dioxopiperidin-3-yl)-1-oxoisoindolin-4-yl)hept-6-yn-1-yl methanesulfonate (SIAIS292017)

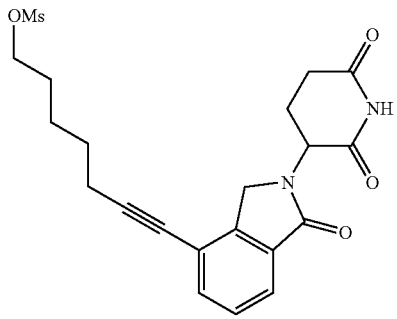 [SMILES: CS(=O)(=O)OCCCCCC#Cc1cccc2c1CN(C1CCC(=O)NC1=O)C2=O]

SIAIS292017 was prepared according to the method of intermediate preparation embodiment 21. The difference was that 6-alkynyl heptanol was used as the starting material. $^1$H NMR (500 MHz, DMSO) δ 10.99 (s, 1H), 7.71 (dd, J=7.6, 0.8 Hz, 1H), 7.64 (dd, J=7.6, 0.9 Hz, 1H), 7.52 (t, J=7.6 Hz, 1H), 5.13 (dd, J=13.3, 5.1 Hz, 1H), 4.45 (d, J=17.7 Hz, 1H), 4.31 (d, J=17.7 Hz, 1H), 4.22 (t, J=6.4 Hz, 2H), 3.15 (d, J=1.4 Hz, 3H), 2.92-2.88 (m, 1H), 2.62-2.56 (m, 1H), 2.51 (t, 4.0 Hz, 2H), 2.48-2.41 (n, 1H), 2.05-1.98 (m, 1H), 1.75-1.70 (n, 2H), 1.63-1.55 (m, 2H), 1.54-1.48 (n, 2H).

Intermediate Preparation Embodiment 25: Preparation of 8-(2-(2,6-dioxopiperidin-3-yl)-1-oxoisoindolin-4-yl)oct-7-yn-1-yl methanesulfonate (SIAIS292020)

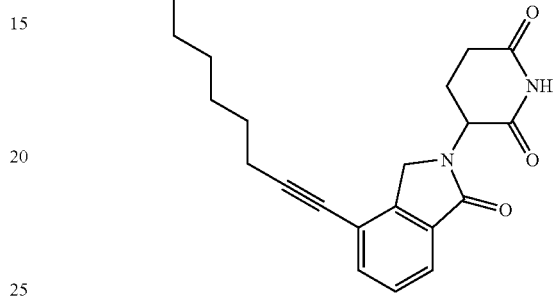

SIAIS292020 was prepared according to the method of intermediate preparation embodiment 21. The difference was that 7-alkynyl octanol was used as the starting material.
$^1$H NMR (500 MHz, DMSO) δ 10.99 (s, 1H), 7.70 (dd, J=7.6, 0.7 Hz, 1H), 7.63 (dd, J=7.6, 0.9 Hz, 1H), 7.51 (dd, J=9.7, 5.5 Hz, 1H), 5.14 (dd, J=13.3, 5.1 Hz, 1H), 4.45 (d, J=17.7 Hz, 1H), 4.31 (d, J=17.6 Hz, 1H), 4.18 (dt, J=6.5, 4.1 Hz, 2H), 2.90 (tt, J=19.0, 5.4 Hz, 1H), 2.60 (d, J=17.6 Hz, 1H), 2.49-2.46 (m, 2H), 2.46-2.40 (m, 1H), 2.05-1.98 (m, 1H), 1.69-1.65 (m, 2H), 1.59-1.55 (m, 2H), 1.48-1.38 (m, 4H).

Intermediate Preparation Embodiment 26: Preparation of 9-(2-(2,6-dioxopiperidin-3-yl)-1-oxoisoindolin-4-yl)non-8-yn-1-yl methanesulfonate (SIAIS255127)

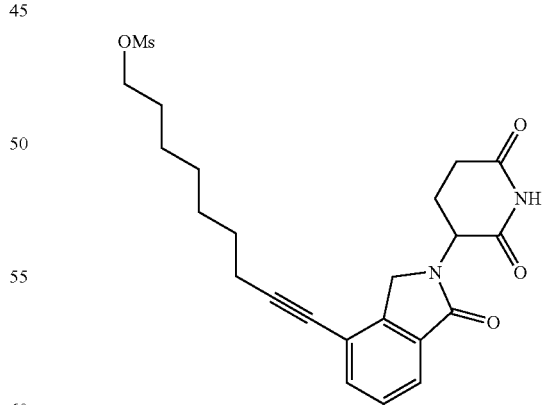

SIAIS255127 was prepared according to the method of intermediate preparation embodiment 21. The difference was that 8-alkynyl nonanol was used as the starting material. $^1$H NMR (500 MHz, DMSO) δ 11.00 (s, 1H), 7.70 (d, J=7.4 Hz, 1H), 7.63 (d, J=7.0 Hz, 1H), 7.52 (t, J=7.6 Hz, 1H), 5.14 (dd, J=13.3, 5.1 Hz, 1H), 4.44 (d, J=17.6 Hz, 1H), 4.30 (d, J=17.6 Hz, 1H), 4.18 (t, J=6.5 Hz, 2H), 3.15 (s, 3H), 2.94-2.88 (m, 1H), 2.63-2.57 (m, 1H), 2.47 (d, J=7.1 Hz, 2H), 2.46-2.40 (m, 1H), 2.05-2.01 (m, 1H), 1.68-1.64 (m, 2H), 1.61-1.53 (m, 2H), 1.47-1.40 (m, 2H), 1.40-1.33 (m, 4H).

Intermediate Preparation Embodiment 27: Preparation of 4-(2-(2,6-dioxopiperidin-3-yl)-1-oxoisoindolin-4-yl)butyl methanesulfonate (SIAIS255130)

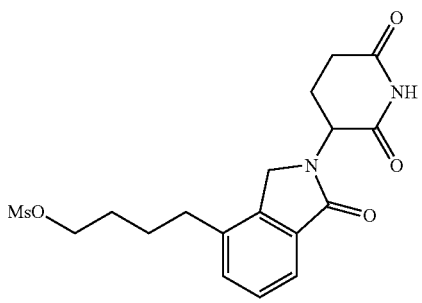 [SMILES: CS(=O)(=O)OCCCCc1cccc2c1CN(C1CCC(=O)NC1=O)C2=O]

According to Scheme 7, in step 1, 3-(4-(4-hydroxybut-1-yn-1-yl)-1-oxoisoindolin-2-yl)piperidine-2,6-dione (0.11 g, 0.35 mmol) was dissolved in 10 mL of ethanol, 10% Pd/C (5 mg) and PtO$_2$ (5 mg) were added as catalysts, and the mixture was reacted at 50° C. under hydrogen atmosphere for 12 h, filtered, the solvent was evaporated under reduced pressure to obtain intermediate 3-(4-(4-hydroxybutyl)-1-oxoisoindolin-2-yl)piperidine-2,6-dione as a light yellow solid, m=0.11 g.

In step 2, referring to step 2 of the preparation of intermediate SIAIS255120. A light yellow solid was obtained, m=0.11 g. $^1$H NMR (500 MHz, DMSO-d$_6$) δ 11.00 (s, 1H), 7.65-7.53 (m, 2H), 7.50-7.46 (m, 2H), 5.14 (dd, J=13.3, 5.2 Hz, 1H), 4.47 (d, J=17.1 Hz, 1H), 4.31 (d, J=17.1 Hz, 1H), 4.24 (t, J=5.9 Hz, 2H), 3.16 (s, 3H), 2.93 (ddd, J=17.4, 13.7, 5.4 Hz, 1H), 2.69 (t, J=7.3 Hz, 2H), 2.66-2.58 (m, 1H), 2.42 (m, 1H), 2.02 (m, 1H), 1.71 (dt, J=10.5, 4.9 Hz, 4H).

Intermediate Preparation Embodiment 28: Preparation of 2-((2-(2,6-dioxopiperidin-3-yl)-1,3-dioxoisoindolin-4-yl)oxy)acetic acid (SIAIS172101B)

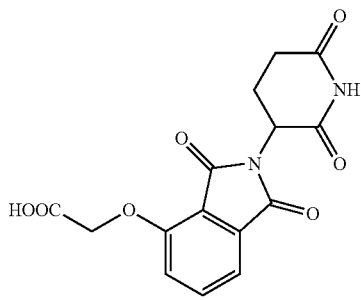 [SMILES: O=C(O)COc1cccc2c1C(=O)N(C1CCC(=O)NC1=O)C2=O]

Step 1: tert-butyl 2-((2-(2,6-dioxopiperidin-3-yl)-1,3-dioxoisoindolin-4-yl)oxy) acetate (SIAIS180152) was prepared according to scheme 8: compound 2-(2,6-dioxopiperidin-3-yl)-4-hydroxyisoindoline-1,3-dione (412 mg, 1.50 mmol), tert-butyl bromoacetate (350 mg, 1.80 mmol), anhydrous sodium bicarbonate (190 mg, 2.25 mmol), potassium iodide (25 mg, 0.15 mmol) and anhydrous DMF (10 mL) were added to a 50 mL egg-shaped flask together, the temperature was slowly increased to 60° C. and stirred for 12 h. After the reaction, water was added to the reaction flask, extracted with ethyl acetate, the organic phases were combined, washed with water and saturated brine, dried over anhydrous sodium sulfate, the reaction solvent was evaporated under reduced pressure, the sample was mixed with silica gel, and the crude product was purified by column chromatography (eluent: 40% EA/PE) to obtain the compound (SIAIS180152), the product was a light yellow solid, 520 mg, with a yield of 89%. $^1$H NMR (500 MHz, DMSO) δ 11.11 (s, 1H), 7.82-7.78 (m, 1H), 7.48 (d, J=7.1 Hz, 1H), 7.38 (d, J=8.5 Hz, 1H), 5.10 (dd, J=12.8, 5.4 Hz, 1H), 4.97 (s, 2H), 2.95-2.83 (m, 1H), 2.62-2.52 (m, 2H), 2.08-1.98 (m, 1H), 1.44-1.43 (m, 9H). HRMS (ESI) m/z: Calculated for C$_{19}$H$_{21}$N$_2$O$_7^+$ [M+H]$^+$, 389.1343; found: 389.1339.

Step 2: 2-((2-(2,6-Dioxopiperidin-3-yl)-1,3-dioxoisoindolin-4-yl)oxy)acetic acid (SIAIS172101B) was prepared according to scheme 8:

The obtained compound SIAIS180152 (500 mg, 1.29 mmol), TFA (2 mL) and anhydrous dichloromethane (10 mL) were added together into a 50 mL egg-shaped flask, and then the mixture was stirred at room temperature for 2 hours. After the reaction was completed, the reaction solvent was removed under reduced pressure, and the obtained crude product was prepared by a C$_{18}$ reversed-phase column. The eluent (v/v): acetonitrile/(water+0.1% TFA)=10%-100%, acetonitrile was evaporated under reduced pressure, the residue was freeze-dried to obtain the target compound (SIAIS172101B), the product was a white solid, 400 mg, with a yield of 92%. $^1$H NMR (500 MHz, DMSO) δ 13.25 (s, 1H), 11.11 (s, 1H), 7.79 (dd, J=8.5, 7.3 Hz, 1H), 7.47 (d, J=7.2 Hz, 1H), 7.39 (d, J=8.6 Hz, 1H), 5.10 (dd, J=12.8, 5.4 Hz, 1H), 4.98 (s, 2H), 2.93-2.85 (m, 1H), 2.63-2.51 (m, 2H), 2.08-2.00 (m, 1H). HRMS (ESI) m/z: Calculated for C$_{15}$H$_{13}$N$_2$O$_7^+$ [M+H]$^+$, 333.0717; found: 333.0719.

Intermediate Preparation Embodiment 29

Preparation of 2-(2-((2-(2,6-dioxopiperidin-3-yl)-1-oxoisoindolin-4-yl)thio)ethoxy)acetic acid (SIAIS1213129)

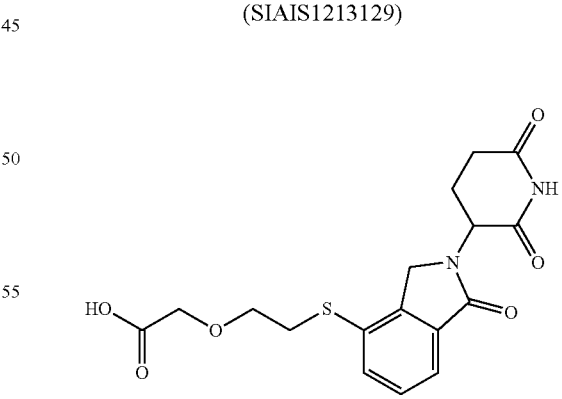

According to Scheme 13, the compound Lenalidomide thiophenol (0.724 mmol, 1 equiv) was added to a 50 mL egg-shaped flask, and then anhydrous N,N-dimethylformamide (10 mL) and anhydrous potassium carbonate (1.448 mmol, 2 equiv) were added sequentially, the corresponding substrate substituted by p-toluenesulfonate (0.869 mmol, 1.2 equiv) as a linker was slowly added dropwise under stirring at room temperature, and then stirred at room temperature for 0.5 h after the dropwise addition. After the reaction of the raw materials was completed, the mixture was filtered to remove insoluble materials and the sample was directly loaded on a $C_{18}$ reversed phase column for separation, eluent: 10%-100% (v1: v2) acetonitrile: water, the solvent was removed under reduced pressure to obtain the corresponding tert-butanol ester intermediate product; the corresponding tert-butanol ester intermediate compound was added to a 25 mL egg-shaped flask, followed by dichloromethane (1 mL) and trifluoroacetic acid (3 mL), and the mixture was stirred at room temperature for 1 h. The solvent was evaporated under reduced pressure, and water was added to freeze-dry to obtain the corresponding target product. The target compound SIAIS1213129 (light yellow solid, 148 mg, yield: 54%) was obtained. $^1$H NMR (500 MHz, $CDC_{13}$) δ 8.90 (s, 1H), 7.81 (d, J=7.5 Hz, 1H), 7.68 (d, J=7.7 Hz, 1H), 7.54 (t, J=7.7 Hz, 1H), 5.33 (dd, J=13.4, 5.1 Hz, 1H), 4.60 (d, J=17.2 Hz, 1H), 4.47 (d, J=17.2 Hz, 1H), 4.11 (s, 2H), 3.78-3.73 (m, 1H), 3.72-3.66 (m, 1H), 3.22 (t, J=6.2 Hz, 2H), 2.98-2.93 (m, 1H), 2.90-2.82 (m, 1H), 2.53-2.43 (m, 1H), 2.32-2.25 (m, 1H). HRMS (ESI) m/z: Calculated for $C_{17}H_{19}N_2O_6S^+$ [M+H]$^+$, 379.0958; found: 379.0963.

Intermediate Preparation Embodiment 30

Preparation of 2-(2-(2-((2-(2,6-dioxopiperidin-3-yl)-1-oxoisoindolin-4-yl)thio) ethoxy)ethoxy) acetic acid (SIAIS1213131)

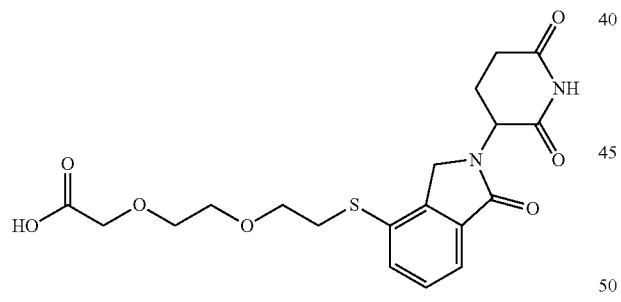

SIAIS1213131 was prepared according to the method of intermediate preparation embodiment 29. The difference was that the substrate substituted by p-toluenesulfonate used as the raw material was tert-butyl 2-(2-(2-(toluenesulfonyloxy)ethoxy)ethoxy)acetate. The target compound SIAIS1213131 (light yellow oil, 158 mg, yield: 52%) was obtained. $^1$H NMR (500 MHz, CDCl$_3$) δ 8.77 (s, 1H), 7.68 (d, J=7.5 Hz, 1H), 7.53 (d, J=7.7 Hz, 1H), 7.42 (t, J=7.7 Hz, 1H), 5.21 (dd, J=13.4, 5.1 Hz, 1H), 4.41 (d, J=17.1 Hz, 1H), 4.32 (d, J=17.1 Hz, 1H), 4.06 (s, 2H), 3.65-3.59 (m, 4H), 3.54 (t, J=4.1 Hz, 2H), 3.11 (t, J=6.1 Hz, 2H), 2.88-2.83 (m, 1H), 2.81-2.76 (m, 1H), 2.42-2.34 (m, 1H), 2.20-2.14 (m, 1H). HRMS (ESI) m/z: Calculated for $C_{19}H_{23}BN_2O_7S^+$ [M+H]$^+$, 423.1200; found: 423.1205.

Intermediate Preparation Embodiment 31

Preparation of 2-(2-(2-(2-((2-(2,6-dioxopiperidin-3-yl)-1-oxoisoindolin-4-yl)thio) ethoxy)ethoxy) ethoxy)acetic acid (SIAIS1213133)

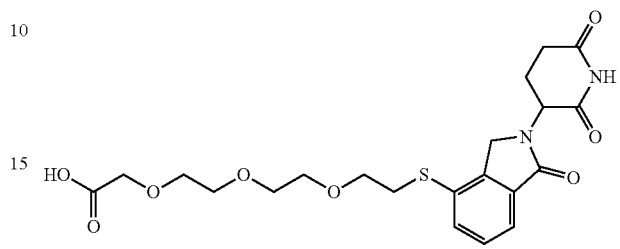

SIAIS1213133 was prepared according to the method of intermediate preparation embodiment 29. The difference was that the substrate substituted by p-toluenesulfonate used as the raw material was tert-butyl 2-(2-(2-(2-(toluenesulfonyloxy)ethoxy)ethoxy)ethoxy)acetate. The target compound SIAIS1213133 (light yellow oil, 149 mg, yield: 44%) was obtained. $^1$H NMR (500 MHz, CDCl$_3$) δ 8.91 (s, 1H), 7.75 (d, J=7.5 Hz, 1H), 7.61 (d, J=7.6 Hz, 1H), 7.50 (t, J=7.7 Hz, 1H), 5.29 (dd, J=13.4, 5.1 Hz, 1H), 4.49 (d, J=17.0 Hz, 1H), 4.39 (d, J=17.1 Hz, 1H), 4.17-4.15 (m, 2H), 3.72-3.63 (m, 101-1), 3.20 (t, J=6.3 Hz, 2H), 2.96-2.90 (m, 1H), 2.90-2.82 (m, 1H), 2.50-2.44 (m, 1H), 2.28-2.22 (m, 1H). HRMS (ESI) m/z: Calculated for $C_{21}H_{27}N_2O_8S^{\alpha}$ [M+H]$^+$, 467.1483; found: 467.1467.

Intermediate Preparation Embodiment 32

14-((2-(2,6-dioxopiperidin-3-yl)-1-oxoisoindolin-4-yl)thio)-3,6,9,12-tetraoxatetradecanoic acid (SIAIS1213135)

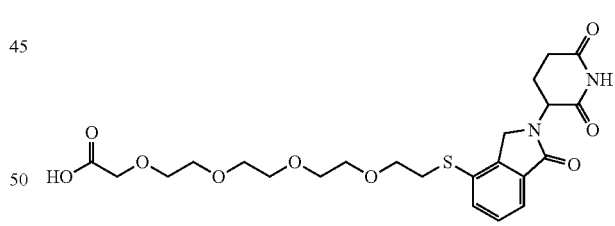

SIAIS1213135 was prepared according to the method of intermediate preparation embodiment 29. The difference was that the substrate substituted by p-toluenesulfonate used as the raw material was tert-butyl 14-(toluenesulfonyloxy)-3,6,9,12-tetraoxatetradecanoate. The target compound SIAIS1213135 (light yellow oil, 181 mg, yield: 49%) was obtained. $^1$H NMR (500 MHz, CDCl$_3$) δ 8.61 (s, 1H), 7.78 (dd, J=7.6, 0.7 Hz, 1H), 7.63 (dd, J=7.8, 0.8 Hz, 1H), 7.50 (t, J=7.0 Hz, 1H), 5.29 (dd, J=13.3, 5.1 Hz, 1H), 4.50 (d, J=17.0 Hz, 1H), 4.40 (d, J=16.9 Hz, 1H), 4.15 (s, 2H), 3.72-3.66 (m, 14H), 3.19 (t, J=6.6 Hz, 2H), 2.95-2.93 (m, 1H), 2.91-2.86 (m, 1H), 2.52-2.46 (m, 1H), 2.28-2.24 (m, 1H). HRMS (ESI) m/z: Calculated for $C_{23}H_{31}N_2O_9S^+$ [M+H]$^+$, 511.1745; found: 511.1749.

Intermediate Preparation Embodiment 33

Preparation of 174(2-(2,6-dioxopiperidin-3-yl)-1-oxoisoindolin-4-yl)thio)-3,6,9,12,15-pentaoxaheptadecanoic acid (SIAIS1213137)

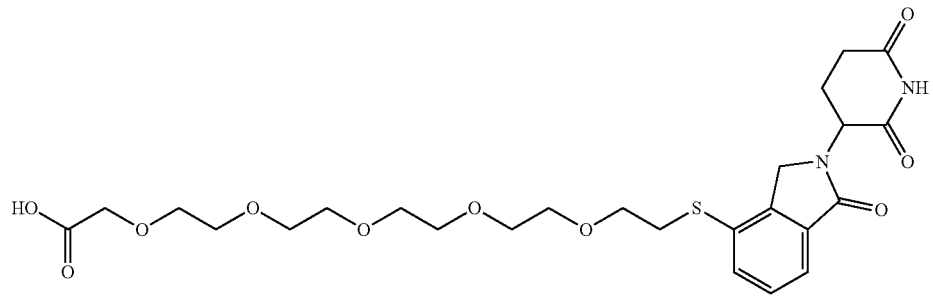 [SMILES: O=C(O)COCCOCCOCCOCCOCCSc1cccc2c1CN(C1CCC(=O)NC1=O)C2=O]

SIAIS1213133 was prepared according to the method of intermediate preparation embodiment 29. The difference was that the substrate substituted by p-toluenesulfonate used as the raw material was tert-butyl 17-(toluenesulfonyloxy)-3,6,9,12,15-pentoxaheptadecanoate. The target compound SIAIS1213137 (light yellow oil, 209 mg, yield: 52%) was obtained. $^1$H NMR (500 MHz, CDCl$_3$) δ 8.71 (s, 1H), 7.77 (d, J=7.0 Hz, 1H), 7.64 (dd, J=7.7, 0.7 Hz, 1H), 7.54-7.49 (m, 1H), 5.31 (dd, J=13.4, 5.1 Hz, 1H), 4.50 (d, J=17.0 Hz, 1H), 4.40 (d, J=17.0 Hz, 1H), 4.17 (s, 2H), 3.76-3.74 (m, 2H), 3.70-3.66 (m, 12H), 3.64-3.61 (m, 4H), 3.20 (t, J=6.5 Hz, 2H), 2.98-2.94 (m, 1H), 2.90-2.85 (m, 1H), 2.53-2.43 (m, 1H), 2.30-2.25 (m, 1H). HRMS (ESI) m/z: Calculated for C$_{25}$H$_{35}$N$_2$O$_{10}$S$^+$ [M+H]$^+$, 569.1800; found: 569.1814.

Intermediate Preparation Embodiment 34

Preparation of 2-((2-(2,6-dioxopiperidin-3-yl)-1-oxoisoindolin-4-yl)thio)acetic acid (SIAIS171090)

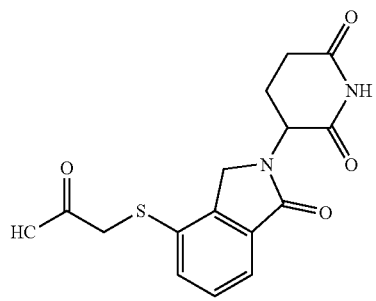 [SMILES: CC(=O)CSc1cccc2c1CN(C1CCC(=O)NC1=O)C2=O]

The compound SIAIS171090 was prepared according to the method in Scheme 12, the difference was that the brominated substrate used as the linker was tert-butyl 2-bromoacetate. The target compound SIAIS171090 (white solid, 77 mg, total yield of step 3: 64%) was obtained. $^1$H NMR (500 MHz, DMSO) δ 12.88 (s, 1H), 11.00 (s, 1H), 7.68-7.45 (m, 3H), 5.15-5.13 (m, 1H), 4.32 (dd, J=56.2, 17.3 Hz, 2H), 3.94 (s, 2H), 2.95-2.91 (m, 1H), 2.63-2.59 (m, 1H), 2.49-2.39 (m, 1H), 2.08-1.92 (m, 1H). HRMS (ESI) m/z: Calculated for C$_{15}$H$_{15}$N$_2$O$_5$S$^+$ [M+H]$^+$, 335.0696; found: 334.8134.

Intermediate Preparation Embodiment 35

Preparation of 3-((2-(2,6-dioxopiperidin-3-yl)-1-oxoisoindolin-4-yl)thio)propionic acid (SIAIS171086)

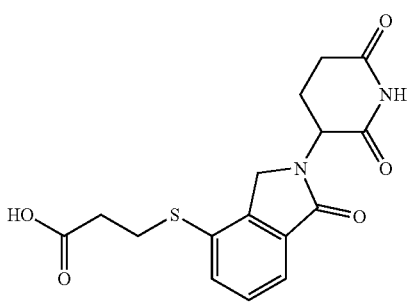 [SMILES: O=C(O)CCSc1cccc2c1CN(C1CCC(=O)NC1=O)C2=O]

The compound SIAIS171086 was prepared according to the method in Scheme 12, the difference was that the brominated substrate used as the linker wasTertt-butyl 3-bromopropionate. The target compound SIAIS171086 (white solid, 40 mg, total yield of step 3: 32%) was obtained. $^1$H NMR (500 MHz, DMSO) δ 10.99 (s, 1H), 7.70-7.55 (m, 3H), 5.13 (dd, J=13.3, 5.1 Hz, 1H), 4.40-4.18 (m, 2H), 3.24 (t, J=7.0 Hz, 2H), 2.95-2.87 (m, 1H), 2.63-2.53 (m, 3H), 2.47-2.34 (m, 1H), 2.05-1.95 (m, 1H). HRMS (ESI) m/z: Calculated for C$_{16}$H$_{17}$N$_2$O$_5$S$^+$ [M+H]$^+$, 349.0853; found: 348.8166.

Intermediate Preparation Embodiment 36

Preparation of 4-((2-(2,6-dioxopiperidin-3-yl)-1-oxoisoindolin-4-yl)thio)butanoic acid (SIAIS171089)

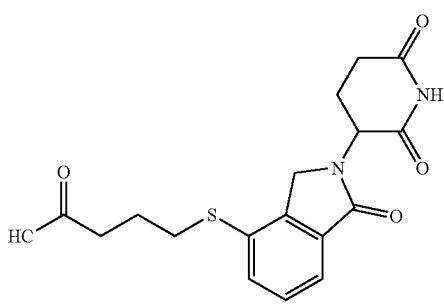 [SMILES: CC(=O)CCCSc1cccc2c1CN(C1CCC(=O)NC1=O)C2=O]

The compound SIAIS171089 was prepared according to the method in Scheme 12, the difference was that the brominated substrate used as the linker was tert-butyl 4-bromobutyrate. The target compound SIAIS171089 (white solid, 50 mg, total yield of step 3: 38%) was obtained. NMR (500 MHz, DMSO) δ 12.15 (s, 1H), 10.99 (s, 1H), 7.71-7.49 (m, 3H), 5.13 (dd, J=13.3, 5.1 Hz, 1H), 4.41-4.18 (m, 2H), 3.10 (t, J=7.3 Hz, 2H), 2.92-2.88 (m, 1H), 2.61-2.59 (m, 1H), 2.49-2.42 (m, 1H), 2.38 (t, J=7.2 Hz, 2H), 2.05-1.96 (m, 1H), 1.84-1.74 (m, 2H). HRMS (ESI) m/z: Calculated for $C_{17}H_{19}N_2O_5S^+$ [M+H]$^+$, 363.1009; found: 362.8160.

Intermediate Preparation Embodiment 37

Preparation of 5-((2-(2,6-dioxopiperidin-3-yl)-1-oxoisoindolin-4-yl)thio)pentanoic acid (SIAIS171079)

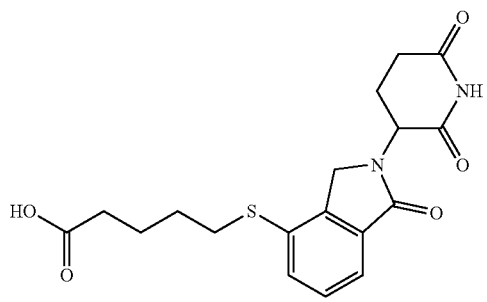 [SMILES: O=C(O)CCCCSc1cccc2c1CN(C1CCC(=O)NC1=O)C2=O]

The compound SIAIS171079 was prepared according to the method in Scheme 12, the difference was that the brominated substrate used as the linker was tert-butyl 5-bromopentanoate. The target compound SIAIS171079 (white solid, 30 mg, total yield of step 3:22%) was obtained. $^1$H NMR (500 MHz, DMSO) δ 12.01 (s, 1H), 10.98 (s, 1H), 7.66-7.55 (m, 3H), 5.12 (dd, J=13.3, 5.1 Hz, 1H), 4.37-4.18 (m, 2H), 3.10-3.05 (m, 2H), 2.95-2.84 (m, 1H), 2.65-2.61 (m, 1H), 2.48-2.38 (m, 1H), 2.27-2.20 (m, 3H), 1.63-1.59 (m, 4H). HRMS (ESI) m/z: Calculated for $C_{18}H_{21}N_2O_5S^+$ [M+H]$^+$, 377.1166; found: 376.8981.

Intermediate Preparation Embodiment 38

Preparation of 6-((2-(2,6-dioxopiperidin-3-yl)-1-oxoisoindolin-4-yl)thio)hexanoic acid (SIAIS171091)

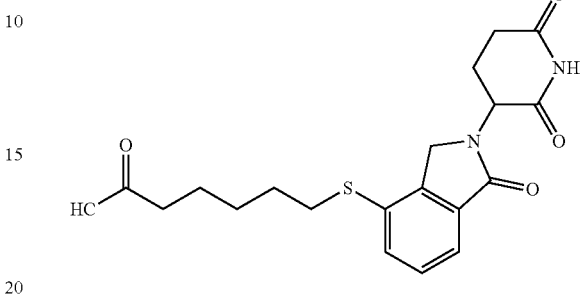

The compound SIAIS171091 was prepared according to the method in Scheme 12, the difference was that the brominated substrate used as the linker was tert-butyl 6-bromohexanoate. The target compound SIAIS171091 (white solid, 75 mg, total yield of step 3: 53%) was obtained. $^1$H NMR (500 MHz, DMSO) δ 11.98 (s, 1H), 10.98 (s, 1H), 7.59-7.52 (m, 3H), 5.12 (dd, J=13.4, 5.1 Hz, 1H), 4.26 (dd, J=40.9, 20.5 Hz, 2H), 3.07 (t, J=7.3 Hz, 2H), 2.96-2.84 (m, 1H), 2.64-2.60 (m, 1H), 2.48-2.39 (m, 1H), 2.19-2.15 (m, 2H), 2.02-2.00 (m, 1H), 1.70-1.35 (m, 6H). HRMS (ESI) m/z: Calculated for $C_{19}H_{23}N_2O_5S^+$ [M+H]$^+$, 391.1322; found: 390.8150.

Intermediate Preparation Embodiment 39

Preparation of 7-((2-(2,6-dioxopiperidin-3-yl)-1-oxoisoindolin-4-yl)thio)heptanoic acid (SIAIS171092)

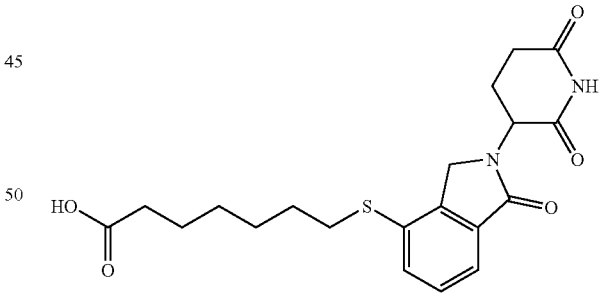

The compound SIAIS171092 was prepared according to the method in Scheme 12, the difference was that the brominated substrate used as the linker was tert-butyl 7-bromoheptanoate. The target compound SIAIS171092 (white solid, 79 mg, total yield of step 3: 54%) was obtained. $^1$H NMR (500 MHz, DMSO) δ 11.99 (s, 1H), 10.98 (s, 1H), 7.66-7.45 (m, 3H), 5.12 (dd, J=13.3, 5.1 Hz, 1H), 4.26 (dd, J=40.9, 20.5 Hz, 2H), 3.07 (t, J=7.3 Hz, 2H), 2.97-2.83 (m, 1H), 2.63-2.60 (m, 1H), 2.47-2.35 (m, 1H), 2.18 (t, J=7.3 Hz, 2H), 2.06-1.93 (m, 1H), 1.65-1.20 (m, 8H). HRMS (ESI) m/z: Calculated for $C_{20}H_{25}N_2O_5S^+$[M+H]$^+$, 405.1479; found: 404.8155.

Intermediate Embodiment 40: Preparation of 3-(4-((5-bromopentyl)thio)-1-oxoisoindolin-2-yl)piperidine-2,6-dione (SIAIS1216049)

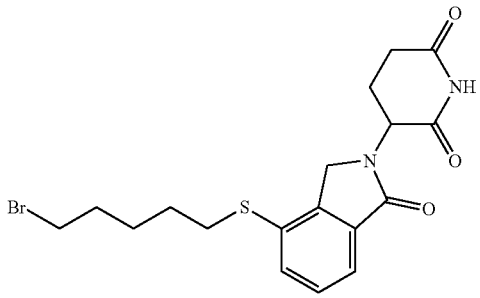 [SMILES: O=C1CCC(N2Cc3c(SCCCCCBr)cccc3C2=O)C(=O)N1]

According to Scheme 13, the compound Lenalidomide thiophenol (0.344 mmol, 1 equiv), potassium carbonate (0.688 mmol, 2 equiv) and DMF (5 mL) were added to a 50 mL two-necked flask. After the system was ventilated with argon, the corresponding substrate substituted by halogen (0.413 mmol, 1.2 equiv) was added, then the mixture was stirred at room temperature for 1 h. After the reaction was completed, the insoluble substance was removed by filtration, and the residue was separated by a $C_{18}$ reversed phase column. The eluent (v/v): acetonitrile/(water) =10%-100%, and the solvent was removed under reduced pressure to obtain the corresponding target compound. $^1$H NMR (500 MHz, DMSO) δ 11.01 (s, 1H), 7.64 (dd, J=7.5, 0.9 Hz, 1H), 7.59-7.51 (m, 2H), 5.13 (dd, J=13.3, 5.1 Hz, 1H), 4.36 (d, J=17.4 Hz, 1H), 4.21 (d, J=17.4 Hz, 1H), 3.52 (t, J=6.6 Hz, 2H), 3.10 (t, J=7.1 Hz, 2H), 2.95-2.87 (m, 1H), 2.63-2.55 (m, 1H), 2.48-2.41 (m, 1H), 2.03-1.97 (m, 1H), 1.86-1.76 (m, 2H), 1.66-1.58 (m, 2H), 1.57-1.48 (m, 2H). HRMS (ESI) m/z: Calculated for $C_{18}H_{22}BrN_2O_3S^+$ [M+H]$^+$, 425.0529; found: 425.0535.

Intermediate Embodiment 41: Preparation of 3-(4-((6-bromohexyl)thio)-1-oxoisoindolin-2-yl)piperidine-2,6-dione (SIAIS1216133)

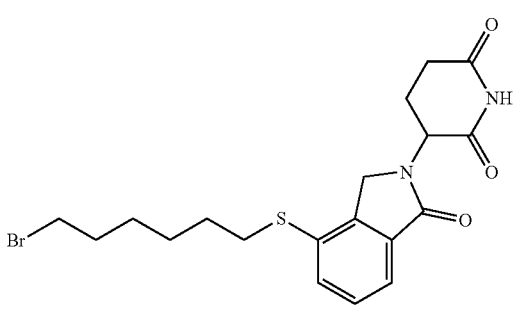 [SMILES: O=C1CCC(N2Cc3c(SCCCCCCBr)cccc3C2=O)C(=O)N1]

According to the method in Scheme 13, the compound SIAIS1216133 was prepared under understandable appropriate conditions in the art, the difference was that the used halogenated substrate was 1,6-dibromohexane. The target compound SIAIS1216133 (white solid, 339 mg, yield: 38%) was obtained. $^1$H NMR (500 MHz, DMSO) δ 11.01 (s, 1H), 7.63 (dd, J=7.5, 1.2 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.59 (d, J=17.4 Hz, 1H), 2.49-2.41 (n, 1H), 2.04-1.97 (n, 1H), 1.82-1.74 (n, 2H), 1.63-1.56 (m, 2H), 1.46-1.36 (m, 4H). HRMS (ESI) m/z: Calculated for $C_{19}H_{24}BrN_2O_3S^+$ [M+H]$^+$, 439.0686; found value, 439.0680.

Intermediate Embodiment 42: Preparation of 3-(4-((7-bromoheptyl)thio)-1-oxoisoindolin-2-yl)piperidine-2,6-dione (SIAIS1216135)

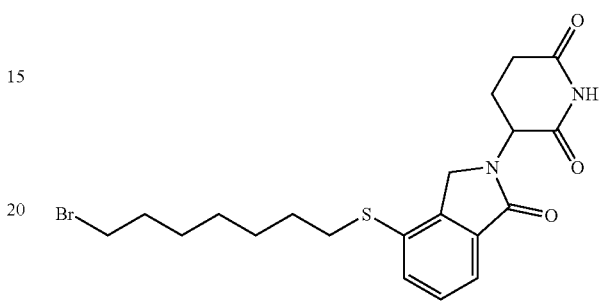

According to the method in Scheme 13, the compound SIAIS1216135 was prepared under understandable appropriate conditions in the art, the difference was that the halogenated substrate used was 1,7-dibromoheptane. The target compound SIAIS1216135 (white solid, 212 mg, yield: 23%) was obtained. $^1$H NMR (500 MHz, DMSO) δ 11.02 (s, 1H), 7.63 (dd, J=7.5, 0.9 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.63-2.56 (m, 1H), 2.49-2.40 (m, 1H), 2.04-1.97 (m, 1H), 1.82-1.73 (m, 2H), 1.63-1.56 (m, 2H), 1.44-1.27 (m, 6H). HRMS (ESI) m/z: Calculated for $C_{20}H_{26}BrN_2O_3S^+$ [M+H]$^+$, 453.0842; found: 453.0840.

Intermediate Embodiment 43: Preparation of 3-(4-((4-bromobutyl)thio)-1-oxoisoindolin-2-yl)piperidine-2,6-dione (SIAIS213134)

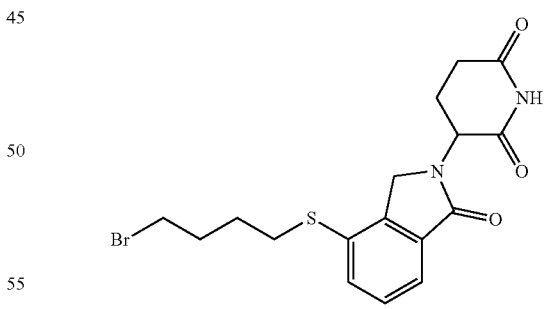

According to the method in Scheme 13, the compound SIAIS213134 was prepared under understandable appropriate conditions in the art, the difference was that the halogenated substrate used was 1,4-dibromoheptane. The target compound SIAIS213134 (light yellow solid, 170 mg, yield: 38.1%) was obtained. NMR (500 MHz, CDCl$_3$) δ 8.00 (s, 1H), 7.74 (t, J=8.7 Hz, 1H), 7.55-7.44 (n, 2H), 5.23 (dd, J=13.4, 5.2 Hz, 1H), 4.39 (d, J=17.3 Hz, 1H), 4.33 (d, J=17.4 Hz, 1H), 3.48-3.35 (m, 2H), 3.01 (dd, J=20.7, 13.5 Hz, 2H), 2.97-2.81 (m, 2H), 2.44-2.38 (m, 1H), 2.28-2.19 (m, 1H), 2.09-1.96 (m, 2H), 1.89-1.86 (m, 2H). LCMS (ESI) m/z: Calculated for C$_{17}$H$_{20}$BrN$_2$O$_3$S$_+$ [M+H]$^+$, 411.0373; found: 411.0371.

Intermediate Embodiment 44: Preparation of 3-(4-(2-bromoethylthio)-1-oxoisoindolin-2-yl)piperidine-2,6-dione (SIAIS213137)

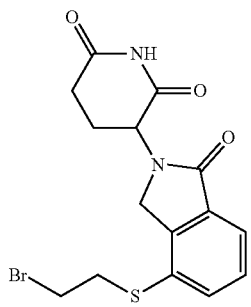 [SMILES: O=C1CCC(N2Cc3c(SCCBr)cccc3C2=O)C(=O)N1]

According to the method in Scheme 13, the compound SIAIS213137 was prepared under understandable appropriate conditions in the art, the difference was that the brominated substrate used as the linker was 1,2-dibromoethane. The target compound SIAIS213137 (light yellow solid, 78 mg, yield: 18.7%) was obtained. $^1$H NMR (500 MHz, CDCl$_3$) δ 8.00 (s, 1H), 7.83-7.76 (m, 1H), 7.57 (t, J=7.1 Hz, 1H), 7.50 (dd, J=17.4, 9.8 Hz, 1H), 5.23 (dt, J=15.9, 7.9 Hz, 1H), 4.46 (d, J=16.5 Hz, 1H), 4.37-4.27 (m, 1H), 3.51-3.43 (m, 2H), 3.41-3.33 (m, 2H), 2.94 (d, J=15.1 Hz, 1H), 2.90-2.78 (m, 1H), 2.46-2.35 (m, 1H), 2.29-2.20 (m, 1H). LCMS (ESI) m/z: Calculated for C$_{15}$H$_{16}$BrN$_2$O$_3$S$^+$ [M+H]$^+$, 383.0060; found: 383.0068.

Intermediate Embodiment 45: Preparation of 3-(4-((4-(bromomethyl)benzyl)thio)-1-oxoisoindolin-2-yl)piperidine-2,6-dione (SIAIS1220141)

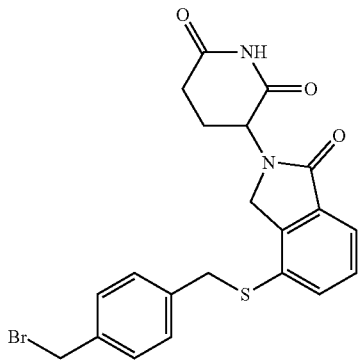 [SMILES: O=C1CCC(N2Cc3c(SCc4ccc(CBr)cc4)cccc3C2=O)C(=O)N1]

According to the method in Scheme 13, the compound SIAIS1220141 was prepared under understandable appropriate conditions in the art, the difference was that the halogenated substrate used was 1,4-bis(bromomethyl)benzene. The target compound SIAIS1220141 (light yellow solid, 247 mg, yield: 27%) was obtained. $^1$H NMR (500 MHz, DMSO) δ 11.00 (s, 1H), 7.67 (dd, J=7.7, 0.7 Hz, 1H), 7.58 (d, J=6.9 Hz, 1H), 7.50 (t, J=7.6 Hz, 1H), 7.43-7.31 (m, 4H), 5.10 (dd, 13.3, 5.1 Hz, 1H), 4.67 (s, 2H), 4.34 (s, 2H), 4.24 (d, J=17.4 Hz, 1H), 4.13 (d, J=17.4 Hz, 1H), 2.95-2.86 (m, 1H), 2.58 (d, J=16.6 Hz, 1H), 2.45-2.35 (m, 1H), 2.00-1.94 (m, 1H). HRMS (ESI) m/z: Calculated for C$_{21}$H$_{20}$BrN$_2$O$_3$S$^+$ [M+H]$^+$, 459.0373; found: 459.0370.

Intermediate Embodiment 46: Preparation of 5-(2-(2,6-dioxopiperidin-3-yl)-1-oxoisoindolin-4-yl)pentyl methanesulfonate (SIAIS350020)

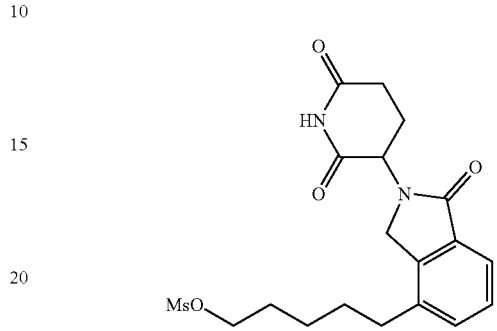

SIAIS350020 was prepared according to the method in intermediate preparation embodiment 27, the difference was that 3-(4-(5-hydroxybut-1-yn-1-yl)-1-oxoisoindolin-2-yl)piperidine-2,6-dione was used as the starting material. The product was a light yellow solid, 1.0 g, with a yield of 73.5%. $^1$H NMR (500 MHz, DMSO) δ 10.99 (s, 1H), 7.56 (dt, J=7.8, 3.9 Hz, 1H), 7.51-7.36 (m, 2H), 5.13 (dd, J=13.3, 5.1 Hz, 1H), 4.39 (dd, J=78.5, 17.1 Hz, 2H), 4.19 (t, J=6.4 Hz, 2H), 3.15 (s, 3H), 2.99-2.85 (m, 1H), 2.71-2.55 (m, 3H), 2.47-2.35 (m, 1H), 2.07-1.95 (m, 1H), 1.77-1.58 (m, 4H), 1.47-1.35 (m, 2H). LCMS (ESI) m/z: Calculated for C$_{19}$H$_{25}$N$_2$O$_6$S$^+$ [M+H]$^+$, 409.1428; found: 409.30.

Intermediate Embodiment 47: Preparation of 5-(2-(2,6-dioxopiperidin-3-yl)-1,3-dioxoisoindolin-4-yl)pent-4-yn-1-yl methanesulfonate (SIAIS292006)

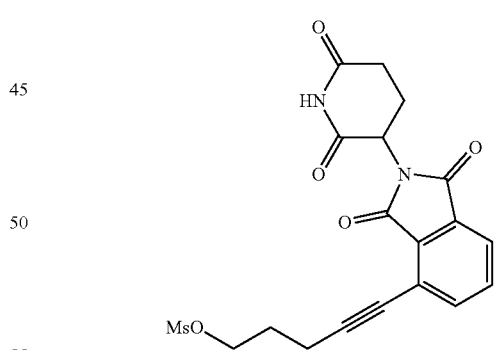

SIAIS292006 was prepared according to the method in intermediate LM preparation embodiment 21, the difference was that 4-bromo-2-(2,6-dioxopiperidin-3-yl)isoindoline-1,3-dione was used instead of 3-(4-bromo-1-oxoisoindolin-2-yl)piperidine-2,6-dione, and 4-alkynyl pentanol was used instead of 3-alkynyl butanol as the starting materials. $^1$H NMR (500 MHz, DMSO-d$_6$) δ 11.13 (s, 1H), 8.00-7.80 (m, 3H), 5.16 (dd, J=12.9, 5.4 Hz, 1H), 4.36 (t, J=6.1 Hz, 2H), 3.21 (s, 3H), 2.89 (ddd, J=18.1, 13.8, 5.4 Hz, 1H), 2.64 (t, J=7.0 Hz, 2H), 2.61-2.50 (m, 2H), 2.10-2.02 (m, 1H), 1.99 (p, J=6.6 Hz, 2H).

Preparation Embodiments of Compounds of the Present Disclosure

Embodiment 1: Preparation of 8-(4-(4-((2-(2,6-di-oxopiperidin-3-yl)-1-oxoisoindolin-4-yl)amino-acetyl)piperazin-1-yl)piperidin-1-yl)-9-ethyl-6,6-dimethyl-11-oxo-6,11-dihydro-5H-benzo[b]carbazole-3-carbonitrile (SIAIS262091)

According to Scheme 9, at room temperature, in the reaction flask, the corresponding ALK inhibitor, namely Alectinib derivative C (0.031 mmol, 1 equiv), intermediate LM (SIAIS1204057) (0.031 mmol, 1 equiv), HATU (0.0372 mmol, 1.2 equiv), 2 mL of DMF, DIPEA (0.093 mmol, 3 equiv) were added successively, the mixture was reacted at room temperature overnight. The reaction was detected by TLC until the reaction was completed, prepared and separated by HPLC (eluent (v/v): acetonitrile/(water+0.05% HCl)=10% -100%), the acetonitrile was spun off, and freeze-dried to obtain the final target compound (SIAIS262091) (yellow solid, 9.7 mg, yield: 40%). $^1$H NMR (500 MHz, DMSO) δ 12.85 (s, 1H), 11.10 (s, 1H), 11.03 (s, 1H), 8.31 (d, J=8.2 Hz, 1H), 8.06 (s, 1H), 8.01 (s, 1H), 7.61 (dd, J=8.1, 1.3 Hz, 1H), 7.37 (s, 1H), 7.31 (t, J=7.7 Hz, 1H), 7.00 (d, J=7.3 Hz, 1H), 6.79 (d, J=8.1 Hz, 1H), 5.13 (dd, J=13.3, 5.0 Hz, 1H), 4.50 (d, J=13.5 Hz, 1H), 4.32 (d, J=13.5 Hz, 1H), 4.23-4.09 (m, 4H), 3.68-3.57 (m, 3H), 3.33 (d, J=11.2 Hz, 3H), 3.21 (t, J=11.9 Hz, 2H), 3.05 (s, 1H), 2.96-2.89 (m, 1H), 2.83 (t, J=10.6 Hz, 2H), 2.72 (q, J=7.4 Hz, 2H), 2.63-2.61 (m, 1H), 2.38-2.35 (m, 1H), 2.24 (s, 2H), 2.04-2.01 (m, 1H), 1.93 (s, 2H), 1.76 (s, 6H), 1.29 (t, J=7.5 Hz, 3H). HRMS (ESI) m/z: Calculated for $C_{45}H_{49}N_8O_5^+$ [M+H]$^+$, 781.3820; found: 781.3834.

Embodiment 2: Preparation of 8-(4-(4-(4-((2-(2,6-dioxopiperidin-3-yl)-1-oxoisoindolin-4-yl)amino)butyryl)piperazin-1-yl)piperidin-1-yl)-9-ethyl-6,6-dimethyl-11-oxo-6,11-dihydro-5H-benzo[b]carbazole-3-carbonitrile According the method in Embodiment 1, and under understandable appropriate conditions in the art, the target compound (SIAIS262092) (yellow solid, 9.9 mg, yield: 39%) was prepared using Alectinib derivative C and intermediate LM (SIAIS1204085). $^1$H NMR (500 MHz, DMSO) δ 12.92 (s, 1H), 11.33 (s, 1H), 11.05 (s, 1H), 8.32 (d, J=8.2 Hz, 1H), 8.06 (s, 1H), 8.01 (s, 1H), 7.61 (dd, J=8.1, 1.2 Hz, 1H), 7.37 (s, 1H), 7.32 (t, J=7.7 Hz, 1H), 6.97 (d, J=7.4 Hz, 1H), 6.84 (d, J=8.1 Hz, 1H), 5.13 (dd, J=13.3, 5.1 Hz, 1H), 4.53 (d, J=13.0 Hz, 1H), 4.27 (d, J=17.2 Hz, 1H), 4.15 (d, J=17.2 Hz, 1H), 4.09 (d, J=13.3 Hz, 1H), 3.59-3.55 (m, 4H), 3.31 (d, J=11.0 Hz, 4H), 3.21-3.15 (m, 3H), 3.09 (d, J=9.7 Hz, 1H), 3.01-2.89 (m, 2H), 2.82 (t, J=11.1 Hz, 2H), 2.71 (q, J=7.4 Hz, 2H), 2.66-2.59 (m, 1H), 2.38-2.28 (m, 1H), 2.21 (s, 2H), 2.08-2.01 (m, 1H), 1.95-1.81 (m, 4H), 1.77 (s, 6H), 1.29 (t, J=7.5 Hz, 3H). HRMS (ESI) m/z: Calculated for $C_{47}H_{53}N_8O_5^+$ [M+H]$^+$, 809.4133; found: 809.4126.

Embodiment 3: Preparation of 8-(4-(4-(5-((2-(2,6-dioxopiperidin-3-yl)-1-oxoisoindolin-4-yl)amino)pentanoyl)piperazin-1-yl)piperidin-1-yl)-9-ethyl-6,6-dimethyl-11-oxo-6,11-dihydro-5H-benzo[b]carbazole-3-carbonitrile According to the method in Embodiment 1, and under understandable appropriate conditions in the art, the target compound (SIAIS262093) (yellow solid, 10.6 mg, yield: 42%) was prepared using Alectinib derivative C and intermediate LM (SIAIS1210133). $^1$H NMR (500 MHz, DMSO) δ 13.01 (s, 1H), 11.54 (s, 1H), 11.05 (s, 1H), 8.32 (d, I=8.2 Hz, 1H), 8.06 (s, 1H), 8.02 (s, 1H), 7.61 (dd, J=8.2, 1.3 Hz, 1H), 7.38-7.33 (m, 2H), 7.05 (d, J=7.3 Hz, 1H), 6.91 (d, J=7.7 Hz, 1H), 5.13 (dd, J=13.3, 5.1 Hz, 1H), 4.51 (d, J=13.3 Hz, 1H), 4.32 (d, J=17.3 Hz, 1H), 4.21 (d, J=17.2 Hz, 1H), 3.66 (t, J=12.7 Hz, 2H), 3.55 (t, J=12.8 Hz, 2H), 3.31 (d, J=11.1 Hz, 3H), 3.19 (s, 3H), 3.11 (s, 1H), 3.00-2.89 (m, 2H), 2.82 (s, 2H), 2.71 (q, J=7.4 Hz, 2H), 2.63 (d, J=16.6 Hz, 1H), 2.43 (s, 2H), 2.37-2.29 (m, 1H), 2.27-2.19 (m, 2H), 2.09-2.00 (m, 1H), 1.99-1.88 (m, 2H), 1.77 (s, 6H), 1.64 (d, J=2.6 Hz, 4H), 1.29 (t, J=7.5 Hz, 3H). HRMS (ESI) m/z: Calculated for $C_{48}H_{55}N_8O_5^+$ [M+H]$^+$, 823.4290; found: 823.4285.

Embodiment 4: Preparation of 8-(4-(4-(7-((2-(2,6-dioxopiperidin-3-yl)-1-oxoisoindolin-4-yl)amino)heptanoyl)piperazin-1-yl)piperidin-1-yl)-9-ethyl-6,6-dimethyl-11-oxo-6,11-dihydro-5H-benzo[b]carbazole-3-carbonitrile According to the method in Embodiment 1, under understandable appropriate conditions in the art, the target compound (SIAIS262095) (yellow solid, 10.8 mg, yield: 42%) was prepared using Alectinib derivative C and intermediate LM (SIAIS1204063). $^1$H NMR (500 MHz, DMSO) δ 12.88 (s, 1H), 11.12 (s, 1H), 11.04 (s, 1H), 8.32 (d, J=8.2 Hz, 1H), 8.06 (s, 1H), 8.01 (s, 1H), 7.61 (dd, J=8.1, 1.3 Hz, 1H), 7.37 (s, 1H), 7.31 (t, J=7.7 Hz, 1H), 6.96 (d, J=7.4 Hz, 1H), 6.79 (d, J=8.0 Hz, 1H), 5.13 (dd, J=13.3, 5.1 Hz, 1H), 4.51 (d, J=13.6 Hz, 1H), 4.26 (d, J=17.2 Hz, 1H), 4.15 (d, J=17.2 Hz, 1H), 4.09 (d, J=12.7 Hz, 1H), 3.43-3.25 (m, 6H), 3.14-3.10 (m, 4H), 2.96-2.92 (m, 2H), 2.82 (s, 2H), 2.71 (t, J=7.5 Hz, 2H), 2.62 (d, J=16.8 Hz, 1H), 2.38 (t, J=7.5 Hz, 2H), 2.34-2.31 (m, 1H), 2.23 (d, J=9.9 Hz, 2H), 2.07-2.02 (m, 1H), 1.91 (d, J=11.2 Hz, 2H), 1.77 (s, 6H), 1.61-1.55 (m, 2H), 1.52 (d, J=6.4 Hz, 2H), 1.41-1.31 (m, 4H), 1.29 (t, J=7.5 Hz, 3H). HRMS (ESI) m/z: Calculated for $C_{50}H_{59}N_8O_5^+$ [M+H]$^+$, 851.4603; found: 851.4605.

Embodiment 5: Preparation of 8-(4-(4-(2-((2-(2,6-dioxopiperidin-3-yl)-1,3-dioxoisoindolin-4-yl)oxy)acetyl)piperazin-1-yl)piperidin-1-yl)-9-ethyl-6,6-dimethyl-11-oxo-6,11-dihydro-5H-benzoiblcarbazole-3-carbonitrile According to the method in Embodiment 1, under understandable appropriate conditions in the art, the target compound (SIAIS293010) (yellow solid, 8.8 mg, yield: 36%) was prepared using Alectinib derivative C and intermediate LM (SIAIS172101B). $^1$H NMR (500 MHz, DMSO) δ 12.86 (s, 1H), 11.11 (s, 1H), 11.04 (s, 1H), 8.31 (d, J=8.2 Hz, 1H), 8.07 (s, 1H), 8.02 (s, 1H), 7.62 (dd, J=8.1, 1.3 Hz, 1H), 7.38 (s, 1H), 7.32 (t, J=7.7 Hz, 1H), 7.01 (d, J=7.3 Hz, 1H), 6.79 (d, J=8.1 Hz, 1H), 5.13 (dd, J=13.3, 5.0 Hz, 1H), 4.24-4.09 (m, 4H), 3.69-3.57 (m, 3H), 3.34 (d, J=11.2 Hz, 3H), 3.22 (t, J=11.9 Hz, 2H), 3.06 (s, 1H), 2.97-2.89 (m, 1H), 2.84 (t, J=10.6 Hz, 2H), 2.73 (q, J=7.4 Hz, 2H), 2.65-2.61 (m, 1H), 2.39-2.35 (m, 1H), 2.25 (s, 2H), 2.06-2.01 (m, 1H), 1.94 (s, 2H), 1.77 (s, 6H), 1.29 (t, J=7.5 Hz, 3H). HRMS (ESI) m/z: Calculated for $C_{45}H_{46}N_7O_7^+$ [M+H]$^+$, 796.3453; found: 796.3446.

Embodiment 6: Preparation of N-(1-(3-cyano-9-ethyl-6,6-dimethyl-11-oxo-6,11-dihydro-5H-benzo[b]carbazole-8-yl)piperidin-4-yl)-5-((2-(2,6-dioxopiperidin-3-yl)-1-oxoisoindolin-4-yl)amino)valeramide According to the method in Embodiment 1, and under understandable appropriate conditions in the art, the target compound (SIAIS293012) (yellow solid, 8.3 mg, yield: 45%) was prepared using Alectinib derivative B and intermediate LM (SIAIS1210133). $^1$H NMR (500 MHz, DMSO) δ 12.74 (s, 1H), 11.01 (s, 1H), 8.32 (d, J=8.1 Hz, 1H), 8.04 (s, 1H), 8.00 (s, 1H), 7.82 (d, J=7.7 Hz, 1H), 7.60 (dd, J=8.1, 1.4 Hz, 1H), 7.37 (s, 1H), 7.29 (t, J=7.7 Hz, 1H), 6.93 (d, J=7.2 Hz, 1H), 6.76 (d, J=8.0 Hz, 1H), 5.11 (dd, J=13.3, 5.1 Hz, 1H), 4.24 (d, J=17.2 Hz, 1H), 4.14 (d, J=17.1 Hz, 1H), 3.74 (s, 1H), 3.18-3.09 (m, 4H), 2.95-2.88 (m, 1H), 2.84 (t, J=11.2 Hz, 2H), 2.70 (q, J=7.4 Hz, 2H), 2.61 (d, J=17.0 Hz, 1H), 2.34-2.26 (m, 1H), 2.10 (t, J=7.3 Hz, 2H), 2.04-2.02 (m, 1H), 1.86 (d, J=10.6 Hz, 2H), 1.76 (s, 6H), 1.63-1.54 (m, 6H), 1.27 (t, J=7.5 Hz, 3H). HRMS (ESI) m/z: Calculated for $C_{44}H_{48}N_7O_5^+$[M+H]$^+$, 754.3711; found: 754.3710.

Embodiment 7: Preparation of 8-(4-(4-(5-(2-(2,6-dioxopiperidin-3-yl)-1-oxoisoindolin-4-Apent-4-yn-1-yl)piperazin-1-yl)piperidin-1-yl)-9-ethyl-6,6-dimethyl-11-oxo-6,11-dihydro-5H-benzo[b]carbazole-3-carbonitrile (SIAIS293001)

According to Scheme 10, at room temperature, in the reaction flask, corresponding ALK inhibitor, namely Alectinib derivative C (0.03 mmol, 1 equiv), intermediate LM (SIAIS255121) (0.045 mmol, 1.5 equiv), NaI (0.036 mmol, 1.2 equiv), 2 mL of NMP, DIPEA (0.09 mmol, 3 equiv) were added sequentially and the mixture was reacted at 80° C. overnight. The reaction was detected by LC-MS until the reaction was completed, prepared and separated by HPLC (eluent (v/v): acetonitrile/(water+0.05% HCl)=10% -100%), the acetonitrile was spun off, and freeze-dried to obtain the final target compound (SIAIS293001) (yellow solid, 8.9 mg, yield: 36%). $^1$H NMR (500 MHz, DMSO) δ 13.02 (s, 1H), 12.43 (s, 1H), 11.00 (s, 1H), 8.32 (d, J=8.1 Hz, 1H), 8.07 (s, 1H), 8.01 (s, 1H), 7.73-7.71 (m, 1H), 7.64-7.61 (m, 1H), 7.55 (t, J=7.6 Hz, 1H), 7.37 (s, 1H), 5.18 (dd, J=13.1, 5.1 Hz, 1H), 4.57 (d, J=17.8 Hz, 1H), 4.40 (d, J=17.8 Hz, 1H), 3.85 (s, 4H), 3.59-3.41 (m, 6H), 3.33 (d, J=11.1 Hz, 4H), 2.99-2.89 (m, 1H), 2.84 (t, J=11.3 Hz, 2H), 2.73 (q, J=7.4 Hz, 2H), 2.67-2.63 (m, 2H), 2.58 (d, J=13.3 Hz, 1H), 2.25 (s, 2H), 2.12-2.08 (m, 1H), 2.04-1.86 (m, 4H), 1.78 (s, 6H), 1.30 (t, J=7.5 Hz, 3H). HRMS (ESI) m/z: Calculated for $C_{48}H_{52}N_7O_4^+$ [M+H]$^+$, 790.4075; found: 790.4074.

Embodiment 8: Preparation of 8-(4-(4-(6-(2-(2,6-dioxopiperidin-3-yl)-1-oxoisoindolin-4-yl)hex-5-yn-1-yl)piperazin-1-yl)piperidin-1-yl)-9-ethyl-6,6-dimethyl-11-oxo-6,11-dihydro-5H-benzo[b]carbazole-3-carbonitrile According to the method in Embodiment 7, and under understandable appropriate conditions in the art, the target compound (SIAIS293002) (yellow solid, 9.2 mg, yield: 37%) was prepared using Alectinib derivative C and intermediate LM (SIAIS255119). $^1$H NMR (500 MHz, DMSO) δ 12.98 (s, 1H), 10.99 (s, 1H), 8.31 (d, J=8.1 Hz, 1H), 8.06 (s, 1H), 8.00 (s, 1H), 7.72 (d, J=7.5 Hz, 1H), 7.68 (d, J=7.5 Hz, 1H), 7.60 (dd, J=8.1, 1.2 Hz, 1H), 7.53 (t, J=7.6 Hz, 1H), 7.37 (s, 1H), 5.16 (dd, J=13.1, 5.1 Hz, 1H), 4.53 (d, J=17.7 Hz, 1H), 4.38 (d, J=17.8 Hz, 1H), 3.59 (d, J=11.5 Hz, 8H), 3.51-3.41 (m, 2H), 3.33 (d, I=11.2 Hz, 2H), 3.22 (s, 2H), 2.96-2.90 (m, 1H), 2.83 (d, J=11.4 Hz, 2H), 2.72 (q, J=7.4 Hz, 2H), 2.63 (s, 1H), 2.57 (t, J=6.6 Hz, 2H), 2.25 (d, J=9.7 Hz, 2H), 2.05-2.02 (m, 1H), 1.97-1.92 (m, 4H), 1.77 (s, 6H), 1.66 (d, J=7.4 Hz, 2H), 1.28 (d, J=7.5 Hz, 3H). HRMS (ESI) m/z: Calculated for $C_{49}H_{54}N_7O_4^+$ [M+H]$^+$, 804.4232; found: 804.4244.

Embodiment 9: Preparation of 8-(4-(4-(7-(2-(2,6-dioxopiperidin-3-yl)-1-oxoisoindolin-4-yl)hept-6-yn-1-yl)piperazin-1-yl)piperidin-1-yl)-9-ethyl-6,6-dimethyl-11-oxo-6,11-dihydro-5H-benzo[b]carbazole-3-carbonitrile According to the method in Embodiment 7, and under understandable appropriate conditions in the art, the target compound (SIAIS293014) (yellow solid, 9.2 mg, yield: 36%) was prepared using Alectinib derivative C and intermediate LM (SIAIS292017). $^1$H NMR (500 MHz, DMSO) δ 12.98 (s, 1H), 11.00 (s, 1H), 8.32 (d, J=8.2 Hz, 1H), 8.06 (s, 1H), 8.01 (s, 1H), 7.72 (d, J=7.0 Hz, 1H), 7.66 (d, J=6.9 Hz, 1H), 7.60 (dd, J=8.2, 1.3 Hz, 1H), 7.53 (t, J=7.6 Hz, 1H), 7.37 (s, 1H), 5.16 (dd, J=13.2, 5.0 Hz, 1H), 4.48 (d, J=17.7 Hz, 1H), 4.34 (d, J=17.7 Hz, 1H), 3.80 (d, J=16.0 Hz, 4H), 3.66 (s, 2H), 3.33 (d, J=11.3 Hz, 4H), 3.17 (s, 2H), 2.95-2.89 (m, 1H), 2.84 (t, J=11.2 Hz, 2H), 2.72 (q, J=7.4 Hz, 2H), 2.62 (d, J=18.2 Hz, 1H), 2.25 (d, J=10.3 Hz, 2H), 2.06-1.91 (m, 4H), 1.77 (d, J=7.2 Hz, 9H), 1.68-1.59 (m, 2H), 1.49 (t, J=14.7 Hz, 2H), 1.29 (t, J=7.0 Hz, 3H). HRMS (ESI) m/z: Calculated for $C_{50}H_{56}N_7O_4^+$ [M+H]$^+$, 818.4388; found: 818.4384.

Embodiment 10: Preparation of 8-(4-(4-(8-(2-(2,6-dioxopiperidin-3-yl)-1-oxoisoindolin-4-yl)oct-7-yn-1-yl)piperazin-1-yl)piperidin-1-yl)-9-ethyl-6,6-dimethyl-11-oxo-6,11-dihydro-5H-benzo[b]carbazole-3-carbonitrile According to the method in Embodiment 7, and under understandable appropriate conditions in the art, the target compound (SIAIS293003) (yellow solid, 9.4 mg, yield: 36%) was prepared using Alectinib derivative C and intermediate LM (SIAIS292020). $^1$H NMR (500 MHz, MeOD) δ 8.41 (d, J=8.0 Hz, 1H), 8.20 (s, 1H), 7.86 (s, 1H), 7.75 (d, J=7.5 Hz, 1H), 7.67-7.59 (m, 2H), 7.55 (d, J=8.1 Hz, 1H), 7.51 (t, J=7.5 Hz, 1H), 7.40 (s, 1H), 5.20 (dd, J=13.1, 4.8 Hz, 1H), 4.53 (d, J=17.6 Hz, 1H), 4.48 (d, J=16.8 Hz, 1H), 3.85 (s, 4H), 3.44 (dd, J=54.9, 44.3 Hz, 9H), 2.94 (t, J=11.1 Hz, 3H), 2.83-2.78 (m, 31-1), 2.58-2.49 (m, 3H), 2.29 (s, 2H), 2.20 (d, J=7.8 Hz, 1H), 2.01 (d, J=12.8 Hz, 2H), 1.84 (s, 2H), 1.80 (s, 6H), 1.73-1.66 (m, 2H), 1.60 (s, 2H), 1.51 (d, J=6.9 Hz, 2H), 1.34 (t, J=7.3 Hz, 3H). HRMS (ESI) m/z: Calculated for $C_{51}H_{58}N_7O_4^+$ [M+H]$^+$, 832.4545; found: 832.4541.

Embodiment 11: Preparation of 8-(4-(4-(9-(2-(2,6-dioxopiperidin-3-yl)-1-oxoisoindolin-4-yl)non-8-yn-1-yl)piperazin-1-yl)piperidin-1-yl)-9-ethyl-6,6-dimethyl-11-oxo-6,11-dihydro-5H-benzo[b]carbazole-3-carbonitrile According to the method in Embodiment 7, and under understandable appropriate conditions in the art, the target compound (SIAIS293004) (yellow solid, 10.1 mg, yield: 39%) was prepared using Alectinib derivative C and intermediate LM (SIAIS255127). $^1$H NMR (500 MHz, DMSO) δ 12.99 (s, 1H), 11.01 (s, 1H), 8.34 (d, J=8.2 Hz, 1H), 8.08 (s, 1H), 8.02 (s, 1H), 7.74 (d, J=7.0 Hz, 1H), 7.67 (d, J=6.9 Hz, 1H), 7.61 (dd, J=8.2, 1.3 Hz, 1H), 7.54 (t, J=7.6 Hz, 1H), 7.38 (s, 1H), 5.15 (dd, J=13.2, 5.0 Hz, 1H), 4.48 (d, J=17.7 Hz, 1H), 4.35 (d, J=17.7 Hz, 1H), 3.81 (d, J=16.0 Hz, 4H), 3.67 (s, 2H), 3.35 (d, J=11.3 Hz, 4H), 3.18 (s, 2H), 2.96-2.89 (m, 1H), 2.85 (t, J=11.2 Hz, 21-1), 2.72 (q, J=7.4 Hz, 2H), 2.63 (d, J=18.2 Hz, 1H), 2.27 (d, J=10.3 Hz, 2H), 2.06-1.93 (m, 4H), 1.85-1.80 (m, 4H), 1.79 (d, J=7.2 Hz, 9H), 1.69-

1.59 (m, 2H), 1.49 (t, J=14.7 Hz, 2H), 1.30 (t, J=7.0 Hz, 3H). HRMS (ESI) m/z: Calculated for $C_{52}H_{60}N_7O_4^+$ [M+H]$^+$, 846.4701; found: 846.4698.

Embodiment 12: Preparation of 8-(4-(4-(4-(2-(2,6-dioxopiperidin-3-yl)-1-oxoisoindolin-4-yl)butyl)piperazin-1-yl)piperidin-1-yl)-9-ethyl-6,6-dimethyl-11-oxo-6,11-dihydro-5H-benzo[b]carbazole-3-carbonitrile According to the method in Embodiment 7, and under understandable appropriate conditions in the art, the target compound (SIAIS293005) (yellow solid, 9.4 mg, yield: 39%) was prepared using Alectinib derivative C and intermediate LM (SIAIS255130). $^1$H NMR (500 MHz, DMSO) δ 13.00 (s, 1H), 11.01 (s, 1H), 8.32 (d, J=8.1 Hz, 1H), 8.06 (s, 1H), 8.01 (s, 1H), 7.62-7.58 (m, 2H), 7.50 (dd, J=13.3, 7.0 Hz, 2H), 7.37 (s, 1H), 5.15 (dd, J=13.3, 5.1 Hz, 1H), 4.53 (d, J=17.0 Hz, 1H), 4.34 (d, J=17.1 Hz, 1H), 3.80 (d, J=18.8 Hz, 4H), 3.66 (s, 4H), 3.33 (d, J=11.4 Hz, 4H), 2.96-2.90 (m, 1H), 2.84 (t, J=11.7 Hz, 2H), 2.75-2.70 (m, 4H), 2.63-2.60 (m, 1H), 2.25 (d, J=9.4 Hz, 2H), 2.07-2.02 (m, 1H), 2.01-1.87 (m, 4H), 1.80 (d, J=7.6 Hz, 2H), 1.77 (s, 6H), 1.74-1.65 (m, 2H), 1.29 (d, J=7.1 Hz, 3H). HRMS (ESI) m/z: Calculated for $C_{47}H_{54}N_7O_4^+$ [M+H]$^+$, 780.4232; found: 780.4223.

Embodiment 13: Preparation of 8-(4-(4-(5-((2-(2,6-dioxopiperidin-3-yl)-1,3-dioxoisoindolin-4-yl)amino)pentyl)piperazin-1-yl)piperidin-1-yl)-9-ethyl-6,6-di methyl-11-oxo-6,11-dihydro-5H-benzo[b]carbazole-3-carbonitrile According to the method in Embodiment 7, and under understandable appropriate conditions in the art, the target compound (SIAIS293008) (yellow solid, 9.1 mg, yield: 36%) was prepared using Alectinib derivative C and intermediate LM (SIAIS264016). $^1$H NMR (500 MHz, DMSO) δ 12.97 (s, 1H), 11.10 (s, 1H), 8.31 (d, J=8.1 Hz, 1H), 8.06 (s, 1H), 8.00 (s, 1H), 7.59 (t, J=7.7 Hz, 2H), 7.36 (s, 1H), 7.13 (d, J=8.6 Hz, 1H), 7.03 (d, J=7.0 Hz, 1H), 6.59 (s, 1H), 5.06 (dd, J=12.7, 5.2 Hz, 1H), 3.80 (d, J=15.7 Hz, 6H), 3.33 (d, J=7.1 Hz, 6H), 3.16 (s, 2H), 2.92-2.81 (m, 4H), 2.74-2.70 (m, 2H), 2.61-2.58 (m, 2H), 2.24 (s, 2H), 2.05-1.90 (m, 5H), 1.77 (s, 8H), 1.63 (s, 2H), 1.42 (d, J=6.6 Hz, 2H), 1.29 (t, J=6.5 Hz, 3H). HRMS (ESI) m/z: Calculated for $C_{48}H_{55}N_8O_5^+$ [M+H]$^+$, 823.4290; found: 823.4288.

Embodiment 14: Preparation of 8-(4-(4-(6-4(2-(2,6-dioxopiperidin-3-yl)-1,3-dioxoisoindolin-4-yl)amino)hexyl)piperazin-1-yl)piperidin-1-yl)-9-ethyl-6,6-dimethyl-11-oxo-6,11-dihydro-5H-benzo[b]carbazole-3-carbonitrile According to the method in Embodiment 7, and under understandable appropriate conditions in the art, the target compound (SIAIS293009) (yellow solid, 8.6 mg, yield: 33%) was prepared using Alectinib derivative C and intermediate LM (SIAIS264018). $^1$H NMR (500 MHz, DMSO) δ 12.95 (s, 1H), 11.10 (d, J=3.6 Hz, 2H), 8.32 (d, J=8.2 Hz, 1H), 8.07 (s, 1H), 8.01 (s, 1H), 7.60 (s, 1H), 7.37 (s, 1H), 7.12 (d, J=8.6 Hz, 1H), 7.09 (d, J=8.6 Hz, 1H), 7.02 (d, J=6.7 Hz, 1H), 6.55 (s, 1H), 5.08-5.04 (m, 1H), 3.60-3.43 (m, 4H), 3.38 (t, J=6.5 Hz, 2H), 3.36-3.27 (m, 6H), 3.16 (d, J=13.3 Hz, 2H), 2.93-2.81 (m, 4H), 2.76-2.69 (m, 2H), 2.59 (d, J=17.8 Hz, 2H), 2.25 (d, J=10.5 Hz, 2H), 2.07-1.90 (m, 5H), 1.77 (d, J=5.8 Hz, 8H), 1.59-1.55 (m, 4H), 1.43-1.40 (m, 2H), 1.28 (d, J=7.5 Hz, 3H). HRMS (ESI) m/z: Calculated for $C_{49l}-157N_8O_5^+$ [M+H]$^+$, 837.4446; found: 837.4452.

Embodiment 15: Preparation of 3-(4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-1-oxoisoindolin-2-yl)piperidine-2,6-dione According to the method in Embodiment 7, and under understandable appropriate conditions in the art, the target compound (SIAIS262039) (yellow solid, 15.2 mg, yield: 47%) was prepared using Brigatinib derivative C and intermediate LM (SIAIS255121). $^1$H NMR (500 MHz, MeOD) δ 8.38-8.25 (m, 1H), 8.11 (s, 1H), 7.77 (d, J=7.5 Hz, 1H), 7.70 (dd, J=14.0, 7.8 Hz, 1H), 7.66 (d, J=7.6 Hz, 1H), 7.60 (s, 1H), 7.52 (t, J=7.6 Hz, 1H), 7.43 (t, J=7.1 Hz, 1H), 7.00 (s, 1H), 6.81 (s, 1H), 5.21 (dd, J=13.2, 5.3 Hz, 1H), 4.60 (d, J=17.9 Hz, 1H), 4.53 (d, J=17.7 Hz, 1H), 3.94 (d, J=11.8 Hz, 2H), 3.90 (s, 3H), 3.69-3.34 (m, 10H), 3.29-3.00 (m, 3H), 2.99-2.87 (m, 1H), 2.79 (d, J=17.6 Hz, 1H), 2.70 (t, J=6.7 Hz, 2H), 2.60 (dd, J=13.3, 4.4 Hz, 1H), 2.32 (d, J=12.1 Hz, 2H), 2.23-2.13 (m, 3H), 2.08 (s, 2H), 1.88 (d, J=13.6 Hz, 6H). HRMS (ESI) m/z: Calculated for $C_{46}H_{54}ClN_9O_5^+$ [M+H]$^+$, 878.3669; found: 878.3661.

Embodiment 16: Preparation of 3-(4-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)hex-1-yn-1-yl)-1-oxoisoindolin-2-yl)piperidine-2,6-dione According to the method in Embodiment 7, under understandable appropriate conditions in the art, the target compound (SIAIS262040) (yellow solid, 16.1 mg, yield: 49%) was prepared using Brigatinib derivative C and intermediate LM (SIAIS255119). $^1$H NMR (500 MHz, MeOD) δ 8.31 (s, 1H), 8.10 (s, 1H), 7.76 (d, J=7.1 Hz, 1H), 7.70 (dd, J=14.4, 7.6 Hz, 1H), 7.64 (d, J=7.6 Hz, 1H), 7.60 (s, 1H), 7.51 (t, J=7.7 Hz, 1H), 7.42 (t, J=7.6 Hz, 1H), 6.96 (s, 1H), 6.77 (s, 1H), 5.21 (dd, J=13.3, 5.2 Hz, 1H), 4.58 (d, J=17.6 Hz, 1H), 4.52 (d, J=17.5 Hz, 1H), 3.92 (s, 2H), 3.89 (s, 3H), 3.49 (dd, J=88.4, 29.3 Hz, 10H), 3.16 (s, 3H), 2.97-2.87 (m, 1H), 2.80 (dd, J=11.0, 8.7 Hz, 1H), 2.62 (dd, J=15.2, 8.4 Hz, 3H), 2.29 (d, J=10.8 Hz, 2H), 2.19 (dd, J=9.1, 3.9 Hz, 1H), 2.02 (s, 4H), 1.88 (d, J=13.6 Hz, 6H), 1.76 (dd, J=14.8, 7.3 Hz, 2H). HRMS (ESI) m/z: Calculated for $C_{47}H_{56}ClN_9O_5P^+$ [M+H]$^+$, 892.3825; found: 892.3821.

Embodiment 17: Preparation of 3-(4-(7-(4-(1-(4-((5-chloro-4-((2-(dimethylphosphono)phenyl)amino)pyrimidin-2-yl)amino)-3-methoxyphenyl)piperidin-4-yl)piperazin-1-yl)hept-1-yn-1-yl)-1-oxoisoindolin-2-yl)piperidine-2,6-dione According to the method in Embodiment 7, under understandable appropriate conditions in the art, the target compound (SIAIS293015) (yellow solid, 9.5 mg, yield: 40%) was prepared by using Brigatinib derivative C and intermediate LM (SIAIS292017). $^1$H NMR (500 MHz, MeOD) δ 8.32 (s, 1H), 8.09 (s, 1H), 7.75 (d, J=7.7 Hz, 1H), 7.70 (dd, J=13.9, 7.8 Hz, 1H), 7.61 (t, J=7.9 Hz, 2H), 7.51 (t, J=7.6 Hz, 1H), 7.42 (t, J=7.4 Hz, 1H), 6.95 (s, 1H), 6.78 (s, 1H), 5.19 (dd, J=13.3, 5.1 Hz, 1H), 4.54 (d, J=17.5 Hz, 1H), 4.48 (d, J=17.5 Hz, 1H), 3.91 (d, J=14.5 Hz, 5H), 3.77-3.36 (m, 8H), 3.28-3.21 (m, 3H), 3.16 (s, 2H), 2.92 (ddd, J=18.6, 13.7, 5.3 Hz, 1H), 2.79 (d, J=15.6 Hz, 1H), 2.60-2.53 (m, 3H), 2.26 (d, J=12.1 Hz, 2H), 2.22-2.16 (m, 1H), 2.04-1.96 (m, 2H), 1.87 (t, J=10.6 Hz, 8H), 1.73 (dd, J=14.5, 7.1 Hz, 2H), 1.67-1.59 (m, 2H). HRMS (ESI) m/z: Calculated for $C_{48}H_{58}ClN_9O_5P^+$ [M+H]$^+$, 906.3982; found: 906.3981.

Embodiment 18: Preparation of 3-(4-(8-(4-(1-(4-((5-chloro-4-((2-(dimethylphosphono)phenyl)amino) pyrimidin-2-yl)amino)-3-methoxyphenyl)piperidin-4-yl)piperazin-1-yl)oct-1-yn-1-yl)-1-oxoisoindolin-2-yl)piperidine-2,6-dione According to the method in Embodiment 7, under understandable appropriate conditions in the art, the target compound (SIAIS293017) (yellow solid, 9.4 mg, yield: 39%) was prepared by using Brigatinib derivative C and intermediate LM (SIAIS292020). $^1$H NMR (500 MHz, DMSO) δ 11.00 (s, 1H), 9.11 (s, 3H), 8.25 (s, 1H), 7.71 (d, J=7.6 Hz, 1H), 7.63 (t, J=10.8 Hz, 2H), 7.53 (t, J=7.6 Hz, 1H), 7.43 (s, 1H), 7.25 (s, 1H), 6.86 (s, 1H), 6.67 (s, 1H), 5.16 (dd, J=13.3, 5.1 Hz, 1H), 4.46 (d, J=17.4 Hz, 1H), 4.33 (d, J=17.6 Hz, 1H), 3.91 (s, 4H), 3.81 (s, 3H), 3.78-3.75 (m, 3H), 3.38-3.28 (m, 6H), 2.95-2.89 (m, 2H), 2.60 (s, 1H), 2.24 (s, 2H), 1.99 (dd, J=10.9, 6.7 Hz, 3H), 1.80 (d, J=13.6 Hz, 8H), 1.60 (d, J=7.4 Hz, 2H), 1.47 (s, 4H), 1.39 (d, J=6.4 Hz, 4H). HRMS (ESI) m/z: Calculated for $C_{49}H_{60}ClN_9O_5P^+$ [M+H]$^+$, 920.4138; found: 920.4141.

Embodiment 19: Preparation of 3-(4-(9-(4-(1-(4-((5-chloro-4-((2-(dimethylphosphono)phenyl)amino) pyrimidin-2-yl)amino)-3-methoxyphenyl)piperidin-4-yl)piperazin-1-yl)non-1-yn-1-yl)-1-oxoisoindolin-2-yl)piperidine-2,6-dione According to the method in Embodiment 8, under understandable appropriate conditions in the art, the target compound (SIAIS293018) (yellow solid, 10.2 mg, yield: 42%) was prepared by using Brigatinib derivative C and intermediate LM (SIAIS255127). $^1$H NMR (500 MHz, DMSO) δ 12.02 (s, 1H), 11.01 (s, 1H), 9.31 (s, 2H), 8.29 (s, 1H), 7.71 (d, J=7.6 Hz, 1H), 7.68-7.61 (m, 2H), 7.53 (t, J=7.6 Hz, 1H), 7.44 (s, 2H), 7.27 (t, J=7.3 Hz, 1H), 6.90 (s, 1H), 6.74 (s, 1H), 5.16 (dd, J=13.3, 5.1 Hz, 1H), 4.46 (d, J=17.6 Hz, 1H), 4.31 (d, J=17.7 Hz, 1H), 3.91 (s, 4H), 3.37 (d, J=7.2 Hz, 9H), 2.97-2.88 (m, 3H), 2.62 (d, J=18.9 Hz, 1H), 2.45 (d, J=4.7 Hz, 1H), 2.25 (s, 2H), 1.98 (ddd, J=41.3, 24.0, 6.3 Hz, 5H), 1.80 (d, J=13.6 Hz, 8H), 1.74 (s, 2H), 1.59 (dd, J=14.6, 7.3 Hz, 2H), 1.46-1.42 (m, 2H), 1.36 (s, 2H). HRMS (ESI) m/z: Calculated for $C_{50}H_{62}ClN_9O_5P^+$ [M+H]$^+$, 934.4295; found: 934.4300.

Embodiment 20: Preparation of 4-(2-(4-(1-(4-((5-chloro-4-((2-(dimethylphosphono)phenyl)amino) pyrimidin-2-yl)amino)-3-methoxyphenyl)piperidin-4-yl)piperazin-1-yl)-2-oxoethoxy)-2-(2,6-dioxopiperidin-3-yl))isoindoline-1,3-dione According to the method in Embodiment 1, under understandable appropriate conditions in the art, the target compound (SIAIS293016) (yellow solid, 6.2 mg, yield: 40%) was prepared using Brigatinib derivative C and intermediate LM (SIAIS172101B). $^1$H NMR (500 MHz, DMSO) δ 12.12 (s, 1H), 11.87 (s, 1H), 11.11 (s, 1H), 9.74 (d, J=75.2 Hz, 1H), 8.33 (s, 1H), 7.78 (dd, J=8.4, 7.4 Hz, 1H), 7.66 (dd, J=13.7, 7.7 Hz, 1H), 7.53-7.37 (m, 4H), 7.28 (dd, J=14.7, 7.6 Hz, 1H), 7.04 (s, 1H), 6.86 (s, 1H), 5.26 (d, J=11.3 Hz, 2H), 5.16-5.09 (m, 1H), 4.43 (s, 2H), 4.12 (s, 2H), 4.20 (s, 2H), 3.83 (s, 3H), 3.55 (dd, J=28.5, 18.2 Hz, 4H), 3.30 (d, J=12.6 Hz, 2H), 3.13-2.98 (m, 3H), 2.88 (dd, J=12.2, 4.6 Hz, 1H), 2.59 (d, J=20.1 Hz, 1H), 2.31 (s, 2H), 2.21-1.89 (m, 4H), 1.80 (d, J=13.7 Hz, 6H). HRMS (ESI) m/z: Calculated for $C_{43}H_{48}ClN_9O_5P^+$ [M+H]$^+$, 884.3047; found: 884.3038.

Embodiment 21: Preparation of 3-(4-((6-((1-(4-((5-chloro-4-((2-(dimethylphosphono)phenyl)amino) pyrimidin-2-yl)amino)-3-methoxyphenyl)piperidin-4-yl)amino)hexyl)thio)-1-oxoisoindolin-2-yl) piperidine-2,6-dione (SIAIS293110)

According to Scheme 15, Brigatinib derivative B (20 mg, 0.04 mmol) was dissolved in 2 mL of NMP, and SIAIS1216133 (22.8 mg, 0.052 mmol), NaI (9 mg, 0.08 mmol) and DIPEA (10.3 mg, 0.08 mmol) were added sequentially, the mixture was heated to 80° C., and reacted overnight. 0.10 mL of water was added to quench the reaction, the mixture was prepared and separated by HPLC (eluent(v/v): acetonitrile/(water+0.05% HCl) =10% -100%), most of the acetonitrile and water were evaporated under reduced pressure, and freeze-dried to obtain the final target compound (SIAIS293110) (yellow solid, 14.4 mg, 42%). HRMS (ESI) $C_{43}H_{53}ClN_9O_5PS^+$[M+H]$^+$, calculated: 859.3280; found: 859.3275.

Embodiment 22: Preparation of 3-(4-(5-((1-(4-((5-chloro-4-((2-(dimethylphosphono)phenyl)amino) pyrimidin-2-yl)amino)-3-methoxyphenyl)piperidin-4-yl)amino)pent-1-yn-1-yl)-1-oxoisoindolin-2-yl) piperidine-2,6-dione (SIAIS293093)

According to the method in Embodiment 7, under understandable appropriate conditions in the art, the target compound (SIAIS293093) (yellow solid, 10.2 mg, yield: 42%) was prepared by using Brigatinib derivative B and intermediate LM (SIAIS255121). $^1$H NMR (500 MHz, Methanol-d$_4$) δ 8.27 (s, 1H), 8.15 (s, 1H), 7.79 (d, J=7.7 Hz, 2H), 7.75-7.68 (m, 3H), 7.61 (s, 1H), 7.55 (t, J=7.9 Hz, 2H), 7.28 (d, J=8.7 Hz, 1H), 5.23 (d, J=12.4 Hz, 1H), 4.62 (d, J=17.7 Hz, 1H), 4.55 (d, J=17.4 Hz, 1H), 4.02 (s, 3H), 3.92-3.87 (m, 7H), 2.95 (s, 1H), 2.86-2.73 (m, 3H), 2.59-2.55 (m, 3H), 2.43 (s, 2H), 2.22 (s, 1H), 2.14 (s, 2H), 1.89 (d, J=13.4 Hz, 6H). HRMS (ESI) m/z: Calculated for $C_{42}H_{47}ClN_8O_5P^+$ [M+H]$^+$, 809.3090; found: 809.3092.

Embodiment 23: Preparation of 3-(4-((4-((4-(1-(4-((5-chloro-4-((2-(dimethylphosphono)phenyl)amino) pyrimidin-2-yl)amino)-3-methoxyphenyl)piperidin-4-yl)piperazin-1-yl)methyl)benzyl)thio)-1-oxoisoindolin-2-yl)piperidine-2,6-dione (SIAIS293189)

According to the method of Embodiment 21, under understandable appropriate conditions in the art, the target compound (SIAIS293189) (yellow solid, 9.2 mg, yield: 38%) was prepared using Brigatinib derivative C and intermediate LM (SIAIS1220141). $^1$H NMR (500 MHz, Methanol-d$_4$) δ 8.28 (s, 1H), 8.16 (s, 1H), 7.79 (d, J=7.7 Hz, 2H), 7.76-7.68 (m, 3H), 7.62 (s, 1H), 7.57 (t, J=7.9 Hz, 2H), 7.27 (d, J=8.7 Hz, 1H), 7.25-7.21 (m, 4H), 5.21 (d, J=12.4 Hz, 1H), 4.65 (s, 2H), 4.32 (s, 2H), 4.24 (d, J=17.4 Hz, 1H), 4.13 (d, J=17.4 Hz, 1H), 4.03 (s, 3H), 3.93-3.83 (m, 9H), 2.96-2.86 (m, 1H), 2.57 (d, J=16.6 Hz, 1H), 2.46-2.35 (m, 1H), 2.13-2.08 (m, 4H), 2.01-1.95 (m, 1H), 1.87 (d, J=13.4 Hz, 6H). HRMS (ESI) m/z: Calculated for $C_{49}H_{56}ClN_9O_5PS^+$[M+H]$^+$, 948.3546; found: 948.3548.

Embodiment 24: Preparation of 8-(4-(4-(4-((2-(2,6-dioxopiperidin-3-yl)-1-oxoisoindolin-4-yl)thio)butyl)piperazin-1-yl)piperidin-1-yl)-9-ethyl-6,6-dimethyl-11-oxo-6,11-dihydro-5H-benzo[b]carbazole-3-carbonitrile (SIAIS293060)

According to the method in Embodiment 21, under understandable appropriate conditions in the art, the target compound (SIAIS293060) (yellow solid, 9.8 mg, yield: 41%) was prepared using Alectinib derivative C and intermediate LM (SIAIS213134). $^1$H NMR (500 MHz, Methanol-$d_4$) δ 8.42 (d, J=8.1 Hz, 1H), 8.23 (s, 1H), 7.89 (s, 1H), 7.67 (dd, J=7.5, 3.7 Hz, 2H), 7.59-7.54 (m, 2H), 7.45 (s, 1H), 5.19 (dd, J=13.4, 5.2 Hz, 1H), 4.49 (d, J=17.3 Hz, 1H), 4.45 (d, J=17.4 Hz, 1H), 3.94 (s, 4H), 3.59 (s, 2H), 3.44 (d, J=12.7 Hz, 2H), 3.29-3.24 (m, 2H), 3.15-3.05 (m, 2H), 3.01-2.91 (m, 3H), 2.83 (q, J=7.7 Hz, 3H), 2.59-2.52 (m, 1H), 2.36 (s, 1H), 2.24-2.16 (m, 1H), 2.11-2.03 (m, 2H), 1.81 (d, J=13.6 Hz, 8H), 1.78-1.64 (m, 2H), 1.64-1.49 (m, 2H), 1.48-1.43 (m, 2H), 1.35 (d, J=6.6 Hz, 3H). HRMS (ESI) m/z: Calculated for $C_{47}H_{54}N_7O_4S^+$ [M+H]$^+$, 812.3953; found: 812.3951.

Embodiment 25: Preparation of 8-(4-(4-(5-(2-(2,6-dioxopiperidin-3-yl)-1-oxoisoindolin-4-yl)pentyl)piperazin-1-yl)piperidin-1-yl)-9-ethyl-6,6-dimethyl-11-oxo-6,11-dihydro-5H-benzo[b]carbazole-3-carbonitrile (SIAIS350083)

According to the method of Embodiment 7, and under understandable appropriate conditions in the art, the target compound (SIAIS350083) (gray solid, 3.0 mg, yield: 18.2%) was prepared using Alectinib derivative C and intermediate LM (SIAIS350020). $^1$H NMR (500 MHz, MeOD) δ 8.40 (d, J=8.2 Hz, 1H), 8.20 (s, 1H), 7.86 (s, 1H), 7.66 (dd, J=7.1, 1.4 Hz, 1H), 7.60-7.46 (m, 3H), 7.42 (s, 1H), 5.20 (dd, J=13.4, 5.2 Hz, 1H), 4.53 (dd, J=35.1, 17.0 Hz, 2H), 3.76 (d, J=178.8 Hz, 10H), 3.42 (d, J=12.1 Hz, 2H), 3.27 (d, J=8.7 Hz, 2H), 2.93 (dt, J=13.6, 8.8 Hz, 3H), 2.83-2.77 (m, 4H), 2.58 (dt, J=13.4, 8.7 Hz, 1H), 2.35 (d, J=9.3 Hz, 2H), 2.24-2.15 (m, 1H), 2.06 (d, J=8.7 Hz, 2H), 1.91-1.73 (m, 10H), 1.49 (d, J=5.3 Hz, 2H), 1.35 (t, J=7.5 Hz, 3H). HRMS (ESI) m/z: Calculated for $C_{48}H_{56}N_7O_4^+$ [M+H]$^+$, 794.4388; found: 794.4387.

Embodiment 26: Preparation of 8-(4-(5-(2-(2,6-dioxopiperidin-3-yl)-1-oxoisoindolin-4-yl)pentyl)piperazin-1-yl)-9-ethyl-6,6-dimethyl-11-oxo-6,11-dihydro-5H-benzo[b]carbazole-3-carbonitrile (SIAIS350081)

According to the method in Embodiment 7, and under understandable appropriate conditions in the art, the target compound (SIAIS350081) (white solid, 6.0 mg, yield: 37.5%) was prepared using Alectinib derivative A and intermediate LM (SIAIS350020). $^1$H NMR (500 MHz, MeOD) δ 8.40 (d, J=8.2 Hz, 1H), 8.23 (s, 1H), 7.87 (s, 1H), 7.67 (d, J=6.0 Hz, 1H), 7.59-7.46 (m, 3H), 7.43 (s, 1H), 5.20 (dd, J=13.3, 5.1 Hz, 1H), 4.52 (q, J=16.9 Hz, 2H), 3.68 (d, J=12.0 Hz, 2H), 3.49-3.34 (m, 4H), 3.27-3.15 (m, 4H), 2.93 (ddd, J=18.5, 13.5, 5.4 Hz, 1H), 2.87-2.76 (m, 5H), 2.53 (tt, J=13.6, 6.8 Hz, 1H), 2.20 (dd, J=9.0, 3.7 Hz, 1H), 1.88-1.77 (m, 10H), 1.51 (dt, J=15.4, 7.9 Hz, 2H), 1.35 (t, J=7.5 Hz, 3H). HRMS (ESI) m/z: Calculated for $C_{43}H_{47}N_6O_4^+$ [M+H]$^+$, 711.3653; found: 711.3652.

Embodiment 27: Preparation of 3-(4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pentyl)-1-oxoisoindolin-2-yl)piperidine-2,6-dione (SIAIS352008)

Preparation method 1: compound SIAIS262039 (10 mg, 11.4 µmot) was dissolved in 2 mL of THF and 3 mL of MeOH; PtOz (5 mg), Pd/C (5 mg) and acetic acid (50 mg) were added, the system was ventilated with hydrogen three times, heated to 50° C., and reacted overnight. After LCMS detected that there was no raw material in the reaction, filtered, the filtrate was concentrated to dryness, 1.0 mL of acetonitrile and 0.20 mL of water were added, the mixture was prepared and separated by HPLC (eluent(v/v): acetonitrile/(water+0.05% HCl))=10% -100%), acetonitrile and most of water were evaporated under reduced pressure, and freeze-dried to obtain the final target compound (SIAIS352008) (white solid, 4.5 mg, 46%). HRMS (ESI) $C_{46}H_{58}ClN_9O_5P^+$[M+H]$^+$, calculated: 882.3982; actual found: 882.3988.

Preparation method 2: according to the method in Embodiment 7, under understandable appropriate conditions in the art, the target compound (SIAIS352008) (white solid, 10.0 mg, yield: 38.8%) was prepared using Brigatinib derivative C and intermediate LM (SIAIS350020). $^1$H NMR (500 MHz, DMSO) δ 12.18 (d, J=198.4 Hz, 3H), 10.99 (s, 1H), 9.33 (s, 1H), 8.33 (d, J=67.0 Hz, 2H), 7.70-7.54 (m, 2H), 7.52-7.33 (m, 4H), 7.26 (t, J=7.2 Hz, 1H), 6.78 (d, J=83.1 Hz, 2H), 5.15 (dd, J=13.3, 5.1 Hz, 1H), 4.42 (dd, J=86.3, 17.2 Hz, 2H), 3.92 (d, J=10.5 Hz, 2H), 3.80 (d, J=12.7 Hz, 7H), 3.66-3.41 (m, 5H), 3.13 (s, 2H), 2.93 (ddd, J=18.3, 11.8, 5.0 Hz, 3H), 2.71-2.56 (m, 3H), 2.44 (dd, J=13.4, 4.5 Hz, 1H), 2.25 (d, J=9.3 Hz, 21-1), 2.08-1.86 (m, 3H), 1.80 (d, J=13.6 Hz, 8H), 1.70-1.60 (m, 2H), 1.38 (d, J=7.0 Hz, 2H). LCMS (ESI) m/z: Calculated for $C_{46}H_{58}ClN_9O_5P^+$ [M+H]$^+$, 882.3982; found: 882.54.

Embodiment 28: Preparation of 4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-2-(2,6-dioxopiperidin-3-yl)isoindoline-1,3-dione (SIAIS352010)

According to the method in Embodiment 1, and under understandable appropriate conditions in the art, the target compound (SIAIS352010) (yellow solid, 6.42 mg, 20%) was prepared using Alectinib derivative C and intermediate LM (SIAIS292006). $^1$H NMR (500 MHz, DMSO-$d_6$) δ 11.16 (s, 1H), 8.47 (s, 1H), 8.16 (s, 1H), 7.95 (dd, J=24.3, 8.4 Hz, 2H), 7.59 (t, J=10.4 Hz, 1H), 7.42 (s, 2H), 7.18 (s, 1H), 6.67 (d, J=77.8 Hz, 2H), 5.17 (d, J=14.0 Hz, 1H), 4.06 (s, 1H), 3.84-3.78 (m, 3H), 3.50 (s, 14H), 2.90 (t, J=14.2 Hz, 1H), 2.79 (s, 2H), 2.20 (s, 2H), 2.07 (s, 2H), 1.78 (d, J=13.5 Hz, 6H). HRMS (ESI) $C_{46}H_{52}ClN_9O_6P^+$[M+H]$^+$, calculated: 892.3461; found: 892.3469.

Embodiment 29: Preparation of 3-(4-((2-(4-(1-(4-((5-chloro-4-((2-(dimethylphosphono)phenyl)amino)pyrimidin-2-yl)amino)-3-methoxyphenyl)piperidin-4-yl)piperazin-1-yl)ethyl)thio)-1-oxoisoindolin-2-yl)piperidine-2,6-dione (SIAIS352011)

According to the method in Embodiment 7, under understandable appropriate conditions in the art, the target compound (SIAIS352011) was prepared using Alectinib derivative C and intermediate LM (SIAIS213137) (yellow-brown solid, 9.0 mg, 39%). $^1$H NMR (500 MHz, DMSO-$d_6$) δ 11.93 (d, J=121.1 Hz, 2H), 10.99 (s, 1H), 8.34 (d, J=36.2 Hz, 2H), 7.83 (d, J=7.6 Hz, 1H), 7.65 (q, J=7.4, 7.0 Hz, 2H), 7.57 (t, J=7.5 Hz, 1H), 7.44 (d, J=11.8 Hz, 2H), 7.27 (d, J=7.1 Hz, 1H), 6.85 (d, J=84.6 Hz, 2H), 5.15 (dd, J=12.8, 5.1 Hz, 1H), 4.34-4.23 (m, 2H), 3.93 (s, 6H), 3.56 (s, 6H), 3.38 (s, 2H), 3.30 (td, J=7.1, 1.9 Hz, 2H), 3.19-3.08 (m, 2H), 2.96 (s, 4H), 2.72-2.56 (m, 2H), 2.28 (s, 3H), 2.18 (t, J=8.1 Hz, 1H), 2.00 (s, 3H), 1.90 (p, J=7.6 Hz, 1H), 1.87-1.74 (m, 8H). HRMS (ESI) $C_{43}H_{52}ClN_9O_5PS^+$[M+H]$^+$, calculated: 872.3233; found: 872.3240.

Embodiment 30: Preparation of 3-(4-((2-(2-(2-(4-(1-(4-((5-chloro-4-((2-(dimethylphosphono)phenyl)amino)pyrimidin-2-yl)amino)-3-methoxyphenyl)piperidin-4-yl)piperazin-1-yl)-2-oxoethoxy)ethoxy)ethyl)amino)-1-oxoisoindolin-2-yl)piperidine-2,6-dione (SIAIS352054)

According to the method in Embodiment 1, under understandable appropriate conditions in the art, the target compound (SIAIS352054) (white solid, 6.0 mg, yield: 18%) was prepared by using Brigatinib derivative C and intermediate LM (SIAIS1204123). $^1$H NMR (500 MHz, Methanol-$d_4$) δ 8.24 (d, J=6.4 Hz, 1H), 8.15 (s, 1H), 7.82-7.72 (m, 2H), 7.71-7.60 (m, 4H), 7.57-7.43 (m, 2H), 7.26-7.12 (m, 1H), 5.22 (ddd, J=20.8, 13.3, 5.2 Hz, 1H), 5.01-4.97 (m, 1H), 4.76-4.63 (m, 2H), 4.16 (s, 2H), 3.98 (d, J=3.5 Hz, 2H), 3.94 (d, J=2.1 Hz, 2H), 3.69 (m, 12H), 3.23 (q, J=7.4 Hz, 3H), 3.01-2.68 (m, 4H), 2.63-2.43 (m, 5H), 2.21 (ddt, J=12.7, 5.2, 2.8 Hz, 1H), 1.87 (d, J=13.5 Hz, 8H). HRMS (ESI) m/z: Calculated for $C_{47}H_{59}ClN_{10}O_8P^+$ [M+H]$^+$, 957.3938; found: 957.3946.

Embodiment 31: Preparation of 3-(4-((2-(2-(2-(2-(4-(1-(4-((5-chloro-4-((2-(dimethylphosphonyl)phenyl)amino)pyrimidin-2-yl)amino)-3-methoxyphenyl)piperidin-4-yl)piperazin-1-yl)-2-oxoethoxy)ethoxy)ethoxy)ethyl)amino)-1-oxoisoindolin-2-yl)piperidine-2,6-dione (SIAIS352055)

According to the method in Embodiment 1, and under understandable appropriate conditions in the art, the target compound (SIAIS352055) (white solid, 6.5 mg, yield: 19%) was prepared using Brigatinib derivative C and intermediate LM (SIAIS1204127). $^1$H NMR (500 MHz, Methanol-$d_4$) δ 8.22 (d, J=8.3 Hz, 2H), 7.74 (dd, J=13.2, 7.3 Hz, 2l1), 7.67-7.58 (m, 4H), 7.50 (d, J=7.3 Hz, 1H), 7.43 (s, 1H), 7.15 (s, 1H), 5.44-5.06 (m, -1H), 4.75 (s, 1H), 4.69-4.58 (m, 2H), 4.31 (s, 2H), 4.16-4.05 (m, 2H), 4.01-3.92 (m, 6H), 3.89 (s, 2H), 3.70 (d, J=6.9 Hz, 13H), 3.21 (s, 3H), 2.90-2.77 (m, 21-1), 2.55 (d, J=10.6 Hz, 5H), 2.23 (s, 1H), 1.87 (d, J=13.4 Hz, 8l1). HRMS (ESI) m/z: Calculated for $C_{49}H_{63}ClN_{10}O_8P^+$ [M+H]$^+$, 1001.4200; found: 1001.4211.

Embodiment 32: Preparation of 3-(4-((14-(4-(1-(4-((5-chloro-4-((2-(dimethylphosphono)phenyl)amino)pyrimidin-2-yl)amino)-3-methoxyphenyl)piperidin-4-yl)piperazin-1-yl)-14-oxo-3,6,9,12-tetraoxatetradecyl)amino)-1-oxoisoindolin-2-yl)piperidine-2,6-dione (SIAIS352056)

According to the method in Embodiment 1, under understandable appropriate conditions in the art, the target compound (SIAIS352056) (white solid, 6.2 mg, yield: 17%) was prepared using Brigatinib derivative C and intermediate LM (SIAIS1204131). $^1$H NMR (500 MHz, Methanol-$d_4$) δ 8.20 (s, 2H), 7.72 (td, J=15.6, 14.8, 7.5 Hz, 2H), 7.67-7.59 (m, 4H), 7.49 (d, J=7.7 Hz, 2H), 7.04 (dd, J=22.6, 8.6 Hz, 1H), 5.19 (dd, J=13.3, 5.2 Hz, 1H), 4.78-4.54 (m, 3H), 4.12-4.02 (m, 3H), 4.02-3.91 (m, 5H), 3.83-3.53 (m, 18H), 3.23 (q, J=7.4 Hz, 3H), 3.02-2.88 (m, 2H), 2.80 (ddd, J=17.6, 4.6, 2.4 Hz, 1H), 2.62-2.45 (m, 4H), 2.36 (s, 3H), 2.22 (dtd, J=12.2, 5.0, 2.2 Hz, 2H), 1.87 (dd, J=13.6, 1.4 Hz, 6H). HRMS (ESI) m/z: Calculated for $C_{51}H_{67}ClN_{10}O_{10}P^+$ [M+H]$^+$, 1045.4464; found: 1045.4466.

Embodiment 33: Preparation of 3-(4-((17-(4-(1-(4-((5-chloro-4-((2-(dimethylphosphono)phenyl)amino)pyrimidin-2-yl)amino)-3-methoxyphenyl)piperidin-4-yl)piperazin-1-yl)-17-oxo-3,6,9,12,15-pentaoxaheptadecyl)amino)-1-oxoisoindolin-2-yl)piperidine-2,6-dione (SIAIS352057)

According to the method in Embodiment 1, under understandable appropriate conditions in the art, the target compound (SIAIS352057) (white solid, 7.2 mg, yield: 19%) was prepared using Brigatinib derivative C and intermediate LM (SIAIS1204135). $^1$H NMR (500 MHz, Methanol-$d_4$) δ 8.34 (s, 1H), 8.08 (s, 1H), 7.59 (s, 2H), 7.41-7.21 (m, 4H), 7.00 (dd, J=21.9, 8.0 Hz, 1H), 6.85 (s, 1H), 6.68 (d, J=8.8 Hz, 1H), 5.16 (dd, J=13.3, 5.4 Hz, 2H), 4.47-4.33 (m, 4H), 4.09 (s, 2H), 3.94 (s, 2H), 3.88 (d, J=7.4 Hz, 4H), 3.72 (q, J=6.0, 5.2 Hz, 8H), 3.65-3.58 (m, 6H), 3.47 (p, J=5.1, 4.4 Hz, 6H), 3.23 (q, J=7.4 Hz, 3H), 2.97-2.86 (m, 4H), 2.84-2.74 (m, 2H), 2.57-2.43 (m, 2H), 2.24-2.15 (m, 2H), 1.88 (d, J=13.5 Hz, 8H). HRMS (ESI) m/z: Calculated for $C_{53}H_{71}ClN_{10}O_{11}P^+$ [M+H]$^+$, 1089.4724; found: 1089.4730.

Embodiment 34: Preparation of 3-(4-(4-(4-(1-(4-((5-chloro-4-((2-(dimethylphosphono)phenyl)amino)pyrimidin-2-yl)amino)-3-methoxyphenyl)piperidin-4-yl)piperazin-1-yl)butyl)-1-oxoisoindolin-2-yl)piperidine-2,6-dione (SIAIS352059)

Brigatinib derivative C (11.6 mg, 0.02 mmol) was dissolved in 2 mL of NMP, SIAIS255130 (8.0 mg, 0.02 mmol), NaI (3.0 mg, 0.02 mmol) and DIPEA (15.7 mg, 0.12 mmol) were added sequentially, the mixture was heated to 90° C., and reacted overnight. 0.10 mL of water was added to quench the reaction, the mixture was prepared and separated by HPLC (eluent (v/v): acetonitrile/(water+0.05% HCl)=10% -100%), acetonitrile and most of water were evaporated under reduced pressure, and freeze-dried to obtain the final target compound (SIAIS352059) (yellow solid, 2.2 mg, 12%). $^1$H NMR (500 MHz, DMSO-$d_6$) δ 10.99 (s, 1H), 8.40 (s, 1H), 8.25 (s, 1H), 7.63 (dd, J=14.0, 7.8 Hz, 1H), 7.58 (d, J=6.8 Hz, 1H), 7.52-7.38 (m, 4H), 7.25 (s, 1H), 6.86 (s, 1H), 6.69 (s, 1H), 5.15 (dd, J=13.2, 5.1 Hz, 2H), 4.50 (d, J=17.1 Hz, 1H), 4.33 (d, J=17.1 Hz, 2H), 3.92 (d, J=11.8 Hz, 7H), 3.50 (s, 5H), 3.13 (s, 2H), 2.93 (s, 3H), 2.70-2.61 (m, 3H), 2.25 (s, 2H), 2.07-1.99 (m, 2H), 1.94 (s, 2H), 1.80 (d, J=13.5 Hz, 8H), 1.72-1.60 (m, 2H), 1.37 (t, J=8.0 Hz, 2H). HRMS (ESI) $C_{45}H_{56}ClN_9O_5P^+$ [M+H]$^+$, calculated: 868.3825; found: 868.3833.

Embodiment 35: Preparation of 8-(4-(5-((2-(2,6-dioxopiperidin-3-yl)-1-oxoisoindolin-4-yl)amino)pentanoyl)piperazin-1-yl)-9-ethyl-6,6-dimethyl-11-oxo-6,11-dihydro-5H-benzo[b]carbazole-3-carbonitrile (SIAIS352107)

According to the method in Embodiment 1, and under understandable appropriate conditions in the art, the target compound (SIAIS352107) (white solid, 7.2 mg, yield: 19%)

was prepared using Alectinib derivative A and intermediate LM (SIAIS1210133). $^1$H NMR (500 MHz, Methanol-d$_4$) δ 8.40 (d, J=8.2 Hz, 1H), 8.21 (s, 1H), 7.88-7.84 (m, 1H), 7.77 (d, J=7.5 Hz, 1H), 7.68 (t, J=7.7 Hz, 1H), 7.59 (d, J=8.0 Hz, 1H), 7.54 (dd, J=8.2, 1.4 Hz, 1H), 7.41 (s, 1H), 5.22 (dd, J=13.3, 5.2 Hz, 1H), 4.77-4.60 (m, 2H), 3.87-3.73 (m, 4H), 3.50 (td, J=7.1, 2.6 Hz, 2H), 3.08 (dt, J=17.0, 4.9 Hz, 4H), 2.93 (ddd, J=18.5, 13.6, 5.4 Hz, 1H), 2.88-2.76 (m, 3H), 2.58 (t, J=6.5 Hz, 2H), 2.51 (td, J=13.2, 4.6 Hz, 1H), 2.29-2.15 (tn, 1H), 1.93-1.76 (m, 10H), 1.35 (t, J=7.5 Hz, 3H). HRMS (ESI) m/z: Calculated for $C_{43}H_{46}ClN_7O_5P^+$ [M+H]$^+$, 740.3555; found: 740.3557.

Embodiment 36: preparation of N-(1-(4-((5-chloro-4-((2-(dimethylphosphono)phenyl)amino)pyrimidin-2-yl)amino)-3-methoxyphenyl)piperidin-4-yl)-2-((2-(2,6-dioxopiperidin-3-yl)-1-oxoisoindolin-4-yl)thio)-N-methylacetamide (SIAIS353007)

According to the method in Embodiment 1, under understandable appropriate conditions in the art, the target compound SIAIS353007 (white solid, 10 mg, yield: 62%) was prepared using SIAIS220029B and intermediate LM (SIAIS171090). $^1$H NMR (500 MHz, DMSO-d$_6$) δ 11.00 (s, 1H), 8.44 (br.s, 1H), 8.22-8.18 (m, 1H), 7.77-7.72 (m, 2H), 7.65-7.58 (n, 3H), 7.57-7.52 (m, 1H), 7.49-7.42 (m, 1H), 7.22 (br.s, 1H), 5.16-7.13 (m, 1H), 4.44 (d, J=15.0 Hz, 2H), 4.29 (d, J=15.0 Hz, 2H), 4.16 (s, 2H), 3.83 (s, 3H), 2.94 (s, 3H), 2.75 (s, 1H), 2.66-2.58 (m, 2H), 2.47-2.42 (m, 2H), 2.05-2.01 (n, 2H), 1.80 (s, 3H), 1.78 (s, 3H), 1.68-1.64 (m, 2H). HRMS: Calculated for $C_{40}H_{44}ClN_8O_6PS$ [M+H]$^+$ 831.2531, found: 831.2571.

The preparation method of the starting material SIAIS220029B was as follows:

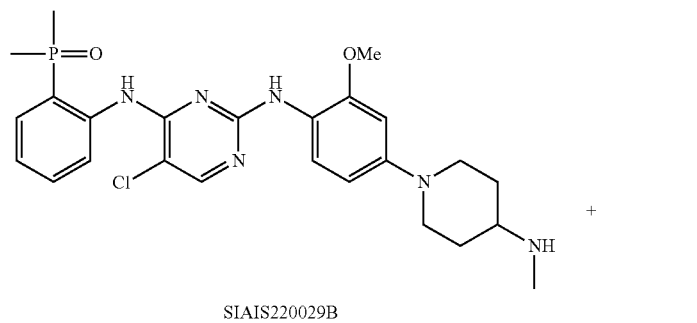

SIAIS220029B +

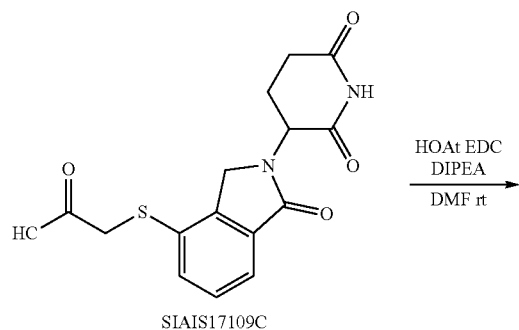

SIAIS17109C

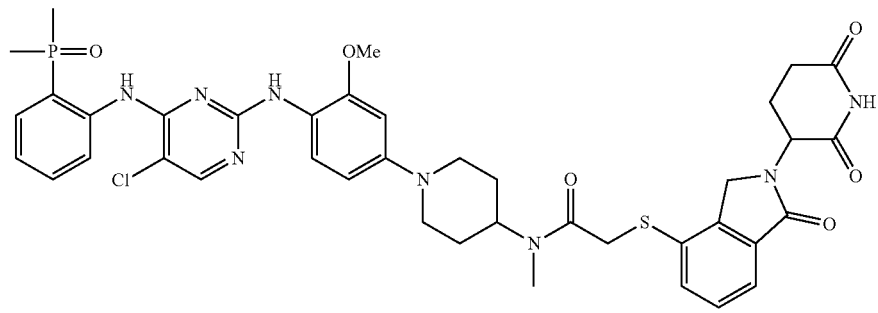

SIAIS353007

Scheme 16

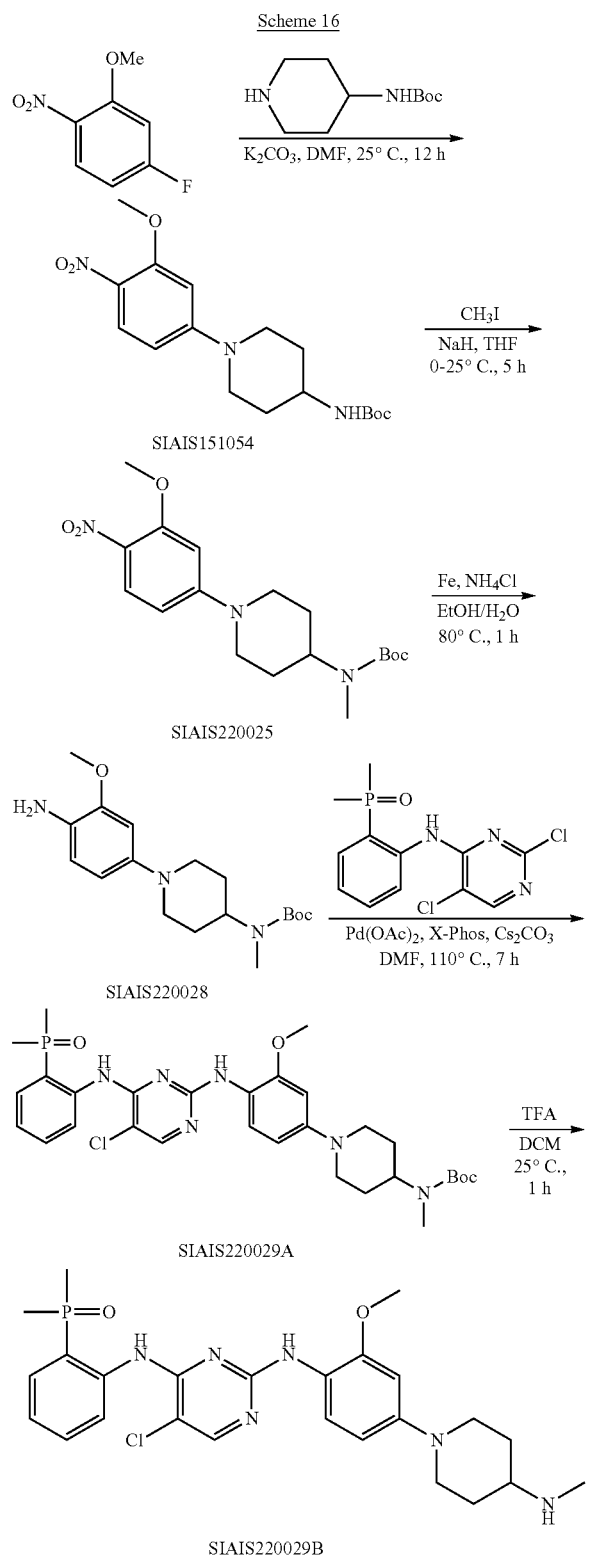

Step 1: tert-butyl (1-(3-methoxy-4-nitrophenyl)piperidin-4-yl)carbamate (SIAIS151054) was prepared according to Scheme 16:

Under open conditions, 5-fluoro-2-nitroanisole (7 g, 40.9 mmol) was dissolved in 60 mL of DMF solution, and K$_2$CO$_3$ (8.4 g, 60.8 mmol), N-tert-butoxycarbonylpiperazine (9.1 g, 48.9 mmol) were added sequentially, the mixture was stirred at room temperature overnight. After the reaction was completed, quenched with water, extracted with ethyl acetate, the organic phase was washed with water, washed with saturated brine, dried over anhydrous sodium sulfate, spin-dried, beaten with mixed solvent of petroleum ether: ethyl acetate=5:1, filtered with sand core to obtain the yellow target solid SIAIS151054 (yellow solid, 1.81 g, 88%). $^1$H NMR (500 MHz, CDCl$_3$) δ 7.99 (t, J=8.9 Hz, 1H), 6.41 (dd, J=9.4, 2.5 Hz, 1H), 6.30 (d, f 2.5 Hz, 1H), 4.49 (s, 1H), 3.94 (s, 3H), 3.86-3.82 (m, 2H), 3.71 (s, 1H), 3.09-3.00 (m, 2H), 2.11-2.03 (m, 2H), 1.89-1.75 (m, 2H), 1.45 (s, 9H).

Step 2: tert-butyl (1-(4-amino-3-methoxyphenyl)piperidin-4-yl)(methyl)carbamate (SIAIS220025) was prepared according to Scheme 16:

The compound (SIAIS151054) (1 g, 2.85 mmol) and anhydrous tetrahydrofuran (15 mL) were added to a 100 mL three-necked flask together. Subsequently, the system was ventilated with nitrogen for three times. Under ice-water bath, NaH (60% in oil, 342 mg, 8.55 mmol) was added in batches. After the addition, the stirring was kept under ice-water bath for 1 hour. Subsequently, methyl iodide (2 g, 14.25 mmol) was slowly added dropwise to the reaction system, and the dropwise addition was completed, and the mixture was stirred at room temperature for 5 hours. After the reaction was completed, water was added slowly to the reaction solution in an ice-water bath to quench, extracted with ethyl acetate, washed with water, washed with saturated brine, dried over anhydrous sodium sulfate, and concentrated under reduced pressure to obtain the crude product (SIAIS220025). The crude product was not purified and directly used in the next step. A yellow oil was obtained, 1000 mg, with a yield of 96%. $^1$H NMR (500 MHz, CDCl$_3$) δ 7.99 (d, J=9.4 Hz, 1H), 6.42 (dd, J=9.4, 2.5 Hz, 1H), 6.31 (d, J=2.4 Hz, 1H), 4.38-4.20 (m, 1H), 3.98 (d, J=13.0 Hz, 2H), 3.94 (s, 3H), 3.01 (t, J=12.0 Hz, 2H), 2.72 (s, 31-1), 1.80-1.72 (m, 4H), 1.47 (s, 9H). HRMS (ESI) m/z: Calculated for C$_{18}$H$_{28}$N$_3$O$_5^+$ [M+H]$^+$, 366.2023; found: 366.2019.

Step 3: tert-butyl (1-(3-methoxy-4-nitrophenyl)piperidin-4-yl)(methyl)carbamate (SIAIS220028) was prepared according to Scheme 16:

The substrate (SIAIS220025) (900 mg, 2.46 mmol), ethanol (15 mL) and water (5 mL) were added together into a 100 mL egg-shaped flask, then ammonium chloride (520 mg, 9.84 mmol) and iron powder (700 mg, 12.30 mmol) were added. After the addition, the temperature was slowly raised to reflux, and the mixture was stirred for 2 h; after the reaction was completed, the reaction solution was concentrated under reduced pressure, and then water was added to the system, the mixture was extracted with dichloromethane, the combined organic phase was washed with water, washed with saturated brine, and dried over anhydrous sodium sulfate, concentrated under reduced pressure to obtain the crude product (SIAIS220028), the crude product was used directly in the next step without further purification as an off-white solid, 700 mg, yield: 85%. $^1$H NMR (500 MHz, CDCl$_3$) δ 6.63 (d, J=8.3 Hz, 1H), 6.52 (d, J=2.4 Hz, 1H), 6.42 (dd, J=8.3, 2.4 Hz, 1H), 3.83 (s, 3H), 3.56-3.50 (m, 3H), 2.77 (s, 3H), 2.70 (t, J=11.5 Hz, 2H), 1.91-1.83 (m, 2H), 1.75-1.70 (m, 2H), 1.47 (s, 9H). HRMS (ESI) m/z: Calculated for C$_{18}$H$_{30}$N$_3$O$_3^+$ [M+H]$^+$, 336.2282; found: 336.2286.

Step 4: tert-butyl (1-(4-((5-chloro-44(2-(dimethylphosphono)phenyl)amino)pyrimidin-2-yl)amino)-3-methoxyphenyl)piperidin-4-yl)(methyl)carbamate (SIAIS220029A) was prepared according to Scheme 16:

At room temperature, in a 100 mL egg-shaped flask, AP26113 intermediate (405 mg, 1.28 mmol), SIAIS220028 (410 mg, 1.22 mmol), Pd(OAc)$_2$ (29 mg, 0.13 mmol), X-Phos (64 mg, 0.13 mmol), cesium carbonate (1.260 g, 3.84 mmol) and anhydrous DMF (10 mL) were added sequentially, then the system was ventilated with argon for three times. The reaction solution was slowly heated to 110° C. and stirred for 7 hours. After the reaction was completed, filtered with suction, water was added, and the mixture was extracted with ethyl acetate, then the organic phase was washed with water, dried over anhydrous sodium sulfate, the solvent was evaporated under reduced pressure, mixed with silica gel, and the crude product was purified by column chromatography (eluent: 3% MeOH/DCM) to obtain the target compound SIAIS220029 as a brown solid, 300 mg, yield: 38%. $^1$H NMR (500 MHz, CDCl$_3$) δ 10.80 (s, 1H), 8.62 (dd, J=8.4, 4.4 Hz, 1H), 8.09 (d, J=9.5 Hz, 2H), 7.49 (t, J=7.9 Hz, 1H), 7.31-7.27 (m, 1H), 7.12 (dd, J=10.4, 4.3 Hz, 1H), 6.56 (d, J=2.1 Hz, 1H), 6.50 (dd, J=8.8, 2.3 Hz, 1H), 4.30-4.10 (m, 1H), 3.88 (d, J=8.4 Hz, 3H), 3.65 (d, J=12.2 Hz, 2H), 2.78 (s, 3H), 2.84-2.72 (m, 2H), 1.93-1.86 (m, 2H), 1.85 (s, 3H), 1.82 (s, 3H), 1.79-1.73 (m, 2H), 1.48 (s, 9H). HRMS (ESI) m/z: Calculated for $C_{30}H_{41}ClN_6O_4P^+$ [M+H]$^+$, 615.2610; found: 615.2606.

Step 5: compound SIAIS220029B was prepared according to Scheme 16:

At room temperature, in a 50 mL egg-shaped flask, SIAIS220029A (250 mg, 0.40 mmol), DCM (6 mL) and trifluoroacetic acid (2 mL) were added sequentially, and then the mixture was reacted at room temperature for 1 h. The reaction was detected by LC-MS until the reaction was completed, the reaction solvent and trifluoroacetic acid were evaporated under reduced pressure, and then 10 mL of 10% MeOH/DCM solution was added, and then the mixture was adjusted to pH=8-9 with saturated NaHCO$_3$ solution, and extracted with dichloromethane. The organic phase was dried over anhydrous sodium sulfate and spin-dried to obtain the crude compound SIAIS220029B. Without further purification, the crude compound was directly used to prepare the target compound SIAIS353007.

Embodiment 37: preparation of N-(1-(4-((5-chloro-4-((2-(dimethylphosphono)phenyl)amino)pyrimidin-2-yl)amino)-3-methoxyphenyl)piperidin-4-yl)-6-((2-(2,6-dioxopiperidin-3-yl)-1-oxoisoindolin-4-yl)thio)-N-methylhexanamide (SIAIS353009)

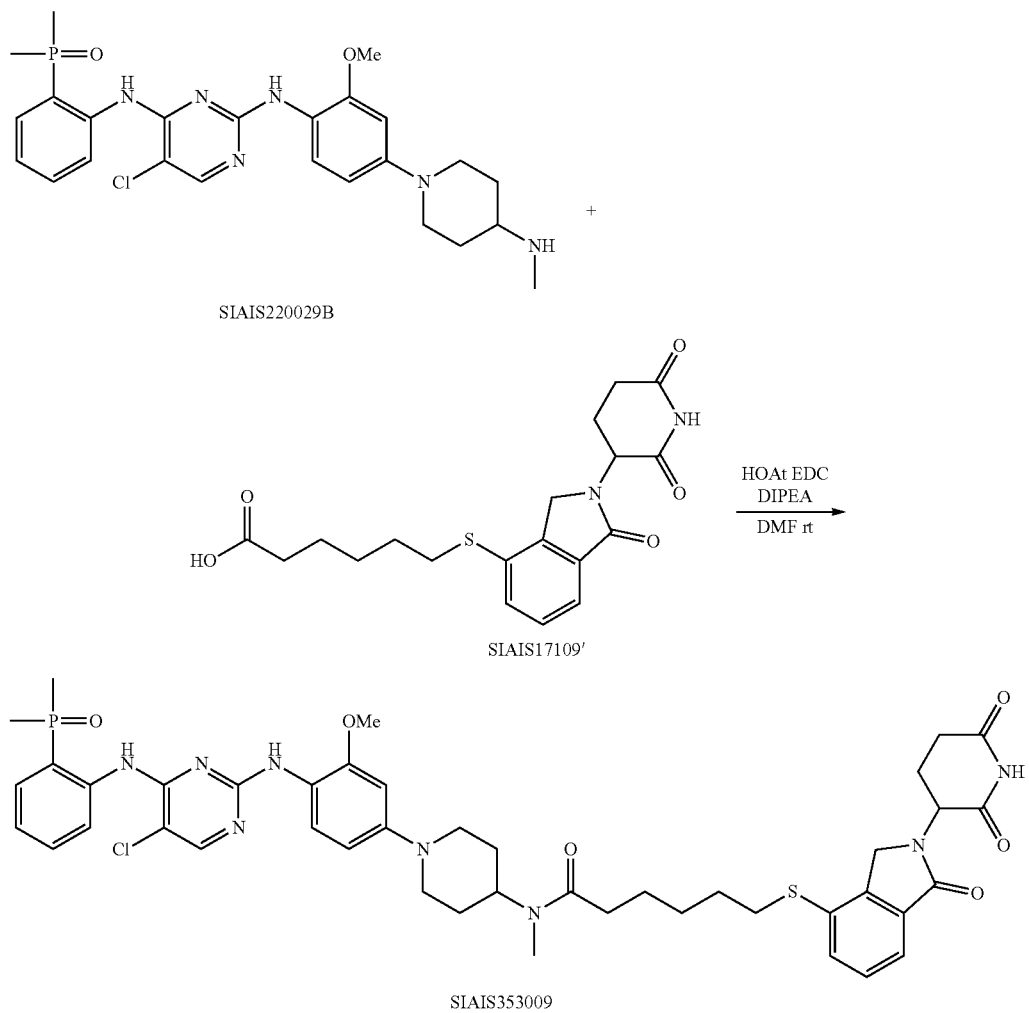

According to the method in Embodiment 1, under understandable appropriate conditions in the art, the target compound SIAIS353009 (white solid, 7 mg, yield: 41%) was prepared using SIAIS220029B and intermediate LM (SIAIS171091). $^1$H NMR (500 MHz, DMSO-$d_6$) δ 10.99 (s, 1H), 8.43 br.s, 1H), 8.21 (s, 1H), 7.65-7.62 (m, 2H), 7.61-7.52 (m, 3H), 7.49-7.42 (m, 2H), 7.24-7.19 (m, 2H), 5.18-5.08 (m, 1H), 4.36 (d, J=15.0 Hz, 1H), 4.22 (d, J=15.0 Hz, 1H), 3.83 (s, 3H), 3.72-3.68 (m, 2H), 3.11-3.07 (m, 3H), 2.94-2.91 (m, 21-1), 2.84 (s, 3H), 2.71 (s, 1H), 2.61-2.55 (m, 2H), 2.44-2.35 (m, 2H), 2.31-2.29 (m, 2H), 2.06-1.96 (m, 2H), 1.80 (s, 3H), 1.78 (s, 3H), 1.66-1.60 (m, 3H), 1.56-1.52 (m, 2H), 1.46-1.42 (m, 2H). HRMS: Calculated for $C_{44}H_{52}ClN_8O_6PS$ [M+H]$^+$ 887.3157, found: 887.3172.

Embodiment 38: preparation of 3-(4-((6-((1-(4-((5-chloro-4-((2-(dimethylphosphono)phenyl)amino) pyrimidin-2-yl)amino)-3-methoxyphenyl)piperidin-4-yl)(methyl)amino)hexyl)thio)-1-oxoisoindolin-2-yl)piperidine-2,6-dione (SIAIS353041)

According to the method in Embodiment 7, and under understandable appropriate conditions in the art, the target compound SIAIS353041 (white solid, 10 mg, yield: 59%) was prepared using SIAIS220029B and intermediate LM (SIAIS1216133). $^1$H NMR (500 MHz, Methanol-$d_4$) δ 8.27-8.15 (m, 2H), 7.76-7.71 (m, 1H), 7.69-7.63 (m, 3H), 7.59-7.53 (m, 2H), 7.49-7.46 (m, 1H), 7.32 (s, 1H), 7.06 (d, J=10.0 Hz, 1H), 5.19-5.15 (m, 1H), 4.45 (q, J=15.0 Hz, 2H), 3.95 (s, 3H), 3.90-3.86 (m, 2H), 3.82-3.74 (m, 1H), 3.65-3.53 (m, 2H), 3.45 (t, J=5.0 Hz, 1H), 3.28-3.24 (m, 1H), 3.18-3.09 (m, 3H), 2.89 (s, 3H), 2.85-2.80 (m, 2H), 2.60-2.51 (m, 1H), 2.37-2.33 (m, 4H), 2.22-2.16 (m, 1H), 2.06-2.02 (m, 1H), 1.89 (s, 3H), 1.86 (s, 3H), 1.79-1.70 (m, 4H), 1.58-1.53 (m, 2H). HRMS: Calculated for $C_{44}H_{54}ClN_8O_5PS$ [M+H]$^+$ 873.3364, found: 873.3354.

Embodiment 39: preparation of 3-(4-((4-((1-(4-((5-chloro-4-((2-(dimethylphosphono)phenyl)amino) pyrimidin-2-yl)amino)-3-methoxyphenyl)piperidin-4-yl) (methyl)amino)butyl)thio)-1-oxoisoindolin-2-yl)piperidine-2,6-dione (SIAIS353043)

According to the method in Embodiment 7, and under understandable appropriate conditions in the art, the target compound SIAIS353043 (white solid, 4.5 mg, yield: 28%) was prepared using SIAIS220029B and intermediate LM (SIAIS213134). NMR (500 MHz, Methanol-$d_4$) δ 8.21 (s, 2H), 7.77-7.73 (m, 2H), 7.69-7.66 (m, 2H), 7.59-7.53 (m, 2H), 7.52-7.46 (m, 1H), 7.35 (s, 1H), 7.09 (d, J=10.0 Hz, 1H), 5.21-5.15 (m, 1H), 4.50 (q, J=15.0 Hz, 2H), 3.97 (s, 3.91-3.82 (m, 3H), 3.76-3.74 (m, 2H), 3.65-3.53 (m, 2H), 3.26-3.19 (m, 3H), 2.92 (s, 3H), 2.85-2.80 (m, 1H), 2.60-2.56 (m, 1H), 2.46-2.335 m, 4H), 2.25-2.16 (m, 1H), 2.06-2.02 (m, 2H), 1.91 (s, 3H), 1.88 (s, 3H)), 1.84-1.78 (m, 2H). HRMS: Calculated for $C_{42}H_{50}ClN_8O_5PS$ [M+H]$^+$ 845.3051, found: 845.3078.

Embodiment 40: preparation of 3-(4-((5-((1-(4-((5-chloro-4-((2-(dimethylphosphono)phenyl)amino) pyrimidin-2-yl)amino)-3-methoxyphenyl)piperidin-4-yl)(methyl)amino)pentyl)thio)-1-oxoisoindolin-2-yl)piperidine-2,6-dione (SIAIS353044)

According to the method in Embodiment 7, under understandable appropriate conditions in the art, the target compound SIAIS353044 (white solid, 5.4 mg, yield: 32%) was prepared using SIAIS220029B and intermediate LM (SIAIS1216049). NMR (500 MHz, Methanol-$d_4$) δ 8.28-8.19 (m, 2H), 7.78-7.70 (m, 2H), 7.68-7.63 (m, 2H), 7.62-7.54 (m, 2H), 7.51-7.48 (m, 1H), 7.32 (br.s, 1H), 7.07 (d, J=10.0 Hz, 1H), 5.21-5.17 (m, 1H), 4.48 (q, J=15.0 Hz, 2H), 3.97 (s, 3H), 3.91-3.88 (n, 2H), 3.82-3.73 (m, 4H), 3.62-3.55 (m, 2H), 3.20-3.07 (m, 3H), 2.91 (s, 3H), 2.85-2.79 (m, 1H), 2.59-2.55 (n, 1H), 2.42-2.33 (m, 4H), 2.24-2.20 (m, 1H), 1.91 (s, 3H), 1.88 (s, 3H), 1.81-1.75 (m, 2H), 1.62-1.58 (m, 2H). HRMS: Calculated for $C_{43}H_{52}ClN_8O_5PS$ [M+H]$^+$ 859.3208, found: 859.3254.

Embodiment 41: preparation of 3-(4-(5-((1-(4-((5-chloro-4-((2-(dimethylphosphono)phenyl)amino) pyrimidin-2-yl)amino)-3-methoxyphenyl)piperidin-4-yl)(methyl)amino)pent-1-yn-1-yl)-1-oxoisoindolin-2-yl)piperidine-2,6-dione (SIAIS353050)

Scheme 17

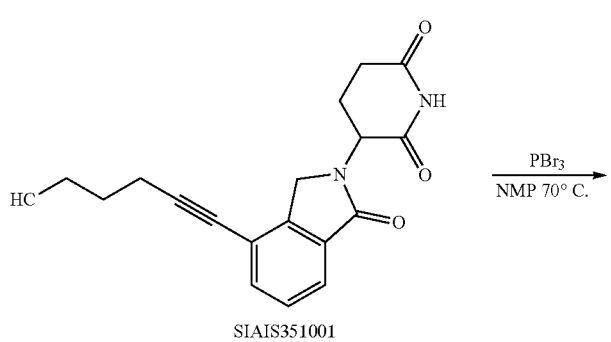

SIAIS351001

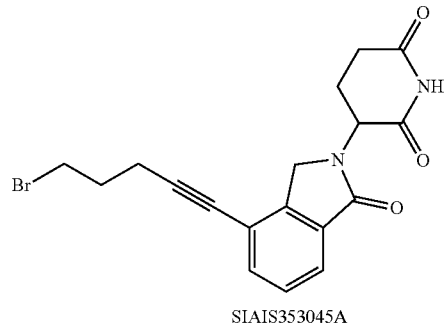

SIAIS353045A

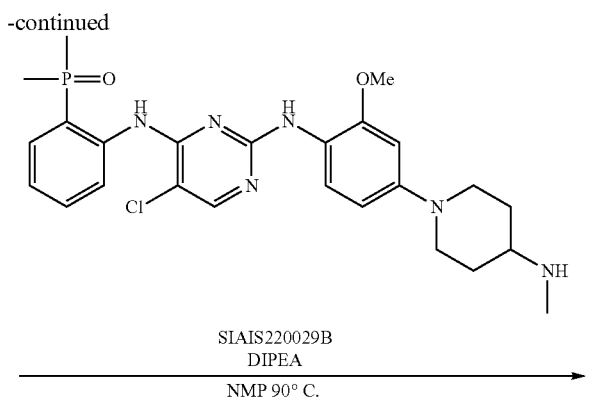

SIAIS220029B
DIPEA
NMP 90° C.

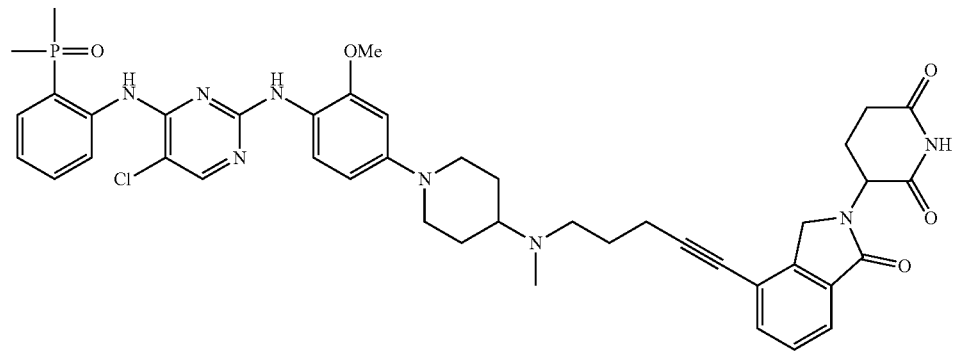

SIAIS353050

Step 1: compound SIAIS353045A was prepared according to Scheme 17.

Compound SIAIS351001 (50 mg, 0.15 mmol) was dissolved in NMP (2 mL), and phosphorus tribromide (42 mg, 0.15 mmol) was added at room temperature. The mixture was heated to 70° C. and stirred at this temperature for 24 hours. The reaction solution was cooled to room temperature, and was prepared and separated by high performance liquid chromatography (hydrochloric acid system) to obtain a white solid SIAIS353045A (20 mg, yield: 33%). MS m/z: 389.2, 391.2 [M+H].

Step 2: compound SIAIS220029B (15 mg, 29.13 μmol), SIAIS353045A (11 mg, 29.13 μmol) were dissolved in NMP (2 mL); diisopropylethylamine (8 mg, 58.25 μmol) was added at room temperature. The mixture was heated to 90° C. and stirred at this temperature for 18 hours. The reaction solution was cooled to room temperature and prepared and separated by high performance liquid chromatography (hydrochloric acid system) to obtain a white solid SIAIS353050 (4.7 mg, yield: 20%). $^1$H NMR (500 MHz, Methanol-$d_4$) δ 8.21-8.16 (m, 2H), 7.78-7.72 (m, 2H), 7.70-7.65 (m, 2H), 7.64-7.58 (m, 1H), 7.54-7.48 (m, 2H), 7.39 (br.s, 1H), 7.12 (d, J=10.0 Hz, 1H), 5.24-5.18 (m, 1H), 4.58 (q, J=15.0 Hz, 2H), 3.95 (s, 3H), 3.88-3.86 (m, 3H), 3.73-3.68 (m, 2H), 3.58-3.53 (m, 1H), 2.98 (s, 3H), 2.91-2.88 (m, 1H), 2.79-2.73 (m, 3H), 2.61-2.57 (m, 1H), 2.45-2.41 (m, 4H), 2.21-2.18 (m, 4H), 1.88 (s, 3H), 1.85 (s, 3H). HRMS: Calculated for $C_{43}H_{48}ClN_8O_5P$ [M+H]$^+$ 823.3174, found: 823.3156.

Embodiment 42: 4-(1-(4-(4-((5-chloro-4-((2-(dimethylphosphono)phenyl)amino)pyrimidin-2-yl)amino)-3-methoxyphenyl)piperidin-4-yl)-N-(4-((2-(2,6-dioxopiperidin-3-yl)-1-oxoisoindolin-4-yl)thio)butyl)piperazine-1-carboxamide (SIAIS353062)

Scheme 18

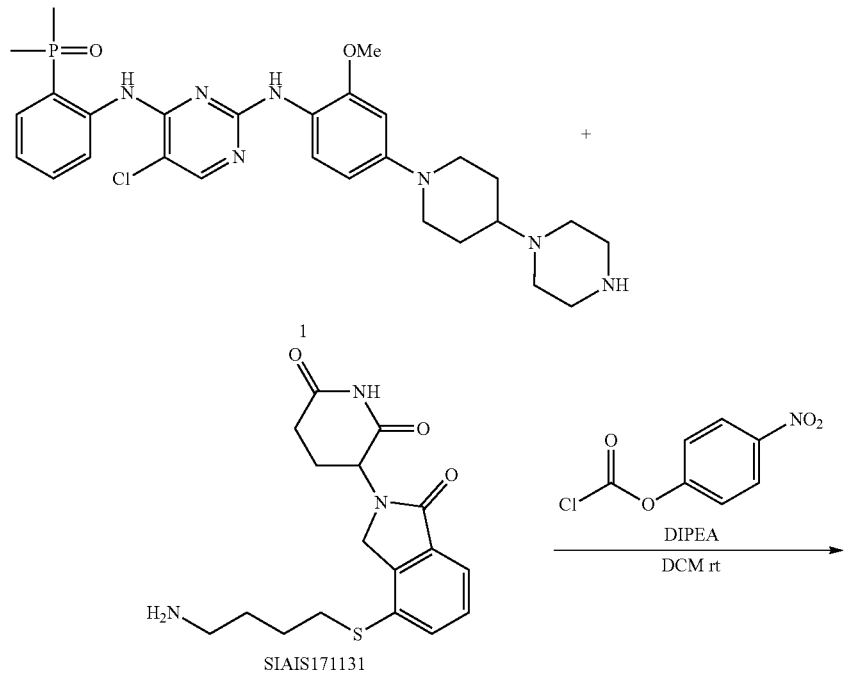

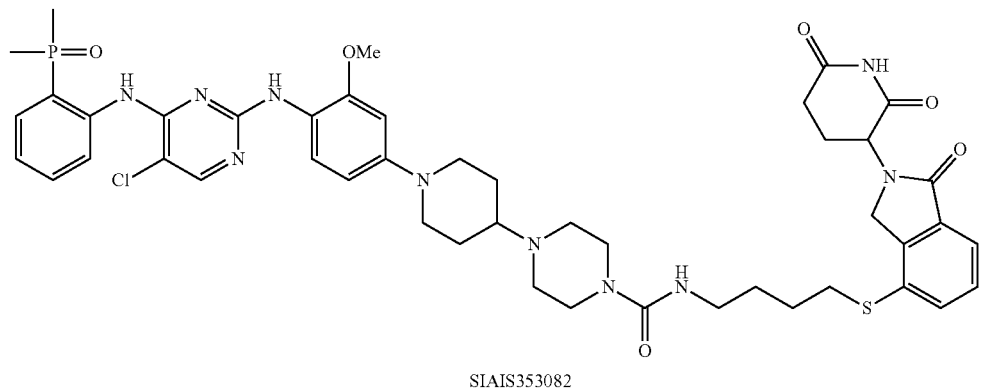

Compound SIAIS171131 (7 mg, 17.54 μmol), diisopropylethylamine (7 mg, 52.62 μmop were dissolved in anhydrous dichloromethane (2 mL), p-nitrophenyl chloroformate (7 mg, 17.54 μmop was added to the solution at room temperature. After the mixture was stirred for 2 hours, a solution of Brigatinib derivative C (10 mg, 17.54 μmol) in dichloromethane (2 mL) was added to the solution. The reaction solution was stirred for 16 hours and quenched by water (5 mL), extracted with dichloromethane (10 mL×3), the combined organic phase was dried over anhydrous sodium sulfate, filtered, and the filtrate was concentrated under reduced pressure. The residue was prepared and separated by high performance liquid chromatography (hydrochloric acid system) to obtain a white solid SIAIS353062 (8 mg, yield: 50%). $^1$H NMR (500 MHz, Methanol-$d_4$) δ 8.21 (br.s, 1H), 8.03 (s, 1H), 7.67-7.58 (m, 1H), 7.56-7.52 (m, 2H), 7.50-7.47 (m, 1H), 7.46-7.44 (m, 1H), 7.36 (m, 2H), 6.94 (br.s, 1H), 6.74 (d, J=10.0 Hz, 1H), 5.09-5.03 (m, 1H), 4.36 (q, J=15.0 Hz, 2H), 4.07 (br.s, 2H), 3.87-3.82 (m, 2H), 3.81 (s, 3H), 3.54-3.45 (m, 3H), 3.37-3.34 (m, 3H), 3.15-3.08 (m, 4H), 3.05-2.88 (m, 4H), 2.73 (s, 3H), 2.49-2.44 (m, 1H), 2.31-2.25 (m, 5H), 2.14-2.06 (m, 1H), 2.04-1.99 (m, 2H), 1.96-1.92 (m, 3H), 1.80 (s, 3H), 1.77 (s, 3H). HRMS: Calculated for $C_{46}H_{56}ClN_{10}O_6PS$ [M+H]$^+$ 943.3531, found: 943.3516.

The preparation method of the starting material compound SIAIS171131 was as follows:

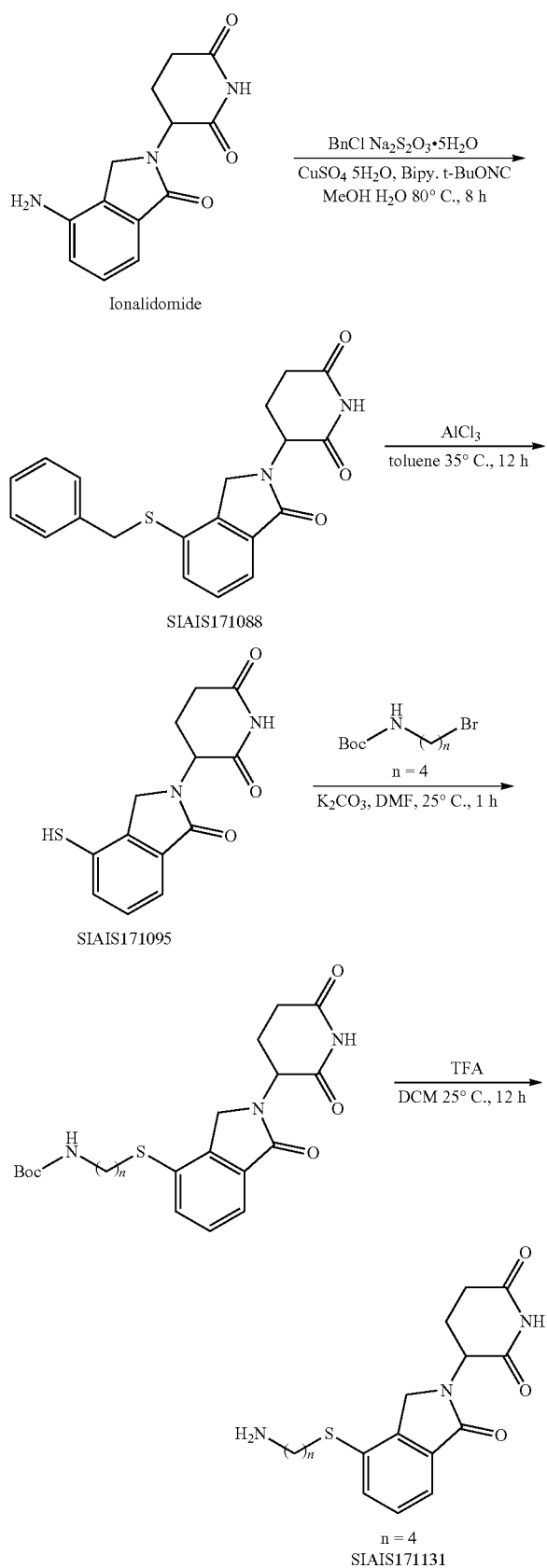

Step 1: preparation of 3(4-(benzylthio)-1-ozoisoindolin-2-yl)piperidine-2,6-dione (SIAIS171088):

sodium thiosulfate pentahydrate (53.7 g, 216.3 mmol), benzyl chloride (27.4 g, 216.3 mmol), copper sulfate pentahydrate (77.4 mg, 0.31 mmol) and bipyridine (0.72 g, 4.6 mmol) were added together in a 500 mL egg-shaped flask containing methanol (120 mL) and water (120 mL), the temperature was then slowly raised to 80° C. and the mixture was stirred for 2 hours. Then the reaction solution was cooled to room temperature and 3-(4-amino-1-oxoisoindolin-2-yl)piperidine-2,6-dione (namely Lenalidomide) (8.0 g, 30.9 mmol) was added, and finally tert-butyl nitrite (4.78 g, 46.4 mmol) was slowly added dropwise. After the dropwise addition was completed, the temperature was raised to 80° C. again and the mixture was stirred for 8 hours. After the reaction was completed, the reaction solution was cooled to room temperature, water (200 mL) was added, the mixture was extracted with ethyl acetate (2×200 mL), the organic phases were combined, washed with water (2×50 mL), washed with saturated brine (50 mL), and dried over anhydrous sodium sulfate, the solvent was evaporated under reduced pressure, the crude product was purified by column chromatography (eluent (v/v): petroleum ether/ethyl acetate=1:2) to obtain the target compound (SIAIS171088) (white solid, 6.8 g, yield: 60%). $^1$H NMR (500 MHz, CDCl$_3$) δ 8.07 (s, 1H), 7.75 (t, J=7.3 Hz, 1H), 7.55 (dd, J=7.4, 6.8 Hz, 1H), 7.49-7.41 (m, 1H), 7.27-7.17 (m, 5H), 5.20-5.17 (m, 1H), 4.22 (d, J=16.5 Hz, 1H), 4.15-4.04 (m, 2H), 3.92 (d, J=16.5 Hz, 1H), 2.95-2.74 (m, 2H), 2.32-2.22 (m, 1H), 2.17-2.11 (m, 1H). HRMS (ESI) m/z: Calculated for C$_{20}$H$_{19}$N$_2$O$_3$S$^+$ [M+H]$^+$, 367.1111; found: 367.1402.

Step 2: preparation of 3-(4-mercapto-1-oxoisoindolin-2-yl)piperidine-2,6-dione (SIAIS171095):

anhydrous aluminum trichloride (2.61 g, 19.6 mmol) and anhydrous toluene (70 mL) were added to a 250 mL egg-shaped flask, and the compound (SIAIS171088) (1.8 g, 4.9 mmol) was slowly added with stirring, and the addition was completed, the mixture was stirred overnight at 35° C. After the reaction was completed, 20% citric acid aqueous solution was slowly added under stirring, a large amount of solid was precipitated, and then the mixture was filtered by suction, the filter cake was washed with water and ethyl acetate, and the filter cake was dried to obtain the target compound (SIAIS171095) (white solid, 1.15 g, yield: 85%). NMR (500 MHz, DMSO) δ 11.01 (s, 1H), 7.82-7.39 (m, 3H), 5.73 (s, 1H), 5.21-5.04 (m, 1H), 4.40-4.20 (m, 2H), 2.99-2.85 (m, 1H), 2.67-2.56 (m, 1H), 2.47-2.30 (m, 1H), 2.05-1.95 (m, 1H). HRMS (ESI) m/z: Calculated for C$_{13}$H$_{13}$N$_2$O$_3$S$^+$ [M+H]$^+$, 277.0641; found: 276.8348.

Steps 3 and 4:

compound SIAIS171095 (0.36 mmol, 1 equiv) was added to a 10 mL reaction flask, then anhydrous N,N-dimethylformamide (2 mL) and anhydrous potassium carbonate (0.72 mmol, 2 equiv) were added, and tert-butyl (4-bromobutyl) carbamate (0.43 mmol, 1.2 equiv) was added slowly with stirring at room temperature, after the dropwise addition, the mixture was stirred at room temperature for 1 h. After the reaction of the raw materials was completed, the crude product was separated by a reversed-phase C18 column, eluent (v/v): acetonitrile/(water+0.05% TFA)=10% -100%, the solvent was evaporated under reduced pressure, and the Boc-protected alkylation intermediate product was obtained by freeze-drying.

The obtained Boc-protected alkylation intermediate product was added to a 10 mL reaction flask, then anhydrous dichloromethane (2 mL) and trifluoroacetic acid (2 mL) were added, and the mixture was stirred at room temperature for 12 h. The reaction solvent was evaporated under reduced pressure, the crude product was separated by reversed-phase $C_{18}$ column, the eluent (v/v): acetonitrile/(water+0.05% TFA)=10% -100%, the solvent was evaporated under reduced pressure, and freeze-dried to obtain compound SIAIS171131 (light yellow solid, 76 mg, the total yield of two steps was 60%). $^1$H NMR (500 MHz, DMSO) δ 10.99 (s, 1H), 7.81-7.47 (m, 6H), 5.13 (dd, J=13.3, 5.1 Hz, 1H), 4.25 (dd, J=31.3, 15.7 Hz, 2H), 3.20-3.03 (m, 2H), 2.96-2.85 (m, 1H), 2.85-2.80 (m, 2H), 2.63-2.60 (m, 1H), 2.46-2.30 (m, 1H), 2.06-1.94 (m, 1H), 1.71-1.56 (m, 4H). HRMS (ESI) m/z: Calculated for $C_{17}H_{22}N_3O_3S^+$ [M+H]$^+$, 348.1376; found: 348.1381.

Biological Activity Detection Experiment

Material:

Halt protease and phosphatase inhibitor (Thermo Fisher)

Cell TITER BLUE Detection Kit (Promega)

Cell TITER GLO Detection Kit (Promega)

CCK8 (WST) reagent (Dojindo Chemistry Research Institute, Japan)

RPMI1640 (GIBICO company)

Fetal Bovine Serum (GIBICO Company)

Penicillin-Streptomycin (GIBICO company)

SuperSignal West Pico Chemiluminescent Substrate (Thermo Fisher)

SuperSignal West Femto Maximum Sensitivity Substrate (Thermo Fisher)

Cycloheximide (Sigma)

Antibody:

Most of the antibodies used in the experiment were purchased from Cell Signaling Technology, including p-ALK (#6962S), ALK(#36335), AKT(#40605), pAKT (473)(#4691S), pERK(222/224) (#4370), ERK(9107S). Antibodies of Tubulin and GAPDH were purchased from Abeam Company.

Cell

The ALK gene rearrangement positive cell line used was SR cells (NPM-ALK, human anaplastic large cell lymphoma cells). MDA-MB231 was a triple-negative breast cancer cell. Both SR cells and MDA-MB231 cells were purchased from ATCC. The 293T cells overexpressing EML4-ALK G1202R were the cells constructed and verified for correct expression by this laboratory.

Construction of 293T Cells Overexpressing EML4-ALK G1202R

The method of cell construction refers to the "Refined Molecular Biology Experiment Guide" (Fourth Edition) (Author: (US) F. M. Osber and other editors, Science Press, publication date 2005-01).

Figure 3:
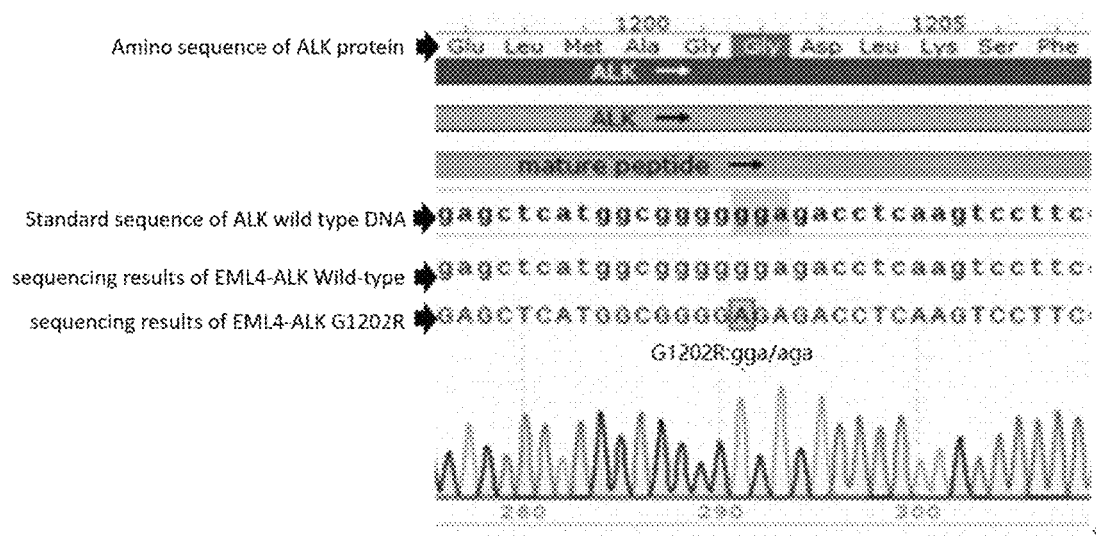
FIG. 3 shows the RT-PCR sequencing results of the constructed 293T cell line with the G1202R mutation EML4-ALK. The results proved that 293T cells express EML4-ALK cDNA and carry G1202R transition (GGA=>AGA).

The main steps were as follows: TrizoL was used to extract RNA from H3122 cells, and the RNA was reverse transcribed into cDNA with reverse transcriptase. EML4-ALK (GenBank number: AB663645.1) full-length cDNA was cloned on the pLVX lentiviral expression plasmid (Clonetech) by PCR, and the G1202R point mutation was introduced on the cDNA expressing EML4-ALK using the KOD point mutation kit (TOYOBO). The lentiviral plasmid containing the EML4-ALK G1202R point mutation was virus-coated with pSPAX2, pMD2.G, and 293T cells were infected with the virus. The 293T stable expression cell line was obtained by screening the cells with 2 μg/ML puromycin. Subsequently, RNA was extracted from the cells and reverse transcribed into cDNA. The EML4-ALK was amplified by PCR, and the product was sequenced to verify that it contained the EML4-ALK G1202R mutation, which proved that the EML4-ALK with the G1202R mutation was exogenously expressed in the 293T cell line. The sequencing results showed the correct point mutations. The results are shown in FIG. 3, which shows the RT-PCR sequencing results of the 293T cell line with the EML4-ALK G1202R mutation.

Cell Culture

The tumor cell line used was daily cultured in a 37° C. incubator containing 5% $CO_2$. The medium was RPMI1640 supplemented with 10% FCS and Penicillin-Streptomycin. The cells used were identified as correct cells by STR cells and were negative for mycoplasma through routine inspections.

Western Blot

Tumor cells were seeded in a 24-well plate containing 1 ml of RPMI1640 medium at 1.5-3×10^5 cells/well. The next day, the cells were treated with different concentrations of drugs. After 16 hours, the supernatant was removed and the cells were washed with PBS. The cells were placed on ice and the cells were treated with RIPA protein lysate containing Halt protease and phosphatase inhibitors. The lysate was centrifuged at 10000RPM at 4° C. for 10 minutes, and the supernatant was collected. The same amount of protein was added to the 4×SDS sample solution, denatured at 95° C. for 5 minutes and freezen to −20° C., or protein electrophoresis was directly performed. GenScript, a 4-20% gradient protein precast gel was used as the electrophoresis gel. The electrophoresis tank and related components were purchased from Bio-rad, and the electrophoresis conditions were equal pressure 120 v for 2 hours. PVDF membrane was used for the transfer membrane, and the transfer membrane system was placed on ice with an equal current of 400 mA for one hour. After transferring the membrane, it was sealed with TBST+5% milk powder for half an hour. For the specific steps of immunoblotting, refer to the antibody instructions of Cell Signaling Technology. The $DC_{50}$ (half degradation concentration) of the compounds of the present disclosure are shown in Table 4 and Table 5.

$DC_{50}$ (the drug concentration corresponding to protein degradation to 50%) calculation: according to the gray value of the Western blotting band after the drug is processed, the relationship curve between the drug concentration and the gray value is fitted by Prism GraphPad software to calculate the drug concentration range corresponding half of the gray value.

Determination of Compound of Half Inhibitory Concentration ($IC_{50}$)

The $IC_{50}$ of the compound of the present disclosure was determined using Promega's Cell Titer Blue, Cell Titer GLO or commercially available WST reagents. The specific steps were as follows: the cells were seeded in a 96-well plate containing 100 microliters of RPMI medium containing serum at a number of 2000 cells/well. On the second day, the original drug and the compound of the present disclosure were serially diluted and added to the cells. After 72 hours of treatment with the compound of the present disclosure, the cell activity detection reagent was added to the culture medium for cell activity determination according to the instructions. The negative control was DMSO, and the positive control was the original drug, and the cells were treated in the same manner as the compound of the present disclosure. The growth inhibition of the compounds of the present disclosure on cells was plotted by Prism Graphpad software and the $IC_{50}$ of the compounds of the present disclosure was counted from it. The results are shown in Tables 4-7 below.

Experimental Results

In this study, the compounds of the present disclosure were developed based on different ALK inhibitors. By selecting the compounds of the present disclosure designed and developed based on ALK inhibitors such as Alecitinib, Brigatinib, etc., to study the expression level of the target protein, it was found that the compounds of the present disclosure designed and developed using different inhibitors had different degrees of regulatory effects on ALK protein. The compound of the present disclosure could not only promote the degradation of ALK protein, but also inhibit the proliferation of ALK mutation-positive cells, and could be developed into therapeutic drugs for tumor patients. The specific experimental data are shown below.

I. Research on Compounds of the Present Disclosure Based on Alectinib

We have successfully developed compounds of the present disclosure based on Alectinib. Such compounds can not only promote the degradation of ALK protein, but also inhibit the activity of ALK kinase, and have an inhibitory effect on the proliferation of some ALK mutation-positive cells.

1. 1 Research on Proliferation Inhibition of ALK Mutation-Positive Cells by the Compounds of the Present Disclosure Based on Alectinib We conducted dose-dependent experiments on the designed and synthesized compounds of the present disclosure in SR cells. The cells contained NPM-ALK fusion gene mutation and were highly sensitive to ALK inhibitors. The cells were treated with different concentrations of compounds (starting at 10 µM, 3 times dilution factor, 10 concentrations). After 72 hours, the cells were detected using CCK8 reagent (WST). The experiment was repeated more than 3 times, and the specific results are shown in Table 4.

The compound of the present disclosure developed based on Alectinib that we designed and developed could well inhibit the proliferation of anaplastic large cell lymphoma cells (Table 4). The half inhibitory concentration of Alectinib on SR cells was 17 nM. The compound of the present disclosure we have developed maintained a better inhibitory effect than the original drug Alectinib; the half inhibitory concentration of some compounds of the present disclosure were significantly lower than that of the original drug, for example, the compound (SIAIS262091) inhibited cell proliferation at about 0.34 nM.

TABLE 4

The $IC_{50}$ (half inhibitory concentration) of the compounds of the present disclosure and the $DC_{50}$ (half degradation concentration) of some of the compounds of the present disclosure based on the Alectinib series in lymphoma cell lines

| Cell line | Name of test compound | Reagent | $IC_{50}$ (nM) | $DC_{50}$ (nM) |
|---|---|---|---|---|
| SR | Alectinib | WST | 16.96 ± 11.06 | |
| SR | Alectinib derivative C (SIAIS184192) | WST | 10.1 ± 4.3 | |
| SR | SIAIS262091 | WST | 0.34 ± 0.2 | 0.05-0.5 |
| SR | SIAIS262092 | WST | 1.37 ± 0.87 | |
| SR | SIAIS262093 | WST | 2.65 ± 1.72 | |
| SR | SIAIS262095 | WST | 3.2 ± 1.93 | |
| SR | SIAIS293001 | WST | 2.7 | 0.05-0.5 |
| SR | SIAIS293002 | WST | 2.9 | |
| SR | SIAIS293014 | WST | 3.2 | |
| SR | SIAIS293004 | WST | 9.5 | |
| SR | SIAIS293005 | WST | 1.9 | |
| SR | SIAIS293008 | WST | 5.2 | |
| SR | SIAIS293009 | WST | 15.1 | |
| SR | SIAIS293010 | WST | 2.0 | 0.05-0.5 |

TABLE 4-continued

The $IC_{50}$ (half inhibitory concentration) of the compounds of the present disclosure and the $DC_{50}$ (half degradation concentration) of some of the compounds of the present disclosure based on the Alectinib series in lymphoma cell lines

| Cell line | Name of test compound | Reagent | $IC_{50}$ (nM) | $DC_{50}$ (nM) |
|---|---|---|---|---|
| SR | Alectinib derivative B (SIAIS184193) | WST | 9.1 ± 5.5 | |
| SR | SIAIS293012 | WST | 10.3 ± 5.1 | |
| SR | SIAIS350081 | WST | 6.5 ± 4.0 | |
| SR | SIAIS350083 | WST | 1.1 ± 0.7 | |
| SR | SIAIS293060 | WST | 0.1 ± 0.02 | |

1. 2 Research on the Expression Level of Target Protein ALK by the Compounds of the Present Disclosure Based on Alectinib We studied the total ALK protein in the anaplastic large cell lymphoma cell line SR by the compounds of the present disclosure which we had designed and synthesized based on Alectinib. SR cells had NPM-ALK fusion gene mutation, and the results of protein degradation were shown in FIG. 1. The cells with different concentrations (0, 10, 50, 100, 500 nM) of Alectinib were first treated in SR cells for 16 hours. Western blotting was used on cell lysate to detect the effect of Alectinib on the content of ALK protein (FIG. 1). The results showed that ALK protein was not degraded by Alectinib itself. The degradation study on the ALK target protein by the developed compounds of the present disclosure based on Alectinib derivatives C was shown in (FIG. 1). In SR cells, the original drug Alectinib had no degradation effect on ALK protein at concentrations up to 500 nM. However, almost all the compounds of the present disclosure developed by us had a significant degradation effect on the ALK target protein at a concentration of 5 nM. The selected compounds of the present disclosure had a significant degradation effect on the ALK protein at 5 nM. The selected compound of the present disclosure, such as SIAIS262091 had a degradation effect on ALK protein from less than 0.005 nM. Some selected compounds of the present disclosure, such as SIAIS293010, showed a degradation effect on ALK protein starting from 0.5 nM. It further showed that the compounds of the present disclosure designed and developed by us had a good degradation effect on the ALK target protein.

II. Research on the Compounds of the Present Disclosure Based on Brigatinib

We have successfully developed compounds of the present disclosure based on Brigatinib. Such compounds can not only promote the degradation of ALK protein, but also have an inhibitory effect on the proliferation of ALK mutation-positive cells.

1. 1 Research on Proliferation Inhibition of ALK Mutation-Positive Cells by the Compounds of the Present Disclosure Based on Brigatinib We conducted dose-dependent experiments on the designed and synthesized compounds of the present disclosure in SR cells. The cells contained NPM-ALK fusion gene mutation and were highly sensitive to ALK inhibitors. The cells were treated with different concentrations of compounds (starting at 10 µM, 3 times dilution factor, 10 concentrations). After 72 hours, the cells were detected using CCK8 reagent (WST). The experiment was repeated more than 3 times, and the specific results are shown in Table 5.

The compound of the present disclosure developed based on Brigatinib that we designed and developed could well inhibit the proliferation of anaplastic large cell lymphoma cells (Table 5). The half inhibitory concentration of Brigatinib on SR cells was 6.9 nM. The compounds of the present disclosure we have developed maintained an inhibitory effect comparable to that of the original drug Brigatinib; the half inhibitory concentration of some compounds of the present disclosure were significantly lower than that of the original drug, for example, the compound (SIAIS262039) inhibited cell proliferation at about 1 nM.

TABLE 5

The $IC_{50}$ (half inhibitory concentration) of the compounds of the present disclosure and the $DC_{50}$ (half degradation concentration) of some of the compounds of the present disclosure based on the Brigatinib series in lymphoma cell lines

| Cell line | Name of test compound | Reagent | IC50 (nM) | $DC_{50}$ (nM) |
|---|---|---|---|---|
| SR | Brigatinib | WST | 6.9 | |
| SR | Brigatinib derivative C (SIAIS164005) | WST | 11.1 | |
| SR | SIAIS262039 | WST | 1.0 | 0.0005-0.05 |
| SR | SIAIS262040 | WST | 1.1 | 0.05-0.5 |
| SR | SIAIS293015 | WST | 1.2 | |
| SR | SIAIS293017 | WST | 1.5 | 0.5-5 |
| SR | SIAIS293018 | WST | 2.0 | 0.05-0.5 |
| SR | SIAIS293016 | WST | 7.2 | |
| SR | SIAIS293189 | WST | 0.1 ± 0.02 | 0.05-0.5 |
| SR | SIAIS293093 | WST | 1.3 | |
| SR | SIAIS352008 | WST | 2.1 ± 1.2 | 0.05-0.5 |
| SR | SIAIS352010 | WST | 19.0 ± 5.8 | |
| SR | SIAIS352011 | WST | 1.2 ± 0.3 | 0.5-5 |
| SR | SIAIS352054 | WST | 22.0 ± 10.9 | |
| SR | SIAIS352055 | WST | 15.0 ± 4.4 | |
| SR | SIAIS352056 | WST | 84.5 ± 17.3 | |
| SR | SIAIS352057 | WST | 102.5 ± 43.9 | |
| SR | SIAIS352059 | WST | 1.1 ± 0.3 | |
| SR | SIAIS353007 | WST | 17.1 ± 10.9 | |
| SR | SIAIS353009 | WST | 10.5 ± 5.6 | |
| SR | SIAIS353041 | WST | 0.5 ± 0.2 | |
| SR | SIAIS353043 | WST | 0.9 ± 0.2 | |
| SR | SIAIS353044 | WST | 1.1 ± 0.2 | |
| SR | SIAIS353050 | WST | 4.8 ± 0.1 | |
| SR | SIAIS353062 | WST | 0.6 ± 0.4 | |
| SR | SIAIS293110 | WST | 0.33 ± 0.11 | |

Figure 2:
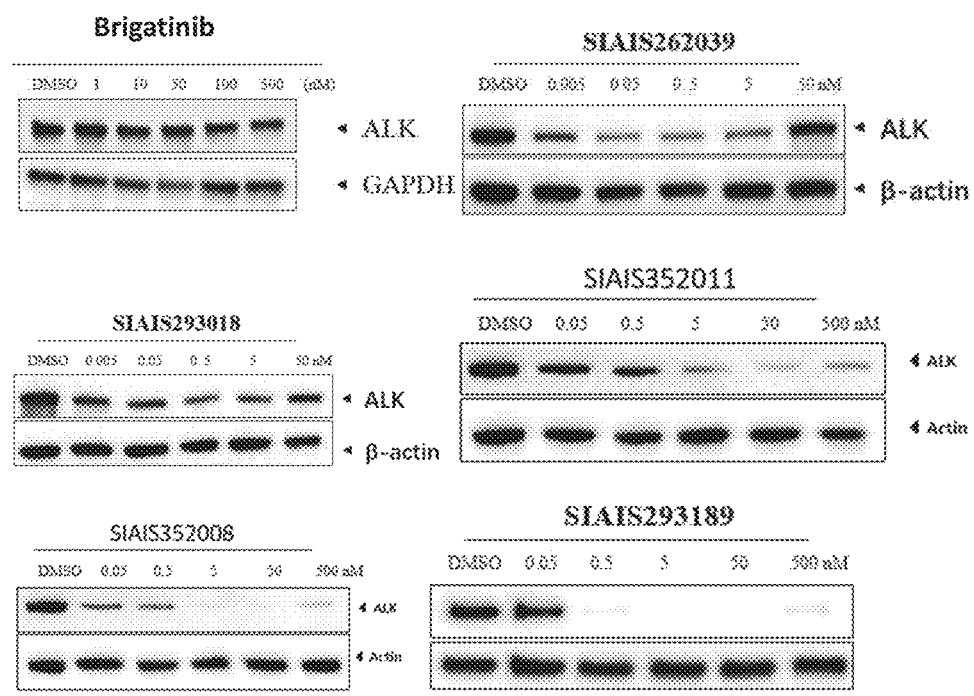
FIG. 2 shows the study of the Brigatinib-derived compounds of the present disclosure (SR cell line) using Western-blot assay. Compared with the commercial parent inhibitor Brigatinib, the compound of the present disclosure can effectively degrade ALK protein.

2. 2 Research on the Expression Level of Target Protein ALK by the Compounds of the Present Disclosure Based on Brigatinib We studied the total ALK protein in the anaplastic large cell lymphoma cell line SR by the compounds of the present disclosure which we had designed and synthesized based on Brigatinib. SR cells had NPM-ALK fusion gene mutation, and the results of protein degradation were shown in FIG. 2. The cells with different concentrations (0, 10, 50, 100, 500 nM) of Brigatinib were first treated in SR cells for 16 hours. Western blotting was used on cell lysate to detect the effect of Brigatinib on the content of ALK protein (FIG. 2). The results showed that ALK protein was not degraded by Brigatinib itself. The degradation study on the ALK target protein by the developed compounds of the present disclosure based on Brigatinib derivatives C was shown in (FIG. 2). In SR cells, the original drug Brigatinib and Brigatinib derivative C(SIAIS164005) had no degradation effect on ALK protein at a concentration of up to 500 nM. However, at a concentration of 50 nM, almost all the compounds of the present disclosure developed by us had a significant degradation effect on the ALK target protein. The selected compounds of the present disclosure had a significant degradation effect on the ALK protein at 5 nM. The selected compound of the present disclosure such as SIAIS262039 had a degradation effect on ALK protein from less than 0.005 nM. Some selected compounds of the present disclosure, such as SIAI5293018, showed a degradation effect on ALK protein starting from 5 nM. It further showed that the compounds of the present disclosure designed and developed by us had a good degradation effect on the ALK target protein.

III. Study on the Proliferation Inhibition of the Compounds of the Present Disclosure Based on Alectinib and Brigatinib in 293T Cells Overexpressing EML4-ALK G1202R We used the compound of the present disclosure in 293T cells overexpressing EML4-ALK G1202R, and the results showed that the proliferation inhibitory activity of ALK protein degrading agents on ALKTKI-resistant G1202R cells was significantly better than that of FDA-approved drugs (Table 6).

TABLE 6

$IC_{50}$ (half inhibitory concentration) of the compounds of the present disclosure based on Alectinib and Brigatinib series in 293T cells overexpressing EML4-ALK G1202R

| Cell line | Name of test compound | Reagent | $IC_{50}$ (nM) |
|---|---|---|---|
| EML4ALK-G1202R | Alectinib | WST | 242.45 ± 2.19 |
| EML4ALK G1202R | Brigatinib | WST | 473.25 ± 129 |
| EML4ALK G1202R | SIAIS293189 | WST | 99.51 ± 8.62 |

IV. Study on Cell Proliferation of the Compounds of the Present Disclosure Based on Alectinib and Brigatinib in MDA-MB-231

The disclosed compound we developed had a good proliferation inhibitory effect on the triple-negative breast cancer MDA-MB-231 cell line (Table 7).

TABLE 7

$IC_{50}$ (half inhibitory concentration) of the compounds of the present disclosure based on Alectinib and Brigatinib series in MDA-MB-231 cell line

| Cell line | Name of test compound | Reagent | $IC_{50}$ (nM) |
|---|---|---|---|
| MDA-MB-231 | Alectinib | WST | 2265 ± 800.32 |
| MDA-MB-231 | Brigatinib | WST | 381 ± 41.04 |
| MDA-MB-231 | SIAIS262039 | WST | 22.5 ± 2.26 |
| MDA-MB-231 | SIAIS293093 | WST | 190.67 ± 106.46 |
| MDA-MB-231 | SIAIS352008 | WST | 4.5 ± 0.5 |
| MDA-MB-231 | SIAIS352011 | WST | 4.9 ± 1.04 |
| MDA-MB-231 | SIAIS352059 | WST | 75 ± 57.97 |

The basic principles, main features and advantages of the present disclosure have been shown and described above. Those skilled in the art should understand that the present disclosure is not limited to the foregoing embodiments, and they can make various changes, substitutions and alterations herein without departing from the spirit and scope of the present disclosure. These changes, substitutions and alterations fall within the scope of the present disclosure. The scope of protection claimed in the present disclosure is defined by the appended claims and their equivalents.

The invention claimed is:

1. A compound represented by formula (I):

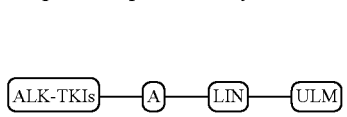

formula (I)

wherein ALK-TKIs are covalently connected to LIN through group A, and wherein ULM is covalently connected to LIN;

wherein group A represents C(O) or is absent;

ALK-TKIs represent the structure of the following formula (Ia), formula (Ib), formula (Ic), formula (Id), formula (Ie) or formula (If):

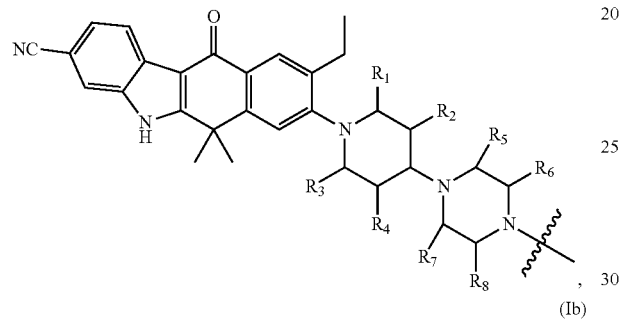

(Ia)

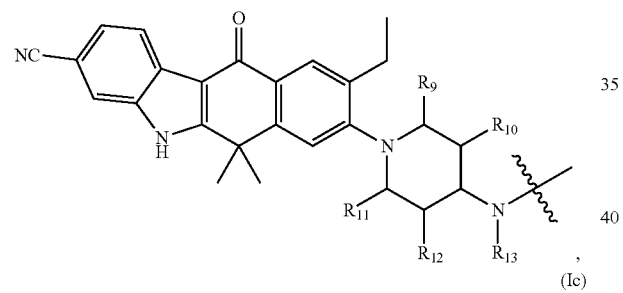

(Ib)

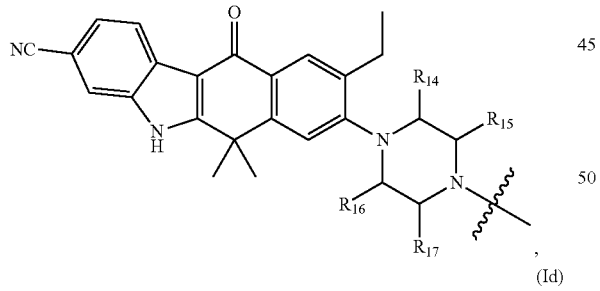

(Ic)

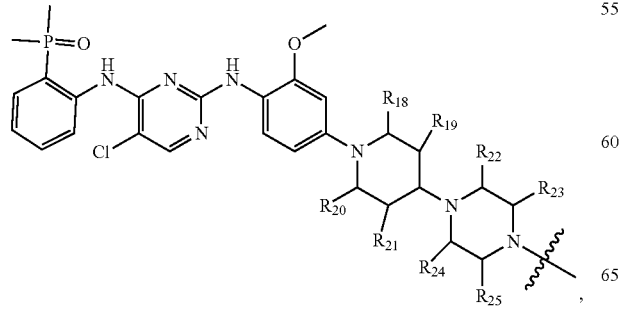

(Id)

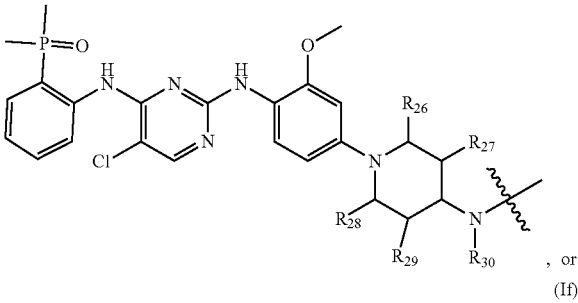

(Ie)

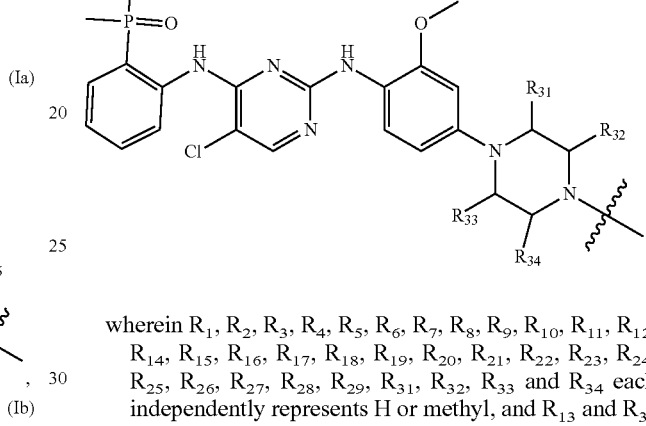

(If)

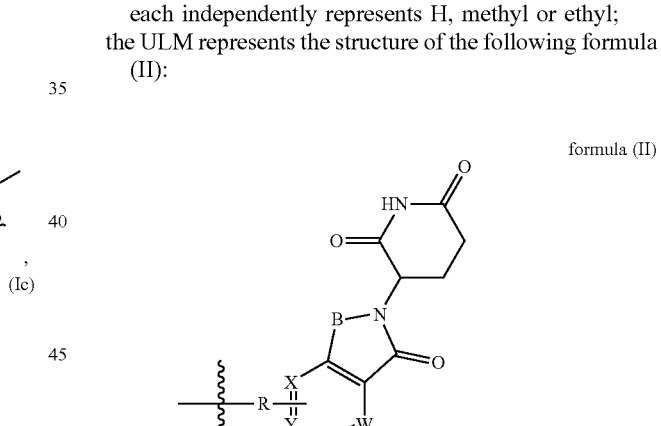

wherein $R_1$, $R_2$, $R_3$, $R_4$, $R_5$, $R_6$, $R_7$, $R_8$, $R_9$, $R_{10}$, $R_{11}$, $R_{12}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{31}$, $R_{32}$, $R_{33}$ and $R_{34}$ each independently represents H or methyl, and $R_{13}$ and $R_{30}$ each independently represents H, methyl or ethyl;

the ULM represents the structure of the following formula (II):

formula (II)

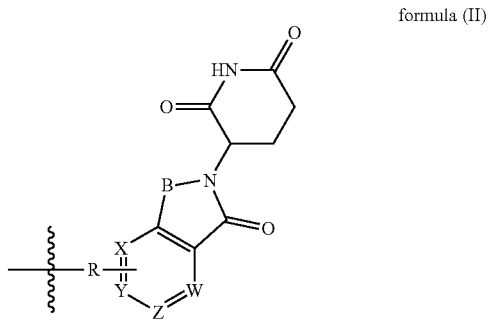

wherein

B represents $CH_2$ or C(O); X, Y, Z, and W are the same or different and each independently represents CH or N; and R represents ethynylene; and LIN is a linking group and represents —U-alkylene-, wherein the alkylene is linear or branched alkylene optionally interrupted one or more times by one or more groups selected from the following groups: C(O)NH, NHC(O), O, NH, alkynylene, alkenylene, cycloalkylene, arylene, heterocyclylene, heteroarylene, or any combination thereof, wherein the linear or branched alkylene is optionally substituted by one or more substituents, and the group U represents C(O), or the group U is absent;

or a salt thereof, an enantiomer thereof, a stereoisomer thereof, a solvate thereof, a polymorph thereof.

2. The compound represented by formula (I) as defined in claim 1, or the salt thereof, the enantiomer thereof, the stereoisomer thereof, the solvate thereof, the polymorph thereof, wherein the compound represented by formula (I) is also the compound represented by formula (Ia-1), formula (Ib-1), formula (Ic-1), formula (Id-1), formula (Ie-1) or formula (If-1):
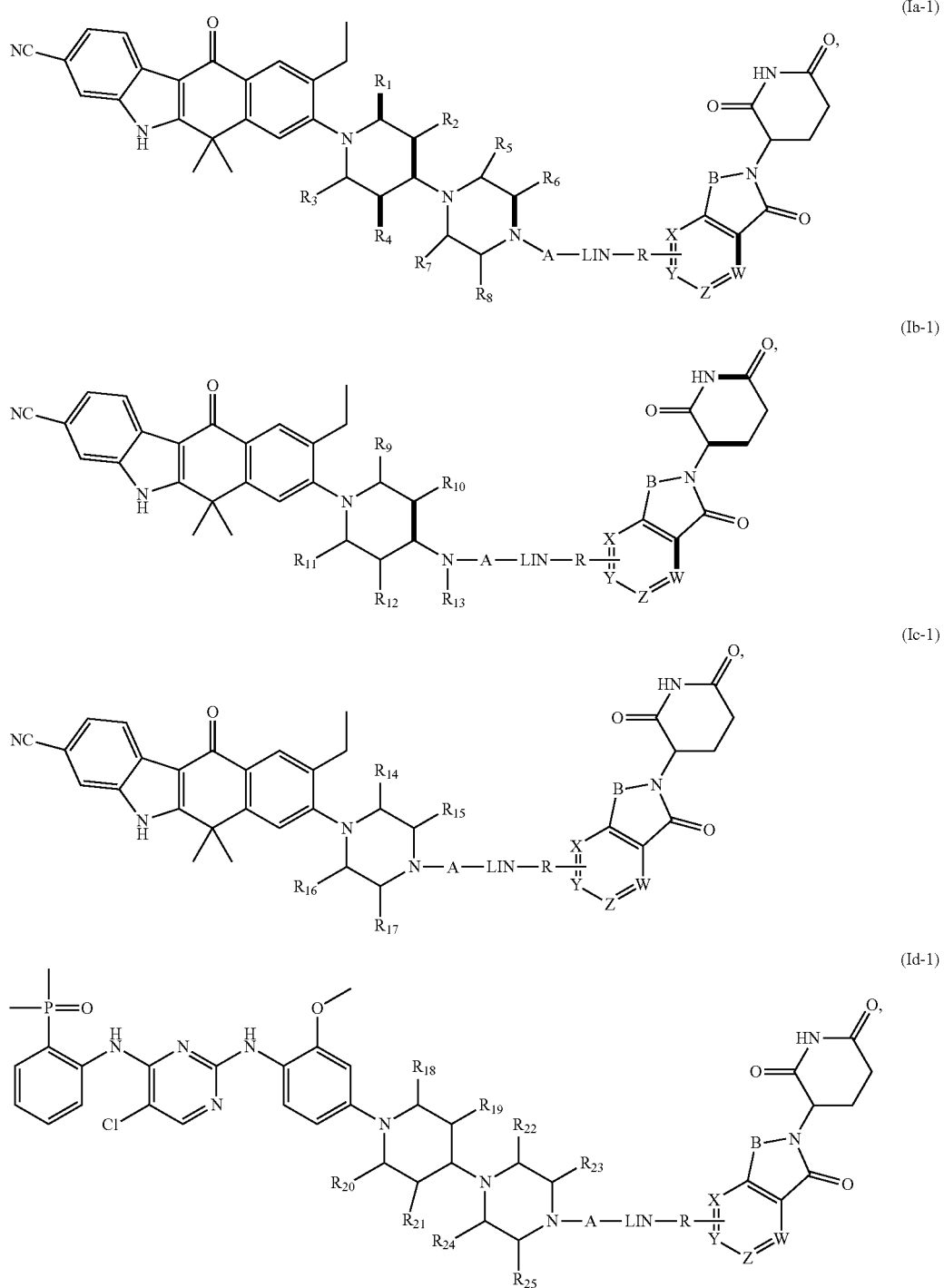

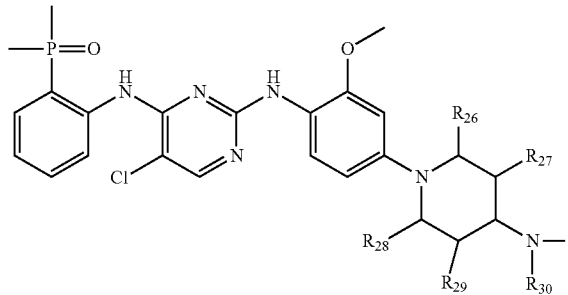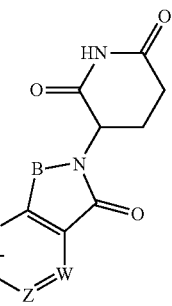

(Ie-1)

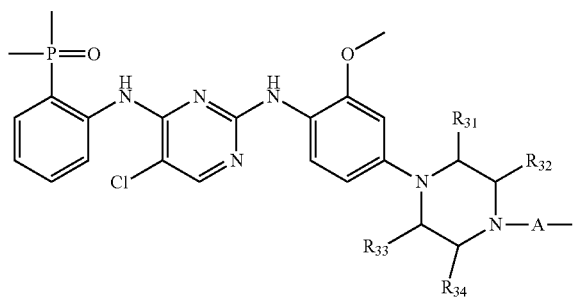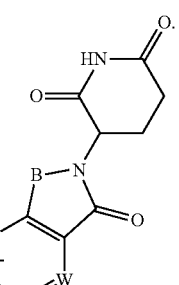

(If-1)

3. The compound represented by formula (I) as defined in claim 1, or the salt thereof, the enantiomer thereof, the stereoisomer thereof, the solvate thereof, the polymorph thereof, wherein the B represents CH2 or C(O); X, Y, Z, and W each independently represents CH; and R represents ethynylene.

4. The compound represented by formula (I) as defined in claim 1, or the salt thereof, the enantiomer thereof, the stereoisomer thereof, the solvate thereof, the polymorph thereof, wherein the LIN represents:

—U—$C_{1-30}$ alkylene-, —U—$(CH_2)_{n1}$—C(O)NH—$(CH_2)_{n2})_{m1}$—, —U—$(CH_2)_{n1}$—(NHC(O)—$(CH_2)_{n2})_{m1}$, —U—$(CH_2)_{n1}$—$(O(CH_2)_{n2})_{m1}$—, —U—$(CH_2)_{n1}$—$(O(CH_2)_{n2})_{m1}$—$(O(CH_2)_{n3})_{m2}$—, —U—$(CR_{a1}R_{a2})_{n1}$—$(O(CR_{a3}R_{a4})_{n2})_{m1}$—, —U—$(CR_{a5}R_{a6})_{n1}$—$(O(CR_{a7}R_{a8})_{n2})_{m1}$—$(O(CR_{a9}R_{a10})_{n3})_{m2}$—, —U—$(CH_2)_{n1}$—C(O)NH—$(CH_2)_{n2})_{m1}$—$(O(CH_2)_{n3})_{m2}$—, —U—$(CH_2)_{n1}$—(O$(CH_2)_{n2})_{m1}$—O—$(CH_2)_{n3}$—C(O)NH—$(CH_2)_{n4}$—(O$(CH_2)_{n5})_{m2}$—O—$(CH_2)_{n6}$—, —U—$(CR_{a11}R_{a12})_{n1}$—$(O(CR_{a13}R_{a14})_{n2})_{m1}$—O—$(CR_{a15}R_{a16})_{n3}$—C(O)NH—$(CR_{a17}R_{a18})_{n4}$—$(O(CR_{a19}R_{a20})_{n5})_{m2}$—O—$(CR_{a21}R_{a22})_{n6}$—, —U—$(CR_{a23}R_{a24})_{n1}$—C(O)NH—$(O(CR_{a25}R_{a26})_{n2})_{m1}$—, —U—$(CH_2)_{n1}$—(NHC(O)—$(CH_2)_{n2})_{m1}$—$(O(CH_2)_{n3})_{m2}$—, linear or branched —U-alkylene chain-having the carbon chain interrupted one or more times by one or more groups selected from alkynylene, alkenylene, cycloalkylene, arylene, heterocyclylene or heteroarylene or any combination thereof, or —U—$(CH_2)_{n1}$—$(O(CH_2)_{n2})_{m1}$- having alkylene carbon chain interrupted one or more times by one or more groups selected from arylene, heterocyclylene, heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represents H, linear or branched $C_1$-$C_{10}$ alkyl or $C_3$-$C_{10}$ cycloalkyl, wherein in the same LIN, $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, or $R_{a23}$, $R_{a24}$, $R_{a25}$, $R_{a26}$ are not H at the same time;

n1, n2, n3, n4, n5, n6, m1, m2 each independently represents an integer of 1, 2, 3, 4, 5, 6, 7, 8, 9, 10, 11, 12, 13, 14, 15, 16, 17, 18, 19 or 20; and the group U represents C(O), or the group U is absent; and wherein, the alkylene in the LIN is optionally substituted by one or more substituents.

5. The compound represented by formula (I) as defined in claim 4, or the salt thereof, the enantiomer thereof, the stereoisomer thereof, the solvate thereof, the polymorph thereof, wherein, the LIN represents —U—$C_{1-30}$ alkylene chain-, and the $C_{1-30}$ alkylene chain is optionally substituted by one or more substituents selected from hydroxyl, amino, mercapto, halogen or any combination thereof, or the LIN represents —U—$(CH_2)_{n1}$—C(O)NH—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20, or the LIN represents —U—$(CH_2)_{n1}$—NHC(O)—$(CH_2)_{n2}$—, wherein n1 and n2 each independently represents an integer of 1, 2, 3, 4, 5, 6, 7, 8, 9, 10, 11, 12, 13, 14, 15, 16, 17, 18, 19, or 20.

6. The compound represented by formula (I) as defined in claim 4, or the salt thereof, the enantiomer thereof, the stereoisomer thereof, the solvate thereof, the polymorph thereof, wherein the LIN represents:

—U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—;

—U—(CH₂)₂₃—; —U—(CH₂)₂₄—; —U—(CH₂)₂₅—; —U—(CH₂)₂₆—; —U—(CH₂)₂₇—; —U—(CH₂)₂₈—; —U—(CH₂)₂₉—; or —U—(CH₂)₃₀—;
wherein the group U represents C(O), or the group U is absent,
or the LIN represents: —U—CH₂C(O)NHCH₂—, —U—CH₂C(O)NH(CH₂)₂—, —U—CH₂C(O)NH(CH₂)₃—, —U—CH₂C(O)NH(CH₂)₄—, —U—CH₂C(O)NH(CH₂)₅—, —U—CH₂C(O)NH(CH₂)₆—, —U—CH₂C(O)NH(CH₂)₇—, —U—CH₂C(O)NH(CH₂)₈—, —U—CH₂C(O)NH(CH₂)₉—, —U—(CH₂C(O)NH(CH₂)₁₀—, —U—(CH₂)₂C(O)NHCH₂—, —U—(CH₂)₂C(O)NH(CH₂)₂—, —U—(CH₂)₂C(O)NH(CH₂)₃—, —U—(CH₂)₂C(O)NH(CH₂)₄—, —U—(CH₂)₂C(O)NH(CH₂)₅—, —U—(CH₂)₂C(O)NH(CH₂)₆—, —U—(CH₂)₂C(O)NH(CH₂)₇—, —U—(CH₂)₂C(O)NH(CH₂)—, —U—(CH₂)₃C(O)NHCH₂—, —U—(CH₂)₃C(O)NH(CH₂)₂—, —U—(CH₂)₃C(O)NH(CH₂)₃—, —U—(CH₂)₃C(O)NH(CH₂)₄—, —U—(CH₂)₃C(O)NH(CH₂)₅—, —U—(CH₂)₃C(O)NH(CH₂)₆—, —U—(CH₂)₃C(O)NH(CH₂)₇—, —U—(CH₂)₃C(O)NH(CH₂)₃—, —U—(CH₂)₄C(O)NHCH₂—, —U—(CH₂)₄C(O)NH(CH₂)₂—, —U—(CH₂)₄C(O)NH(CH₂)₃—, —U—(CH₂)₄C(O)NH(CH₂)₄—, —U—(CH₂)₄C(O)NH(CH₂)₅—, —U—(CH₂)₄C(O)NH(CH₂)₆—, —U—(CH₂)₅C(O)NHCH₂—, —U—(CH₂)₅C(O)NH(CH₂)₂—, —U—(CH₂)₅C(O)NH(CH₂)₃—, —U—(CH₂)₅C(O)NH(CH₂)₄—, —U—(CH₂)₅C(O)NH(CH₂)₅—, —U—(CH₂)₅C(O)NH(CH₂)₆—, —U—(CH₂)₆C(O)NHCH₂—, —U—(CH₂)₆C(O)NH(CH₂)₂—, —U—(CH₂)₆C(O)NH(CH₂)₃—, —U—(CH₂)₆C(O)NH(CH₂)₄—, —U—(CH₂)₆C(O)NH(CH₂)₅—, —U—(CH₂)₆C(O)NH(CH₂)₆—, —U—(CH₂)₆C(O)NH(CH₂)₇—, —U—(CH₂)₇C(O)NHCH₂—, —U—(CH₂)₇C(O)NH(CH₂)₂—, —U—(CH₂)₇C(O)NH(CH₂)₃—, —U—(CH₂)₇C(O)NH(CH₂)₄—, —U—(CH₂)₇C(O)NH(CH₂)₅—, —U—(CH₂)₇C(O)NH(CH₂)₆—, —U—(CH₂)₇C(O)NH(CH₂)₇—, —U—(CH₂)₈C(O)NHCH₂—, —U—(CH₂)₈C(O)NH(CH₂)₂—, —U—(CH₂)₈C(O)NH(CH₂)₃—, —U—(CH₂)₈C(O)NH(CH₂)₄—, —U—(CH₂)₈C(O)NH(CH₂)₅—, —U—(CH₂)₉C(O)NH(CH₂)₆—, —U—(CH₂)C(O)NH(CH₂)₇—, —U—(CH₂)C(O)NH(CH₂)—, —U—(CH₂)₉C(O)NHCH₂—, —U—(CH₂)₉C(O)NH(CH₂)₂—, —U—(CH₂)₉C(O)NH(CH₂)₃—, —U—(CH₂)₉C(O)NH(CH₂)₄—, —U—(CH₂)₉C(O)NH(CH₂)₅—, —U—(CH₂)₉C(O)NH(CH₂)₆—, —U—(CH₂)₉C(O)NH(CH₂)₇—, —U—(CH₂)₉C(O)NH(CH₂)₈—, —U—(CH₂)₉C(O)NH(CH₂)₉—, —U—(CH₂)₁₀C(O)NHCH₂—, —U—(CH₂)₁₀C(O)NH(CH₂)₂—, —U—(CH₂)₁₀C(O)NH(CH₂)₃—, —U—(CH₂)₁₀C(O)NH(CH₂)₄—, —U—(CH₂)₁₀C(O)NH(CH₂)N- or —U—(CH₂)₁₀C(O)NH(CH₂)₁₀—, or the LIN represents: —U—CH₂NHC(O)CH—, —U—CH₂NHC(O)(CH₂)₂—, —U—CH₂NHC(O)(CH₂)₃—, —U—CH₂NHC(O)(CH₂)₄—, —U—CH₂NHC(O)(CH₂)₅—, —U—CH₂NHC(O)(CH₂)₆—, —U—CH₂NHC(O)(CH₂)₇—, —U—CH₂NHC(O)(CH₂)₈—, —U—CH₂NHC(O)(CH₂)₉—, —U—CH₂NHC(O)(CH₂)₃—, —U—(CH₂)₂NHC(O)CH₂—, —U—(CH₂)₂NHC(O)(CH₂)₂—, —U—(CH₂)₂NHC(O)(CH₂)₃—, —U—(CH₂)₂NHC(O)(CH₂)₄—, —U—(CH₂)₂NHC(O)(CH₂)₅—, —U—(CH₂)₃NHC(O)CH₂—, —U—(CH₂)₃NHC(O)(CH₂)₂—, —U—(CH₂)₃NHC(O)(CH₂)₃—, —U—(CH₂)₃NHC(O)(CH₂)₄—, —U—(CH₂)₃NHC(O)(CH₂)₅—, —U—(CH₂)₄NHC(O)CH₂—, —U—(CH₂)₄NHC(O)(CH₂)₂—, —U—(CH₂)₄NHC(O)(CH₂)₃—, —U—(CH₂)₄NHC(O)(CH₂)₄—, —U—(CH₂)₄NHC(O)(CH₂)₅—, —U—(CH₂)₄NHC(O)(CH₂)₆—, —U—(CH₂)₄NHC(O)(CH₂)₇—, —U—(CH₂)₅NHC(O)CH₂—, —U—(CH₂)₅NHC(O)(CH₂)₂—, —U—(CH₂)₅NHC(O)(CH₂)₃—, —U—(CH₂)₅NHC(O)(CH₂)₄—, —U—(CH₂)₅NHC(O)(CH₂)₅—, —U—(CH₂)₅NHC(O)(CH₂)₆—, —U—(CH₂)₆NHC(O)CH₂—, —U—(CH₂)₆NHC(O)(CH₂)₂—, —U—(CH₂)₆NHC(O)(CH₂)₃—, —U—(CH₂)₆NHC(O)(CH₂)₄—, —U—(CH₂)₆NHC(O)(CH₂)₅—, —U—(CH₂)₆NHC(O)(CH₂)₆—, —U—(CH₂)₆NHC(O)(CH₂)₇—, —U—(CH₂)₇NHC(O)CH₂—, —U—(CH₂)₇NHC(O)(CH₂)₂—, —U—(CH₂)₇NHC(O)(CH₂)₃—, —U—(CH₂)₇NHC(O)(CH₂)₄—, —U—(CH₂)₇NHC(O)(CH₂)₅—, —U—(CH₂)₇NHC(O)(CH₂)₆—, —U—(CH₂)₇NHC(O)(CH₂)₇—, —U—(CH₂)₈NHC(O)CH₂—, —U—(CH₂)₉NHC(O)(CH₂)₂—, —U—(CH₂)NHC(O)(CH₂)₃—, —U—(CH₂)NHC(O)(CH₂)—, —U—(CH₂)₉NHC(O)CH₂—, —U—(CH₂)₉NHC(O)(CH₂)₂—, —U—(CH₂)₉NHC(O)(CH₂)₃—, —U—(CH₂)₉NHC(O)(CH₂)₉—, or —U—(CH₂)₁₀NHC(O)(CH₂)₁₀—.

7. The compound represented by formula (I) as defined in claim 1, or the salt thereof, the enantiomer thereof, the stereoisomer thereof, the solvate thereof, the polymorph thereof, wherein the compound is selected from:
- 8-(4-(4-(4-(2-(2,6-dioxopiperidin-3-yl)-1-oxoisoindolin-4-yl)but-3-yn-1-yl)piperazin-1-yl)piperidin-1-yl)-9-ethyl-6,6-dimethyl-11-oxo-6,11-dihydro-5H-benzo[b]carbazole-3-carbonitrile;
- 8-(4-(4-(5-(2-(2,6-dioxopiperidin-3-yl)-1-oxoisoindolin-4-yl)pent-4-yn-1-yl)piperazin-1-yl)piperidin-1-yl)-9-ethyl-6,6-dimethyl-11-oxo-6,11-dihydro-5H-benzo[b]carbazole-3-carbonitrile;
- 8-(4-(4-(6-(2-(2,6-dioxopiperidin-3-yl)-1-oxoisoindolin-4-yl)hex-5-yn-1-yl)piperazin-1-yl)piperidin-1-yl)-9-ethyl-6,6-dimethyl-11-oxo-6,11-dihydro-5H-benzo[b]carbazole-3-carbonitrile;
- 8-(4-(4-(7-(2-(2,6-dioxopiperidin-3-yl)-1-oxoisoindolin-4-yl)hept-6-yn-1-yl)piperazin-1-yl)piperidin-1-yl)-9-ethyl-6,6-dimethyl-11-oxo-6,11-dihydro-5H-benzo[b]carbazole-3-carbonitrile;
- 8-(4-(4-(8-(2-(2,6-dioxopiperidin-3-yl)-1-oxoisoindolin-4-yl)oct-7-yn-1-yl)piperazin-1-yl)piperidin-1-yl)-9-ethyl-6,6-dimethyl-11-oxo-6,11-dihydro-5H-benzo[b]carbazole-3-carbonitrile;
- 8-(4-(4-(9-(2-(2,6-dioxopiperidin-3-yl)-1-oxoisoindolin-4-yl)non-8-yn-1-yl)piperazin-1-yl)piperidin-1-yl)-9-ethyl-6,6-dimethyl-11-oxo-6,11-dihydro-5H-benzo[b]carbazole-3-carbonitrile;
- 3-(4-(4-(4-(1-(4-((5-chloro-4-((2-(dimethylphosphono)phenyl)amino)pyrimidin-2-yl)amino)-3-methoxyphenyl)piperidin-4-yl)piperazin-1-yl)but-1-yn-1-yl)-1-oxoisoindolin-2-yl)piperidine-2,6-dione;
- 3-(4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-1-oxoisoindolin-2-yl)piperidine-2,6-dione;
- 3-(4-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)hex-1-yn-1-yl)-1-oxoisoindolin-2-yl)piperidine-2,6-dione;

3-(4-(7-(4-(1-(4-((5-chloro-4-((2-(dimethylphosphono)phenyl)amino)pyrimidin-2-yl)amino)-3-methoxyphenyl)piperidin-4-yl)piperazin-1-yl)hept-1-yn-1-yl)-1-oxoisoindolin-2-yl)piperidine-2,6-dione;

3-(4-(8-(4-(1-(4-((5-chloro-4-((2-(dimethylphosphono)phenyl)amino)pyrimidin-2-yl)amino)-3-methoxyphenyl)piperidin-4-yl)piperazin-1-yl)oct-1-yn-1-yl)-1-oxoisoindolin-2-yl)piperidine-2,6-dione;

3-(4-(9-(4-(1-(4-((5-chloro-4-((2-(dimethylphosphono)phenyl)amino)pyrimidin-2-yl)amino)-3-methoxyphenyl)piperidin-4-yl)piperazin-1-yl)non-1-yn-1-yl)-1-oxoisoindolin-2-yl)piperidine-2,6-dione;

8-(4-(4-(6-(2-(2,6-dioxopiperidin-3-yl)-1-oxoisoindolin-5-yl)hex-5-ynoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(7-(2-(2,6-dioxopiperidin-3-yl)-1-oxoisoindolin-5-yl)hept-6-ynoyl)piperazin-1-yl)piperidin-1-yl)-9-ethyl-6,6-dimethyl-11-oxo-6,11-dihydro-5H-benzo[b]carbazole-3-carbonitrile;

2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(5-(2-(2,6-dioxopiperidin-3-yl)-1-oxoisoindolin-4-yl)pent-4-yn-1-yl)acetamide;

2-(4-(1-(3-cyano-9-ethyl-6,6-dimethyl-11-oxo-6,11-dihydro-5H-benzo[b]carbazole-8-yl)piperidin-4-yl)piperazin-1-yl)-N-(6-(2-(2,6-dioxopiperidin-3-yl)-1-oxoisoindolin-4-yl)hex-5-yn-1-yl)acetamide;

2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(5-(2-(2,6-dioxopiperidin-3-yl)-1-oxoisoindolin-4-yl)pent-4-yn-1-yl)acetamide;

2-(4-(1-(4-((5-chloro-4-((2-(dimethylphosphono)phenyl)amino)pyrimidin-2-yl)amino)-3-methoxyphenyl)piperidin-4-yl)piperazin-1-yl)-N-(6-(2-(2,6-dioxopiperidin-3-yl)-1-oxoisoindolin-4-yl)hex-5-yn-1-yl)acetamide;

3-(4-(4-((1-(4-((5-chloro-4-((2-(dimethylphosphono)phenyl)amino)pyrimidin-2-yl)amino)-3-methoxyphenyl)piperidin-4-yl)amino)but-1-yn-1-yl)-1-oxoisoindolin-2-yl)piperidine-2,6-dione;

3-(4-(5-((1-(4-((5-chloro-4-((2-(dimethylphosphono)phenyl)amino)pyrimidin-2-yl)amino)-3-methoxyphenyl)piperidin-4-yl)amino)pent-1-yn-1-yl)-1-oxoisoindolin-2-yl)piperidine-2,6-dione;

3-(4-(6-((1-(4-((5-chloro-4-((2-(dimethylphosphono)phenyl)amino)pyrimidin-2-yl)amino)-3-methoxyphenyl)piperidin-4-yl)amino)hex-1-yn-1-yl)-1-oxoisoindolin-2-yl)piperidine-2,6-dione;

3-(4-(7-((1-(4-((5-chloro-4-((2-(dimethylphosphono)phenyl)amino)pyrimidin-2-yl)amino)-3-methoxyphenyl)piperidin-4-yl)amino)hept-1-yn-1-yl)-1-oxoisoindolin-2-yl)piperidine-2,6-dione;

3-(4-(8-((1-(4-((5-chloro-4-((2-(dimethylphosphono)phenyl)amino)pyrimidin-2-yl)amino)-3-(methoxyphenyl)piperidin-4-yl)amino)oct-1-yn-1-yl)-1-oxoisoindolin-2-yl)piperidine-2,6-dione;

3-(4-(9-((1-(4-((5-chloro-4-((2-(dimethylphosphono)phenyl)amino)pyrimidin-2-yl)amino)-3-methoxyphenyl)piperidin-4-yl)amino)non-1-yn-1-yl)-1-oxoisoindolin-2-yl)piperidine-2,6-dione;

3-(5-(5-((1-(4-((5-chloro-4-((2-(dimethylphosphono)phenyl)amino)pyrimidin-2-yl)amino)-3-methoxyphenyl)piperidin-4-yl)amino)pent-1-yn-1-yl)-1-oxoisoindolin-2-yl)piperidine-2,6-dione;

3-(5-(6-((1-(4-((5-chloro-4-((2-(dimethylphosphono)phenyl)amino)pyrimidin-2-yl)amino)-3-methoxyphenyl)piperidin-4-yl)amino)hex-1-yn-1-yl)-1-oxoisoindolin-2-yl)piperidine-2,6-dione;

3-(5-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-1-oxoisoindolin-2-yl)piperidine-2,6-dione;

3-(5-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)hex-1-yn-1-yl)-1-oxoisoindolin-2-yl)piperidine-2,6-dione;

4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)pent-1-yn-1-yl)-2-(2,6-dioxopiperidin-3-yl)isoindoline-1,3-dione;

3-(4-(5-((1-(4-((5-chloro-4-((2-(dimethylphosphono)phenyl)amino)pyrimidin-2-yl)amino)-3-methoxyphenyl)piperidin-4-yl)(methyl)amino)pent-1-yn-1-yl)-1-oxoisoindolin-2-yl)piperidine-2,6-dione;

8-(4-(4-(5-(2-(2,6-dioxopiperidin-3-yl)-1-oxoisoindolin-4-yl)pent-4-ynoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(6-(2-(2,6-dioxopiperidin-3-yl)-1-oxoisoindolin-4-yl)hex-5-ynoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(7-(2-(2,6-dioxopiperidin-3-yl)-1-oxoisoindolin-4-yl)hept-6-ynoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(8-(2-(2,6-dioxopiperidin-3-yl)-1-oxoisoindolin-4-yl)oct-7-ynoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(9-(2-(2,6-dioxopiperidin-3-yl)-1-oxoisoindolin-4-yl)non-8-ynoyl)piperazin-1-yl)piperidin-1-yl)-9-ethyl-6,6-dimethyl-11-oxo-6,11-dihydro-5H-benzo[b]carbazole-3-carbonitrile;

3-(4-(5-(4-(1-(4-((5-chloro-4-((2-(dimethylphosphono)phenyl)amino)pyrimidin-2-yl)amino)-3-methoxyphenyl)piperidin-4-yl)piperazin-1-yl)-5-oxopent-1-yn-1-yl)-1-oxoisoindolin-2-yl)piperidine-2,6-dione;

3-(4-(6-(4-(1-(4-((5-chloro-4-((2-(dimethylphosphono)phenyl)amino)pyrimidin-2-yl)amino)-3-methoxyphenyl)piperidin-4-yl)piperazin-1-yl)-6-oxohex-1-yn-1-yl)-1-oxoisoindolin-2-yl)piperidine-2,6-dione;

3-(4-(7-(4-(1-(4-((5-chloro-4-((2-(dimethylphosphono)phenyl)amino)pyrimidin-2-yl)amino)-3-methoxyphenyl)piperidin-4-yl)piperazin-1-yl)-7-oxohept-1-yn-1-yl)-1-oxoisoindolin-2-yl)piperidine-2,6-dione;

3-(4-(8-(4-(1-(4-((5-chloro-4-((2-(dimethylphosphono)phenyl)amino)pyrimidin-2-yl)amino)-3-methoxyphenyl)piperidin-4-yl)piperazin-1-yl)-8-oxooct-1-yn-1-yl)-1-oxoisoindolin-2-yl)piperidine-2,6-dione; or 3-(4-(9-(4-(1-(4-((5-chloro-4-((2-(dimethylphosphono)phenyl)amino)pyrimidin-2-yl)amino)-3-methoxyphenyl)piperidin-4-yl)piperazin-1-yl)-9-oxonon-1-yn-1-yl)-1-oxoisoindolin-2-yl)piperidine-2,6-dione.

8. A pharmaceutical composition, comprising the compound represented by formula (I) as defined in claim 1, the pharmaceutically acceptable salt thereof, the enantiomer thereof, the stereoisomer thereof, the solvate thereof or the polymorph thereof, and at least one pharmaceutically acceptable carrier.

9. A method for the treatment or prevention of anaplastic large cell lymphoma or triple negative breast cancer, comprising administering an effective amount of the compound represented by formula (I) as defined in claim 1, the pharmaceutically acceptable salt thereof, the enantiomer thereof, the stereoisomer thereof, the solvate thereof or the polymorph thereof to a subject.

* * * * *